(12) United States Patent
Dixon et al.

(10) Patent No.: US 11,839,544 B2
(45) Date of Patent: Dec. 12, 2023

(54) HEART VALVE SEALING DEVICES AND DELIVERY DEVICES THEREFOR

(71) Applicant: Edwards Lifesciences Corporation, Irvine, CA (US)

(72) Inventors: Eric Robert Dixon, Villa Park, CA (US); Lauren R. Freschauf, Mission Viejo, CA (US); Rachel Liat David Foreman, Orange, CA (US); Rachel Ann Gohres, Costa Mesa, CA (US); Michael J. Popp, Irvine, CA (US); Chris J. Okos, Huntington Beach, CA (US); Eric Michael Oberwise, Newport Beach, CA (US); Steven M. Ford, Laguna Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 346 days.

(21) Appl. No.: 17/160,307

(22) Filed: Jan. 27, 2021

(65) Prior Publication Data
US 2021/0145571 A1 May 20, 2021

Related U.S. Application Data

(63) Continuation of application No. PCT/US2020/018115, filed on Feb. 13, 2020.

(60) Provisional application No. 62/944,325, filed on Dec. 5, 2019, provisional application No. 62/805,847, filed on Feb. 14, 2019.

(51) Int. Cl.
*A61F 2/24* (2006.01)

(52) U.S. Cl.
CPC ............ *A61F 2/246* (2013.01); *A61F 2/2463* (2013.01); *A61F 2/2466* (2013.01); *A61F 2220/0008* (2013.01); *A61F 2220/0091* (2013.01)

(58) Field of Classification Search
CPC ...... A61F 2/246; A61F 2/2463; A61F 2/2466; A61F 2220/0008; A61F 2220/0091;
(Continued)

(56) References Cited

U.S. PATENT DOCUMENTS

| 3,874,388 A | 4/1975 | King et al. |
| 4,340,091 A | 7/1982 | Skelton et al. |

(Continued)

FOREIGN PATENT DOCUMENTS

| CN | 1142351 A | 2/1997 |
| CN | 106175845 A | 12/2016 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Keri J Nelson
*Assistant Examiner* — Rebecca Lynee Zimmerman
(74) *Attorney, Agent, or Firm* — Thomas C. Richardson

(57) ABSTRACT

Valve repair devices and systems configured to detect proper valve leaflet insertion. The device/system can have a pair of paddles and a clasp attached to each of the paddles. The clasps may have a fixed arm attached to the paddle, a movable arm connected to the fixed arm that is movable between an open position and a closed position, and an indicator arm connected to at least one of the fixed arm and the movable arm. The indicator arm can move between a first position when not engaged with a leaflet and a second, engaged position when engaged with the leaflet. Movement of the indicator arm from the first position to the second, engaged position indicates capture of a leaflet of the native valve by the pair of paddles.

18 Claims, 342 Drawing Sheets

(58) Field of Classification Search
CPC ........ A61F 2250/001; A61F 2250/0037; A61F 2/2454; A61F 2/2496; A61F 2250/0002; A61F 2250/0096
See application file for complete search history.

(56) References Cited

U.S. PATENT DOCUMENTS

| | | | |
|---|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,569,062 B1 | 8/2009 | Kuehn et al. |
| 7,618,449 B2 | 11/2009 | Tremulis et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,824,443 B2 | 11/2010 | Salahieh et al. |
| 7,981,123 B2 | 7/2011 | Seguin |
| 7,988,724 B2 | 8/2011 | Salahieh et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,172,856 B2 | 5/2012 | Eigler et al. |
| 8,206,437 B2 | 6/2012 | Bonhoeffer et al. |
| 8,216,301 B2 | 7/2012 | Bonhoeffer et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,740,918 B2 | 6/2014 | Seguin |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 9,034,032 B2 | 5/2015 | McLean et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |

(56) References Cited

U.S. PATENT DOCUMENTS

| | | |
|---|---|---|
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0287304 A1 | 11/2009 | Dahlgren et al. |
| 2010/0022823 A1* | 1/2010 | Goldfarb ............ A61B 17/0401 600/37 |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |

(56) References Cited

U.S. PATENT DOCUMENTS

| | | |
|---|---|---|
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0092661 A1 | 4/2018 | Prabhu |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361416 A1 | 11/2021 | Stearns |
| 2021/0361422 A1 | 11/2021 | Gross et al. |
| 2021/0361428 A1 | 11/2021 | Dixon |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |

(56) References Cited

U.S. PATENT DOCUMENTS

| | | |
|---|---|---|
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0313433 A1 | 10/2022 | Ma et al. |
| 2023/0014540 A1 | 1/2023 | Metchik et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2146050 A5 | 2/1973 |
| FR | 9711600 | 3/1997 |
| WO | 2014064694 A2 | 5/2014 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban & Vogel, Germany.

Batista RJ et al., "Partial left ventriculectomy to treat end-stage heart disease", Ann Thorac Surg., vol. 64, Issue—3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977, Elsevier, United States.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.

Fucci et al., "Improved results with mitral valve repair using new surgical techniques", Eur J Cardiothorac Surg. 1995;Issue 9, vol. 11, pp. 621-626.

Inoune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue—3, pp. 240-245, Mar. 1998.

Pavcnik et al. "Development and Initial Experimental Evaluation of a Prosthetic Aortic Valve for Transcatheter Placement," Radiology, vol. 183, No. 1, pp. 151-154, Apr. 1, 1992. Elsevier, United States.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et al., "Compassionate use of the PASCAL transcatheter mitral valve repair system for patients with severe mitral regurgitation: a multicentre, prospective, observational, first-in-man study," Lancet, vol. 390, pp. 773-780, Aug. 19, 2017, Lancet, United States.

Rashkind et al., "Creation of an Atrial Septal Defect Without Thoracotomy: A Palliative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", vol. 13, No. 4, pp. 363-367, Dec. 1986, Texas Heart Institute Journal, Interventional Cardiology, Houston, TX.

Reul RM et al., "Mitral valve reconstruction for mitral insufficiency", Prog Cardiovasc Dis., vol. 39, Issue—6, May-Jun. 1997.

Rösch et al., "The Birth, Early Years and Future of Interventional Radiology," Journal of Vascular and Interventiona Radiology, vol. 14, No. 7, pp. 841-853, Jul. 1, 2003, Elsevier, United States.

(56) References Cited

OTHER PUBLICATIONS

Sabbah et al., "Mechanical Factors in the Degeneration of Porcine Bioprosthetic Valves: An Overview", Journal of Cardiac Surgery, vol. 4, No. 4, pp. 302-309, Dec. 1989.
Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.
Serruys et al., "Stenting of coronary arteries. Are we the sorcerer's apprentice?", European Heart Journal, vol. 10, No. 9 pp. 774-782, Sep. 1, 1989, The European Society of Cardiology, Oxford University Press, United Kingdom.
Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.
Uchida et al., "Modifications of Gianturco Expandable Wire Stents", Technical Note, American Roentgen Ray Society, pp. 1185-1187, May 1988.
Umaña JP et al., "'Bow-tie' mitral valve repair: an adjuvant technique for ischemic mitral regurgitation', Ann Thorac Surg., vol. 66, Issue—6, pp. 1640-1646, Nov. 1998.
Urban, Philip MD, "Coronary Artery Stenting", pp. 5-47, © 1991, ISBN: 2-88049-054-5, Editions Medecine et Hygiene, Geneva, Switzerland.
Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.
Wheatley, David J., "Valve Prosthesis", Rob & Smith's Operative Surgery—Cardiac Surgery, vol. 91, No. 2, pp. 415-424, Feb. 1, 1987, Butterworth Scientific, London, UK.
Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.

\* cited by examiner

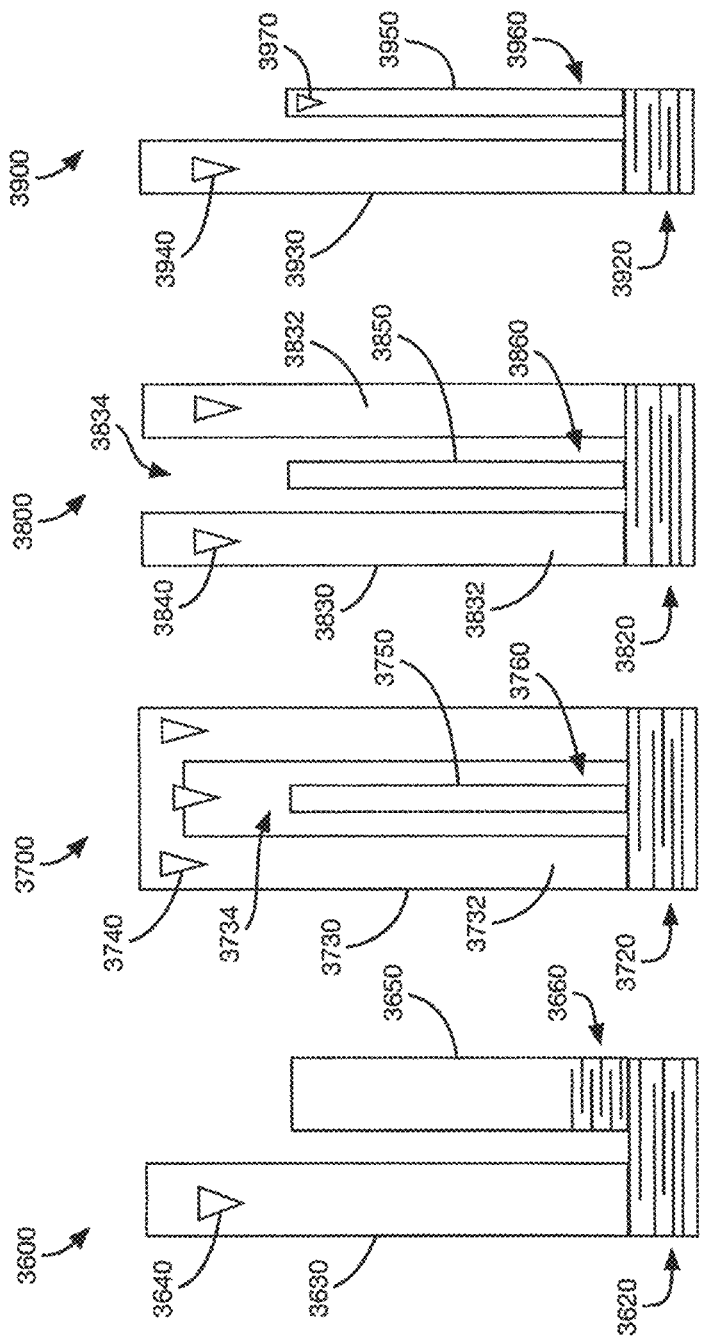

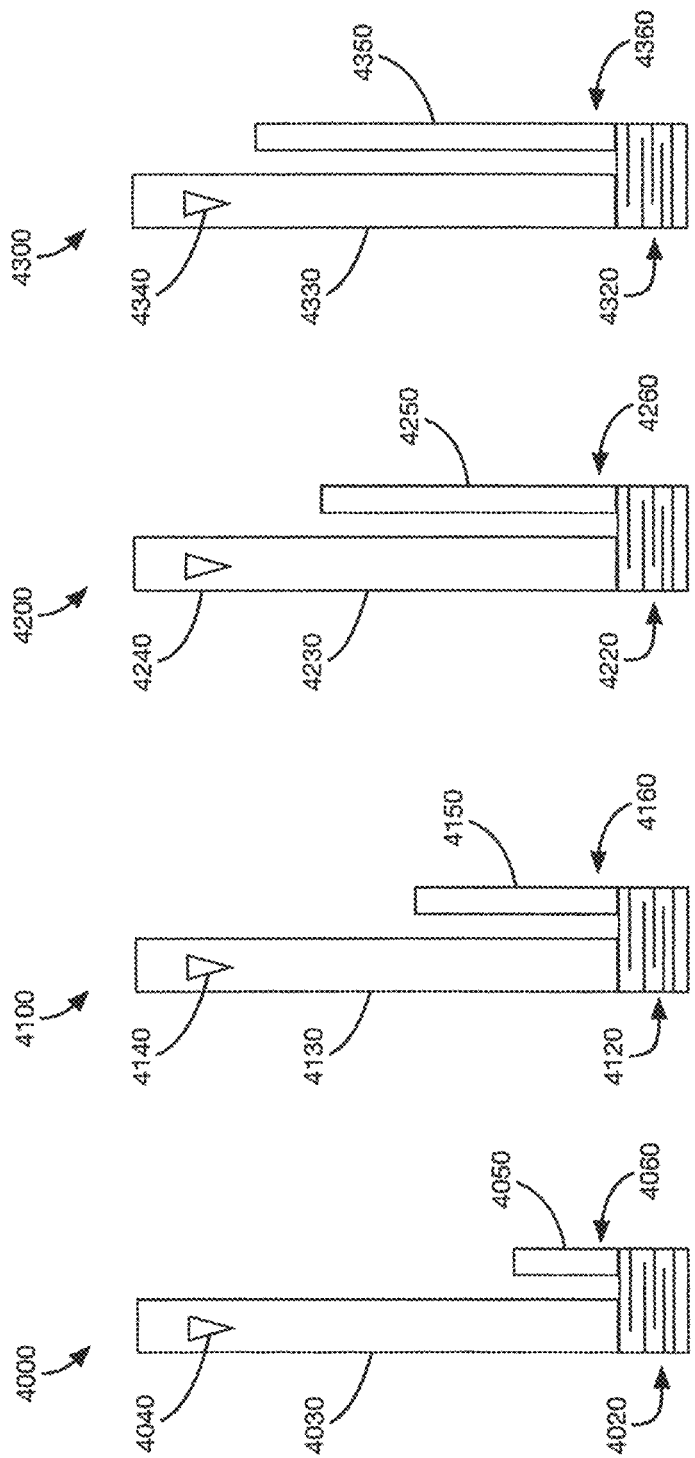

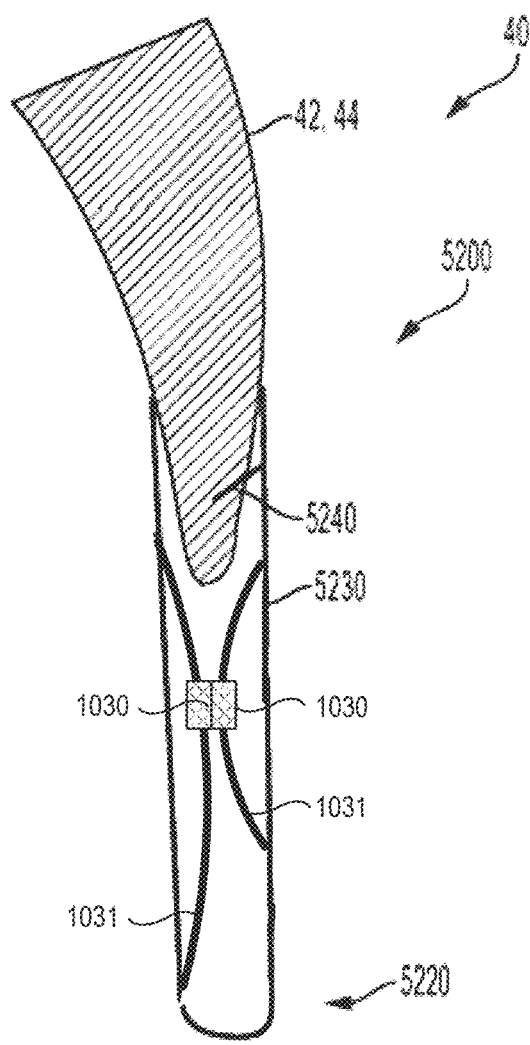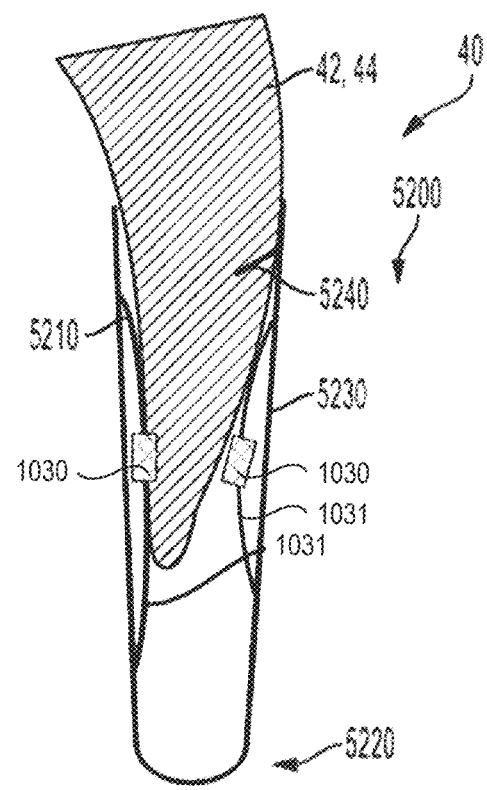
FIG. 108C
FIG. 109C

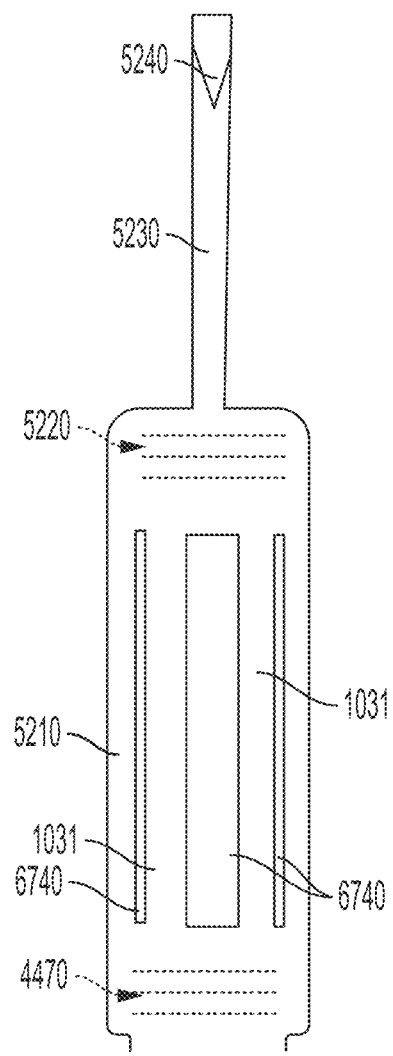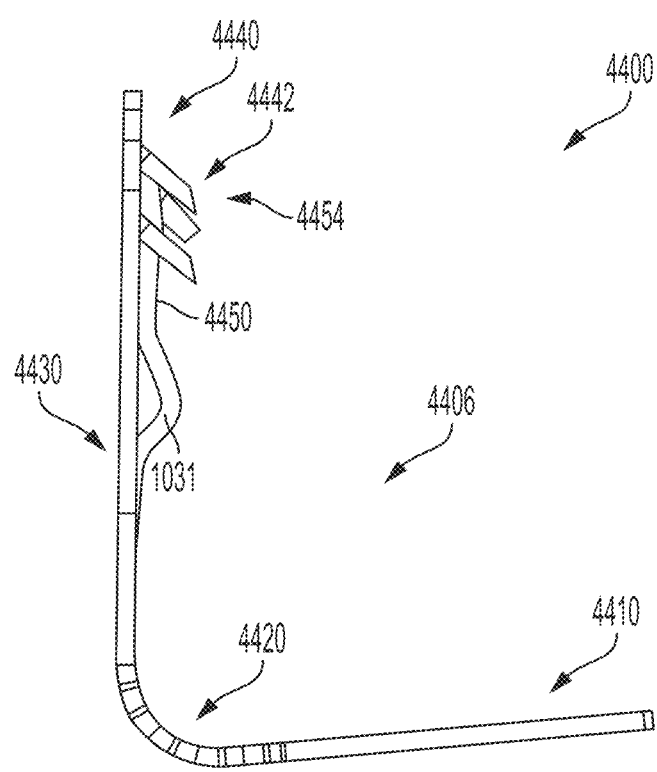
FIG. 110
FIG. 111

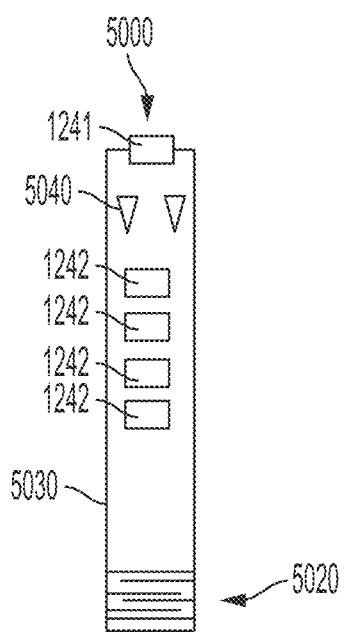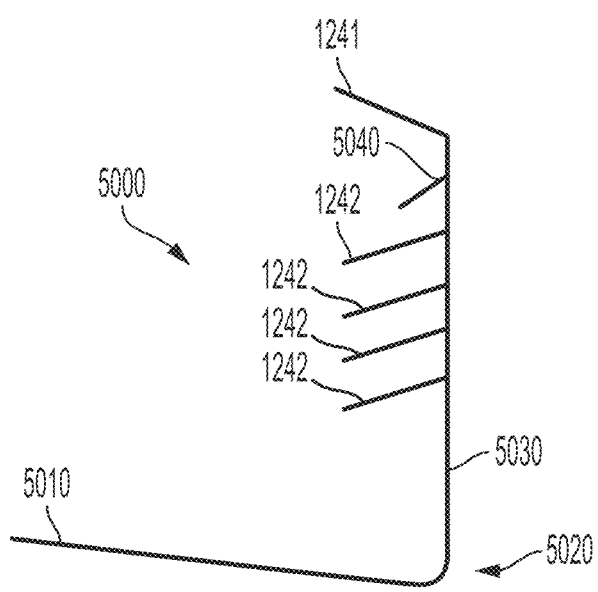
FIG. 123A
FIG. 124A

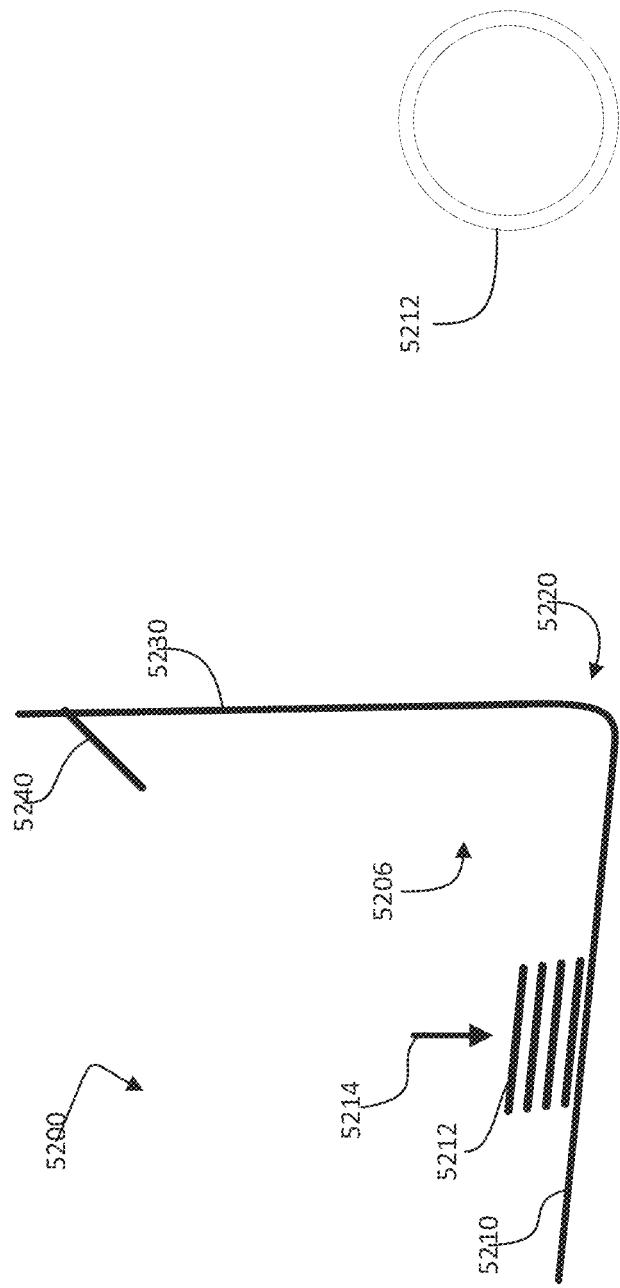

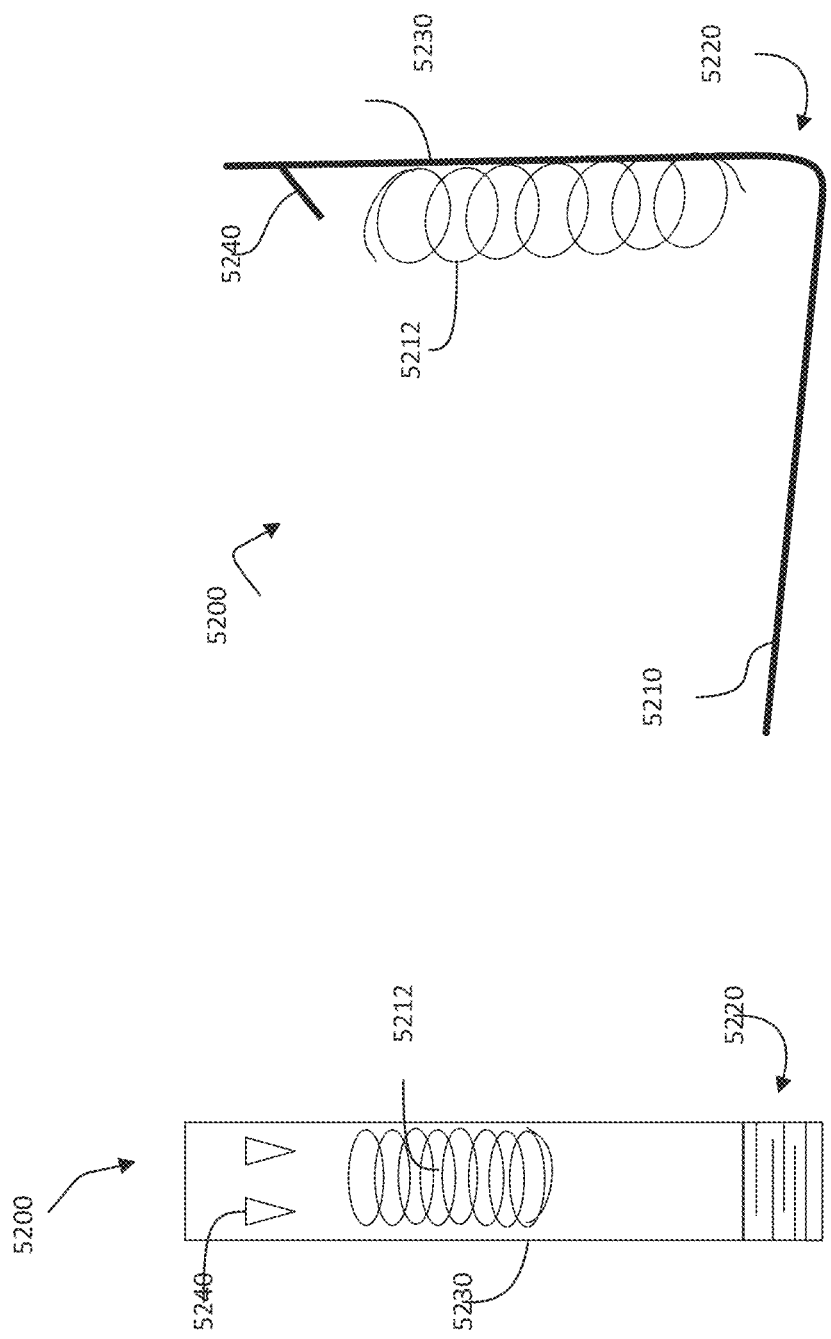

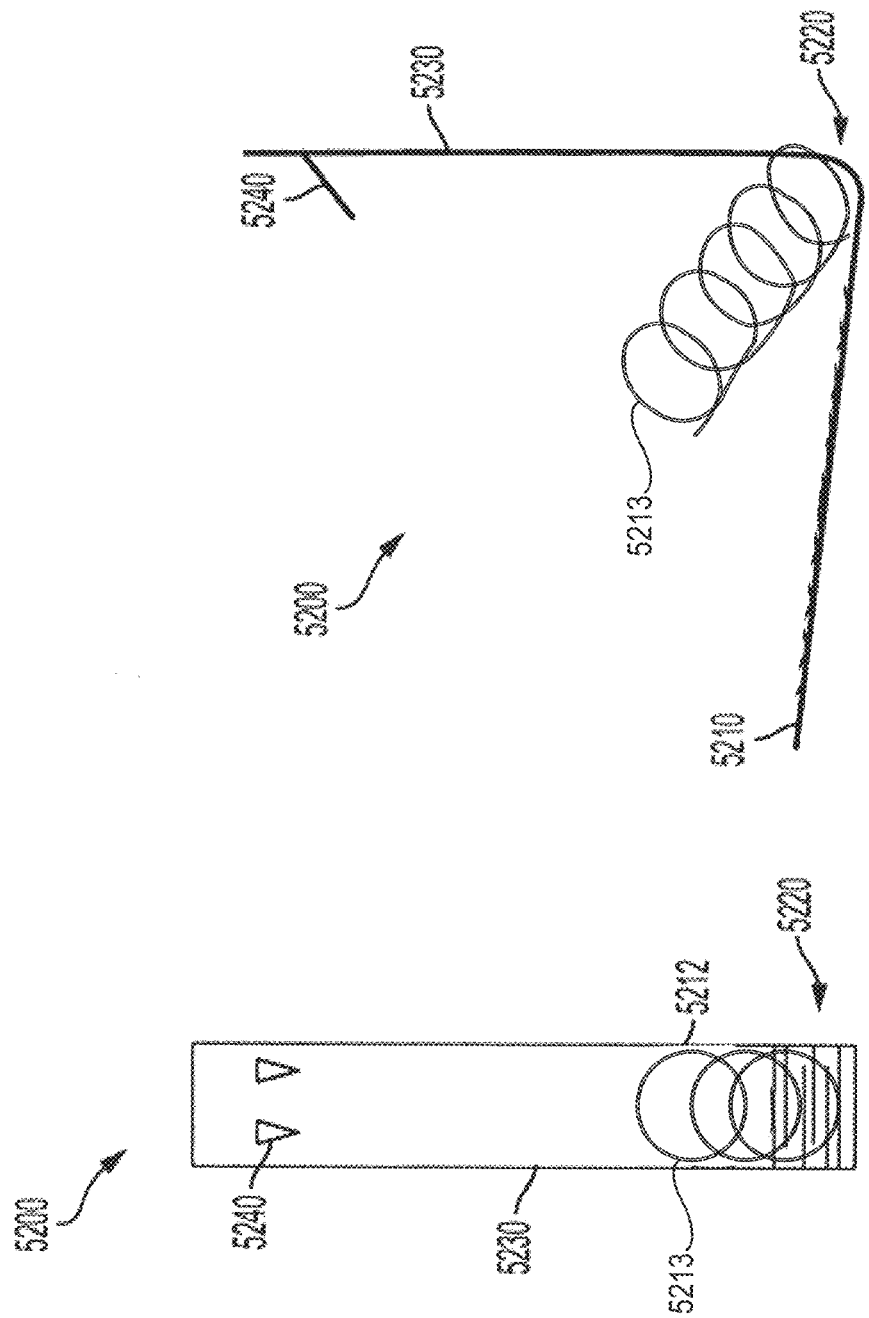

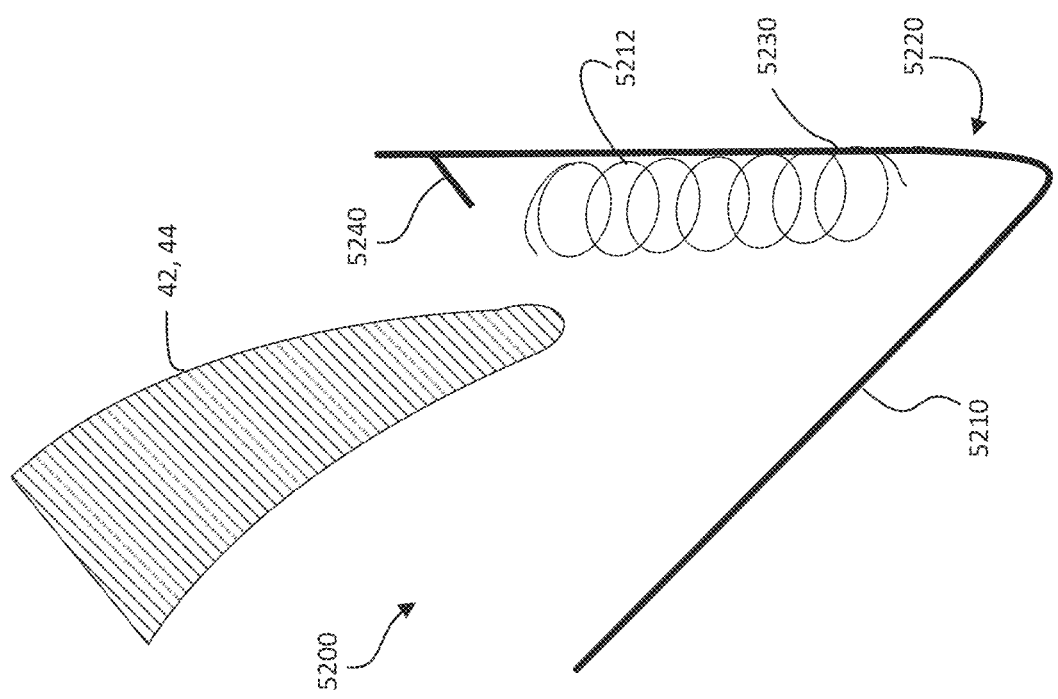

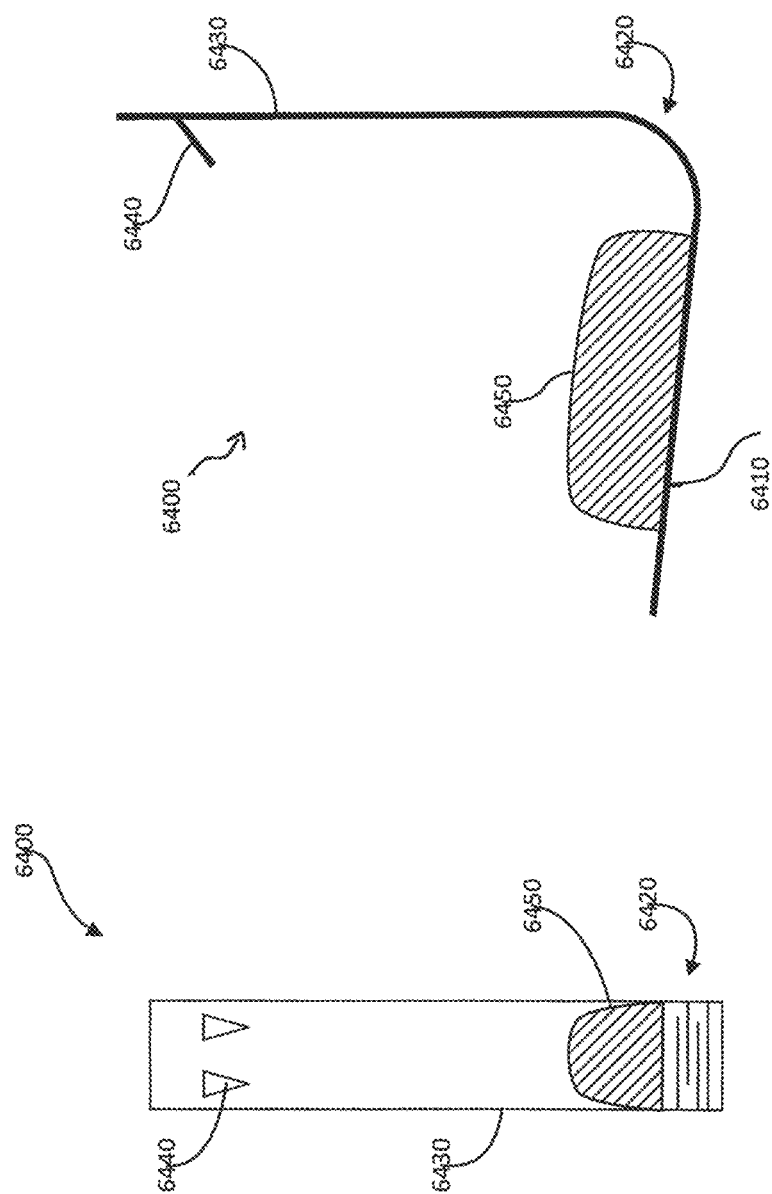

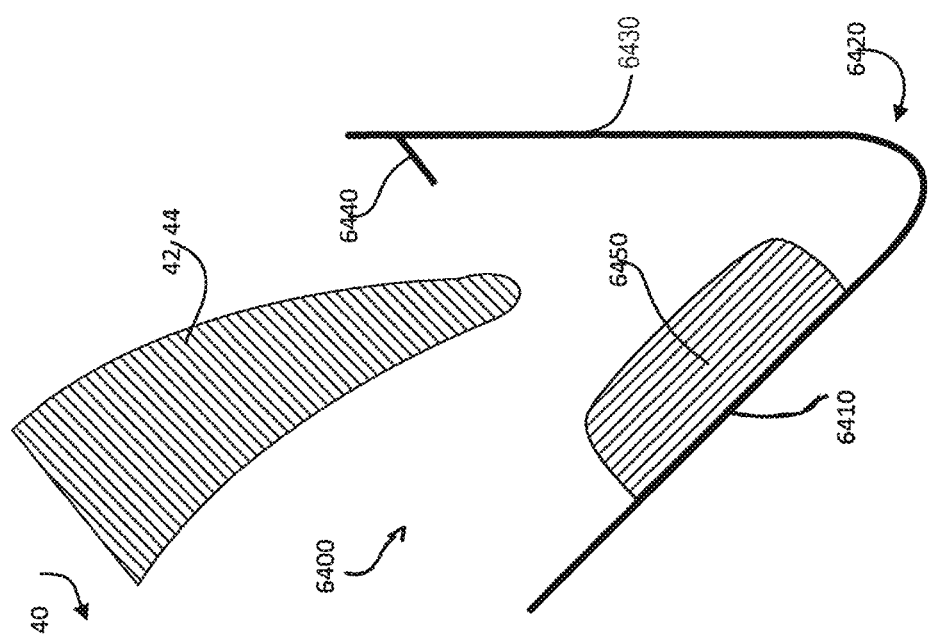

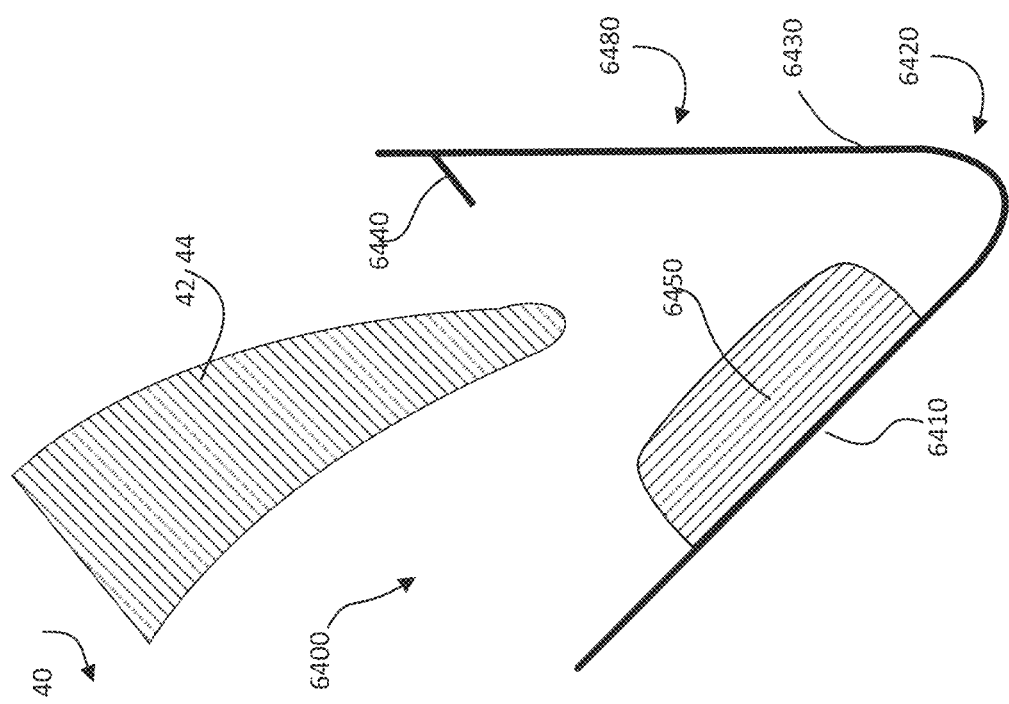

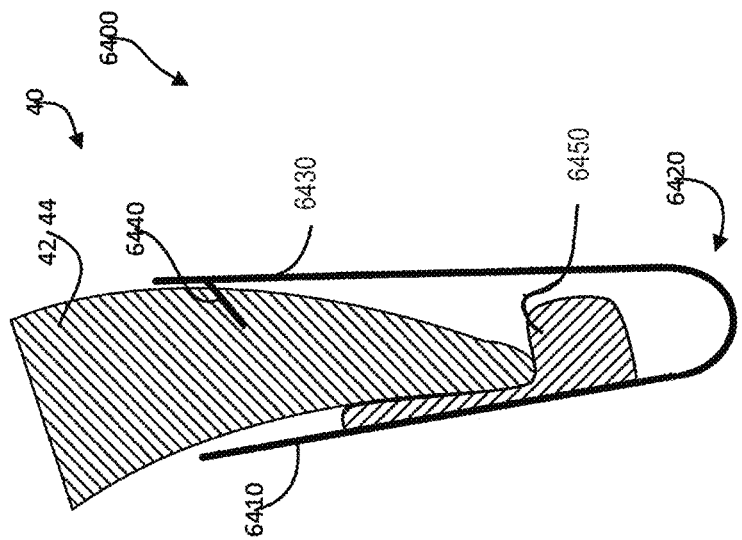

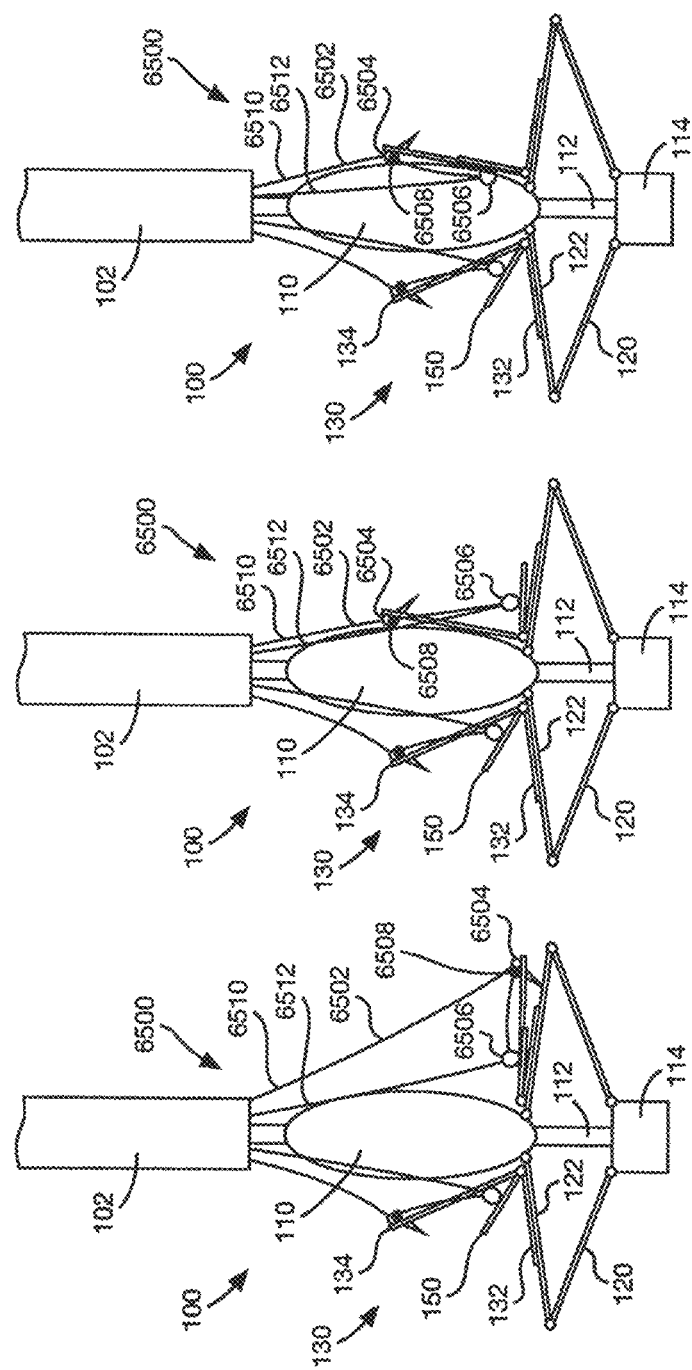

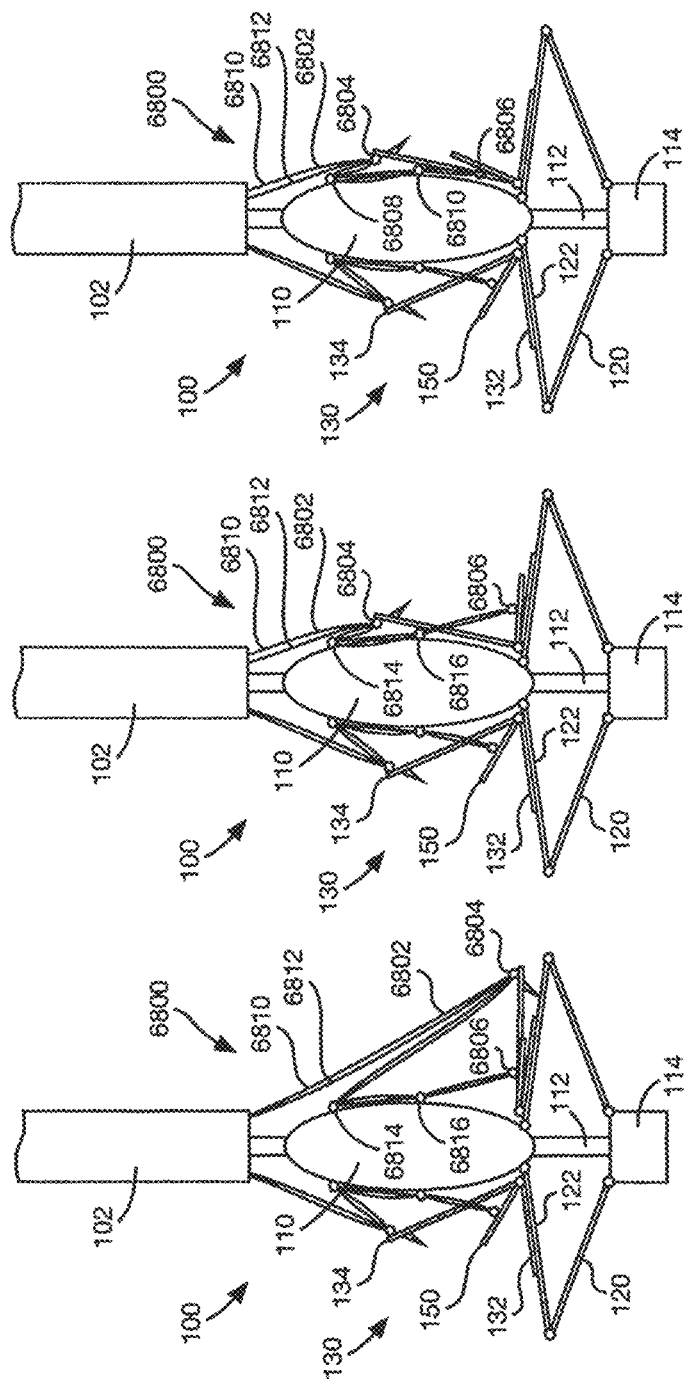

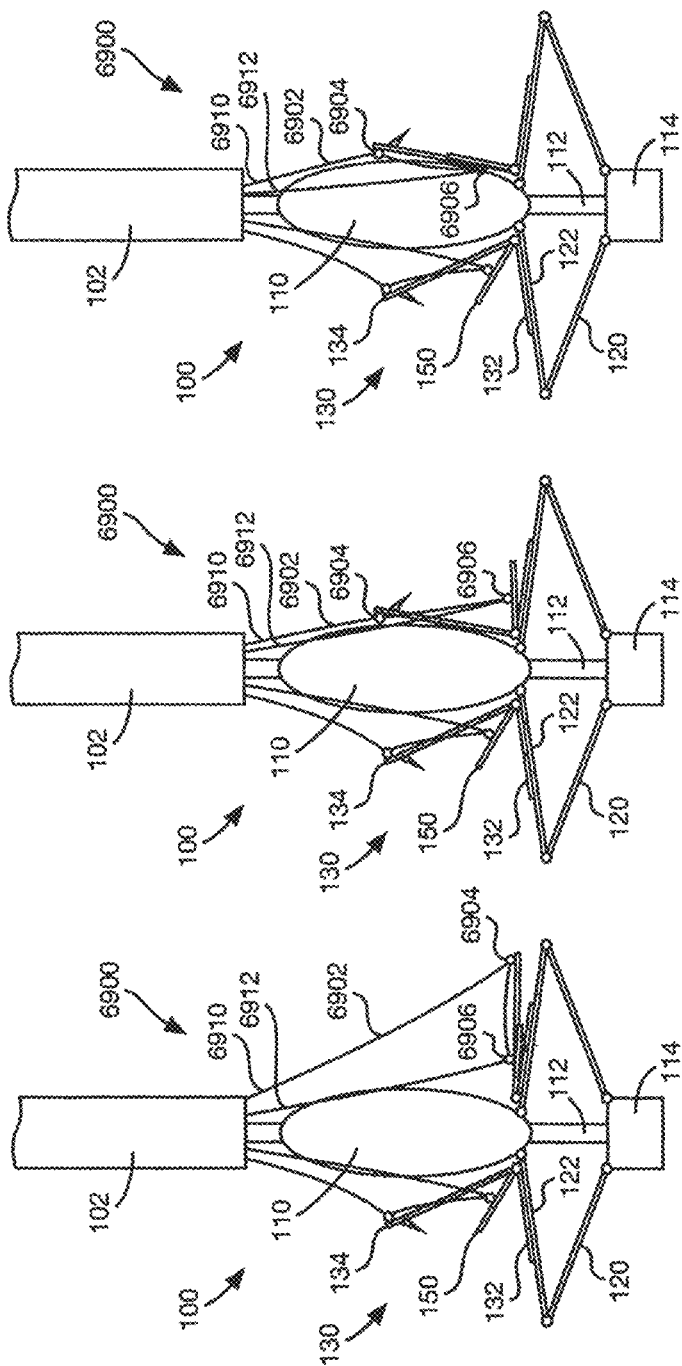

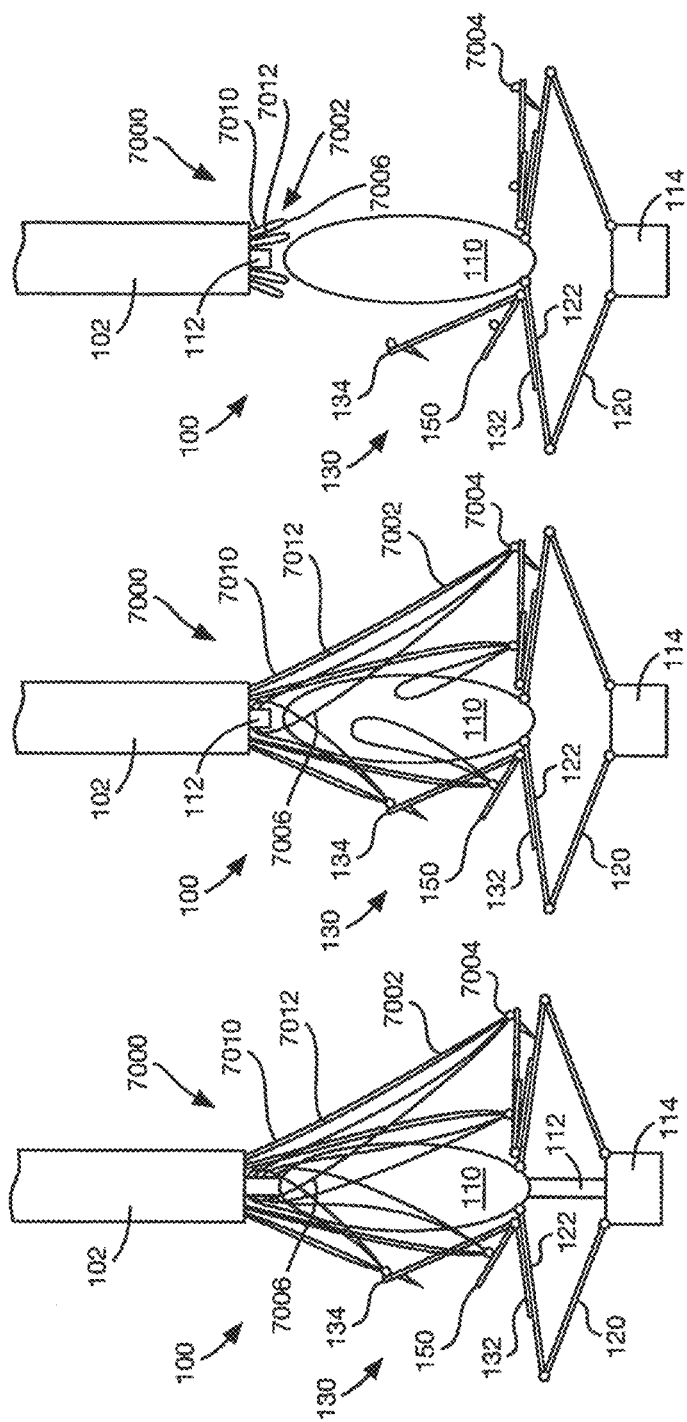

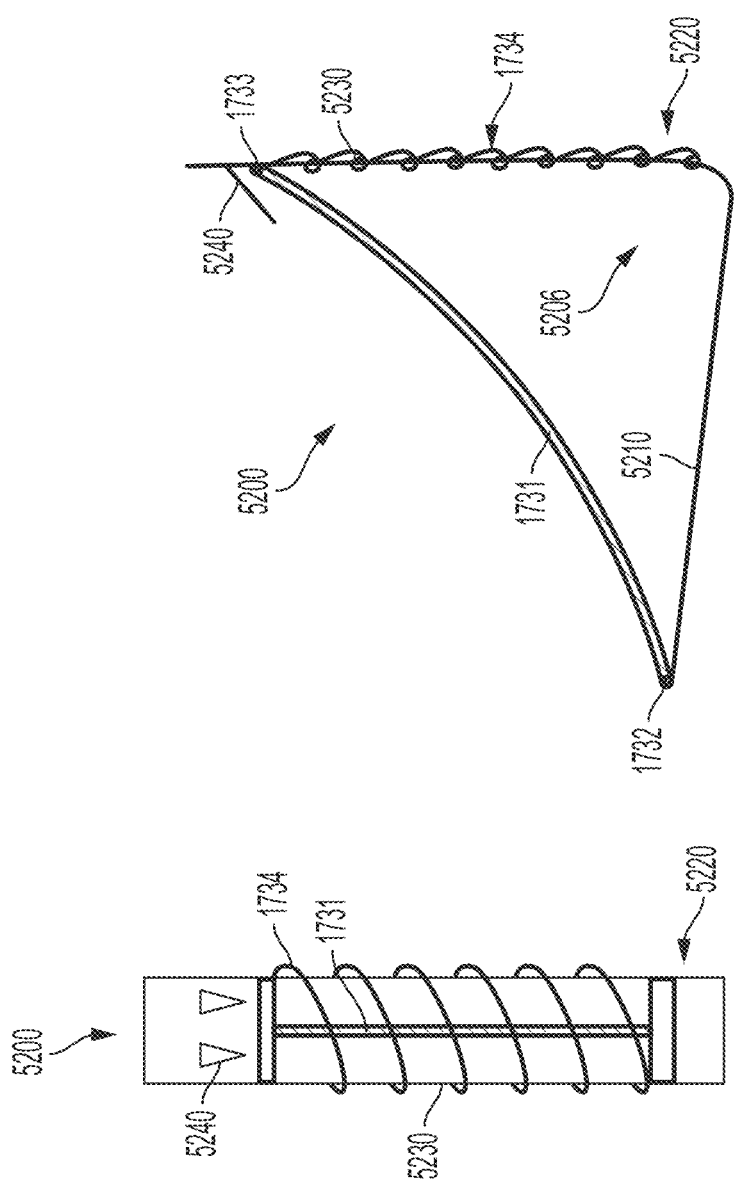

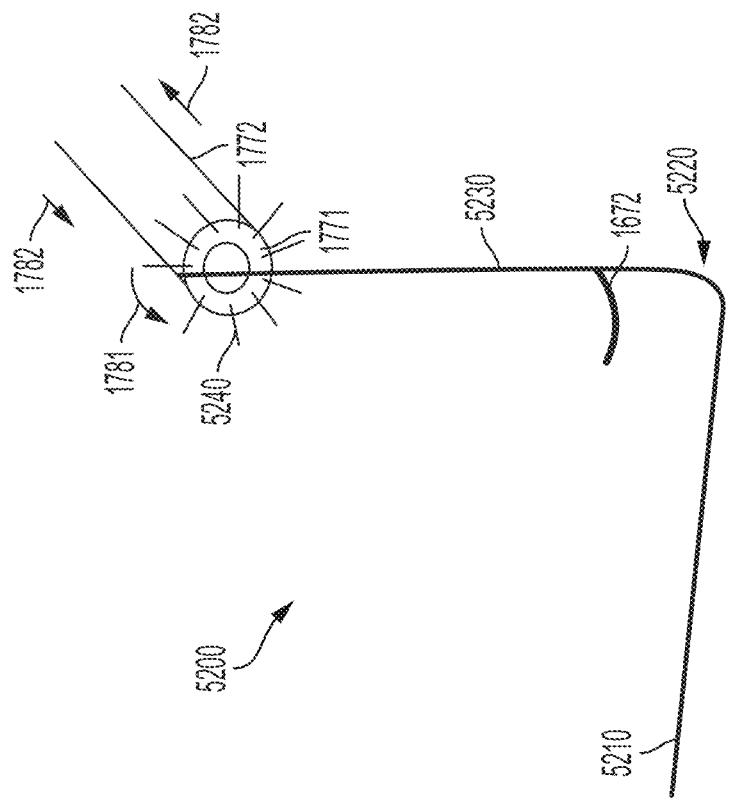
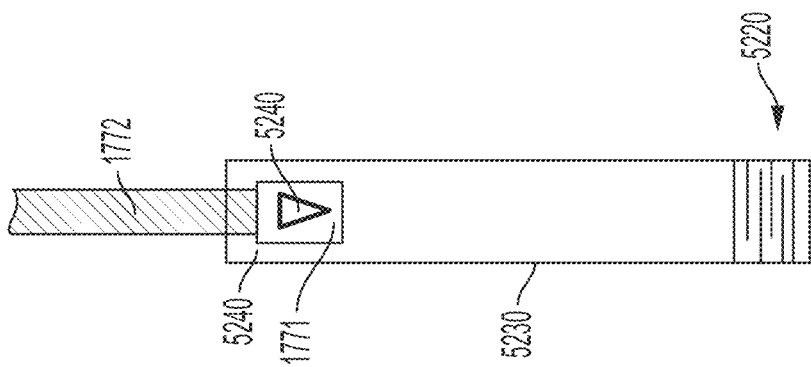

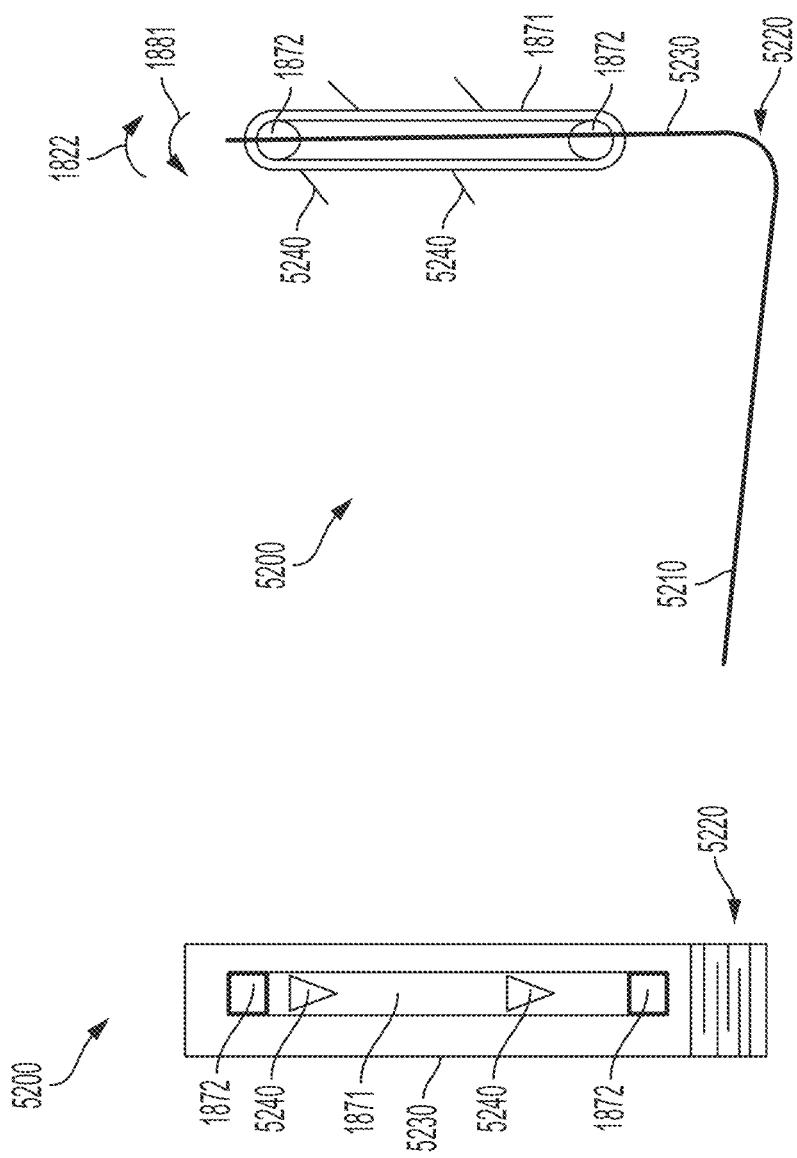

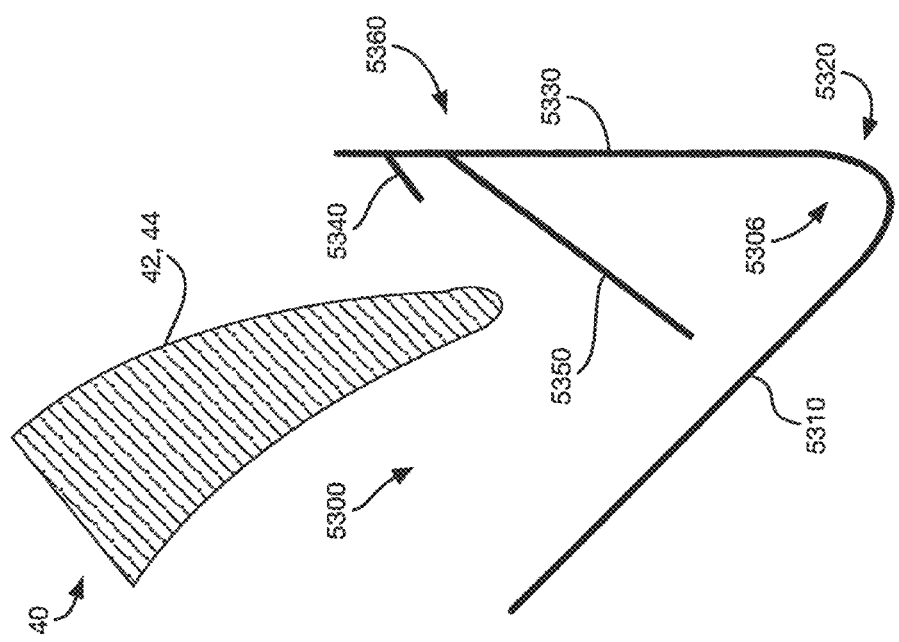

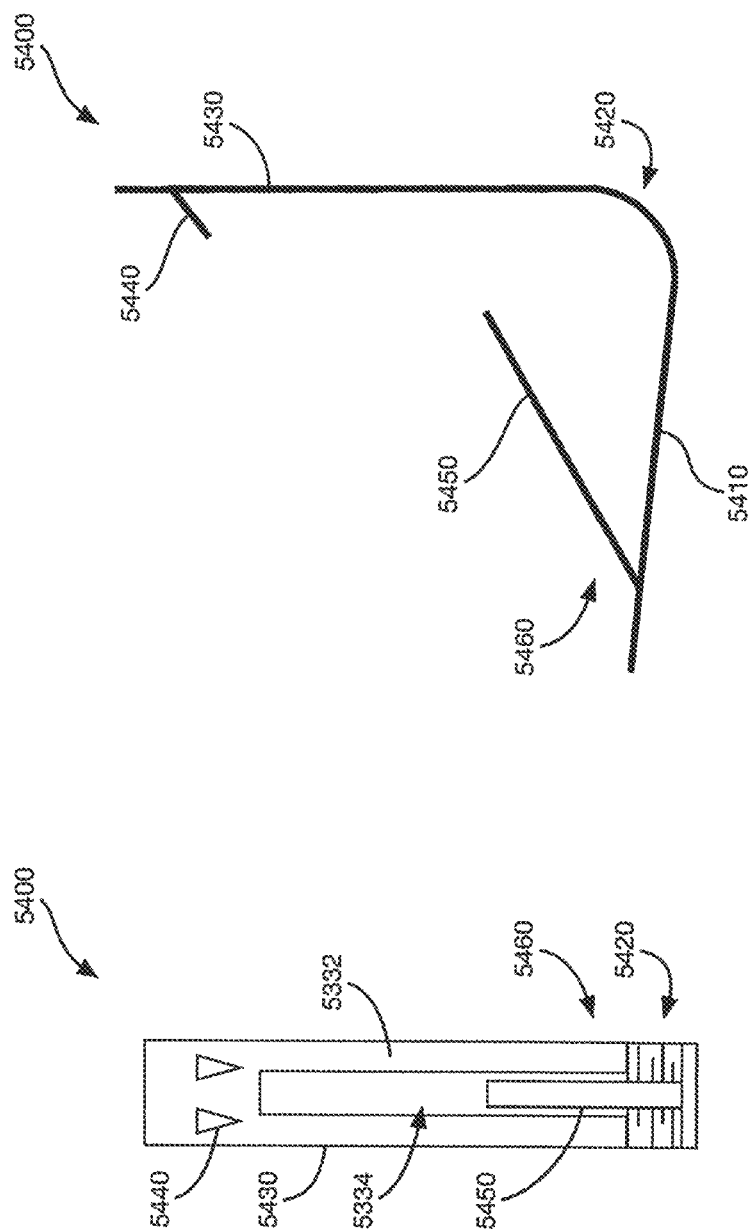

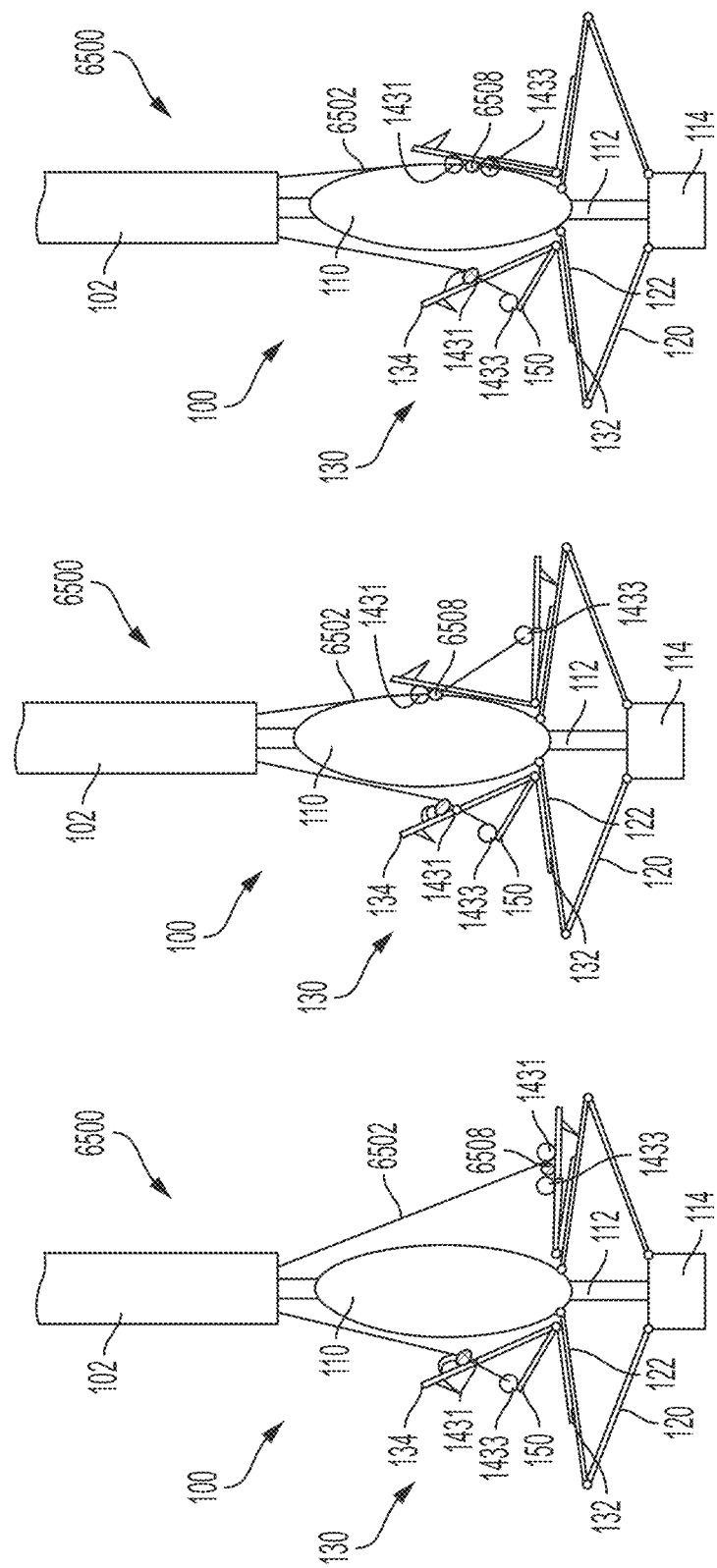

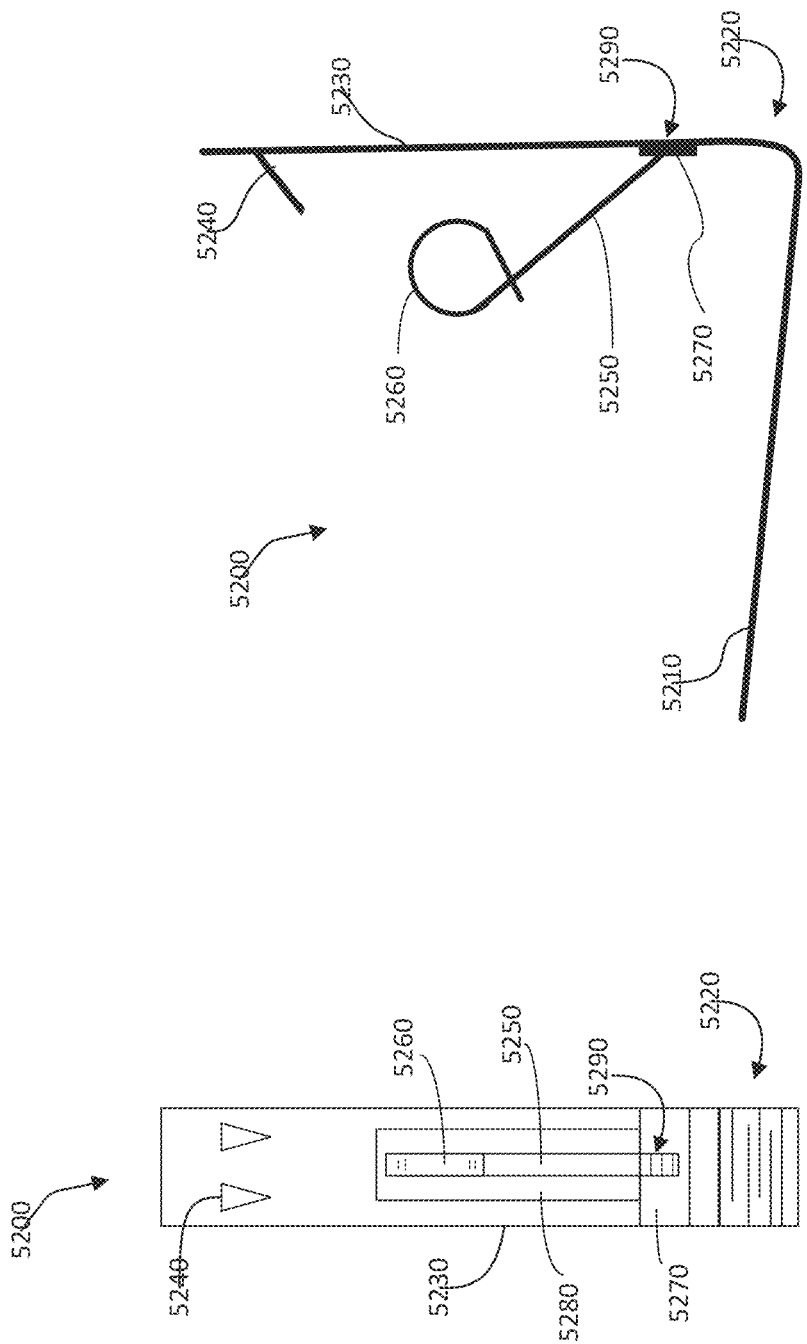

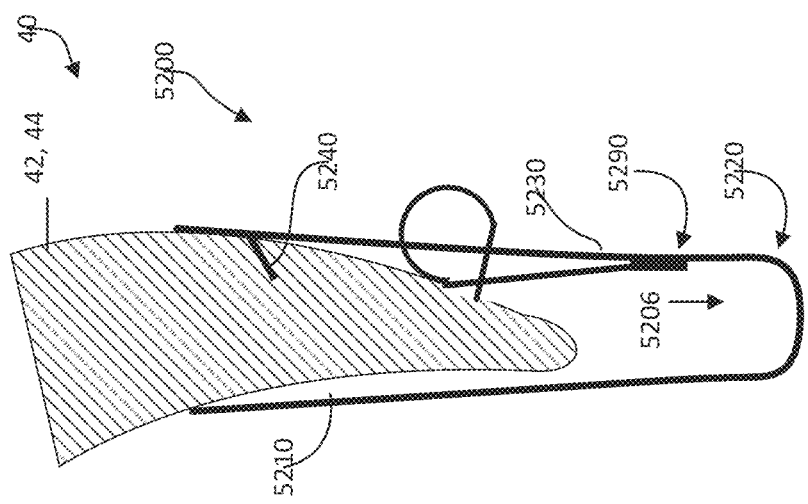

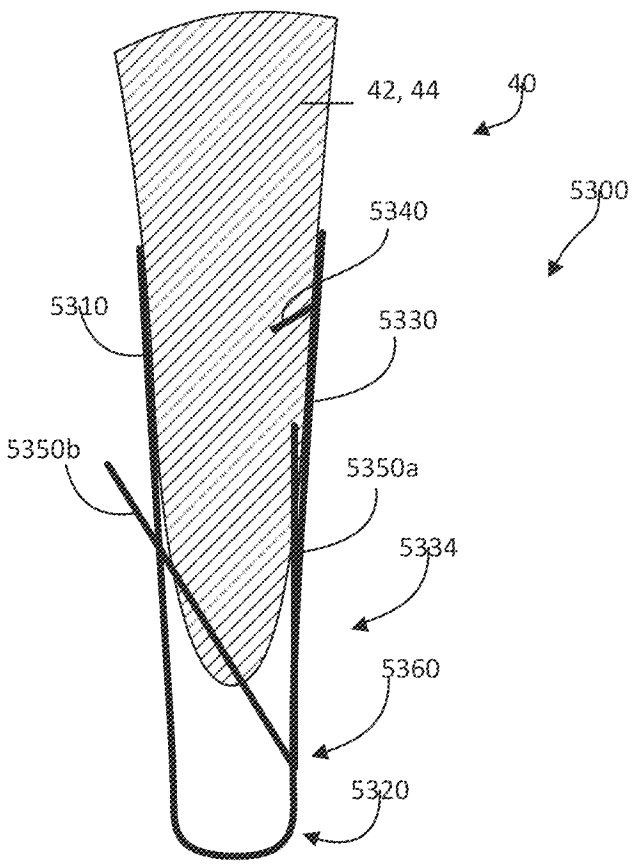

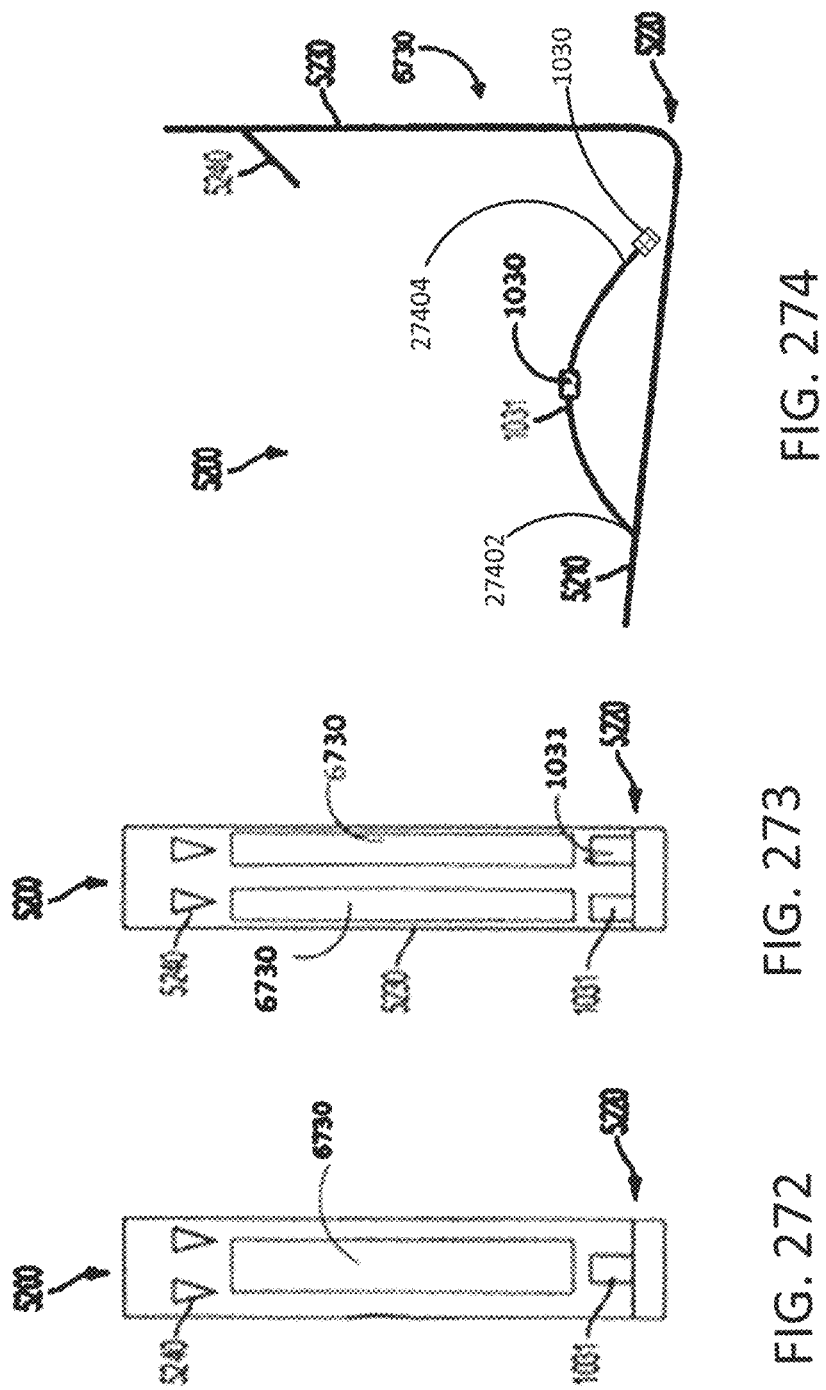

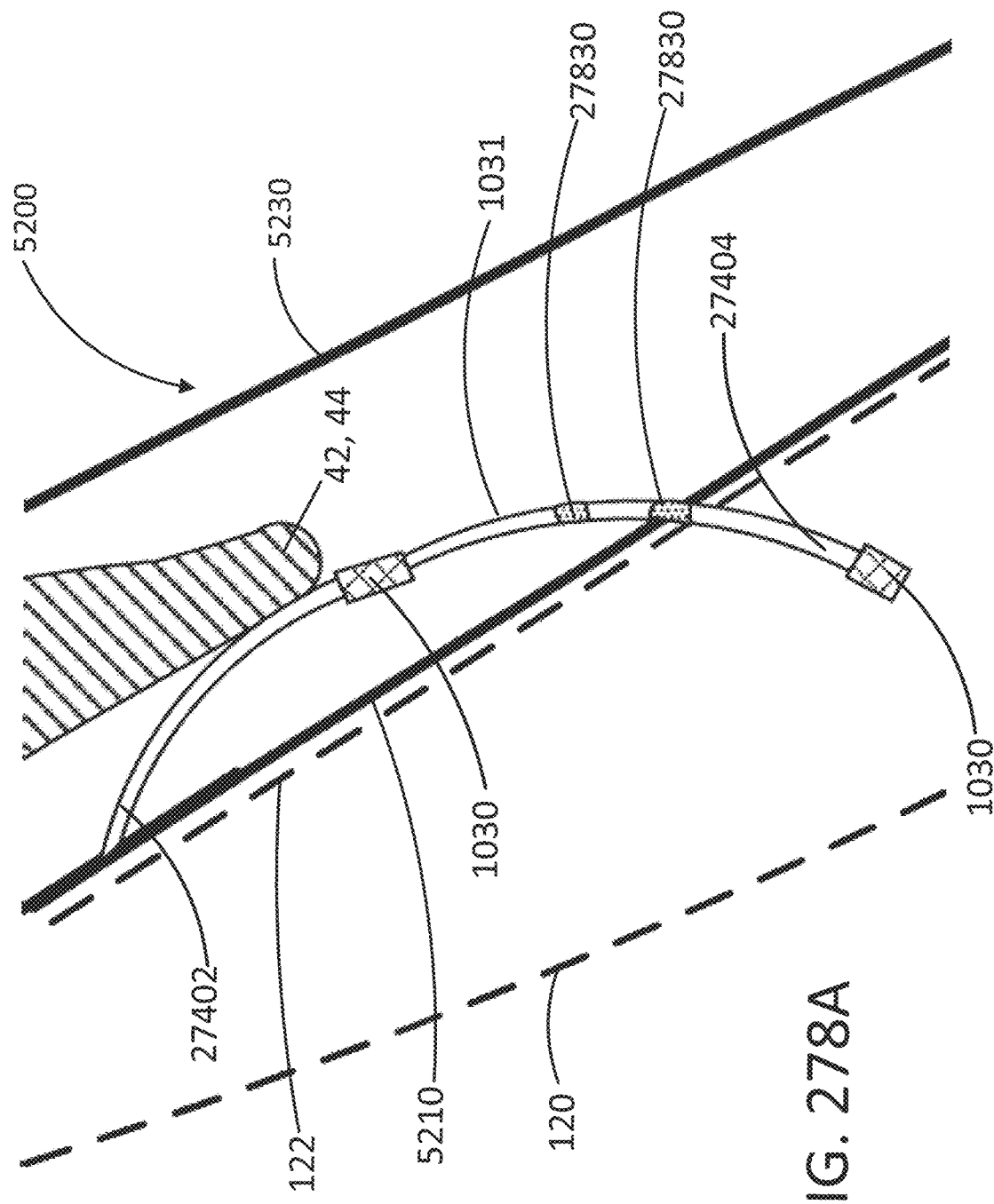

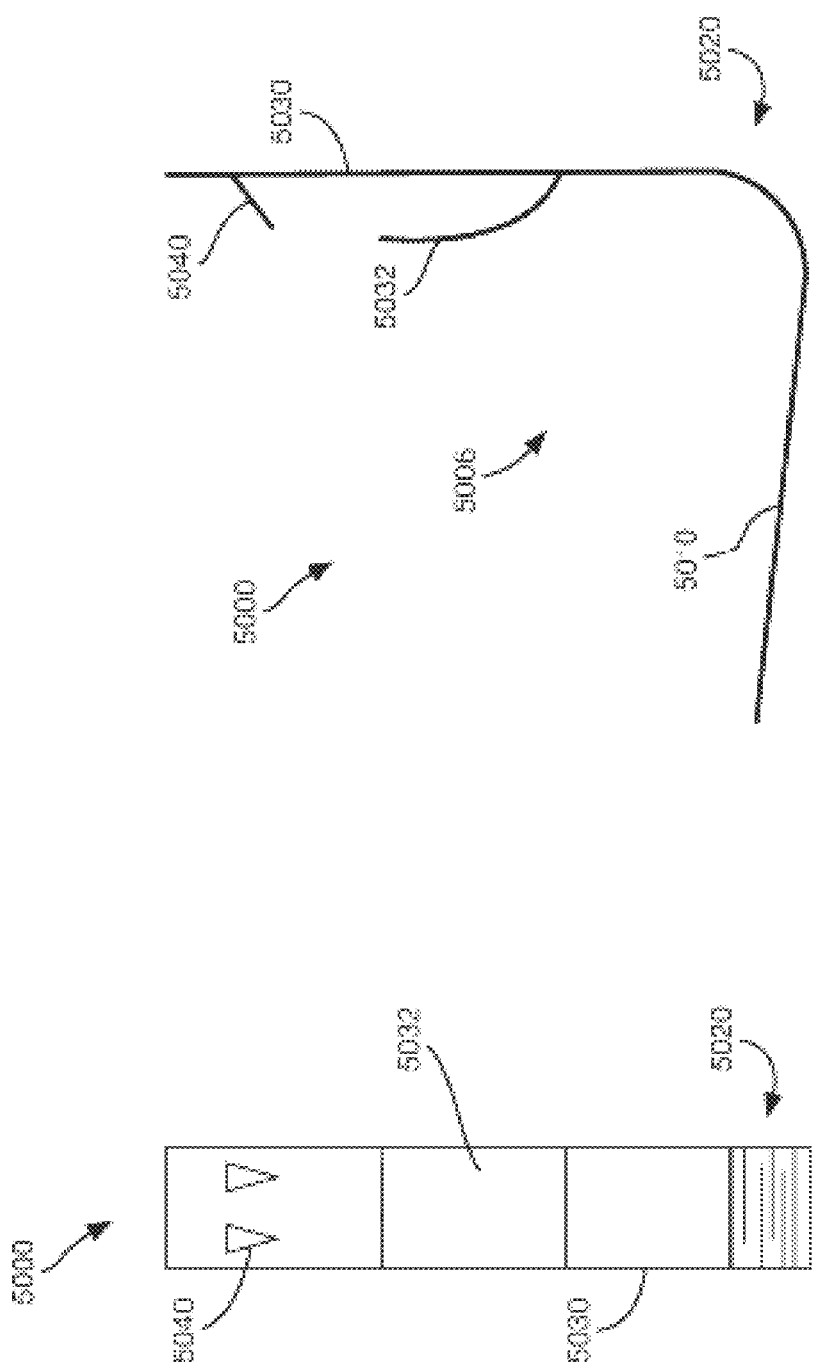

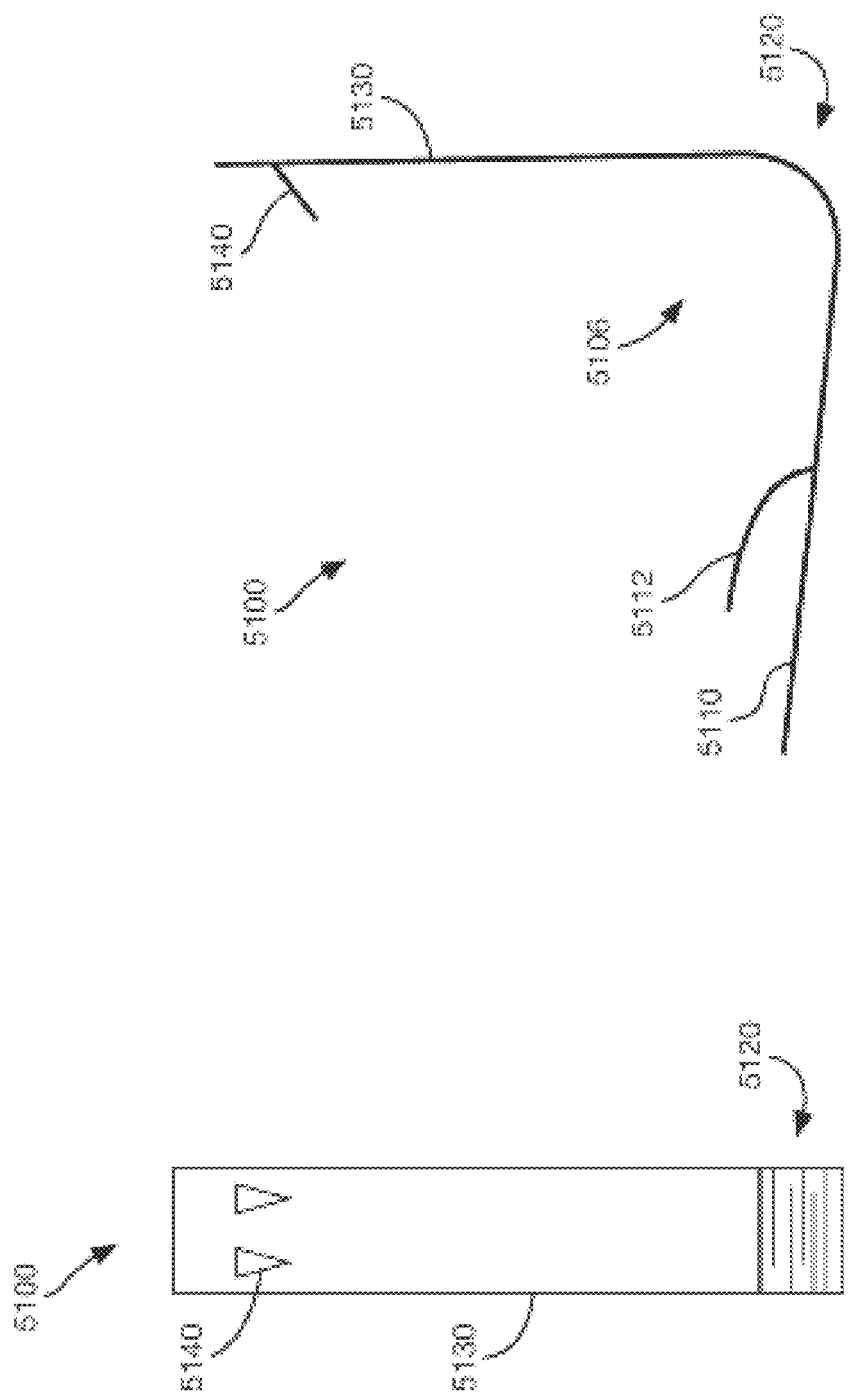

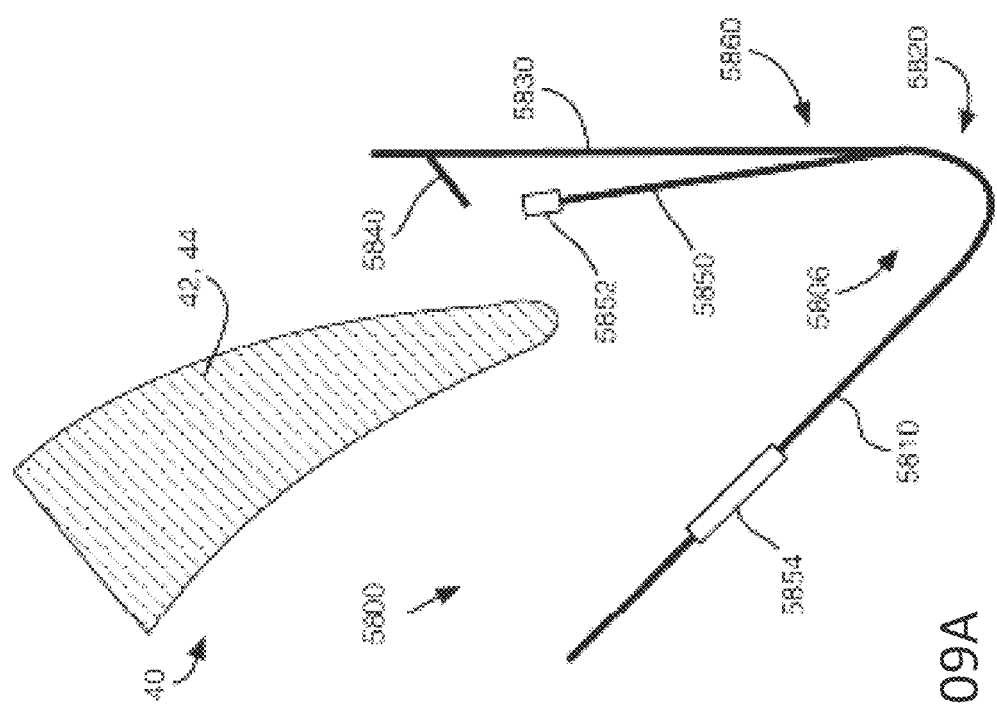

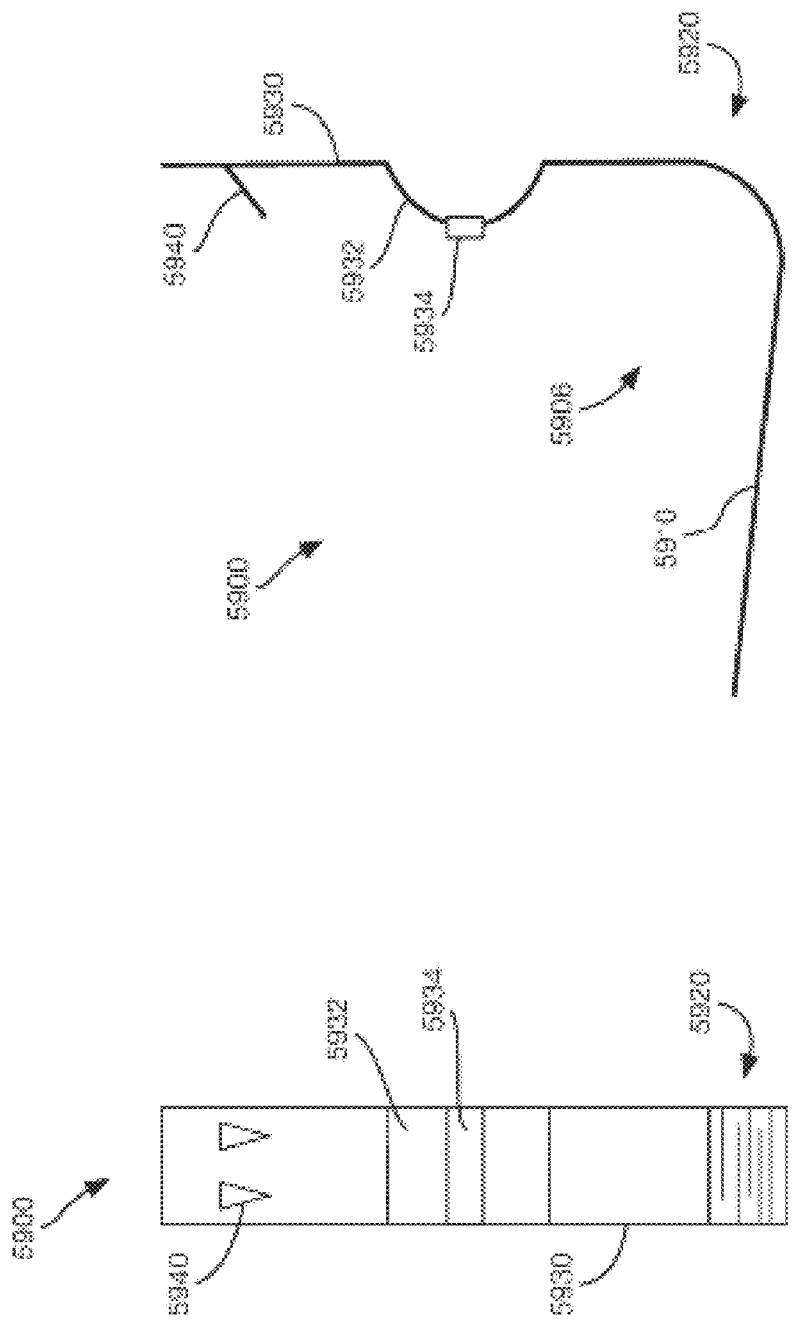

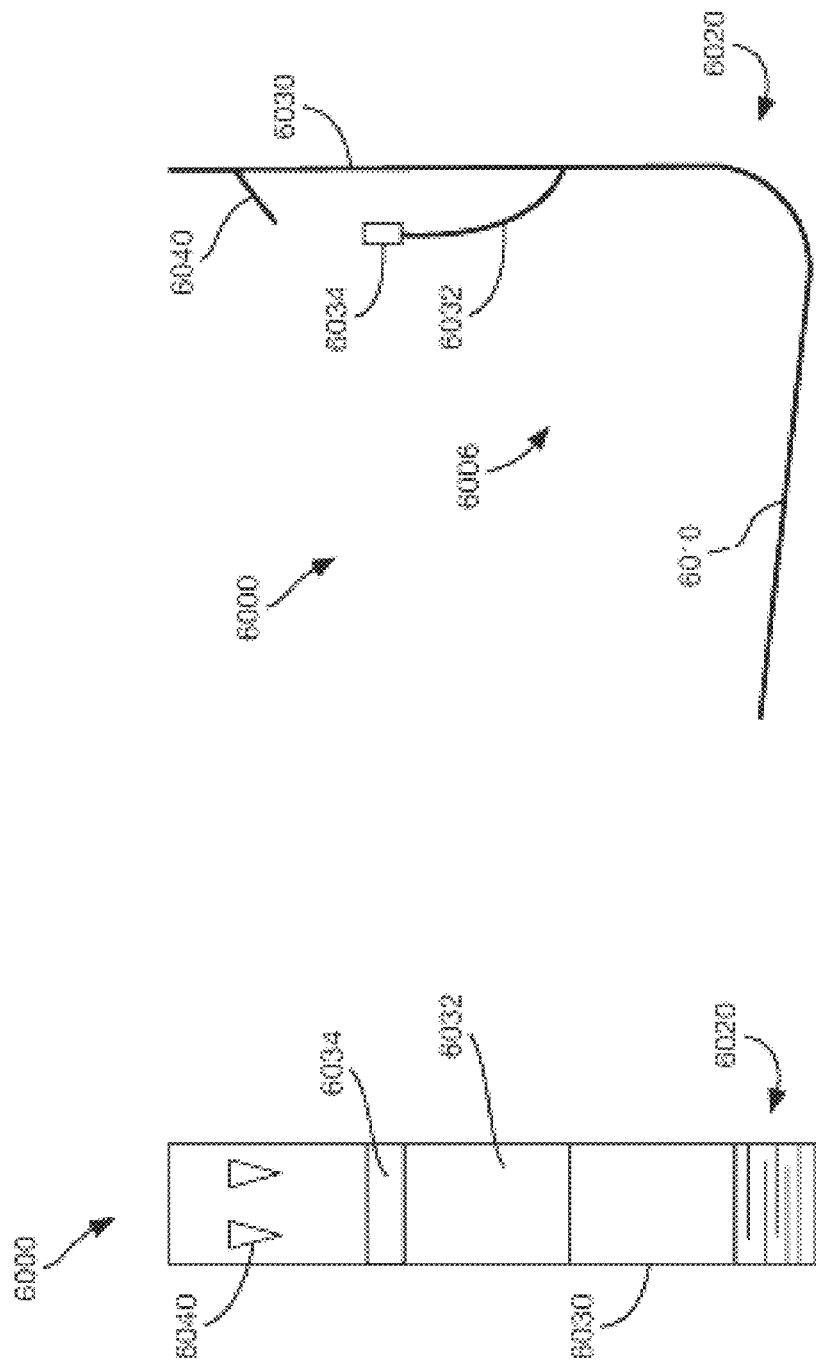

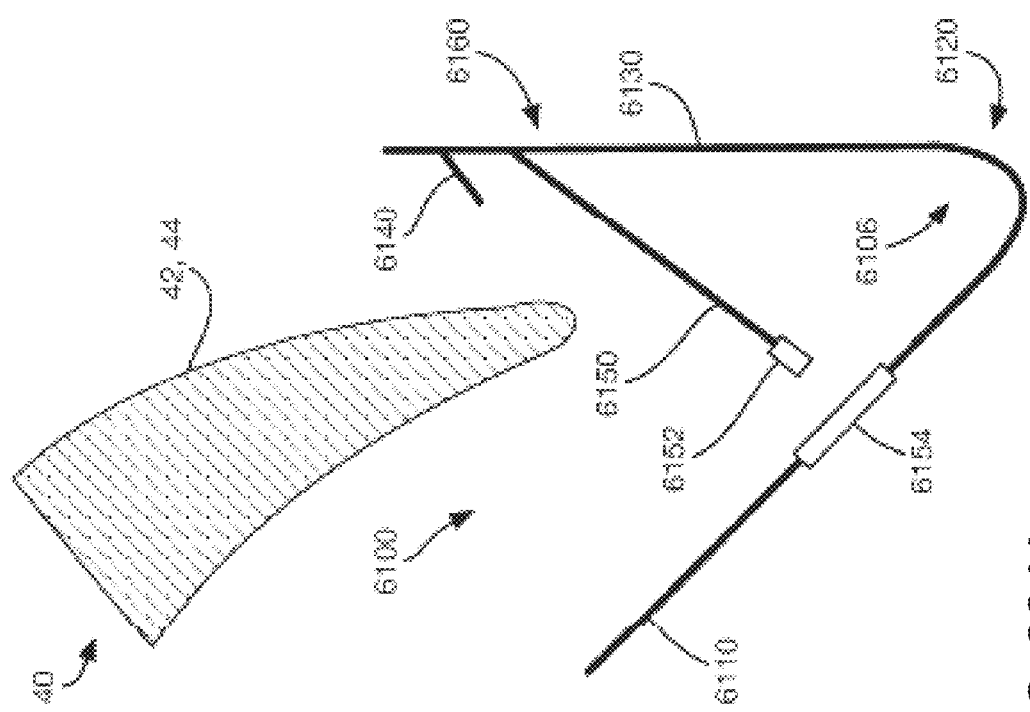

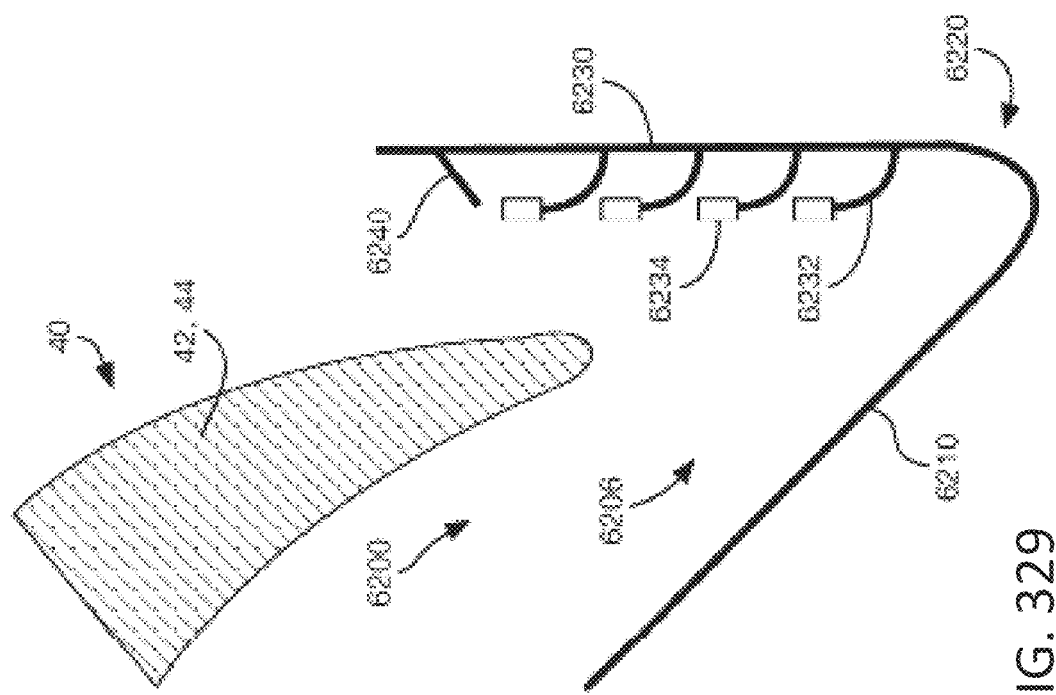

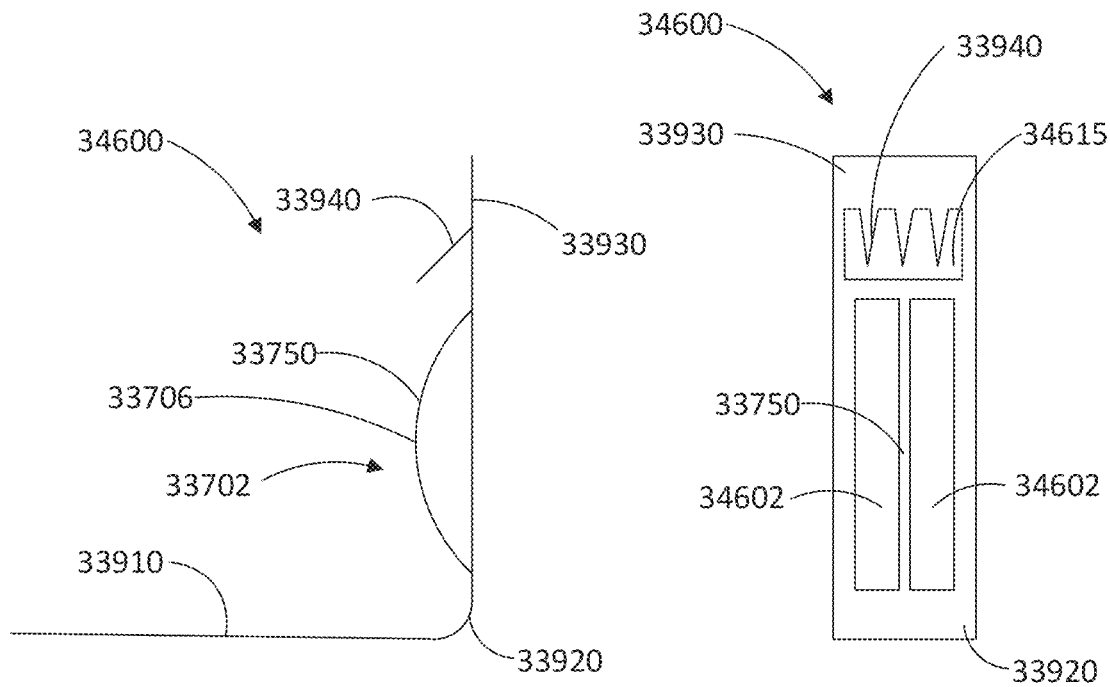
FIG. 346
FIG. 348
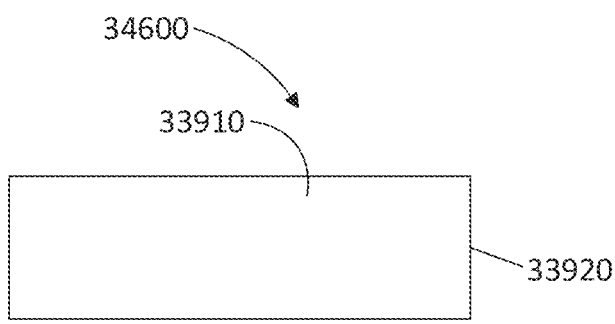
FIG. 347

HEART VALVE SEALING DEVICES AND DELIVERY DEVICES THEREFOR

CROSS-REFERENCE TO RELATED APPLICATIONS

The present application is a continuation of PCT Application No. PCT/US2020/018115 filed on Feb. 13, 2020 titled "Heart Valve Sealing Devices and Delivery Devices Therefor," which claims priority to U.S. Provisional Application Ser. No. 62/805,847, filed on Feb. 14, 2019, titled "Heart Valve Sealing Devices and Delivery Devices Therefor" and U.S. Provisional Patent Application Ser. No. 62/944,325, filed on Dec. 5, 2019, titled "Leaflet Depth Indicators," which are all incorporated herein by reference in their entireties for all purposes.

BACKGROUND

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, disease, etc. Such damage to the valves can result in serious cardiovascular compromise or death. Damaged valves can be surgically repaired or replaced during open heart surgery. However, open heart surgeries are highly invasive, and complications may occur. Transvascular techniques can be used to introduce and implant prosthetic devices in a manner that is much less invasive than open heart surgery. As one example, a transvascular technique useable for accessing the native mitral and aortic valves is the trans-septal technique. The trans-septal technique comprises advancing a catheter into the right atrium (e.g., inserting a catheter into the right femoral vein, up the inferior vena cava and into the right atrium). The septum is then punctured, and the catheter passed into the left atrium. A similar transvascular technique can be used to implant a prosthetic device within the tricuspid valve that begins similarly to the trans-septal technique but stops short of puncturing the septum and instead turns the delivery catheter toward the tricuspid valve in the right atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Valvular regurgitation involves the valve improperly allowing some blood to flow in the wrong direction through the valve. For example, mitral regurgitation occurs when the native mitral valve fails to close properly and blood flows into the left atrium from the left ventricle during the systolic phase of heart contraction. Mitral regurgitation is one of the most common forms of valvular heart disease. Mitral regurgitation can have many different causes, such as leaflet prolapse, dysfunctional papillary muscles, stretching of the mitral valve annulus resulting from dilation of the left ventricle, more than one of these, etc. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close, and regurgitation is present.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

In one example embodiment, a heart valve treatment device or system is configured to detect aspects pertaining to valve leaflet insertion (e.g., depth of leaflet insertion, thickness of leaflet tissue captured, etc.). The device/system can have an indicator that moves, is positioned, and/or changes shape in response to engagement with the valve leaflet. When the position of the indicator indicates that the valve leaflet is properly positioned in the device/system, the device/system can be closed.

In one example embodiment, a heart valve treatment device/system or valve repair device/system for repairing a native valve of a patient includes a clasp and a leaflet indicator. The clasp (e.g., all or a portion thereof) is moveable to form an opening or leaflet receiving area. The opening or leaflet receiving area can be formed between two portions of the clasp (e.g., a fixed arm and a movable arm, etc.), between the clasp or a portion thereof and another portion of the device, between the clasp and a paddle of the device, between the clasp and an anchor of the device, between a movable arm of the clasp and a paddle of the device, etc. The leaflet indicator is moveable, is re-positionable, and/or changes shape or configuration in the opening or receiving area to indicate whether a leaflet of the native valve is inserted into the opening or receiving area to at least a minimum desired insertion depth and/or a minimum desired tissue thickness. The leaflet indicator can be configured the same as or similar to any of the indicators shown in any of the figures or described anywhere in this disclosure. For example, the leaflet indicator can comprise one or more indicator arms, one or more radiopaque markers, one or more springs, one or more levers, one or more snap-through portions, one or more tabs, one or more pads, one or more coils, one or more deflectable portions, one or more hoops or hoop-shaped portions, one or more flattenable indicators, one or more indicator wings, etc.

The heart valve treatment device/system or valve repair device/system can include one or more of the features or components described with respect to other devices shown in any of the figures or described anywhere in this disclosure. For example, in some implementations, the device/system includes one or more of an anchor portion, anchor, coaption portion, coaption element, paddle, pair of paddles, plurality of paddles, delivery sheath, delivery catheter, actuation element, shaft, actuation lines/sutures, cap, collar, cover, braided material, strip of material, etc.

In some implementations, the device/system comprises a shaft and a proximal portion (e.g., collar, coaption portion, coaption element, disk, cover, post, tube, etc.) that the shaft extends through, and a cap attached to the shaft such that the cap can be moved by the shaft away from the proximal portion. In some implementations, the device/system also includes a pair of paddles attached to the cap. The device/system can be configured such that movement of the cap toward the proximal portion causes the pair of paddles to move to the closed position, and movement of the cap away from the proximal portion causes the pair of paddles to move to the open position. In some implementations, the device/system further includes a coaption element configured to fill space between leaflets of a native valve.

In one example embodiment, a heart valve treatment device/system or valve repair device/system for repairing a native valve of a patient includes a clasp and a plurality of indicator arms. The clasp (e.g., all or a portion thereof) is moveable to form an opening or leaflet receiving area. The opening or leaflet receiving area can be formed between two portions of the clasp (e.g., a fixed arm and a movable arm, etc.), between the clasp or a portion thereof and another portion of the device, between the clasp and a paddle of the device, between the clasp and an anchor of the device, between a movable arm of the clasp and a paddle of the device, etc. In some implementations, the plurality of indicator arms have different lengths and are moveable in the opening or receiving area to indicate whether a leaflet of the native valve is inserted into the opening or receiving area to at least a minimum desired insertion depth and/or a minimum desired tissue thickness.

In one example embodiment, a heart valve treatment device/system or valve repair device/system for repairing a native valve of a patient includes a paddle, a hoop shaped clasp, and an indicator arm. The paddle and the clasp are moveable to form an opening between the clasp and the paddle. The indicator arm is disposed between two sides of the hoop shaped clasp and is moveable in the opening to indicate whether a leaflet of the native valve is inserted into the opening between the paddle and the clasp to at least a minimum desired insertion depth.

In one example embodiment, a heart valve treatment device/system or valve repair device/system for repairing a native valve of a patient includes a clasp and a flattenable indicator. The clasp (e.g., all or a portion thereof) is moveable to form an opening or receiving area. The opening or leaflet receiving area can be formed between two portions of the clasp (e.g., a fixed arm and a movable arm, etc.), between the clasp or a portion thereof and another portion of the device, between the clasp and a paddle of the device, between the clasp and an anchor of the device, between a movable arm of the clasp and a paddle of the device, etc. The flattenable indicator is in the opening or receiving area to indicate whether a leaflet of the native valve is inserted into the opening or receiving area to at least a minimum desired insertion depth and/or a minimum desired tissue thickness.

In one example embodiment, a heart valve treatment device/system or valve repair device/system for repairing a native valve of a patient includes a hoop shaped clasp and an indicator (e.g., an indicator arm, spring, etc.). The clasp (e.g., all or a portion thereof) is moveable to form an opening or receiving area. The opening or leaflet receiving area can be formed between two portions of the clasp (e.g., a fixed arm and a movable arm, etc.), between the clasp or a portion thereof and another portion of the device, between the clasp and a paddle of the device, between the clasp and an anchor of the device, between a movable arm of the clasp and a paddle of the device, etc.

In one embodiment, the indicator spans the hoop shaped clasp and is deformable through the hoop shaped clasp to indicate whether a leaflet of the native valve is inserted into the opening or receiving area to at least a minimum desired insertion depth and/or a minimum desired tissue thickness.

In one embodiment, the indicator comprises an indicator arm disposed between two sides of the hoop shaped clasp. The indicator arm can have a curved portion that is moveable through the hoop shaped clasp to indicate whether a leaflet of the native valve is inserted into the opening or receiving area between the paddle and the clasp to at least a minimum desired insertion depth and/or a minimum desired tissue thickness.

In one embodiment, the indicator comprises a spring disposed or positionable in the opening or receiving area to indicate whether a leaflet of the native valve is inserted into the opening or receiving area between the paddle and the clasp to at least a minimum desired insertion depth and/or a minimum desired tissue thickness.

In one embodiment, the indicator comprises at least one indicator wing that extends outward from a side of the clasp at an angle to indicate whether a leaflet of the native valve is inserted into the opening or receiving area between the paddle and the clasp to at least a minimum desired insertion depth and/or a minimum desired tissue thickness.

In one embodiment, the indicator comprises a first leaflet indicator and a second leaflet indicator that are spaced apart when a leaflet of a native valve is inserted into the opening between the paddle and the clasp to at least a minimum desired insertion depth. In one embodiment, the first leaflet indicator and the second leaflet indicator are in contact in the absence of a leaflet of the native valve in the opening or receiving area between the paddle and the clasp.

In one example embodiment, a heart valve treatment device/system or valve repair device/system for repairing a native valve of a patient includes a clasp and an indicator arm. The clasp (e.g., all or a portion thereof) is moveable to form an opening or leaflet receiving area. The opening or leaflet receiving area can be formed between two portions of the clasp (e.g., a fixed arm and a movable arm, etc.), between the clasp or a portion thereof and another portion of the device, between the clasp and a paddle of the device, between the clasp and an anchor of the device, between a movable arm of the clasp and a paddle of the device, etc. A single actuation line extends from a delivery device to the clasp and the indicator arm. In some implementations, the single actuation line is configured to separately actuates the clasp and the indicator arm.

In one example embodiment, a heart valve treatment device/system or valve repair device/system for repairing a native valve of a patient includes a clasp and a flexible indicator. The clasp (e.g., all or a portion thereof) is moveable to form an opening or leaflet receiving area. The opening or leaflet receiving area can be formed between two portions of the clasp (e.g., a fixed arm and a movable arm, etc.), between the clasp or a portion thereof and another portion of the device, between the clasp and a paddle of the device, between the clasp and an anchor of the device, between a movable arm of the clasp and a paddle of the device, etc. The flexible indicator is fixedly connected to one arm and slidably connected to the other arm.

In one example embodiment, a heart valve treatment device/system or valve repair device/system for repairing a native valve of a patient includes a clasp and at least one indicator. The clasp (e.g., all or a portion thereof) is moveable to form an opening or leaflet receiving area. The opening or leaflet receiving area can be formed between two portions of the clasp (e.g., a fixed arm and a movable arm, etc.), between the clasp or a portion thereof and another portion of the device, between the clasp and a paddle of the device, between the clasp and an anchor of the device, between a movable arm of the clasp and a paddle of the device, etc.

In one embodiment, the at least one indicator extends from the paddle into the opening or leaflet receiving area. In some implementations, the at least one indicator is configured such that when the opening or leaflet receiving area is closed and the indicator is unobstructed, at least a portion of the at least one indicator extends through the clasp. In some implementations, the at least one indicator is also configured such that when the opening or leaflet receiving area is closed and the at least one indicator engages a valve leaflet, a portion of the at least one indicator extends through the paddle.

In one embodiment, the at least one indicator extends from one of the fixed arm and the paddle into the opening or receiving area. The at least one indicator can be configured such that when the opening or receiving area is closed and the indicator is unobstructed, at least a portion of the indicator extends through the moveable arm of the clasp. The at least one indicator can also be configured such that when the opening or receiving area is closed and the indicator engages a valve leaflet, a portion of the indicator extends through the fixed arm of the clasp.

In some implementations, when the opening or receiving area is closed and the at least one indicator engages a valve leaflet, a portion of the at least one indicator extends through a paddle of the device/system. In some implementations, no portion of the at least one indicator extends through the moveable arm of the clasp when the opening or receiving area is closed and the indicator engages a valve leaflet.

In some implementations, the at least one indicator has a fixed end connected to the paddle and a free end. In some implementations, the at least one indicator has a fixed end connected to the fixed arm and a free end. In some implementations, the at least one indicator is integrally formed with the fixed arm of the clasp. The at least one indicator can be curved, straight, angled, spherical, semi-spherical, and/or another shape.

In some implementations, a moveable arm of the clasp includes a cutout that the at least one indicator extends through when the opening or receiving area is closed and the indicator is unobstructed. In some implementations, the fixed arm of the clasp includes a cutout that the at least one indicator extends through. In some implementations, a paddle of the device/system includes a cutout that the at least one indicator extends through when the opening between the paddle and the moveable arm of the clasp is closed and the indicator engages a valve leaflet.

In some implementations, a smaller portion of the at least one indicator extends through the cutout of the paddle when the opening or receiving area (e.g., between a movable arm of the clasp and the paddle) is closed and the indicator is unobstructed, and a larger portion of the at least one indicator extends through the cutout of the paddle when the opening or receiving area is closed and the indicator engages a valve leaflet.

In one example method of implanting a valve repair device an indicator of a clasp is engaged. The indicator is disengaged when a leaflet of the mitral valve is not contacted by the indicator. The clasp is closed when the indicator is engaged, and the leaflet is contacted by the indicator.

In one example method of implanting a valve repair device on a native valve (e.g., on a mitral valve, tricuspid valve, etc.) of a patient an indicator arm of a clasp is actuated. The indicator arm is returned to an unactuated position when a leaflet of the native valve is not engaged by the indicator arm. The clasp of the valve repair device is closed when the leaflet of the native valve is engaged by the actuated indicator arm. In some embodiments, one or more paddles of the valve repair device are closed to bring one or more leaflets of the native valve into contact with a coaption element of the valve repair device. In some embodiments, one or more paddles of the valve repair device are closed to bring the leaflets into contact with each other.

In one example method of implanting a valve repair device an indicator gauge of a clasp measures an engaged depth of a leaflet of the native valve. The indicator gauge is disengaged when the engaged depth is below a desired depth. The clasp is closed when the engaged depth is at least equal to the desired depth.

The above methods can be performed on a living animal or on a simulation, such as on a cadaver, cadaver heart, simulator (e.g. with the body parts, heart, tissue, etc. being simulated), etc.

In one example embodiment, a valve repair device includes a plurality of paddles, a plurality of clasps, and an insertion depth indicator. In some embodiments, the valve repair device can also include a coaption element. The plurality of paddles can be connected to the coaption element and/or another portion of the device. Each paddle has an inner portion and an outer portion. The paddles are moveable between an open position and a closed position. A clasp is attached to each of the plurality of paddles. Each clasp includes a fixed arm, a moveable arm, and a joint or hinge. The fixed arm is attached to the inner portion of the paddle and/or another portion of the valve repair device. The moveable arm and/or the fixed arm can optionally have one or more friction-enhancing portions, such as a barbed portion, ridged portion, textured portion, protrusion portion, etc. The hinge portion connects the moveable arm to the fixed arm. The insertion depth indicator indicates whether a leaflet of the native valve is inserted into an opening of the clasp formed between the fixed and moveable arms to at least a minimum desired insertion depth.

In one example embodiment, a heart valve treatment device/system or valve repair device/system for repairing a native valve of a patient includes a plurality of paddles and a plurality of clasps. The plurality of paddles are moveable between an open position and a closed position. A clasp is attached to each of the paddles. The clasp includes a fixed arm, a moveable arm, a hinge portion, an indicator arm, and an indicator hinge portion. The moveable arm and/or the fixed arm can have one or more friction-enhancing portions, such as a barbed portion, ridged portion, textured portion, protrusion portion, etc. The hinge portion connects the moveable arm to the fixed arm. The indicator arm is connected to the fixed arm by the hinge portion.

In one example embodiment, a heart valve treatment device/system or valve repair device/system for repairing a native valve of a patient includes a plurality of paddles, a plurality of clasps, and a compressible indicator. The paddles are moveable between an open position and a closed position. A clasp is attached to each of the plurality of paddles. Each clasp has a fixed arm, a moveable arm, and a hinge portion. The fixed arm of each clasp is attached to the paddle and/or another portion of the valve repair device. The moveable arm is connected to the fixed arm by a hinge portion. The compressible indicator is configured to engage a leaflet of the native valve.

In one example embodiment, a heart valve treatment device/system or valve repair device/system for repairing a native valve of a patient includes a plurality of paddles, a plurality of clasps, a plurality of indicators, and a plurality of markers. The paddles are moveable between an open position and a closed position. A clasp is attached to each of the paddles. Each clasp includes a fixed arm, a moveable arm, and a hinge portion. The fixed arm of each clasp is attached to a paddle and/or another portion of the valve repair device. The moveable arm and/or the fixed arm can have one or more friction-enhancing portions, such as a barbed portion, ridged portion, textured portion, protrusion portion, etc. The hinge portion connects the moveable arm to the fixed arm. Each marker is attached to the indicator, the fixed arm, and/or the moveable arm.

In one example embodiment, a heart valve treatment device/system or valve repair device/system for repairing a native valve of a patient includes a pair of paddles, a pair of clasps, and an insertion depth gauge. The pair of paddles are moveable between an open position and a closed position. A clasp is attached to each of the paddles. Each clasp includes a fixed arm, a moveable arm, and a hinge portion. The fixed arm is attached to the paddle and/or another portion of the valve repair device. The moveable arm and/or the fixed arm can have one or more friction-enhancing portions, such as a barbed portion, ridged portion, textured portion, protrusion portion, etc. The hinge portion connects the moveable arm to the fixed arm. The insertion depth gauge indicates an insertion depth of a leaflet of the native valve.

In one example embodiment, a heart valve treatment device/system or valve repair device/system for repairing a native valve of a patient includes a pair of paddles, a pair of clasps, an indicator arm, and an actuation suture. The pair of paddles are moveable between an open position and a closed position. A clasp is attached to each of the paddles. Each clasp includes a fixed arm, a moveable arm, and a hinge portion. The fixed arm is attached to the paddle and/or another portion of the valve repair device. The moveable arm and/or the fixed arm can have one or more friction-enhancing portions, such as a barbed portion, ridged portion, textured portion, protrusion portion, etc. The moveable arm is moveable between an open position and a closed position. The hinge portion connects the moveable arm to the fixed arm. An indicator hinge portion connects the indicator arm to the fixed arm of the clasp. In some implementations, the actuation suture extends from a delivery device to first and second moveable loops attached to the moveable clasp arm and the indicator arm, respectively. In some implementations, the moveable clasp arm and the indicator arm are separately actuatable with the single actuation suture.

In one example embodiment, a clasp for a heart valve treatment device/system or valve repair device/system comprises an indicator, such as an insertion depth indicator configured to provide an indication of an insertion depth and/or thickness of a leaflet of a native valve within or adjacent the clasp when the heart valve treatment device is implanted in a native heart valve. The indicator can be configured the same as or similar to any of the indicators shown in any of the figures or described anywhere in this disclosure. For example, the indicator can comprise one or more indicator arms, one or more radiopaque markers, one or more springs, one or more levers, one or more snap-through portions, one or more tabs, one or more pads, one or more coils, one or more deflectable portions, one or more hoops or hoop-shaped portions, one or more flattenable indicators, one or more indicator wings, etc.

In some implementations, the clasp further comprises a fixed arm attachable to the device/system (e.g., to a paddle, anchor, post, arm, extension, cover, etc. of the device/system) and a moveable arm. The fixed arm and/or the moveable arm can include a friction-enhancing portion (e.g., a friction-enhancing element, barbs, protrusions, ridges, textured surface, sticky surface, etc.). A connection portion or hinge portion connects (e.g., jointedly, hingeably, etc.) the moveable arm to the fixed arm.

In some implementations, the indicator or insertion depth indicator is deformable, and a shape of the indicator indicates the insertion depth and/or thickness of the leaflet of the native valve.

In some implementations, the indicator is moveable, and a position of the indicator indicates the insertion depth and/or thickness of the leaflet of the native valve.

In some implementations, the relative position of the indicator and at least one of the fixed arm and the moveable arm indicates the insertion depth of the leaflet of the native valve.

In some implementations, the indicator comprises a plurality of flexible arms (e.g., 2, 3, 4, 5, 6, or more arms) attached to the moveable arm between the clasp hinge portion and the friction-enhancing portion. The insertion depth of the leaflet can be indicated by the number of flexible arms deformed by engagement with the leaflet.

In some implementations, the indicator comprises a plurality of flexible arms (e.g., 2, 3, 4, 5, 6, or more arms) attached to the fixed arm. The insertion depth of the leaflet can be indicated by the number of flexible arms deformed by engagement with the leaflet.

In some implementations, the indicator comprises an indicating pad arranged on at least one of the moveable arm and the fixed arm that is configured to deform when engaged by the leaflet of the native valve. The insertion depth and/or thickness of the leaflet can be indicated by a size of a deformed portion of the indicating pad.

In some implementations, the indicator is actuatable between undeployed and actuated positions. In some implementations, the indicator or actuated or actuatable when the clasp is at least partially open to determine the insertion depth of the leaflet of the native valve.

In some implementations, the insertion depth indicator intersects at least one of the fixed arm and the movable arm when the insertion depth indicator is in the actuated position.

In some implementations, the moveable arm is hoop-shaped, and the friction-enhancing portion comprises longitudinally staggered barbs.

In some implementation, the clasp(s) described above can be included in a heart valve treatment device/system or valve repair device/system. The heart valve treatment device/system or valve repair device/system can include one or more of the features or components shown in any of the figures or described with respect to any of the devices/systems in this disclosure. For example, in some implementations, the device/system includes one or more of an anchor portion, anchor, coaption portion, coaption element, paddle, pair of paddles, plurality of paddles, delivery sheath, delivery catheter, actuation element, shaft, actuation lines/sutures, cap, collar, cover, braided material, strip of material, etc.

In some implementations, the device/system comprises a shaft and a proximal portion (e.g., collar, coaption portion, coaption element, disk, cover, post, tube, etc.) that the shaft extends through, and a cap attached to the shaft such that the cap can be moved by the shaft away from the proximal portion. In some implementations, the device/system also includes a pair of paddles attached to the cap. The device/system can be configured such that movement of the cap toward the proximal portion causes the pair of paddles to move to the closed position, and movement of the cap away from the proximal portion causes the pair of paddles to move to the open position. In some implementations, the device/system further includes a coaption element configured to fill space between leaflets of a native valve.

An understanding of the nature and advantages of the present invention are set forth in the following description and claims, particularly when considered in conjunction with the accompanying drawings in which like parts bear like reference numerals.

BRIEF DESCRIPTION OF THE DRAWINGS

FIGS. 30-33 show front views of example embodiments of clasps for an implantable prosthetic device;

FIGS. 34-47 show an implantable prosthetic device having clasps with indicator arms being delivered and implanted within a native valve;

FIGS. 70-71 show an example embodiment of a clasp for an implantable prosthetic device;

FIGS. 70A-71A show an example embodiment of a clasp for an implantable prosthetic device;

FIGS. 104C, 106C, 108C, and 109C show schematic views of an example embodiment of a clasp having flexible bump indicators on the fixed and moveable arms, for an implantable prosthetic device;

FIG. 110 shows an example embodiment of a moveable arm and fixed arm with flexible curve indicators of a clasp, for an implantable prosthetic device;

FIGS. 111-122 show an example embodiment of a clasp for an implantable prosthetic device having a flexible curved indicator;

FIGS. 123A and 124A show schematic views of an example embodiment of a clasp having deflecting indicators on the moveable arm, for an implantable prosthetic device;

FIGS. 128, 129, and 129B show an example embodiment of a clasp with a spring indicator for an implantable prosthetic device;

FIG. 129C shows an example embodiment of a spring indicator for a clasp;

FIGS. 133A and 134A show an example embodiment of a clasp with a spring indicator for an implantable prosthetic device;

FIGS. 135A, 136A, and 137A show the example clasp of FIGS. 133A and 134A being deployed to engage with a leaflet of a native valve;

FIGS. 133B and 134B show an example embodiment of a clasp with a spring indicator for an implantable prosthetic device;

FIGS. 138 and 139 show an example embodiment of a clasp with an indicator pad for an implantable prosthetic device;

FIGS. 140, 141, and 142 show the example clasp of FIGS. 138 and 139 being deployed to engage with a leaflet of a native valve;

FIGS. 140A, 141A, and 142A show the example clasp of FIGS. 138A and 139A being deployed to engage with a leaflet of a native valve;

FIGS. 155-157 show an example actuation mechanism for use with implantable devices described herein;

FIGS. 158-160 show an example actuation mechanism for use with implantable devices described herein;

FIGS. 161-163 show an example actuation mechanism for use with implantable devices described herein;

FIGS. 164-166 show an example actuation mechanism for use with implantable devices described herein;

FIGS. 172-173 show schematic views of an example embodiment of a clasp having a flexible indicator;

FIGS. 177-178 show schematic views of an example embodiment of a clasp having a barbed wheel to capture tissue;

FIGS. 187-188 show schematic views of an example embodiment of a clasp with a belt;

FIGS. 194-197 show the example clasp of FIGS. 192-193 being deployed to engage a leaflet of a native valve;

FIGS. 198-199 show schematic views of an example embodiment of a clasp having an indicator;

FIGS. 203-205 show an example actuation mechanism for use with implantable devices described herein;

FIGS. 210-214 show schematic views of an example embodiment of a clasp having an indicator arm with a shaped end;

FIGS. 217-220 show the example clasp of FIGS. 215-216 being deployed to engage a leaflet of a native valve;

FIGS. 272-274 are schematic illustrations of example embodiments of a curved indicator having a fixed end connected to an arm of a clasp and a free end;

FIGS. 278A and 279A are enlarged portions of FIGS. 278 and 279 as indicated by the circles in FIGS. 278 and 279;

FIGS. 285-286 show an example embodiment of a clasp for an implantable prosthetic device;

FIGS. 290-291 show an example embodiment of a clasp for an implantable prosthetic device;

FIGS. 292-294 show the clasp of FIGS. 290-291 being deployed to engage with a leaflet of a native valve;

Figure 292:
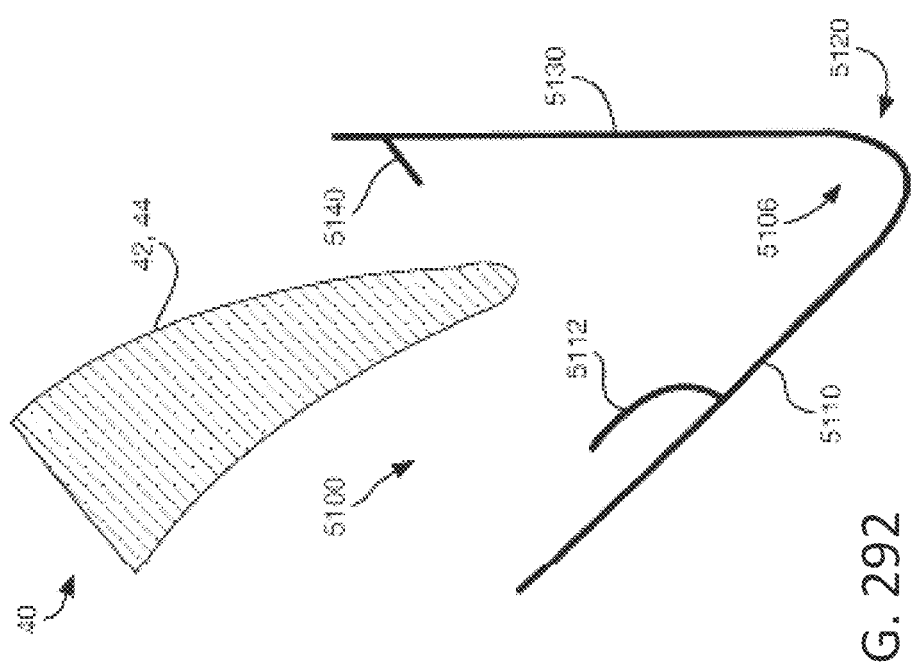
Figure 292A:
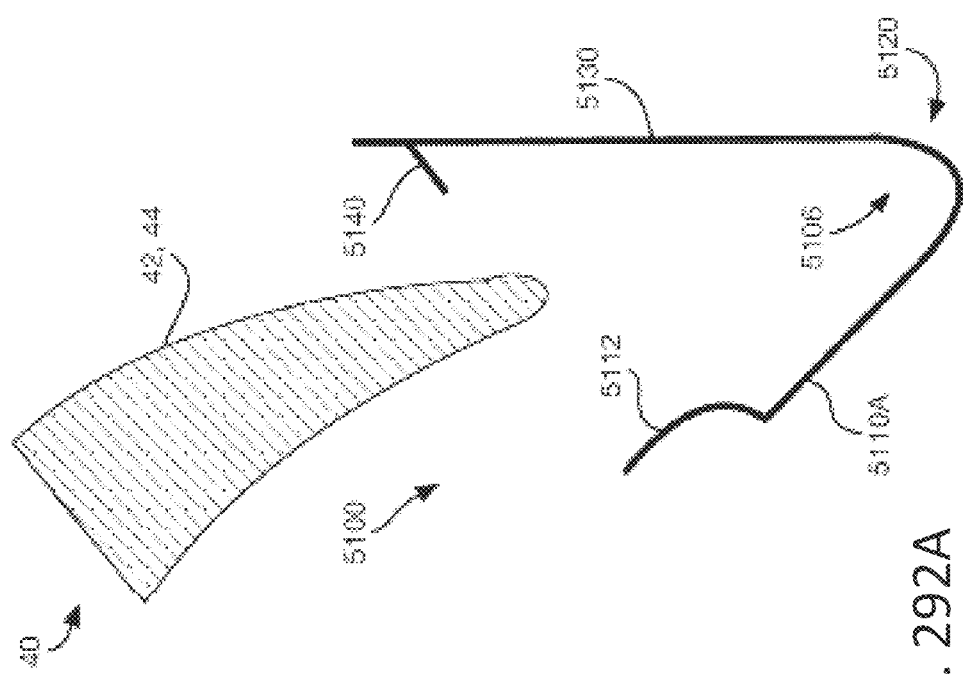
Figure 293:
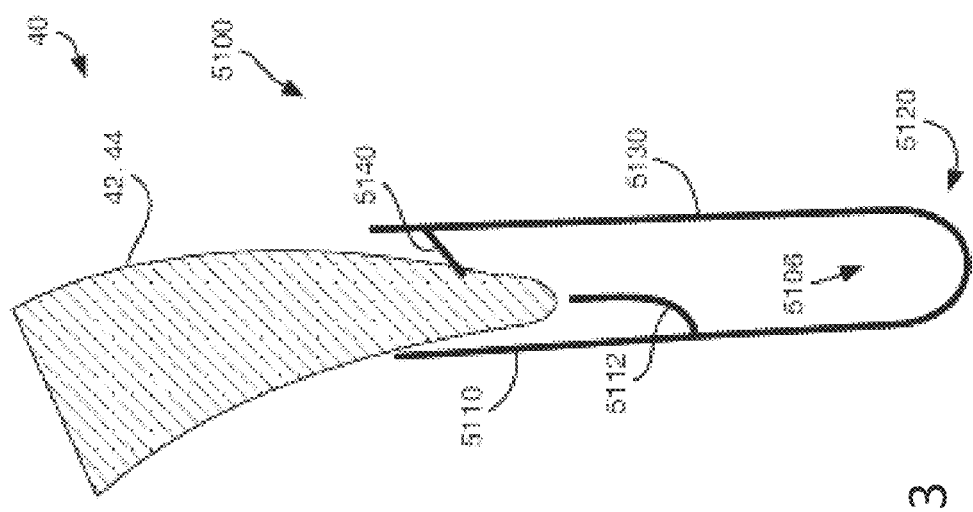
Figure 293A:
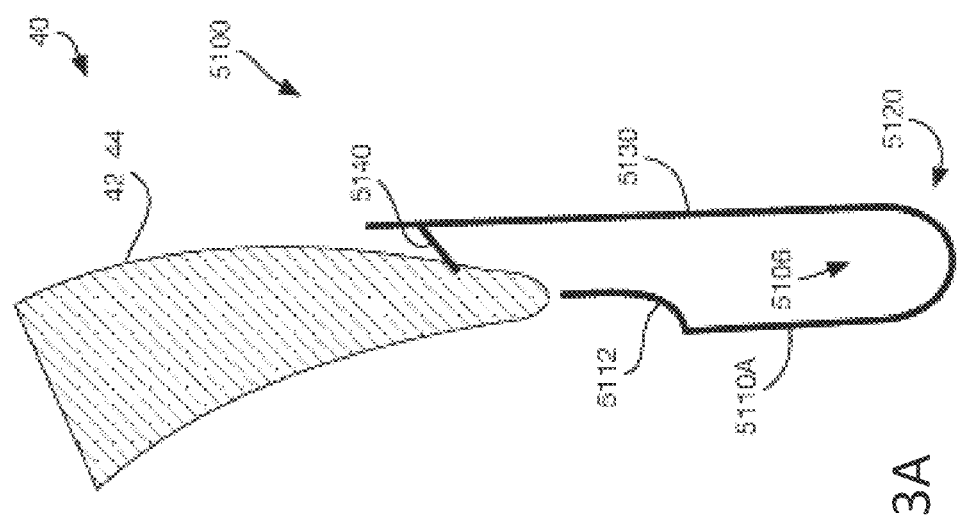
Figure 294:
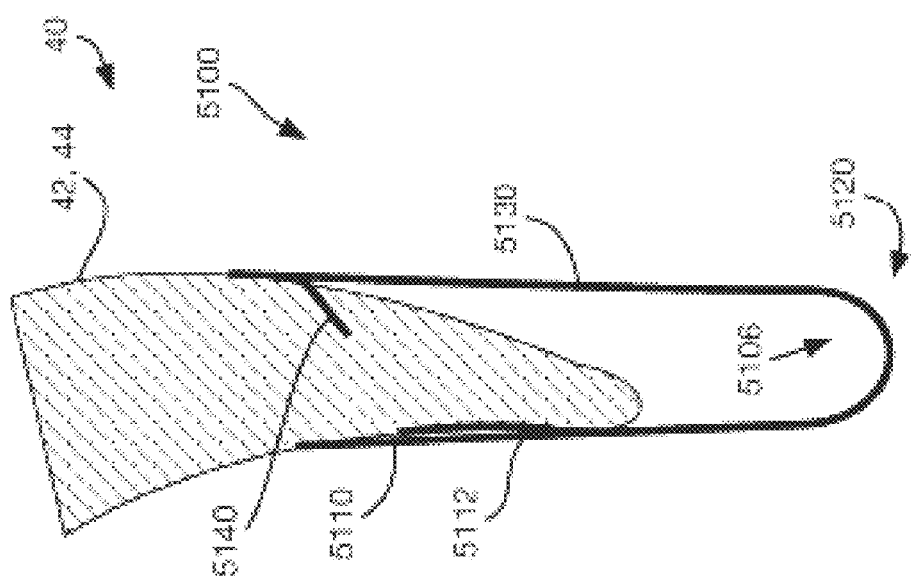
Figure 294A:
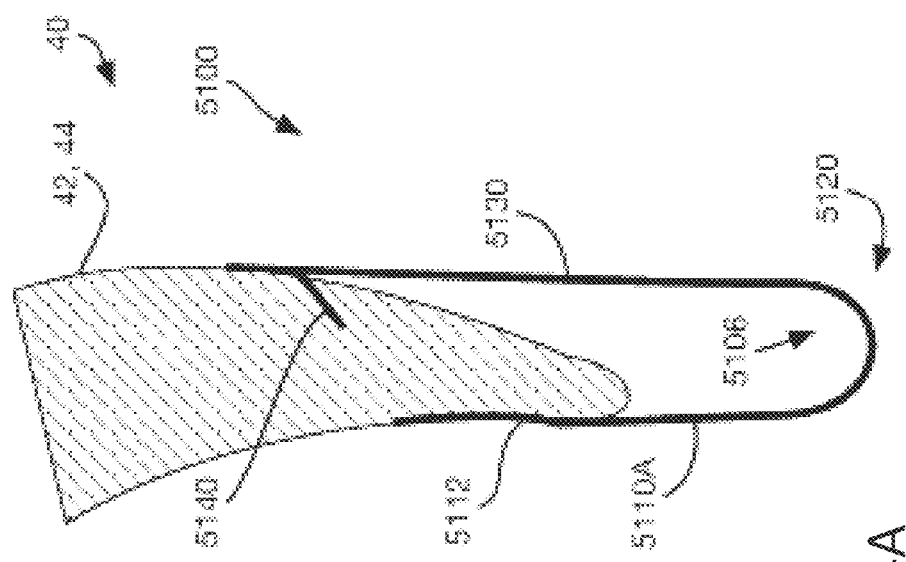
Figure 296:
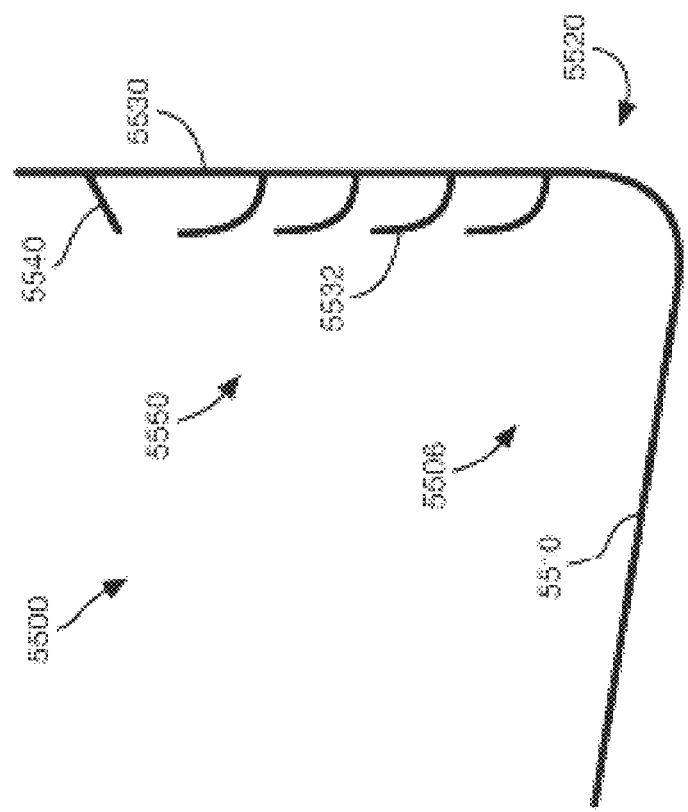
Figure 295:
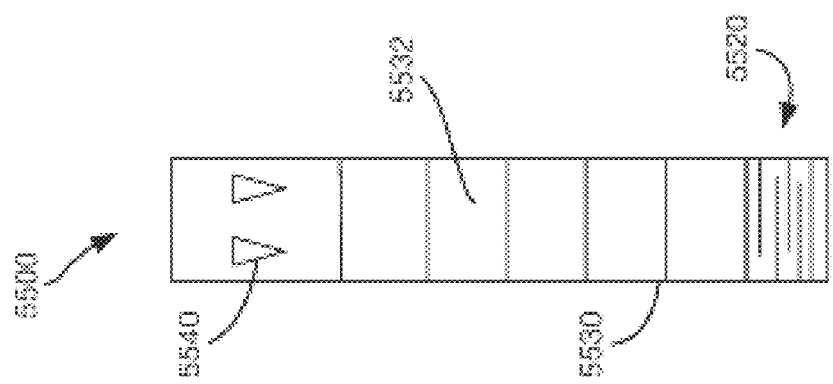
Figure 297:
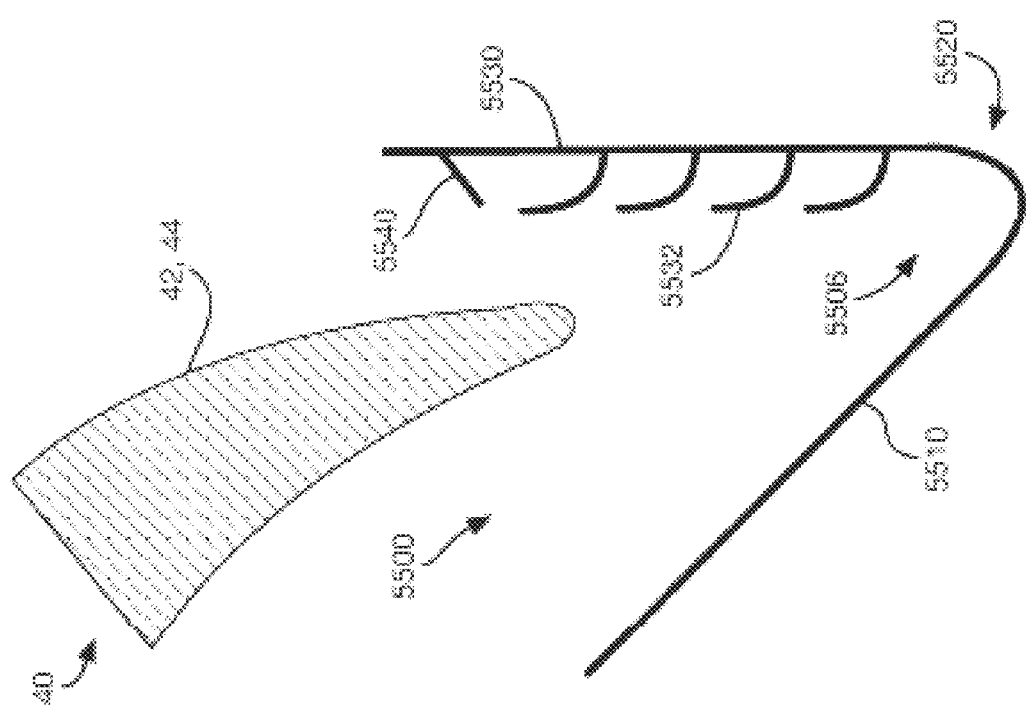
Figure 298:
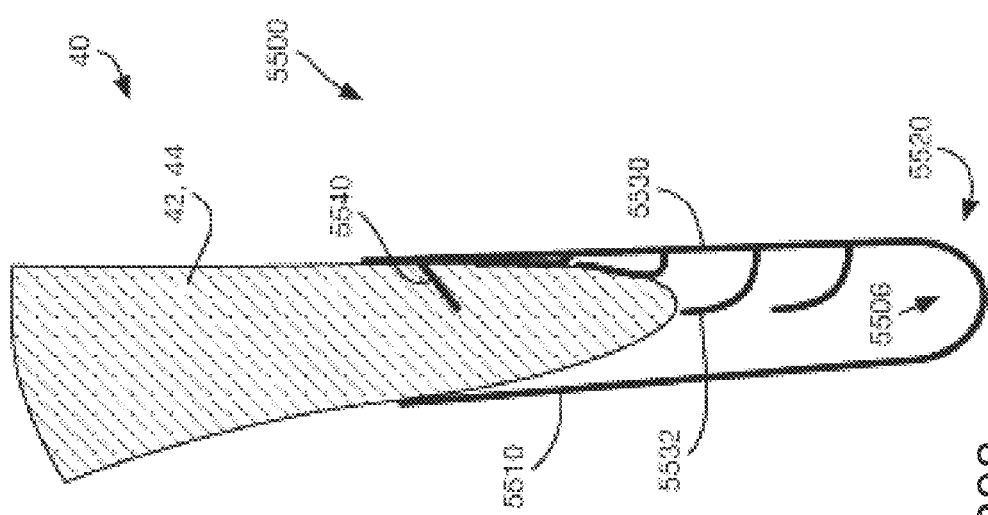
Figure 299:
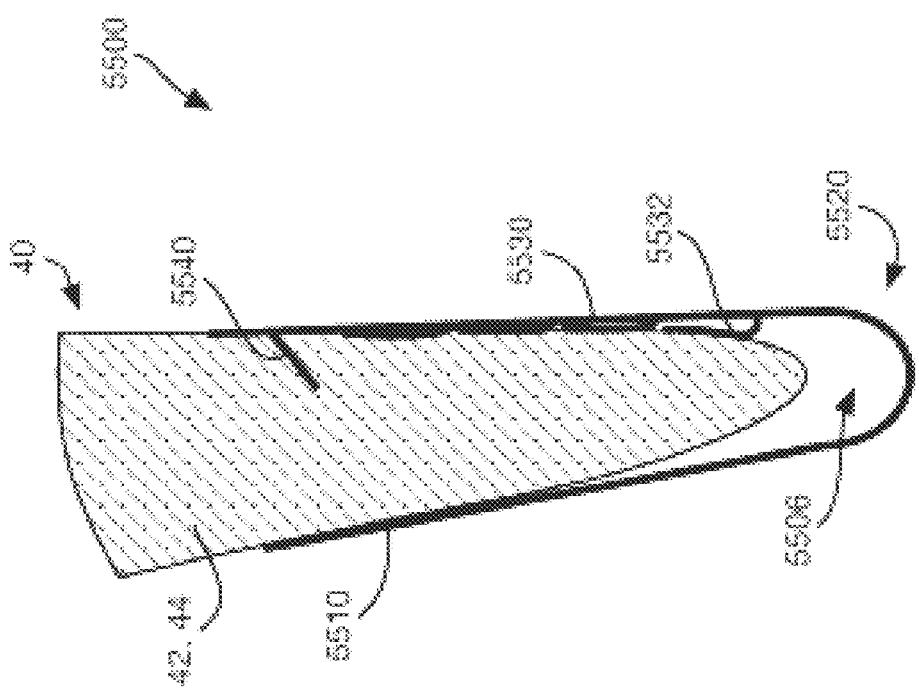
Figure 301:
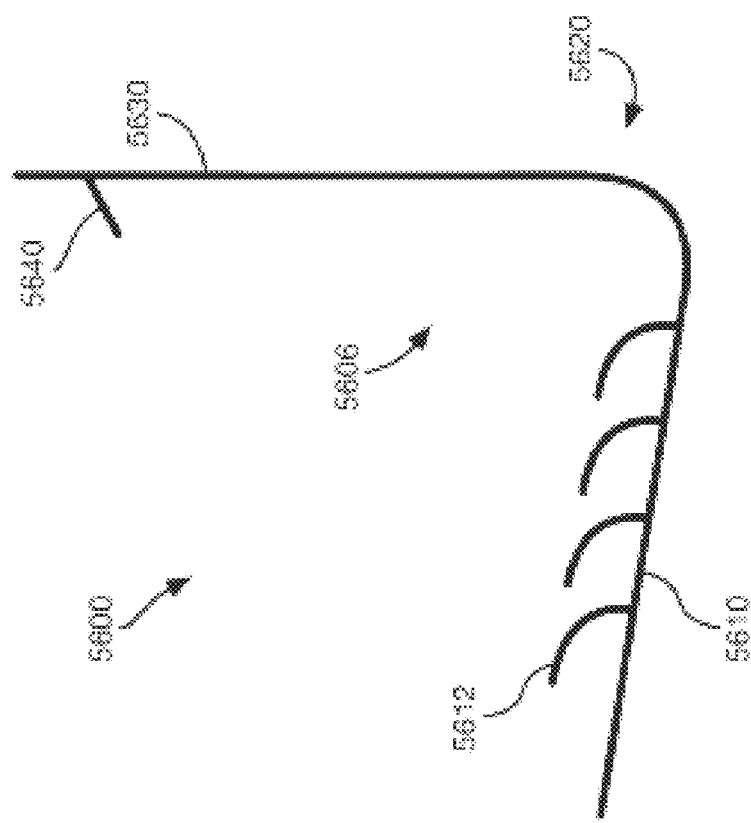
Figure 300:
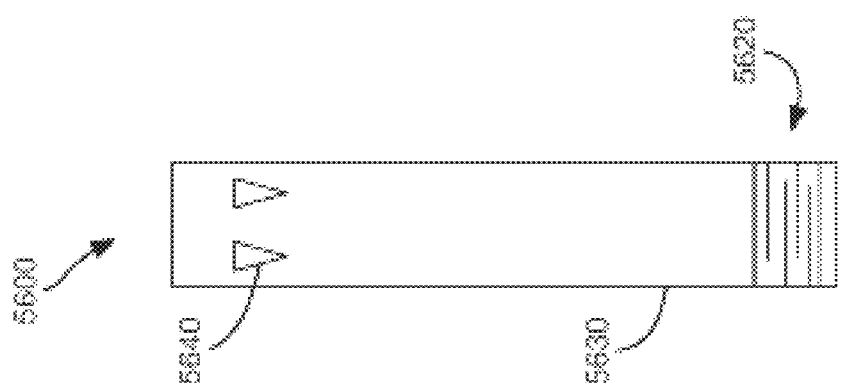
Figure 302:
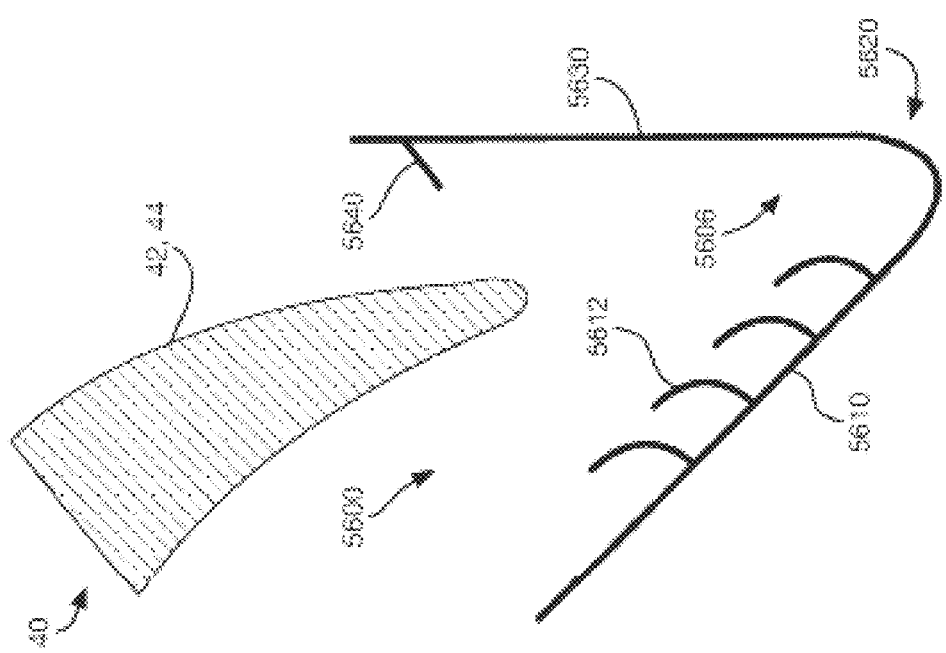
Figure 303:
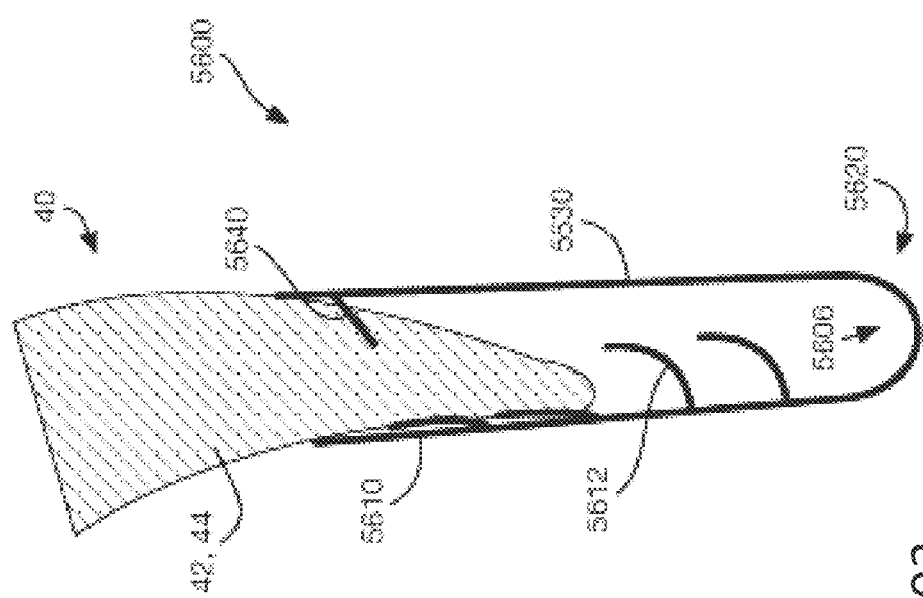
Figure 304:
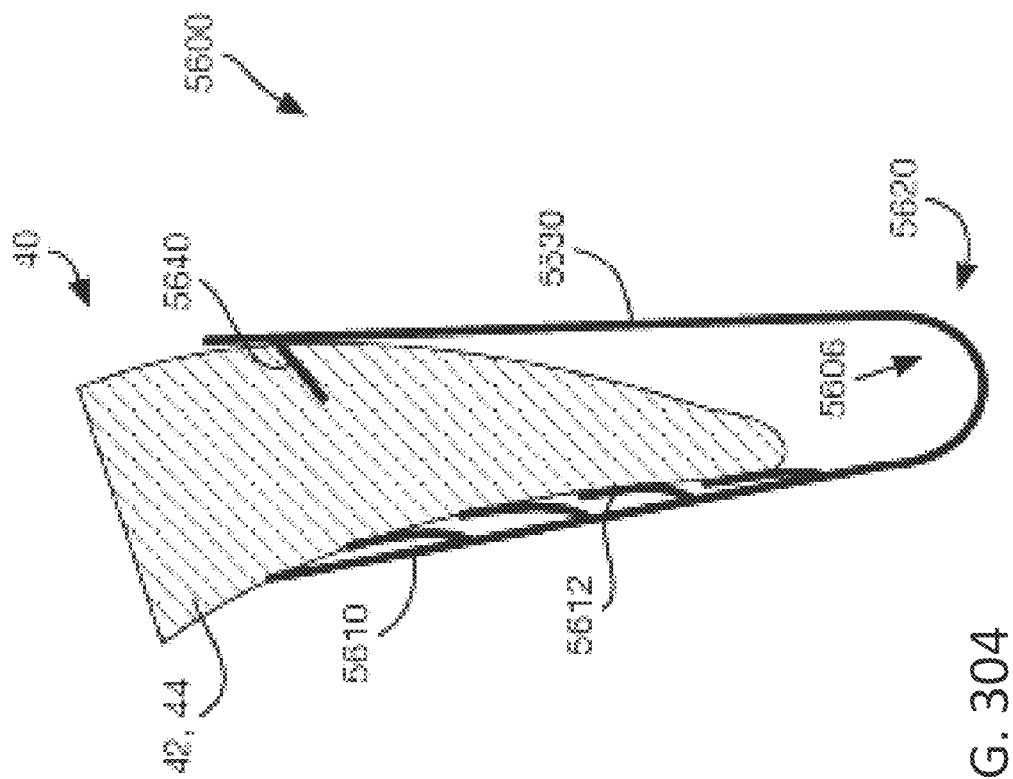
Figure 306:
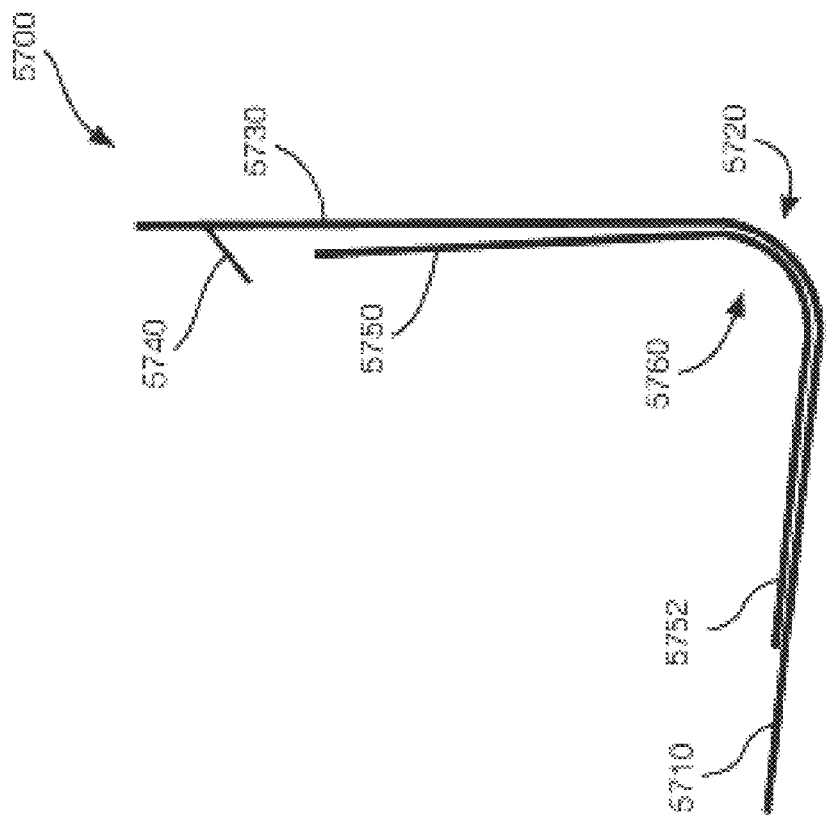
Figure 305:
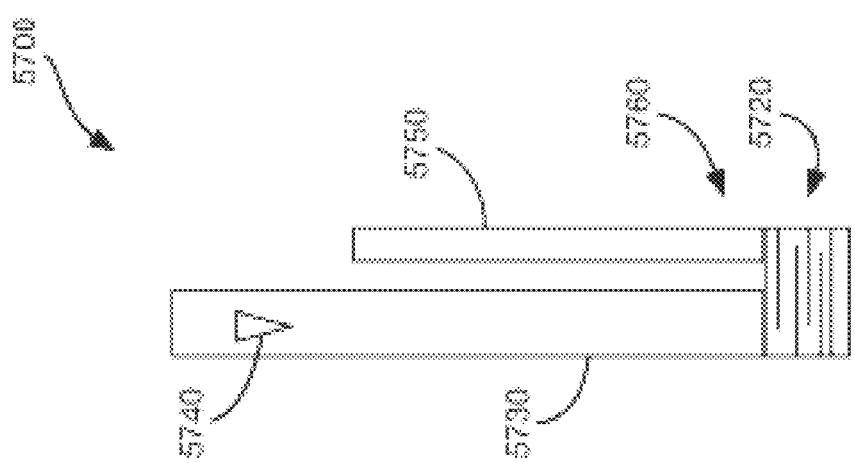
Figure 306A:
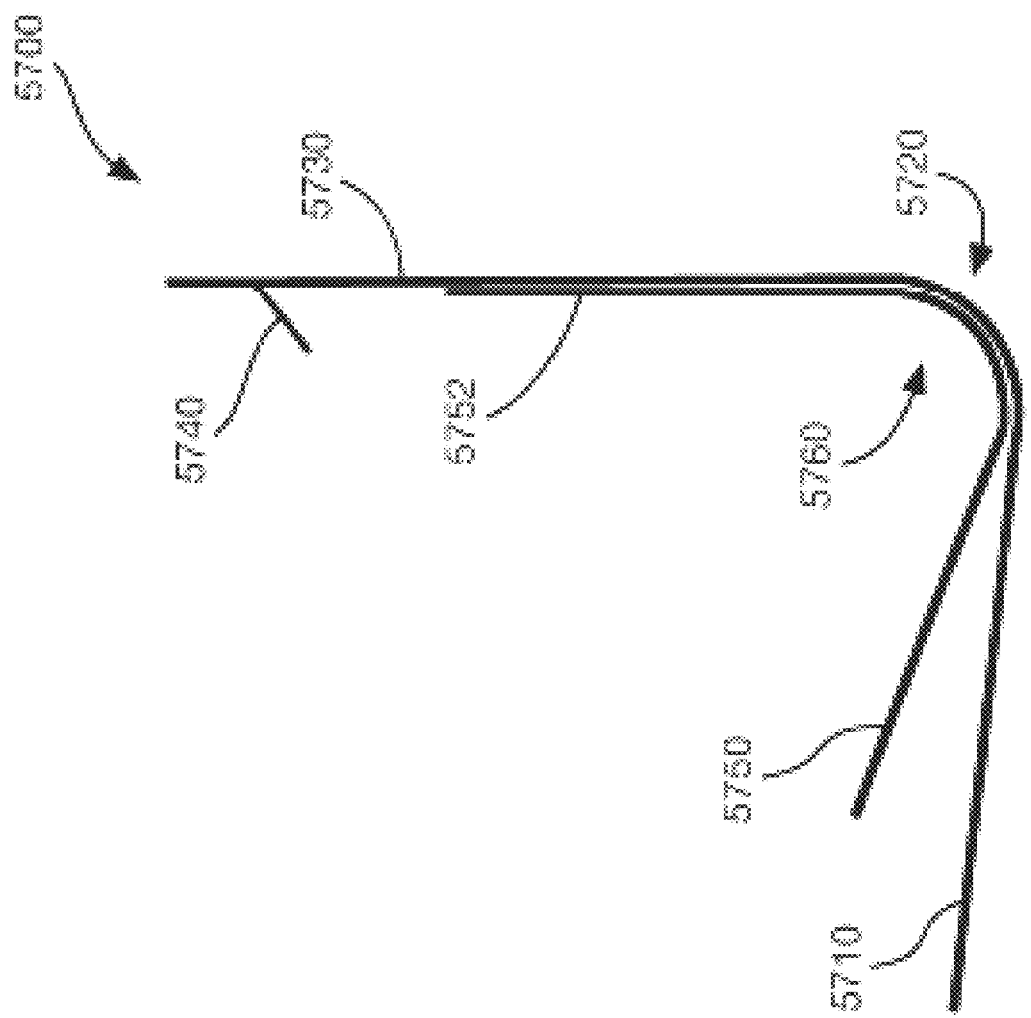
Figure 308:
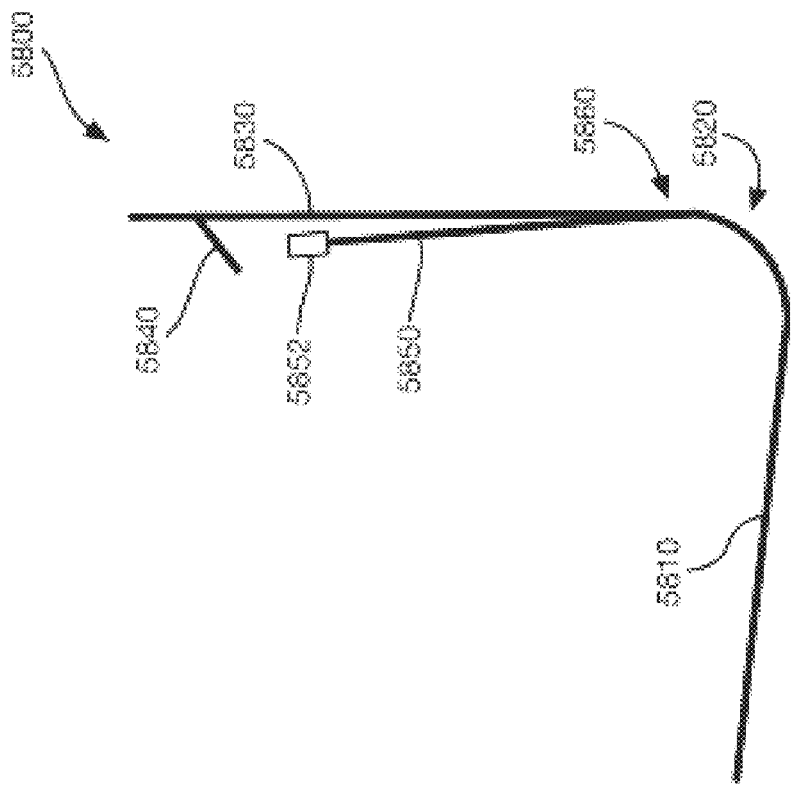
Figure 307:
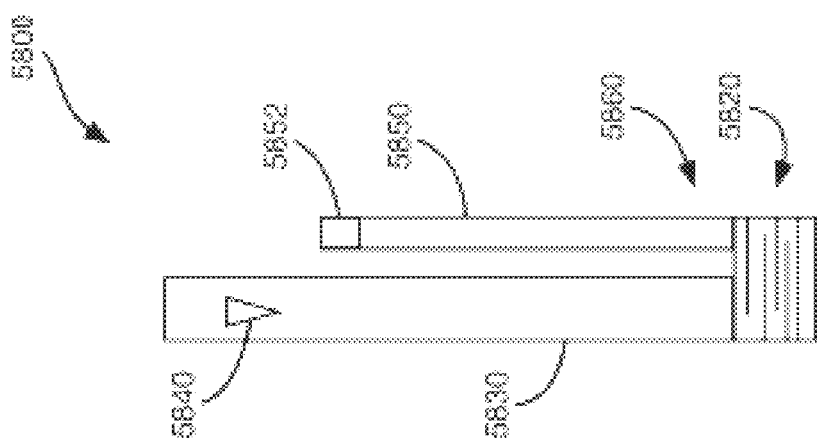
Figure 309:
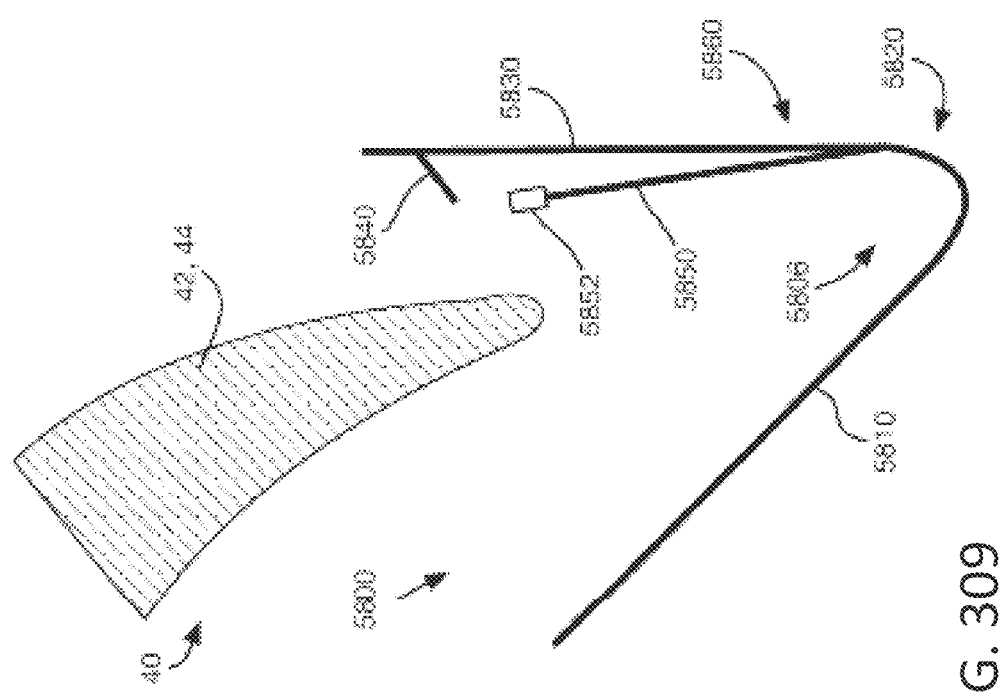
Figure 310:
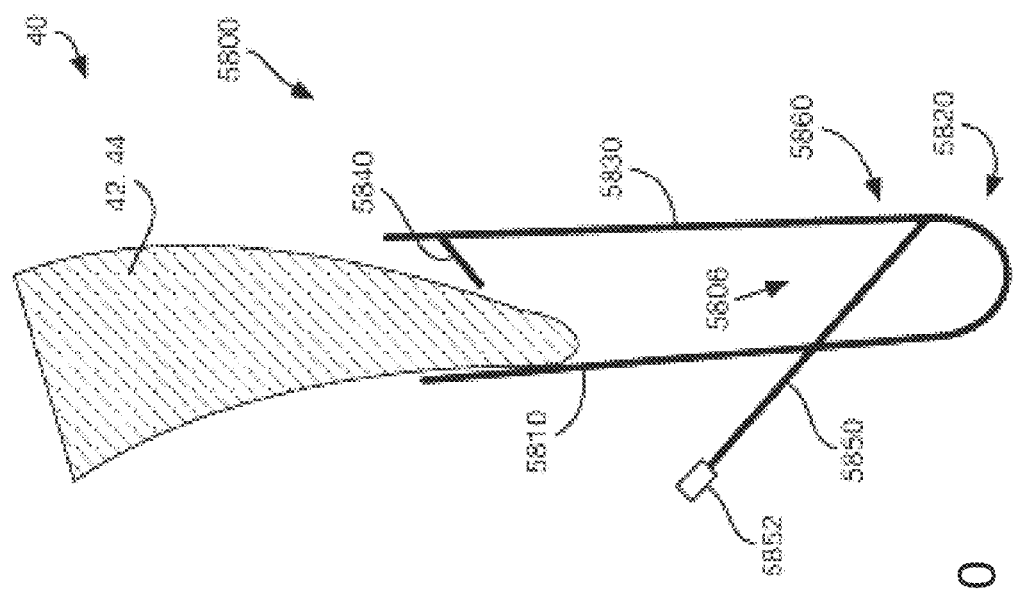
Figure 310A:
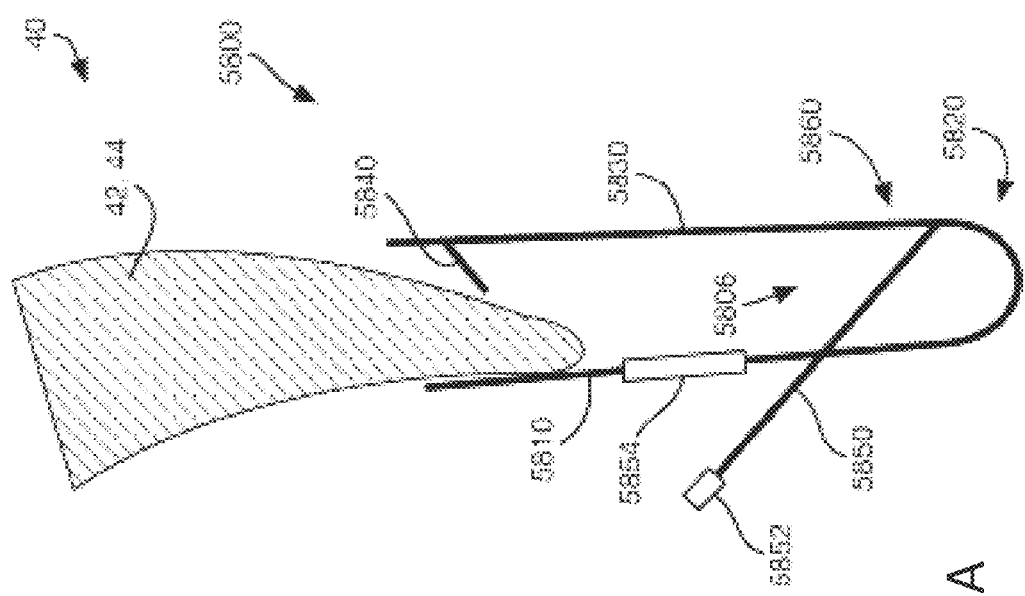
Figure 311:
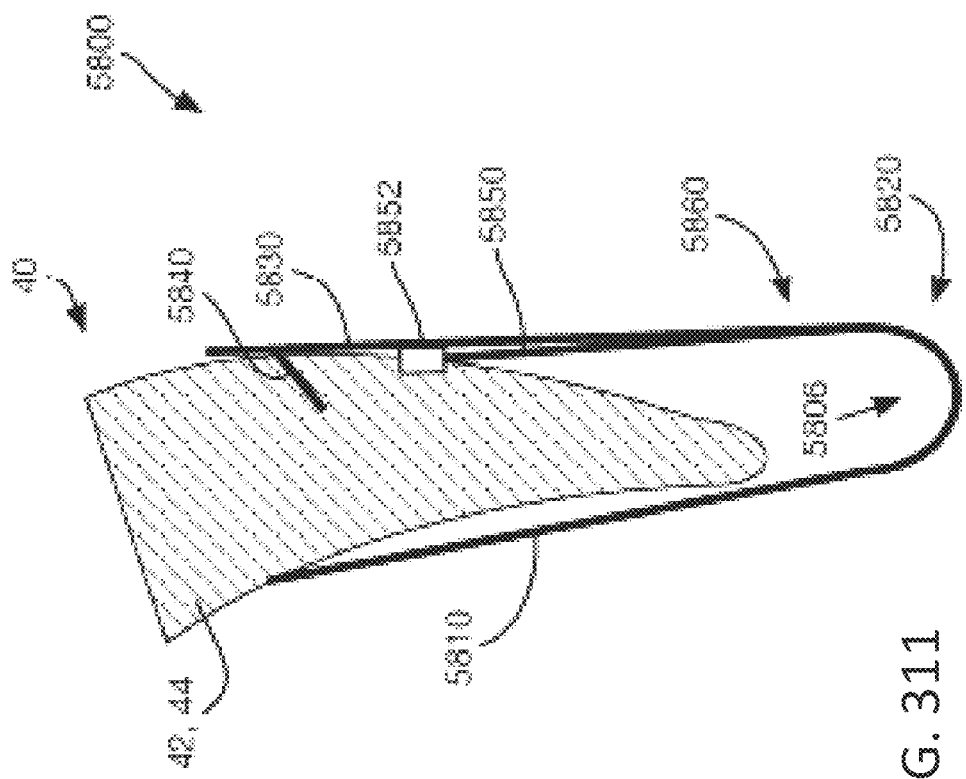
Figure 311A:
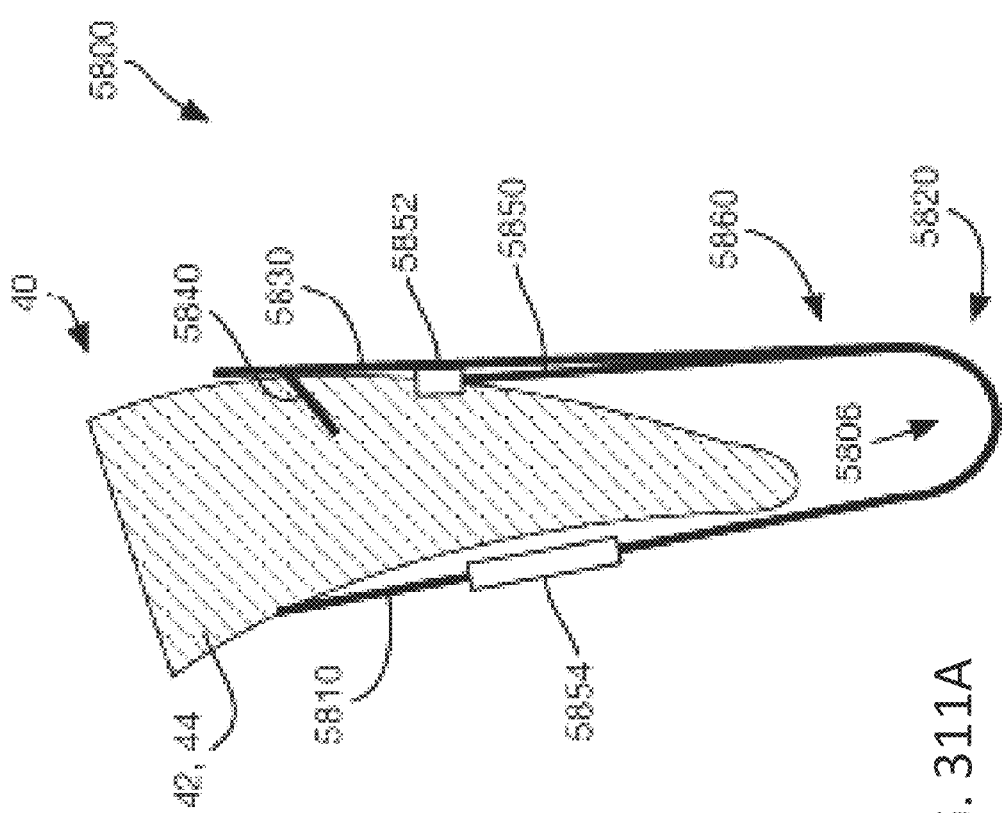
Figure 314:
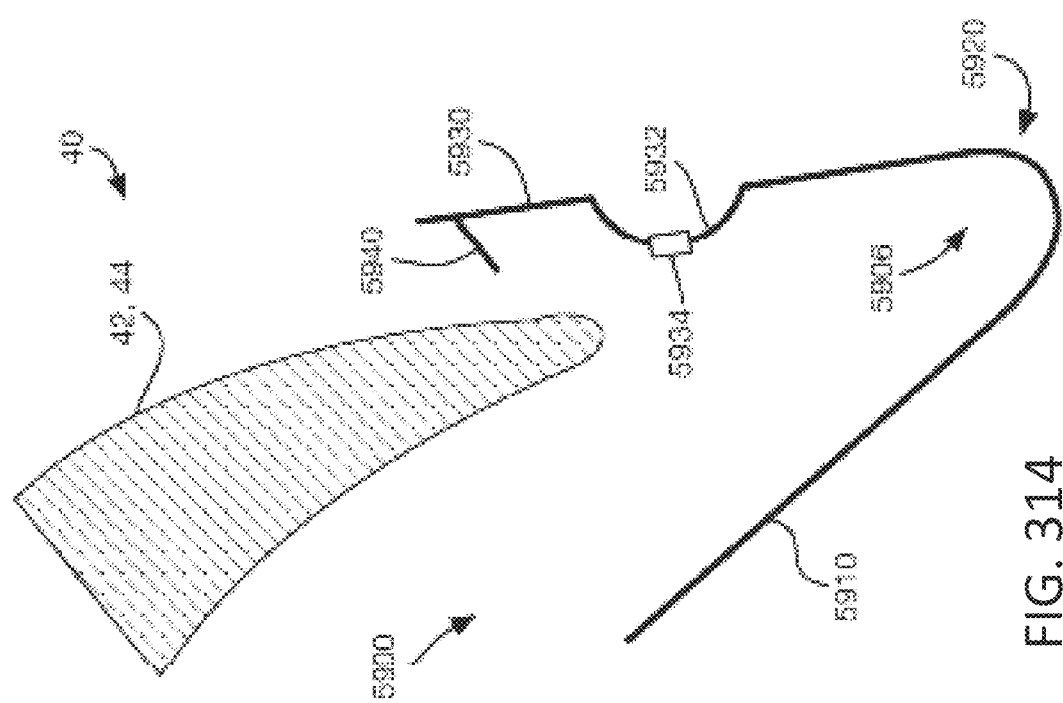
Figure 314A:
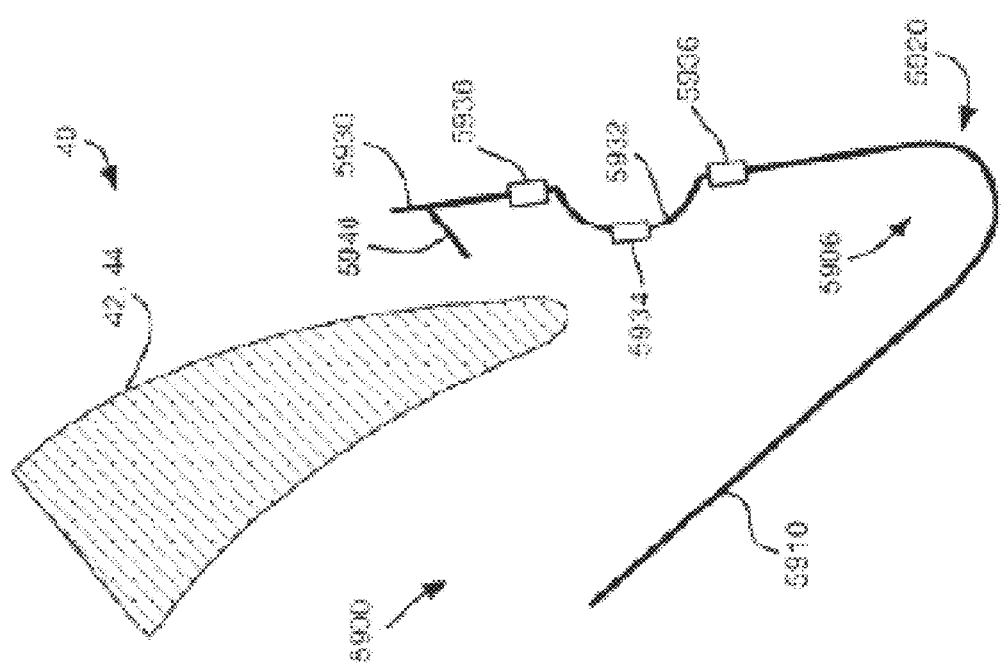
Figure 315:
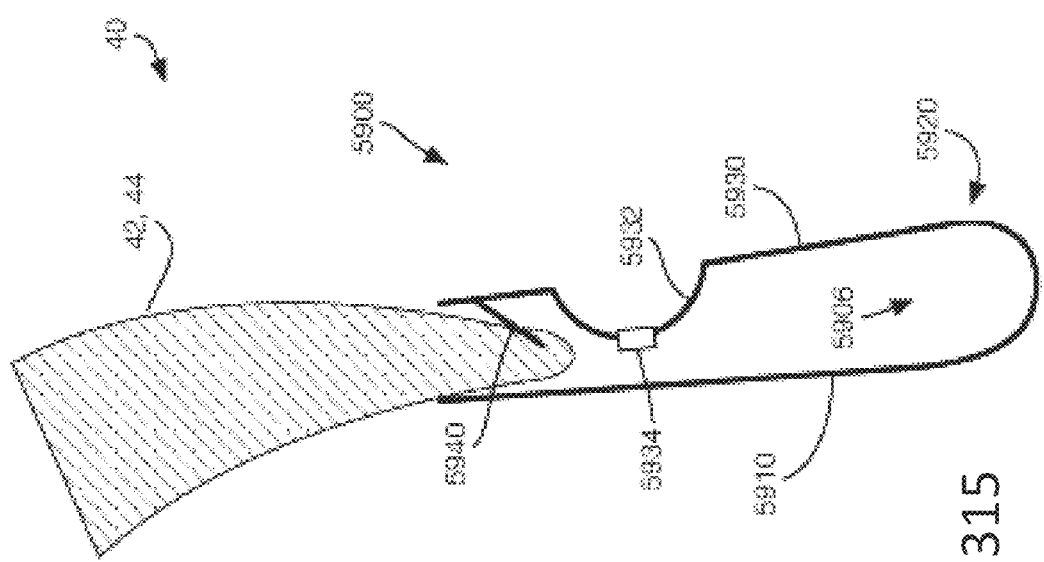
Figure 315A:
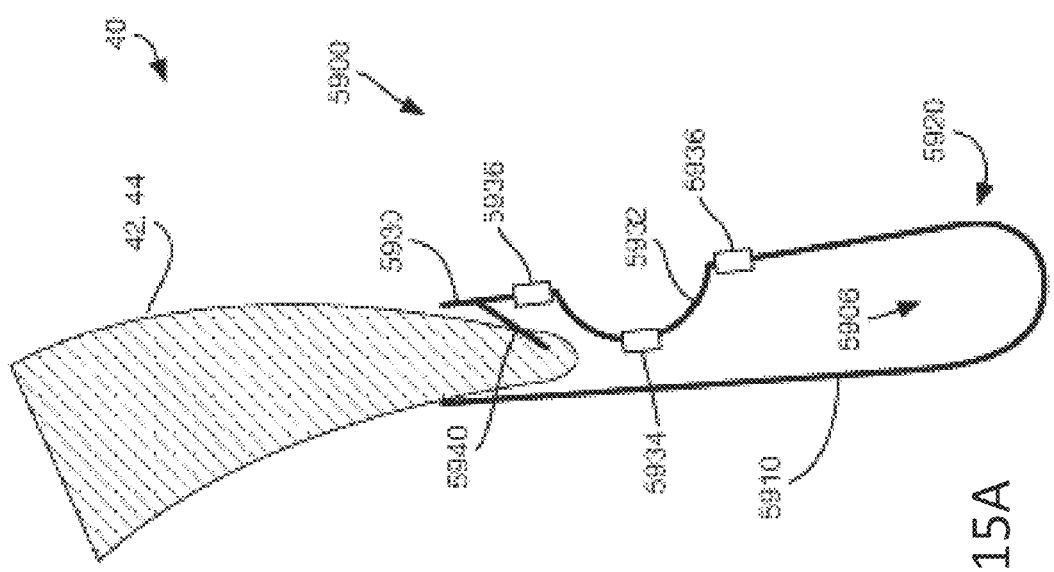
Figure 316:
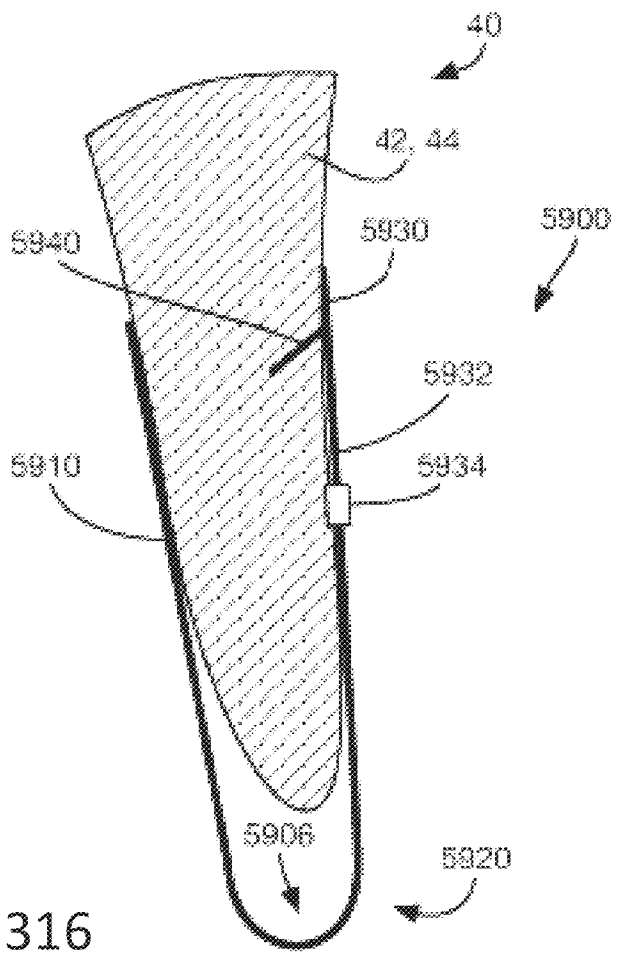
Figure 316A:
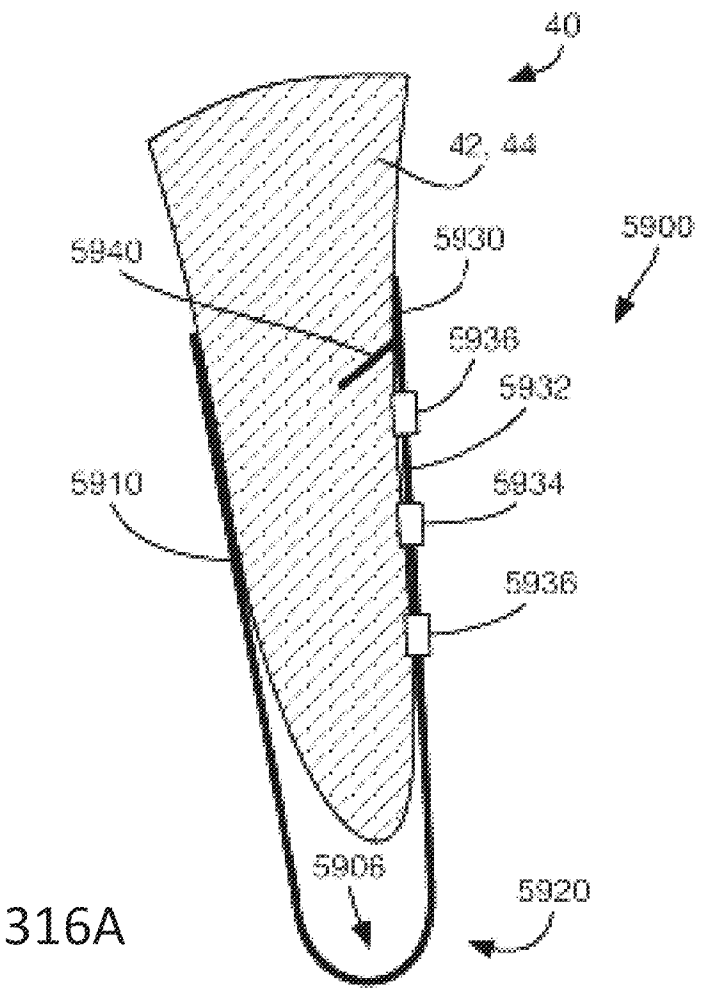
Figure 319:
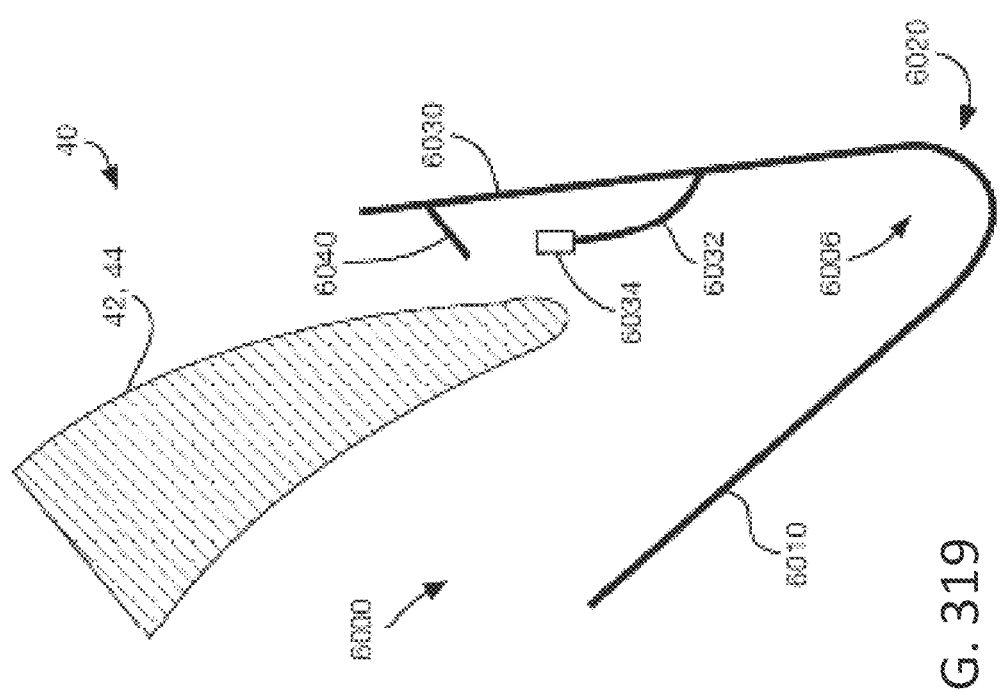
Figure 319A:
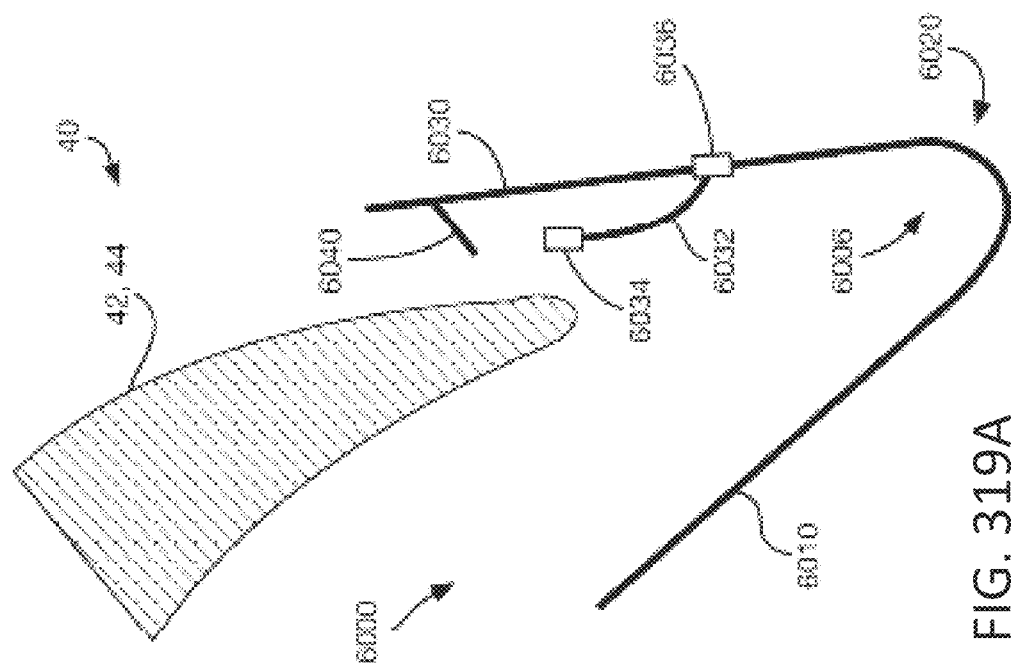
Figure 320:
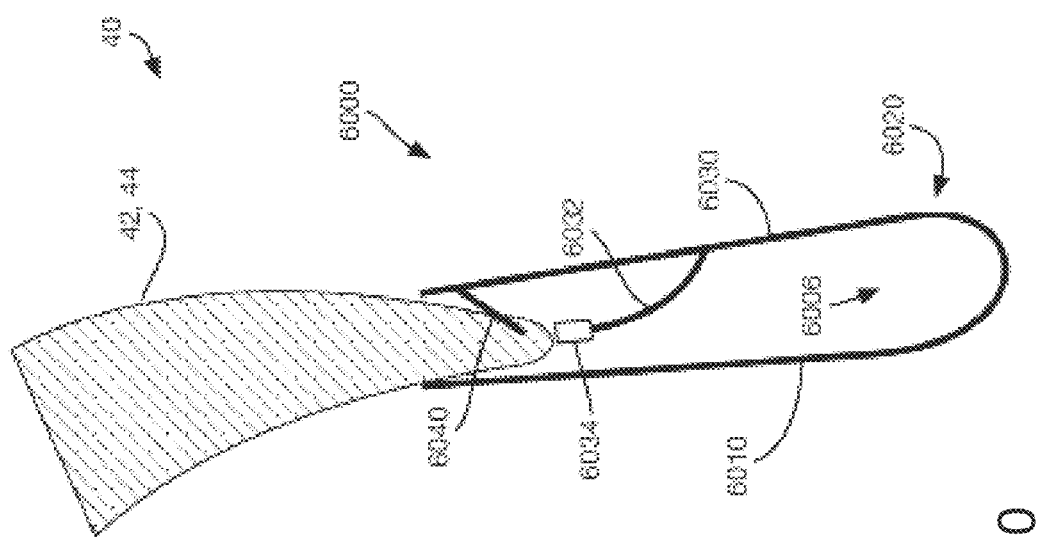
Figure 320A:
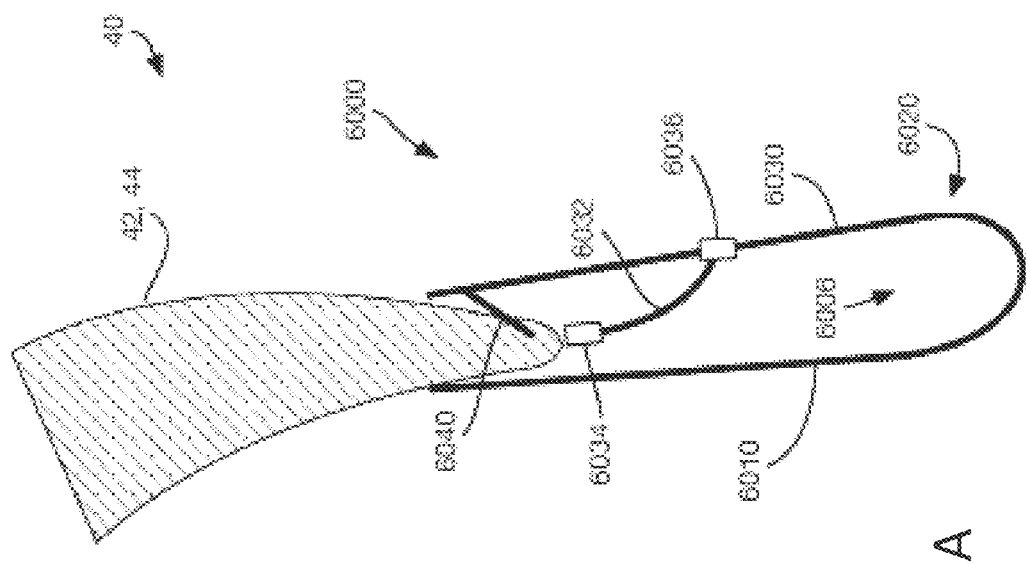
Figure 321:
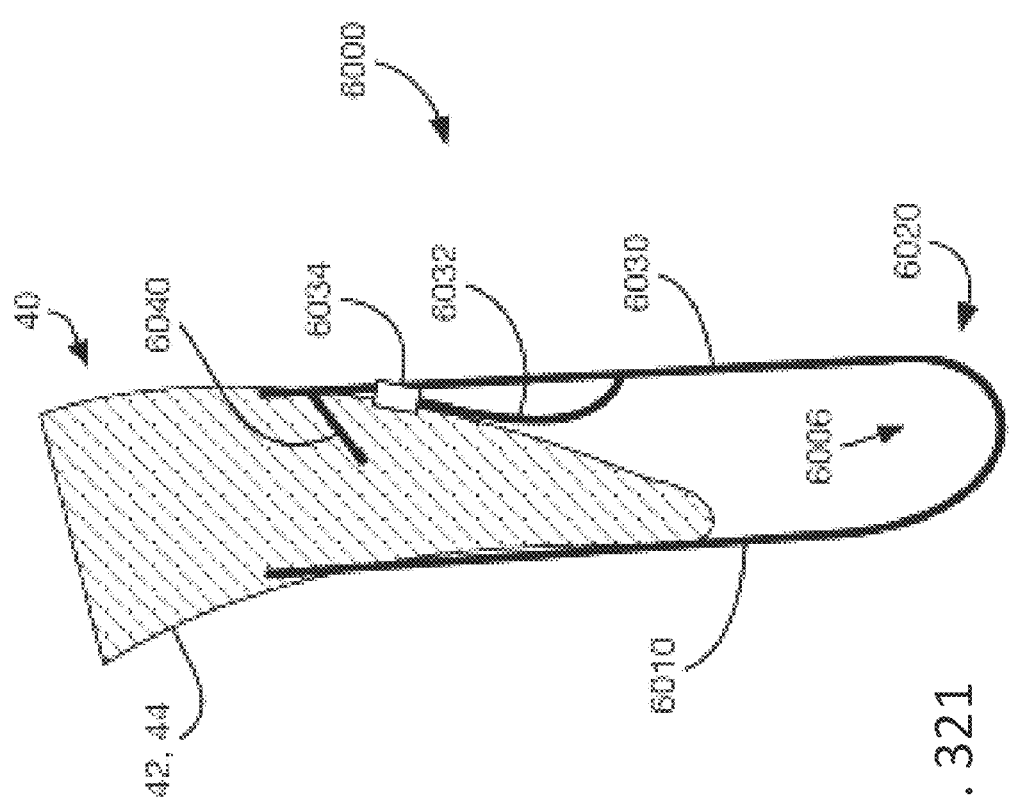
Figure 321A:
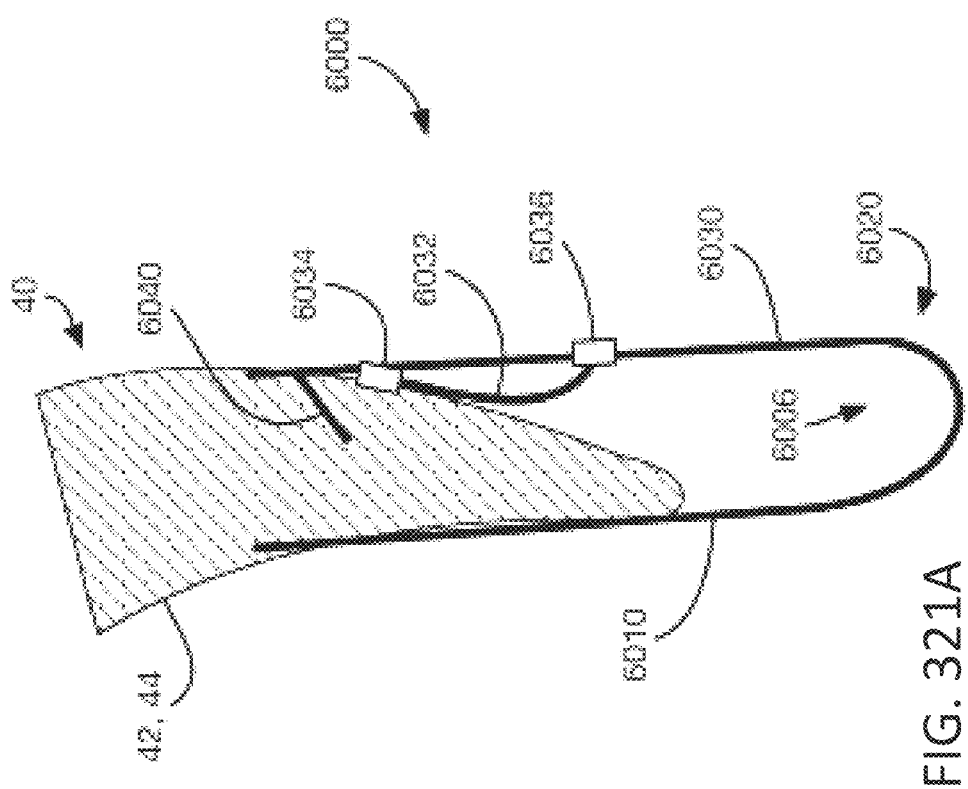
Figure 323:
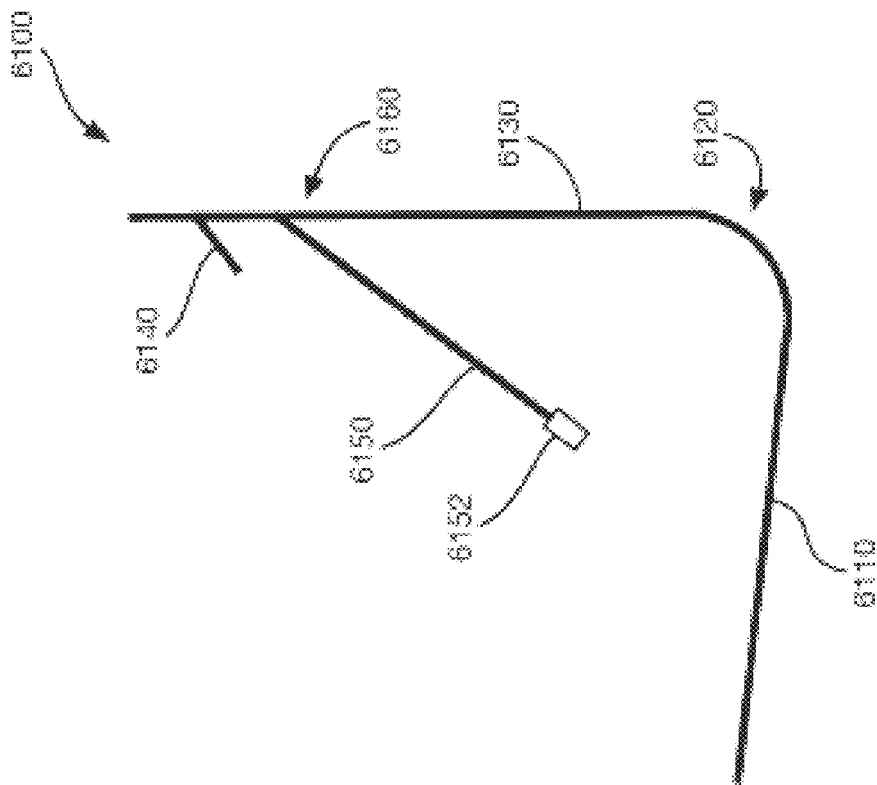
Figure 322:
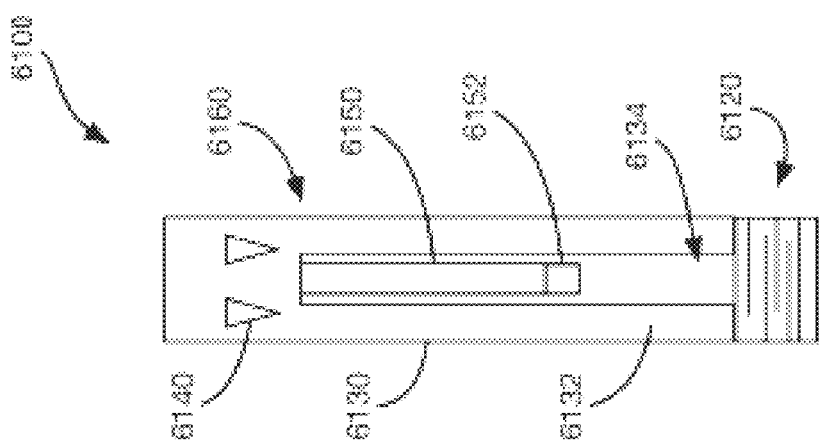
Figure 324:
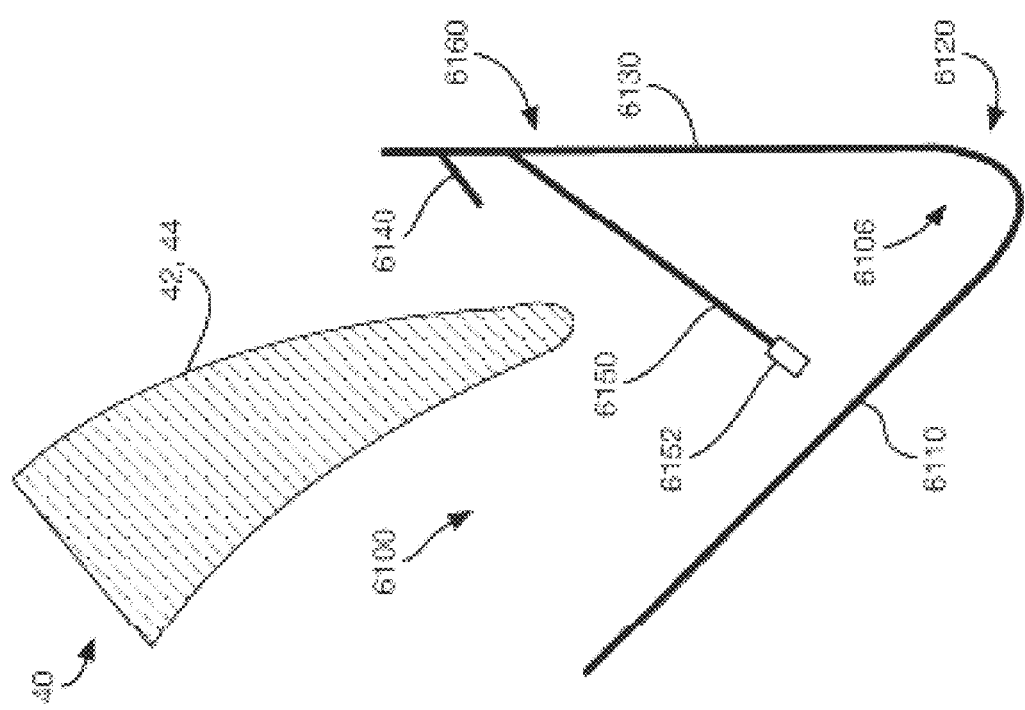
Figure 325:
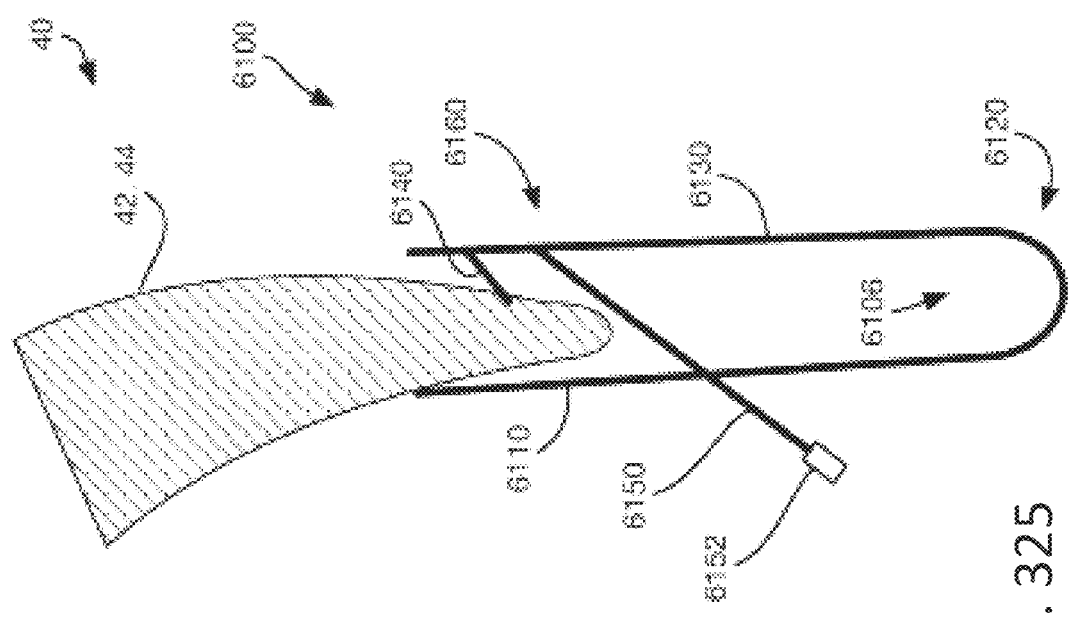
Figure 325A:
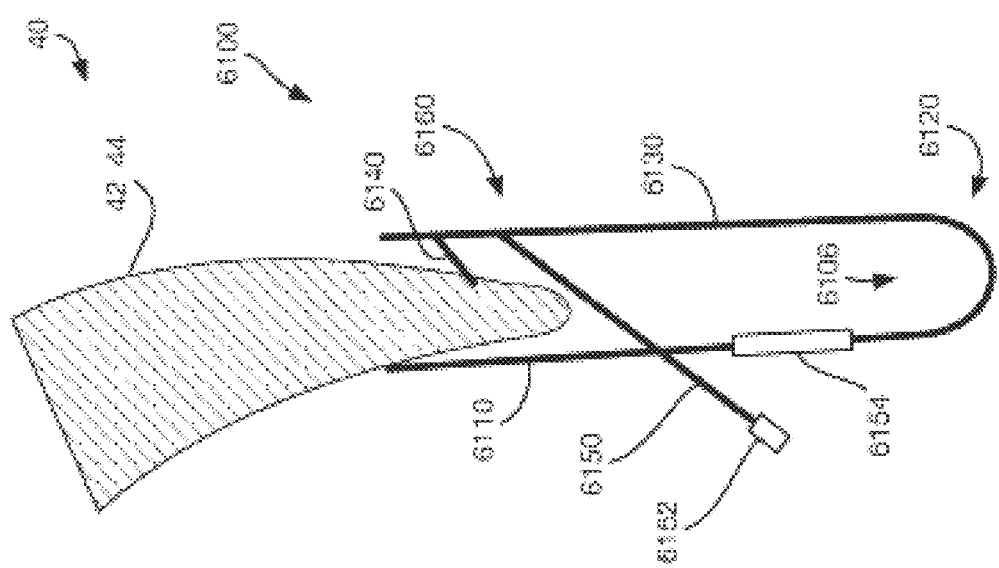
Figure 326:
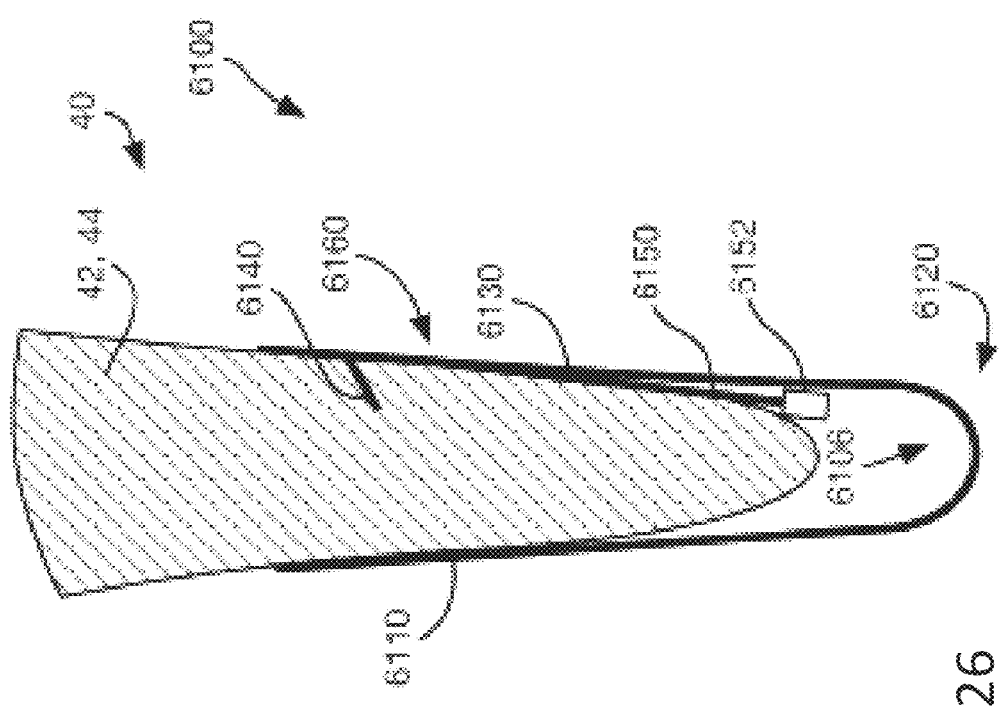
Figure 326A:
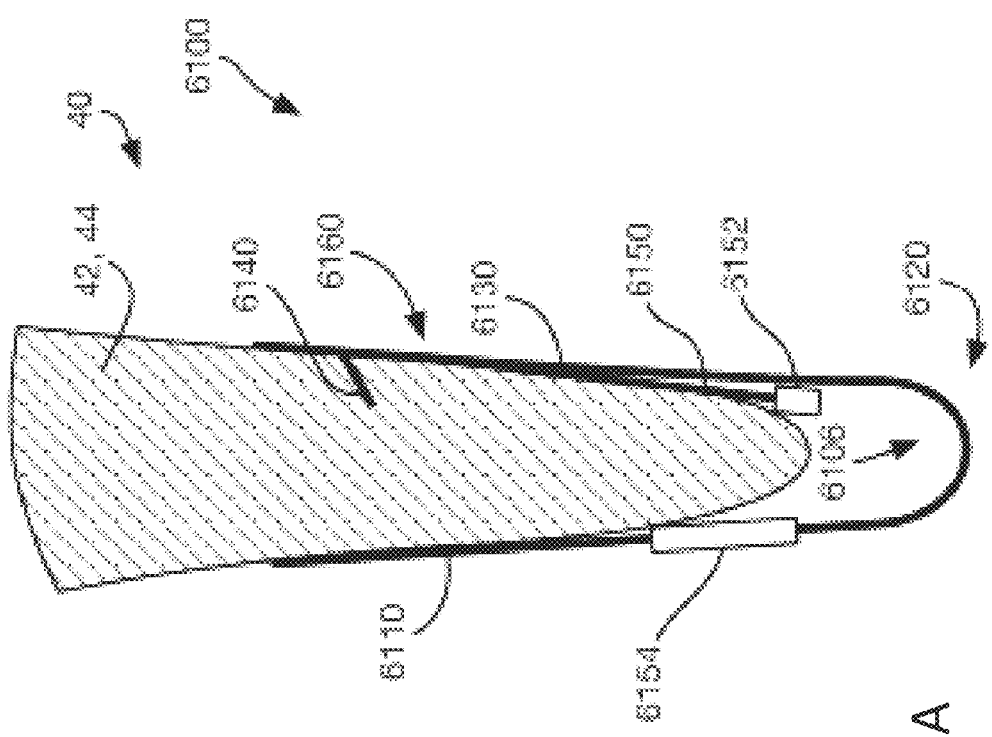
Figure 328:
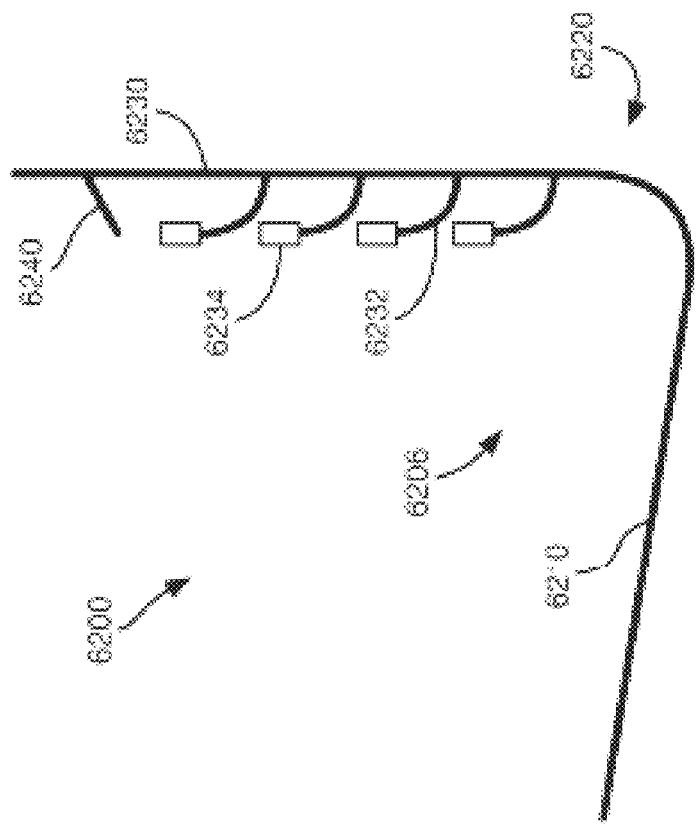
Figure 327:
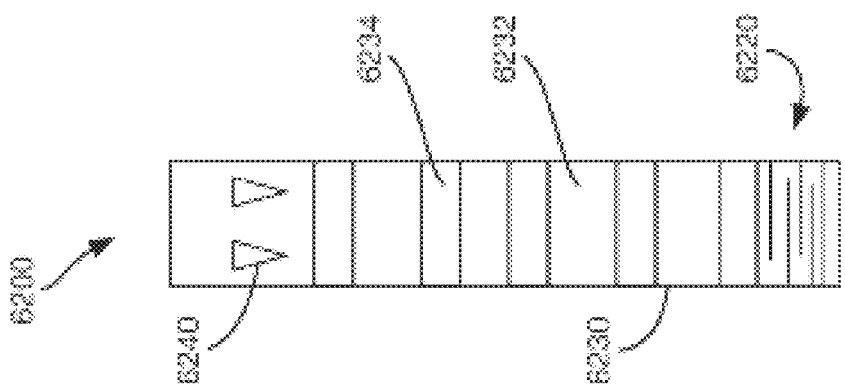
Figure 330:
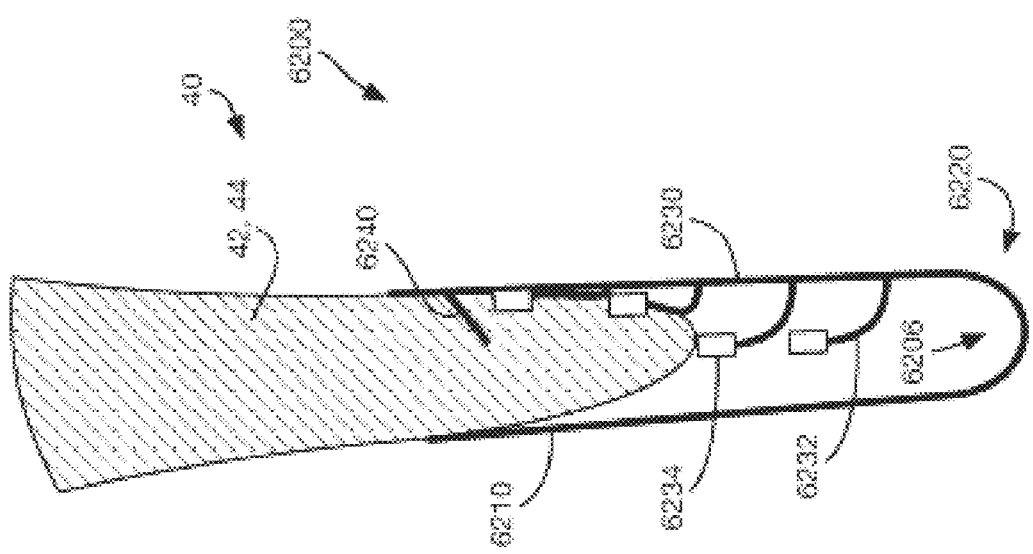
Figure 331:
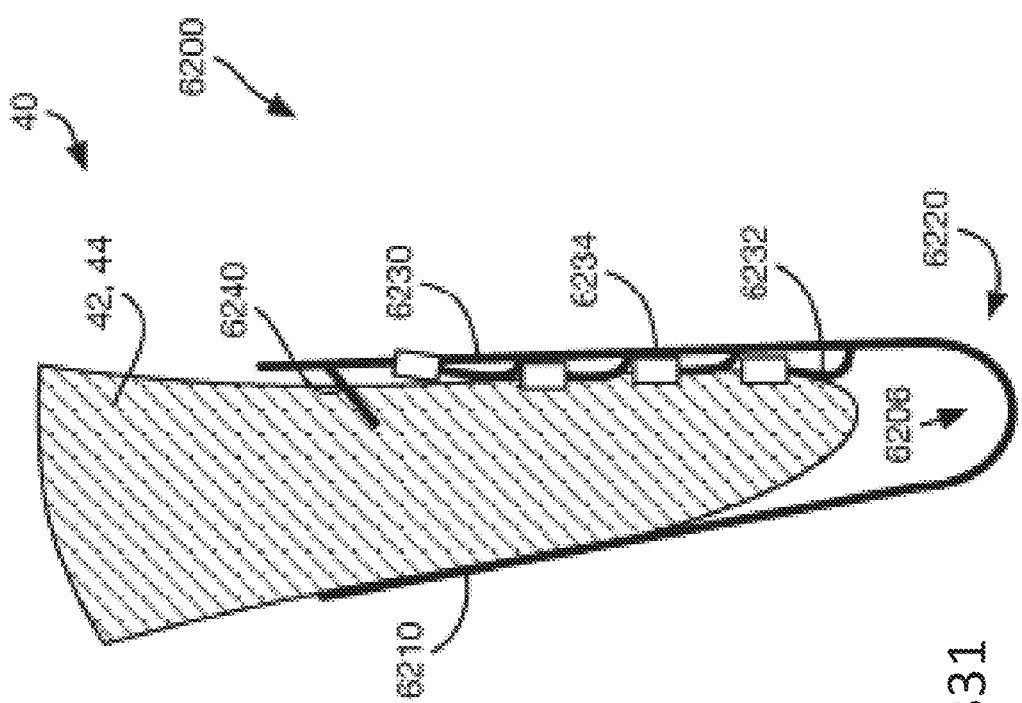
Figure 333:
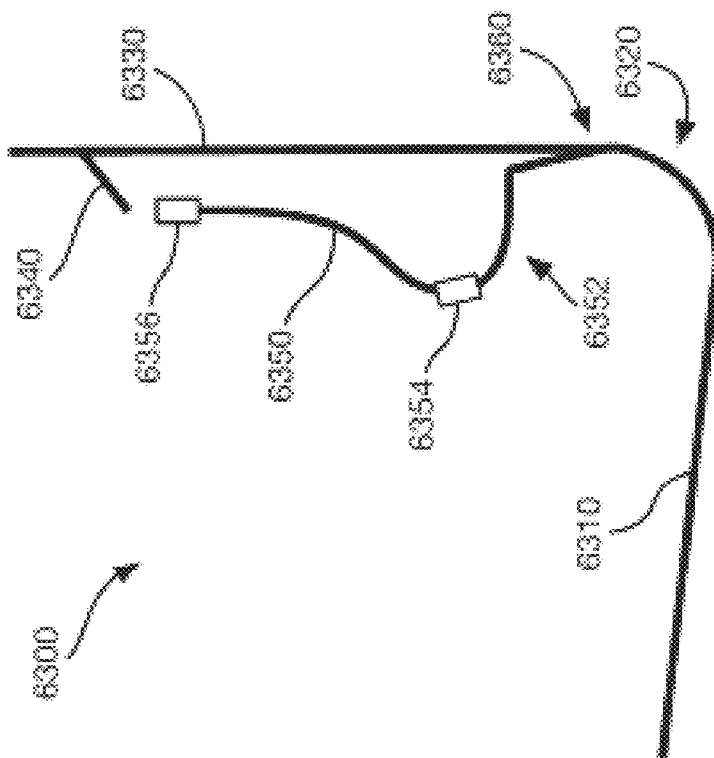
Figure 332:
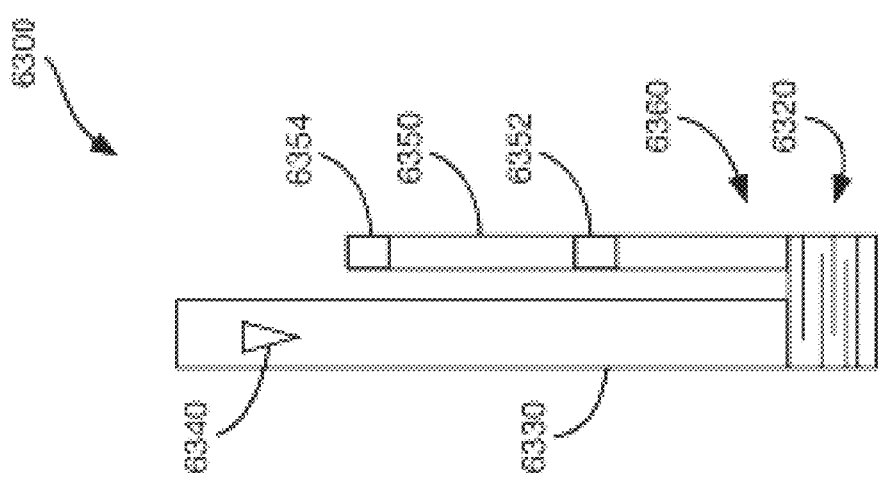
Figure 334:
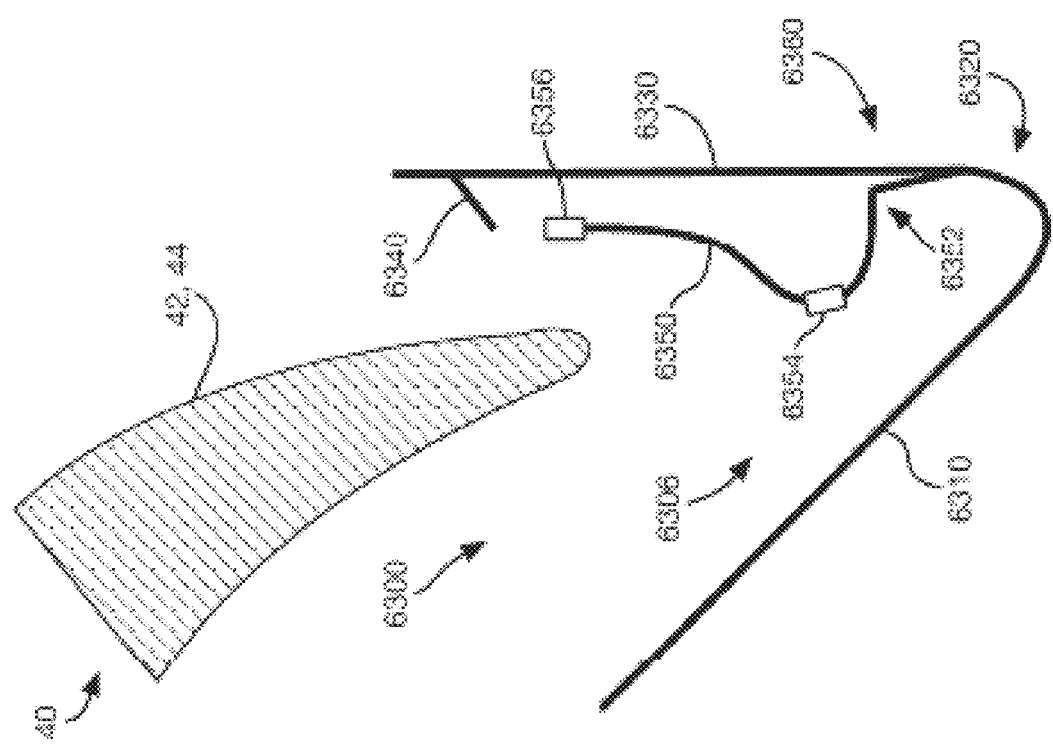
Figure 335:
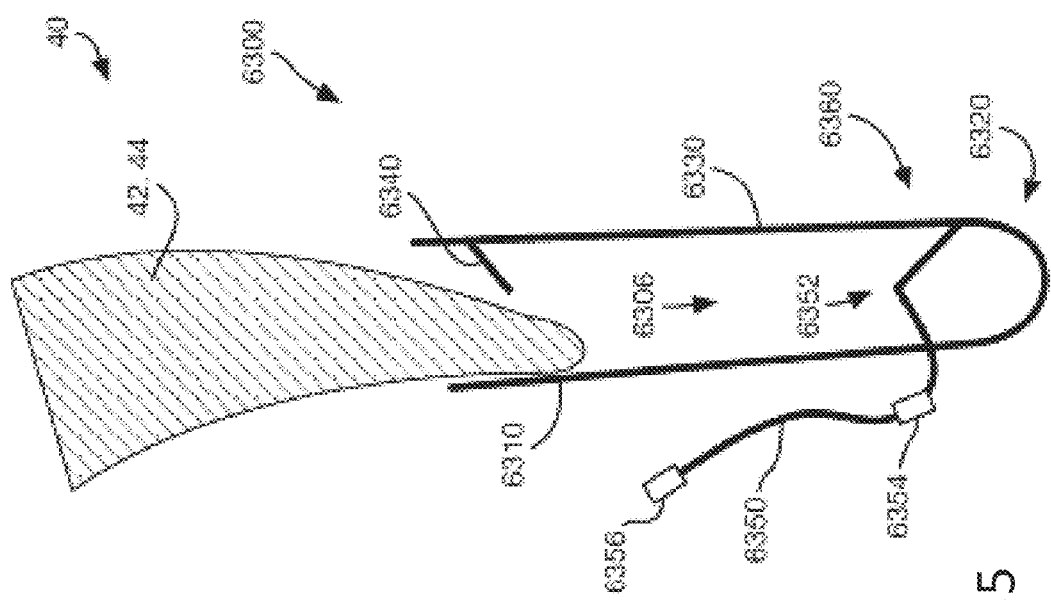
Figure 336:
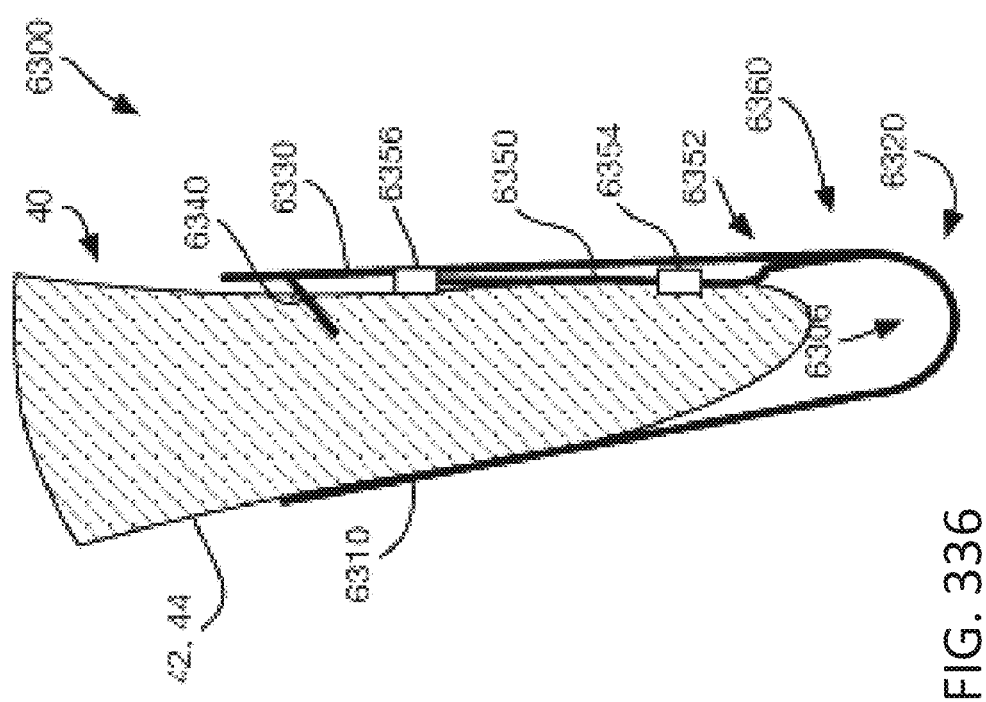
Figure 337:
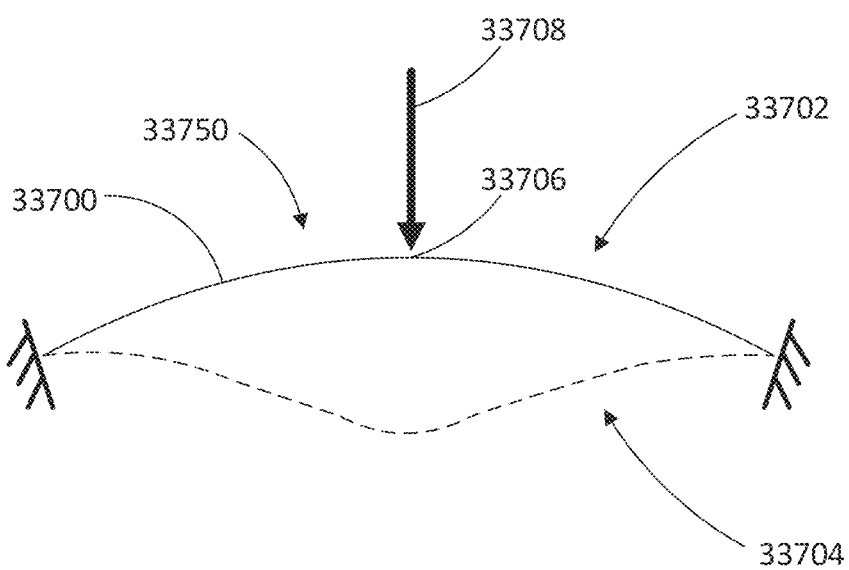
Figure 338:
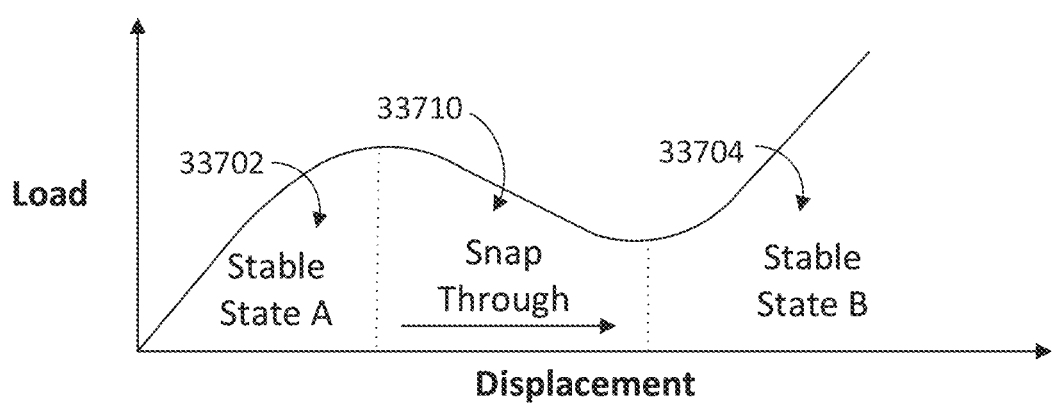
Figure 339:
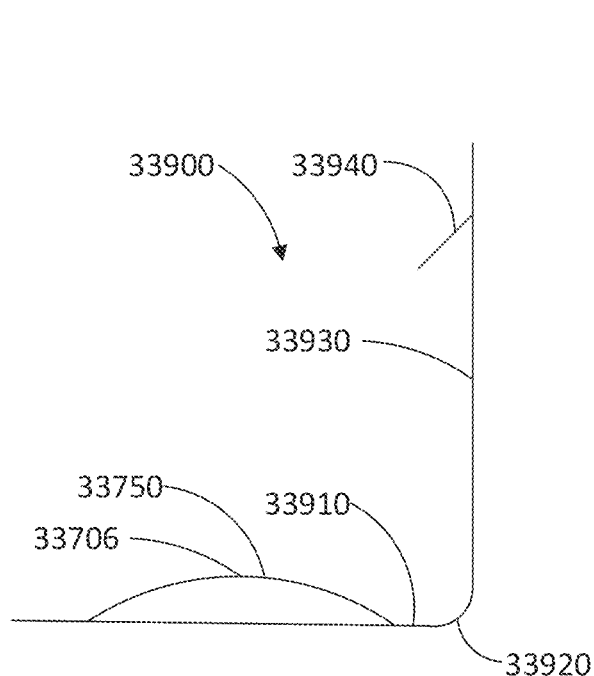
Figure 341:
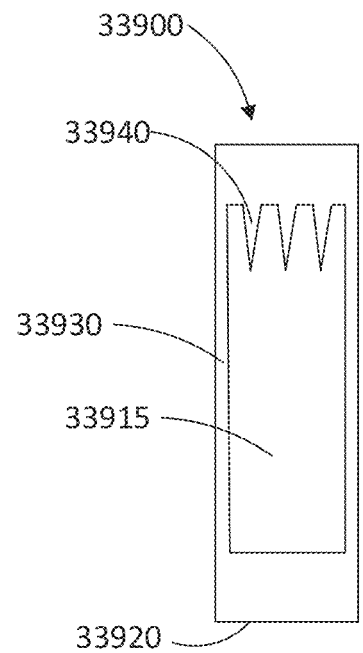
Figure 340:
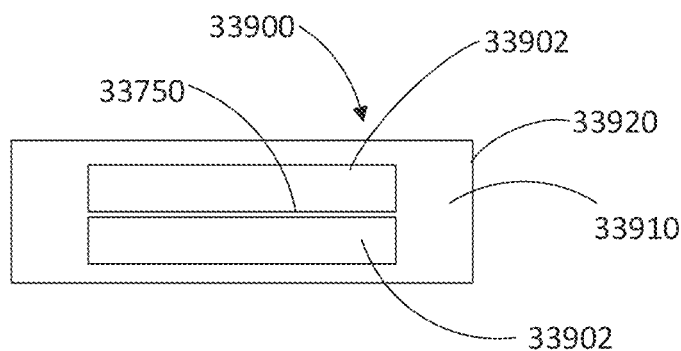
Figure 342:
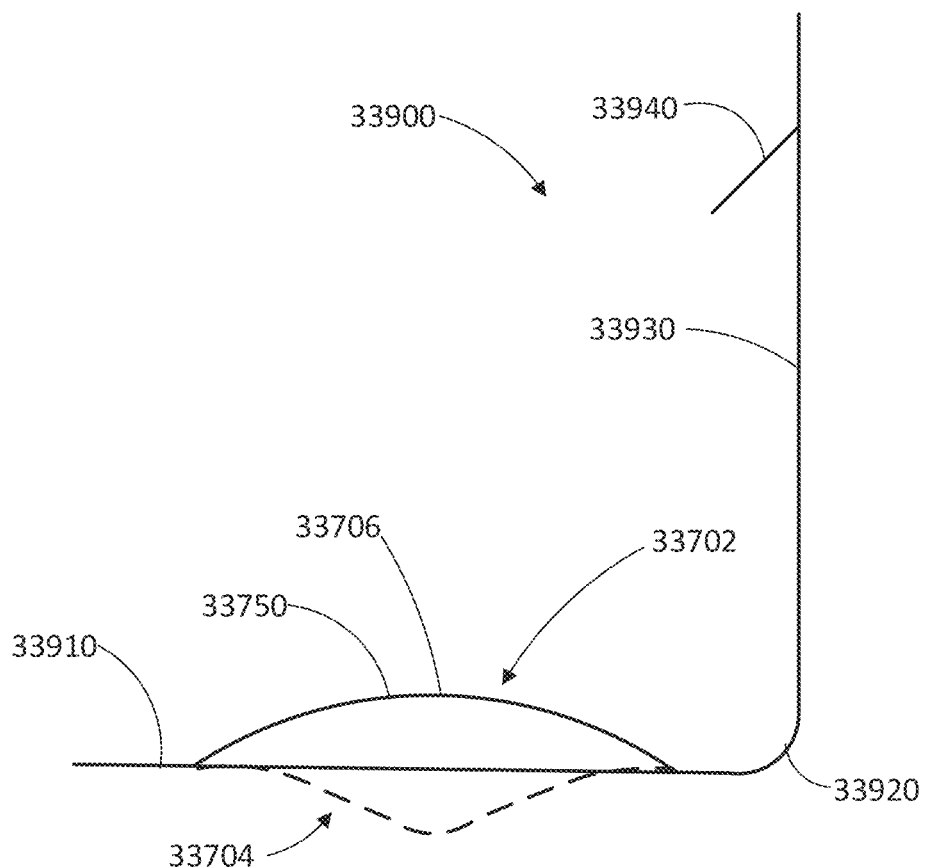
Figure 343:
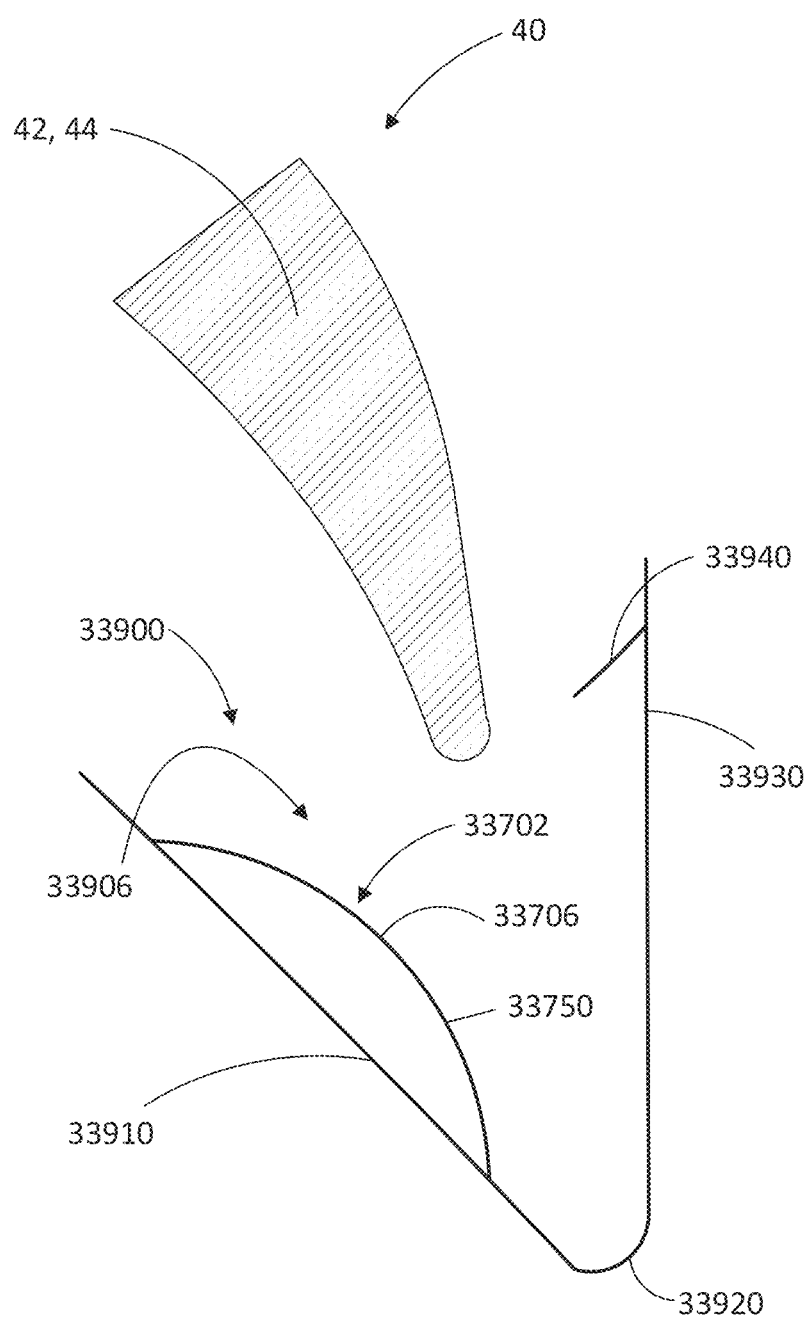
Figure 344:
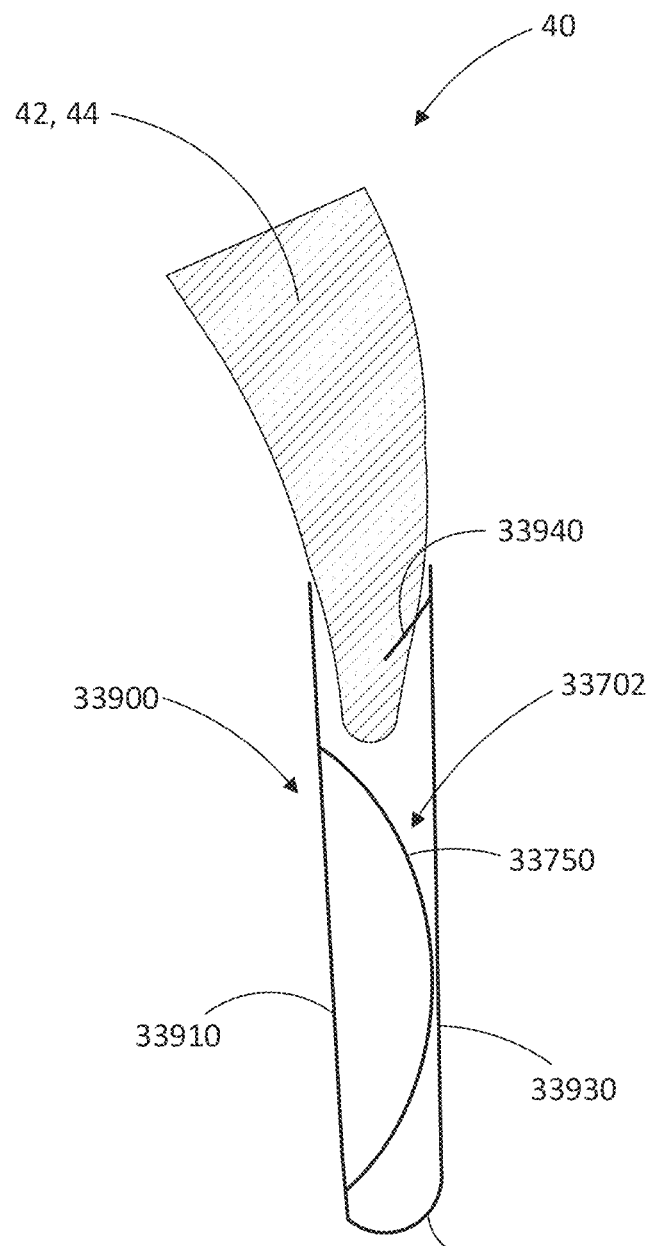
Figure 345:
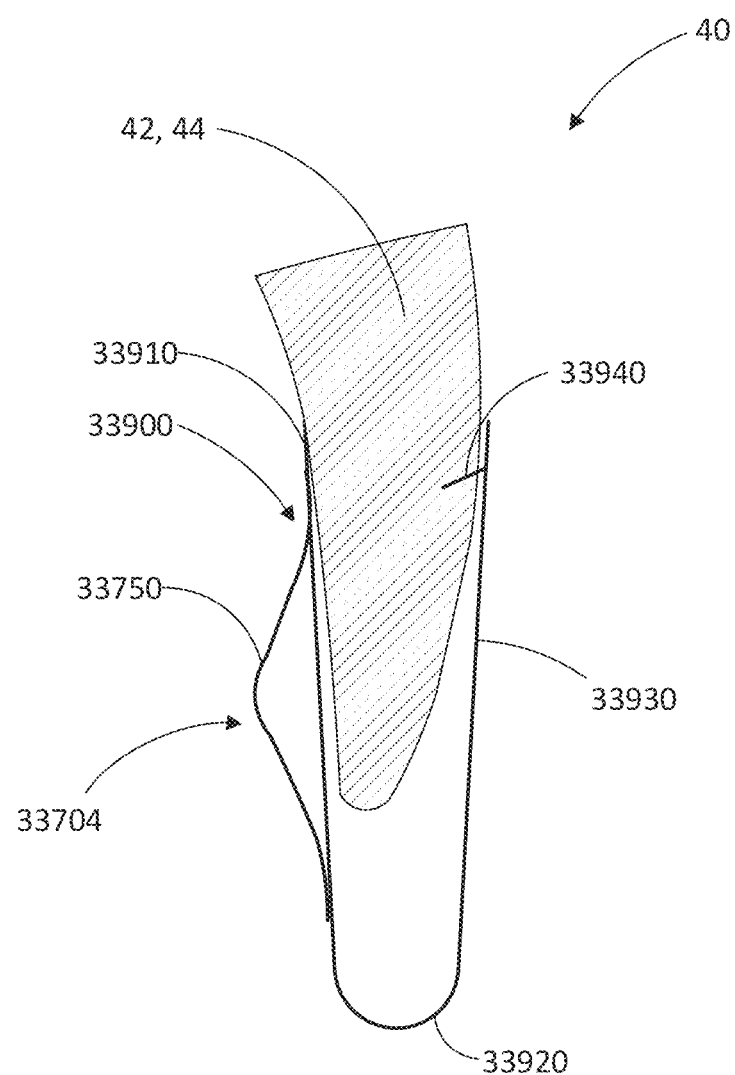
Figure 349:
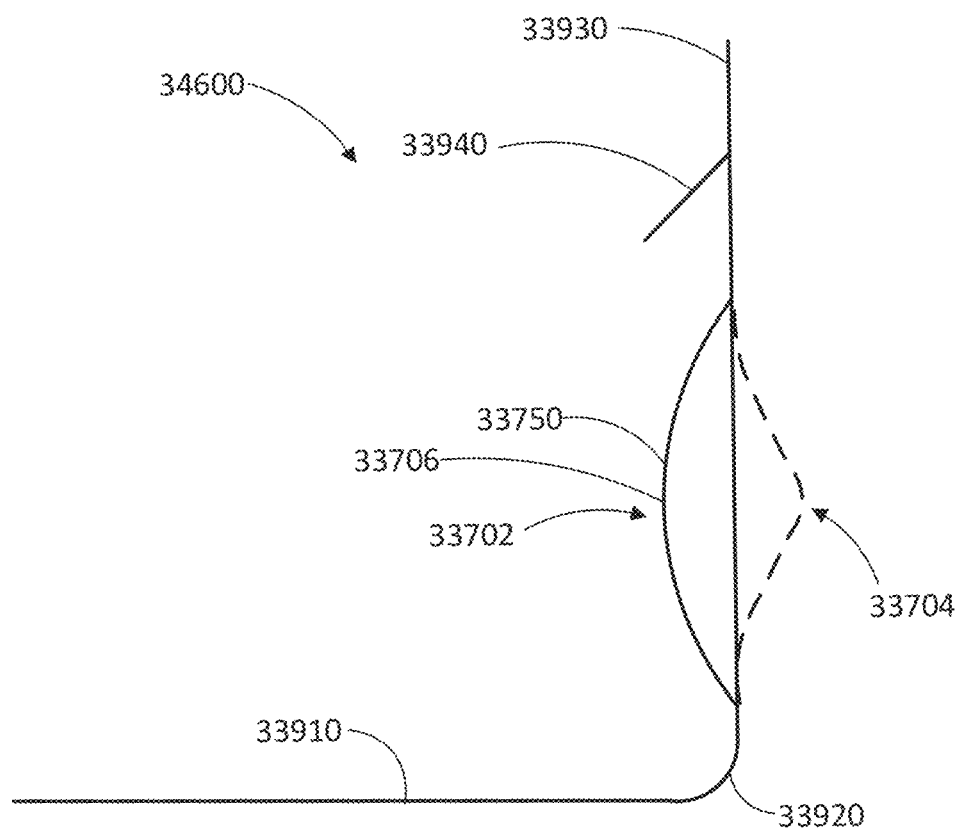
Figure 350:
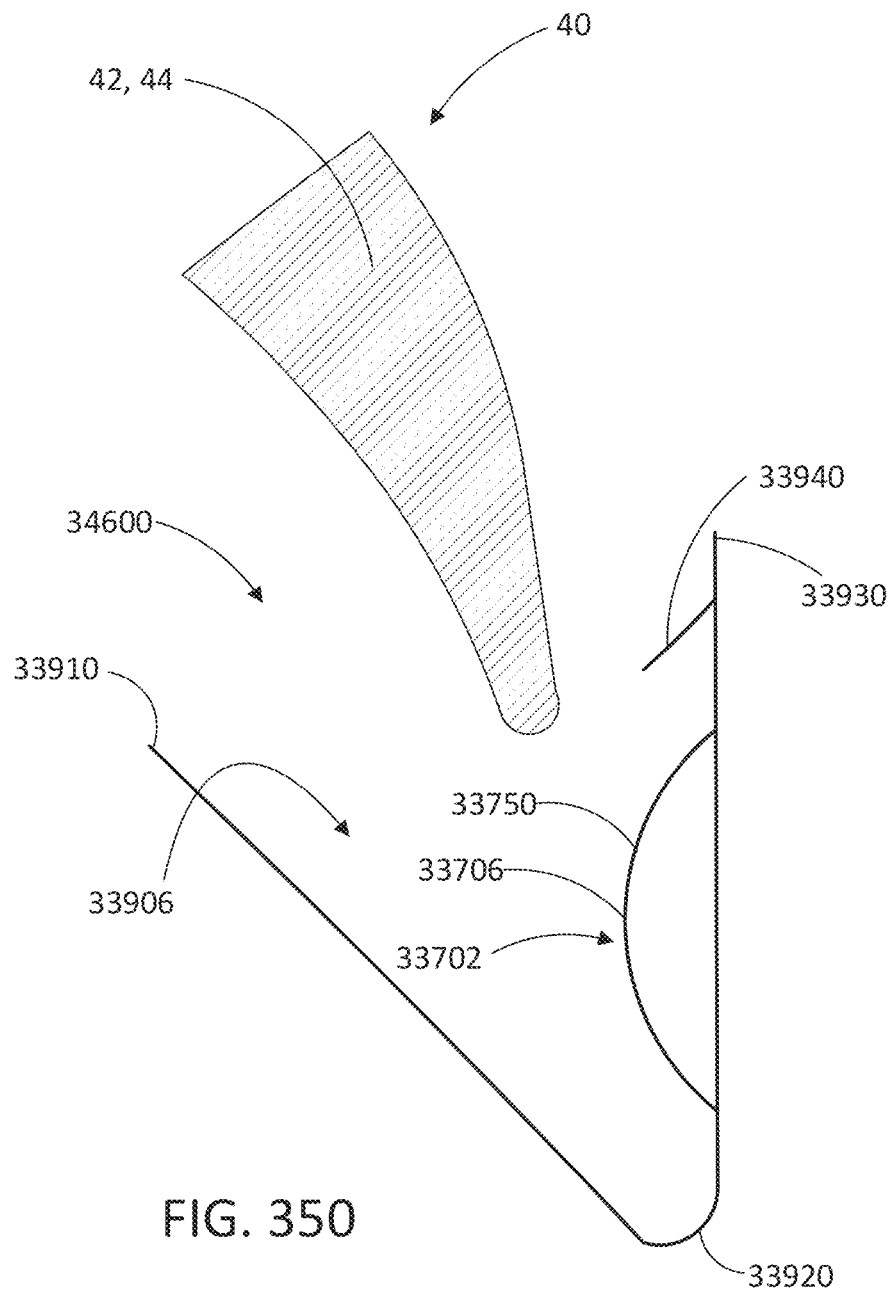
Figure 351:
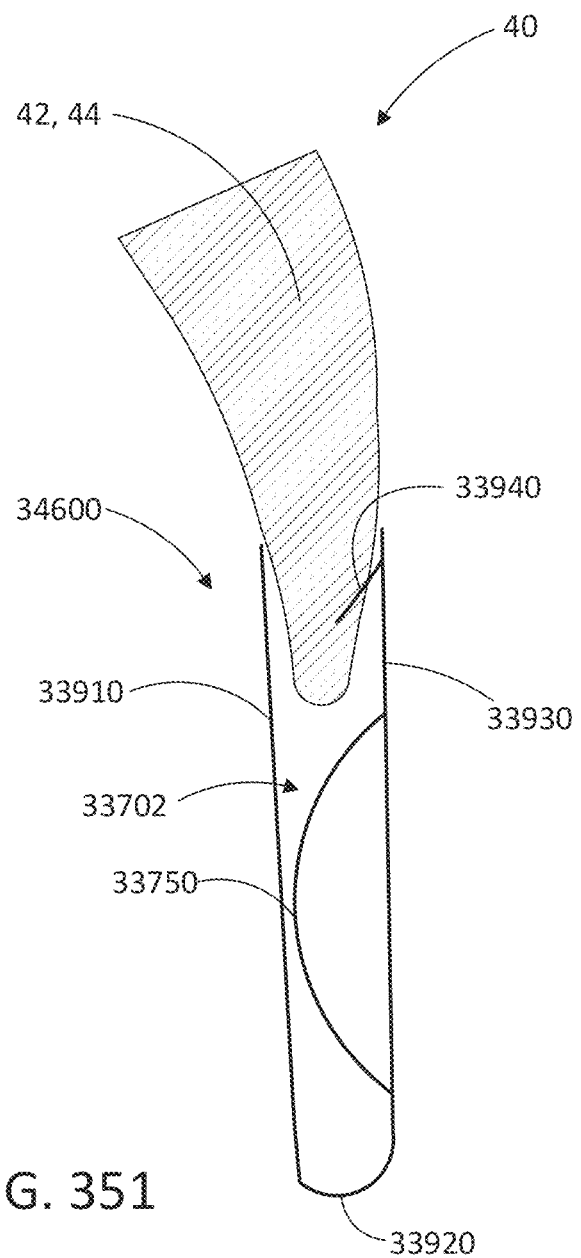
Figure 352:
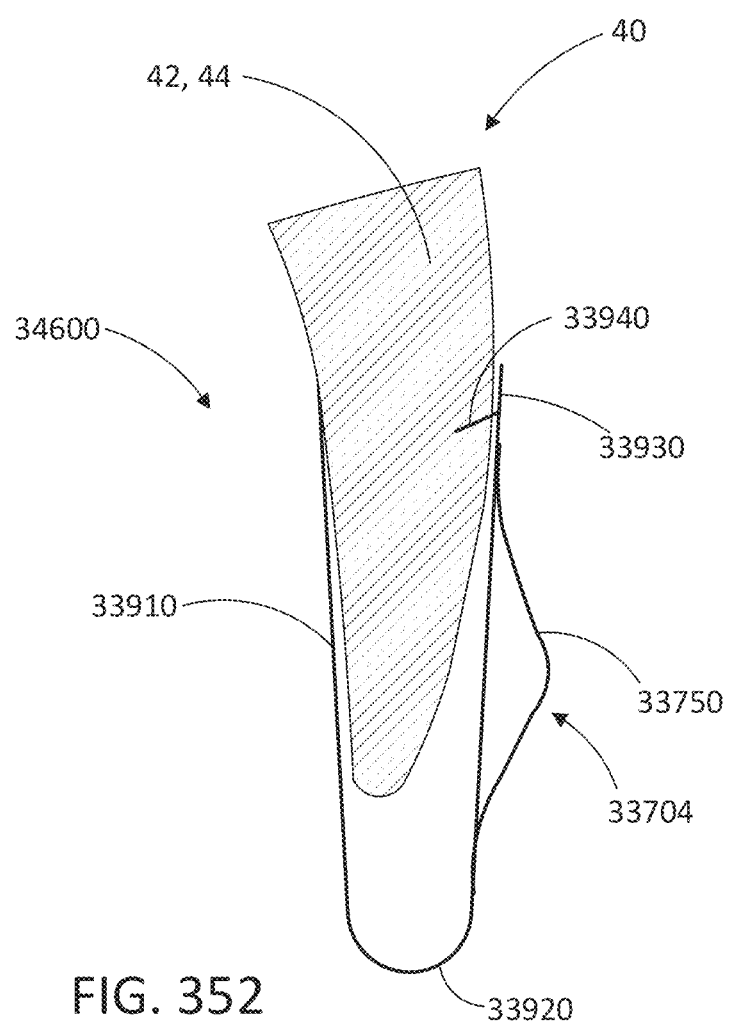
Figure 353A:
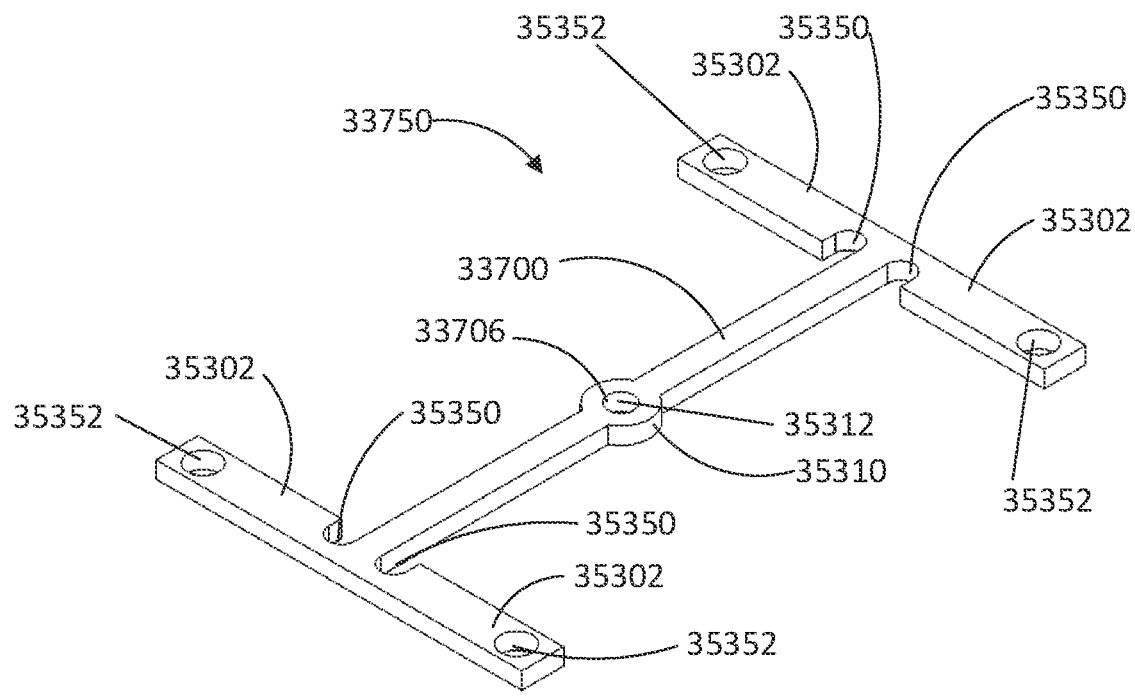
Figure 353B:
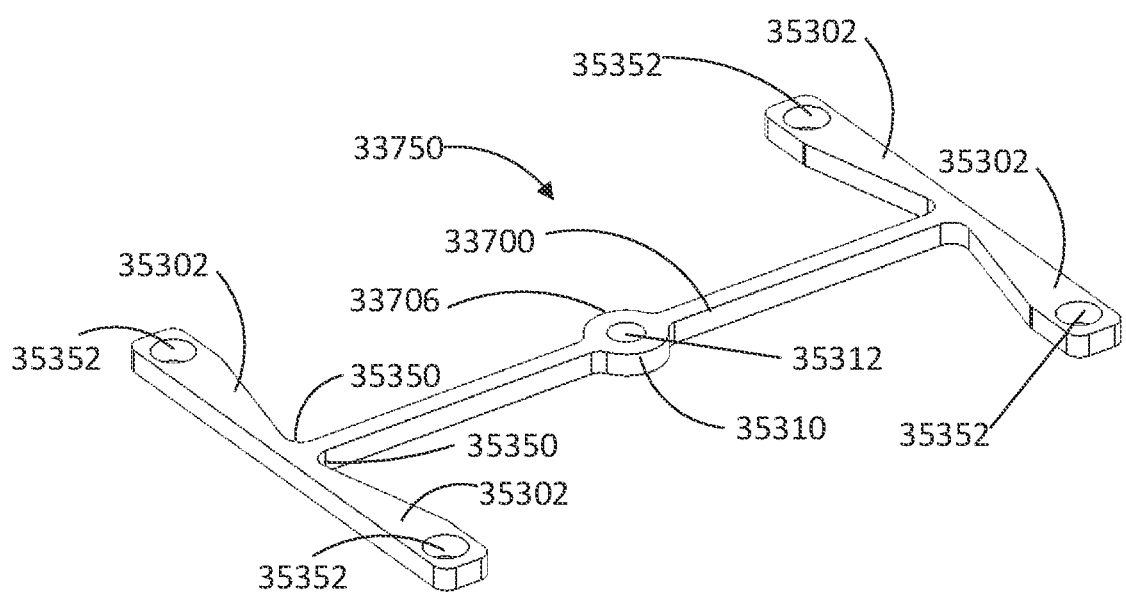
Figure 353C:
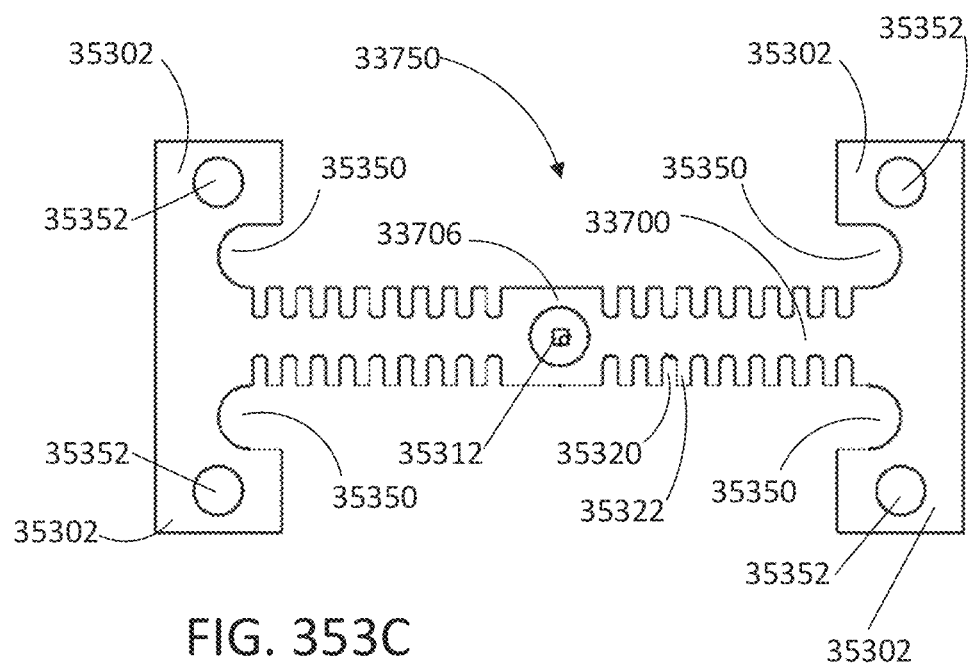
Figure 353D:
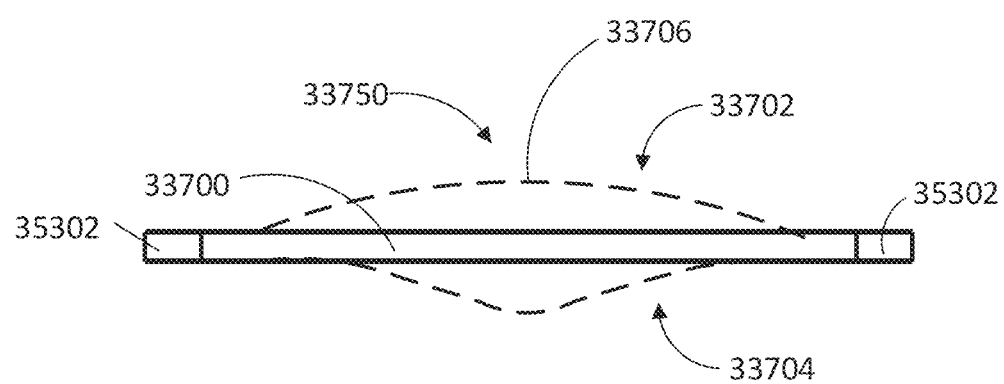

FIGS. 292A, 293A, and 294A show an example embodiment of a clasp for an implantable prosthetic device being deployed to engage with a leaflet of a native valve;

FIGS. 295-296 show an example embodiment of a clasp for an implantable prosthetic device;

FIGS. 297-299 show the clasp of FIGS. 295-296 being deployed to engage with a leaflet of a native valve;

FIGS. 300-301 show an example embodiment of a clasp for an implantable prosthetic device;

FIGS. 302-304 show the clasp of FIGS. 300-301 being deployed to engage with a leaflet of a native valve;

FIGS. 305-306 show an example embodiment of a clasp for an implantable prosthetic device;

FIG. 306A shows an example embodiment of a clasp for an implantable prosthetic device;

FIGS. 307-308 show an example embodiment of a clasp for an implantable prosthetic device;

FIGS. 309-311 show the clasp of FIGS. 307-308 being deployed to engage with a leaflet of a native valve;

FIGS. 309A, 310A, and 311A show an example embodiment of a clasp for an implantable prosthetic device being deployed to engage with a leaflet of a native valve;

FIGS. 312-313 show an example embodiment of a clasp for an implantable prosthetic device;

FIGS. 314-316 show the clasp of FIGS. 312-313 being deployed to engage with a leaflet of a native valve;

FIGS. 314A, 315A, and 316A show an example embodiment of a clasp for an implantable prosthetic device being deployed to engage with a leaflet of a native valve;

FIGS. 317-318 show an example embodiment of a clasp for an implantable prosthetic device;

FIGS. 319-321 show the clasp of FIGS. 317-318 being deployed to engage with a leaflet of a native valve;

FIGS. 319A, 320A, and 321A show an example embodiment of a clasp for an implantable prosthetic device being deployed to engage with a leaflet of a native valve;

FIGS. 322-323 show an example embodiment of a clasp for an implantable prosthetic device;

FIGS. 324-326 show the clasp of FIGS. 322-323 being deployed to engage with a leaflet of a native valve;

FIGS. 324A, 325A, and 326A show an example embodiment of a clasp for an implantable prosthetic device being deployed to engage with a leaflet of a native valve;

FIGS. 327-328 show an example embodiment of a clasp for an implantable prosthetic device;

FIGS. 329-331 show the clasp of FIGS. 327-328 being deployed to engage with a leaflet of a native valve;

FIGS. 332-333 show an example embodiment of a clasp for an implantable prosthetic device;

FIGS. 334-336 show the clasp of FIGS. 332-333 being deployed to engage with a leaflet of a native valve;

FIG. 337 is a schematic illustration of a beam that exhibits snap-through buckling;

FIG. 338 is a graph of load versus displacement of a beam that exhibits snap-through buckling;

FIG. 339 is a profile view of an example embodiment of a clasp for an implantable prosthetic device;

FIG. 340 is a bottom view of the clasp of FIG. 339;

FIG. 341 is a side view of the clasp of FIG. 339;

FIG. 342 illustrates first and second stable states of a snap-through indicator of the clasp of FIG. 339;

FIGS. 343-345 show the clasp of FIGS. 339-342 being deployed to engage with a leaflet of a native valve;

FIG. 346 is a profile view of an example embodiment of a clasp for an implantable prosthetic device;

FIG. 347 is a bottom view of the clasp of FIG. 346;

FIG. 348 is a side view of the clasp of FIG. 346;

FIG. 349 illustrates first and second stable states of a snap-through indicator of the clasp of FIG. 346;

FIGS. 350-352 show the clasp of FIGS. 346-349 being deployed to engage with a leaflet of a native valve;

FIG. 353A illustrates an example embodiment of a flat part useable to make a snap-through indicator;

FIG. 353B illustrates an example embodiment of a flat part useable to make a snap-through indicator;

FIG. 353C illustrates an example embodiment of a flat part useable to make a snap-through indicator; and FIG. 353D illustrates bending of the flat parts of FIGS. 353A-353C to make snap-through indicators and the two stable states of the snap-through indicators.

DETAILED DESCRIPTION

As described herein, when one or more components are described as being connected, joined, affixed, coupled, attached, or otherwise interconnected, such interconnection may be direct as between the components or may be indirect such as through the use of one or more intermediary components. Also, as described herein, reference to a "member," "component," or "portion" shall not be limited to a single structural member, component, or element but can include an assembly of components, members, or elements. Also, as described herein, the terms "substantially" and "about" are defined as at least close to (and includes) a given value or state (preferably within 10% of, more preferably within 1% of, and most preferably within 0.1% of).

A prosthetic device can have a wide variety of different forms. For example, the prosthetic device can have any of the configurations disclosed by PCT Patent Application No. PCT/US2019/055320, filed Oct. 9, 2019 and U.S. Provisional Patent Application Ser. No. 62/744,031, filed on Oct. 10, 2018, which are incorporated herein by reference in their entirety for all purposes. A prosthetic device can have an optional coaptation means or coaption element and at least one anchoring means or anchor. The coaption element is configured to be positioned within the native heart valve orifice to help fill the space between the leaflets and form a more effective seal between the native leaflets, thereby reducing or preventing regurgitation. The coaption element can have a structure that is impervious or resistant to blood and that allows the native leaflets to close around the coaption element during ventricular systole to block blood from flowing from the left or right ventricle back into the left or right atrium, respectively. The prosthetic device can be configured to seal against two or three native valve leaflets; that is, the device may be used in the native mitral (bicuspid) and tricuspid valves. The coaption element is sometimes referred to herein as a spacer because the coaption element can fill a space between improperly functioning native mitral or tricuspid leaflets that do not close completely.

The coaption element (e.g., spacer, coaptation element, etc.) can have various shapes. In some embodiments, the coaption element can have an elongated cylindrical shape having a round cross-sectional shape. In some embodiments, the coaption element can have an oval cross-sectional shape, a crescent cross-sectional shape, a rectangular cross-sectional shape, or various other non-cylindrical shapes. The coaption element can have an atrial portion positioned in or adjacent to the left atrium, a ventricular or lower portion positioned in or adjacent to the left ventricle, and a side surface that extends between the native leaflets. In embodiments configured for use in the tricuspid valve, the atrial or upper portion is positioned in or adjacent to the right atrium, and the ventricular or lower portion is positioned in or adjacent to the right ventricle, and the side surface that extends between the native tricuspid leaflets.

The anchor can be configured to secure the device to one or both of the native leaflets such that the coaption element is positioned between the two native leaflets. In embodiments configured for use in the tricuspid valve, the anchor is configured to secure the device to one, two, or three of the tricuspid leaflets such that the coaption element is positioned between the three native leaflets. In some embodiments, the anchor can attach to the coaption element at a location adjacent the ventricular portion of the coaption element. In some embodiments, the anchor can attach to an actuation element, such as a shaft or actuation wire, to which the coaption element is also attached.

The anchor of the implantable prosthetic device includes clasps to secure the native leaflet tissue between the anchor and the coaption element. Example clasps (e.g., barbed clasps, etc.) include a movable member or arm that is actuatable between open and closed positions relative to a fixed member or arm. The moveable arm is moved away from the fixed arm to form a gap or opening between the moveable and fixed arms for receiving a portion of the native leaflet tissue. Once the leaflet is captured within the gap, the moveable arm is actuated to pinch the leaflet tissue, thereby securing the leaflet within the clasp. Generally, positioning the leaflet further into the opening between the arms of the clasp before actuating the moveable arm to pinch the leaflet allows the moveable arm to engage more of the leaflet tissue. Not only is more of the tissue then engaged by the clasp, but any barbs or other securing members arranged at the distal ends of the moveable or fixed arms are positioned to engage thicker portions of the native leaflet tissue as the tissue is disposed further within the gap. Engaging more and thicker tissue with the clasps ensures a more secure grip on the native leaflet by the clasp.

Determining the depth of native leaflet engagement within the gap between the moveable and fixed arms is a challenge using current imaging technology. In particular, the leaflet tissue moves with each beat of the heart and may be translucent or be visually hard to distinguish from surrounding tissue. In contrast, the clasps (e.g., barbed clasps, etc.) formed from materials, such as metal, are easier to see with imaging devices. Therefore, a surgeon may look at the position and/or of the moveable arm of the clasp to determine whether the clasp has properly engaged the native leaflet. For example, the clasps can be configured so that the moveable arm bounces slightly with each beat of the heart to indicate that the leaflet is captured within the clasp.

Example implantable devices can include an indicator used to determine whether the native leaflet is sufficiently engaged by or within the clasp or barbed clasp during implantation of the implantable prosthetic device. The indicators are visible via imaging devices during implantation. The indicator shows the surgeon that the leaflet is inserted in the opening to a desired capture depth and/or that the leaflet has not reached the desired capture depth. The indicator may be actuatable between an undeployed or starting position and a plurality of actuated positions that are visually distinct so as to indicate to the surgeon whether or not the indicator has engaged the leaflet tissue, and/or the leaflet tissue has reached a desired position or engagement depth. Using an indicator allows the surgeon to look at the indicator and not to the bouncing of the moveable arm to determine that the leaflet is properly engaged. Thus, the pinching force of the clasps can be increased without reducing the ability of the surgeon to determine whether the leaflet is sufficiently engaged.

Referring now to FIGS. 1-6, an implantable prosthetic device 100 is shown in various stages of deployment. The device 100 and associated systems, methods, etc. are described in more detail in International Application Nos. PCT/US2018/028189 and PCT/US2019/055320, the disclosures of which are incorporated herein by reference in their entirety. The device 100 can include any other features for an implantable prosthetic device discussed in the present application, and the device 100 can be positioned to engage valve tissue (e.g., leaflets 20, 22) as part of any suitable valve repair system (e.g., any valve repair system disclosed in the present application).

The device 100 is deployed from a delivery sheath or other means for delivery and can include a coaptation portion or coaption portion 104 and/or an anchor portion 106. The device 100 can be deployed from a delivery sheath and/or can be deployed by a pusher tube or rod 81. In some embodiments, the coaptation portion or coaption portion 104 of the device 100 includes a coaption element 110 that is adapted to be implanted between the leaflets of a native valve (e.g., native mitral valve, native tricuspid valve, etc.) and is slidably attached to an actuation member or actuation element 112 (e.g., an actuation wire, shaft, tube, rod, line, suture, tether, etc.). The anchor portion 106 is actuatable between open and closed conditions and can take a wide variety of forms, such as, for example, paddles, gripping elements, or the like. Actuation of the actuation element or means for actuating 112 opens and closes the anchor portion 106 of the device 100 to grasp the native valve leaflets during implantation. The actuation element or other means for actuation 112 (as well as other actuation elements and means for actuation herein) can take a wide variety of different forms (e.g., as a wire, rod, shaft, tube, screw, suture, line, combination of these, etc.). As one example, the actuation element can be threaded such that rotation of the actuation element moves the anchor portion 106 relative to the coaption portion 104. Or, the actuation element can be unthreaded, such that pushing or pulling the actuation element 112 moves the anchor portion 106 relative to the coaption portion 104.

The anchor portion 106 and/or anchors of the device 100 include outer paddles 120 and inner paddles or gripping elements 122 that are, in some embodiments, connected between a cap 114 and the coaption element or means for coapting 110 by portions 124, 126, 128. The connection portions 124, 126, 128 can be jointed and/or flexible to move between all of the positions described below. The interconnection of the outer paddles 120, the inner paddles 122, the coaption element or means for coapting 110, and the cap 114 by the portions 124, 126, and 128 can constrain the device to the positions and movements illustrated herein.

In some implementations, the actuation member, actuation element, or other means for actuating 112 (e.g., actuation wire, actuation shaft, actuation tube, actuation rod, etc.) extends through the delivery sheath, the pusher tube/rod, and/or a coaption element 110 to the cap 114, e.g., at the distal connection of the anchor portion 106. Extending and retracting the actuation element 112 increases and decreases the spacing between a proximal end of the device and the cap 114 and/or between a coaption element 110 and the cap 114. An optional attaching means or collar (not shown) removably attaches the device and/or a coaption element 110 of the device to the pusher tube or rod 81 and/or delivery sheath 102 so that the actuation element 112 slides along the actuation element 112 during actuation to open and close the paddles 120, 122 of the anchor portion 106. After the device 100 is connected to valve tissue, if the device 100 needs to be removed from the valve tissue, a retrieval device can be used to connect to the collar 115 such that the actuation element can extend through the collar 115 and any coaption element 110 to engage the anchor portion 106 to open the paddles 120, 122 and remove the device 100 from the valve tissue. Examples of retrieval devices that could be used are shown in PCT Application No. PCT/US2019/062391 filed Nov. 20, 2019, which is incorporated herein by reference in its entirety.

Figure 3:
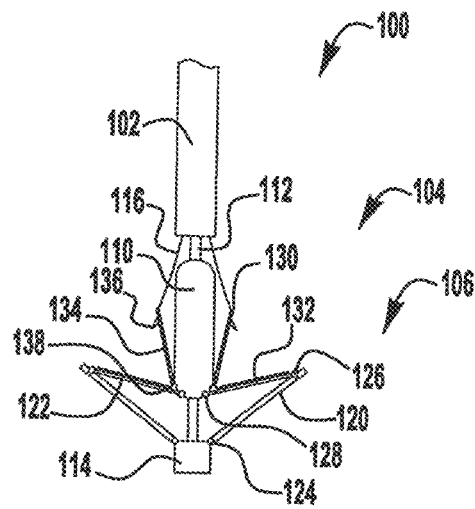

Referring to FIG. 3, the anchor portion and/or anchors include attachment portions for gripping members. The illustrated gripping members comprise clasps 130 that include a base or fixed arm 132, a moveable arm 134, optional barbs or other means for securing 136, and a joint, flex, or hinge portion 138. The fixed arms 132 are attached to the inner paddles 122. In some embodiments, the fixed arms 132 are attached to the inner paddles 122 with the joint, flex, hinge portion 138. disposed proximate a coaption element 110. The clasps or barbed clasps can have flat surfaces and do not fit in a recess of the inner paddle, but are disposed against the surface of the inner paddle 122. The joint, flex, or hinge portion 138 provides a spring force between the fixed and moveable arms 132, 134 of the clasp 130. The joint, flex, or hinge portion 138 can be any suitable flexible portion, joint, or hinge, such as a flexible hinge, a flexible joint, a spring hinge, a pivot hinge, etc. In some embodiments, the joint, flex, or hinge portion 138 is a flexible piece of material integrally formed with the fixed and moveable arms 132, 134. The fixed arms 132 are attached to the inner paddles 122 and remain stationary relative to the inner paddles 122 when the moveable arms 134 are opened to open the clasps 130 and expose the barbs, friction-enhancing elements, or other means for securing 136. In some embodiments, the clasps 130 are opened by applying tension to actuation lines 116 attached to the movable arms or ends of the moveable arms 134, thereby causing the moveable arms 134 to move, flex, and/or pivot on the joint, flex, or hinge portions 138.

During implantation, the paddles 120, 122 can be opened and closed, for example, to grasp or capture the native leaflets (e.g., native mitral valve leaflets, etc.) between the paddles 120, 122 and/or between the paddles 120, 122 and a coaption element or means for coapting 110. The clasps 130 can be used to grasp and/or further secure the native leaflets by engaging the leaflets with barbs, friction-enhancing elements, or means for securing 136 and pinching the leaflets between the moveable and fixed arms 134, 132. The barbs, friction-enhancing elements, or other means for securing 136 of the clasps or barbed clasps 130 increase friction with the leaflets or may partially or completely puncture the leaflets. The actuation lines 116 can be actuated independently so that each clasp 130 can be opened and closed independently. Independent operation allows one leaflet to be grasped or captured at a time, or for the repositioning of a clasp 130 on a leaflet that was insufficiently grasped or captured, without altering a successful grasp on the other leaflet. The clasps 130 not only open and close independent from each other, but they can be opened and closed independent from the position of the inner paddle 122 thereby allowing leaflets to be grasped or captured in a variety of positions as the particular situation requires.

The clasps 130 can be opened independently/separately by pulling on an attached actuation line/suture or other actuation means 116 that extends through the delivery sheath or means for delivery 102 to the clasp 130. The actuation line 116 can take a wide variety of forms, such as, for example, a line, a suture, a wire, a rod, a catheter, or the like. The clasps 130 can be spring loaded or otherwise biased so that in the closed position the clasps 130 continue to provide a pinching force on the grasped or captured native leaflet. This pinching force remains constant regardless of the position of the inner paddles 122. Barbs, friction-enhancing elements, or other means for securing 136 of the clasps or barbed clasps 130 can pierce the native leaflets to further secure the leaflets.

Figure 1:
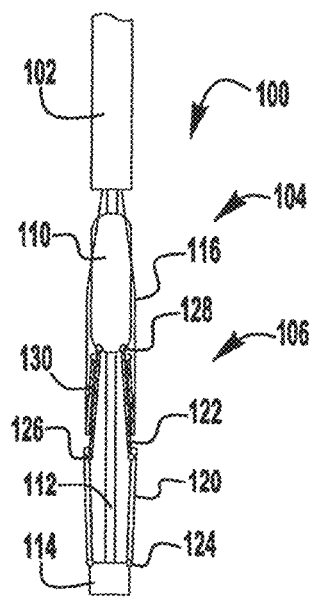
FIGS. 1, 1A, and 2-6 show an implantable prosthetic device, in various stages of deployment.

Referring now to FIG. 1, the device 100 is shown in an elongated or fully-open condition (also called fully-extended or full-bailout condition) for deployment from the delivery sheath. The device 100 is loaded in the delivery sheath in the fully open position, because the fully open position takes up the least space and allows the smallest catheter to be used (or the largest device 100 to be used for a given catheter size).

In some embodiments, the elongated condition the cap 114 is spaced apart from the coaption element or means for coapting 110 such that the paddles 120, 122 of the anchor portion 106 are fully open or extended. In some embodiments, an angle formed between the interior of the outer and inner paddles 120, 122 is approximately 180 degrees. The clasps 130 are kept in a closed condition during deployment through the delivery sheath or means for delivery 102 so that the barbs, friction-enhancing elements, or other means for securing 136 (FIG. 3) do not catch or damage the sheath or tissue in the patient's heart.

Figure 1A:
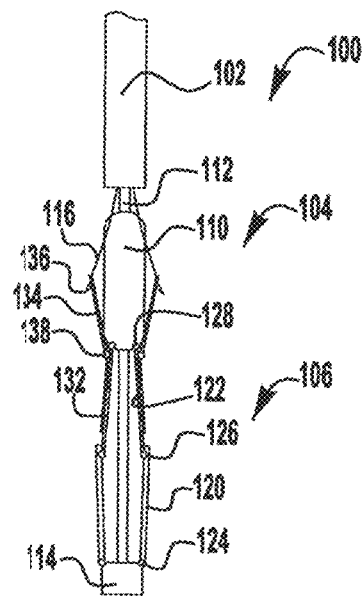

Referring now to FIG. 1A, the device 100 is shown in an elongated detangling condition, similar to FIG. 1, but with the clasps 130 in a fully open position, ranging from about 140 degrees to about 200 degrees, to about 170 degrees to about 190 degrees, or about 180 degrees between fixed and moveable portions of the clasps 130. Fully opening the paddles 120, 122 and the clasps 130 has been found to improve ease of detanglement or detachment from anatomy of the patient, such as the chordae tendineae, during implantation of the device 100.

Figure 2:
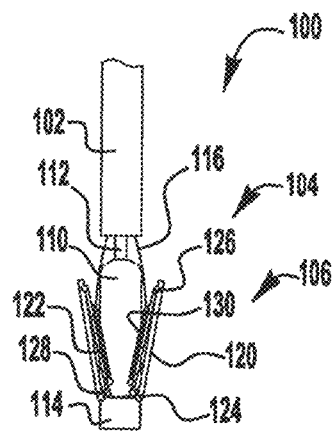

Referring now to FIG. 2, the device 100 is shown in a shortened or fully closed condition. The compact size of the device 100 in the shortened condition allows for easier maneuvering and placement within the heart. To move the device 100 from the elongated condition to the shortened condition, the actuation member or actuation element or other means for actuating 112 is retracted to pull the cap 114 towards a proximal end of the device and/or towards a coaption element 110. The connection portion(s) 126 (e.g., joint(s), hinge(s), flexible connection(s), etc.) between the outer paddle 120 and inner paddle 122 are limited or constrained in movement such that compression forces acting on the outer paddle 120 from the cap 114 being retracted towards the proximal end of the device and/or toward the coaption element 110 cause the paddles or gripping elements 120, 122 to move radially outward. During movement from the open to closed position, the outer paddles 120 maintain an acute angle with the actuation element 112. The outer paddles 120 can optionally be biased toward a closed position. The inner paddles 122 during the same motion move through a considerably larger angle as they are oriented away from the proximal end of the device and/or the coaption element 110 in the open condition and collapse toward the middle of the device in the closed condition (e.g., collapse along the sides of the coaption element 11). In some embodiments, the inner paddles 122 are thinner and/or narrower than the outer paddles 120, and the connection portions 126, 128 (e.g., joints, hinges, flexible connections, etc.) connected to the inner paddles 122 can be thinner and/or more flexible. For example, this increased flexibility can allow more movement than the connection portion 124 connecting the outer paddle 120 to the cap 114. In some embodiments, the outer paddles 120 are narrower than the inner paddles 122. The connection portions 126, 128 connected to the inner paddles 122 can be more flexible, for example, to allow more movement than the connection portion 124 connecting the outer paddle 120 to the cap 114. In some embodiments, the inner paddles 122 can be the same or substantially the same width as the outer paddles Referring now to FIGS. 3-5, the device 100 is shown in a partially open, grasp-ready condition. To transition from the fully closed to the partially open condition, the actuation member or actuation element 112 (e.g., actuation wire, actuation shaft, etc.) is extended to push the cap 114 away from the proximal end of the device (e.g., away from a coaption element 110), thereby pulling on the outer paddles 120, which in turn pull on the inner paddles 122, causing the anchors or anchor portion 106 to partially unfold. The actuation lines 116 are also retracted to open the clasps 130 so that the leaflets can be captured or grasped. In some embodiments, the pair of inner and outer paddles 122, 120 are moved in unison, rather than independently, by a single actuation element 112. Also, the positions of the clasps 130 may be dependent on the positions of the paddles 122, 120. For example, closing the paddles 122, 120 can also close the clasps. In some embodiments, the paddles 120, 122 can be independently controllable. For example, the device 100 can have two actuation elements and two independent caps, such that one independent wire and cap are used to control one paddle, and the other independent wire and cap are used to control the other paddle.

Figure 4:
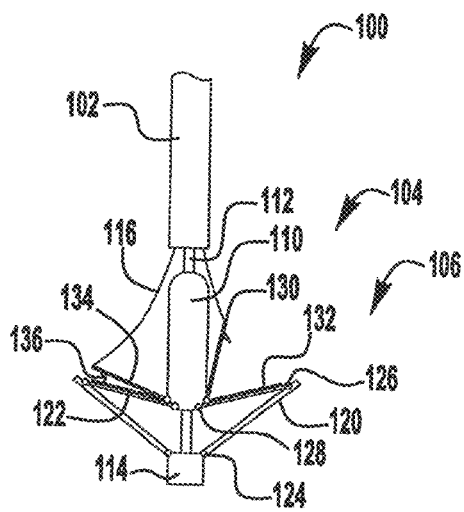
Figure 5:
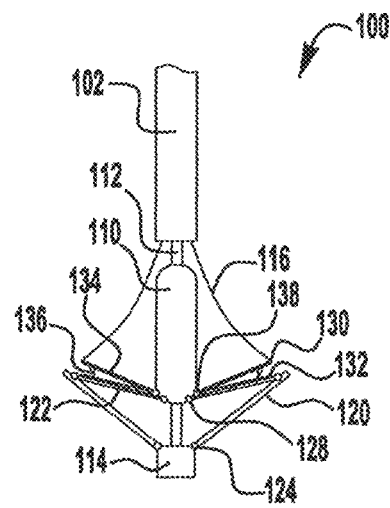

Referring now to FIG. 4, one of the actuation lines 116 is extended to allow one of the clasps 130 to close. Referring now to FIG. 5, the other actuation line 116 is extended to allow the other clasp 130 to close. Either or both of the actuation lines 116 can be repeatedly actuated to repeatedly open and close the clasps 130.

Figure 6:
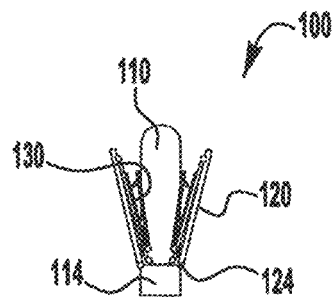

Referring now to FIG. 6, the device 100 is shown in a fully closed and deployed condition. The delivery sheath or means for delivery 102 and actuation element or means for actuating 112 is/are retracted and the paddles 120, 122 and clasps 130 remain in a fully closed position. Once deployed, the device 100 can be maintained in the fully closed position with a mechanical latch or can be biased to remain closed through the use of spring materials, such as steel, other metals, plastics, composites, etc. or shape-memory alloys such as Nitinol. For example, the connection portions 124, 126, 128, the joint portion(s) 138, and/or the inner and outer paddles 122, 120 and/or an additional biasing component (see reference number 224 in FIG. 13) can be formed of metals such as steel or shape-memory alloy, such as Nitinol—produced in a wire, sheet, tubing, or laser sintered powder—and are biased to hold the outer paddles 120 closed around the a center of the device or around a coaption element 110 and the clasps 130 pinched around native leaflets. Similarly, the fixed and moveable arms 132, 134 of the clasps 130 are biased to pinch the leaflets. In some embodiments, the attachment or connection portions 124, 126, 128, joint portion(s) 138, and/or the inner and outer paddles 122, 120 and/or an additional biasing component (see reference number 224 in FIG. 13) can be formed of any other suitably elastic material, such as a metal or polymer material, to maintain the device in the closed condition after implantation.

Figure 7:
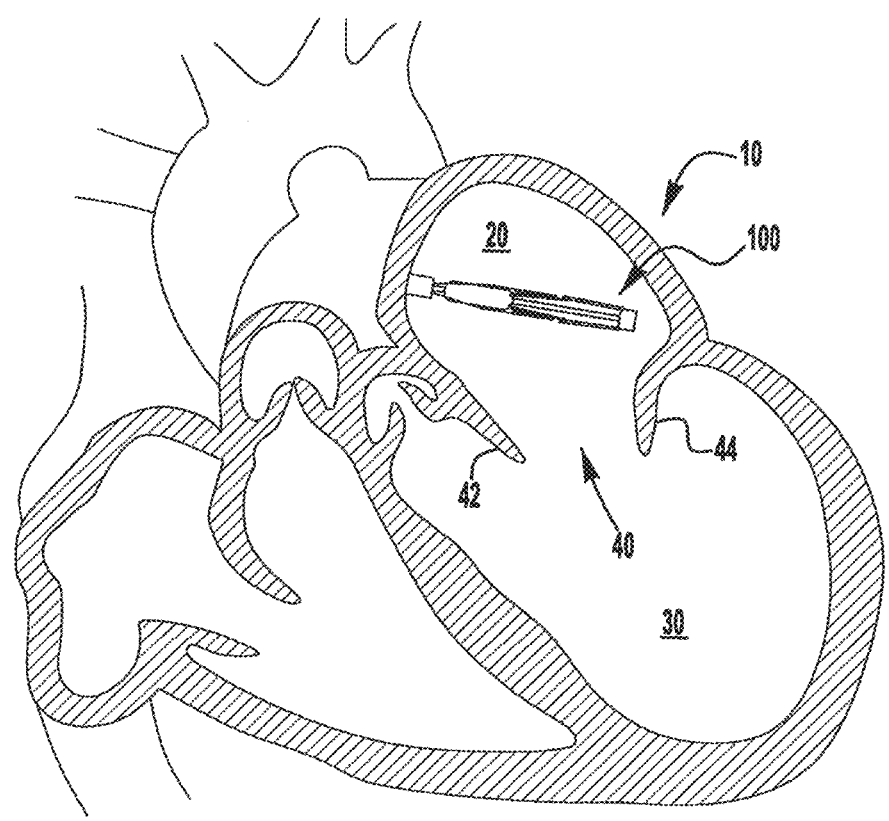
FIGS. 7-12 show the implantable prosthetic device of FIGS. 1-6 being delivered and implanted within a native mitral valve.
Figure 8:
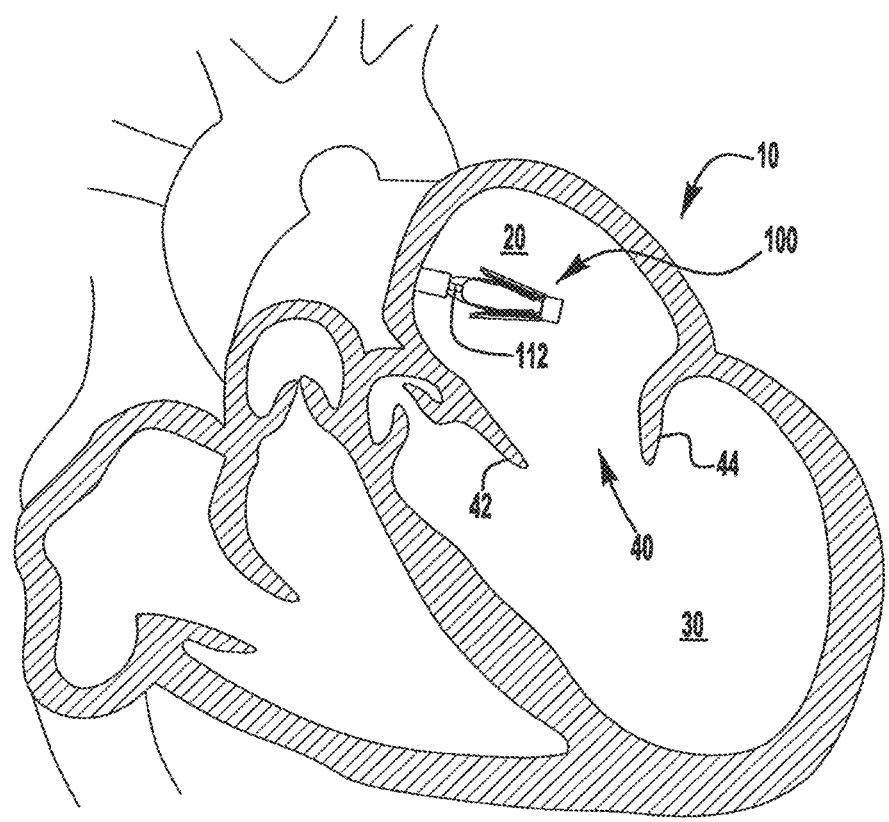
Figure 9:
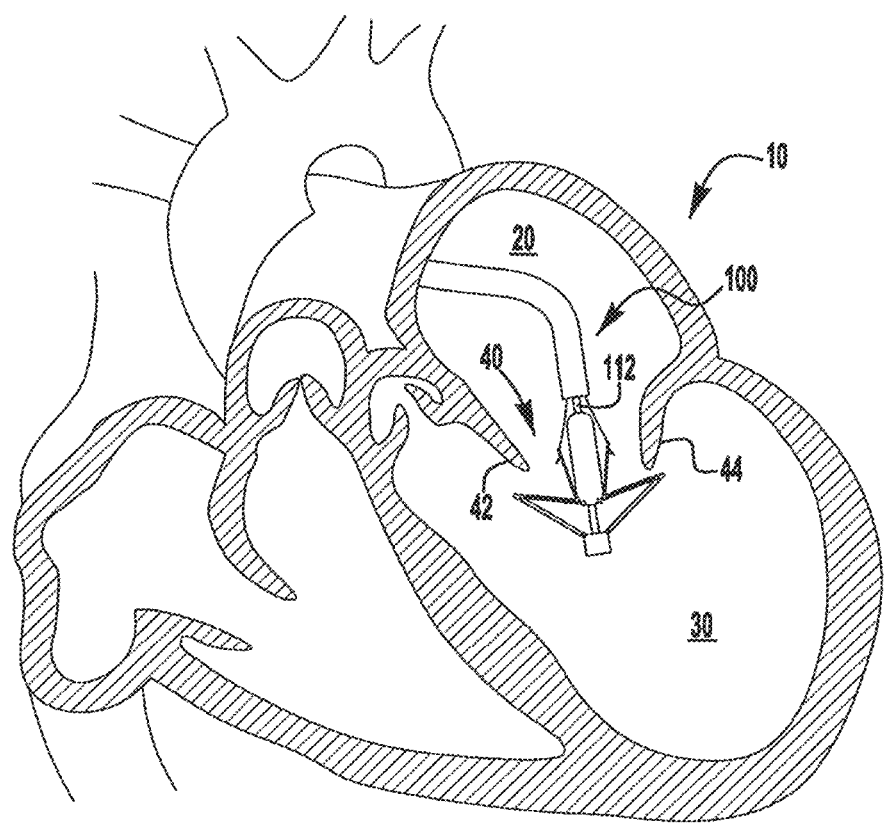
Figure 10:
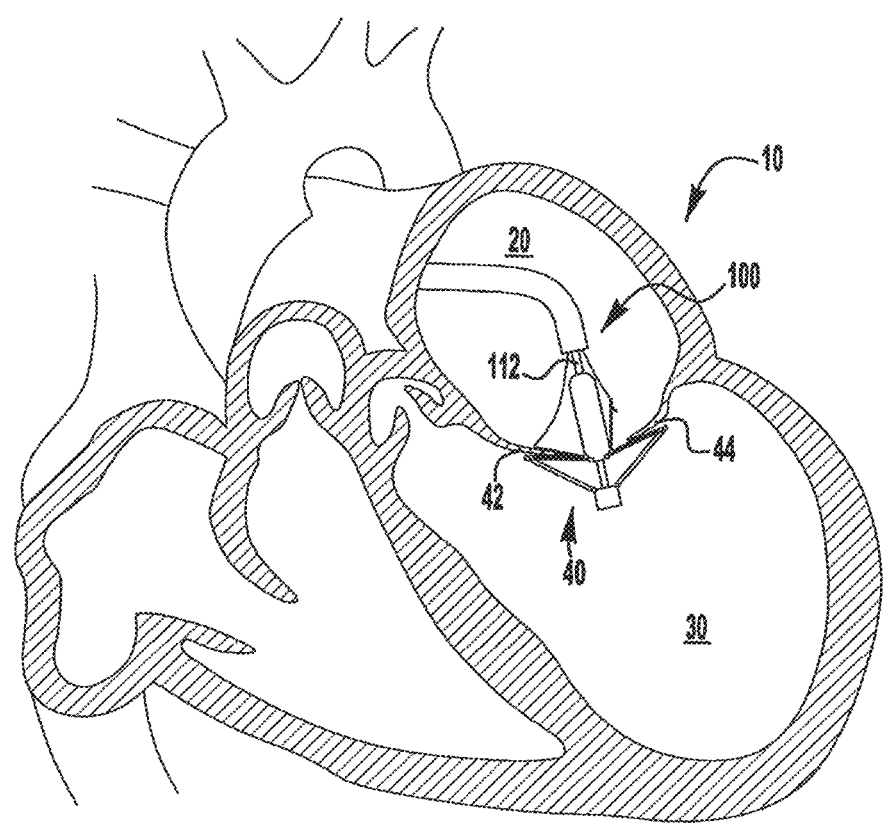
Figure 11:
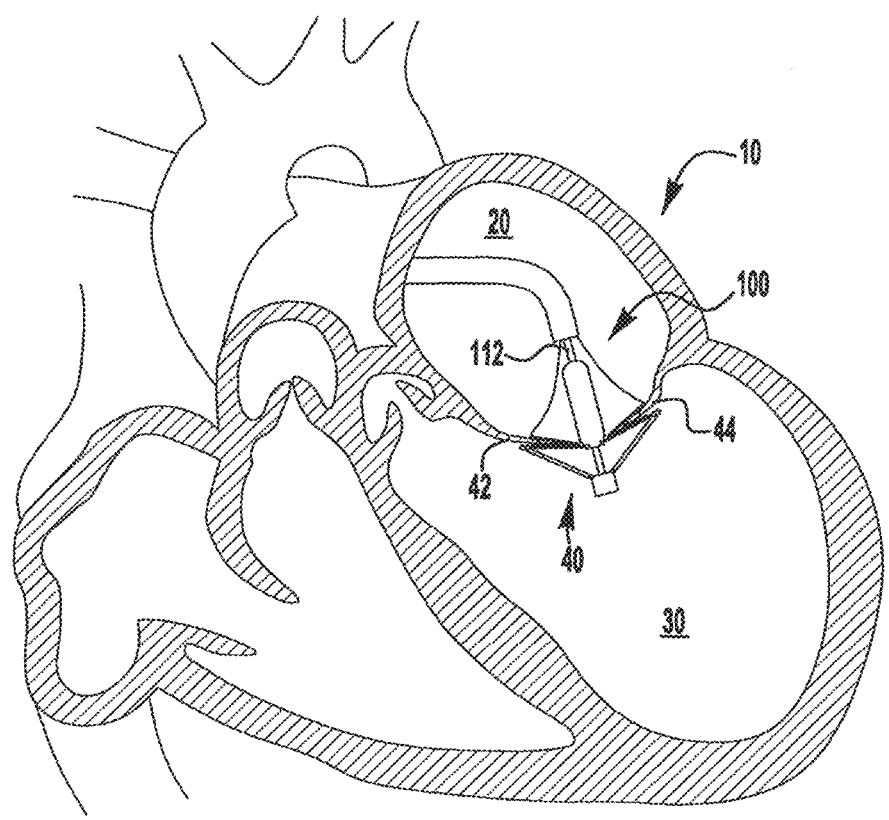
Figure 12:
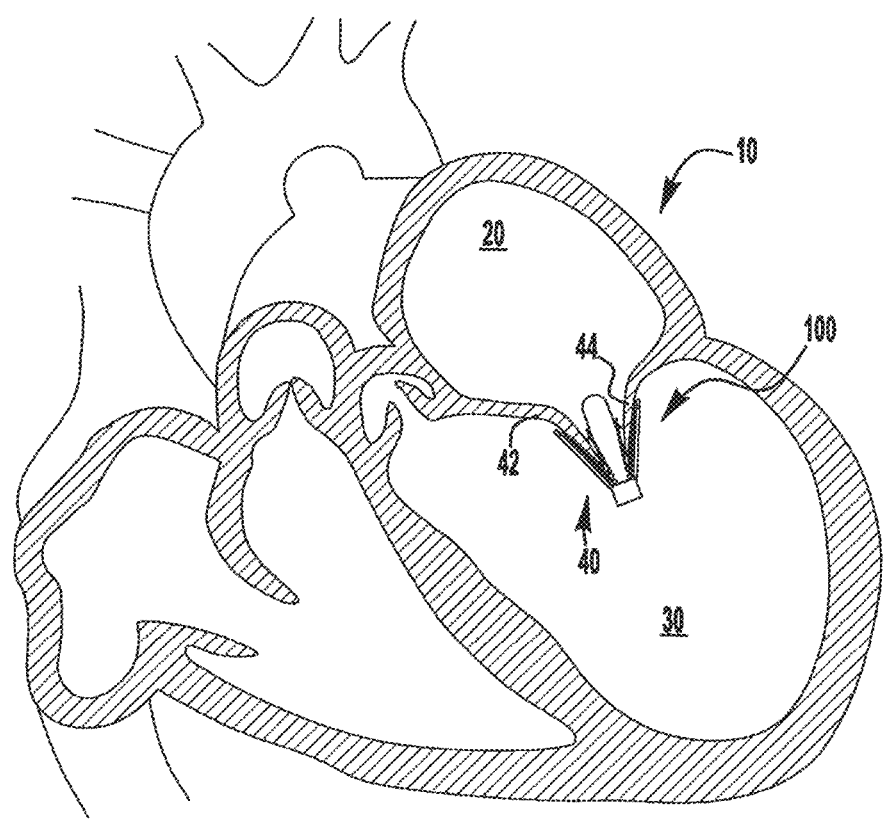

Referring now to FIGS. 7-12, the implantable device 100 of FIGS. 1-6 is shown being delivered and implanted within a native valve or native mitral valve 40 of a heart 10. Referring now to FIG. 7, the delivery sheath is inserted into the left atrium 20 through the septum and the device 100 is deployed from the delivery sheath in the fully open condition. The actuation element 112 is then retracted to move the device 100 into the fully closed condition shown in FIG. 8. As can be seen in FIG. 9, the device 100 is moved into position within the mitral valve 40 into the ventricle 30 and partially opened so that the leaflets 42, 44 can be captured. Referring now to FIG. 10, an actuation line 116 is extended to close one of the clasps 130, capturing a leaflet 42. FIG. 11 shows the other actuation line 116 being then extended to close the other clasp 130, capturing the remaining leaflet 44. Lastly, as can be seen in FIG. 12, the delivery sheath 102 and actuation element 112 are then retracted and the device 100 is fully closed and deployed in the native mitral valve 400.

Figure 13:
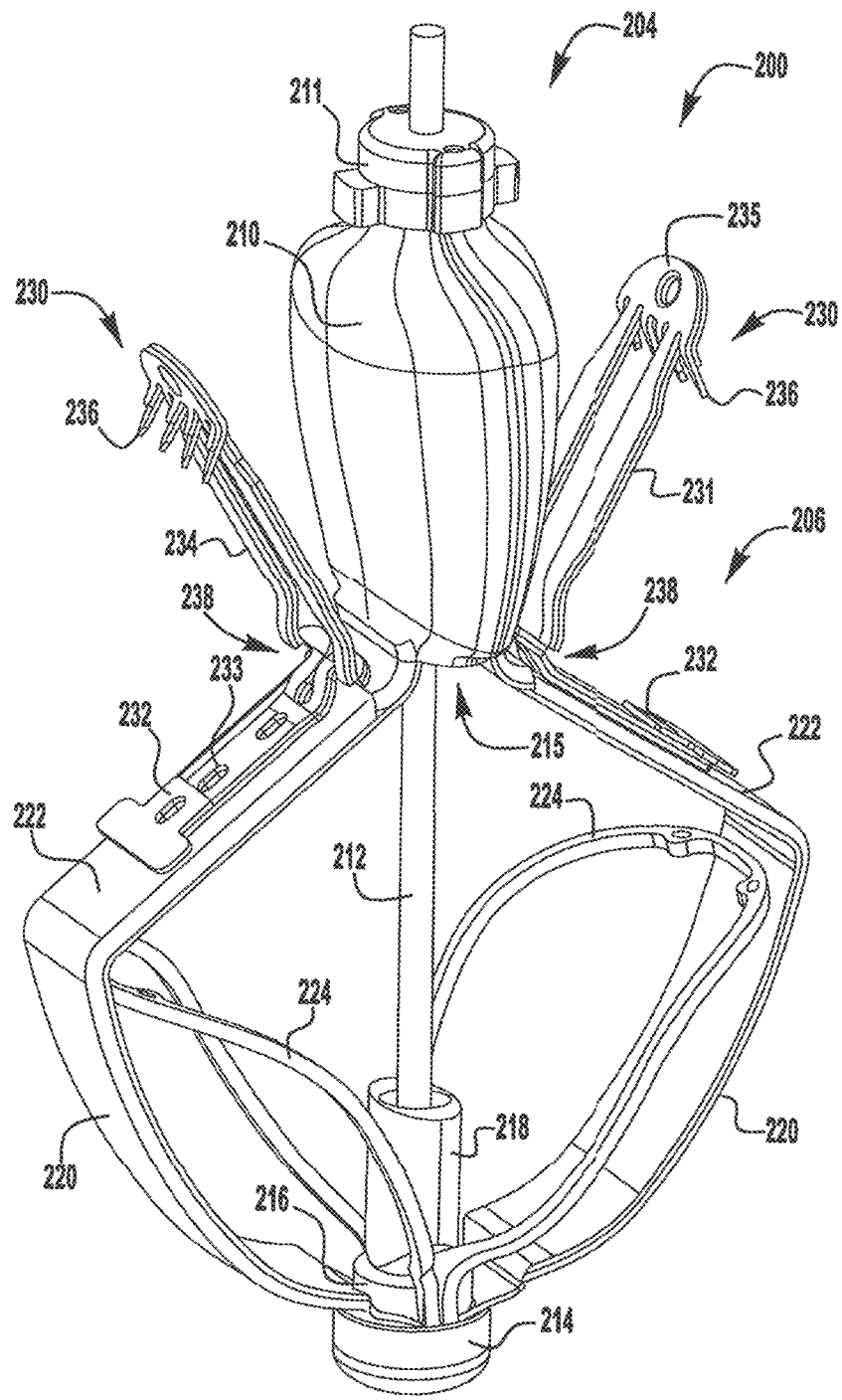
FIGS. 13-13A show an implantable prosthetic device.
Figure 13A:
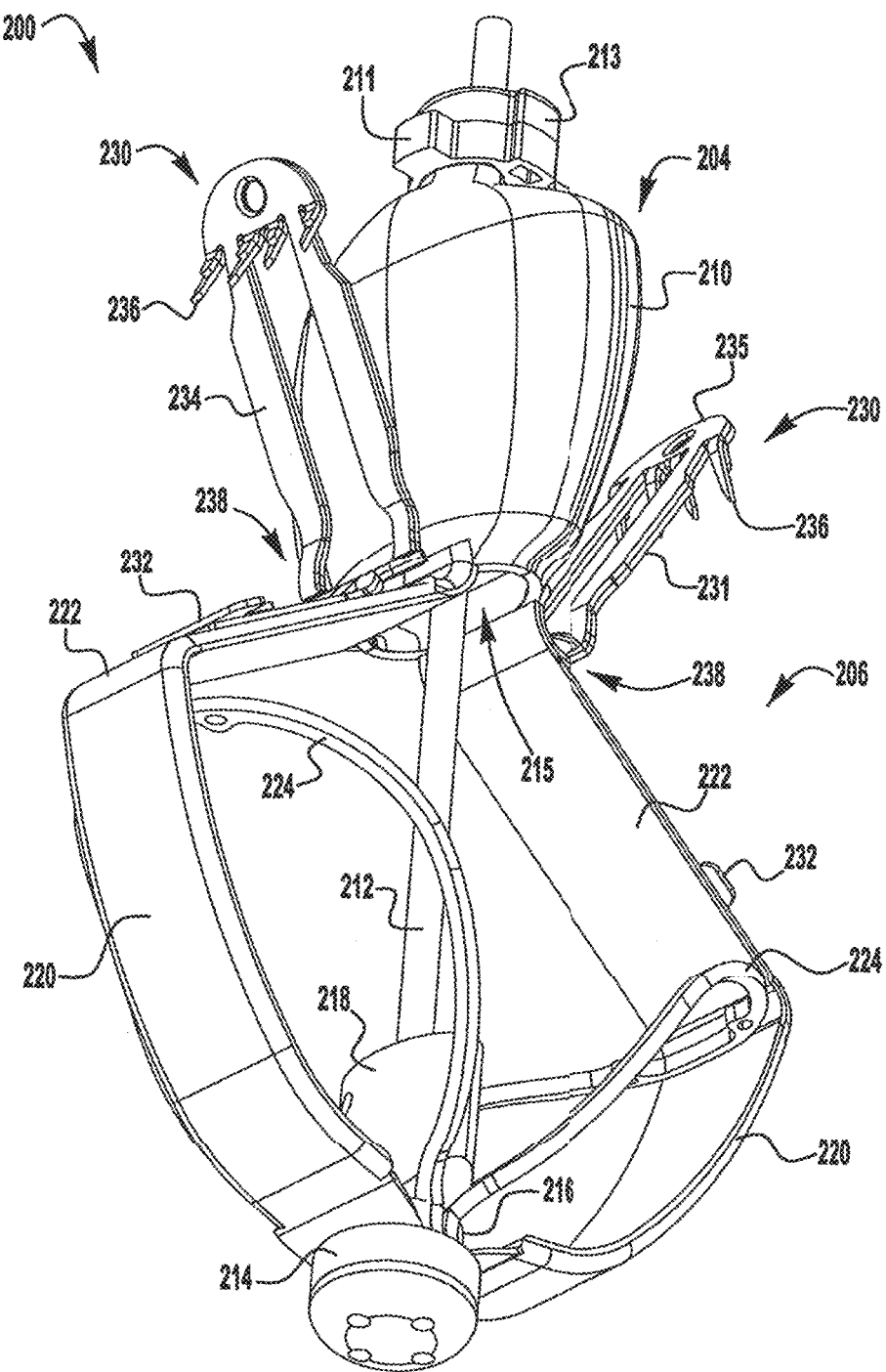

Referring now to FIG. 13, an implantable prosthetic device 200 is shown. The implantable device 200 is one of the many different configurations that the device 100 that is schematically illustrated in FIGS. 1-12 can take. The device 200 is deployed from a delivery sheath (not shown). The device 200 can include a coaption portion 204 and/or an anchor portion 206. The device 200 is loaded in the delivery sheath in the fully open position, because the fully open position takes up the least space and allows the smallest catheter to be used (or the largest device 200 to be used for a given catheter size).

In some embodiments, the coaption portion 204 of the device includes a coaption element 210 for implantation between native leaflets of a native valve that is slidably attached to an actuation element 212 (e.g., actuation wire, rod, shaft, tube, screw, suture, line, combination of these, etc.). The anchors of the device can include outer paddle portions and inner paddle portions. Actuation of the actuation element 212 opens and closes the anchor portion 206 of the device 200 to grasp or capture the native valve leaflets during implantation.

The anchor portion 206 of the device 200 includes outer paddles 220 and inner paddles 222 that are jointedly, flexibly, or hingeably connected to the cap 214 and/or the coaption element 210. The actuation element 212 extends through one, some, or all of the delivery sheath (not shown), a collar 211, and a coaption element 210, and extends to the cap 214 at the distal end of the anchor portion 206. In some embodiments, extending and retracting the actuation element 212 increases and decreases the spacing between the coaption element 210 and the cap 214, respectively.

The collar 211 optionally includes a collar seal 213 that forms a seal around the actuation element 212 during implantation of the device 200, and that seals shut when the actuation element 212 is removed to close or substantially close the device 200 to blood flow through the interior of the coaption element 210 after implantation. In some embodiments, the collar 2011 removably engages and attaches the coaption element 210 to the delivery sheath so that the coaption element 210 slides along the actuation element 212 during actuation to open and close the paddles 220, 222 of the anchor portion 206. In some embodiments, the collar 2011 is held closed around the coaption element 2010 by the actuation element 212, such that removal of the actuation element 212 allows fingers (not shown) of the collar to open, releasing the coaption element 210. In some embodiments, the cap 2014 optionally includes a seal 216 and/or an insert 218 that fit inside an opening 215 of the coaption element 210, the coaption element 210 having a hollow interior. The seal 216 and/or insert 218 maintain the coaption element 210 closed or substantially closed to blood flow when the actuation element 212 is withdrawn and the device 200 is implanted.

The coaption element 210 and/or paddles 220, 222 can comprise and/or be formed from a covering that can be a mesh, woven, braided, or formed in any other suitable way. The covering can be cloth, shape-memory alloy wire—such as Nitinol—to provide shape setting capability, or any other flexible material suitable for implantation in the human body. In some embodiments, paddle frames 224 provide pinching force between the inner paddles 222 and the coaption element 210 and assist in wrapping the leaflets around the sides of the coaption element 210 for a better seal between the coaption element 210 and the leaflets. In some embodiments, the covering extends around the paddle frames 224.

The clasps 230 include a base or fixed arm 232, a moveable arm 234, friction-enhancing elements or barbs 236, and a flex or hinge portion 238. The fixed arms 232 are attached to the inner paddles 222, with the flex or hinge portion 238 disposed proximate a center of the device and/or a coaption element 210. The fixed arms 232 are attached to the inner paddles 222 through holes or slots 233 with sutures (not shown). The fixed arms 232 can be attached to the inner paddles 222 or another portion of the device with any suitable means, such as screws or other fasteners, crimped sleeves, mechanical latches or snaps, welding, adhesive, or the like. The fixed arms 232 remain stationary or substantially stationary relative to the inner paddles 222 when the moveable arms 234 are opened to open the clasps 230 and expose the friction-enhancing elements or barbs 236. The clasps 230 are opened by applying tension to actuation lines (not shown) attached to holes 235 disposed at ends of the moveable arms 234, thereby causing the moveable arms 234 to move, flex, and/or pivot on the joint, flex, or hinge portions 238.

During implantation, the anchors and/or the paddles 220, 222 are opened and closed to capture the native mitral valve leaflets between the anchors and/or the paddles 220, 222 and/or between the anchors or paddles and a coaption element 210. In some embodiments, the clasps 230 (e.g., barbed clasps, etc.) further secure the native leaflets by engaging the leaflets with friction-enhancing elements or barbs 236 and pinching the leaflets between the moveable and fixed arms 234, 232. In some embodiments, friction-enhancing elements or barbs 236 of the clasps 230 increase friction with the leaflets or may partially or completely puncture the leaflets. The actuation lines can be actuated independently so that each clasp 230 can be opened and closed independently. Independent operation allows one leaflet to be grasped/captured at a time, or for the repositioning of a clasp 230 on a leaflet that was insufficiently captured, without altering a successful grasp on the other leaflet. The clasps 230 not only open and close independent from each other but can be fully opened and closed independent from the position of the inner paddle 222, thereby allowing leaflets to be captured in a variety of positions as the particular situation requires.

Referring now to FIGS. 14-23, 23A, and 22B, an implantable device 300 is shown being delivered and implanted within the native mitral valve 40 of the heart 10. The methods and steps shown and/or discussed can be performed on a living animal or on a simulation, such as on a cadaver, cadaver heart, simulator (e.g. with the body parts, heart, tissue, etc. being simulated), etc.

The device 300 can be the same as or similar to implantable device 200 of FIG. 13, though device 300 has a covering over the coaption element 310, clasps 330, inner paddles 322 and/or the outer paddles 320. The device 300 is deployed from a delivery sheath 302. The device can include a coaption portion 304 and/or an anchor portion 306 including a plurality of anchors (e.g., two in the illustrated embodiment, but can be more or less). In some embodiments, the coaption portion 304 of the device can include a coaption element 310 for implantation between the leaflets of a native valve. The coaption element 310 can be slidably attached to an actuation element 312 (actuation wire, actuation shaft, etc.). Actuation of the actuation element 312 opens and closes the anchor portion 306 of the device 300 to capture the native valve leaflets during implantation.

The anchor portion 306 of the device 300 includes outer paddles 320 and inner paddles 322 that are flexibly connected to the cap 314 and/or the coaption element 310. The actuation element 312 extends through one or more of a collar 303 (see FIG. 20), delivery sheath 302, and coaption element 310 to the cap 314 at the distal end of the anchor portion 306. Extending and retracting the actuation element 312 increases and decreases the spacing between the proximal end of the device and the cap 314 and/or between a coaption element 310 and the cap 314. In some embodiments, fingers of the collar 303 removably attach the coaption element 310 to the delivery sheath 302 so that the coaption element 310 slides along the actuation element 312 during actuation to open and close the paddles 320, 322 of the anchor portion 306. In some embodiments, the collar 303 is held closed around the coaption element 310 by the actuation element 312, such that removal of the actuation element 312 allows the fingers of the collar 303 to open, releasing the coaption element 310.

The coaption element 310 and/or paddles 320, 322 are formed from a flexible material that may be a mesh, woven, braided, or formed in any other suitable way. The flexible material can be cloth, shape-memory alloy wire—such as Nitinol—to provide shape setting capability, or any other flexible material suitable for implantation in the human body.

The clasps 330 (illustrated as barbed clasps) include a base or fixed arm 332, a moveable arm 334, and a connection portion or joint, flex, or hinge portion 338. The clasps can be configured as barbed clasps and include barbs 336 (see FIG. 20), or the clasps can include another type of friction-enhancing element, securing element, or means for securing. The fixed arms 332 are attached to the inner paddles 322, with the connection portion or joint, flex, or hinge portion 338. In some embodiments, the connection portion or joint, flex, or hinge portion 338 is disposed proximate a coaption element 310. In some embodiments, sutures (not shown) attach the fixed arms 332 to the inner paddles 322. Though the fixed arms 332 can be attached to the inner paddles 322 with any suitable means, such as screws or other fasteners, crimped sleeves, mechanical latches or snaps, welding, adhesive, or the like. The fixed arms 332 remain stationary or substantially stationary when the moveable arms 334 are opened to open the barbed clasps 330 and expose the barbs 336. The barbed clasps 330 are opened by applying tension to actuation lines 316 attached to the ends of the moveable arms 334, thereby causing the moveable arms 334 to move, flex, and/or pivot on the connection portions or joint, flex, or hinge portions 338.

During implantation, the paddles 320, 322 are opened and closed to capture the native valve leaflets between the paddles 320, 322 and/or between the paddles 320, 322 and a coaption element 310. In some embodiments, the outer paddles 320 have a wide curved shape that fits around the curved shape of the coaption element 310 to more securely grip the leaflets. The curved shape and rounded edges of the outer paddle 320 also prohibits tearing of the leaflet tissue. The clasps 330 can be barbed clasps that further secure the native leaflets by engaging the leaflets with barbs 336 and pinching the leaflets between the moveable and fixed arms 334, 332. The barbs 336 (and/or other friction-enhancing elements) of the clasps 330 increase friction with the leaflets or may partially or completely puncture the leaflets. The actuation lines can be actuated independently so that each clasp 330 can be opened and closed independently. Independent operation allows one leaflet to be captured at a time, or for the repositioning of a clasp 330 on a leaflet that was insufficiently captured, without altering a successful grasp on the other leaflet. The clasps 330 not only open and close independent from each other but can be fully opened and closed independent of the position of the inner paddle 322, thereby allowing leaflets to be grasped and/or captured in a variety of positions as the particular situation requires.

Figure 14:
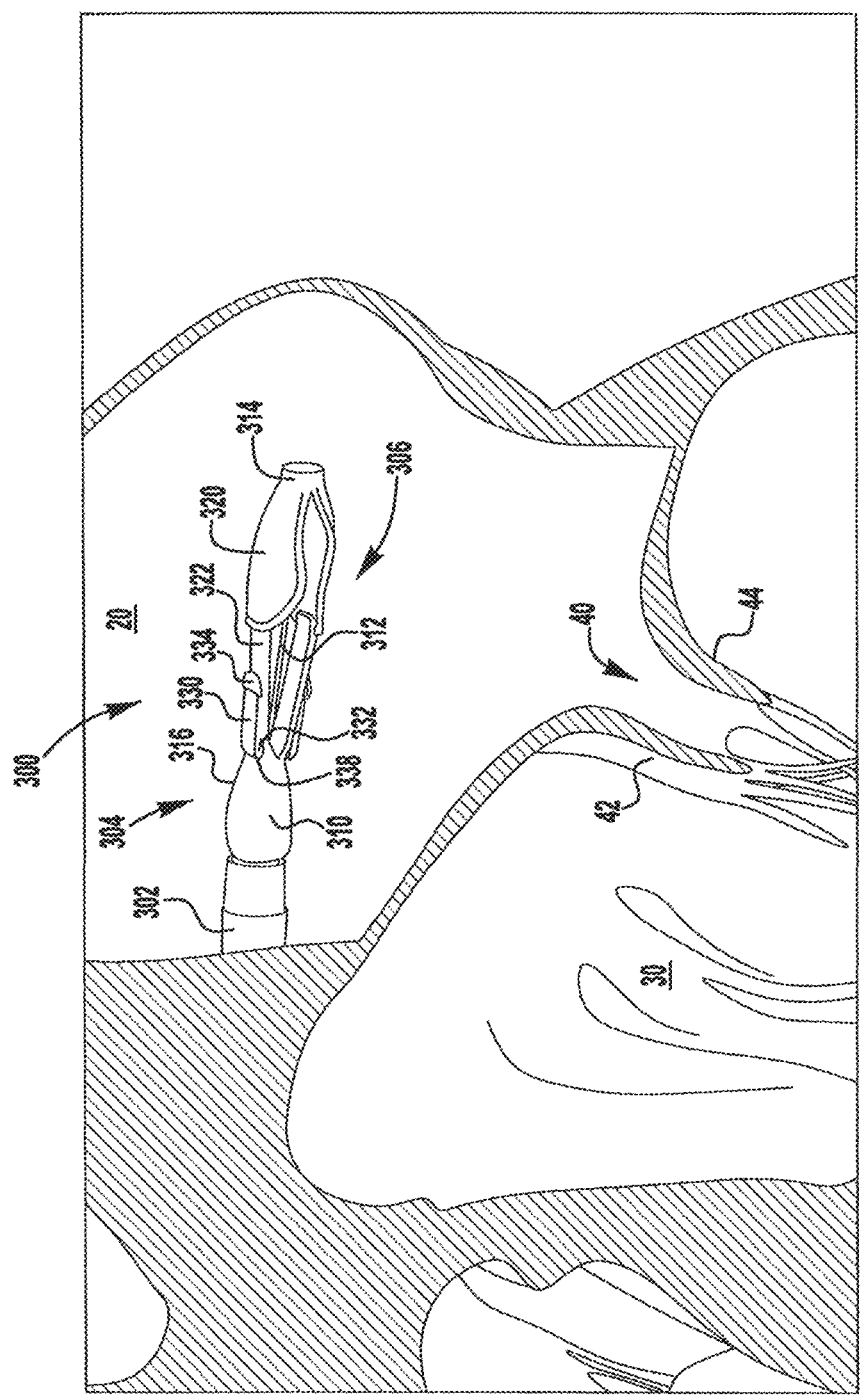
FIGS. 14-23, 23A, and 23B show an implantable prosthetic device being delivered and implanted within a native mitral valve.
Figure 15:
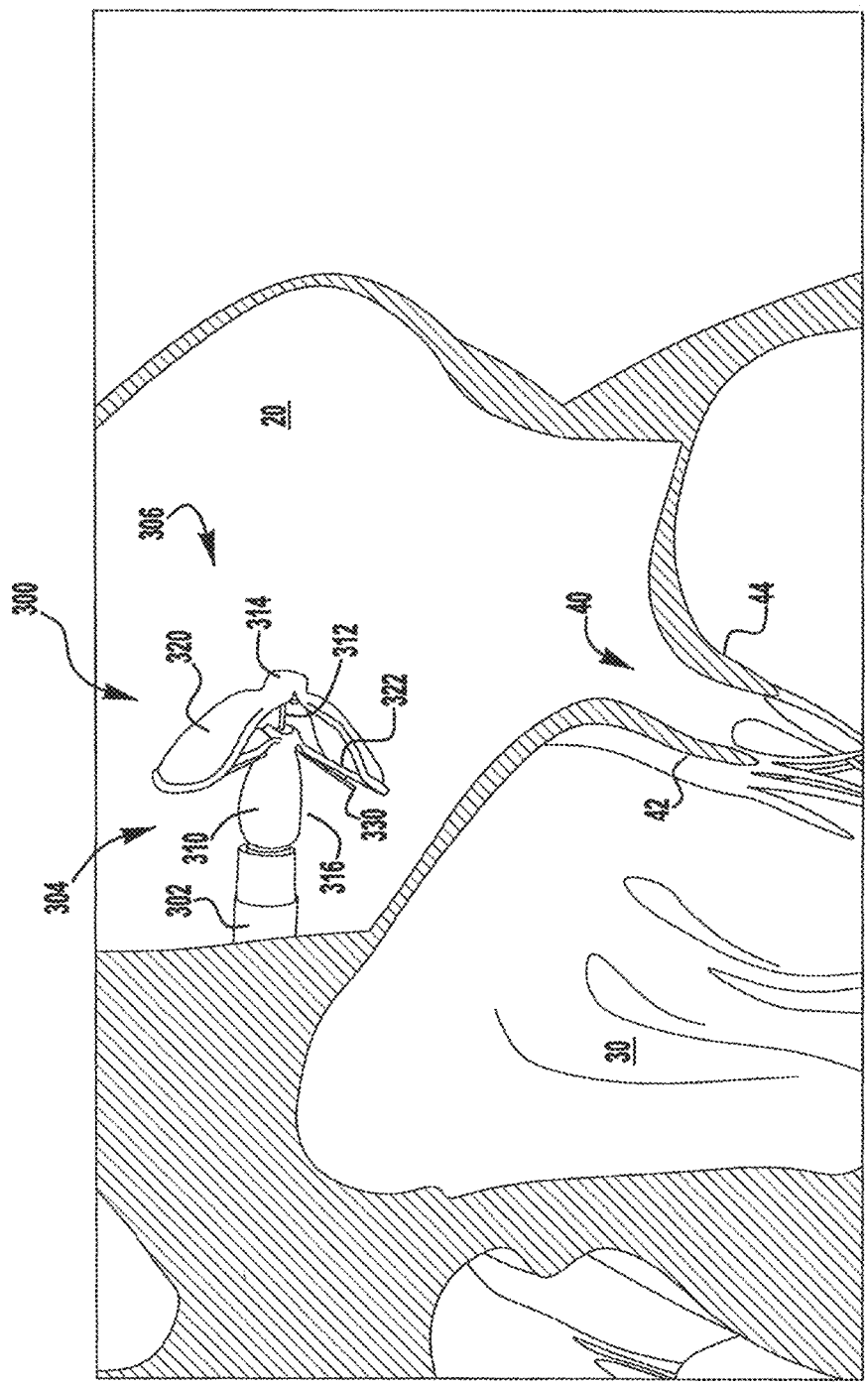
Figure 16:
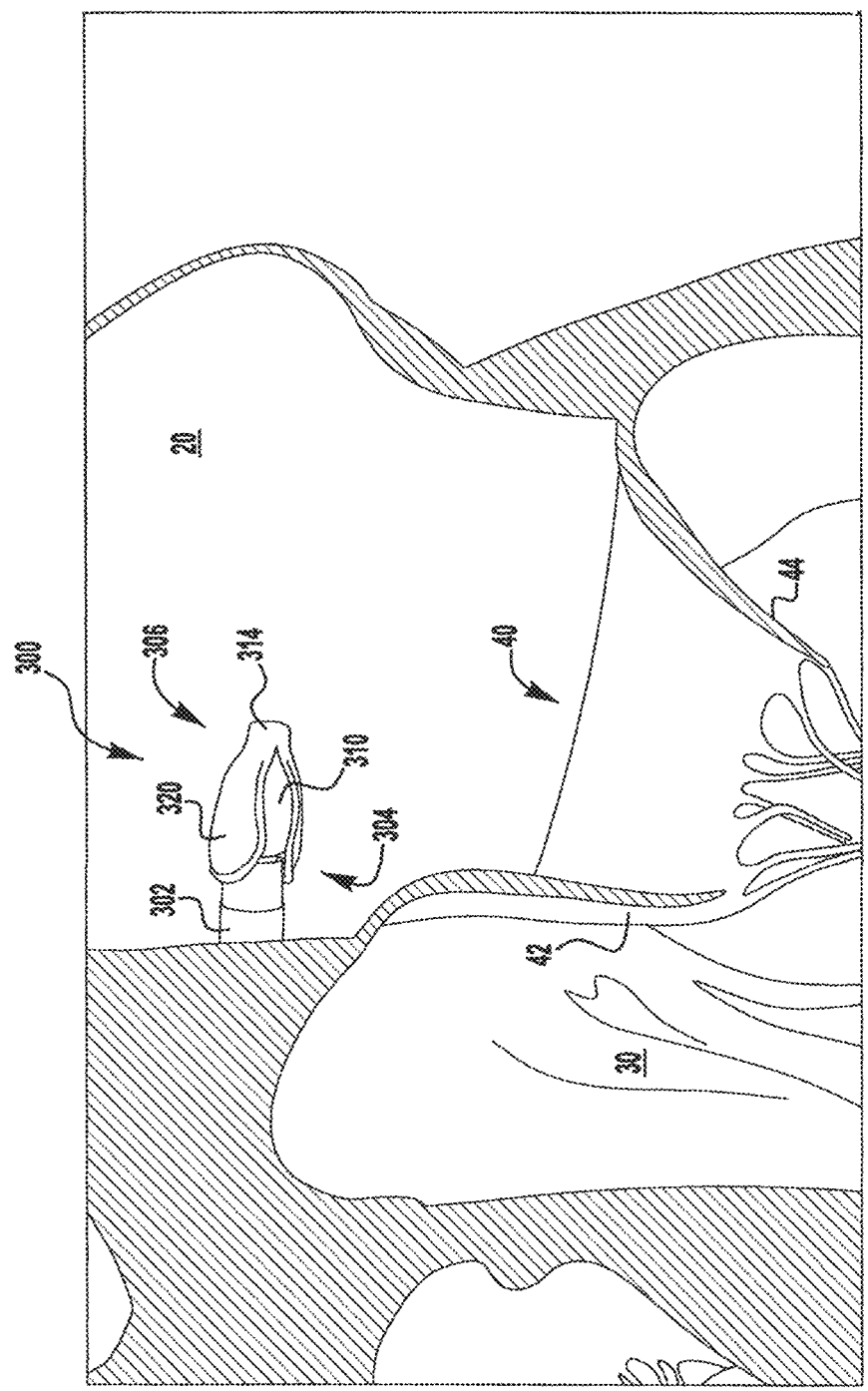
Figure 17:
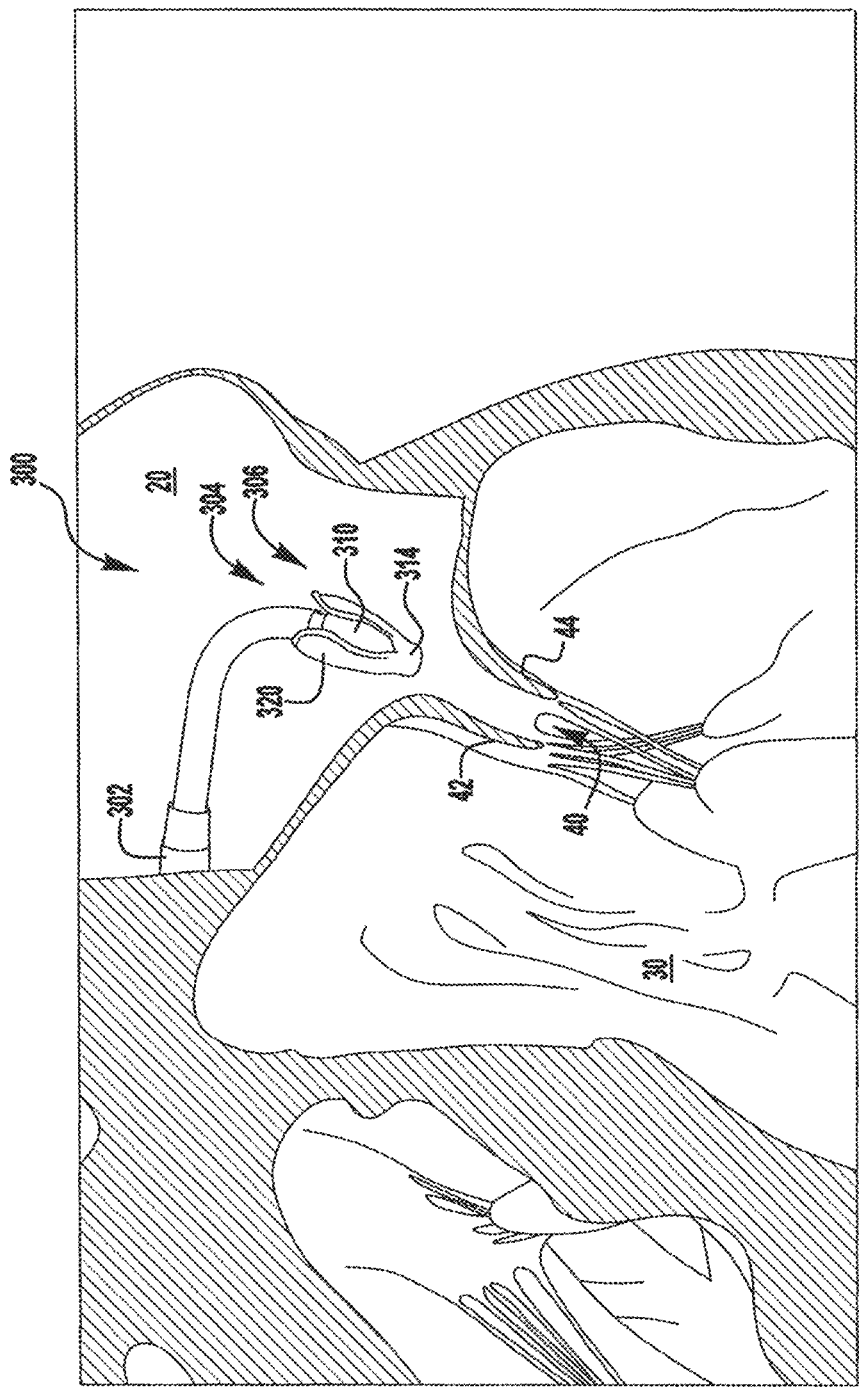
Figure 18:
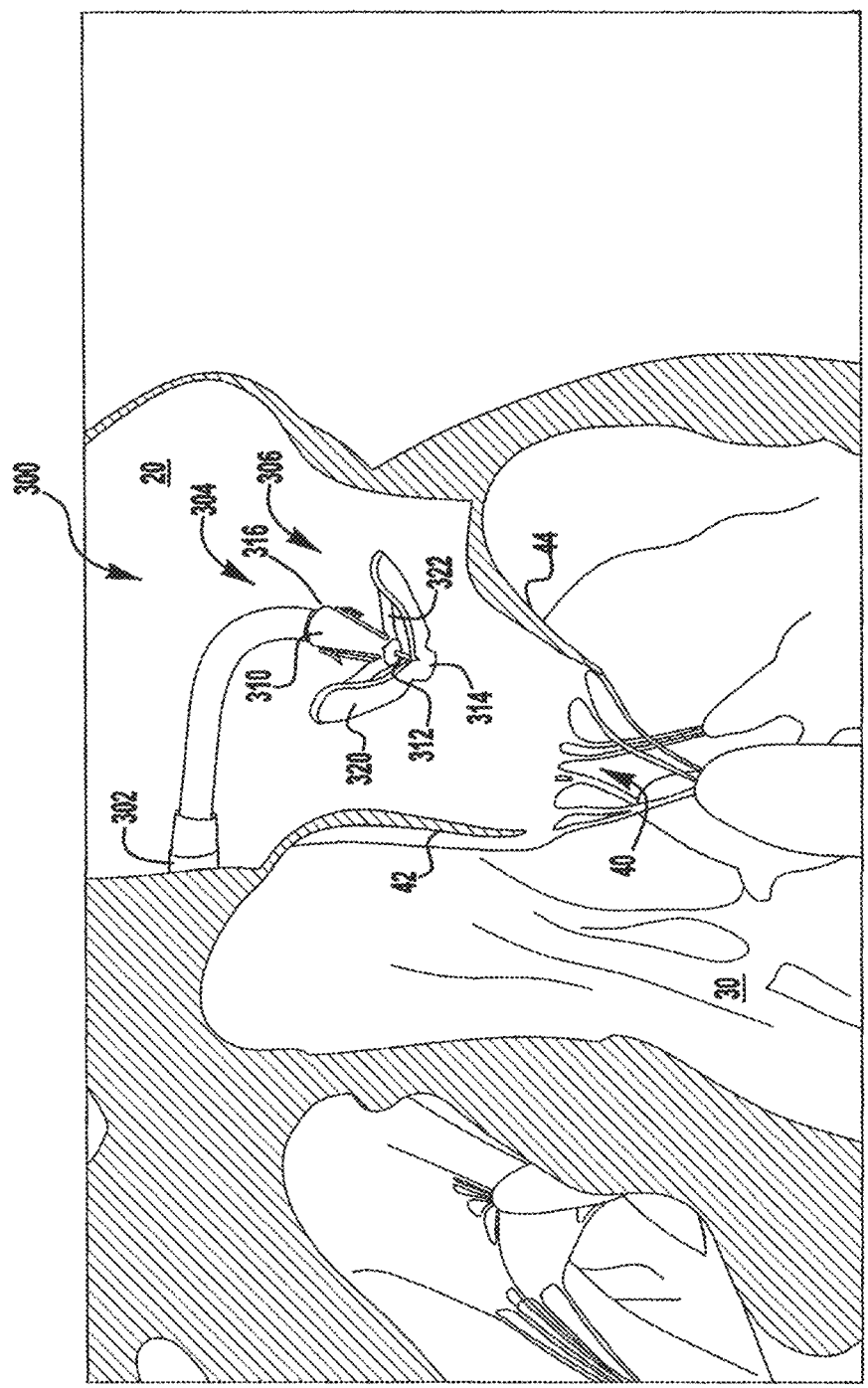
Figure 19:
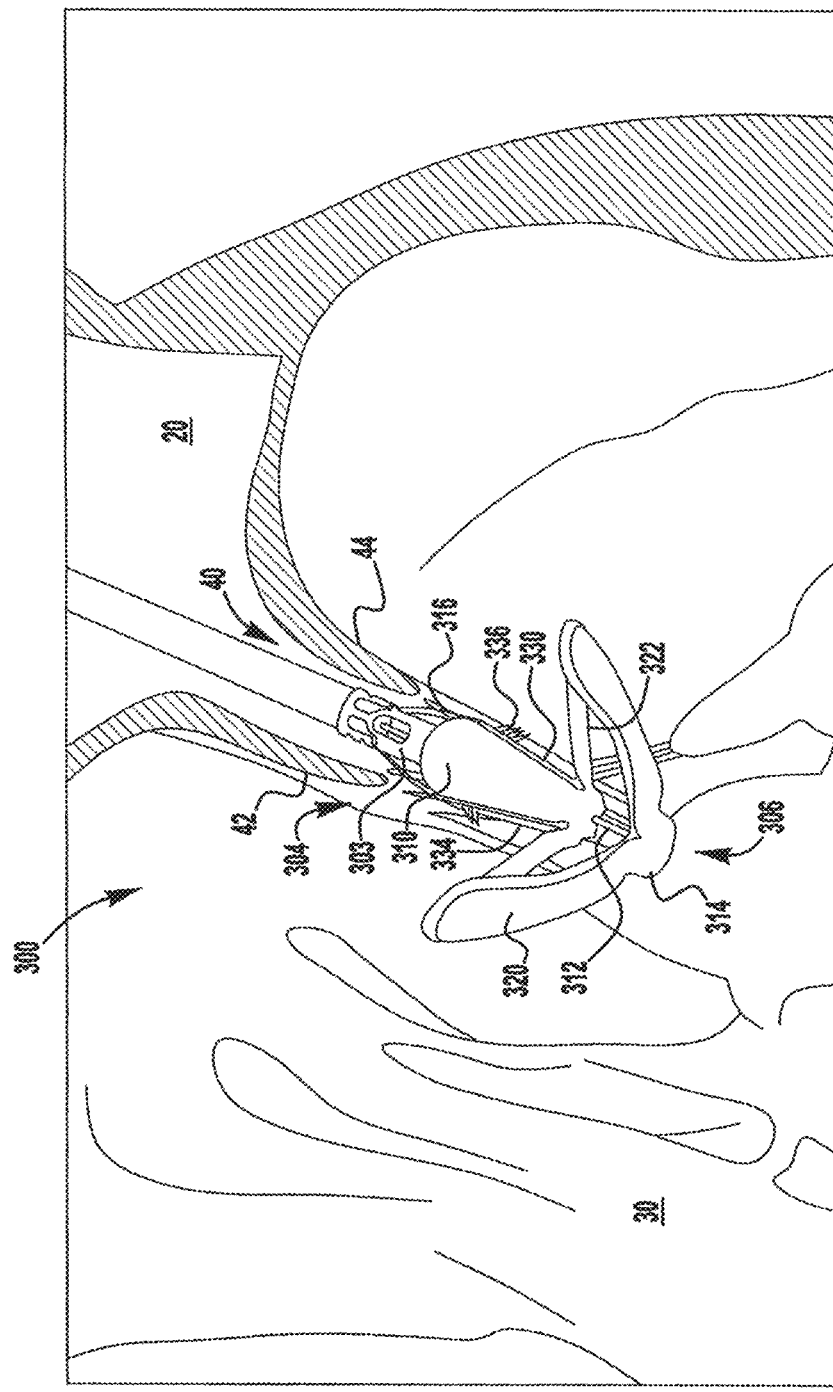
Figure 20:
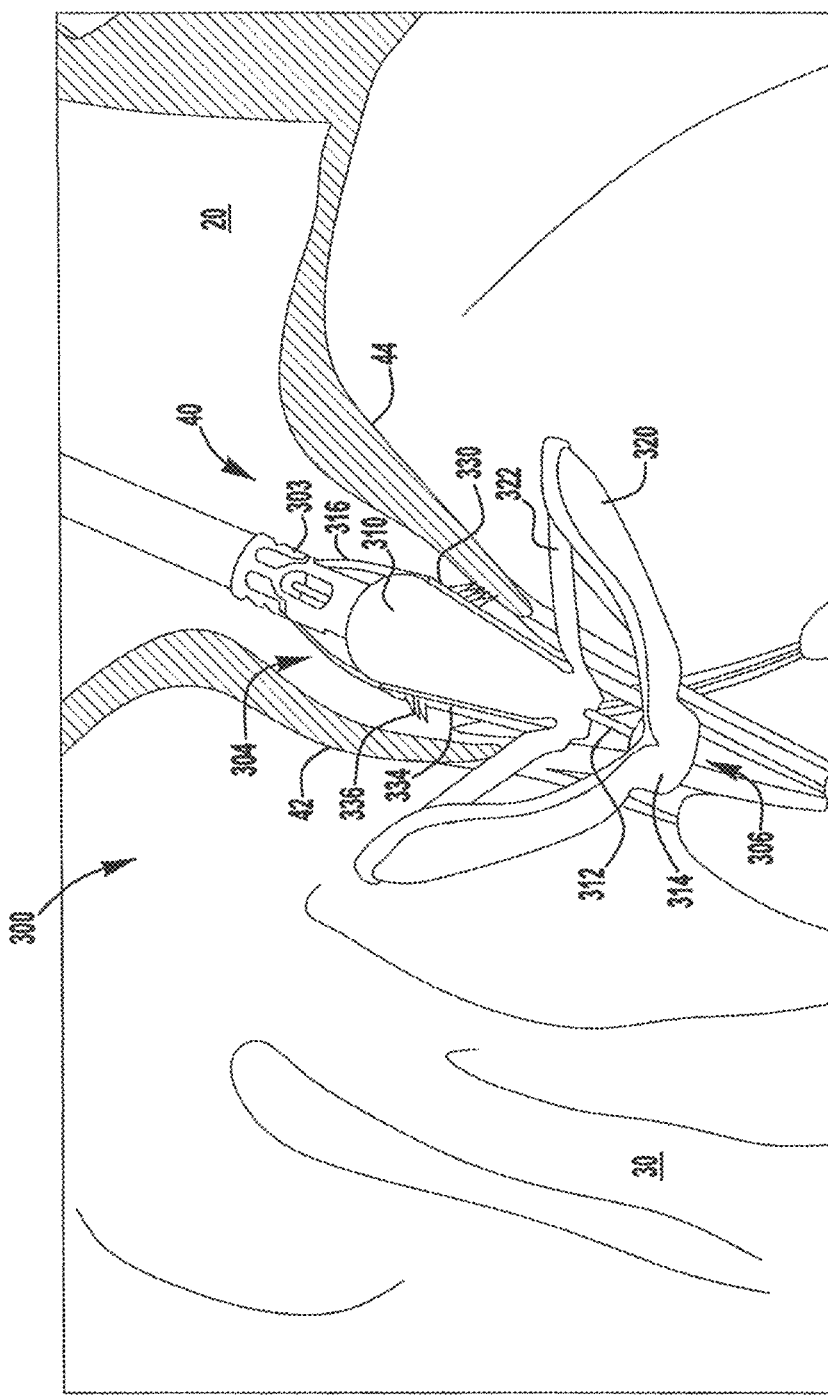
Figure 21:
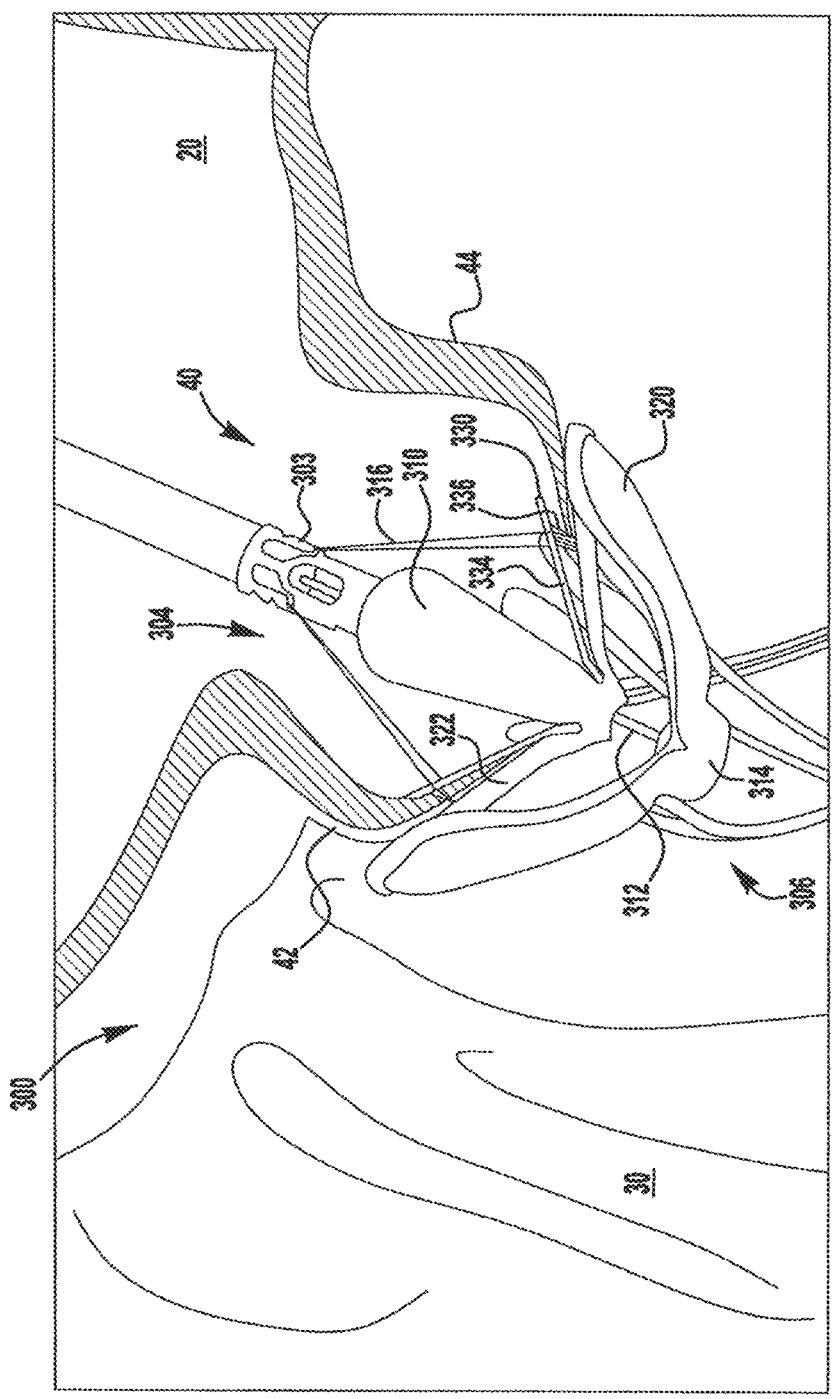
Figure 22:

Figure 23:

Figure 23A:
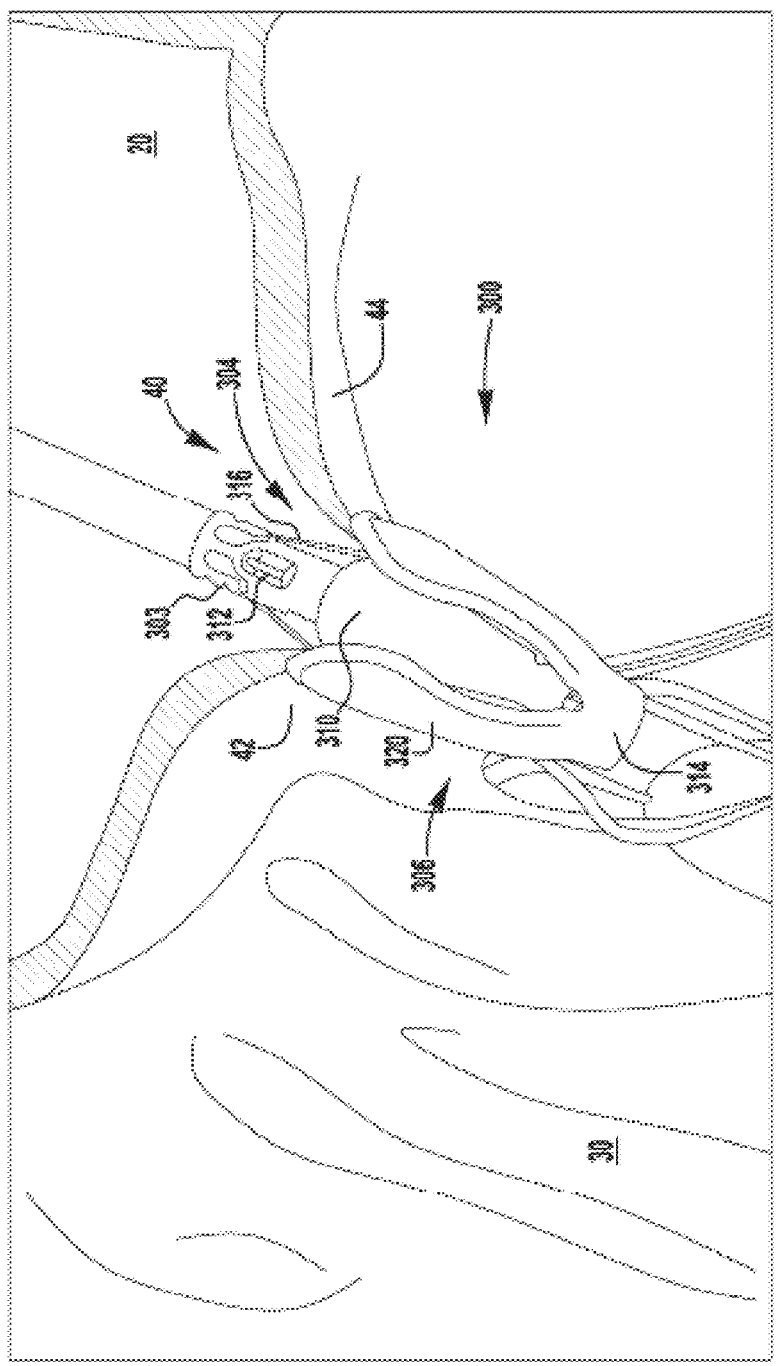
Figure 23B:
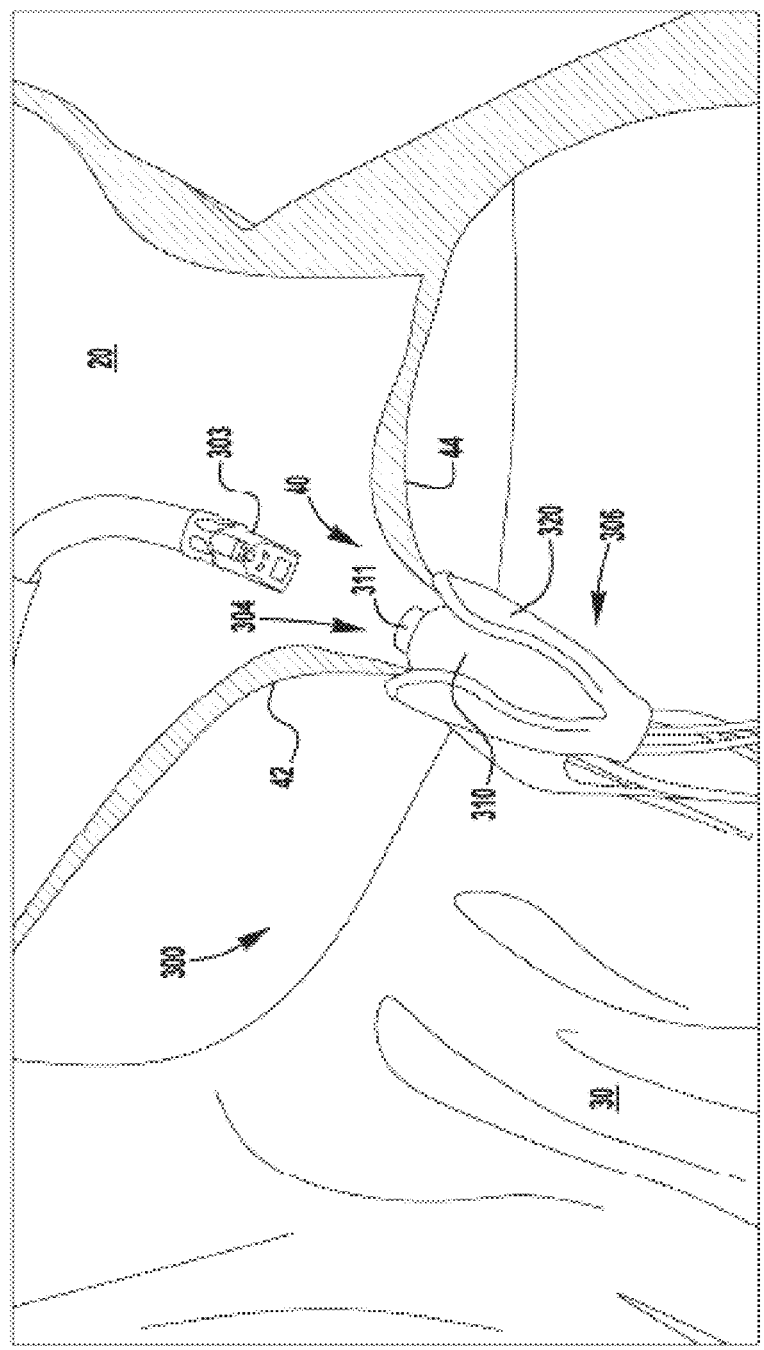

The device 300 is loaded in the delivery sheath in the fully open position, because the fully open position takes up the least space and allows the smallest catheter to be used (or the largest device 300 to be used for a given catheter size). Referring now to FIG. 14, the delivery sheath is inserted into the left atrium 20 through the septum and the device 300 is deployed from the delivery sheath 302 in the fully open condition. The actuation element 312 is then retracted to move the device 300 into the fully closed condition shown in FIGS. 15-16 and then maneuvered towards the native valve, e.g., mitral valve 40 as shown in FIG. 17. Referring now to FIG. 18, when the device 300 is aligned with the native valve 40, the actuation element 312 is extended to open the paddles 320, 322 into the partially opened position and the actuation lines 316 are retracted to open the clasps or barbed clasps 330 to prepare for leaflet capture. Next, as shown in FIGS. 19-20, the partially open device 300 is inserted through the native valve or mitral valve 40 until leaflets are properly positioned in between the inner paddles 322 and the coaption element 310 and inside the open clasps 330. FIG. 21 shows the device 300 with both clasps 330 closed, though the barbs 336 of one clasp 330 missed one of the leaflets 44 or where improperly positioned on the leaflets. As can be seen in FIGS. 22-23, the out of position clasp 330 is opened and closed again to properly capture the missed leaflet 44. When both leaflets 42, 44 are captured properly, the actuation element 312 is retracted to move the device 300 into the fully closed position shown in FIG. 23A. Referring to FIG. 23B, with the device 300 fully implanted in the native valve 40, the actuation element 312 is withdrawn to release the collar 303 from an upper end or plate 311 of the device 300 or of the coaption element 310 to leave the device 300 implanted on the native valve. Once deployed, the device 300 can be maintained in the fully closed position with a mechanical means such as a latch or can be biased to remain closed through the use of spring material, such as steel, and/or shape-memory alloys such as Nitinol. For example, the paddles 320, 322 can be formed of steel or Nitinol shape-memory alloy—produced in a wire, sheet, tubing, or laser sintered powder—and are biased to hold the outer paddles 320 closed, e.g., around the coaption element 310, and the barbed clasps 330 pinching or securing the native leaflets.

Figure 25:
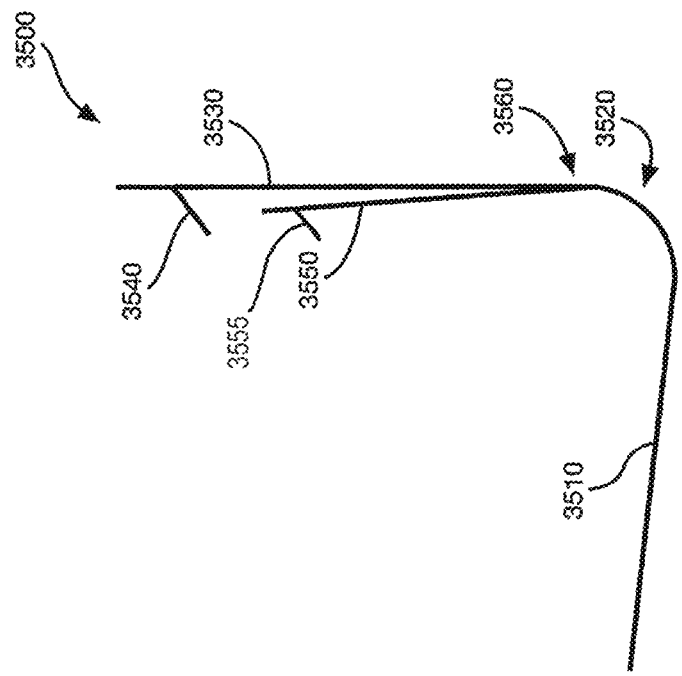
FIGS. 24 and 25 show schematic views of an example embodiment of a clasp for an implantable prosthetic device.
Figure 24:
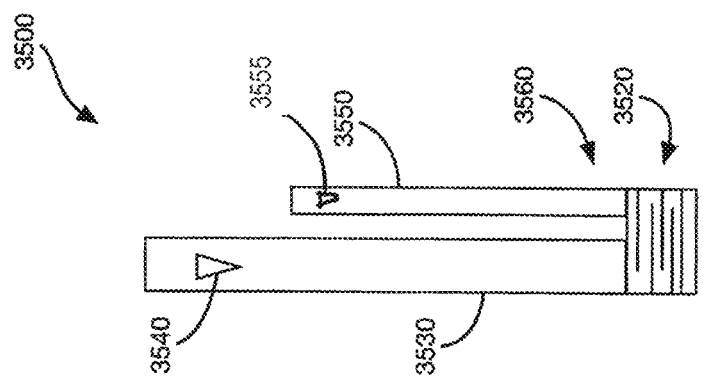

Referring now to FIGS. 24-25, an example clasp 3500 configured as a barbed clasp for use in implantable prosthetic devices, such as devices 100, 200, 300 described above, is shown. While depicted and described as a barbed clasp, the barbed portion 3540 could be substituted with another type of friction-enhancing portion. The clasp 3500 is configured to capture the native tissue when the implantable prosthetic device—e.g., any device described in the present application—is attached to the native tissue. Like the clasps described above, the barbed clasp 3500 includes a fixed arm 3510, a joint, flex, or hinge portion 3520, and a moveable arm 3530 having a barbed portion 3540. The clasp 3500 can be used in any of the implantable prosthetic devices of the present application and can include any of the features or combinations of features of the clasps described herein.

The clasp 3500 also includes an indicator arm 3550 adjacent to the moveable arm 3530 and extending from an indicator flex or hinge portion 3560. In an example embodiment, the indicator arm 3550 and/or the indicator flex or hinge portion 3560 are more resilient and/or flexible than the moveable arm 3530 and/or the moveable arm portion 3520. This increased resilience and/or flexibility allows the indicator arm to bounce, pulse or jump, while the moveable arm 3530 provides a firm grip on the leaflet tissue and does not bounce, pulse or jump. The bounce, pulse or jump of the indicator arm 3550 can be viewed using standard imaging equipment to determine that the clasp is correctly engaged with the leaflet tissue. As such, the indicator function of the indicator arm 3550 can be decoupled from the valve leaflet gripping and securing function of the moveable arm 3530. This decoupling can be applied to any of the embodiments described herein.

Referring to FIGS. 24 and 25, in an example embodiment the indicator flex or hinge portion 3560 allows the indicator arm 3550 to be actuated separately from the moveable arm 3530. The indicator flex or hinge portion 3560 can be formed from a portion of the indicator arm 3550 or can be formed from a series of cutouts.

The indicator arm 3550 can be separately actuated from the moveable arm 3530 to facilitate detection of the depth of engagement of the native leaflet between the moveable arm 3530 and the fixed arm 3510 of the clasp 3500. In the illustrated embodiment, the indicator arm 3550 is narrower than the moveable arm 3530 and has a length that is less than a distance from the joint, flex, or hinge portion 3520 to the barbed portion 3540. The indicator arm can have an optional barb(s) 3555 on it.

The length of the indicator arm 3550 is used to determine a desired minimum engagement depth as measured from the end of the moveable arm 3530 of the clasp 3500. Configuring the length of the indicator arm 3550 to be less than a distance from the joint, flex, or hinge portion 3520 to the barbed portion 3540 ensures that the barbed portion 3540 will engage a leaflet that is positioned at the minimum engagement depth as indicated by the indicator arm 3550. That is, if a native leaflet positioned within the clasp 3500 is engaged by the indicator arm 3550 when the indicator arm 3550 is actuated, then the leaflet will be engaged by the barbed portion 3540 of the moveable arm 3530. The opposite is also true. That is, if a native leaflet positioned within the clasp 3500 is not engaged by the indicator arm 3550 when the indicator arm 3550 is actuated, then the leaflet will not be engaged by the barbed portion 3540 of the moveable arm 3530.

Figure 25A:
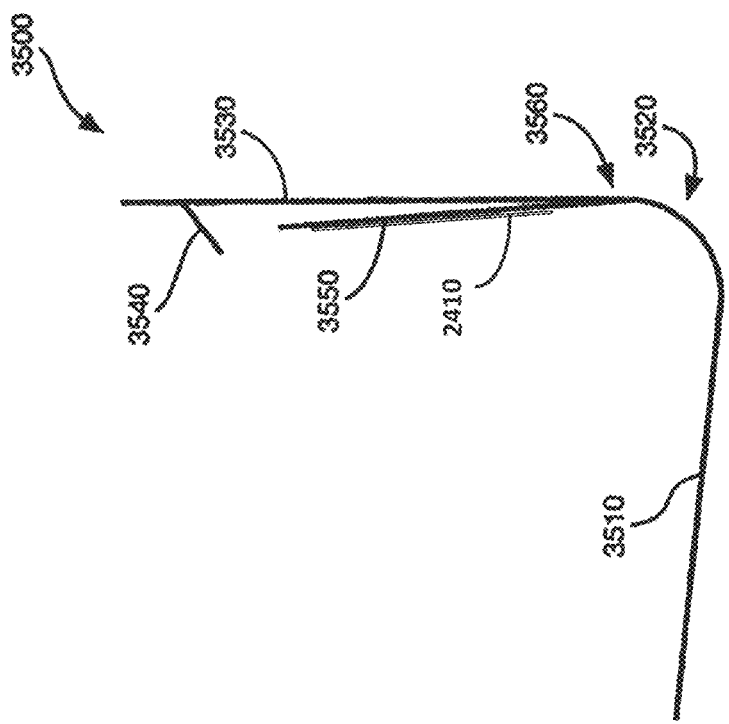
FIGS. 24A and 25A show schematic views of an example embodiment of a clasp for an implantable prosthetic device.
Figure 24A:
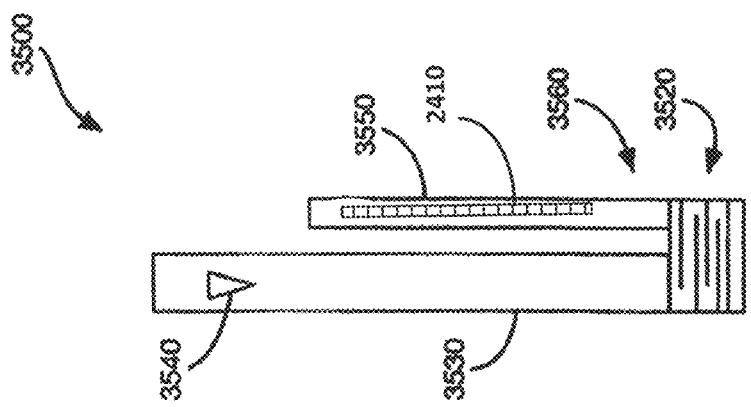

Referring now to FIGS. 24A and 25A, an example embodiment of a clasp such as that illustrated in FIGS. 24 and 25 is shown, with the addition of a radiopaque marker 2410 on the indicator arm 3550. The radiopaque indicator can be printed directly on the bump, a coil wrapped around the bump, or printed on a fabric covering the bump, or otherwise fixed to the bump. The radiopaque indicator can be a platinum coil wrapped around the bump, or it can be radiopaque ink printed on it. In FIGS. 24A and 25A, no barb is shown on the indicator arm, but there can optionally be a barb on the indicator arm as shown in FIGS. 24 and 25.

Figure 26:
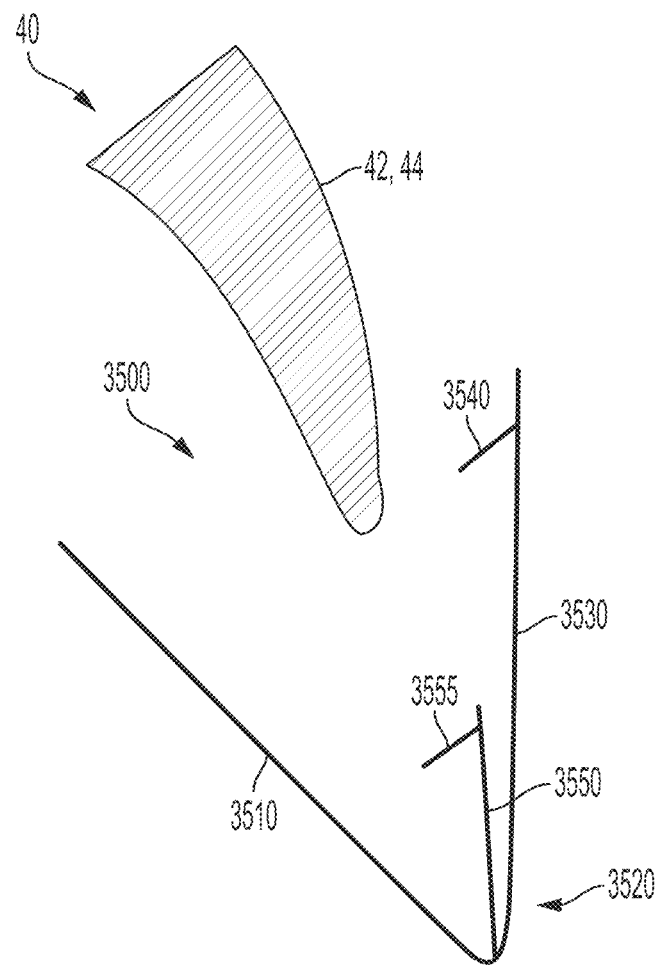
FIGS. 26-29 show the example clasp of FIGS. 24-25 being deployed to engage with a leaflet of a native valve.
Figure 27:
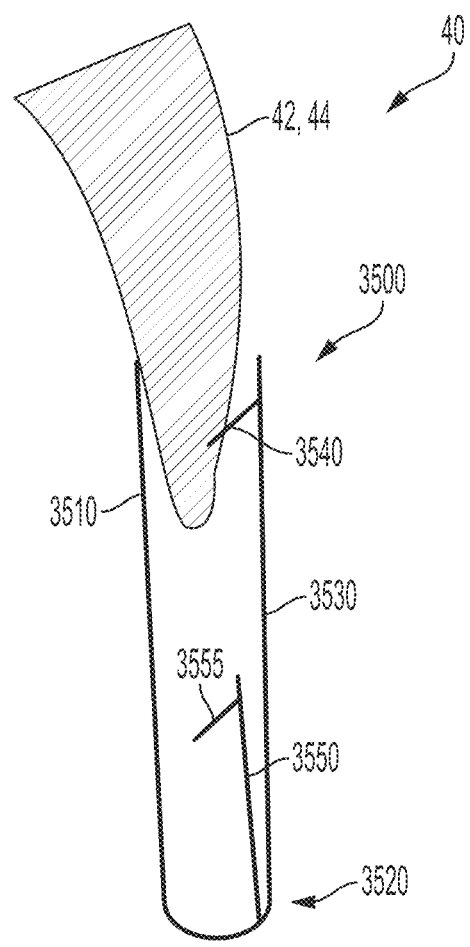

Referring now to FIGS. 26-29, the example clasp or barbed clasp 3500 is shown being deployed within a native valve 40 to secure an implantable device (not shown), such as the devices 100, 200, 300 described above, to one of the native leaflets 42, 44. Referring now to FIG. 26, the barbed clasp 3500 is shown in an open condition with a native leaflet 42, 44 partially inserted into an opening of the barbed clasp 3500 formed between the fixed and moveable arms 3510, 3530. To determine whether the leaflet 42, 44 has reached the desired engagement depth, the indicator arm 3550 can be actuated via an actuation line (not shown). Referring now to FIG. 27, the clasp is shown in a closed configuration, closed on the leaflet 42, 44. The indicator arm 3550 has not yet been actuated.

Figure 28:
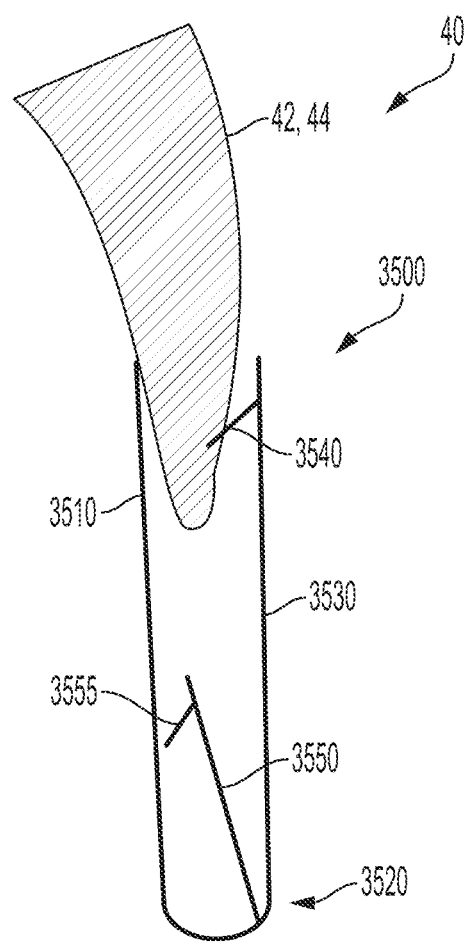

Referring now to FIG. 28, the indicator arm 3550 is shown in an actuated condition. The barb 3540 on the moveable arm 3530 has pierced the native leaflet. Because the leaflet 42, 44 is inserted into the opening of the clasp 3540 about half way between the barbed portion 3540 and the jointed, flexible, or hinged portion 3520 and is not inserted far enough into the clasp to overlap with the length of the indicator arm 3550, the indicator arm 3550 does not engage the leaflet 42, 44. Instead, the indicator arm swings toward the fixed arm 3510. The indicator arm's position is visible via imaging devices used to monitor implantation and deployment of the prosthetic device.

Figure 29:
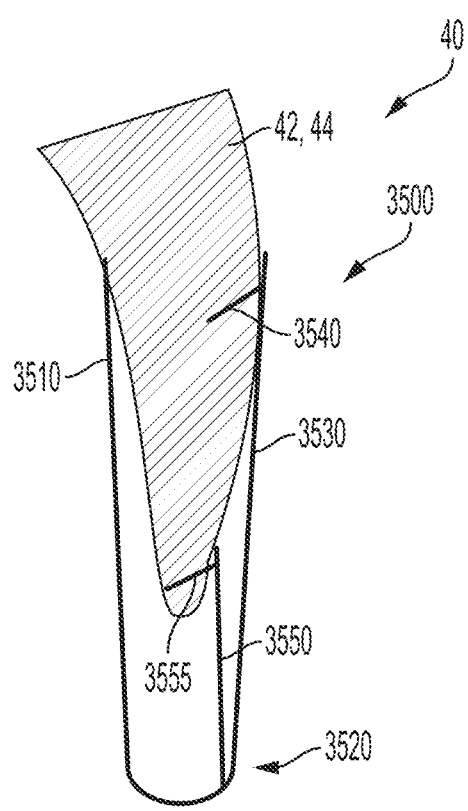
Figure 38:
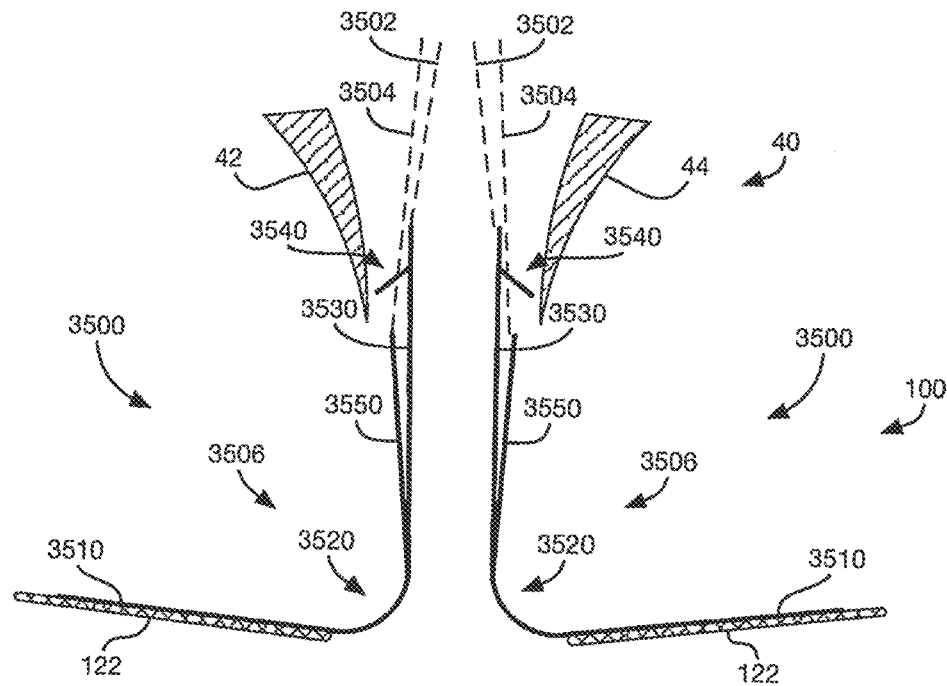

Referring now to FIG. 29, the clasp is closed on the leaflet 42, 44, and the leaflet is positioned deep enough into the clasp 3500 such that it overlaps with the indicator arm 3550. The barb 3540 on the moveable arm 3530 has pierced the native leaflet. The indicator arm rests on the leaflet tissue, and the leaflet prevents the indicator arm from moving all the way toward the fixed arm 3510 of the clasp. The indicator arm as illustrated in FIG. 29 has a barb 3540 to further secure the leaflet in place. In embodiments without a barb on the indicator arm, the indicator arm can bounce with the pulse of the heartbeat, which pulses the leaflet. This pulsing is visible by imaging techniques described above and can be used to indicate to the operator that the leaflet is positioned sufficiently deep into the clasp.

Referring now to FIGS. 30-37, a variety of example arrangements of moveable and indicator arms for clasps are shown. Referring now to FIG. 30, an example clasp 3600, illustrated as a barbed clasp, for use in implantable prosthetic devices, such as devices 100, 200, 300 described above, is shown. Like the barbed clasp 3500 described above, the barbed clasp 3600 includes a fixed arm 3610, a joint, flex, or hinge portion 3620, a moveable arm 3630 having a barbed portion 3640 (though other friction-enhancing portions can be used), and an indicator arm 3650 connected to the joint, flex, or hinge portion 3620 via an indicator flex or hinge portion 3660. The clasp 3600 can be used in any of the implantable prosthetic devices of the present application and can include any of the features or combinations of features of the other clasps described herein.

The indicator arm 3650 has a width that is about the same as a width of the moveable arm 3630, which is wider than the indicator arm 3550 of the clasp 3500, described above. Increasing the width of the indicator arm 3650 increases the area of the arm that can engage the native leaflet. A wider indicator arm 3650 can also help to pinch the native leaflet against the fixed arm when the clasp 3600 is closed. The indicator flex or hinge portion 3660 is similar to the patterned hinge portion 2120 described above which allows the indicator arm 3650 to bend further than the moveable arm 3630 in the closing direction and be shape set in a preloading or shape set position (not shown) to provide increased pinching force when in a closed or engaged position (not shown) in contact with the native leaflet tissue.

Referring now to FIG. 31, an example clasp 3700 for use in implantable prosthetic devices, such as devices 100, 200, 300 described above, is shown. Like the clasp 3500 described above, the clasp 3700 includes a fixed arm 3710, a joint, flex, or hinge portion 3720, a moveable arm 3730 having a barbed portion 3740 (though other friction-enhancing portions can be used), and an indicator arm 3750 connected to the joint, flex, or hinge portion 3720 via an indicator flex or hinge portion 3760. The clasp 3700 can be used in any of the implantable prosthetic devices of the present application and can include any of the features or combinations of features of the other clasps described herein.

The moveable arm 3730 is formed in a hoop or loop shape having two side arms 3732 surrounding a central opening 3734 that extends from the joint, flex, or hinge portion 3720 to the barbed portion 3740 of the moveable arm 3730. The indicator arm 3750 is disposed in the central opening 3734 between the two side arms 3732. Because the moveable arm 3730 spans the full width of the clasp 3700, the barbed portion 3740 of the moveable arm 3730 is as wide as the clasp 3700 so that a larger area of the barbed portion 3740 engages with the native leaflet tissue.

Referring now to FIG. 32, an example clasp 3800 for use in implantable prosthetic devices, such as devices 100, 200, 300 described above, is shown. Like the clasp 3500 described above, the clasp 3800 includes a fixed arm 3810, a joint, flex, or hinge portion 3820, a moveable arm 3830 having a barbed portion 3840 (though other friction-enhancing portions can be used), and an indicator arm 3850 connected to the joint, flex, or hinge portion 3820 via an indicator flex or hinge portion 3860. The clasp 3800 can be used in any of the implantable prosthetic devices of the present application and can include any of the features or combinations of features of the other clasps described herein.

The moveable arm 3830 is formed from two side arms 3832 adjacent to a central opening 3834 that extends from the joint, flex, or hinge portion 3820 to the end of the moveable arm 3830. That is, the central opening 3834 separates the moveable arm 3830 into two independently actuatable side arms 3832 that each include a barbed portion 3840. The indicator arm 3850 is disposed in the central opening 3834 between the two side arms 3832. The barbed portions 3840 of the side arms 3832 span the full width of the clasp 3800 to provide a wide gripping area for the moveable arm 3830 to engage the native leaflet tissue. The side arms 3832 can be independently actuated to allow for lateral variations in thickness of the native leaflet tissue.

Referring now to FIG. 33, an example clasp 3900 for use in implantable prosthetic devices, such as devices 100, 200, 300 described above, is shown. Like the clasp 3500 described above, the clasp 3900 includes a fixed arm 3910, a joint, flex, or hinge portion 3920, a moveable arm 3930 having a barbed portion 3940 (though other friction-enhancing portions can be used), and an indicator arm 3950 having a barbed portion 3970. The indicator arm 3950 is connected to the joint, flex, or hinge portion 3920 via an indicator flex or hinge portion 3960. The clasp 3900 is similar to the clasp 3500 described above, except for the addition of a barbed portion 3970 arranged at the end of the indicator arm 3950. The barbed portion 3970 allows the indicator arm 3950 to aid the moveable arm 3930 in pinching the native leaflet against the fixed arm (not shown). The clasp 3900 can be used in any of the implantable prosthetic devices of the present application and can include any of the features or combinations of features of the other clasps described herein.

Referring now to FIGS. 34-37, example clasps are shown with indicator arms having a length based on percentage of a minimum engagement depth of the clasp. The minimum engagement depth of the clasp is the minimum length of native tissue that should be inserted into the clasp beyond the barbed portion, to ensure a reliable grip on the tissue by the clasp. That is, the minimum engagement depth is the distance between the barbed portion and the joint, flex, or hinge portion of the clasp. The minimum engagement depth for mitral valve tissue can vary depending on a variety of different factors, such as age of the patient, thickness of the tissue, health of the tissue, etc. As such, the minimum engagement depth can vary depending on the patient.

Referring now to FIG. 34, an example clasp 4000 (illustrated as a barbed clasp) for use in implantable prosthetic devices, such as devices 100, 200, 300 described above, is shown. Like the clasp 3500 described above, the clasp 4000 includes a fixed arm 4010, a joint, flex, or hinge portion 4020, a moveable arm 4030 having a barbed portion 4040 (though other friction-enhancing portions can be used), and an indicator arm 4050 connected to the joint, flex, or hinge portion 4020 via an indicator flex or hinge portion 4060. The indicator arm 4050 has a length that is about 25 percent of the maximum engagement depth measured between the joint, flex, or hinge portion 4020 and the barbed portion 4040. Thus, the indicator arm 4050 will not indicate that the native leaflet has reached a desired engagement depth until the leaflet is inserted to at least about 75 percent of the maximum engagement depth. The clasps 4000 can be used in any of the implantable prosthetic devices of the present application and can include any of the features or combinations of features of the other clasps described herein.

Referring now to FIG. 35, an example clasp 4100 for use in implantable prosthetic devices, such as devices 100, 200, 300 described above, is shown. Like the clasp 3500 described above, the clasp 4100 includes a fixed arm 4110, a joint, flex, or hinge portion 4120, a moveable arm 4130 having a barbed portion 4140 (though other friction-enhancing portions can be used), and an indicator arm 4150 connected to the joint, flex, or hinge portion 4120 via an indicator flex or hinge portion 4160. The indicator arm 4150 has a length that is about 50 percent of the maximum engagement depth measured between the joint, flex, or hinge portion 4120 and the barbed portion 4140. Thus, the indicator arm 4150 will not indicate that the native leaflet has reached a desired engagement depth until the leaflet is inserted to at least about 50 percent of the maximum engagement depth. The clasps 4100 can be used in any of the implantable prosthetic devices of the present application and can include any of the features or combinations of features of the other clasps described herein.

Referring now to FIG. 36, an example clasp 4200 for use in implantable prosthetic devices, such as devices 100, 200, 300 described above, is shown. Like the clasp 3500 described above, the clasp 4200 includes a fixed arm 4210, a joint, flex, or hinge portion 4220, a moveable arm 4230 having a barbed portion 4240 (though other friction-enhancing portions can be used), and an indicator arm 4250 connected to the joint, flex, or hinge portion 4220 via an indicator flex or hinge portion 4260. The indicator arm 4250 has a length that is about 75 percent of the maximum engagement depth measured between the joint, flex, or hinge portion 4220 and the barbed portion 4240. Thus, the indicator arm 4250 will not indicate that the native leaflet has reached a desired engagement depth until the leaflet is inserted to at least about 25 percent of the maximum engagement depth. The clasps 4200 can be used in any of the implantable prosthetic devices of the present application and can include any of the features or combinations of features of the other clasps described herein.

Referring now to FIG. 37, an example clasp 4300 for use in implantable prosthetic devices, such as devices 100, 200, 300 described above, is shown. Like the clasp 3500 described above, the clasp 4300 includes a fixed arm 4310, a joint, flex, or hinge portion 4320, a moveable arm 4330 having a barbed portion 4340, and an indicator arm 4350 connected to the joint, flex, or hinge portion 4320 via an indicator flex or hinge portion 4360. The indicator arm 4350 has a length that is about 90 percent of the maximum engagement depth measured between the joint, flex, or hinge portion 4320 and the barbed portion 4340 (though other friction-enhancing portions can be used). Thus, the indicator arm 4350 will not indicate that the native leaflet has reached a desired engagement depth until the leaflet is inserted to at least about 10 percent of the maximum engagement depth. The clasps 4300 can be used in any of the implantable prosthetic devices of the present application and can include any of the features or combinations of features of the other clasps described herein.

Referring now to FIGS. 38-47, example clasps 3500 are shown attached to paddles of an implantable prosthetic device, such as devices 100, 200, 300, and being deployed within a native valve 40 and to secure the device to the native leaflets 42, 44. While the clasps 3500 are shown in FIGS. 93-102, the clasps 3600, 3700, 3800, 3900, 4000, 4100, 4200, and 4300 with indicator arms described above would be attached to the native leaflets in a similar manner as the clasps 3500. The clasps 3500 are attached to paddles 122 of the device 100 that can be moved between opened and closed positions to capture and secure the native leaflets 42, 44 within the device 100, as described above.

Figure 39:
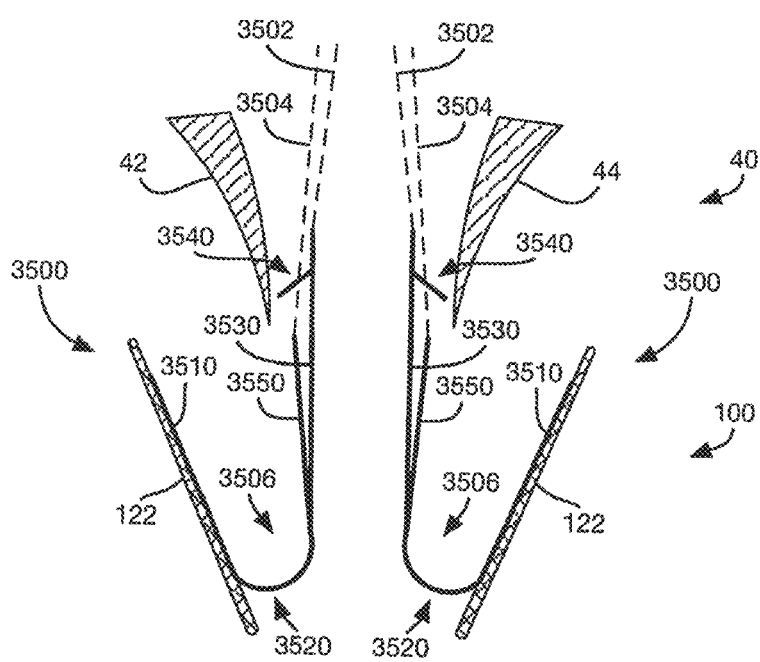

Referring now to FIG. 39, the device 100 is shown deployed through the native mitral valve 40 and the paddles 122 are opened. The clasps 3500 are then opened by applying tension to actuating lines 3502, 3504 attached to the ends of the moveable arms 3530 and the indicator arms 3550, respectively. Opening the clasps 3500 and the paddles 122 as shown in FIG. 39 allows the device 100 to be maneuvered such that the leaflets 42, 44 are at least partially disposed in the opening 3506 formed between the fixed and moveable arms 3510, 3530 of the clasps to facilitate the capture of the leaflets 42, 44 by the clasps 3500.

Referring now to FIG. 39, the paddles 122 and clasps 3500 are partially closed to position the leaflets for detection by the indicating arms 3550 and eventual capture by the clasps 3500. The partially closed position of the paddles 122 and clasps 3500 allows the barbed portions 3540 of the moveable arms 3530 to pinch the leaflets 42, 44 against the fixed arms 3510 without stretching or moving the leaflets 42, 44 so far that the leaflets 42, 44 are pushed aside by the moveable arms 3530 or slip off of the barbed portions 3540 during an attempted leaflet capture.

Figure 40:
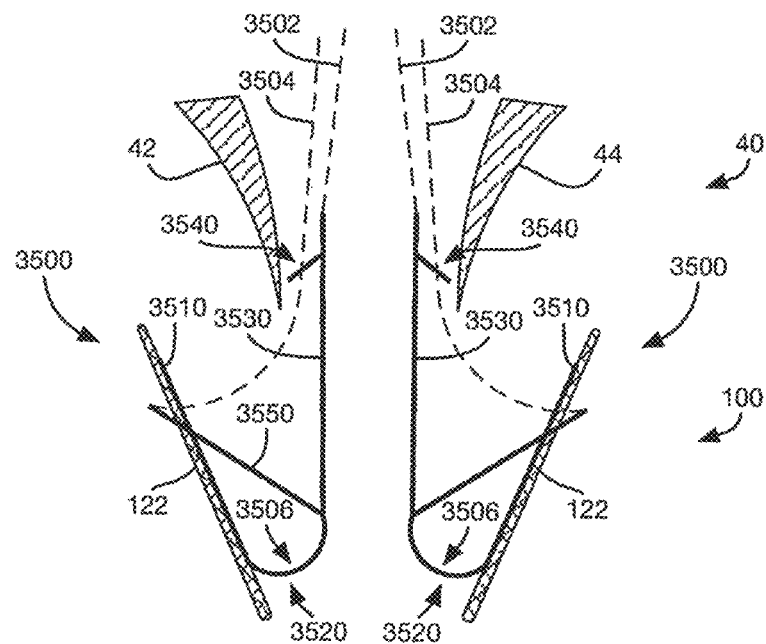

Referring now to FIG. 40, both indicator arms 3550 are actuated by releasing tension on the actuation lines 3504. Both indicator arms 3550 miss or slip off of the leaflets 42, 44 and move to a fully actuated position that is beyond the fixed arms 3510 of the clasps 3500. The indicator arms 3550 crossing the fixed arms 3510 forms an X-shape that is visible via imaging devices used to monitor implantation and deployment of the device.

Figure 41:
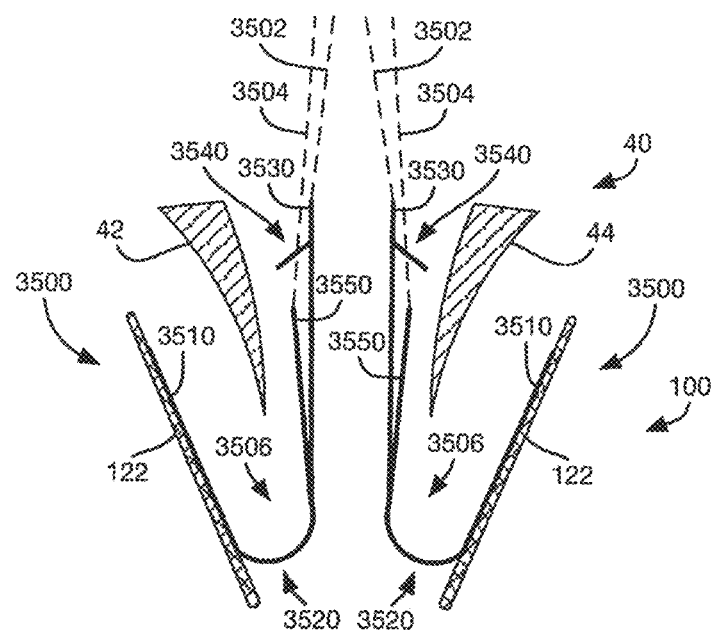
Figure 42:
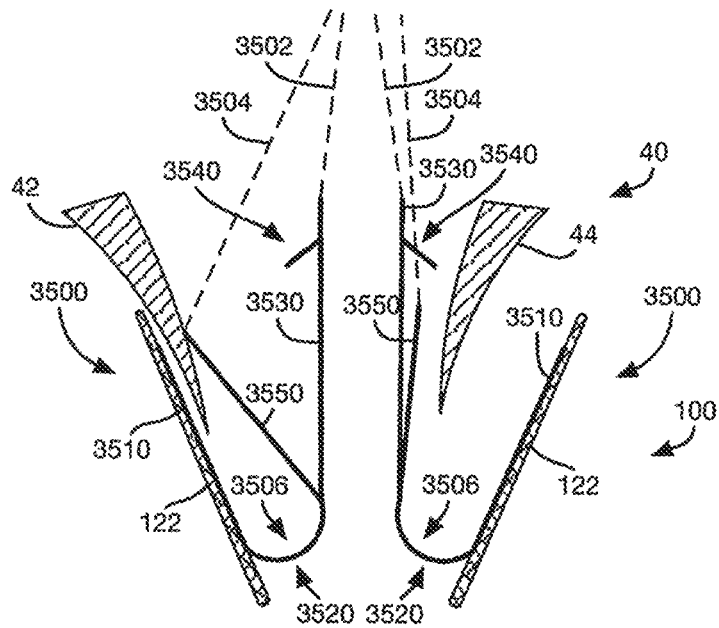
Figure 43:
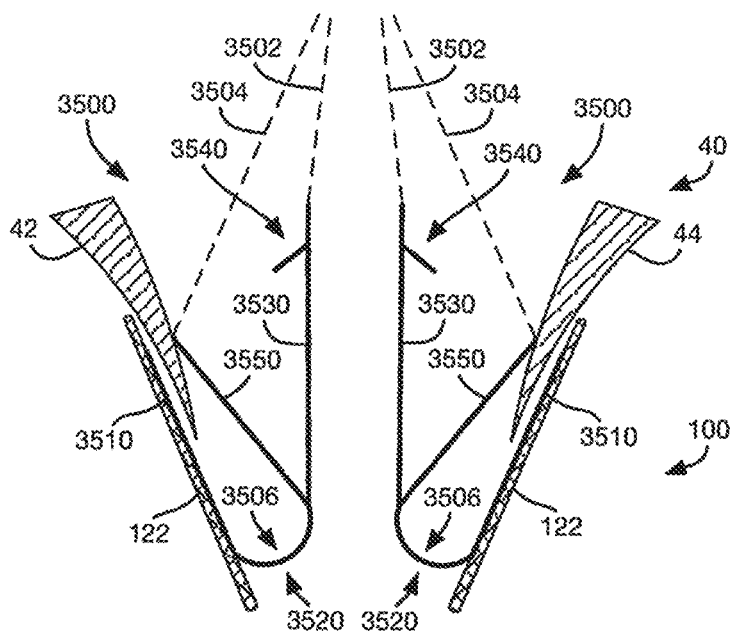
Figure 44:
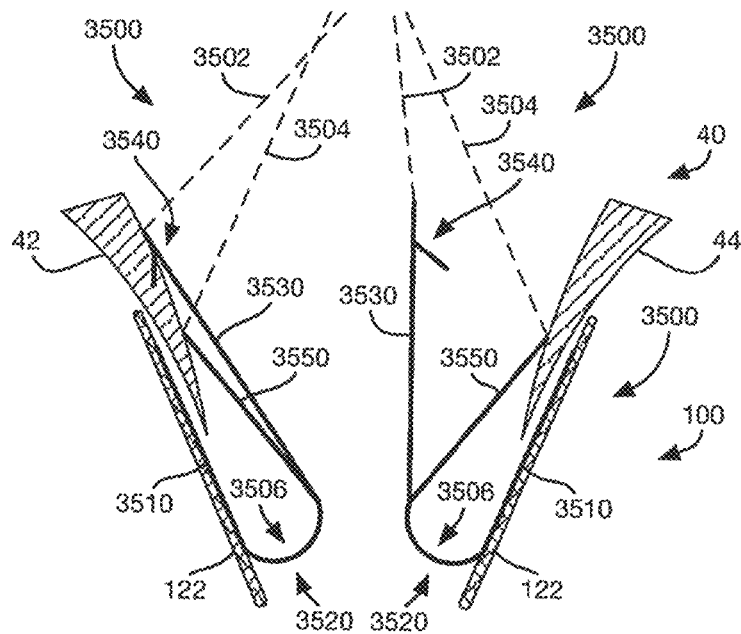
Figure 45:
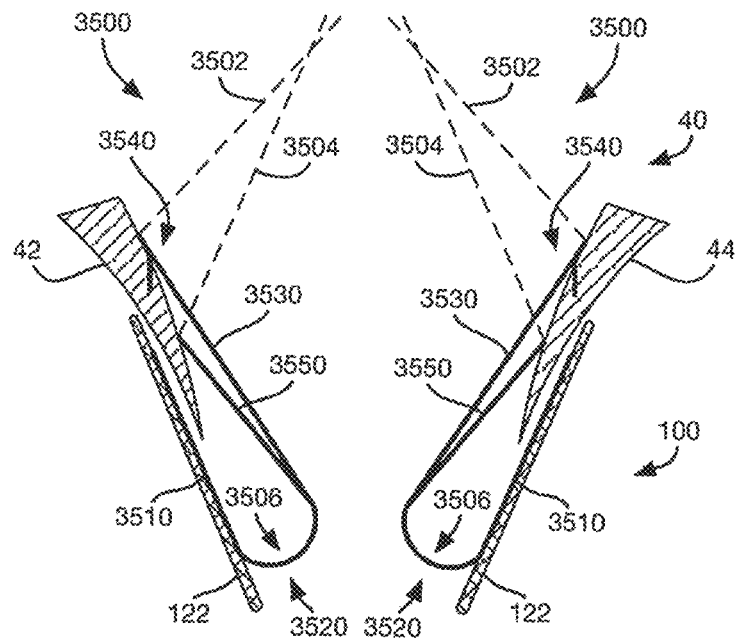
Figure 46:
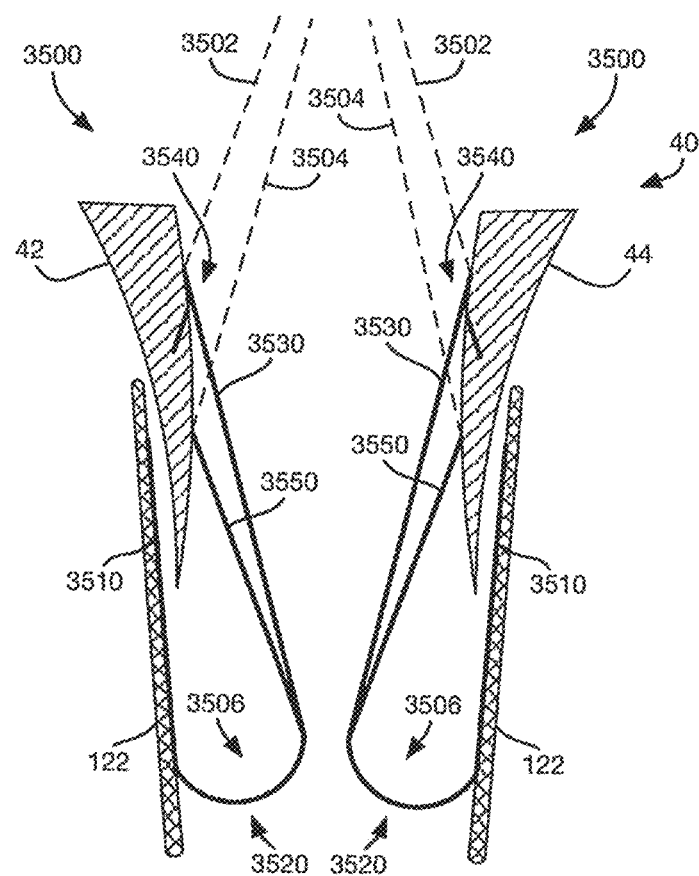

Referring now to FIG. 41, the indicator arms 3550 are retracted by applying tension to the actuation lines 3504 and the device 100 is repositioned so that the leaflets 42, 44 are more deeply inserted into the openings 3506 of the clasps 3500. One of the indicator arms 3550 is then allowed to close by releasing tension on one of the actuating lines 3504, as can be seen in FIG. 42. The indicator arm 3550 engages the leaflet 42 and pinches the leaflet 42 against the fixed arm 3510 and paddle 122. FIG. 43 shows the same with the other indicator arm 3550 being actuated to engage the other leaflet 44 and pinch the leaflet 44 against the other fixed arm 3510 and paddle 122. Engagement with the leaflets 42, 44 prevents the indicator arms 3550 from moving past the fixed arms 3510 of the clasps 3500 to form the X-shape shown in FIG. 40. Thus, the indicator arms 3550 indicate to an observer observing the installation via an imaging device that the leaflets 42, 44 are inserted into the openings 3506 beyond the minimum desired engagement depth that is determined by the length of the indicator arms 3550.

Referring now to FIGS. 44-47, once the indicator arms 3550 indicate that the leaflets 42, 44 are sufficiently inserted into the openings 3506, the moveable arms 3530 are actuated by releasing tension on the actuating lines 3502 so that the leaflets 42, 44 are pinched between the barbed portions 3540 and fixed arms 3510 of each clasp 3500. The paddles 122 are then moved to a fully closed position, shown in FIG. 46, to secure the leaflets firmly within the device 100. The indicators 3550 can be monitored in any of the positions illustrated by FIGS. 42-46. For example, the indicators 3550 will pulse or jump as the heart beats. This pulsing or jumping can be visualized to confirm that the mitral valve repair device is correctly positioned. Since the indicators 3550 are flexible enough to flex or jump as the heart beats, the movable arms 3530 can be made stiff and/or close with a high enough force that closed moveable arms 3530 do not pulse or jump as the heart beats.

Figure 47:
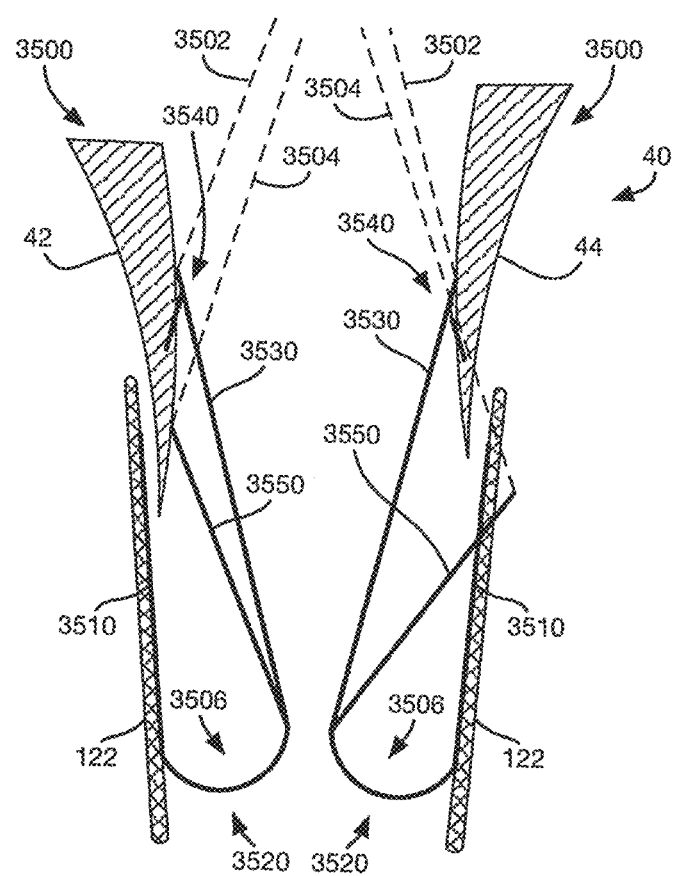

Referring now to FIG. 47, one of the leaflets 44 is shown partially withdrawn from the device 100, which can occur because of movement of the leaflets 42, 44 during the beating of the heart. As can be seen in FIG. 47, the leaflet 44 remains partially secured by the barbed portion 3540. However, the leaflet 44 is no longer secured at or beyond the minimum engagement depth as determined by the length of the indicator arm 3550. Withdrawal of the leaflet 44 allows the indicator arm 3550 to move beyond the fixed arm 3510, thereby forming an X-shape that is visible to an observer using an imaging device. In addition, or instead, the indicator arm 3550 that does not contact the valve leaflet does not pulse or jump as the heart beats. Thus, insufficient retention or slippage of the leaflets 42, 44 from the device 100 can be detected before the device 100 is detached from a delivery device (not shown). Once the slipped leaflet is detected, the clasps 3500 and paddles 122 can be opened and repositioned to better secure the slipped leaflet. In other example embodiments (see FIGS. 221-225), a single actuation line can be used to raise and lower the moveable arm and indicator arm of a clasp.

In some example embodiments, a first moveable arm on a clasp can have a barb and be strong enough to hold the leaflet in place when the first moveable arm is lowered on to the leaflet. The first moveable arm can be raised again if the leaflet is not sufficiently positioned far enough within the leaflet. The barb on the first moveable arm is temporary so that the first moveable arm can be raised and lowered repeatedly until the leaflet is properly positioned. Once the location of the leaflet is sufficiently positioned within the clasp, one or more secondary moveable arms, having a barb or barb region, can be lowered to hold or capture the leaflets in place within the clasp.

Referring now to FIGS. 48-66, an example clasp 4400 for use in implantable prosthetic devices, such as devices 100, 200, 300 described above, is shown. The clasp 4400 has a fixed arm 4410, a patterned flex portion or patterned hinge portion 4420, a moveable arm 4430 formed in the shape of a hoop or loop, and a barbed portion 4440 of the moveable arm 4430. The clasp 4400 also includes an indicator arm 4450 extending from an indicator flex or hinge portion 4460 that joins the indicator arm to the patterned flex or hinge portion 4420. The clasp 4400 can be used in any of the implantable prosthetic devices of the present application and can include any of the features or combinations of features of the other clasps described herein. For example, the clasp 4400 can be laser cut from a flat sheet or a tube of shape-memory alloy, such as Nitinol, and then shape-set into a desired shape.

The illustrated fixed arm 4410 has two tongue portions 4411 that each include holes 4412 for attaching the fixed arm 4410 to an implantable device. A central opening 4454 arranged between the tongue portions 4411 is wider than the indicator arm 4450 so that the indicator arm 4450 can pass through the fixed arm 4410 between the tongue portions 4411 to form an X-shape when viewed from the side (FIG. 51) when the indicator arm 4450 does not engage the leaflet tissue.

The patterned flex portion or patterned hinge portion 4420 is formed from a plurality of spring segments 4422 and cutouts 4424. The two tongue portions 4411 of the fixed arm 4410 extend from one end of the patterned flex portion or patterned hinge portion 4420 and the moveable arm 4430 extends from the other end of the flex or hinge portion 4420.

The moveable arm 4430 of the clasp 4400 has a hoop-like shape. The hoop-shaped moveable arm 4430 includes side beams 4432 that are thinner and more flexible, particularly in the lateral direction. The side beams 4432 include a first flex portion or hinge portion 4434 arranged toward the proximate end of the moveable arm 4430 and a second flex portion or hinge portion 4436 arranged at the distal end of the moveable arm 4430. The first flex or hinge portion 4434 is formed by one or more bends in the side beams 4432. The second flex or hinge portion 4436 includes a thinner—and therefore more flexible—portion to reduce the force required to collapse the clasp 4400. The hoop-shape of the moveable arm 4430 and flexible side arms 4432 allow the moveable arm 4430 to be collapsed by merely retracting the clasp 4400 into a delivery sheath (not shown). In certain embodiments, the expansion and contraction of the clasp 4400 is controlled by actuation lines (not shown).

The hoop-like shape of the moveable arm 4430 provides for a wider barbed portion 4440 that can include more barbs 4442 with the same or greater lateral spacing than other clasps. The wider spacing of the barbs 4442 improves capture of the native leaflets. The barbs 4442 are also longitudinally staggered as a result of their position on the hoop-like shape of the moveable arm 4430. That is, two center barbs 4444 are arranged further away from the joint, flex, or hinge portion 4420 and two outer barbs 4446 are arranged closer to the joint, flex, or hinge portion 4420. The barbed portion 4440 of the moveable arm 4430 also includes holes 4448 for receiving an actuation suture (not shown). In certain embodiments, the hoop shape of the moveable arm 4430 is similar to the shape of wide outer paddles of an implantable device so that pinching forces of the paddles are spread out evenly on the barbs, further improving the retention of the native leaflets. The ends of the barbs 4442 can be further sharpened using any suitable sharpening means.

The indicator arm 4450 includes a beam 4451 that extends from the joint, flex, or hinge portion 4420 in the interior of the hoop-shaped moveable arm 4430 between the two side arms 4432 to a barbed portion 4456. The indicator arm 4450 includes a hole 4452 at the end for receiving an actuation line (not shown) for actuating the indicator arm 4450. The barbed portion 4456 is arranged at the end of the beam 4451 of the indicator arm 4450 and includes at least one barb 4456. The barbed portion 4456 helps the indicator arm 4450 secure the leaflet until the moveable arm 4430 is closed. The barb 4456 can be laser cut from the indicator arm 4450 and bent outwards so that it protrudes away from the indicator arm 4450 at about the same angle as the barbs 4442 protrude from the moveable arm 4430. In some embodiments, the indicator arm 4450 includes barbs that, like the barbs 2244 of the clasp 2200, are cut from a flat sheet of material and then rotated 90 degrees to protrude outward at an angle.

The barbed portion 4456 of the indicator arm 4450 is arranged at a distance from the joint, flex, or hinge portion 4420 such that the barb 4456 of the indicator arm 4450 is longitudinally arranged between the center barbs 4444 and the outer barbs 4446 of the barbed portion 4440. This arrangement ensures that the barbed portion 4440 will engage a leaflet that is engaged by the indicator arm 4450. That is, if a native leaflet positioned within the clasp 4400 is engaged by the barbed portion 4456 of the indicator arm 4450 when the indicator arm 4450 is actuated, then the leaflet will also be engaged by the barbed portion 4440 of the moveable arm 4430. The opposite is also true. That is, if a native leaflet positioned within the clasp 4400 is not engaged by the indicator arm 4450 when the indicator arm 4450 is actuated, then the leaflet will not be sufficiently engaged by the barbed portion 4440 of the moveable arm 4430.

The indicator flex or hinge portion 4460 allows the indicator arm 4450 to be actuated separately from the moveable arm 4430 to facilitate detection of the depth of engagement of the native leaflet arranged between the moveable arm 4430 and the fixed arm 4410 of the clasp 4400. The indicator flex or hinge portion 4460 is similar to the patterned flex/hinge portion 4420 and is formed from a series of spring segments 4462 and cutouts 4464. In some embodiments, the spring force of the indicator flex/hinge portion 4460 is less than the pinching force imparted to the moveable arm 4430 by the joint, flex, or hinge portion 4420 so that the indicator arm 4450 can be actuated many times to detect the position of the leaflet while the moveable arm 4430 with a stronger pinching force is actuated once the leaflet is with barbs is held in a desirable position by the indicator arm 4450. The lower pinching force of the indicator arm 4450 reduces the force imparted onto the leaflet tissue so that the indicator arm 4450 can be repositioned repeatedly and be less likely to puncture or otherwise damage the leaflet tissue. The lower pinching force also allows the indicator arm 4450 to pulse or jump as the heart beats.

Figure 48:
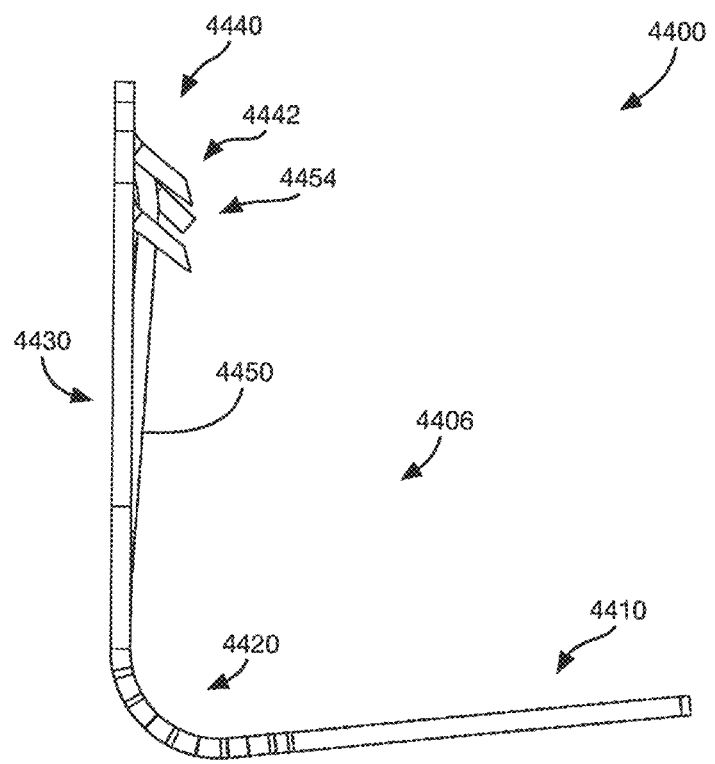
FIGS. 48-61 show an example embodiment of a clasp for an implantable prosthetic device.
Figure 49:
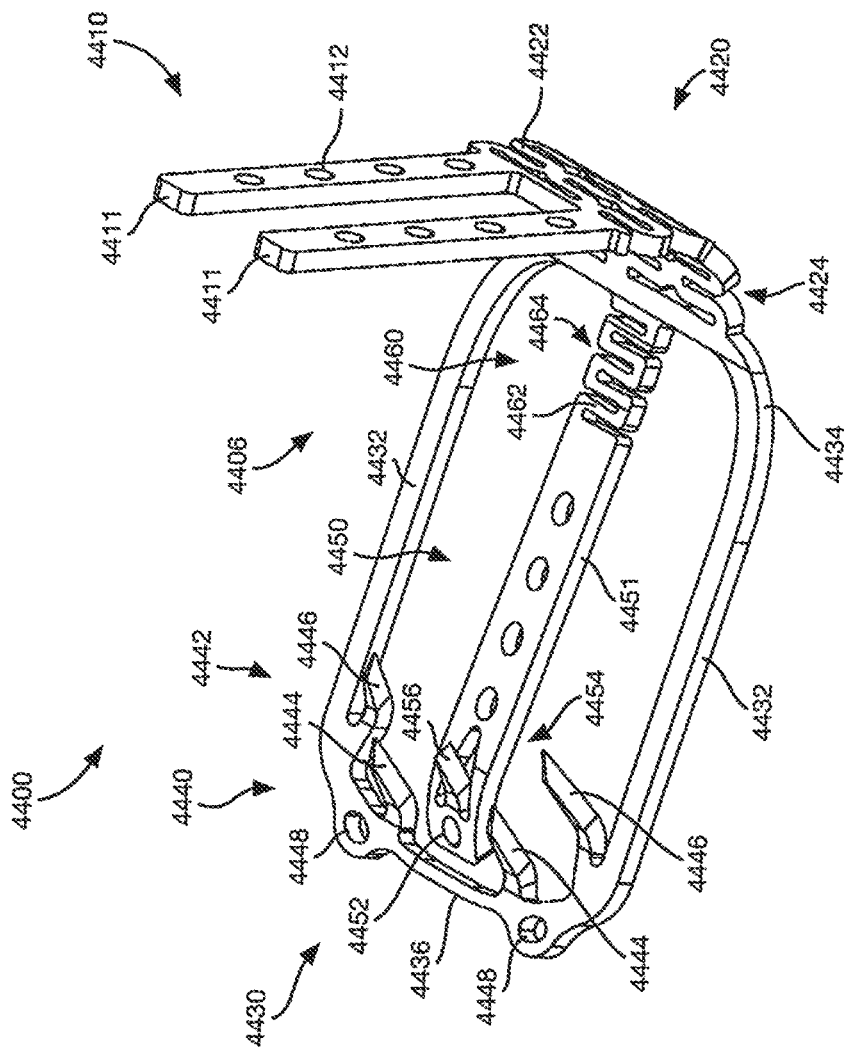
Figure 50:
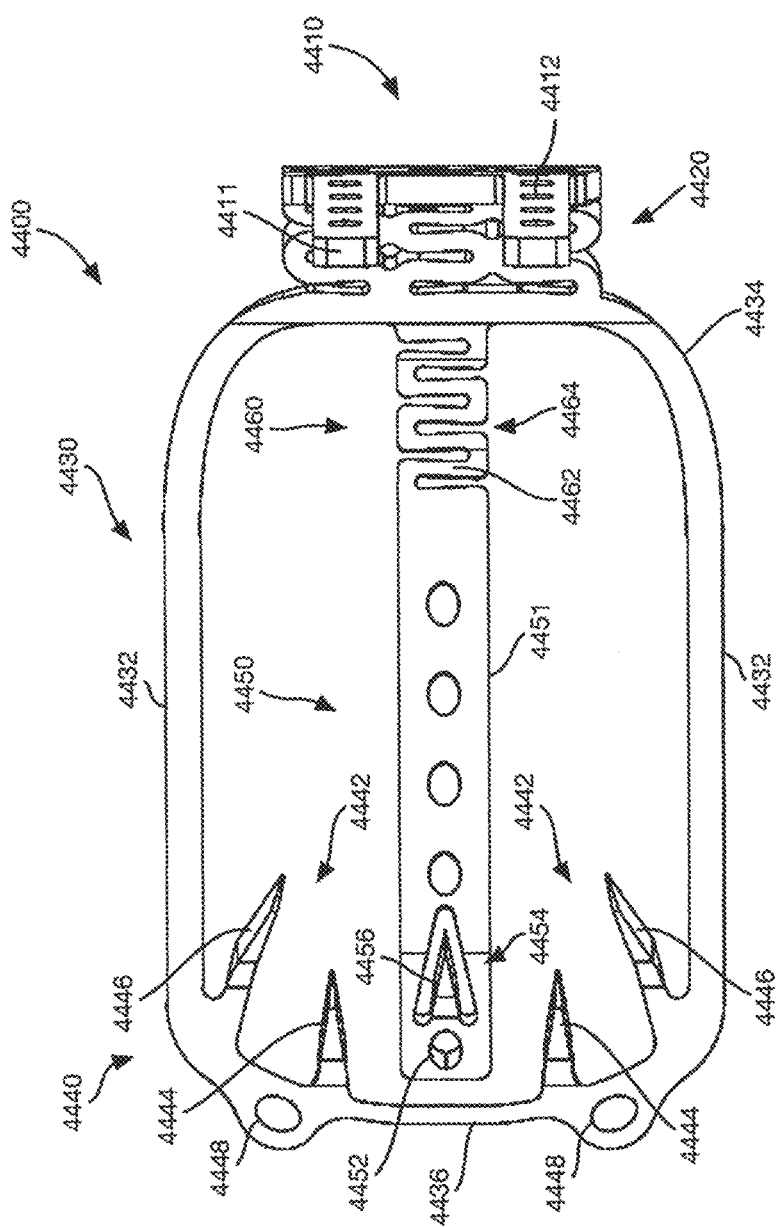

Referring now to FIGS. 48-50, the clasp or clasp 4400 is shown in an open position. The moveable arm 4430 and indicator arm 4450 are biased or spring-loaded in a closing direction and are moved to and held in the open position by tension applied to actuation lines (not shown) attached to the holes 4448, 4452 in each of the moveable arm 4430 and indicator arm 4450, respectively.

Figure 51:
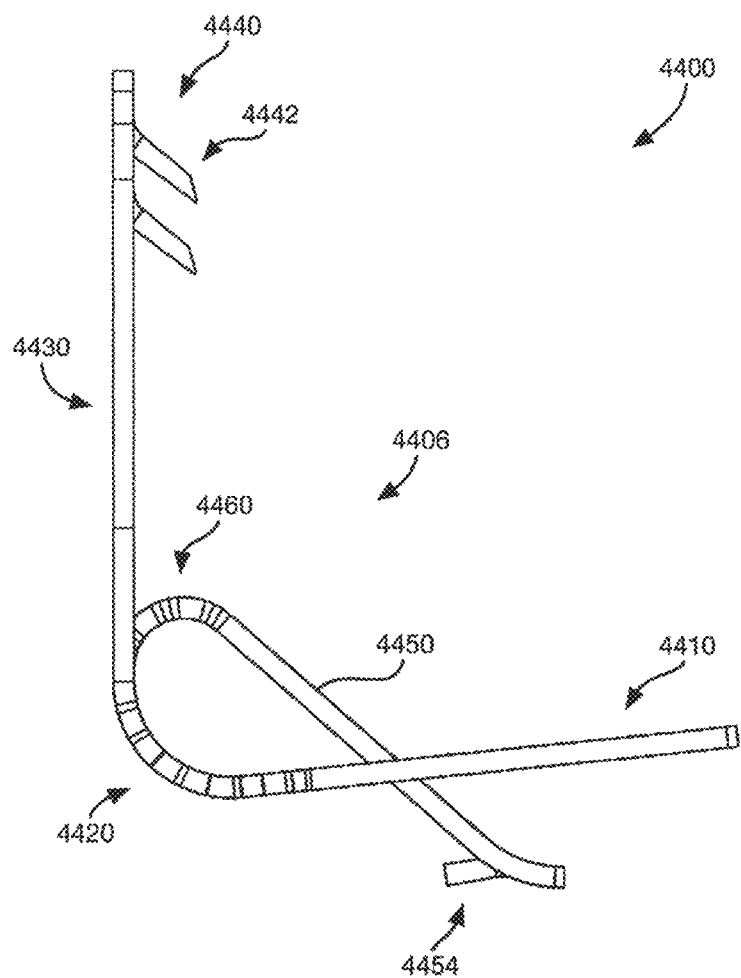
Figure 52:
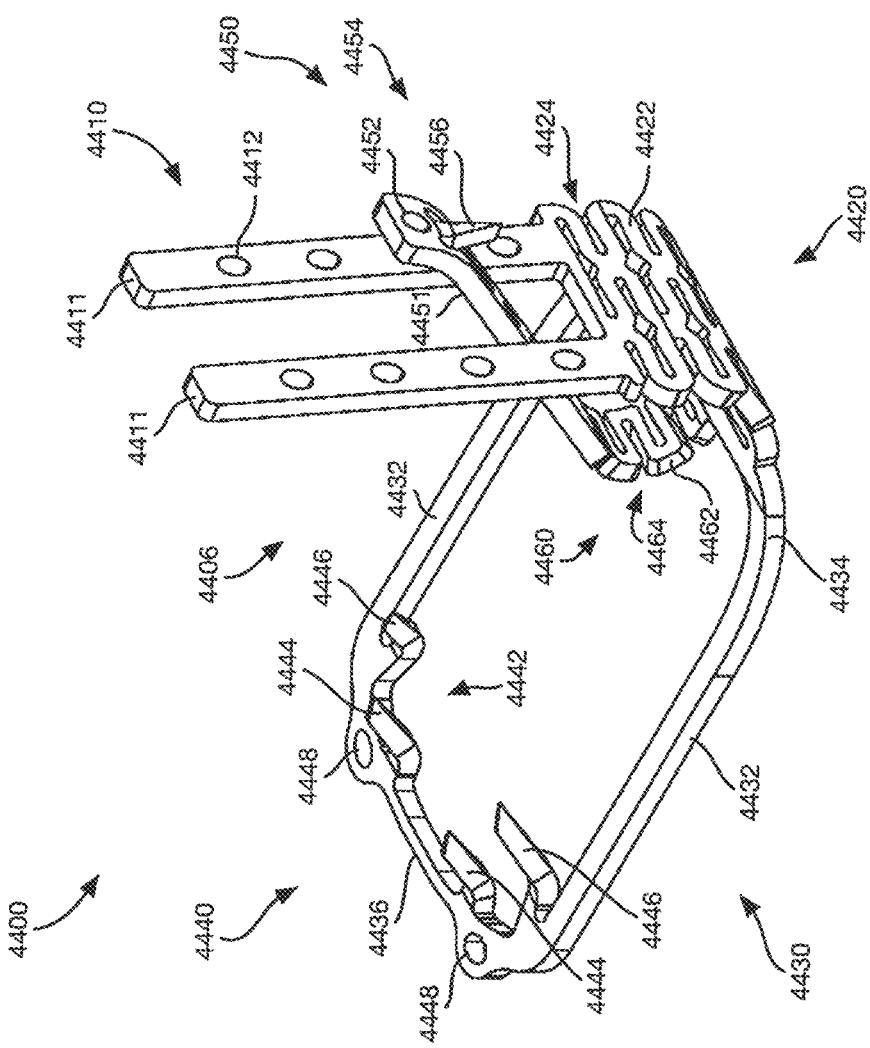

Referring now to FIGS. 51-52, the clasp or barbed clasp 4400 is shown with the indicator arm 4450 in a fully deployed or actuated position, that is, the furthest extent that the indicator arm 4450 is capable of reaching when the indicator arm 4450 does not engage with the leaflet tissue during actuation. The indicator arm 4450 is allowed to actuate in the closing direction when tension on actuation lines (not shown) attached to the hole 4452 in the end of the indicator arm 4450 is decreased. In the fully actuated position, the indicator arm 4450 forms an X-shape with the fixed arm 4410 that is visible via imaging devices so that the operator knows that the indicator arm 4450 has not engaged the leaflet.

Figure 53:
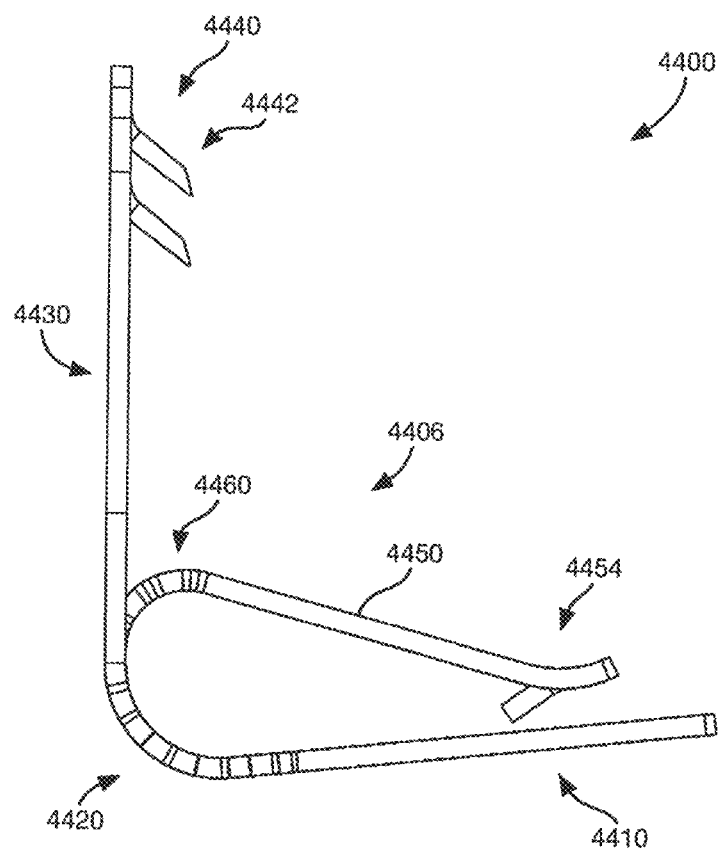
Figure 54:
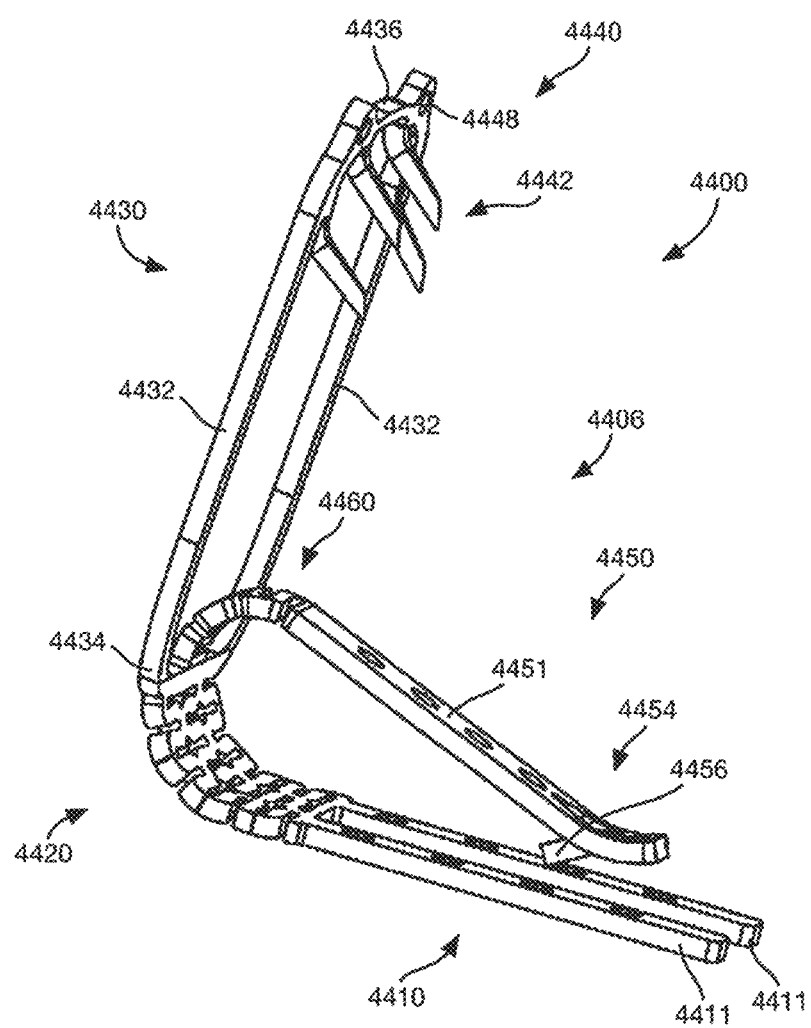
Figure 55:
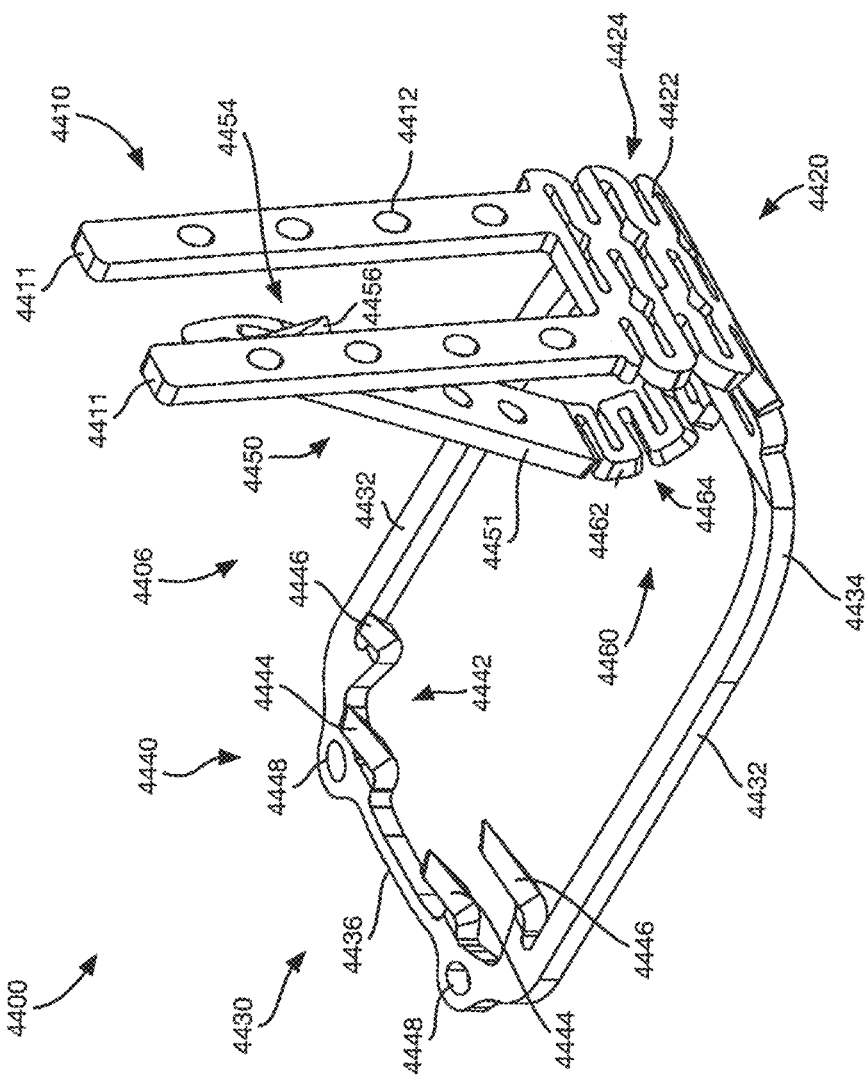

Referring now to FIGS. 53-55, the clasp or barbed clasp 4400 is shown with the indicator arm 4450 in an engaged or closed position. That is, the position that the indicator arm 4450 would be in when the leaflet tissue has been engaged during actuation. The indicator arm 4450 is allowed to actuate in the closing direction when tension on actuation lines (not shown) attached to the hole 4452 in the end of the indicator arm 4450 is decreased. In the closed position, the indicator arm 4450 does not cross the fixed arm 4410 and does not form an X-shape with the fixed arm 4410. Thus, the operator knows that the indicator arm 4450 has engaged the leaflet tissue when the indicator arm 4450 has been actuated and no X-shape is visible when the clasp 4400 is viewed with an imaging device. In addition, or instead, the indicator arm 4450 can be optically monitored to detect pulsing or jumping of the indicator arm as the heart beats. This jumping or bouncing of the indicator arm indicates to the operator that the indicator arm has engaged leaflet tissue.

Figure 56:
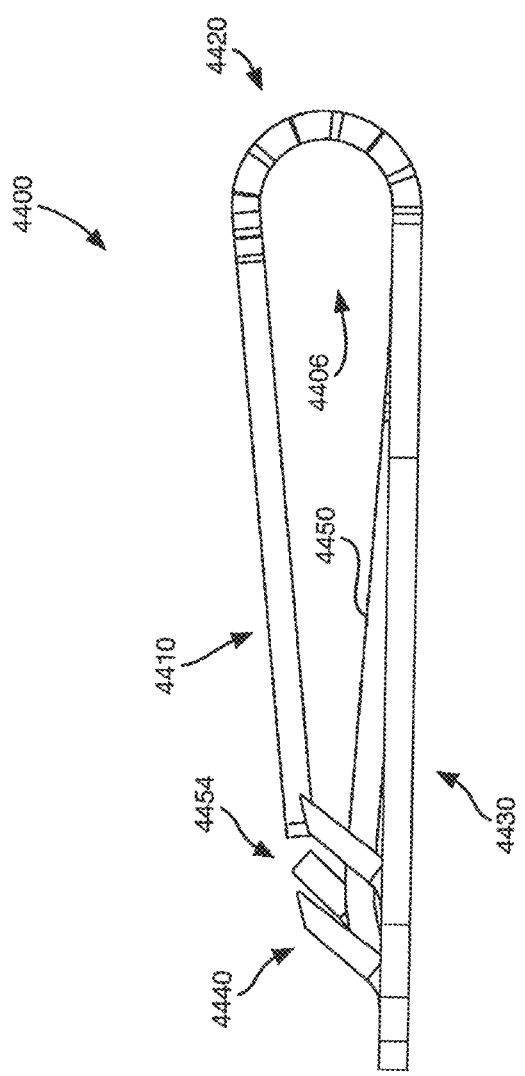
Figure 57:
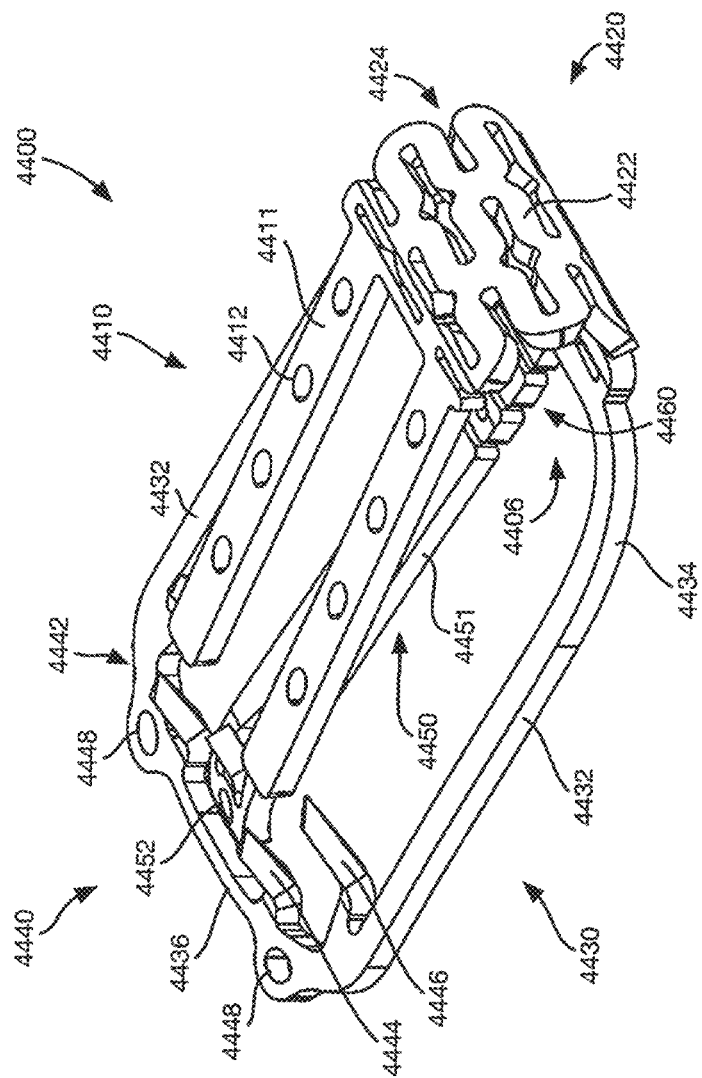
Figure 58:
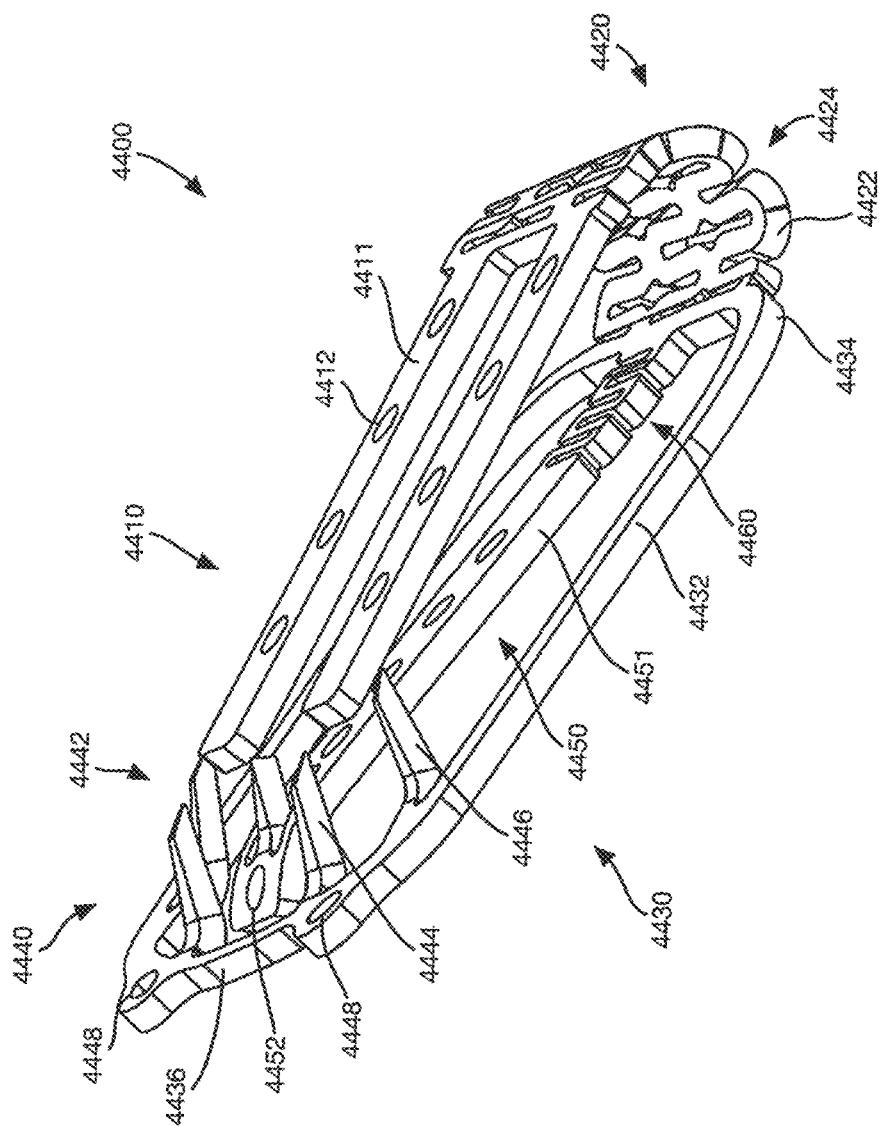

Referring now to FIGS. 56-58, the clasp or barbed clasp 4400 is shown with the moveable arm 4430 and the indicator arm 4450 both in a closed position. When the clasp 4400 is closed, the moveable arm 4430 and the indicator arm 4450 exert a pinching force that retains the native leaflet tissue to be secured within the clasp 4400. Additionally, a tortuous path for retaining the captured leaflet tissue is formed by the fixed arm 4410, the moveable arm 4430, and the barbed portion 4440. The clasp 4400 is biased in the closed direction by the shape-setting of the moveable arm 4430 and the indicator arm 4450 in preloading positions (FIGS. 59-61).

Figure 59:
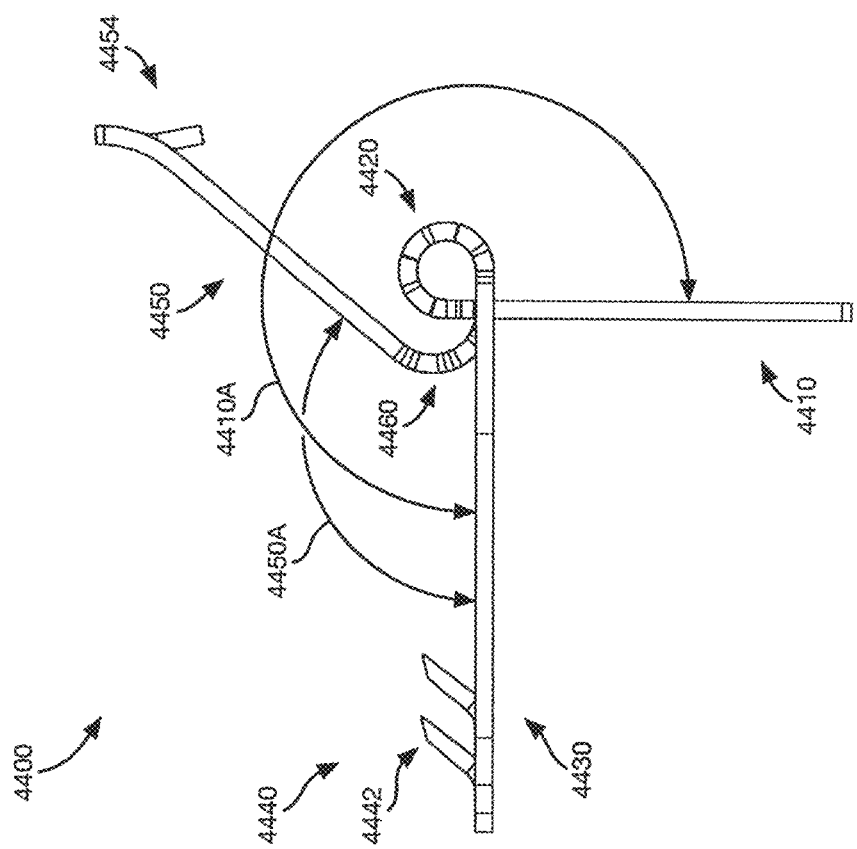
Figure 60:
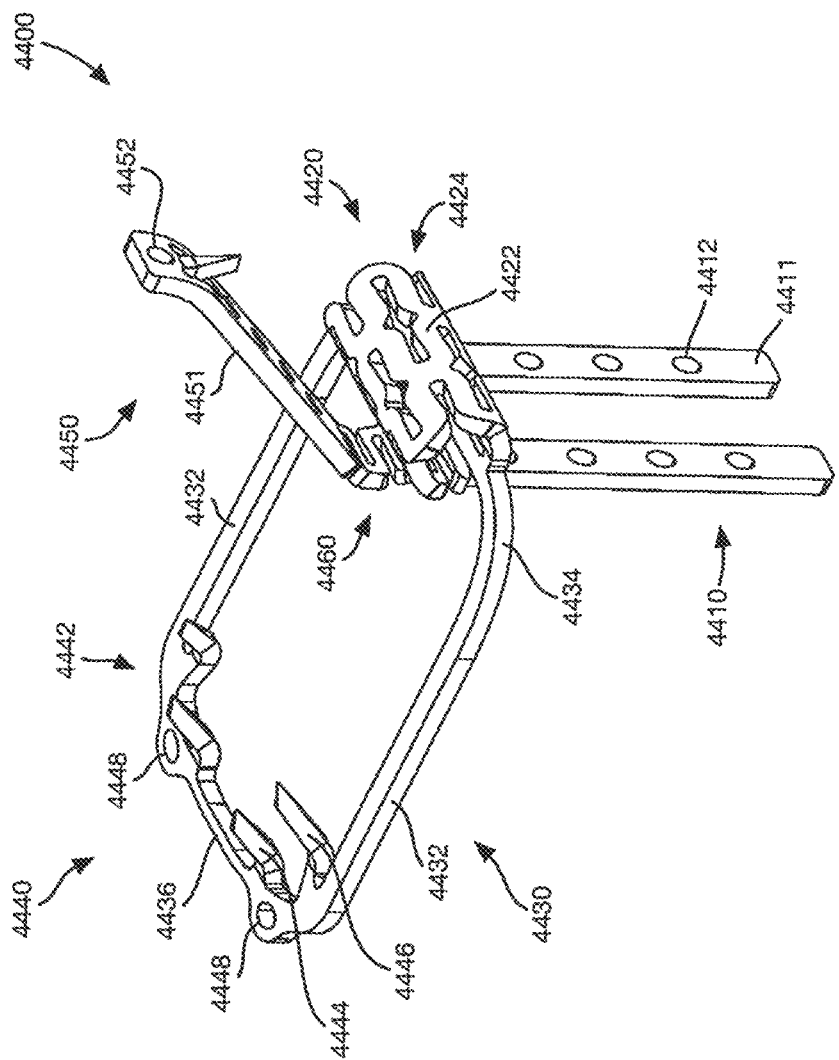
Figure 61:
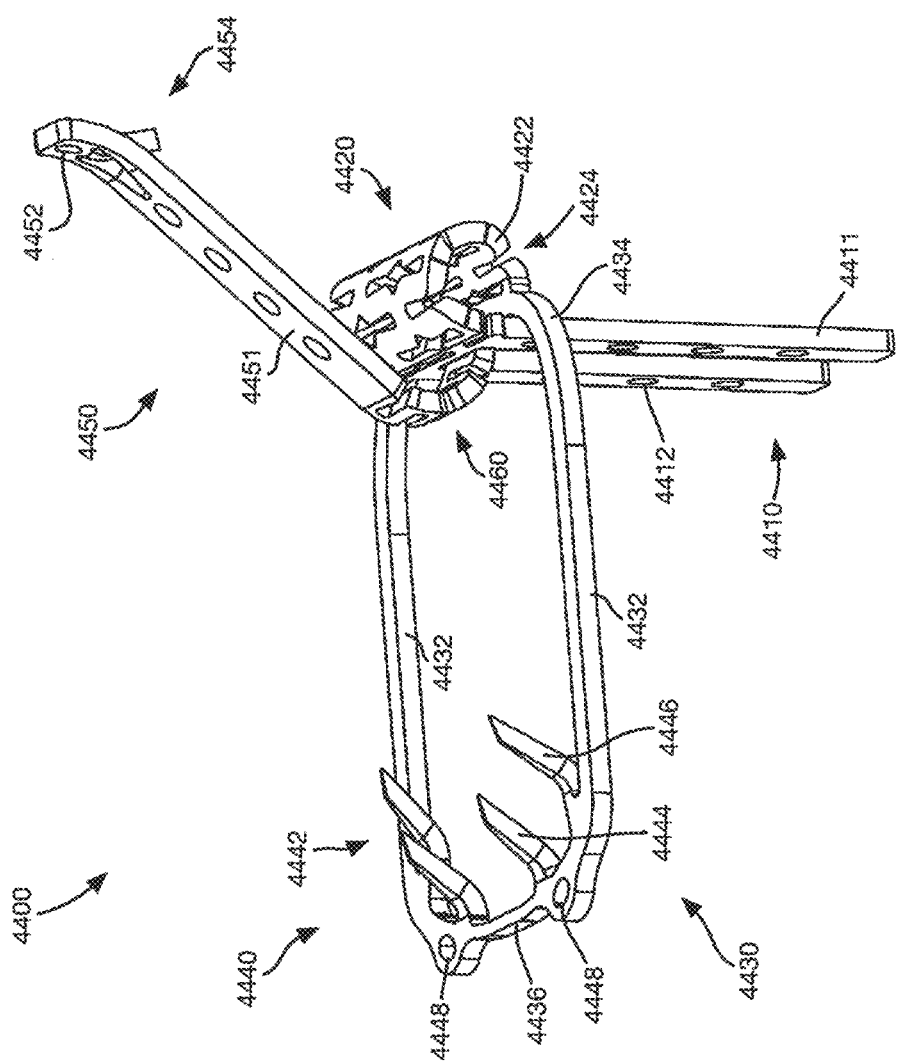

Referring now to FIGS. 59-61, the clasp 4400 is shown with the fixed arm 4410 and the indicator arm 4450 in a shape-setting or preloading position. As has been discussed with respect to other embodiments, shape-setting of the fixed arm 4410 and the indicator arm 4450 relative to the moveable arm 4430 forms a pinching force between the components of the clasp 4400 when the clasp 4400 is in the closed position.

Referring now to FIG. 59, the fixed arm 4410 is shape set at an angle 4410A from the moveable arm 4430. In certain embodiments, the angle 4410A between the neutral and shape-set positions of the tongues 4411 of the fixed arm 4410 is between about 180 to about 270 degrees, or about 270 degrees. To move the fixed arm 4410 into the shape set position, the fixed arm 4410 is bent upward and the tongues 4411 of the fixed arm 4410 are passed through openings in the moveable arm 4430 formed between the side beams 4432 and the indicator arm 4450.

Referring again to FIG. 59, the indicator arm 4450 is shape set at an angle 4450A from the moveable arm 4430. In certain embodiments, the angle 4450A between the neutral and shape-set positions of the beam 4451 of the indicator arm 4450 is between about 90 degrees to about 180 degrees, or between about 100 degrees and about 150 degrees, or about 135 degrees. The shape set position of the indicator arm 4450 is selected such that the indicator arm 4450 will pass between the tongues 4411 of the fixed arm 4410 to form the X-shape described above.

Figure 62:
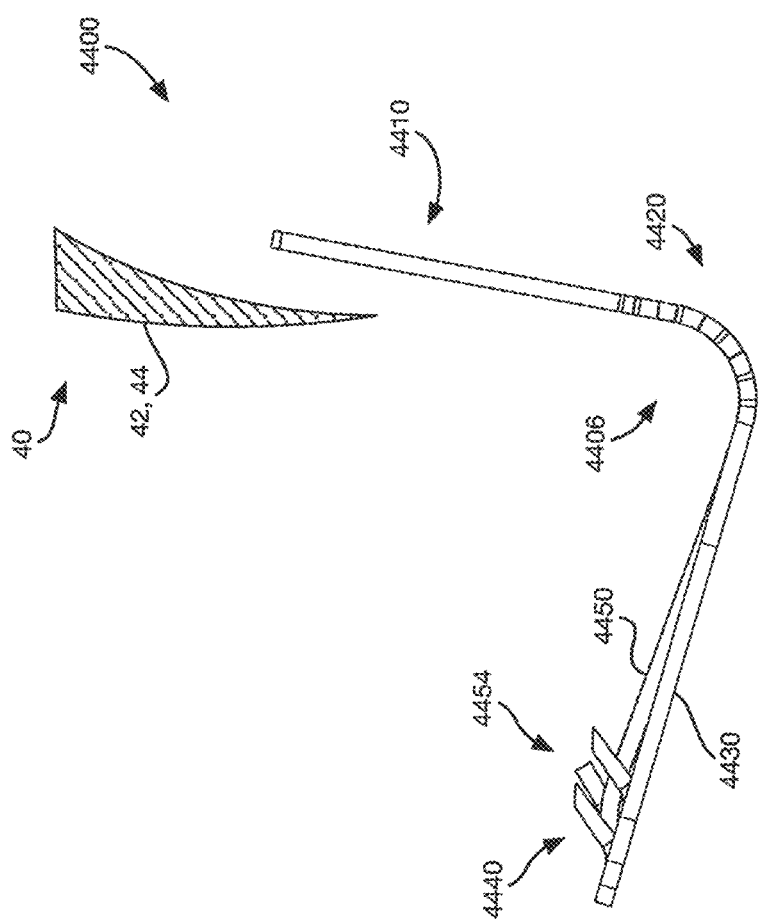
FIGS. 62-66 show an example clasp (which can be configured to be the same as or similar to other barbed clasps herein) being deployed to engage with a leaflet of a native valve.
Figure 63:
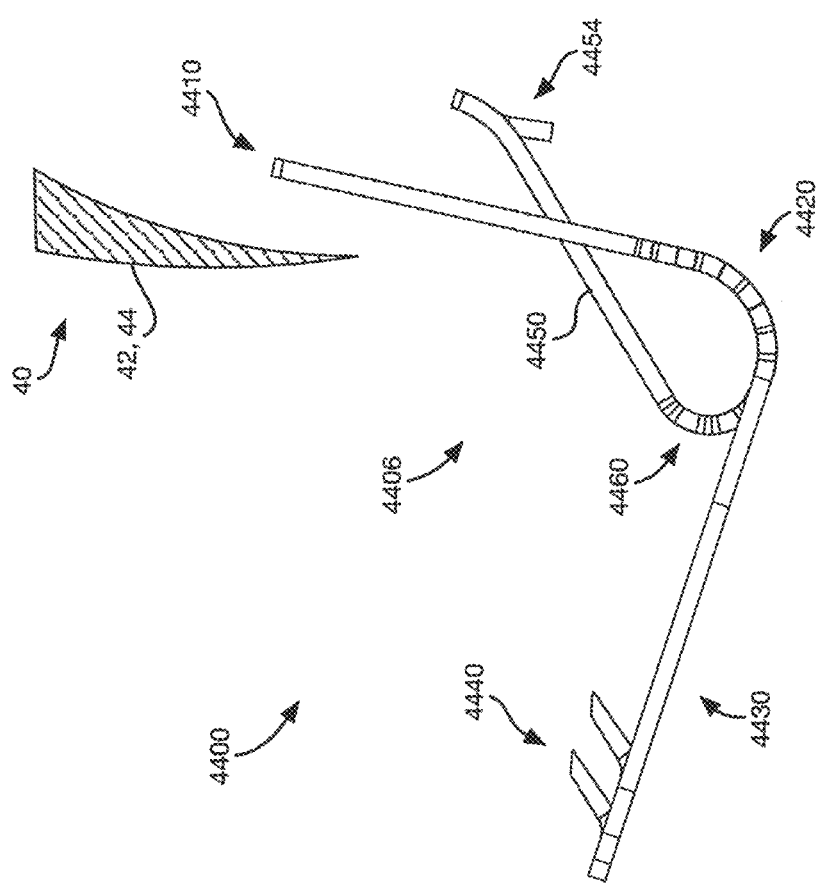
Figure 64:
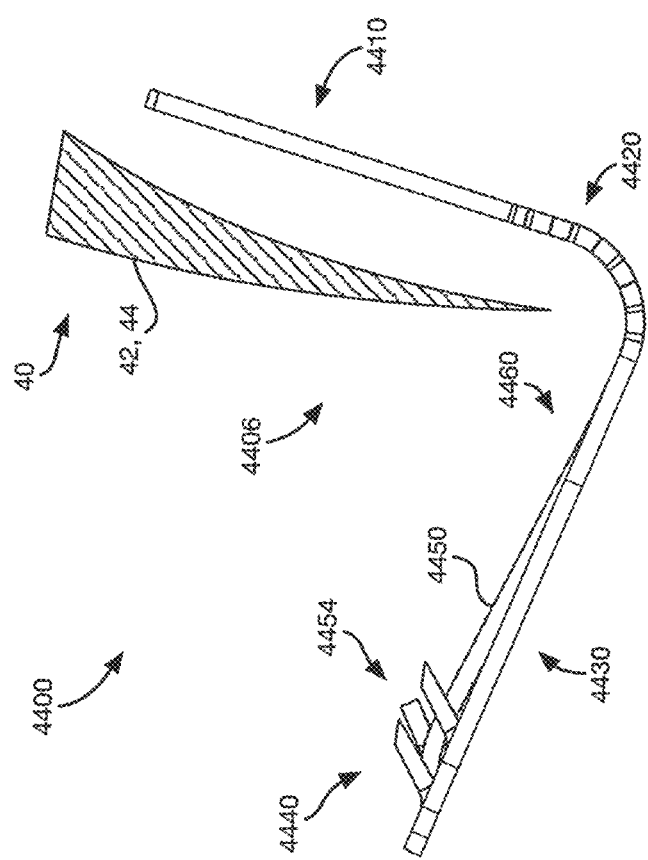
Figure 65:
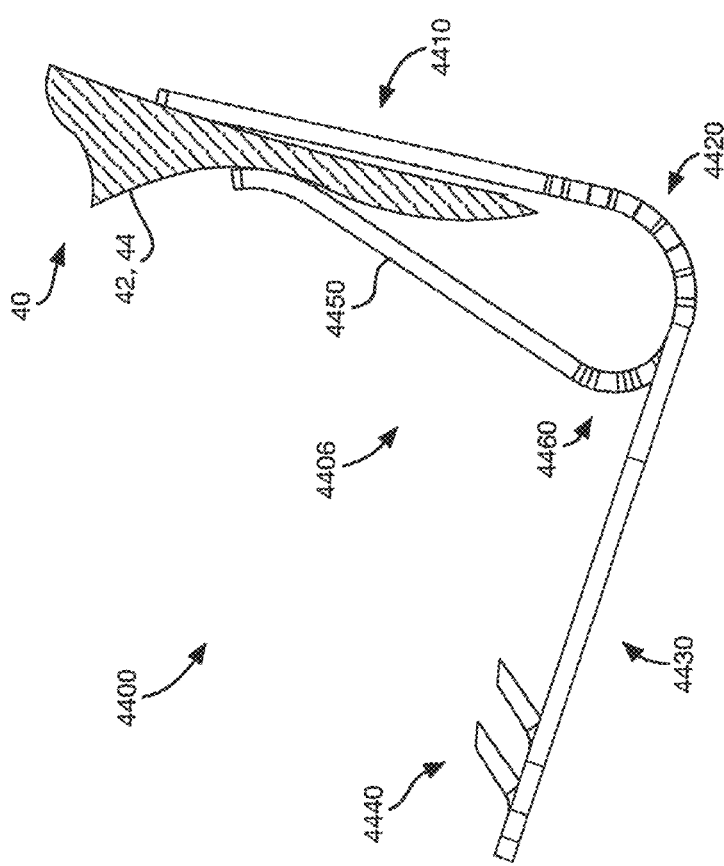

Referring now to FIGS. 62-66, the example clasp or barbed clasp 4400 is shown being deployed within a native valve 40 to secure an implantable device (not shown), such as the devices 100, 200, 300 described above, to one of the native leaflets 42, 44. Referring now to FIG. 62, the clasp 4400 is shown in an open condition with a native leaflet 42, 44 partially inserted into the opening 4406 of the clasp 4400 formed between the fixed and moveable arms 4410, 4430. To determine whether the leaflet 42, 44 has reached the desired engagement depth, the indicator arm 4450 is actuated via actuation lines (see FIG. 41) as shown in FIGS. 63 and 65.

Referring now to FIG. 63, the indicator arm 4450 is actuated by releasing tension on an actuation line (see FIG. 41) connected to the hole 4452 at the end of the indicator arm 4450. Because the leaflet 42, 44 is not at or beyond the minimum engagement depth the indicator arm 4450 misses or slips off of the leaflet 42, 44 and moves to a fully actuated position that is beyond the fixed arm 4410 of the clasps 4400. The indicator arm 4450 crosses the fixed arm 4410 to form an X-shape that is visible via imaging devices used to monitor implantation and deployment of the prosthetic device.

Referring now to FIG. 64, the indicator arm 4450 is retracted by applying tension to the actuation line and the clasp 4400 is repositioned so that the leaflet 42, 44 is more deeply inserted into the opening 4406 of the clasp 4400. The indicator arm 4450 is then actuated by releasing tension on the actuating line, as can be seen in FIG. 65. Because the leaflet 42, 44 has been inserted into the clasp 4400 at or beyond the minimum desired engagement depth, the indicator arm 4450 engages and pinches the leaflet 42, 44 against the fixed arm 4410. Engagement with the leaflet 42, 44 prevents the indicator arm 4450 from moving past the fixed arm 4410 of the clasp 4400 to form the X-shape shown in FIG. 63. In addition, or instead, the indicator arm 4450 can be optically monitored to detect pulsing or jumping of the indicator arm as the heart beats. This jumping or bouncing of the indicator arm indicates to the operator that the indicator arm has engaged leaflet tissue. Thus, the indicator arm 4450 indicates to an observer observing the installation via an imaging device that the leaflet 42, 44 is inserted into the opening 4406 beyond the minimum desired engagement depth that is determined by the length of the indicator arm 4450.

Figure 66:
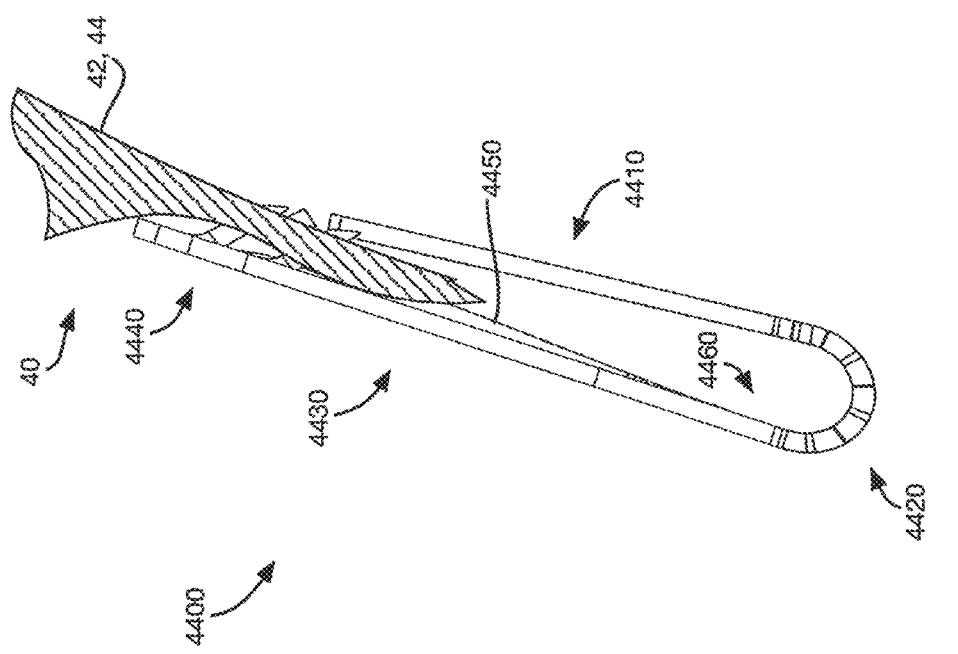

Referring now to FIG. 66, once the indicator arm 4450 indicates that the leaflet 42, 44 is sufficiently inserted into the opening 4406, the moveable arm 4430 is actuated by releasing tension on the actuating line so that the leaflet 42, 44 is pinched between the barbed portion 4440 and the fixed arm 4410 to secure the leaflet 42, 44 firmly within the clasp 4400.

Referring now to FIGS. 84-102, example clasps (often illustrated as barbed clasps, though other friction-enhancing elements other than barbs can be used) are shown with indicating features that are altered by engagement with the native leaflet tissue. For example, the clasps may include bumps or protrusions that flatten when the native leaflet tissue is pressed against the bump. The bump is sufficient in size to be visible via imaging devices so that absence of the bump indicates that the bump has been pressed against the native leaflet tissue. Thus, the engagement depth of the native leaflet can be determined by the position of the bump and whether the bump is visible.

Figure 84:
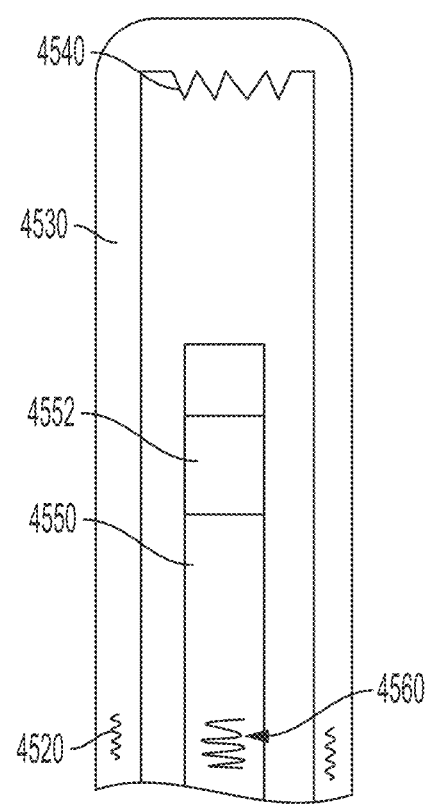
FIG. 84 shows an example embodiment of a clasp having an indicator arm with a curved indicator, for an implantable prosthetic device.

Referring now to FIG. 84, an example embodiment of a portion of a laser cut clasp is illustrated. The clasp can have a moveable arm 4530, a barbed region 4540, and an indicator arm 4550. The moveable arm and the indicator arm each have flexible portions or hinge portions 4520, 4560, respectively. The flexible region 4520 of the moveable arm permits the clasp to be configured to the proper shape for implantation and/or to permit the moveable arm to close on to a fixed arm (see FIGS. 85-89). The flexible region 4560 of the indicator arm permits the indicator arm to drop onto the leaflet and/or to bounce on the leaflet. The indicator arm 4550 can have a flexible bump 4552 on it, that can be flattened to indicate that the leaflet is positioned a sufficient depth within the clasp. The bump 4552 can be positioned at a location on the indicator arm between the free end of the indicator arm and the flexible region 4560. The clasp of which a portion is illustrated in FIG. 84 operates in the manner explained regarding FIGS. 85-89.

Figure 86:
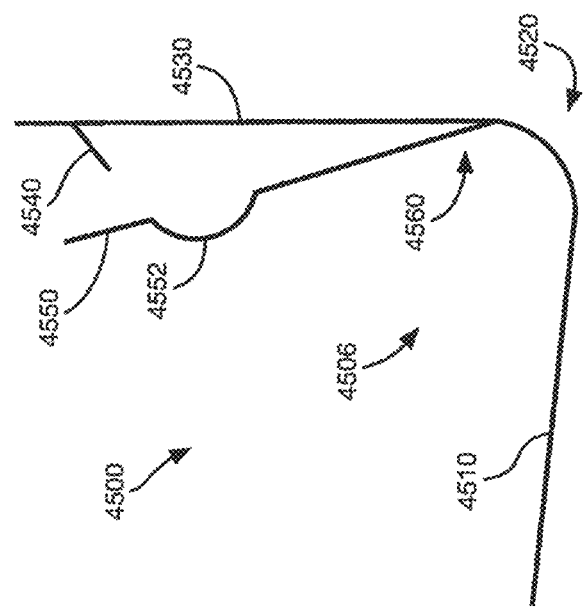
FIGS. 85-86 show schematic views of the example clasp of FIG. 84.
Figure 85:
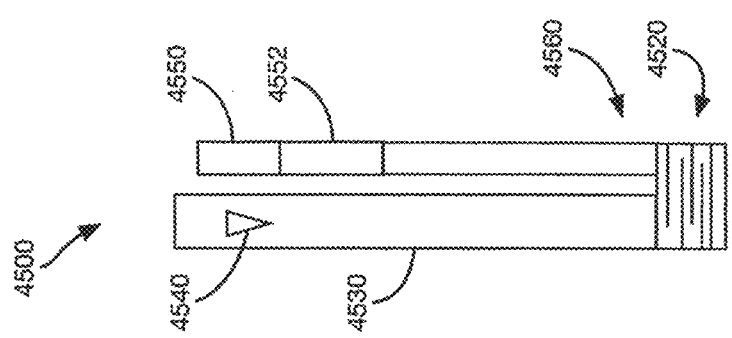

Referring now to FIGS. 85-86, an example clasp 4500 for use in implantable prosthetic devices, such as devices 100, 200, 300 described above, is shown. Like the clasp 3500 described above, the clasp 4500 includes a fixed arm 4510, a joint, flex, or hinge portion 4520, a moveable arm 4530 having a barbed portion 4540 (though other friction-enhancing portions can be used), and an indicator arm 4550 connected to the joint, flex, or hinge portion 4520 via an indicator flex or hinge portion 4560. The indicator arm 4550 includes an indicating feature or bump 4552 that deforms when pressed against the native leaflet tissue to indicate that the leaflet tissue has reached a desired engagement depth. Thus, the indicating feature 4552 will not indicate that the native leaflet has reached a minimum desired engagement depth until the leaflet is inserted at or beyond the location of the indicating feature 4552. Once the leaflet 42, 44 has reached the desired engagement depth, actuation of the indicator arm 4550 presses the indicating feature 4552 against the leaflet tissue 42, 44 to cause the indicating feature 4552 to flatten and thereby indicate that the leaflet 42, 44 has been inserted into the clasp 4500 at or beyond the desired engagement depth. The clasp 4500 can be used in any of the implantable prosthetic devices of the present application and can include any of the features or combinations of features of the other clasps described herein.

Figure 87:
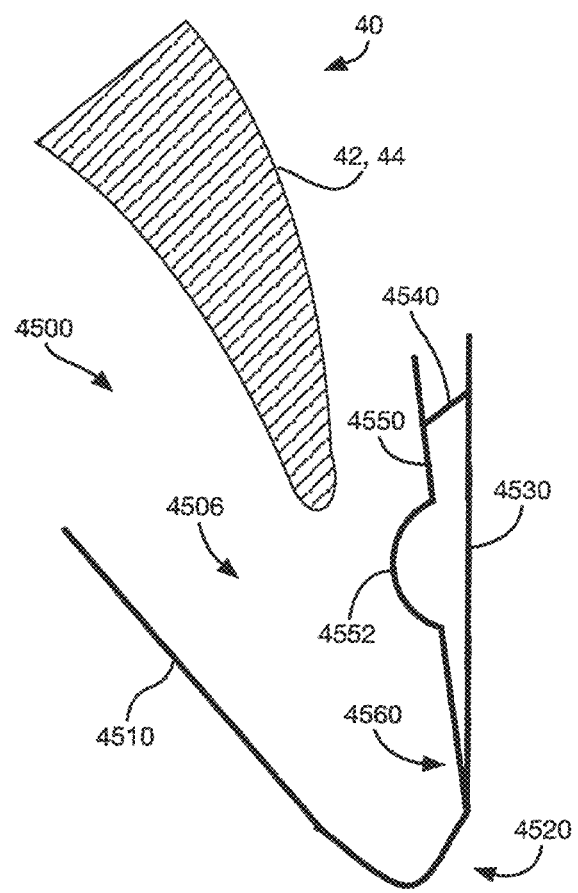
FIGS. 87-90 show the example clasp of FIGS. 85-86 being deployed to engage with a leaflet of a native valve.
Figure 88:
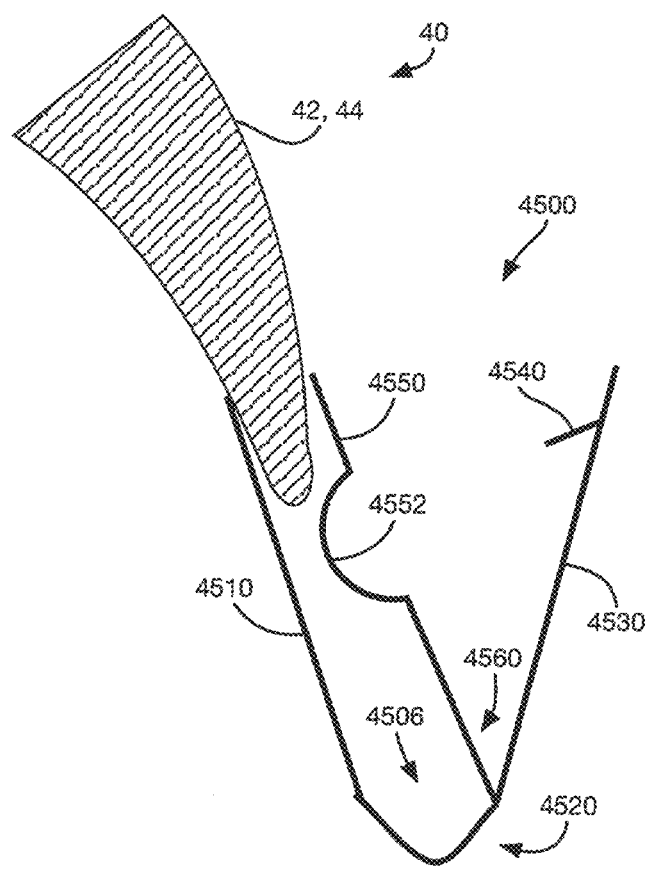
Figure 89:
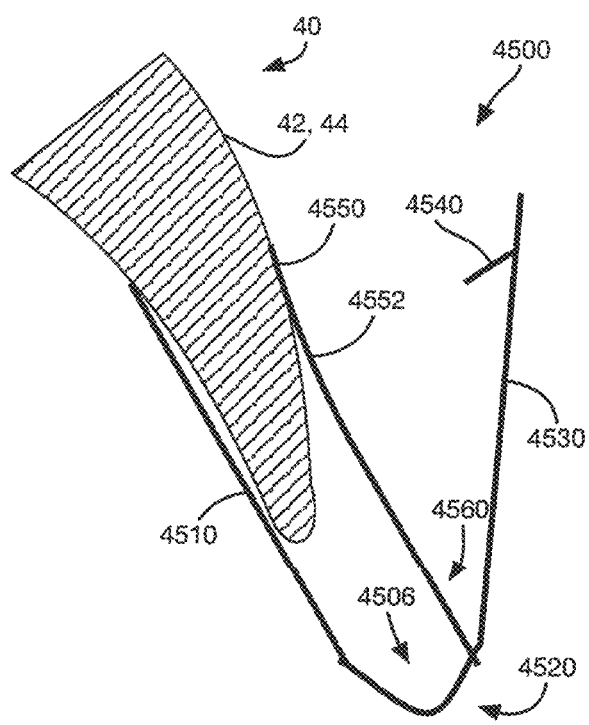

Referring now to FIGS. 87-90, the example clasp 4500 is shown being deployed within a native valve 40 to secure an implantable device (not shown), such as the devices 100, 200, 300 described above, to one of the native leaflets 42, 44. Referring now to FIG. 87, the clasp 4500 is shown in an open condition with a native leaflet 42, 44 partially inserted into an opening 4506 of the clasp 4500 formed between the fixed and moveable arms 4510, 4530. To determine whether the leaflet 42, 44 has reached the desired engagement depth, the indicator arm 4550 is actuated via actuation lines (see FIG. 133) as shown in FIGS. 88-89.

Figure 90:
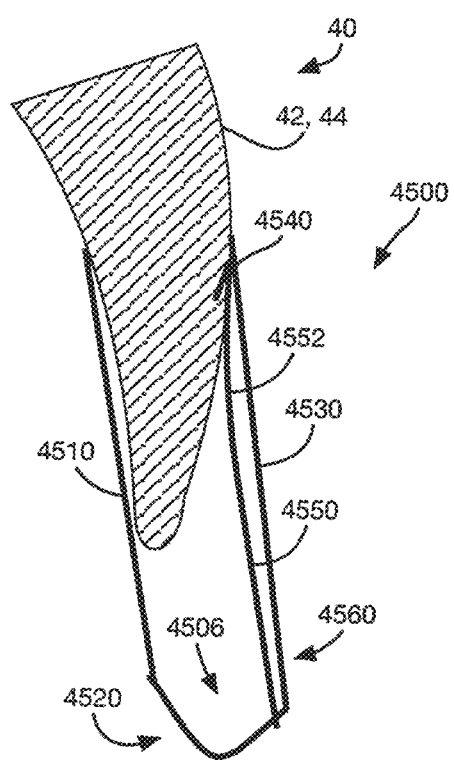

Referring now to FIG. 88, when the indicator arm 4550 is actuated to press the leaflet 42, 44 against the fixed arm 4510, a portion of the indicator arm 4550 may contact the leaflet 42, 44 without contacting the indicating feature 4552 when the engagement depth of the leaflet 42, 44 is less than the minimum engagement depth. As can be seen in FIG. 89, the indicating feature 4552 is deformed or flattened from contact with the leaflet 42, 44 when the leaflet is inserted into the clasp 4500 at or beyond the minimum engagement depth. Referring now to FIG. 90, the indicating feature 4552 is deformed by the leaflet 42, 44 to indicate that the leaflet 42, 44 has been inserted at or beyond the minimum engagement depth. When the leaflet 42, 44 has been moved into the desired position, the moveable arm 4530 is actuated so that the leaflet 42, 44 can be secured within the barbed clasp 4500 by the barbed portion 4540.

Figure 92:
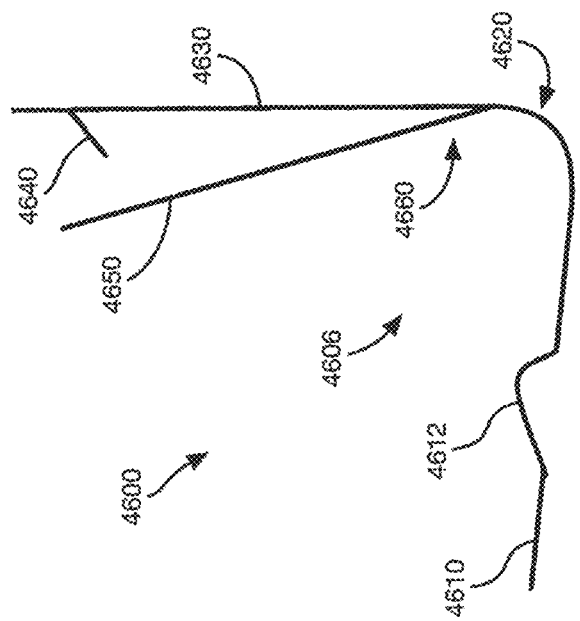
FIGS. 91-92 show a schematic view of an example embodiment of a clasp having an indicator arm and a flexible curve in the fixed arm as an indicator, for an implantable prosthetic device.
Figure 91:
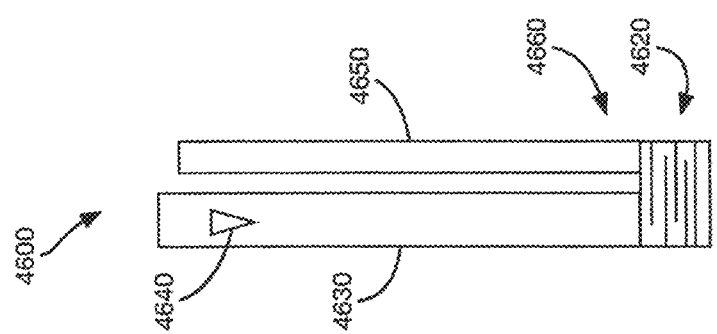

Referring now to FIGS. 91-92, an example clasp 4600 for use in implantable prosthetic devices, such as devices 100, 200, 300 described above, is shown. Like the clasp 3500 described above, the clasp 4600 includes a fixed arm 4610, a joint, flex, or hinge portion 4620, a moveable arm 4630 having a barbed portion 4640 (though other friction-enhancing portions can be used), and an indicator arm 4650 connected to the joint, flex, or hinge portion 4620 via an indicator flex or hinge portion 4660. The fixed arm 4610 includes an indicating feature or bump 4612 that deforms when the native leaflet tissue is pressed against the indicating feature 4612 by the indicating arm 4650 to indicate that the leaflet tissue has reached a minimum desired engagement depth. Thus, the indicating feature 4612 will not indicate that the native leaflet has reached the desired engagement depth until the leaflet is inserted at or beyond the location of the indicating feature 4612. Once the leaflet 42, 44 has reached the desired engagement depth, actuation of the indicator arm 4650 presses the leaflet tissue 42, 44 against the indicating feature 4612 to cause the indicating feature 4612 to flatten and thereby indicate that the leaflet 42, 44 has been inserted into the clasp 4600 at or beyond the desired engagement depth. The clasp 4600 can be used in any of the implantable prosthetic devices of the present application and can include any of the features or combinations of features of the other clasps described herein.

Figure 93:
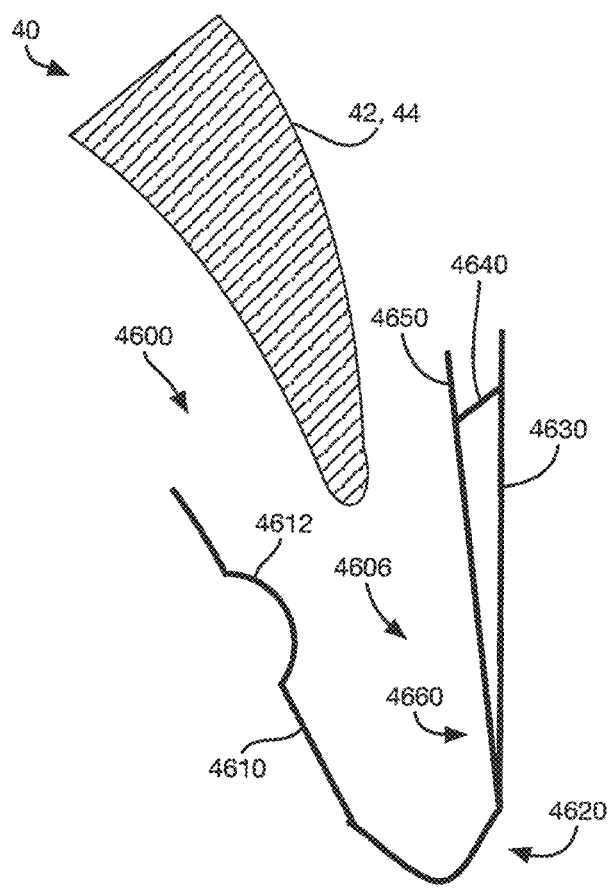
FIGS. 93-96 show the example clasp of FIGS. 91-92 being deployed to engage with a leaflet of a native valve.
Figure 94:
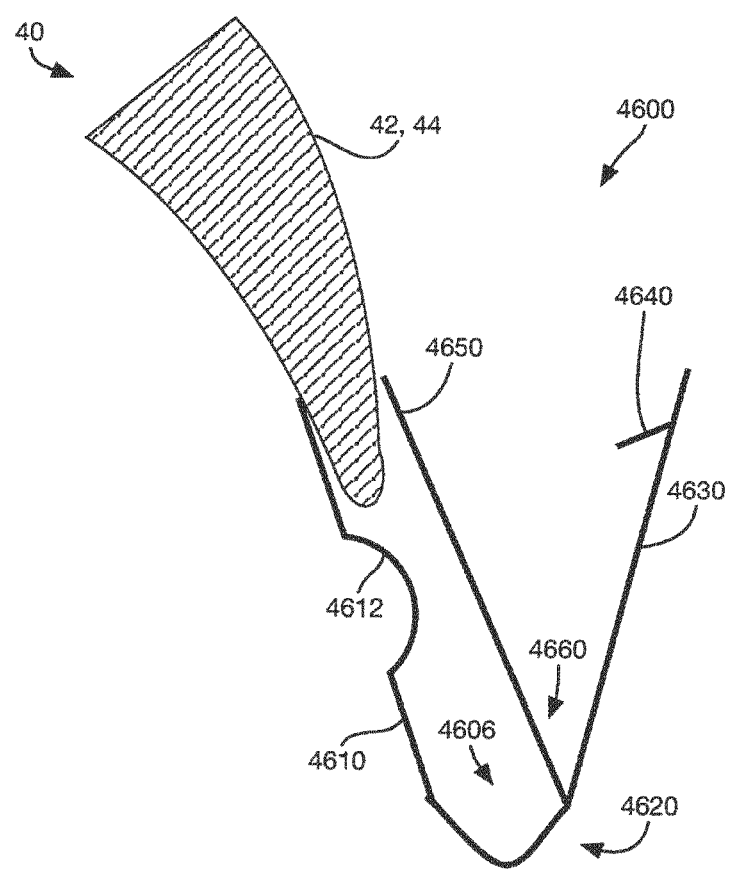
Figure 95:
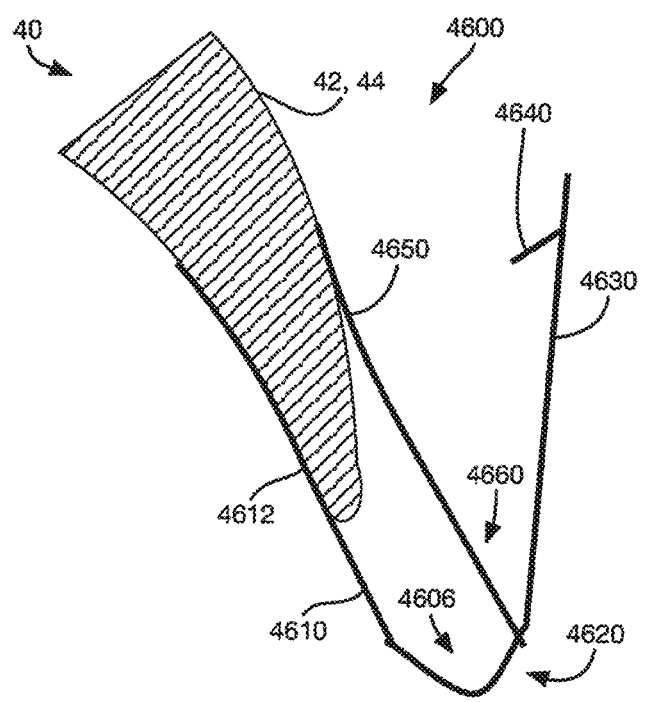

Referring now to FIGS. 93-94, the example clasp 4600 is shown being deployed within a native valve 40 to secure an implantable device (not shown), such as the devices 100, 200, 300 described above, to one of the native leaflets 42, 44. Referring now to FIG. 93, the clasp 4600 is shown in an open condition with a native leaflet 42, 44 partially inserted into an opening 4606 of the clasp 4600 formed between the fixed and moveable arms 4610, 4630. To determine whether the leaflet 42, 44 has reached the desired engagement depth, the indicator arm 4650 is actuated via actuation lines (not shown) as shown in FIGS. 94-95.

Figure 96:
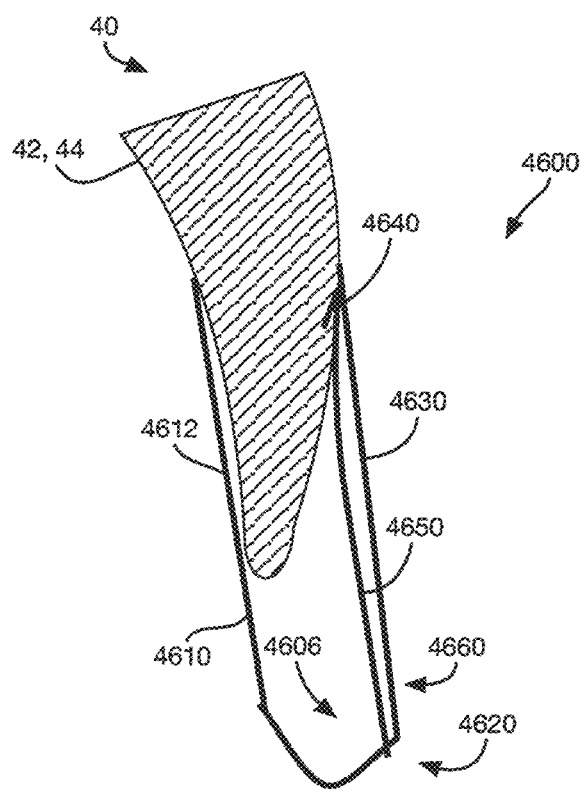

Referring now to FIG. 94, when the indicator arm 4650 is actuated to push the leaflet 42, 44 against the fixed arm 4610, the leaflet 42, 44 may contact a portion of the fixed arm 4610 without contacting the indicating feature 4612 when the engagement depth of the leaflet 42, 44 is less than the minimum engagement depth. As can be seen in FIG. 95, the indicating feature 4612 is deformed or flattened from contact with the leaflet 42, 44 when the leaflet is inserted into the clasp 4600 at or beyond the minimum engagement depth and is pressed against the indicating feature 4612 by the indicating arm 4650. Referring now to FIG. 96, the indicating feature 4612 is deformed by the leaflet 42, 44 to indicate that the leaflet 42, 44 has been inserted at or beyond the minimum engagement depth. When the leaflet 42, 44 has been moved into the desired position, the moveable arm 4630 is actuated so that the leaflet 42, 44 can be secured within the barbed clasp 4600 by the barbed portion 4640.

Figure 98:
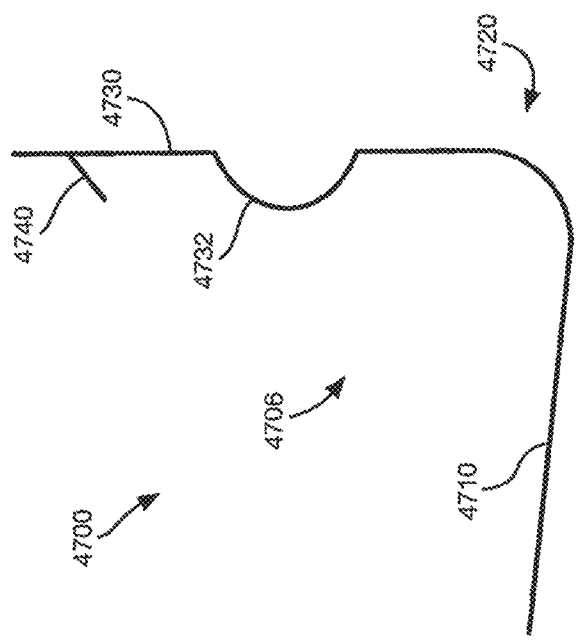
FIGS. 97-98 show a schematic view of an example embodiment of a clasp having a flexible curve indicator in the moveable arm, for an implantable prosthetic device.
Figure 97:
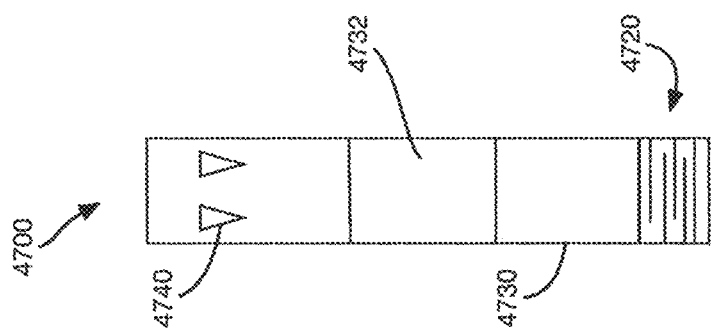

Referring now to FIGS. 97-98, an example clasp 4700 for use in implantable prosthetic devices, such as devices 100, 200, 300 described above, is shown. Like the clasp 3500 described above, the clasp 4700 includes a fixed arm 4710, a joint, flex, or hinge portion 4720, and a moveable arm 4730 having a barbed portion 4740 (though other friction-enhancing portions can be used). The moveable arm 4730 also includes an indicating feature or bump 4732 disposed between the barbed portion 4740 and the joint, flex, or hinge portion 4720. The indicating feature 4732 deforms when the native leaflet tissue is pressed against the indicating feature 4732 by the fixed arm 4710 to indicate that the leaflet tissue has reached a minimum desired engagement depth. Thus, the indicating feature 4732 will not indicate that the native leaflet has reached the desired engagement depth until the leaflet is inserted at or beyond the location of the indicating feature 4732. Once the leaflet 42, 44 has reached the desired engagement depth, actuation of the moveable arm 4730 squeezes the leaflet tissue 42, 44 between the fixed arm 4710 and the indicating feature 4732 to cause the indicating feature 4732 to flatten and thereby indicate that the leaflet 42, 44 has been inserted into the clasp 4700 at or beyond the desired engagement depth. The clasp 4700 can be used in any of the implantable prosthetic devices of the present application and can include any of the features or combinations of features of the other clasps described herein.

Figure 99:
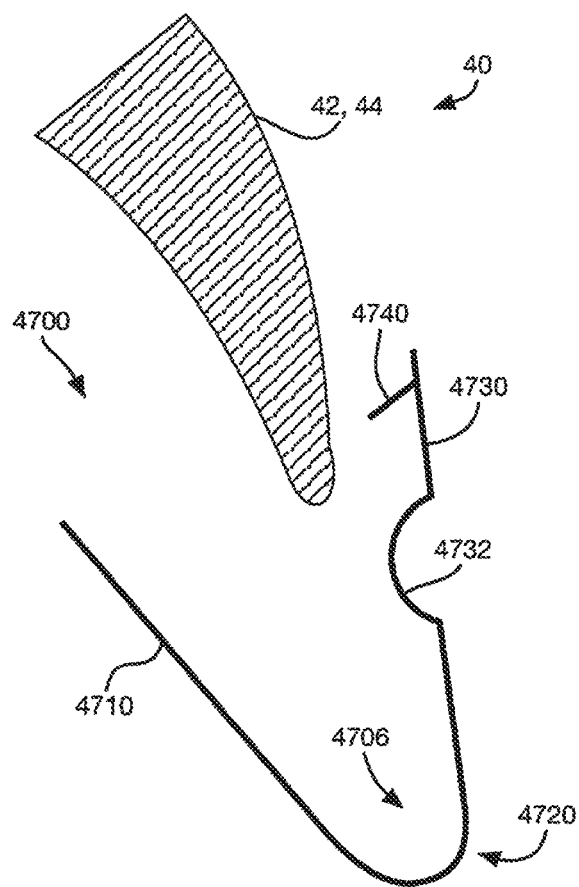
FIGS. 99, 100, and 100A show the example clasp of FIGS. 97-98 being deployed to engage with a leaflet of a native valve.
Figure 100:
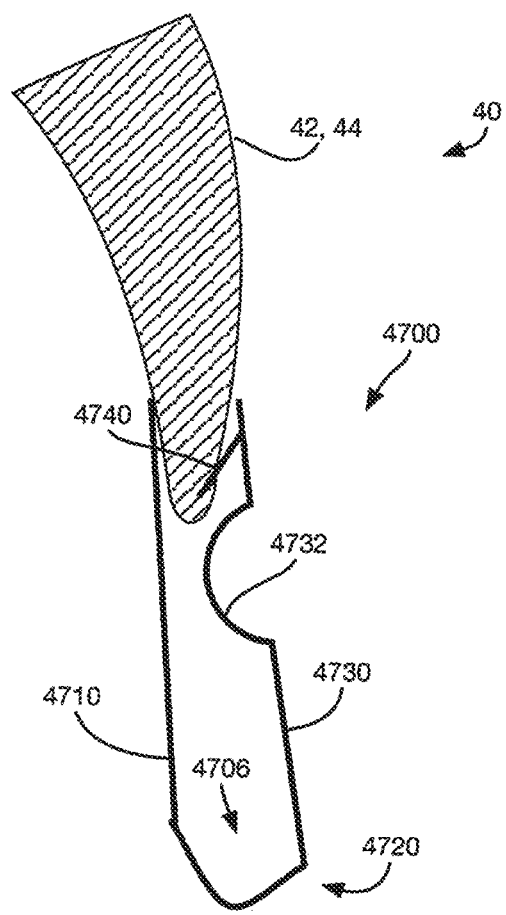

Referring now to FIGS. 99-100, the example barbed clasp 4700 is shown being deployed within a native valve 40 to secure an implantable device (not shown), such as the devices 100, 200, 300 described above, to one of the native leaflets 42, 44. Referring now to FIG. 99, the barbed clasp 4700 is shown in an open condition with a native leaflet 42, 44 partially inserted into an opening 4706 of the barbed clasp 4700 formed between the fixed and moveable arms 4710, 4730. To determine whether the leaflet 42, 44 has reached the desired engagement depth, the moveable arm 4730 is actuated via actuation lines (not shown) as shown in FIG. 100.

Referring FIG. 100, when the moveable arm 4730 is actuated to push the leaflet 42, 44 against the fixed arm 4710, the leaflet 42, 44 may contact a portion of the moveable arm 4730 without contacting the indicating feature 4732 when the engagement depth of the leaflet 42, 44 is less than the minimum desired engagement depth.

Figure 100A:
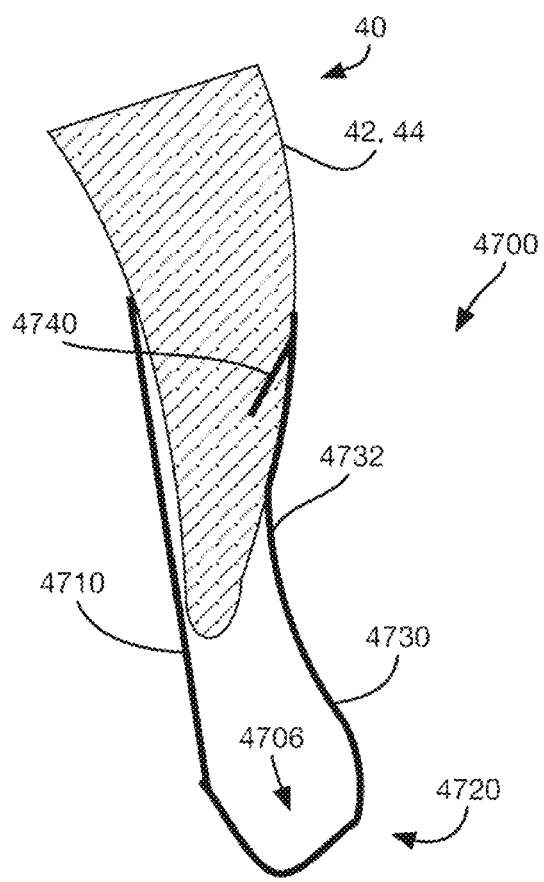

As can be seen in FIG. 100A, the indicating feature 4732 is deformed or flattened from contact with the leaflet 42, 44 when the leaflet 42, 44 is inserted into the clasp 4700 at or beyond the minimum engagement depth and is pressed against the indicating feature 4732. That is, the indicating feature 4732 is deformed by the leaflet 42, 44 to indicate that the leaflet 42, 44 has been inserted at or beyond the minimum engagement depth. In some embodiments, actuation of the moveable arm 4730 also causes the barbed portion 4740 to engage and secure the leaflet 42, 44 within the barbed clasp 4700. If the indicating feature 4732 indicates that the leaflet 42, 44 is not inserted to the desired depth, the clasp 4700 can be opened to allow for repositioning of the leaflet 42, 44.

Figure 101:
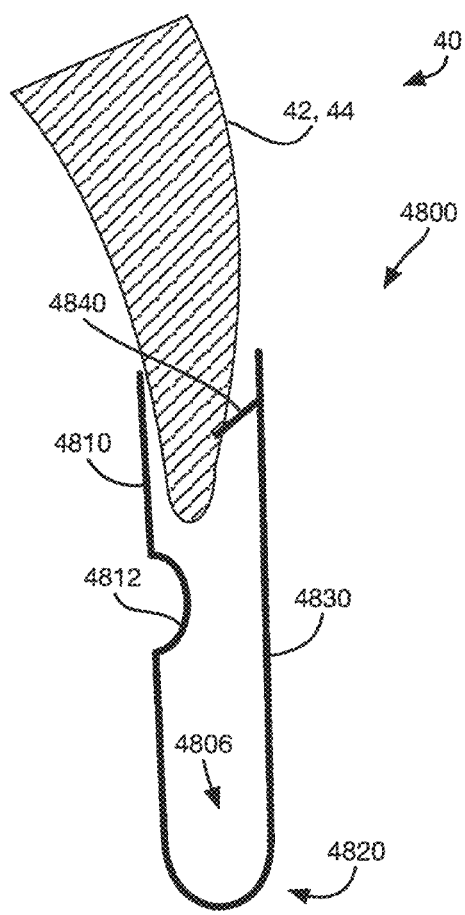
FIGS. 101 and 102 show a schematic view of an example embodiment of a clasp having a flexible curve indicator in the fixed arm, for an implantable prosthetic device.
Figure 102:
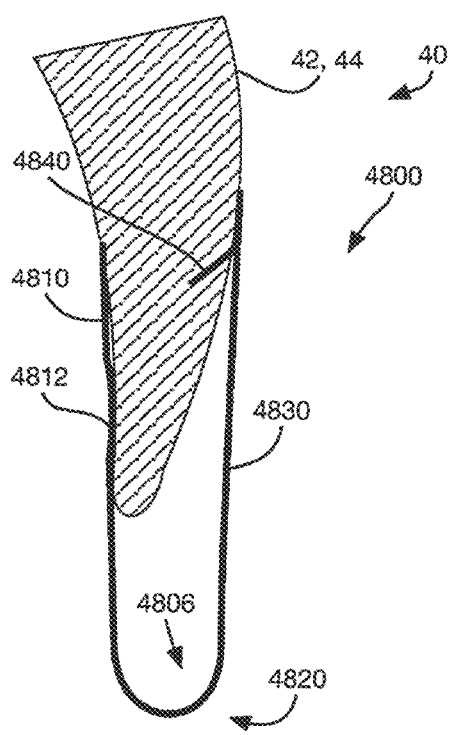

Referring now to FIGS. 101-102, an example clasp 4800 for use in implantable prosthetic devices, such as devices 100, 200, 300 described above, is shown. Like the clasp 3500 described above, the clasp 4800 includes a fixed arm 4810, a joint, flex, or hinge portion 4820, and a moveable arm 4830 having a barbed portion 4840 (though other friction-enhancing portions can be used). The fixed arm 4810 also includes an indicating feature or bump 4812 disposed at a distance from the joint, flex, or hinge portion that is less than a distance between the barbed portion 4840 and the joint, flex, or hinge portion 4820. The indicating feature 4812 deforms when the native leaflet tissue is pressed against the indicating feature 4812 by the moveable arm 4830 to indicate that the leaflet tissue has reached a minimum desired engagement depth. Thus, the indicating feature 4812 will not indicate that the native leaflet 42, 44 has reached the desired engagement depth until the leaflet 42, 44 is inserted at or beyond the location of the indicating feature 4812. Once the leaflet 42, 44 has reached the desired engagement depth, actuation of the moveable arm 4830 squeezes the leaflet tissue 42, 44 against the indicating feature 4812 of the fixed arm 4810 to cause the indicating feature 4812 to flatten and thereby indicate that the leaflet 42, 44 has been inserted into the clasp 4800 at or beyond the desired engagement depth. The clasp 4800 can be used in any of the implantable prosthetic devices of the present application and can include any of the features or combinations of features of the other clasps described herein.

Referring now to FIG. 101, the clasp 4800 is shown with a native leaflet 42, 44 partially inserted into an opening 4806 of the clasp 4800 formed between the fixed and moveable arms 4810, 4830. To determine whether the leaflet 42, 44 has reached the desired engagement depth, the moveable arm 4830 is actuated via actuation lines.

Referring now to FIG. 101, when the moveable arm 4830 is actuated to push the leaflet 42, 44 against the fixed arm 4810, the leaflet 42, 44 may contact a portion of the fixed arm 4810 without contacting the indicating feature 4812 when the engagement depth of the leaflet 42, 44 is less than the minimum desired engagement depth.

As can be seen in FIG. 102, the indicating feature 4812 is deformed or flattened from contact with the leaflet 42, 44 when the leaflet 42, 44 is inserted into the clasp 4800 at or beyond the minimum engagement depth and is pressed against the indicating feature 4812 by the moveable arm 4830. That is, the indicating feature 4812 is deformed by the leaflet 42, 44 to indicate that the leaflet 42, 44 has been inserted at or beyond the minimum engagement depth. In some embodiments, actuation of the moveable arm 4830 also causes the barbed portion 4840 to engage and secure the leaflet 42, 44 within the barbed clasp 4800. If the indicating feature 4812 indicates that the leaflet 42, 44 is not inserted to the desired depth, the barbed clasp 4800 can be opened to allow for repositioning of the leaflet 42, 44.

Figure 103B:
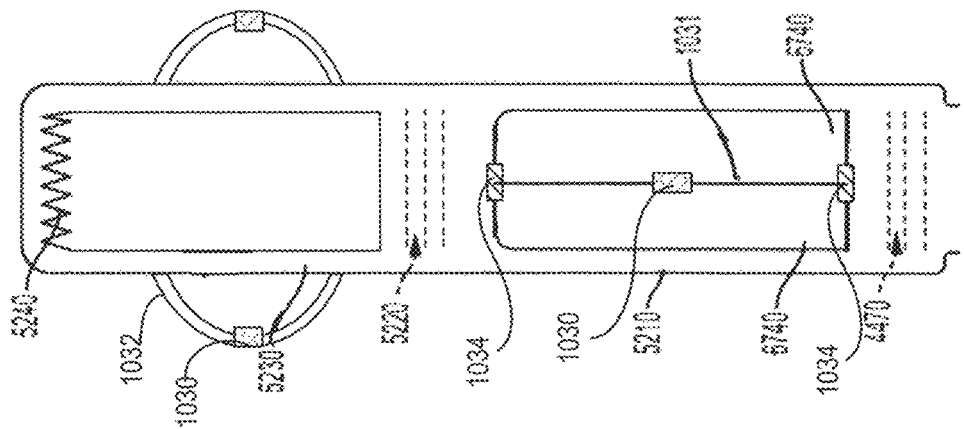
FIGS. 103A-103D show example embodiments of a moveable arm of clasp having various example embodiments of indicators.
Figure 103A:
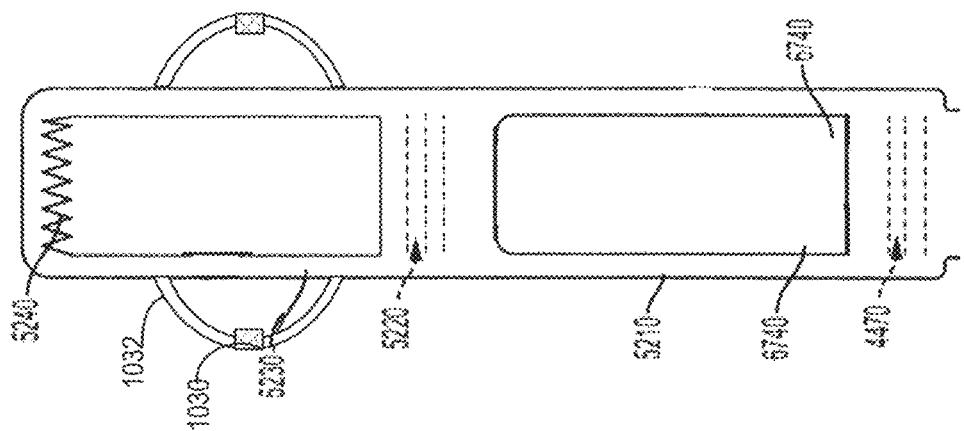
Figure 103:
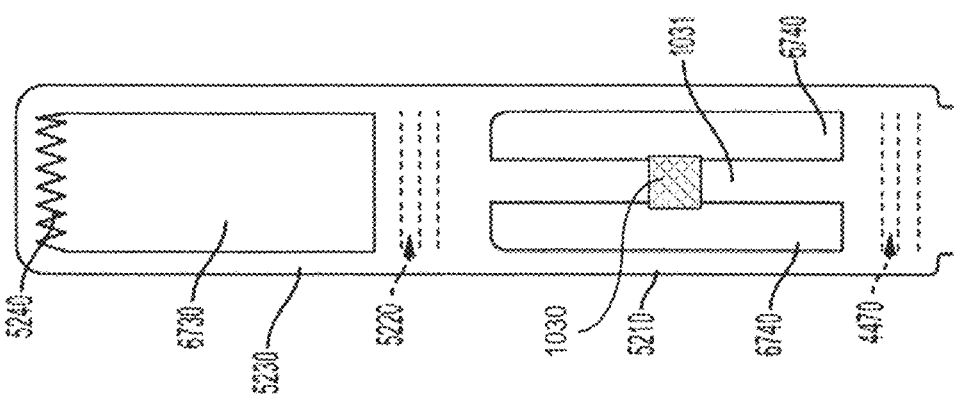
FIG. 103 shows an example embodiment of a moveable arm and an indicator of a clasp.

Referring now to FIG. 103, an example embodiment of a portion of a laser cut clasp is illustrated. In FIG. 103, cut from one sheet is a clasp having a moveable arm 5230, a fixed arm 5210, and a flexible indicator 1031. The moveable arm 5230 has a cut-out opening 6730 and at least one barb 5240, and a flexible section 5220 that permits the moveable arm to bend at the flexible section, to shape set or otherwise position in in the proper configuration to form a clasp. The fixed arm 5210 has two cut-outs 6740 in it that each extend along a length of the fixed arm, and a flexible indicator that extends across a length of the fixed arm, in between the cut-outs 6740. The fixed arm 5210 also can have an optional flexible section 4470 that can be attached to a paddle portion or coaption or spacer portion to allow the paddle and the clasp to optionally be made from a single piece or the clasp and the coaption or spacer portion to optionally be made from a single piece. The flexible indicator 1031 can have an optional indicator element 1030 on it. The optional indicator element 1030 can be a radiopaque marker. The radiopaque marker can be an additional piece attached to the flexible indicator or it can be printed on the flexible indicator or applied to the flexible indicator in the manner of any of the embodiments described herein.

Figure 106:
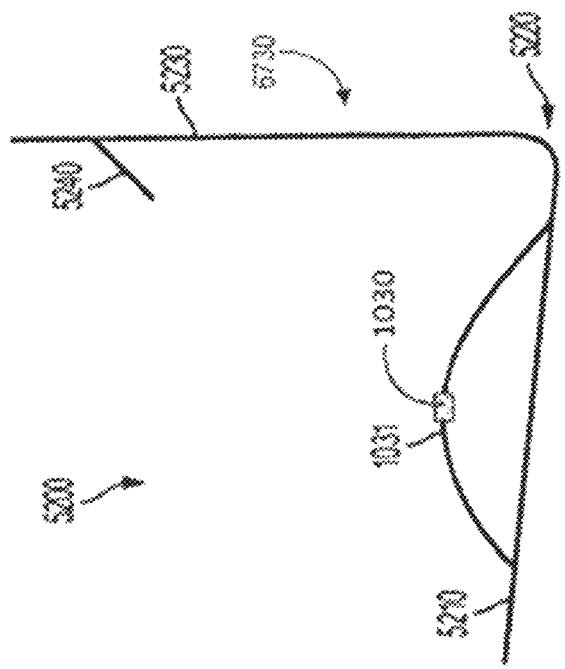
FIGS. 104-106 show schematic views of example embodiments of a clasp having a flexible curve in the fixed arm as an indicator, for an implantable prosthetic device.
Figure 105:
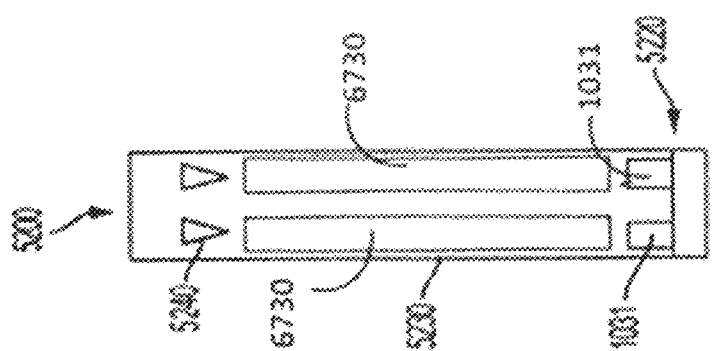
Figure 104:
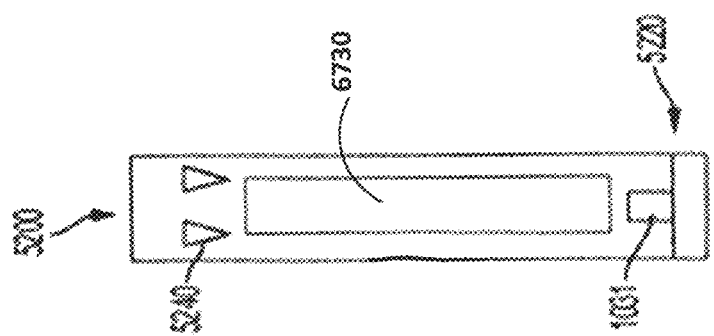

Referring now to FIGS. 104-106, schematic views of example embodiments of a clasp (illustrated as a barbed clasp) for use in an implantable prosthetic device, such as devices 100, 200, and 300 described above, are shown. Like the clasp 3500 described above, the clasp 5200 includes a fixed arm 5210, a joint, flex, or hinge portion 5220, and a moveable arm 5230 having a barbed portion 5240 (though other friction-enhancing portions can be used). The fixed arm 5210 also includes at least one flexible indicator 1031, positioned between cutouts 6740 as shown in FIGS. 103 and 110. FIG. 104 illustrates a schematic view of a clasp that has one flexible indicator 1031 on the fixed arm that fits through an opening 6730 in the moveable arm 5230. FIG. 105 illustrates a schematic view of a clasp that has two flexible indicators 1031 on the fixed arm that fit between two cutout openings 6730 on the moveable arm. When there are a plurality of flexible indicators, the flexible indicators can be aligned or offset along the length of the fixed arm. The flexible indicators can be part of the laser cut clasp or can be attached to the laser-cut clasp frame by welding or rivets or other known means. FIG. 106 illustrates a side schematic view of the embodiments illustrated in FIGS. 104 and 105. From the side view, the clasp appears the same, whether there is one flexible indicator 1031 or two, since the two indicators are aligned in the illustrated example. In FIG. 106, the clasp is in an open position and the flexible indicator is curved into a "bump" configuration. FIGS. 106-109 also illustrates an optional radiopaque indicator 1030 on the flexible bump 1031. The radiopaque indicator can be printed or attached as a separate piece of material to the flexible bump 1031. For example, the radiopaque material can be a coil made of platinum or another radiopaque material. The radiopaque indicator is visible with fluoroscopy and/or other imaging techniques and can assist the user in determining whether the leaflet is properly positioned in the clasp.

The bump 1031 deforms and flattens when the native leaflet tissue is pressed against the bump 1031 by the moveable arm 5230 to indicate that the leaflet tissue has reached a minimum desired engagement depth. Thus, the bump 1031 will not indicate that the native leaflet 42, 44 has reached the desired engagement depth until the leaflet 42, 44 is inserted at or beyond the location of the bump 1031. Once the leaflet 42, 44 has reached the desired engagement depth, actuation of the moveable arm 5230 squeezes the leaflet tissue 42, 44 against the bump 1031 of the fixed arm 5210 to cause the bump 1031 to flatten and thereby indicate that the leaflet 42, 44 has been inserted into the clasp 5200 at or beyond the desired engagement depth. The clasp 5200 can be used in any of the implantable prosthetic devices of the present application and can include any of the features or combinations of features of the other clasps described herein.

Figure 107:
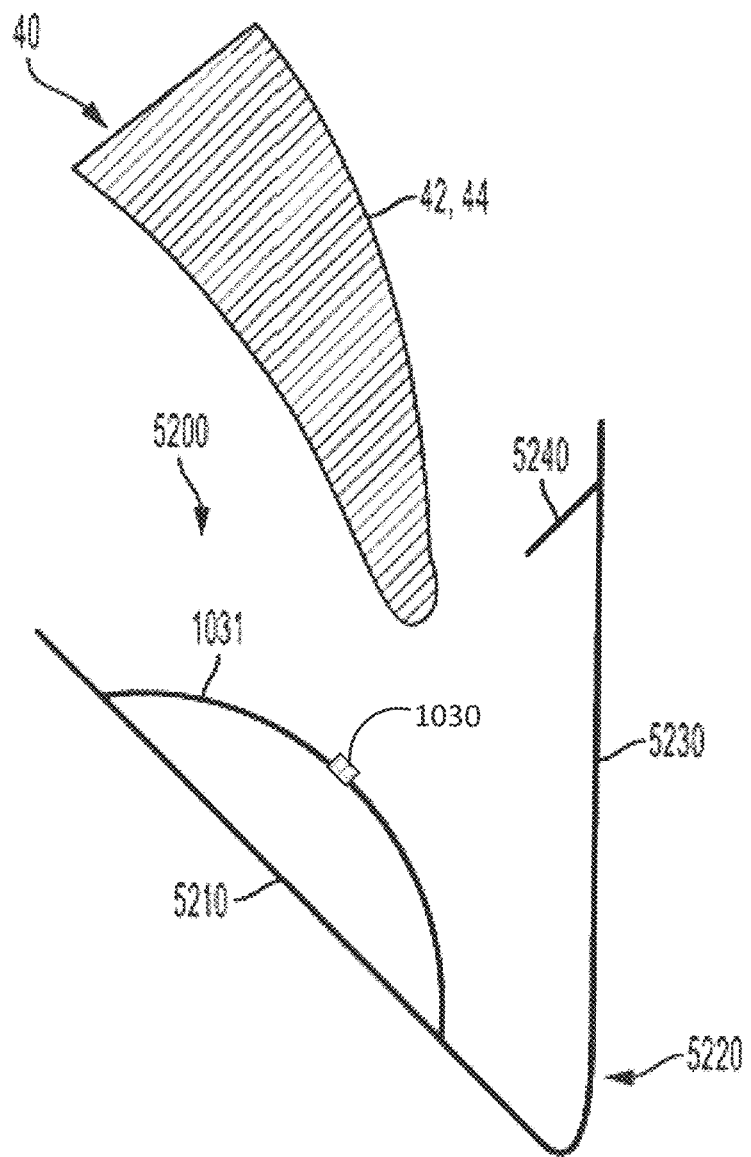
FIGS. 107-109 show the example clasp of FIGS. 104-106 being deployed to engage with a leaflet of a native valve.
Figure 108:
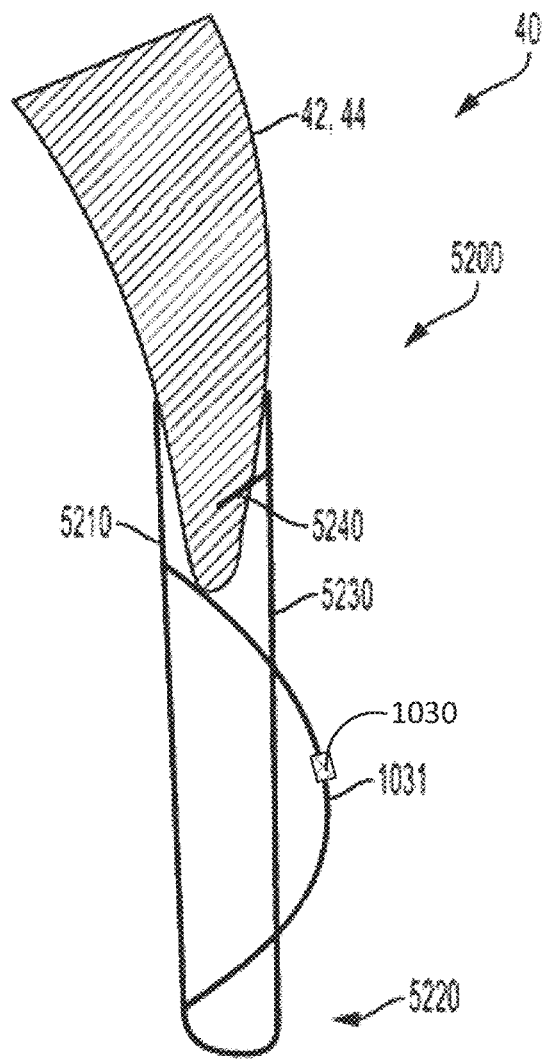
Figure 109:
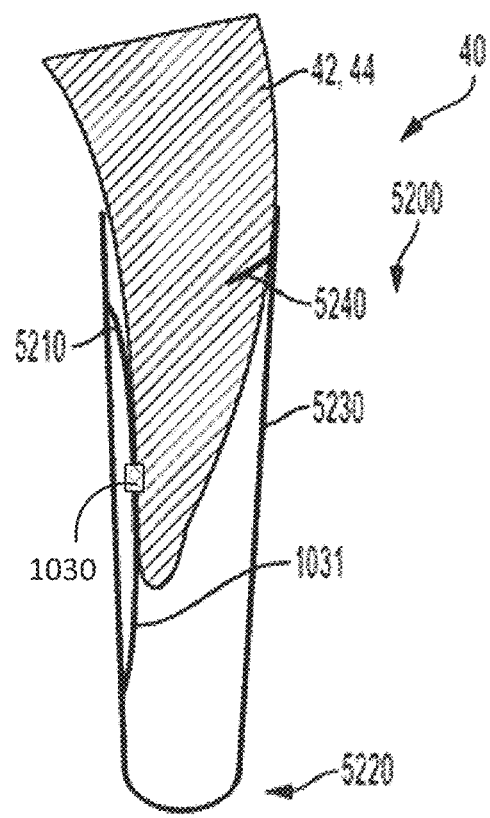

Referring now to FIGS. 107-109, the example clasp 5200 illustrated in FIGS. 104-106 is shown being deployed within a native valve 40 to secure an implantable device (not shown), such as the devices 100, 200, 300 described above, to one of the native leaflets 42, 44. Referring now to FIG. 107, the clasp 5200 is shown in an open condition with a native leaflet 42, 44 partially inserted into an opening of the clasp 5200 formed between the fixed and moveable arms 5210, 5230. In FIGS. 107-109, the bump 1031 can have an optional radiopaque indicator on it. The radiopaque indicator can be printed directly on the bump, a coil wrapped around the bump, or printed on a fabric covering the bump, or otherwise fixed to the bump. The radiopaque indicator can be a platinum coil wrapped around the bump, or it can be radiopaque ink printed on it.

Referring now to FIG. 108, when the moveable arm 5230 is actuated to push the leaflet 42, 44 against the fixed arm 5210, the leaflet 42, 44 may contact a portion of the fixed arm 5210 without contacting the bump 1031 when the engagement depth of the leaflet 42, 44 is less than the minimum engagement depth. As can be seen in FIG. 109, the bump 1031 is deformed or flattened from contact with the leaflet 42, 44 when the leaflet is inserted into the clasp 4600 at or beyond the minimum engagement depth and is pressed against the bump 1031 by the moveable arm 5230.

Referring now to FIGS. 103A-103D, example embodiments of indicators 1031 having optional markers 1030 on a clasp such as the clasp illustrated in FIG. 103, are illustrated. Referring to FIG. 103A, the flexible indicator arms can be flexible "wing" indicators 1032, one attached to each side of the moveable arm 5230. In another example embodiment, a single wing is disposed on only one side of the clasp. The flexible wing indicators can be cut from the same sheet of material as a laser cut clasp or can be separately cut pieces that are attached to the clasp. As with other example embodiments described herein, the indicator arms can have a different thickness than the clasp to provide a different amount of flexibility. The flexible wing indicators can extend outward and inward at an angle from the moveable arm, similar to butterfly wings. The flexible wing indicators can be attached to the moveable arm or the fixed arm. The flexible wing indicators 1032 can each have an optional radiopaque indicator element 1030 on them. As with other example embodiments described herein, the indicator element can be radiopaque and can be printed or otherwise attached to the flexible wing indicators directly, or to fabric covering the flexible wing indicators. The flexible wing indicators extend at an angle from the moveable arm 5230 of the clasp, outwardly away from a longitudinal axis of the clasp, and in toward the center of the clasp toward the fixed arm. When a leaflet is captured by the clasp and applies a force to a flexible wing indicator 1032, the flexible wing indicator flexes back toward the moveable arm (see FIGS. 108A and 109A for schematic illustrations).

Figure 103D:
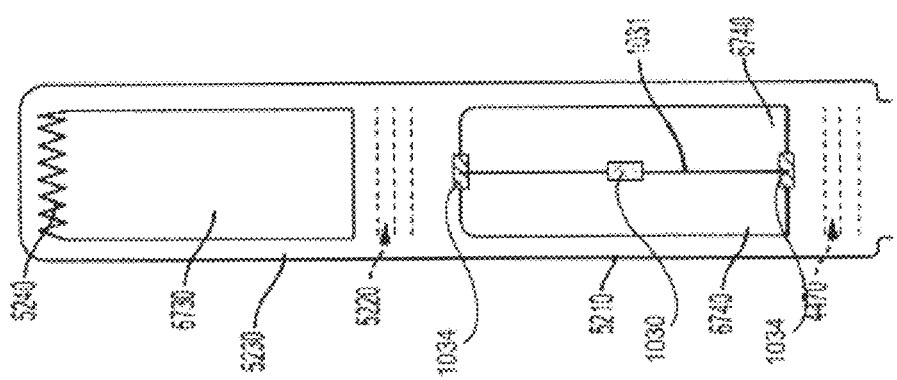

Referring now to FIG. 103B, a flexible wire indicator 1031 can be positioned in the opening 6740 of the fixed arm 5210 of a clasp. This can be in addition to the flexible wing indicators 1032 or can be present without the flexible wing indicators. The flexible wire indicator can be a wire extending along a longitudinal axis of the opening 6740 of the clasp, attached at one end closer to a flex or hinge portion 4470 and attached at the other end closer to the flex or hinge portion 5220. There can be an optional radiopaque marker 1030 positioned along the length of the flexible wire indicator 1031. The wire can be held in place by being secured at attachment points 1034. The attachment point can have the wire indicator attached by welding, suturing, or other known methods of attachment. FIGS. 108B and 109B illustrate schematic views of the example embodiment of the clasp in FIG. 103B when a leaflet is positioned in the clasp a sufficient depth to force the indicators 1031, 1032, to flex. FIG. 103D illustrates an example embodiment having only the flexible wire indicator 1031 without the flexible wing indicators. FIGS. 108D and 109D illustrate schematic views of the example embodiment of the clasp in FIG. 103D when a leaflet is positioned in the clasp a sufficient depth to force the indicator 1031 to flex.

Figure 103C:
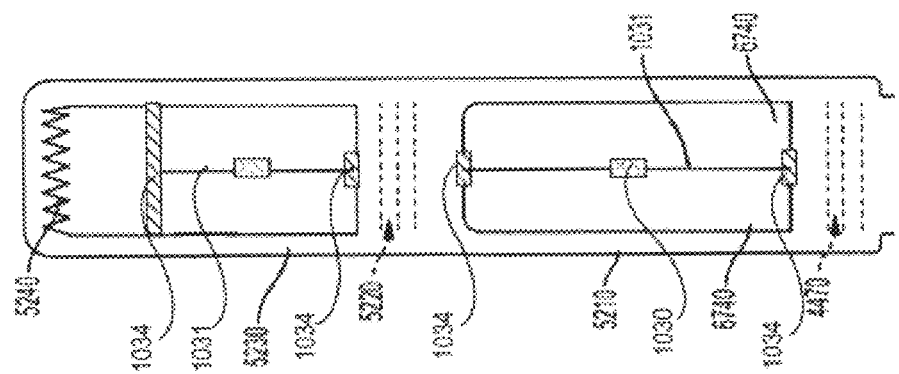

Referring now to FIG. 103C, an example embodiment of a clasp having flexible wire indicators 1031 is illustrated. There can be a flexible wire indicator 1031 extending longitudinally across the opening 6740, having an optional radiopaque indicator 1030 positioned along the wire indicator 1031 and secured to the clasp at attachment points 1034. A flexible wire indicator 1031 can also be positioned longitudinally across the opening 6730 in the moveable arm 5230 in addition to or instead of, the flexible wire indicator in the opening 6740 of the fixed arm. The flexible wire indicator 1031 in the moveable arm opening 6730 can extend partway across the opening and be attached at one end near the flex or hinge portion 5220, and at its other end, at a cross-piece 1033 that extends horizontally across the opening 6740. The cross-piece can have an optional radiopaque indicator printed or attached to it. The flexible wire indicator can have an optional radiopaque marker 1030 positioned along its length. FIGS. 108C and 109C illustrate schematic views of the example embodiment of the clasp in FIG. 103C when a leaflet is positioned in the clasp a sufficient depth to force the indicators 1031 to flex.

Figure 106A:
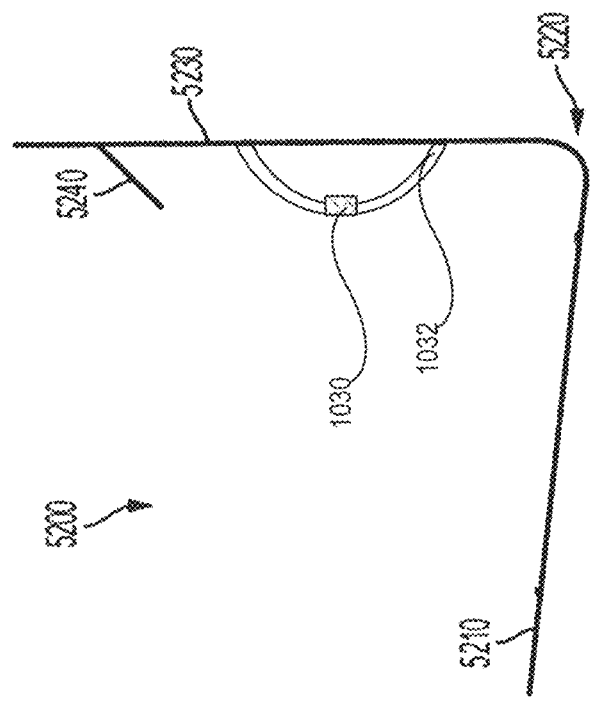
FIGS. 104A, 106A, 108A, and 109A show schematic views of an example embodiment of a clasp having flexible wing indicators on the moveable arm, for an implantable prosthetic device.
Figure 104A:
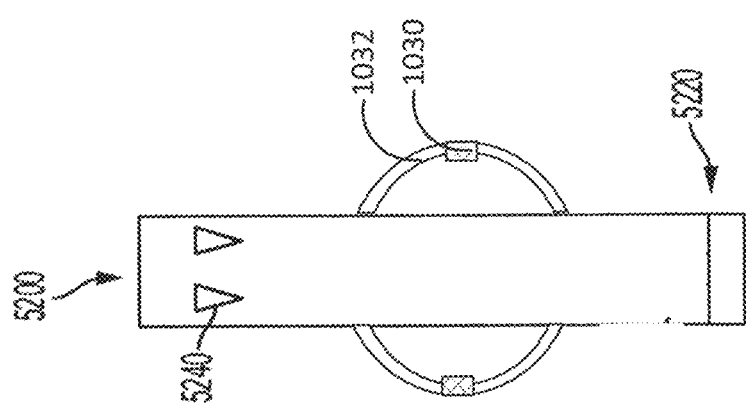

Referring now to FIGS. 104A and 106A, schematic views of example embodiments of a clasp for use in an implantable prosthetic device, such as the example embodiment shown in FIG. 103A having flexible "wing" indicators 1032, one attached to each side of the moveable arm 5230, are illustrated. The flexible wing indicators can extend at an angle, laterally outward from the moveable arm and in toward an end of the fixed arm. While shown here attached to the moveable arm, the flexible wing indicators can optionally be attached to the fixed arm instead. The flexible wing indicators 1032 can each have an optional indicator element 1030 on them. FIG. 106A illustrates a side view of the embodiment illustrated in FIG. 104A. In FIGS. 104A and 106A, the clasp is in an open position and the flexible wing indicators 1032 extend outward from the moveable arm as shown in FIG. 104A and inward toward the portion of the clasp where the leaflet would be positioned as shown in FIG. 106A. An optional radiopaque indicator 1030 on the flexible wing indicators is shown.

The flexible wing indicators 1032 deform and flatten when the native leaflet tissue is pressed against them as the clasp closes to indicate that the leaflet tissue has reached a minimum desired engagement depth in the clasp. In one example embodiment, if the leaflet is inserted off-center in the clasp, only one flexible wing indicator may flex and deform, while the other remains undeformed. The clasp 5200 can be used in any of the implantable prosthetic devices of the present application and can include any of the features or combinations of features of the other clasps described herein.

Figure 108A:
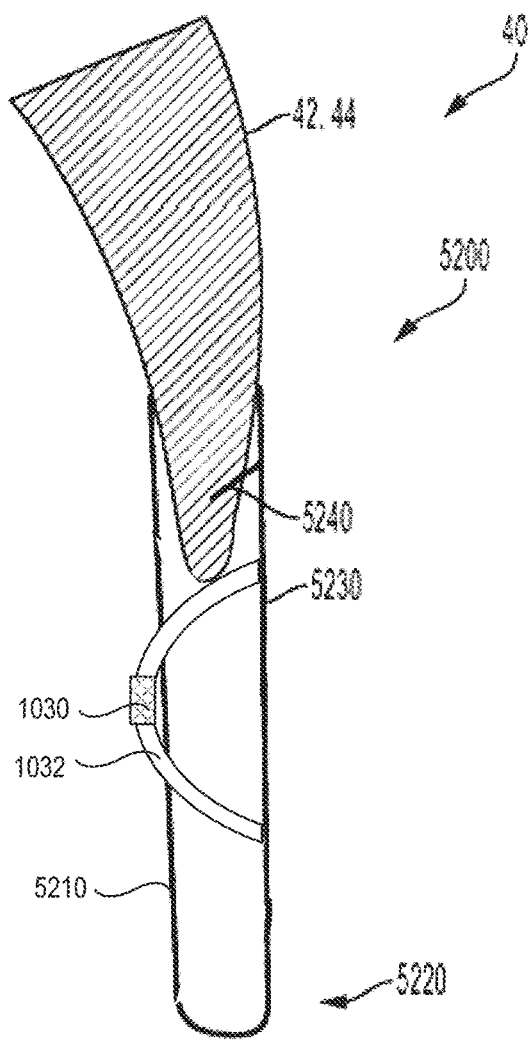
Figure 109A:
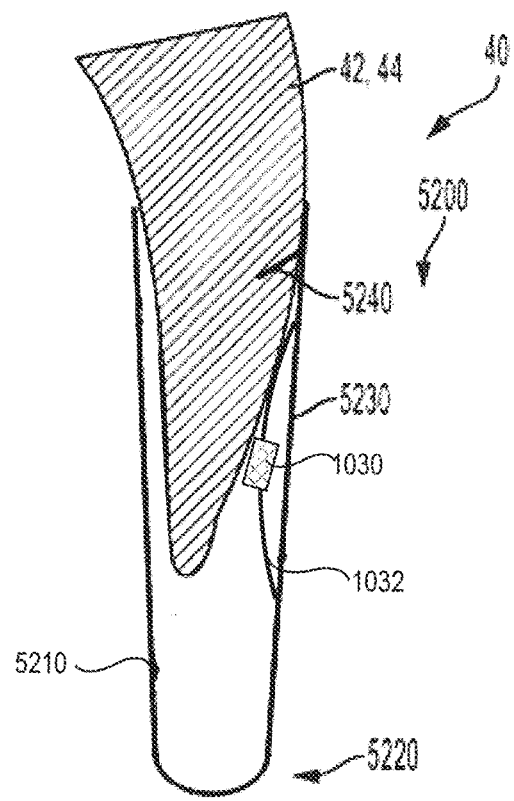
Figure 108B:
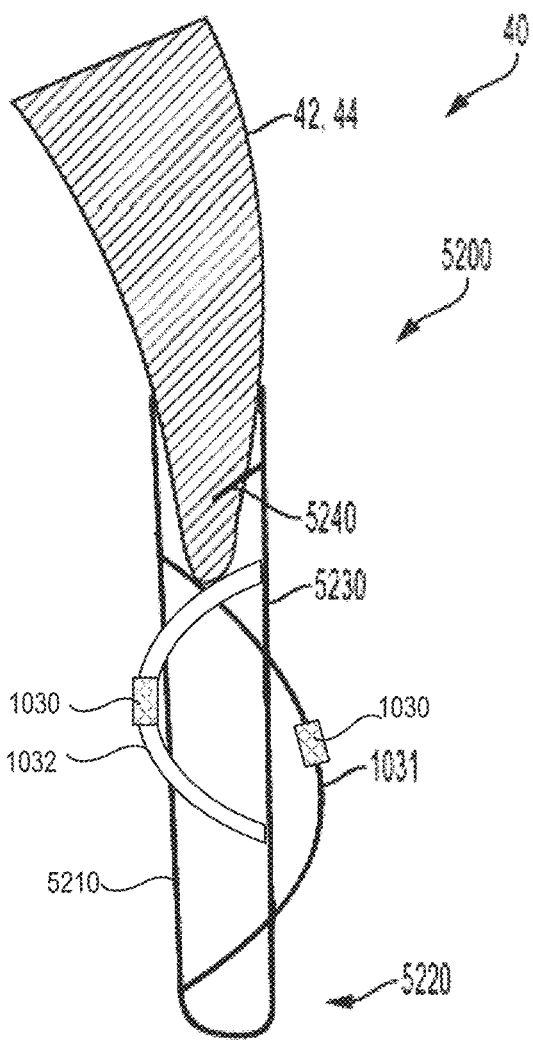
Figure 109B:
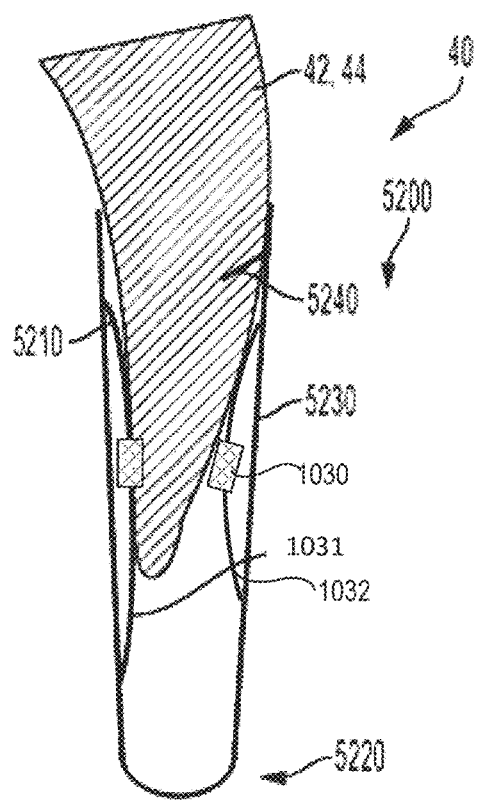
Figure 108D:
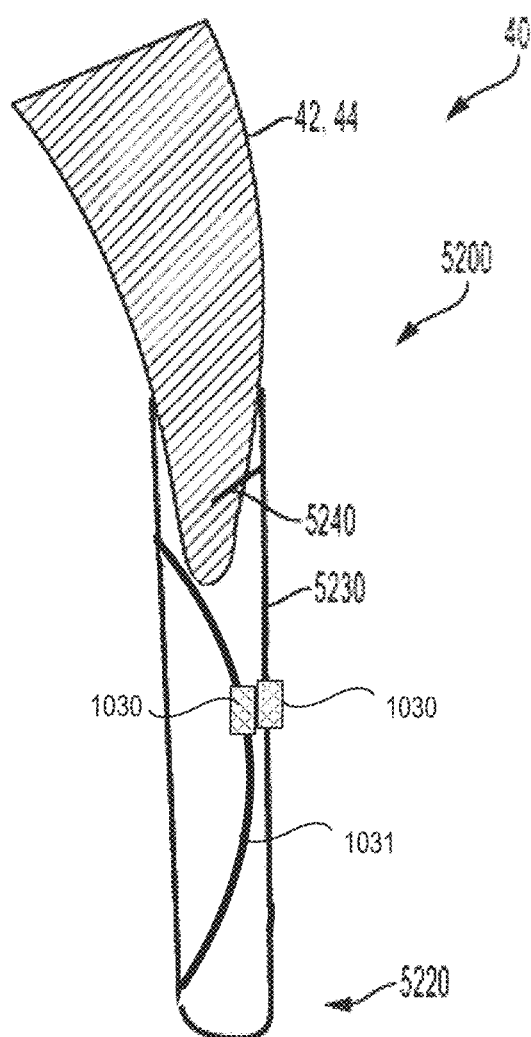
Figure 109D:
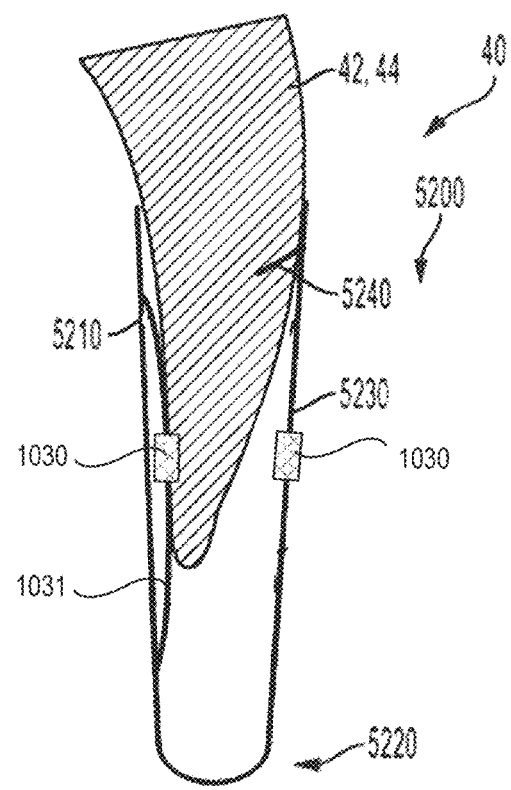

Referring now to FIGS. 108A and 109A, use of the clasp of the example embodiment of FIG. 103A is illustrated. Referring now to FIG. 108A, when the moveable arm 5230 is actuated to push the leaflet 42, 44 against the fixed arm 5210, the leaflet 42, 44 may contact a portion of the fixed arm 5210 and a portion of the moveable arm 5230 without contacting the flexible wing indicators 1032 when the engagement depth of the leaflet 42, 44 is less than the minimum engagement depth. As can be seen in FIG. 109A, the flexible wing indicators 1032 (only one flexible wing indicator is visible in FIG. 109A because the other is directly behind it) are deformed or flattened from contact with the leaflet 42, 44 when the leaflet is inserted into the clasp 4600 at or beyond the minimum engagement depth and is pressed against the flexible wing indicators 1032 by the fixed arm 5210. The location of the optional radiopaque indicating elements 1030 can indicate to the user how much the flexible wing indicators have moved and thus determine the position of the leaflet.

Figure 106B:
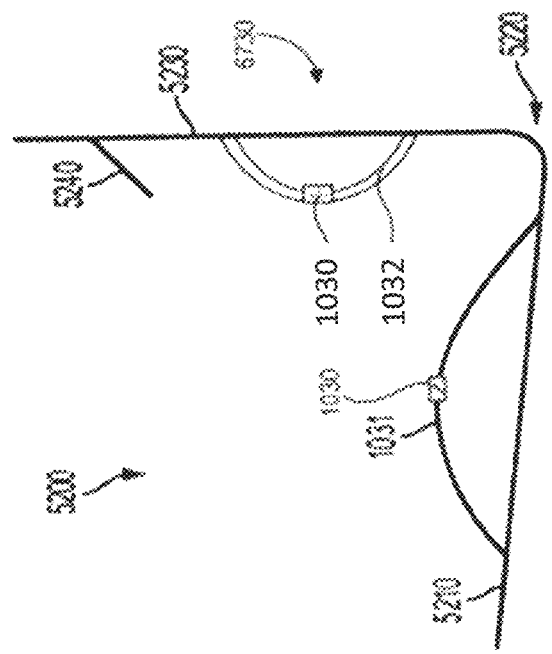
FIGS. 104B, 106B, 108B, and 109B show schematic views of an example embodiment of a clasp having flexible wing indicators on the moveable arm and a flexible indicator on the fixed arm, for an implantable prosthetic device.
Figure 104B:
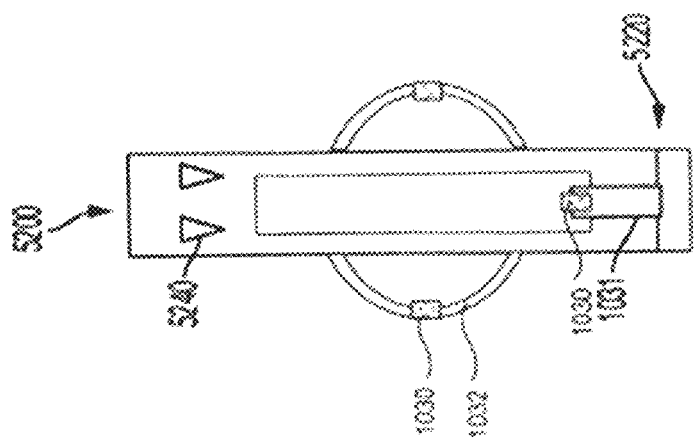

Referring now to FIGS. 104B and 106B, schematic views of an example embodiment of a clasp (illustrated as a barbed clasp) for use in an implantable prosthetic device, such as the example embodiment shown in FIG. 103B having flexible "wing" indicators 1032, one attached to each side of the moveable arm 5230, are illustrated. The flexible wing indicators can extend away from the moveable arm at an angle, and toward an open end of the clasp. While shown here attached to the moveable arm, the flexible wing indicators can optionally be attached to the fixed arm. The flexible wing indicators 1032 can each have an indicator element 1030 on them. FIG. 106B illustrates a side schematic view of the embodiments illustrated in FIG. 104B. In FIGS. 104B and 106B, the clasp is in an open position and the flexible wing indicators 1032 extend outward from the moveable arm as shown in FIG. 104B and inward toward the portion of the clasp where the leaflet would be positioned as shown in FIG. 106B. The wire indicator 1031 that extends longitudinally has a bump configuration when in its resting uncompressed state, such as when the clasp is open. Optional radiopaque indicators 1030 on the flexible wing indicators and on the wire indicators 1031 are shown.

The flexible wing indicators 1032 deform and flatten when the native leaflet tissue is pressed against them as the clasp closes to indicate that the leaflet tissue has reached a minimum desired engagement depth and horizontal position along the clasp. In one example embodiment, if the leaflet is inserted off-center into the clasp, only one flexible wing indicator may flex and deform, while the other remains undeformed. The wire indicator 1031 also flattens and deforms due to the pressure exerted by a leaflet on it if the leaflet is positioned over it when the clasp is closed.

Referring now to FIG. 108B, when the moveable arm 5230 is actuated to push the leaflet 42, 44 against the fixed arm 5210, the leaflet 42, 44 may contact a portion of the fixed arm 5210 and a portion of the moveable arm 5230 without contacting either the flexible wing indicators 1032 or the wire indicator 1031 when the engagement depth of the leaflet 42, 44 is less than the minimum engagement depth. As can be seen in FIG. 109B, the flexible wing indicators 1032 (only one flexible wing indicator is visible in FIG. 109B because the other is directly behind it) and the wire indicator 1031 have deformed or flattened from contact with the leaflet 42, 44 when the leaflet is inserted into the clasp 4600 at or beyond the minimum engagement depth and is pressed against the flexible wing indicators 1032 by the fixed arm 5210, and against the wire indicator 1031 by the moveable arm. The wire indicator can be a wire, or a laser cut sheet attached to the fixed arm, as described in other example embodiments having a flexible bump indicator described herein. The location of the optional radiopaque indicating elements 1030 can indicate to the user how much the flexible wing indicators have moved and thus determine the position of the leaflet.

Figure 106C:
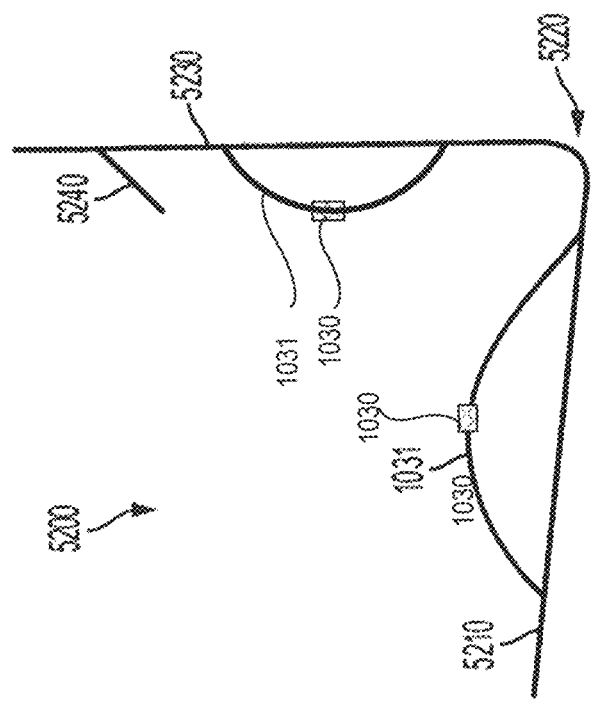
Figure 104C:
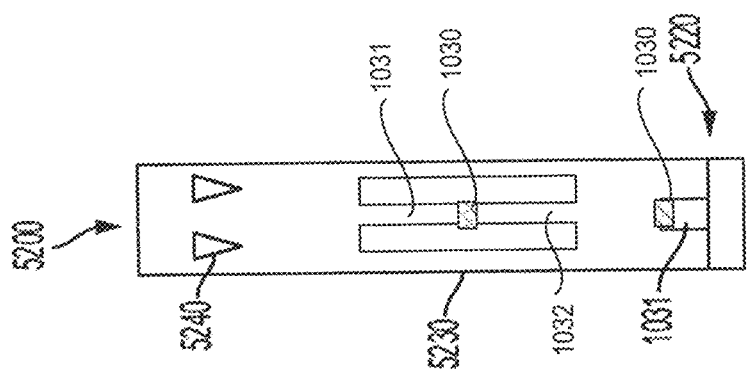

Referring now to FIGS. 104C and 106C, schematic views of example embodiments of a clasp (illustrated as a barbed clasp) for use in an implantable prosthetic device, such as but not limited to the example embodiment shown in FIG. 103C having flexible two wire indicators 1031. Each of the indicators has a bump configuration. One indicator is attached to the moveable arm and one indicator is attached to the fixed arm. The indicators that extend along the moveable arm and the fixed arm can also be laser cut and attached to the arms, in some example embodiments. The wire indicators 1031, can have optional radiopaque indicator elements attached to them, printed on them, and/or wrapped around them. For example, the radiopaque indicator can be a coil made of a radiopaque material wrapped around at least a portion of the wire. FIG. 106C illustrates a side schematic view of the embodiments illustrated in FIG. 104C. In FIGS. 104C and 106C, the clasp is in an open position and the wire indicators 1031 have a bump configuration where the bump extends inward into the clasp toward where the leaflet would be inserted.

Referring now to FIG. 108C, when the moveable arm 5230 is actuated to push the leaflet 42, 44 against the fixed arm 5210, the leaflet 42, 44 may contact a portion of the fixed arm 5210 and a portion of the moveable arm 5230 without contacting either of the wire indicators 1031 when the engagement depth of the leaflet 42, 44 is less than the minimum engagement depth. When the clasp is closed and the leaflet is not at a minimum engagement depth, or there is no leaflet within the clasp at all, the wire indicators 1031 flatten and deform as they press against each other, due to the pressure applied by each wire indicator against the other wire indicator. As is illustrated, the two optional radiopaque indicating elements 1030 become adjacent to one another to provide an indication that the leaflet has not been engaged.

Referring now to FIG. 109C, the wire indicators 1031 deform and flatten against the leaflet when the native leaflet tissue is pressed against them as the clasp closes to indicate that the leaflet tissue has reached a minimum desired engagement depth and horizontal position along the clasp. If the leaflet is not centered over the wire indicator when the clasp is closed, the wire indicator 1031 retains its bump shape and passes through opening 6730 on the moveable arm of the clasp. As is illustrated, the two optional radiopaque indicating elements 1030 are spaced apart to indicate that the leaflet has been engaged.

Figure 106D:
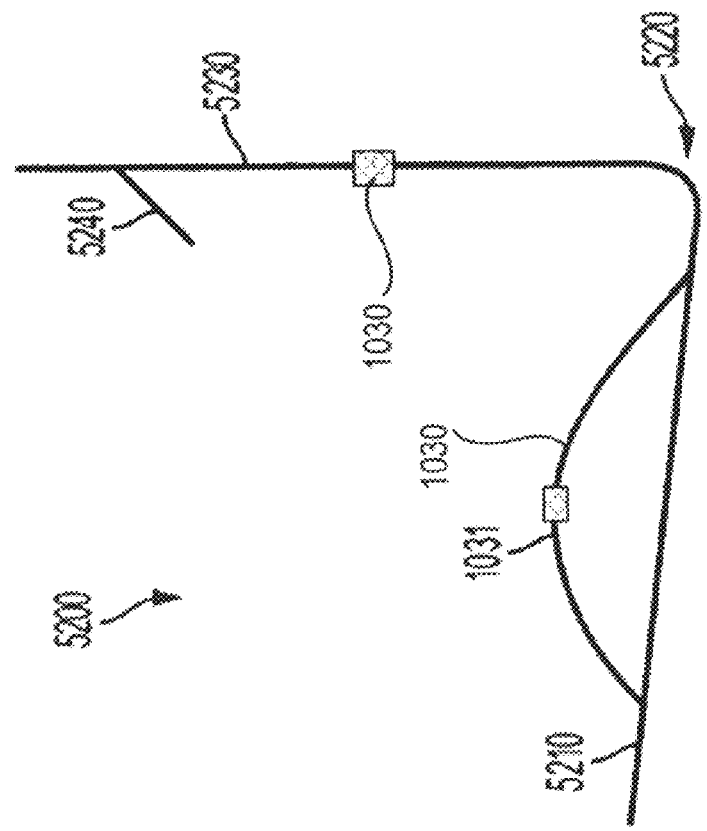
FIGS. 104D, 106D, 108D, and 109D show schematic views of an example embodiment of a clasp having a flexible indicator, for an implantable prosthetic device.
Figure 104D:
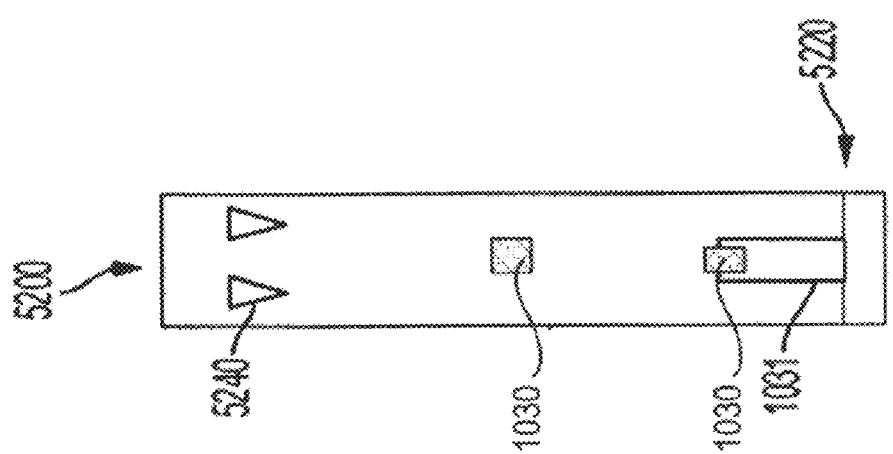

Referring now to FIGS. 104D and 106D, schematic views of example embodiments of a clasp (illustrated as a barbed clasp) for use in an implantable prosthetic device, such as but not limited to the example embodiment shown in FIG. 103D having a flexible indicator 1031 with a bump configuration, is illustrated. The flexible indicator can be a wire indicator. The indicator 1031 can also be laser cut and attached to one of the arms or integrally formed with one of the arms, in some example embodiments. The indicator 1031 can have an optional radiopaque indicator element 1030 attached to or wrapped around it. For example, the radiopaque indicator can be a coil made of a radiopaque material wrapped around at least a portion of the wire. The moveable arm 5230 can also have an optional radiopaque indicator element 1030 on it. FIG. 106D illustrates a side schematic view of the embodiments illustrated in FIG. 104D. In FIGS. 104D and 106D, the clasp is in an open position and the indicator 1031 has a bump configuration where the bump extends into the clasp toward where the leaflet would be inserted.

Referring now to FIG. 108D, when the moveable arm 5230 is actuated to push the leaflet 42, 44 against the fixed arm 5210, the leaflet 42, 44 may contact a portion of the fixed arm 5210 and a portion of the moveable arm 5230 without contacting the wire indicators 1031, when the engagement depth of the leaflet 42, 44 is less than the minimum engagement depth. When the clasp is closed and the leaflet is not at a minimum engagement depth, or there is no leaflet within the clasp at all, the wire indicator 1031 can at least partially flatten and deform due to the pressure applied by the moveable arm against it. In some example embodiments, the wire indicator 1031 can be attached to the moveable arm and is partially flattened by pressure applied to it by the fixed arm. As is illustrated, the two optional radiopaque indicating elements 1030 become adjacent to one another to provide an indication that the leaflet has not been engaged.

Referring now to FIG. 109D, the wire indicator 1031 deforms and flattens against the leaflet when the native leaflet tissue is pressed against them as the clasp closes to indicate that the leaflet tissue has reached a minimum desired engagement depth and horizontal position along the clasp. As is illustrated, the two optional radiopaque indicating elements 1030 are spaced apart to indicate that the leaflet has been engaged.

Figure 106E:
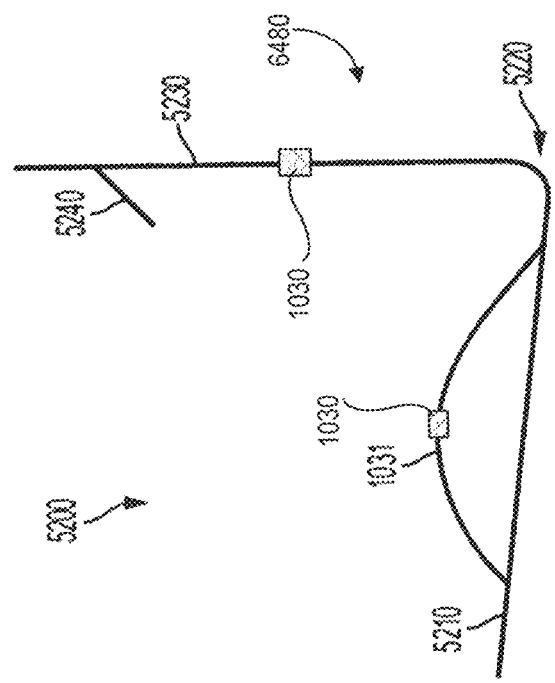
FIGS. 104E, 106E, 108E, and 109E show schematic views of an example embodiment of a clasp having a flexible indicator, for an implantable prosthetic device.
Figure 104E:
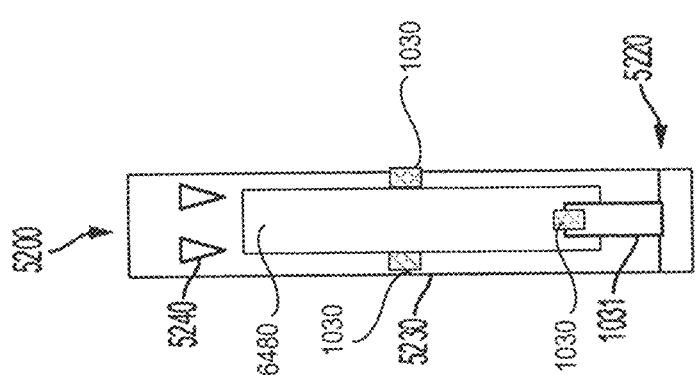

Referring now to FIGS. 104E and 106E, schematic views of an example embodiment of a clasp (illustrated as a barbed clasp) for use in an implantable prosthetic device, having a flexible indicator 1031 with a bump configuration connected to the fixed arm 5210 and an opening 6730 in the moveable arm 5230, is illustrated. The flexible indicator can be a wire indicator. The flexible indicator can also be laser cut and attached to the arms, in some example embodiments. The indicator 1031 can have an optional radiopaque indicator element 1030 attached to or wrapped around it. For example, the radiopaque indicator can be a coil made of a radiopaque material wrapped around at least a portion of the wire. The moveable arm 5230 has an opening 6730 in it and can also have optional radiopaque indicator elements 1030 on the side arms of its frame. FIG. 106E illustrates a side schematic view of the embodiment illustrated in FIG. 104E. In FIGS. 104E and 106E, the clasp is in an open position and the indicator 1031 has a bump configuration where the bump extends inward in the clasp toward where the leaflet would be inserted.

Figure 108E:
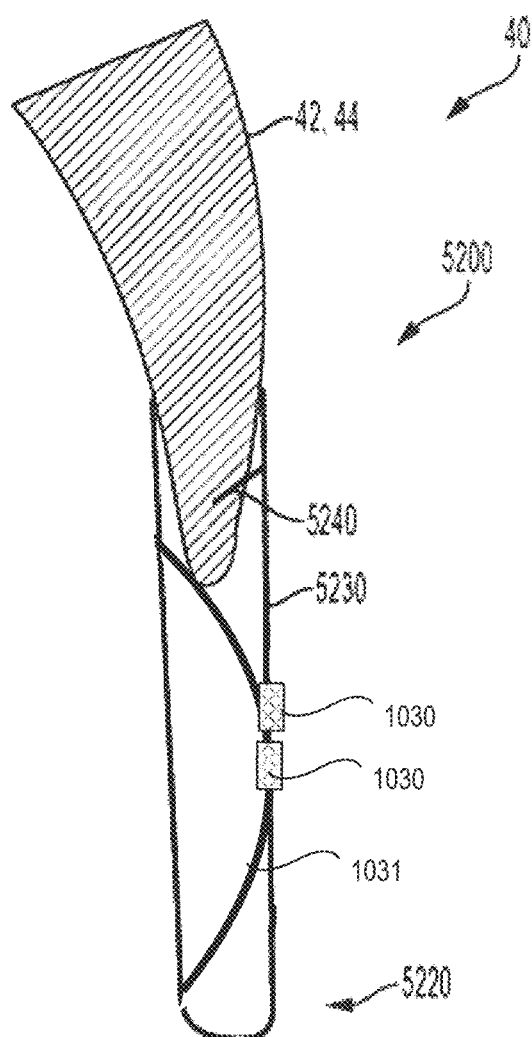

Referring now to FIG. 108E, when the moveable arm 5230 is actuated to push the leaflet 42, 44 against the fixed arm 5210, the leaflet 42, 44 may contact a portion of the fixed arm 5210 and a portion of the moveable arm 5230 without contacting the indicator 1031, when the engagement depth of the leaflet 42, 44 is less than the minimum engagement depth. When the clasp is closed and the leaflet is not at a minimum engagement depth, or there is no leaflet within the clasp at all, the indicator 1031 remains unflattened or only partially flattened and the indicator 1031 can pass into or through the opening 6730 of the moveable arm when the leaflet is not properly inserted in the clasp. As is illustrated, the optional radiopaque indicating elements 1030 become aligned when the indicator 1031 moves into the opening in the moveable arm to provide an indication that the leaflet have not been engaged.

Figure 109E:
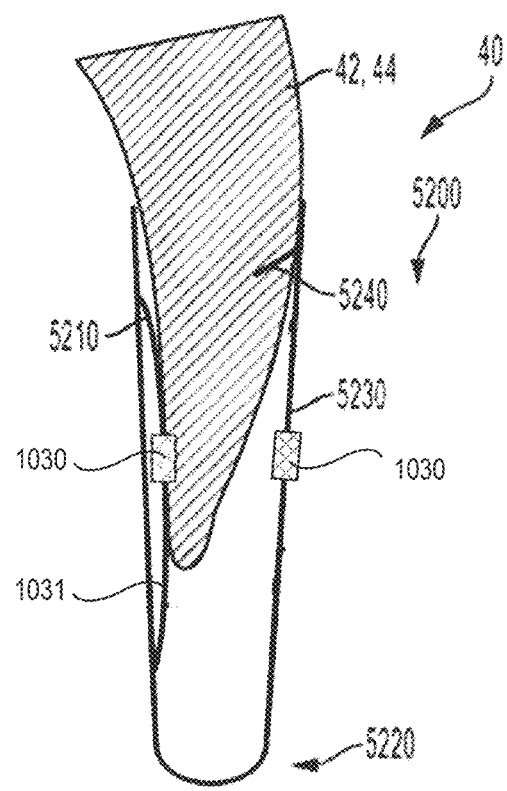

Referring now to FIG. 109E, the wire indicator 1031 deforms and flattens against the leaflet when the native leaflet tissue is pressed against them as the clasp closes to indicate that the leaflet tissue has reached a minimum desired engagement depth in the clasp. As is illustrated, the two optional radiopaque indicating elements 1030 are spaced apart to indicate that the leaflet has been engaged.

FIGS. 226-229 illustrate a variation of the clasp 4400 illustrated by FIGS. 48-66. In the example illustrated by FIGS. 226-229, the clasp includes a flexible wire indicator 1031 extending longitudinally across the hoop shaped moveable arm 4430. One end of the flexible wire indicator 1031 is attached at or near the flex portion or hinge portion 4420 (See FIG. 227), and the other end of the wire is attached at the opposite end of the moveable arm 4430, in between barbs 4444. The clasps 4400 can be used in implantable prosthetic devices, such as devices 100, 200, 300 described above or any other implantable prosthetic device.

The clasp 4400 illustrated by FIGS. 226-229 has a fixed arm 4410, a patterned flex portion or patterned hinge portion 4420, a moveable arm 4430 formed in the shape of a hoop or loop, and a barbed portion 4440 (though other friction-enhancing portions can be used) of the moveable arm 4430. In this embodiment, a leaflet depth indicator can be a flexible feature, that can be a wire indicator 1031 which remains flat in a straight configuration when the clasp is open and when there is no leaflet positioned to overlap it in the closed clasp. When a leaflet is present, the wire indicator 1031 is pressed through the hoop shaped moveable arm 4430. An optional radiopaque coil 1030 can be wrapped around the indicating wire 1031, and can be seen using imaging techniques, such as fluoroscopy. When the indicating wire and coil are seen on the outer side of the moveable arm 4430 of the clasp, the amount of the indicating arm 1031 and/or coil 1030 that is visible indicates the depth of the leaflet to the operator.

The clasp 4400 can include any of the features or combinations of features of the other clasps described herein. The clasp 4400 can be laser cut from a flat sheet or a tube of shape-memory alloy, such as Nitinol, and then shape-set into a desired shape.

The illustrated fixed arm 4410 has two tongue portions 4411 that each include optional holes 4412 for attaching the fixed arm 4410 to an implantable device.

The flex portion or hinge portion 4420 can take a wide variety of different forms. In the illustrated example, the flex or hinge portion 4420 is formed from a plurality of spring segments 4422 and cutouts 4424. Tongue portions 4411 of the fixed arm 4410 extend from one end of the patterned flex portion or patterned hinge portion 4420 and the moveable arm 4430 extends from the other end of the flex or hinge portion 4420.

The moveable arm 4430 of the clasp 4400 has a hoop-like shape. The hoop-shaped moveable arm 4430 includes side beams 4432 that are thinner and more flexible, particularly in the lateral direction. The side beams 4432 include a first flex or hinge portion 4434 arranged toward the proximate end of the moveable arm 4430 and a second flex or hinge portion 4436 arranged at the distal end of the moveable arm 4430. The first flex or hinge portion 4434 is formed by one or more bends in the side beams 4432. The hoop-shape of the moveable arm 4430 and flexible side arms 4432 allow the moveable arm 4430 to be collapsed by merely retracting the clasp 4400 into a delivery sheath (not shown).

The hoop-like shape of the moveable arm 4430 provides for a wider barbed portion 4440 that can include more barbs 4442 with the same or greater lateral spacing than other clasps. The wider spacing of the barbs 4442 improves capture of the native leaflets. The barbs 4442 are also optionally longitudinally staggered as a result of their position on the hoop-like shape of the moveable arm 4430. That is, two center barbs 4444 are arranged further away from the flex or hinge portion 4420 and two outer barbs 4446 are arranged closer to the flex or hinge portion 4420. The barbed portion 4440 of the moveable arm 4430 also includes optional holes 4448 for receiving an actuation suture (not shown). In certain embodiments, the hoop shape of the moveable arm 4430 is similar to the shape of wide outer paddles of an implantable device so that pinching forces of the paddles are spread out evenly on the barbs, further improving the retention of the native leaflets. The ends of the barbs 4442 can be further sharpened using any suitable sharpening means.

Figure 226:
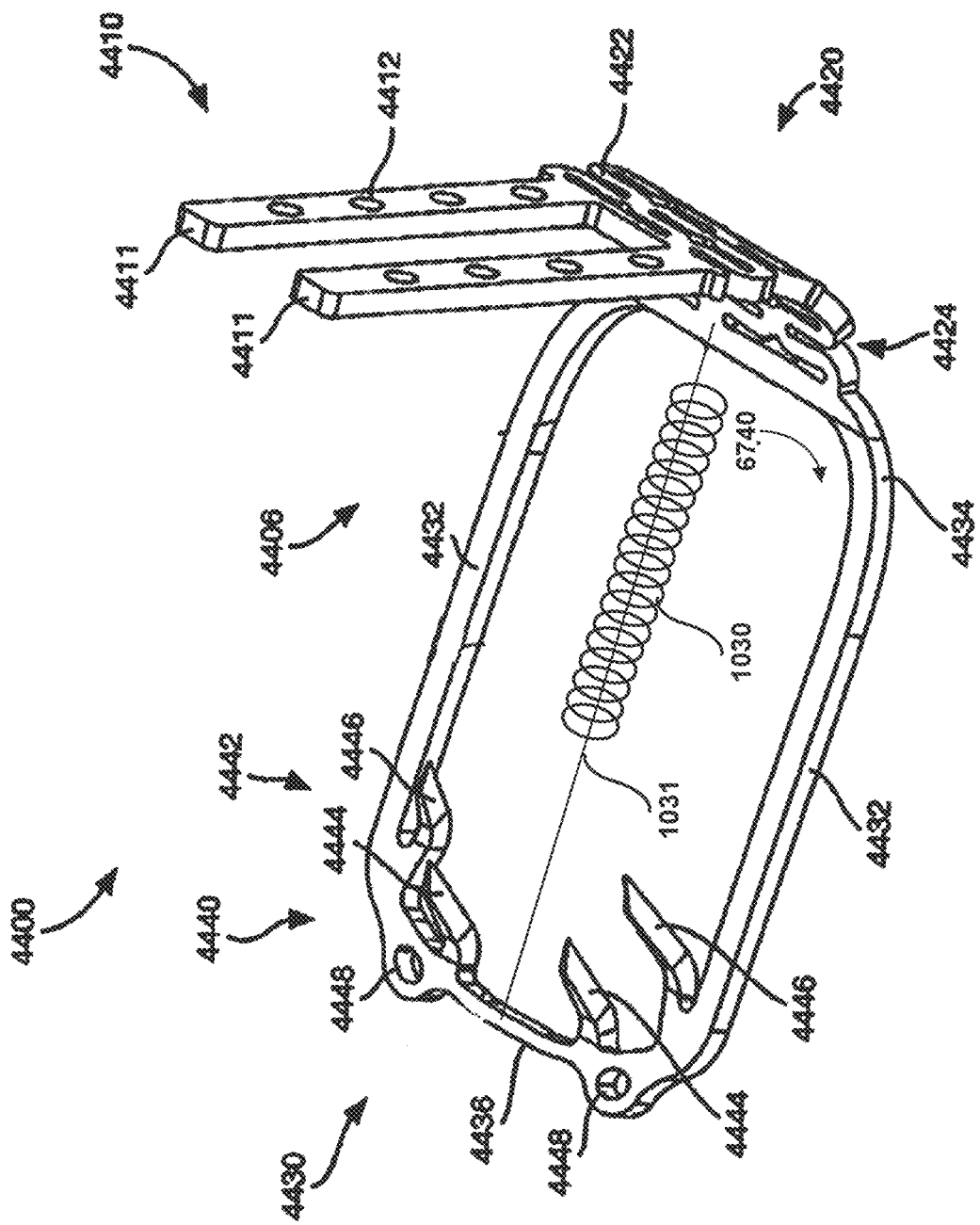
FIGS. 226-229 show a clasp having a flexible wire indicator according to an example embodiment, for an implantable prosthetic device.
Figure 227:
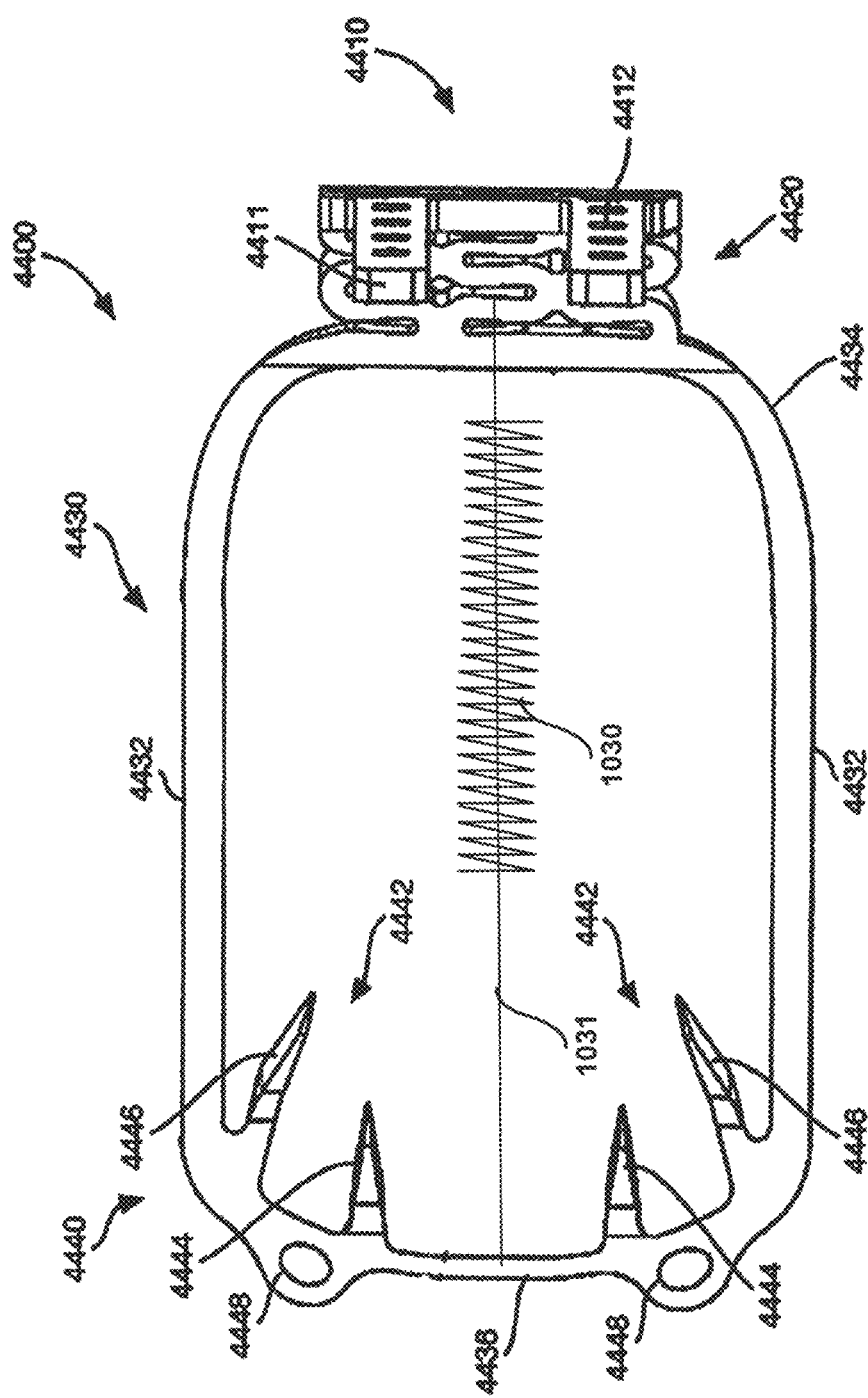

Referring now to FIGS. 226 and 227, the clasp 4400 is shown in an open position. The moveable arm 4430 is biased or spring-loaded in a closing direction and are moved to and held in the open position by tension applied to actuation lines (not shown). The indicating wire 1031 is in a straight undeflected configuration because there is no leaflet engaged in the open clasp in FIGS. 226-227.

Figure 228:
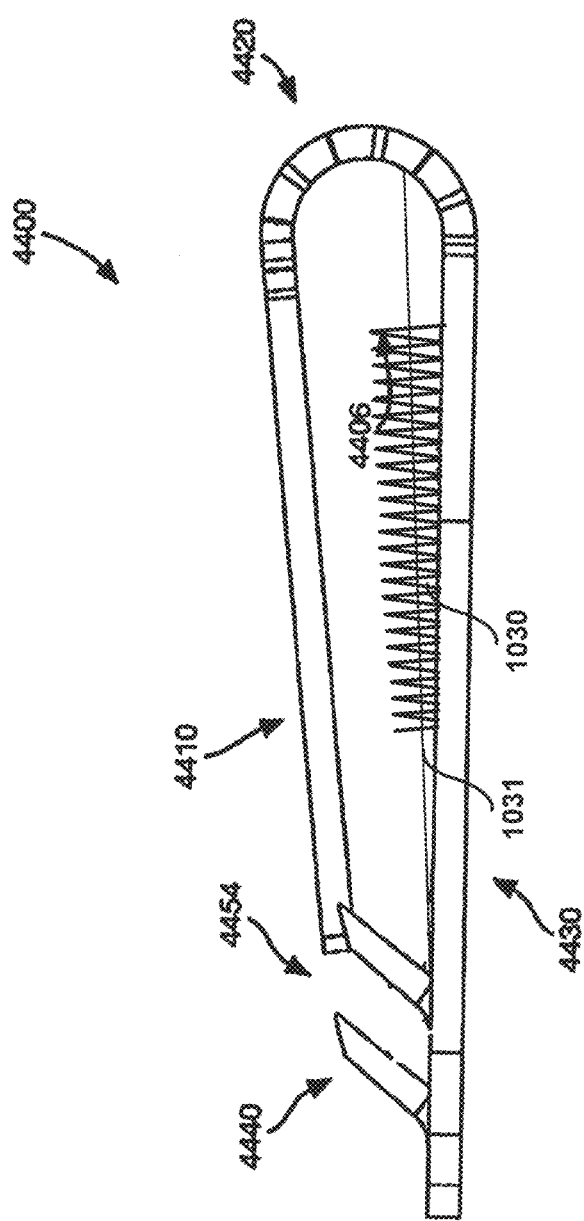

Referring now to FIG. 228, the clasp 4400 is shown in a fully deployed or actuated position, without a leaflet in place. The indicating wire 1031 with optional radiopaque coil 1030 remains undeflected and is positioned on an interior side of the moveable arm 4430 and/or does not extend beyond an outer profile of the moveable arm 4430. The indicating wire 1031 and coil 1030 are not seen outside of the profile of the moveable arm 4430. The absence of the indicator arm outside of the profile of the clasp 4400 by imaging equipment indicates to the operator that a leaflet has not been captured.

Figure 229:
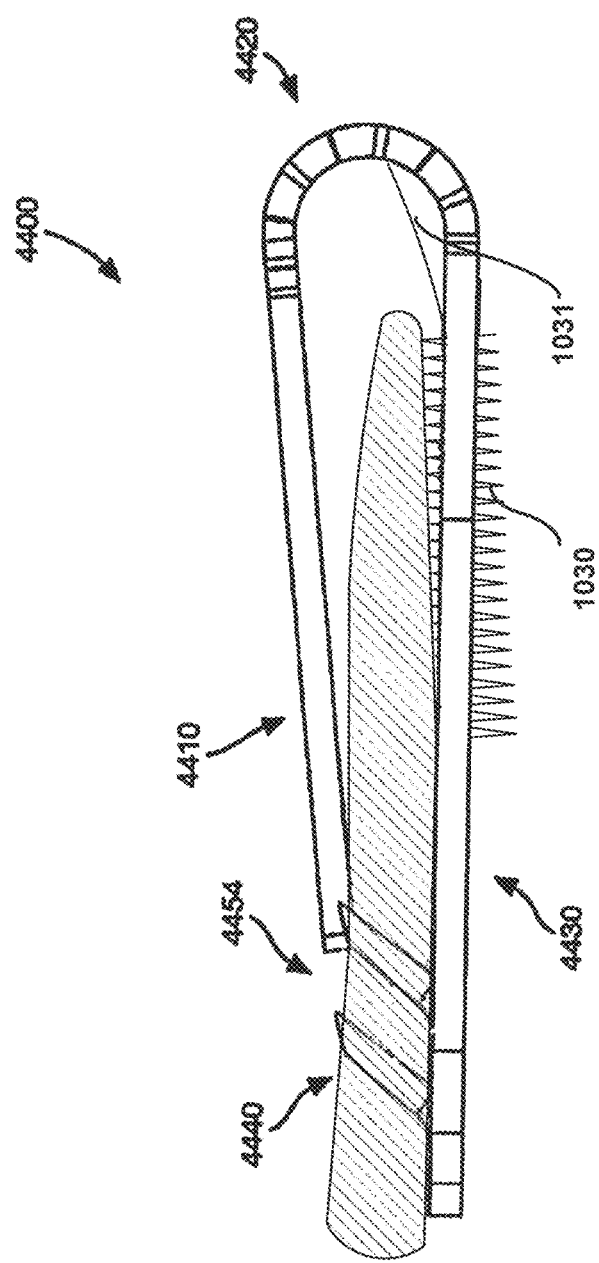

Referring now to FIG. 229, the clasp 4400 is shown with the moveable arm 4430 in a closed position. When the clasp 4400 is closed, the moveable arm 4430 and the indicator arm 4450 exert a pinching force that retains the native leaflet tissue to be secured within the clasp 4400. The clasp 4400 is biased in the closed direction by the shape-setting of the moveable arm 4430 in a preloading position. The closed clasp has captured a sufficient amount of leaflet tissue, that is, the depth of the leaflet in the clasp is sufficient for the clasp to be considered properly positioned, as indicated by the indicating wire 1031 and coil 1030 being deflected through the opening of the hoop shaped moveable arm, such that a portion of the indicating wire 1031 and/or the coil 1030 move past the outside profile of the moveable arm 4430 of the clasp 4400. The indicating wire 1031 and/or coil 1030 beyond the profile of the clasp can be seen on imaging equipment, such as fluoroscopy equipment as represented by FIG. 229 to indicate that the valve leaflet has been properly captured by the clasp 4400.

FIGS. 230-233 illustrate a variation of the clasp 4400 illustrated by FIGS. 48-66. In the example illustrated by FIGS. 230-233, the clasp includes a flexible wire indicator 1031 extending horizontally across the hoop shaped moveable arm 4430. Each end of the wire is attached to a side arm 4432 of the moveable arm 4430. The wire indicator 1031 can be positioned at any location that indicates proper insertion of the native valve leaflets. In one example embodiment, the wire indicator is positioned closer to the flex or hinge region than the barbed region of the clasp. The clasps 4400 can be used in implantable prosthetic devices, such as devices 100, 200, 300 described above or any other implantable prosthetic device.

The clasp 4400 illustrated by FIGS. 230-233 has a fixed arm 4410, a patterned flex portion or patterned hinge portion 4420, a moveable arm 4430 formed in the shape of a hoop or loop, and a barbed portion 4440 of the moveable arm 4430. In this embodiment, a leaflet depth indicator can be a flexible feature, that can be a wire indicator 1031 which remains flat in a straight configuration when the clasp is open and when there is no leaflet positioned to overlap it in the closed clasp. When a leaflet is present, the wire indicator 1031 is pressed through the hoop shaped moveable arm 4430. An optional radiopaque coil 1030 can be wrapped around the indicating wire 1031, and can be seen using imaging techniques, such as fluoroscopy. When the indicating wire and coil are seen on the outer side of the moveable arm 4430 of the clasp, the amount of the indicating arm 1031 and/or coil 1030 that is visible indicates the depth of the leaflet to the operator.

Figure 230:
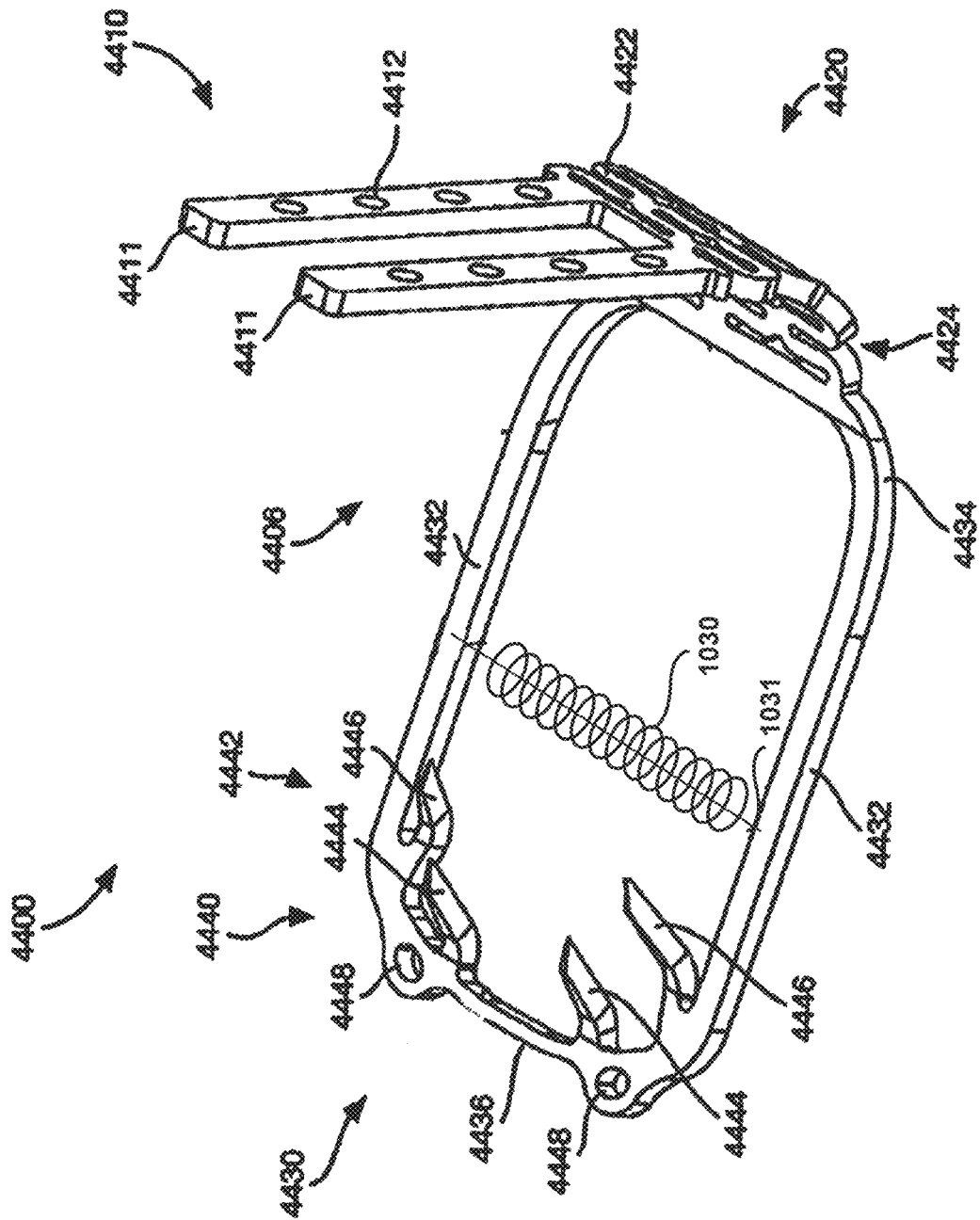
FIGS. 230-233 show a clasp having a flexible wire indicator according to an example embodiment, for an implantable prosthetic device.
Figure 231:
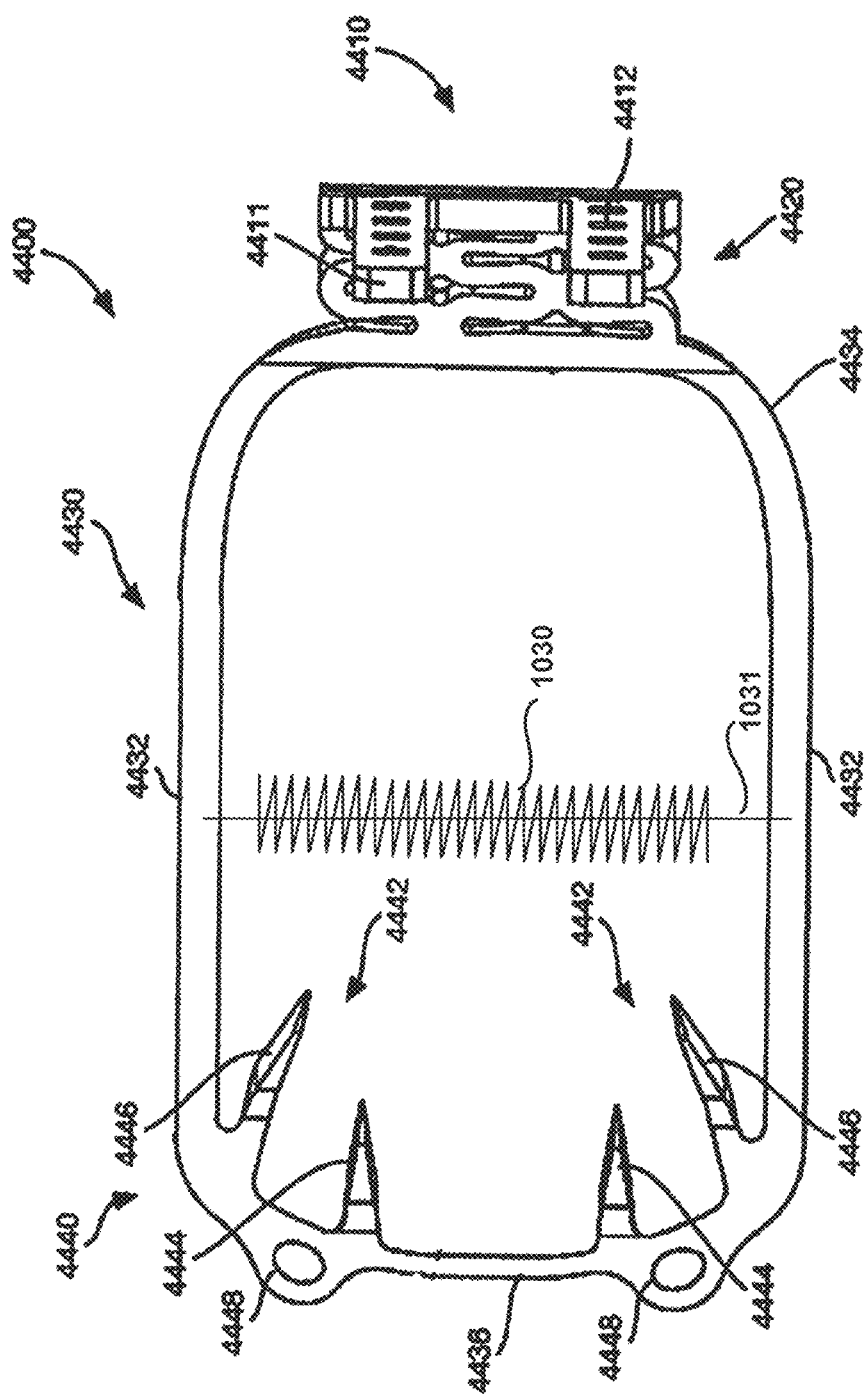

Referring now to FIGS. 230 and 231, the clasp 4400 is shown in an open position. The moveable arm 4430 is biased or spring-loaded in a closing direction and are moved to and held in the open position by tension applied to actuation lines (not shown). The indicating wire 1031 is in a straight undeflected configuration because there is no leaflet engaged in the open clasp in FIGS. 230 and 231.

Figure 232:
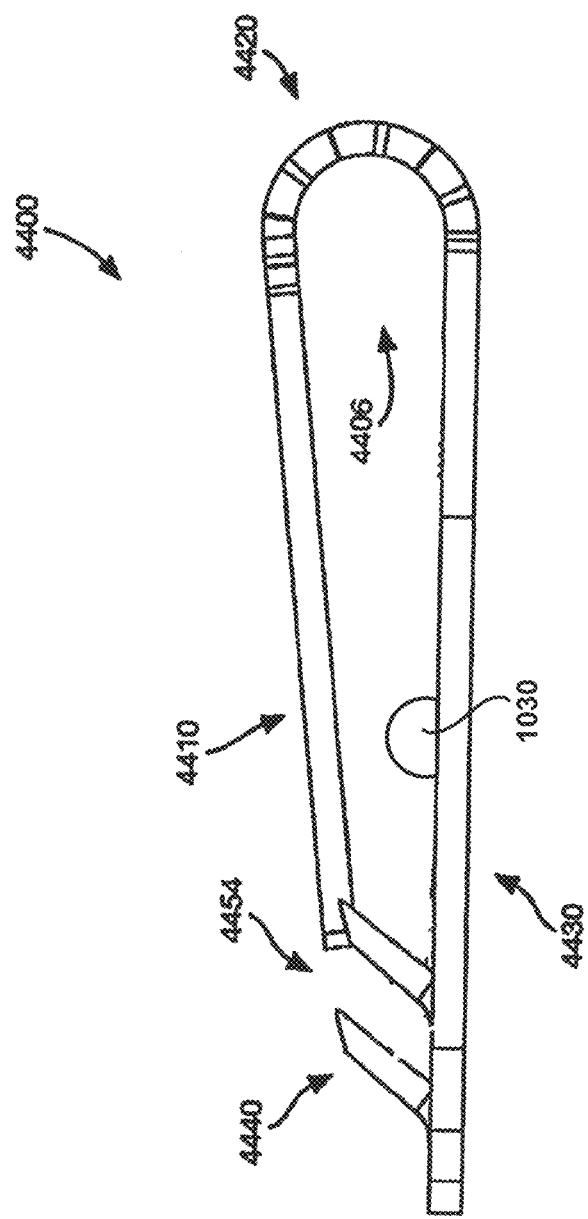

Referring now to FIG. 232, the clasp 4400 is shown in a fully deployed or actuated position, without a leaflet in place. The indicating wire 1031 with optional radiopaque coil 1030 remains undeflected and is positioned on an interior side of the moveable arm and/or does not extend beyond an outer profile of the moveable arm 4430. The indicating wire 1031 and coil 1030 are not seen outside the profile of moveable arm 4430 in FIG. 232. The absence of the indicator arm outside of the profile of the clasp 4400 by imaging equipment indicates to the operator that a leaflet has not been captured.

Figure 233:
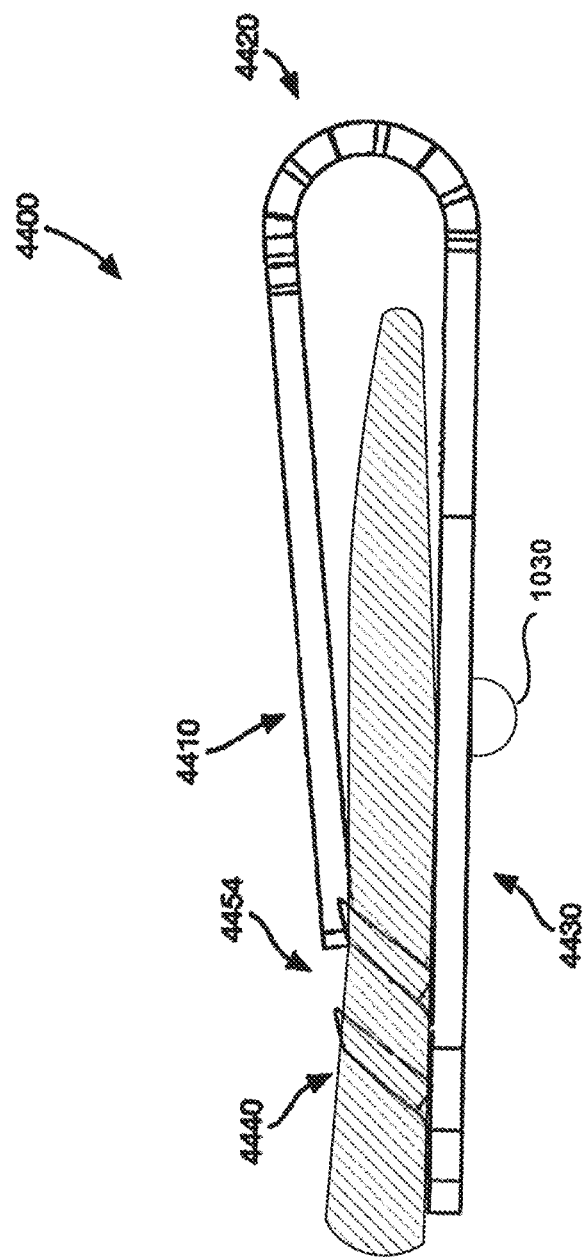

Referring now to FIG. 233, the clasp 4400 is shown with the moveable arm 4430 in a closed position. When the clasp 4400 is closed, the moveable arm 4430 and the indicator arm 4450 exert a pinching force that retains the native leaflet tissue to be secured within the clasp 4400. The clasp 4400 is biased in the closed direction by the shape-setting of the moveable arm 4430 in a preloading position. The closed clasp has captured a sufficient amount of leaflet tissue, that is, the depth of the leaflet in the clasp is sufficient for the clasp to be considered properly positioned, as indicated by the indicating wire 1031 and coil 1030 being deflected through the opening of the hoop shaped moveable arm, such that a portion of the indicating wire 1031 and/or coil 1030 move past the outside profile of the moveable arm 4430 of the clasp 4400. The indicating wire 1031 and/or coil 1030 beyond the profile of the clasp can be seen on imaging equipment, such as fluoroscopy equipment, as represented by FIG. 233 to indicate that the valve leaflet has been properly captured by the clasp 4400.

FIGS. 234-237 illustrate a variation of the clasp 4400 illustrated by FIGS. 48-66. In the example illustrated by FIGS. 234-237, the clasp includes a flexible wire indicator 1031 extending longitudinally across the hoop shaped moveable arm 4430. One end of the flexible wire indicator 1031 is attached near the flex or hinge portion 4420. The other end of the wire is attached to a cross wire 1033 that extends horizontally across the opening of the moveable arm 4430. The crosswire 1033 can be positioned across the middle of the moveable arm, can be positioned closer to the barbed end than the flex or hinge portion, or can be positioned closer to the flex portion or hinged portion than the barbed portion, depending on the minimum leaflet insertion depth. The crosswire 1033 can be replaced with a laser cut sheet component, which can be integrally formed with the clasp or can be a separate piece that is attached to the clasp. The clasps 4400 can be used in implantable prosthetic devices, such as devices 100, 200, 300 described above or with any other implantable prosthetic device.

The clasp 4400 has a fixed arm 4410, a patterned flex portion or patterned hinge portion 4420, a moveable arm 4430 formed in the shape of a hoop or loop, and a barbed portion 4440 of the moveable arm 4430. In this embodiment, a leaflet depth indicator can be a flexible wire 1031 which remains flat in a straight configuration when the clasp is open and when there is no leaflet positioned to against the indicator in the closed clasp. When a leaflet is present, the wire indicator 1031 is pressed through the hoop shaped moveable arm 4430. An optional radiopaque coil 1030 can be wrapped around the indicating wire 1031 and can be seen using imaging equipment, such as fluoroscopy. The indicating wire 1031 and coil 1030 are extend past the periphery or edge on the outer side of the moveable arm 4430 of the clasp 4400 when the clasp is closed on a leaflet that is inserted to a sufficient depth in the clasp. The amount of the indicating arm 1031 and coil 1030 that is exposed past the periphery or outer edge of the moveable arm 4430 indicates the depth of the leaflet to the operator.

Figure 234:
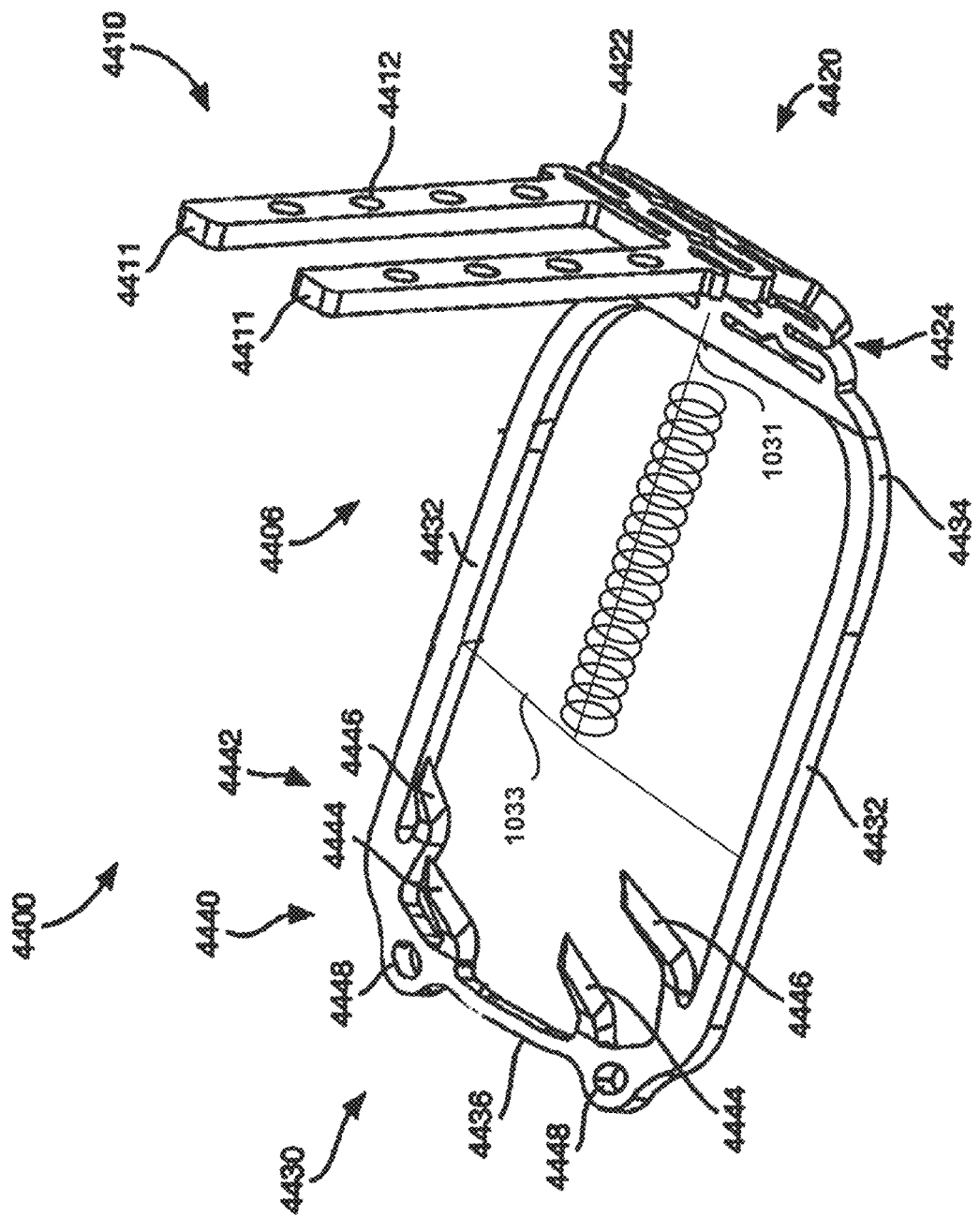
FIGS. 234-237 show a clasp having a flexible wire indicator according to an example embodiment, for an implantable prosthetic device.
Figure 235:
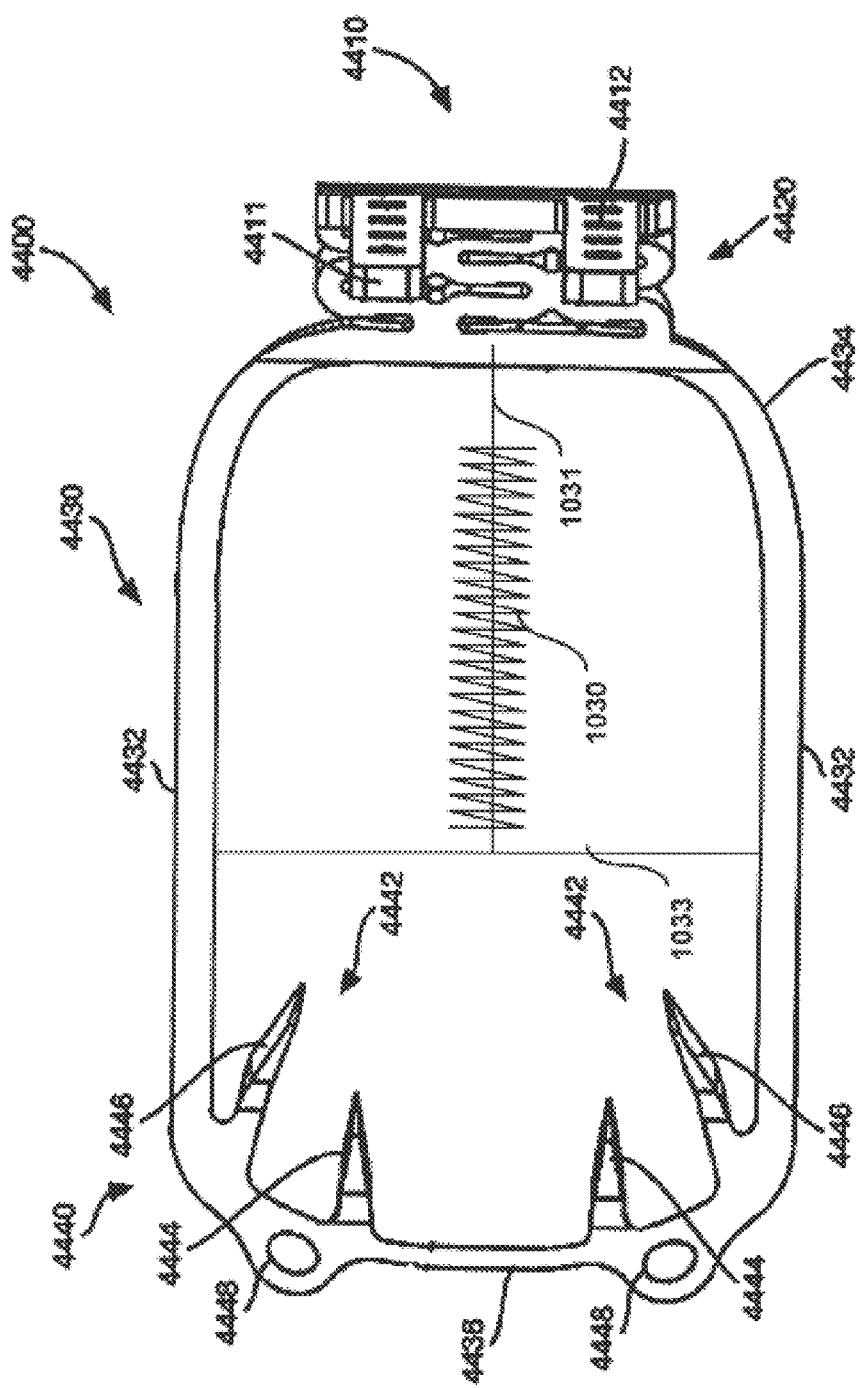

Referring now to FIGS. 234 and 235, the clasp 4400 is shown in an open position. The moveable arm 4430 is biased or spring-loaded in a closing direction and is moved to and held in the open position by tension applied to actuation lines (not shown). The indicating wire 1031 is in a straight undeflected configuration because there is no leaflet engaged in the open clasp in FIGS. 234 and 235.

Figure 236:
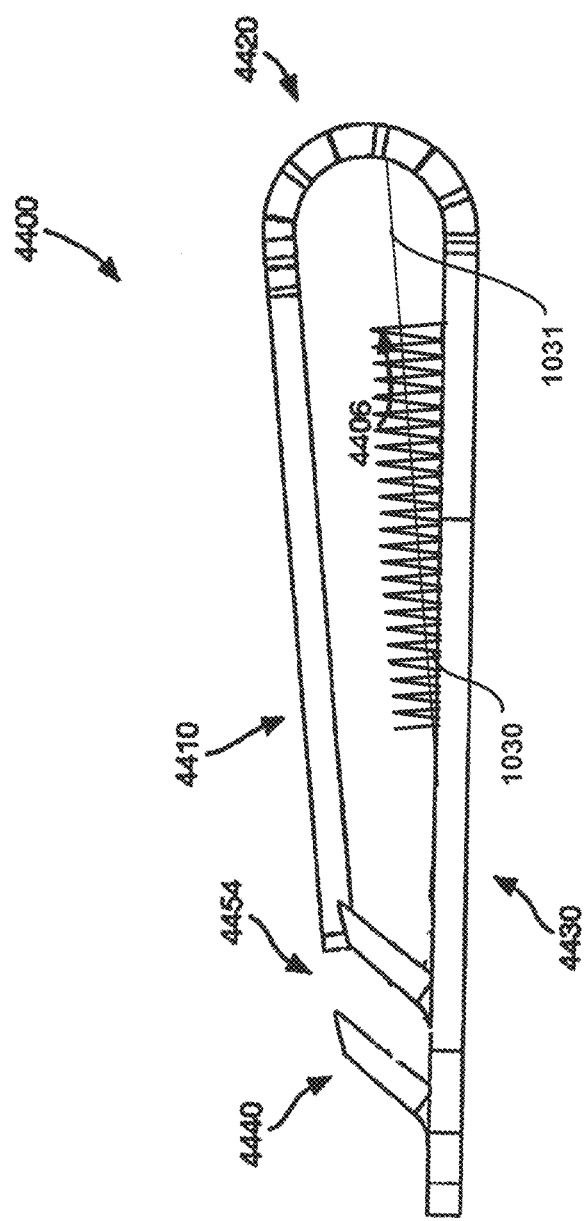

Referring now to FIG. 236, the clasp 4400 is shown in a fully deployed or actuated position, without a leaflet in place. The indicating wire 1031 with optional radiopaque coil 1030 remains undeflected and is positioned on an interior side of the moveable arm 4430. The indicating wire 1031 and coil 1030 are not seen outside of the profile of the moveable arm 4430. The absence of the indicator arm outside of the profile of the clasp by imaging equipment indicates to the operator that a leaflet has not been captured.

Figure 237:
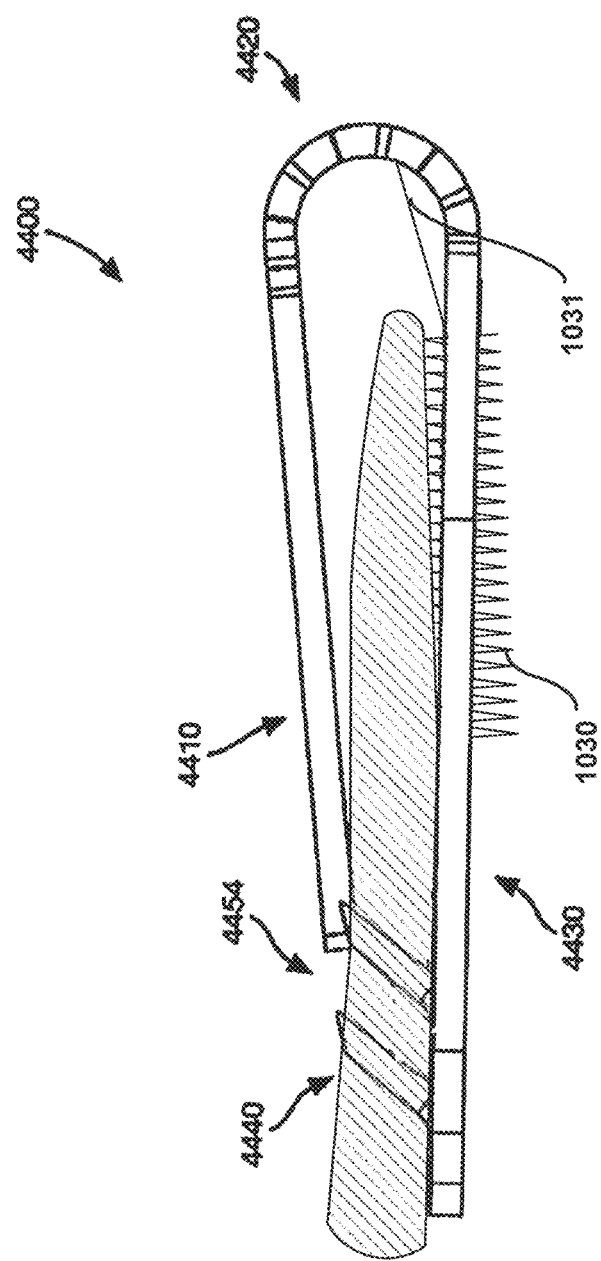

Referring now to FIG. 237, the clasp 4400 is shown with the moveable arm 4430 in a closed position. When the clasp 4400 is closed, the moveable arm 4430 and the indicator arm 4450 exert a pinching force that retains the native leaflet tissue to be secured within the clasp 4400. The clasp 4400 is biased in the closed direction by the shape-setting of the moveable arm 4430 in a preloading position. The closed clasp has captured a sufficient amount of leaflet tissue. That is, the depth of the leaflet in the clasp is sufficient for the clasp to be considered properly positioned, as indicated by the indicating wire 1031 and coil 1030 being deflected through the hoop shaped moveable arm 4430, such that a portion of the indicating wire 1031 and/or the coil 1030 move past the outside profile of the moveable arm 4430 of the clasp 4400. The indicating wire 1031 and/or the coil 1030 beyond the profile of the clasp can be seen on imaging equipment, such as fluoroscopy equipment, as represented by FIG. 237 to indicate that the valve leaflet has been properly captured by the clasp 4400.

FIGS. 238-241 illustrate a variation of the clasp 4400 illustrated by FIGS. 48-66. In the example illustrated by FIGS. 238-241, the clasp has a flexible wire indicator 1031 that loops through openings 2380 in the side beams 4432 of the moveable arm 4430 a plurality of times. The flexible wire indicator 1031 is "laced" or strung through the openings 2380. In the illustrated embodiment, the wire indicator 1031 passes across the hoop shape of the moveable arm with portions 1031a on the inside of the clasp and portions 1031b on the outside of the moveable arm 4430. The portions 1031a of the wire indicator curve and extend inward toward the interior of the clasp. In the illustrated example, the portions 1031b on the outside of the moveable arm extend straight or substantially straight across between the side beams 4432 when the clasp is open. However, in some example embodiments the portions 1031b can have the same or substantially the same shape as the portions 1031a. The clasps 4400 can be used in implantable prosthetic devices, such as devices 100, 200, 300 described above or any other implantable prosthetic device.

The clasp 4400 illustrated by FIGS. 238-241 has a fixed arm 4410, a patterned flex portion of patterned hinge portion 4420, and a moveable arm 4430 formed in the shape of a hoop or loop. In the illustrated embodiment, the interior curved portions 1031*a* are curved in a bump configuration and exterior portions 1031*b* are flat or substantially flat, positioned just exterior to the moveable arm 4430 when the clasp 4400 is open and when there is no leaflet positioned to overlap the indicator when the clasp is closed. In the illustrated example, there are four inner portions 1031*a* and three outer portions 1031*b*. However, there can be any number of inner and outer portions. For example, there can be only one or two of each, or as many as 8-10 of each.

Figure 241:
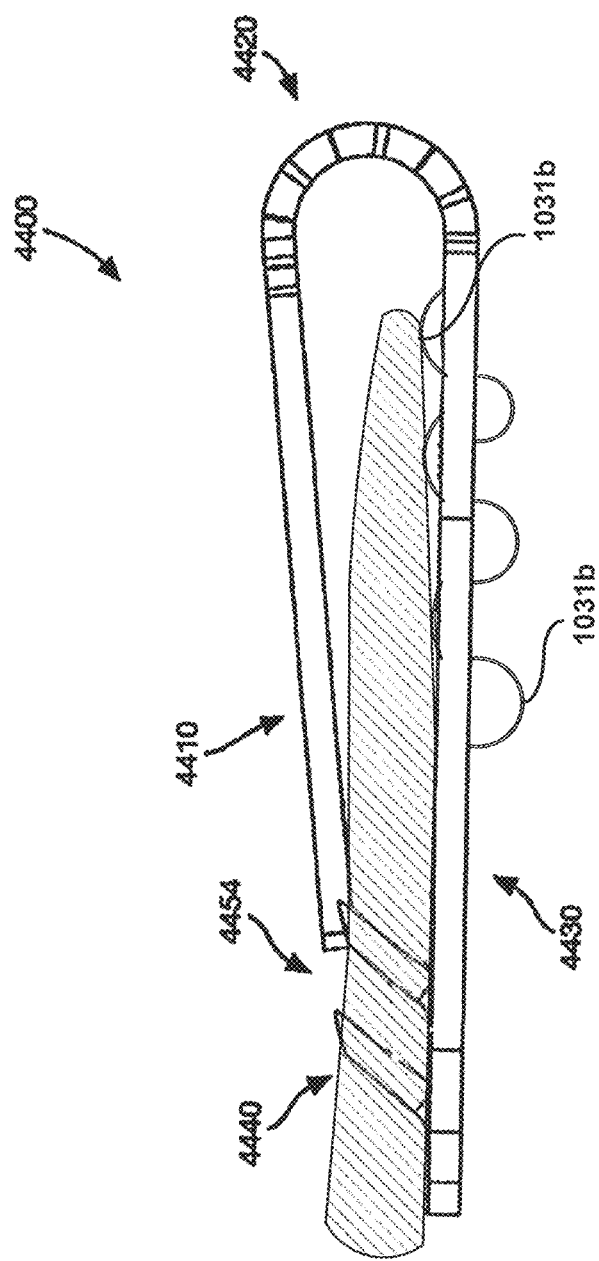

Referring to FIG. 241, when a leaflet is present, the interior curved portions 1031*a* of the wire indicator 1031 are depressed and push the portions 1031*b* outward relative to the moveable arm 4430. The number of portions 1031*b* that are pressed out from the moveable arm 1031*b* indicate the depth of the leaflet to the operator.

Figure 238:
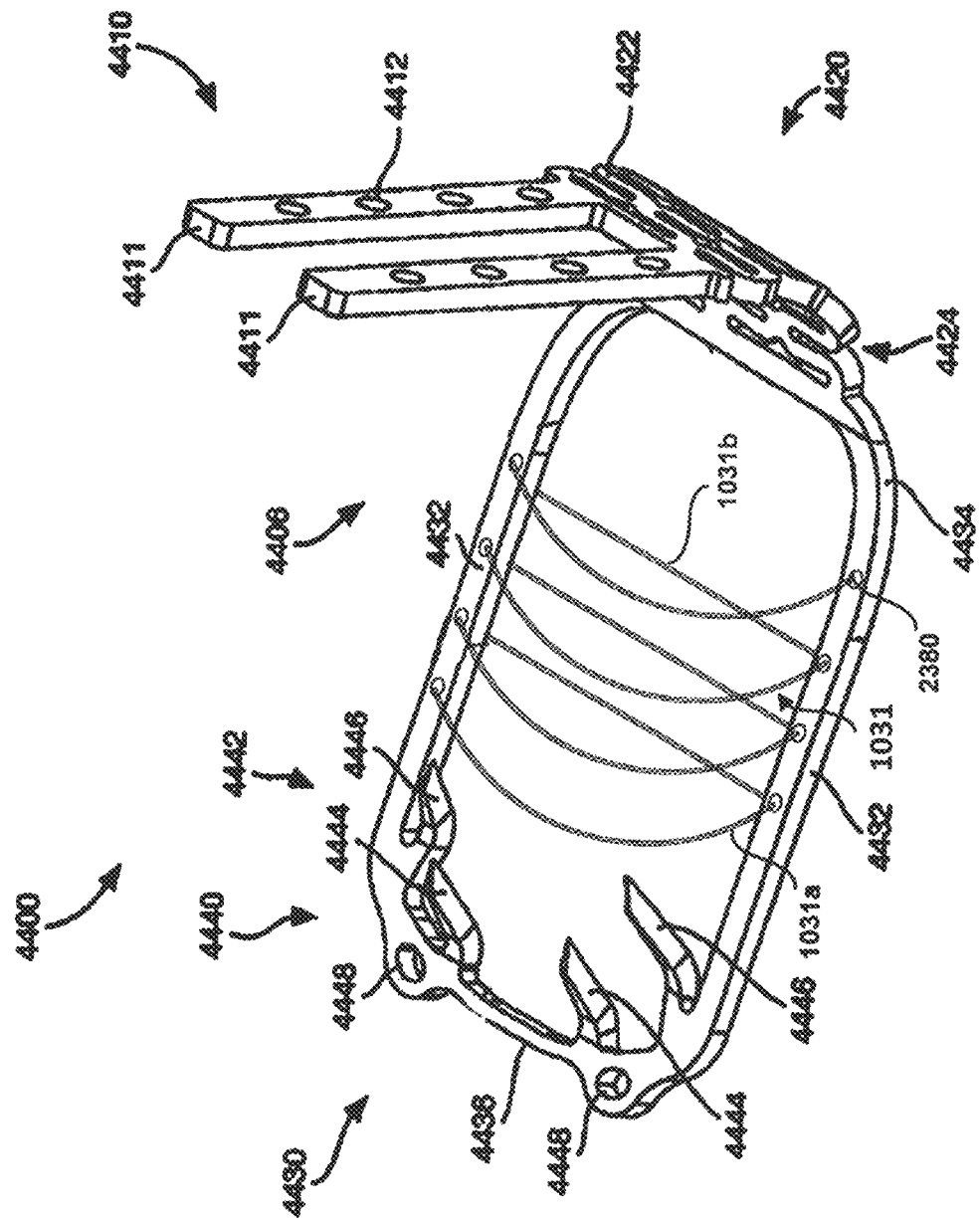
FIGS. 238-241 show a clasp having a flexible wire indicator according to an example embodiment, for an implantable prosthetic device.
Figure 239:
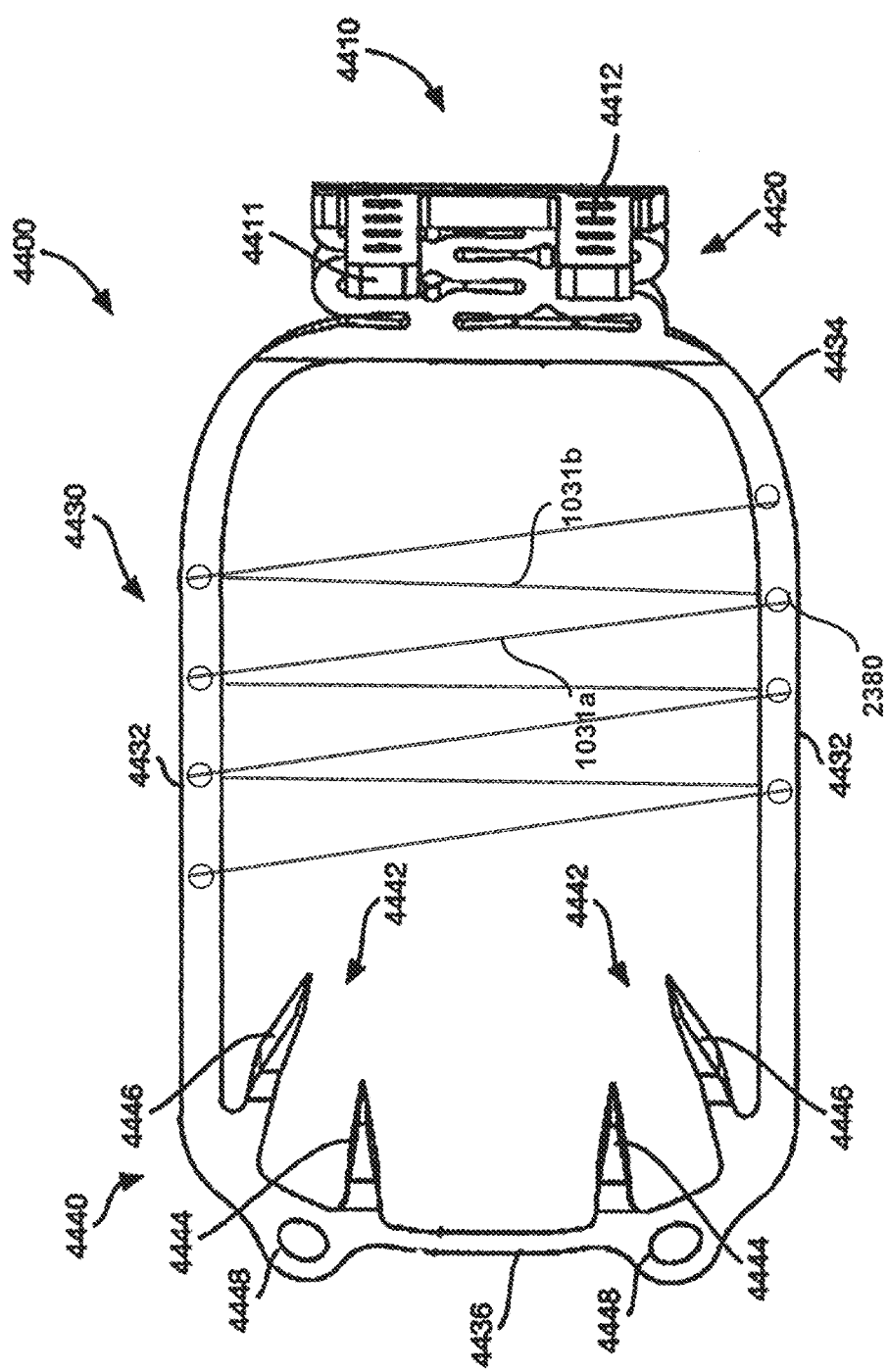

Referring now to FIGS. 238 and 239, the clasp 4400 is shown in an open position. The moveable arm 4430 is biased or spring-loaded in a closing direction and are moved to and held in the open position by tension applied to actuation lines (not shown). The indicating wire 1031 is in an undeflected configuration because there is no leaflet engaged in the open clasp in FIGS. 238 and 239.

Figure 240:
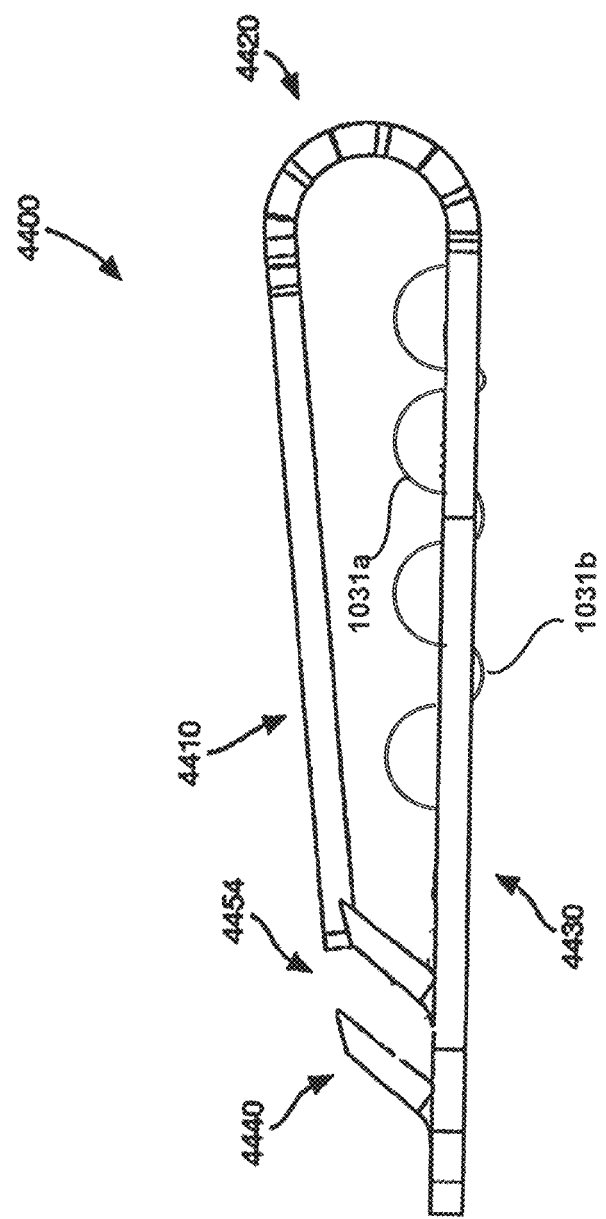

Referring now to FIG. 240, the clasp 4400 is shown in a fully deployed or actuated position, without a leaflet in place. The indicating wire 1031 remains undeflected, and the interior portions 1031*a* remain positioned on an interior side of the fixed arm and the exterior portions 1031*b* are flush or substantially flush with the moveable arm 4430. The absence of the exterior portions 1031*b* extending outward from the moveable arm 4430 on imaging equipment indicates that a leaflet has not been captured.

Referring now to FIG. 241, the clasp 4400 is shown with the moveable arm 4430 in a closed position. When the clasp 4400 is closed, the moveable arm 4430 exerts a pinching force that retains the native leaflet tissue within the clasp 4400. The clasp 4400 is biased in the closed direction by the shape-setting of the moveable arm 4430 in a preloading position. The closed clasp has captured a sufficient amount of leaflet tissue. That is, the depth of the leaflet in the clasp is sufficient for the clasp to be considered properly positioned. The indicating wire 1031 is deflected such that the portions 1031*b* extend outward from the moveable arm 4430. The outwardly extending portions 1031*b* can be seen using imaging equipment, such as fluoroscopy. That is, the interior portions 1031*a* are pressed towards the moveable 4430 arm by the pressure applied from the leaflet, thereby causing the exterior portions 1031*b* to extend further outward from the moveable arm 4430 of the clasp.

In the embodiments described herein, including but not limited to the embodiments described in FIGS. 226-241, the indicator can be a coil over a wire; a flexible, super elastic member with an optional embedded radiopaque marker; protruding members from the clasp body which originate from the flex or hinge region cut from the same continuous sheet as the clasp; and/or a v-shaped radiopaque marker located near the flex or hinge region of the clasp. The indicator can be made of materials that are super-elastic or flexible; i.e., the materials do not undergo plastic deformation upon leaflet capture.

Referring now to FIG. 110, a portion of an example embodiment of a laser cut clasp is illustrated. Similar to the embodiment illustrated in FIG. 103, the clasp has a moveable arm 5230, a fixed arm 5210 and one or more flexible segments to permit shaping and bending of the laser cut sheet into a clasp shape. The moveable arm can have a barb 5240 at the end of it. The fixed arm can have three elongate cut-outs, and two flexible bumps 1031 that serve as indicators. FIG. 105, described above, is the corresponding schematic view to an embodiment having two flexible bumps 1031 such as that in FIG. 110. Thus, FIGS. 106-109 are also representative of operation of the embodiment illustrated in FIG. 110, being positioned and deployed on a native leaflet.

Referring now to FIGS. 111-122, illustrate a variation of the clasp 4400 illustrated by FIGS. 48-66 that has a flexible feature, such as the illustrated bump 1031 that flattens when pressed against leaflet tissue. The clasps 4400 can be used in implantable prosthetic devices, such as devices 100, 200, 300 described above, is shown. The clasp 4400 has a fixed arm 4410, a patterned flex portion or patterned hinge portion 4420, a moveable arm 4430 formed in the shape of a hoop or loop, and a barbed portion 4440 of the moveable arm 4430. The clasp 4400 also includes an indicator arm 4450 extending from an indicator flex or hinge portion 4460 that joins the indicator arm to the flex or hinge portion 4420. In this embodiment, the indicator arm 4450 can have a flexible feature, that can be a bump 1031 that flattens when pressed against leaflet tissue. The clasp 4400 can be used in any of the implantable prosthetic devices of the present application and can include any of the features or combinations of features of the other clasps described herein. The clasp 4400 can be laser cut from a flat sheet or a tube of shape-memory alloy, such as Nitinol, and then shape-set into a desired shape.

The illustrated fixed arm 4410 has two tongue portions 4411 that each include optional holes 4412 for attaching the fixed arm 4410 to an implantable device. A central opening 4454 arranged between the tongue portions 4411 is wider than the indicator arm 4450 so that the indicator arm 4450 can pass through the fixed arm 4410 between the tongue portions 4411 to form an X-shape when viewed from the side (FIG. 106) when the indicator arm 4450 does not engage the leaflet tissue.

The patterned flex portion or patterned hinge portion 4420 is formed from a plurality of spring segments 4422 and cutouts 4424. The two tongue portions 4411 of the fixed arm 4410 extend from one end of the patterned flex/hinge portion 4420 and the moveable arm 4430 extends from the other end of the flex/hinge portion 4420.

The moveable arm 4430 of the clasp 4400 has a hoop-like shape. The hoop-shaped moveable arm 4430 includes side beams 4432 that are thinner and more flexible, particularly in the lateral direction. The side beams 4432 include a first flex or hinge portion 4434 arranged toward the proximate end of the moveable arm 4430 and a second flex or hinge portion 4436 arranged at the distal end of the moveable arm 4430. The first flex or hinge portion 4434 is formed by one or more bends in the side beams 4432. The second flex or hinge portion 4436 includes a thinner—and therefore more flexible—portion to reduce the force required to collapse the clasp 4400. The hoop-shape of the moveable arm 4430 and flexible side arms 4432 allow the moveable arm 4430 to be collapsed by merely retracting the clasp 4400 into a delivery sheath (not shown). In certain embodiments, the expansion and contraction of the clasp 4400 is controlled by actuation lines (not shown).

The hoop-like shape of the moveable arm 4430 provides for a wider barbed portion 4440 that can include more barbs 4442 with the same or greater lateral spacing than other clasps. The wider spacing of the barbs 4442 improves capture of the native leaflets. The barbs 4442 are also longitudinally staggered as a result of their position on the hoop-like shape of the moveable arm 4430. That is, two center barbs 4444 are arranged further away from the flex or hinge portion 4420 and two outer barbs 4446 are arranged closer to the flex or hinge portion 4420. The barbed portion 4440 of the moveable arm 4430 also includes holes 4448 for receiving an actuation suture (not shown). In certain embodiments, the hoop shape of the moveable arm 4430 is similar to the shape of wide outer paddles of an implantable device so that pinching forces of the paddles are spread out evenly on the barbs, further improving the retention of the native leaflets. The ends of the barbs 4442 can be further sharpened using any suitable sharpening means.

The indicator arm 4450 includes a beam 4451 that extends from the flex or hinge portion 4420 in the interior of the hoop-shaped moveable arm 4430 between the two side arms 4432 to a barbed portion 4456. The indicator arm 4450 includes a hole 4452 at the end for receiving an actuation line (not shown) for actuating the indicator arm 4450. The optional barbed portion 4456 is arranged at the end of the beam 4451 of the indicator arm 4450 and includes at least one barb 4456 (when the optional barbed portion is included). The optional barbed portion 4456 helps the indicator arm 4450 secure the leaflet until the moveable arm 4430 is closed. The optional barb 4456 can be laser cut from the indicator arm 4450 and bent outwards so that it protrudes away from the indicator arm 4450 at about the same angle as the barbs 4442 protrude from the moveable arm 4430. In some embodiments, the indicator arm 4450 includes barbs that, like the barbs 2244 of the clasp 2200, are cut from a flat sheet of material and then rotated about 90 degrees to protrude outward at an angle.

The optional barbed portion 4456 of the indicator arm 4450 is arranged at a distance from the flex or hinge portion 4420 such that the barb 4456 of the indicator arm 4450 is longitudinally arranged between the center barbs 4444 and the outer barbs 4446 of the barbed portion 4440. This arrangement ensures that the barbed portion 4440 will engage a leaflet that is engaged by the indicator arm 4450. That is, if a native leaflet positioned within the clasp 4400 is engaged by the barbed portion 4456 of the indicator arm 4450 when the indicator arm 4450 is actuated, then the leaflet will also be engaged by the barbed portion 4440 of the moveable arm 4430.

In the example embodiment illustrated by FIGS. 111-122, when a native leaflet is properly positioned and engaged within the clasp, the bump 1031 will be flattened, to indicate proper depth placement of the leaflet. The opposite is also true. That is, if a native leaflet not properly positioned (i.e. not far enough) within the clasp 4400 the bump 1031 will not be flattened when the indicator arm 4450 is actuated. The bump 1031 can be positioned along the indicator arm at a position in the clasp that indicates the distance within the clasp that the native leaflet must extend to be properly positioned. Thus, the example embodiment illustrated by FIGS. 111-122 provides two indications. First, any engagement of the leaflet with a barb on the indicator arm indicates that the barbs 4444, 4446 will also engage the leaflet (but does not indicate proper insertion depth). Second, compression or flattening of the bump 1031 indicates proper leaflet insertion.

The indicator flex or hinge portion 4460 allows the indicator arm 4450 to be actuated separately from the moveable arm 4430 to facilitate detection of the depth of engagement of the native leaflet arranged between the moveable arm 4430 and the fixed arm 4410 of the clasp 4400. The indicator flex or hinge portion 4460 can be similar to the patterned flex or hinge portion 4420 and can be formed from a series of spring segments 4462 and cutouts 4464. In some embodiments, the spring force of the indicator flex or hinge portion 4460 is less than the pinching force imparted to the moveable arm 4430 by the flex or hinge portion 4420 so that the indicator arm 4450 can be actuated many times to detect the position of the leaflet while the moveable arm 4430 with a stronger pinching force is actuated once the leaflet is held in a desirable position by the indicator arm 4450. The lower pinching force of the indicator arm 4450 reduces the force imparted onto the leaflet tissue so that the indicator arm 4450 can be repositioned repeatedly and be less likely to puncture or otherwise damage the leaflet tissue. The lower pinching force can also allow the indicator arm 4450 to pulse or jump as the heart beats.

Figure 112:
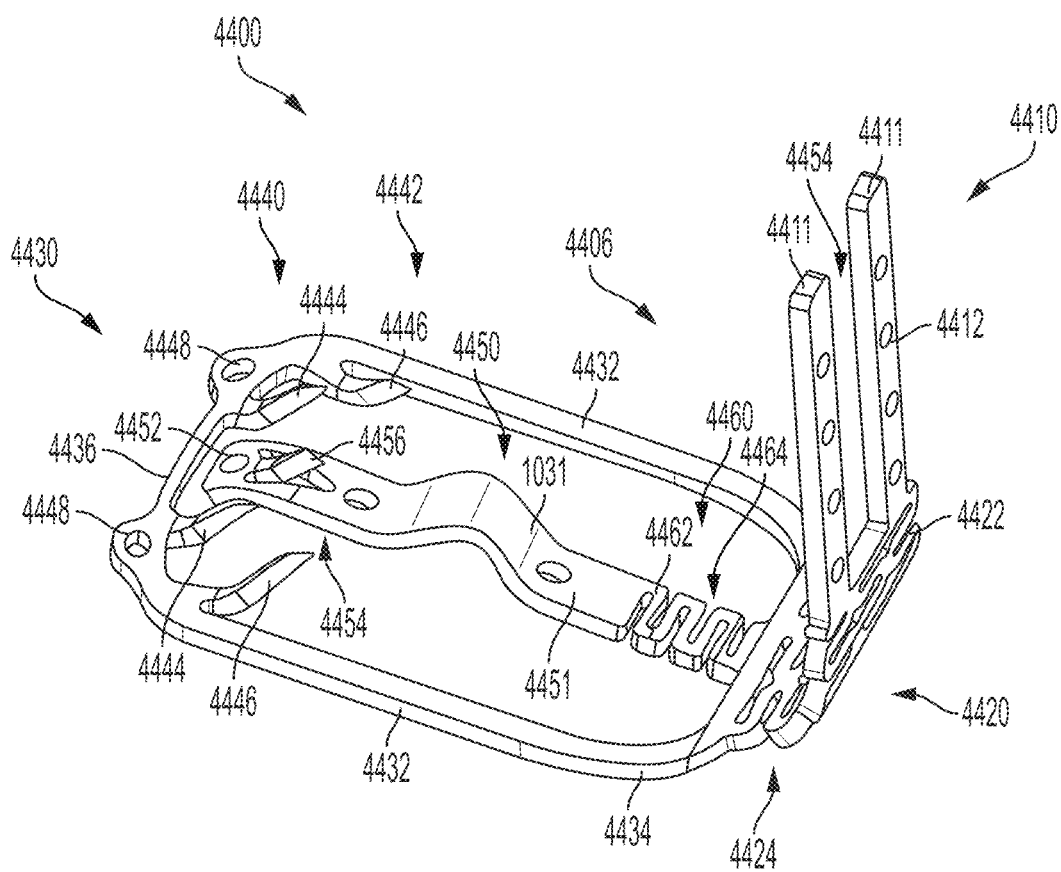
Figure 113:
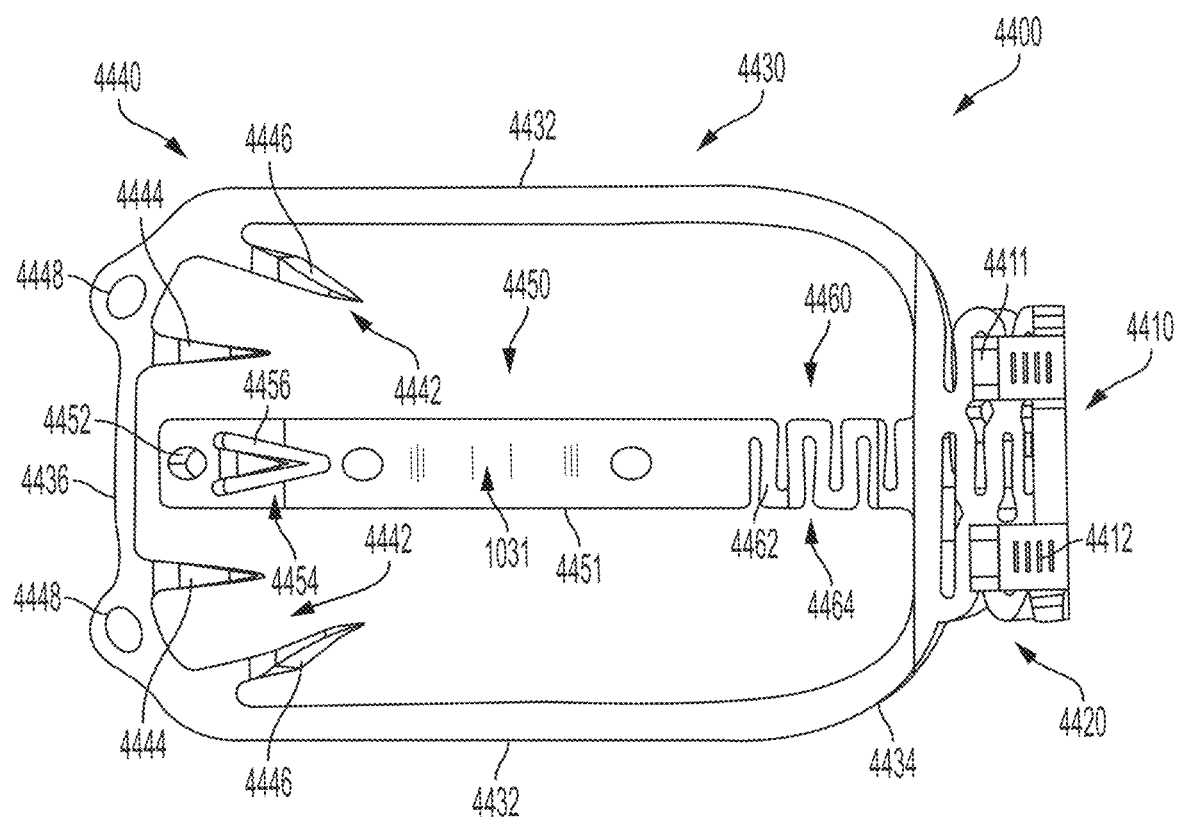

Referring now to FIGS. 111-113, the clasp 4400 is shown in an open position. The moveable arm 4430 and indicator arm 4450 are biased or spring-loaded in a closing direction and are moved to and held in the open position by tension applied to actuation lines (not shown) that can be attached to the holes 4448,4452 in each of the moveable arm 4430 and indicator arm 4450, respectively. The bump 1031 is in its curved bump configuration because there is no leaflet engaged in the open clasp in FIGS. 111-113.

Figure 114:
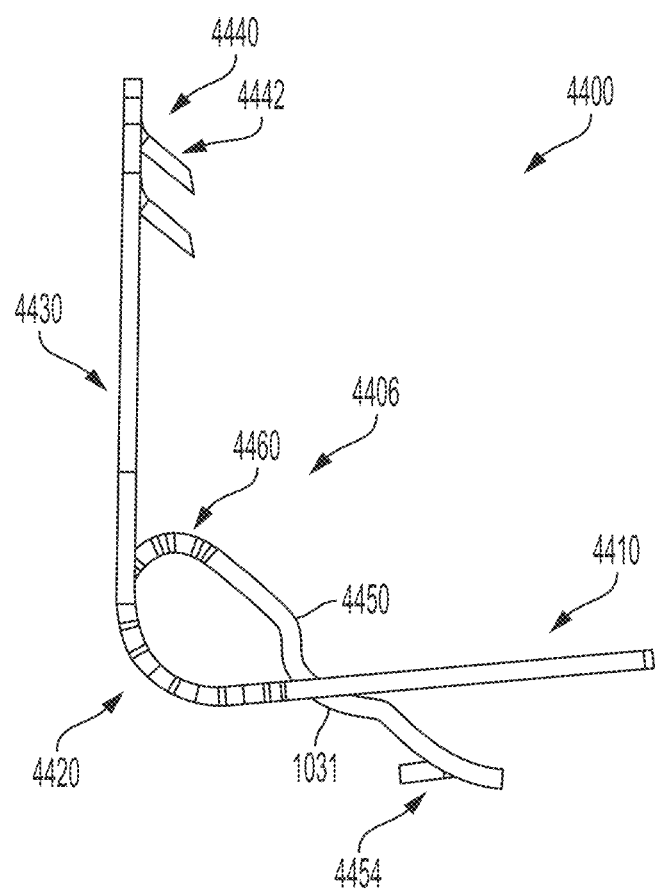
Figure 115:
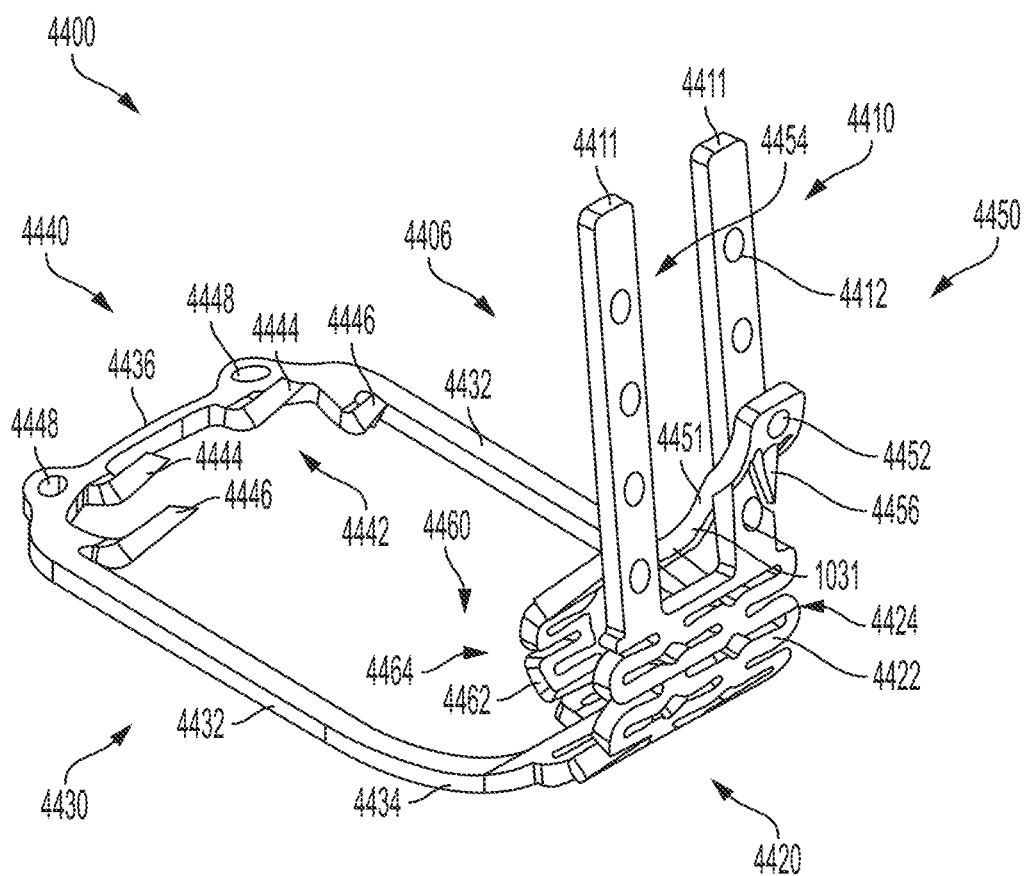
Figure 116:
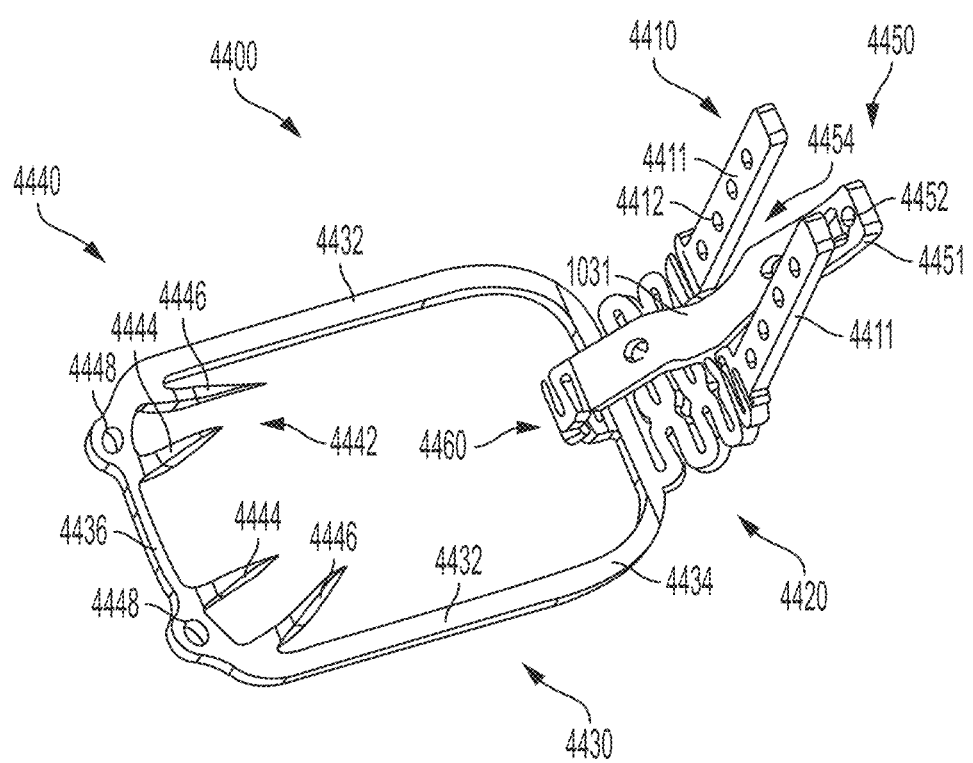

Referring now to FIGS. 114-116, the clasp 4400 is shown with the indicator arm 4450 in a fully deployed or actuated position, that is, the furthest extent that the indicator arm 4450 is capable of reaching when the indicator arm 4450 does not engage with the leaflet tissue during actuation. The indicator arm 4450 is allowed to actuate in the closing direction when tension on actuation lines (not shown) is decreased. In the fully actuated position, the indicator arm 4450 forms an X-shape with the fixed arm 4410 that is visible via imaging devices so that the operator knows that the indicator arm 4450 has not engaged the leaflet at all. Because no leaflet is engaged in the clasp of FIG. 114, the bump 1031 is also in its curved configuration.

Figure 117:
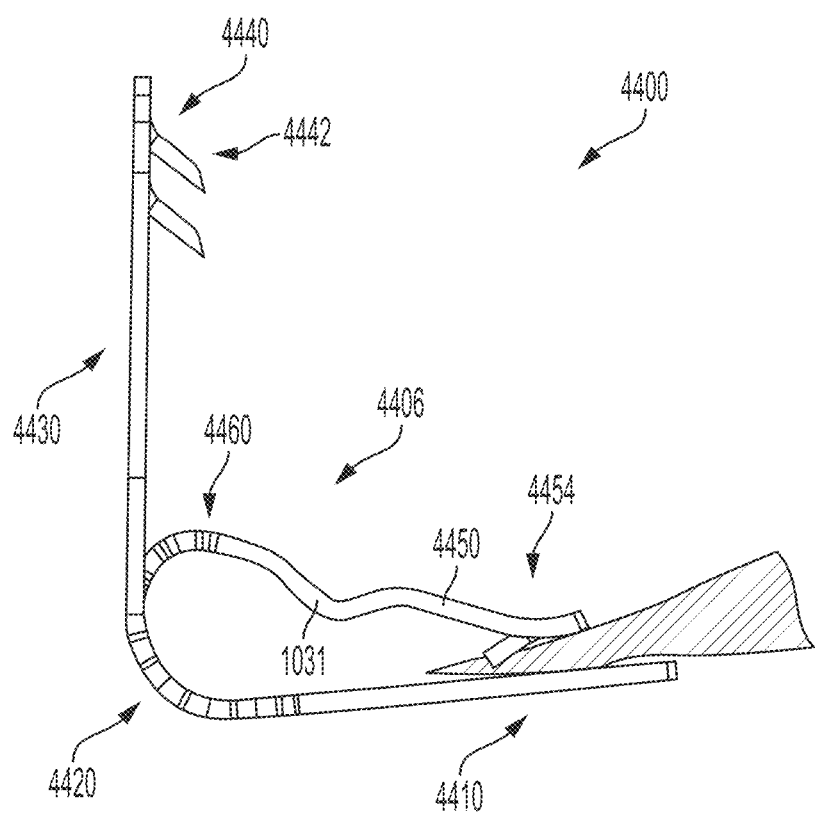
Figure 118:
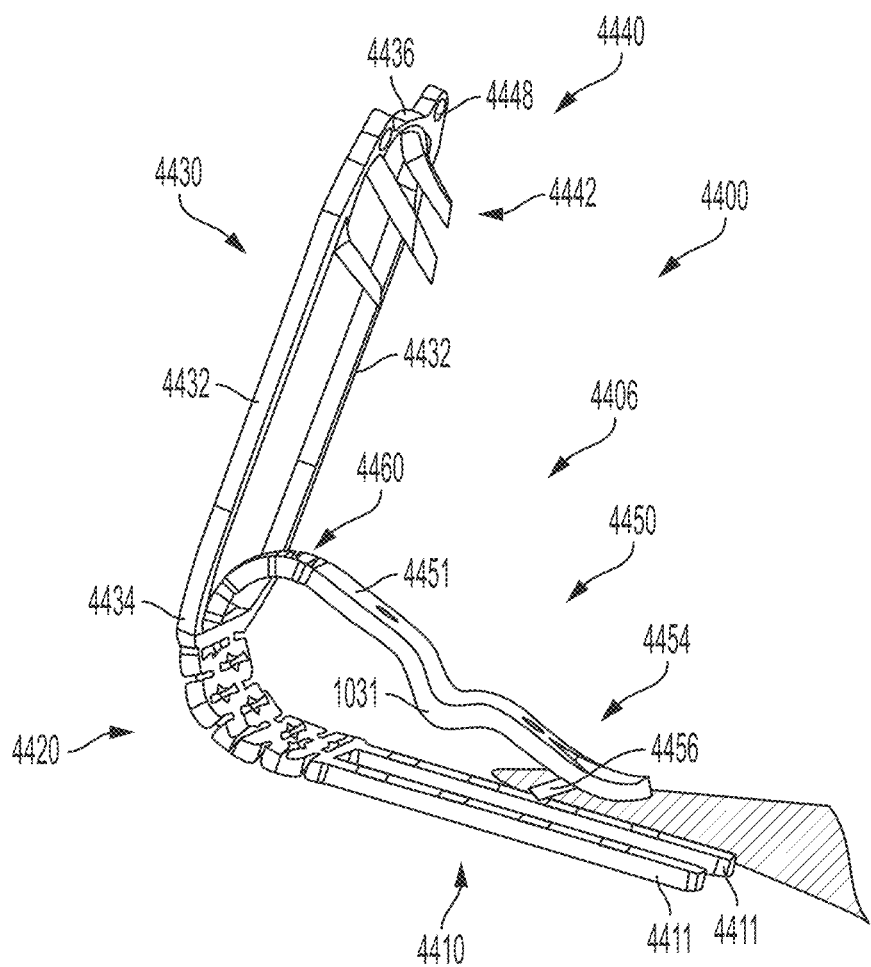
Figure 119:
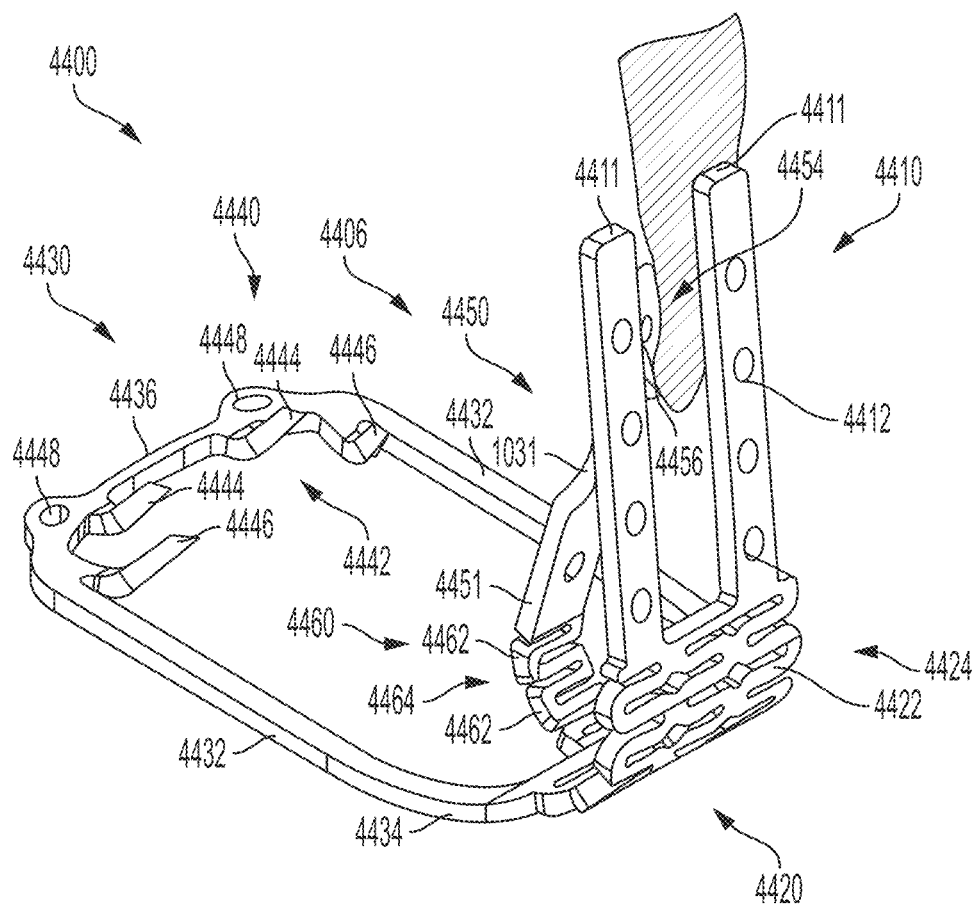

Referring now to FIGS. 117-119, the clasp 4400 is shown with the indicator arm 4450 in an engaged or closed position. That is, the position that the indicator arm 4450 would be in when the leaflet tissue has been engaged during actuation. The indicator arm 4450 is allowed to actuate in the closing direction when tension on actuation lines (not shown) is decreased. In the closed position, the indicator arm 4450 does not cross the fixed arm 4410 and does not form an X-shape with the fixed arm 4410. In the closed position, the leaflet is only partially inserted into the clasp, and thus the bump 1031 on the indicator arm 4450 is not flattened but retains its curved configuration. Thus, the operator knows that the leaflet tissue has been engaged but is not yet positioned a sufficient distance within the clasp to be considered properly positioned.

Figure 120:
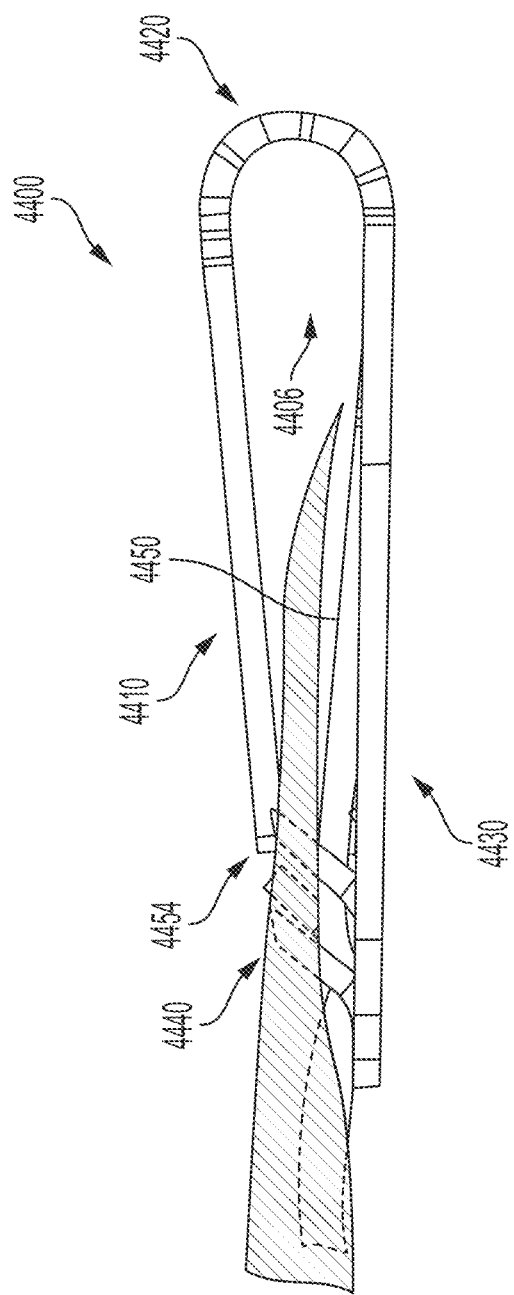
Figure 121:
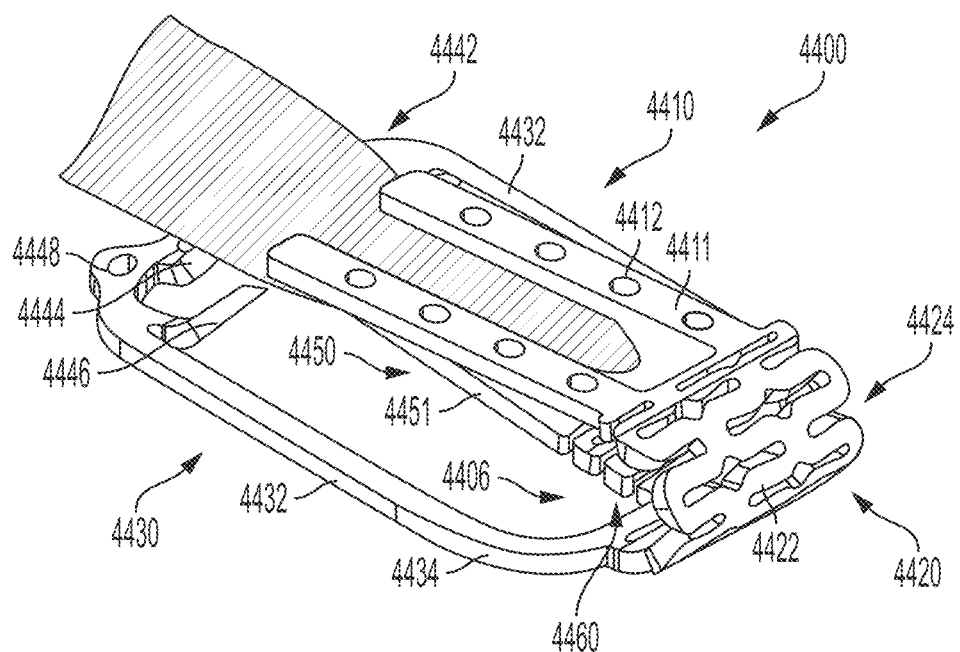
Figure 122:
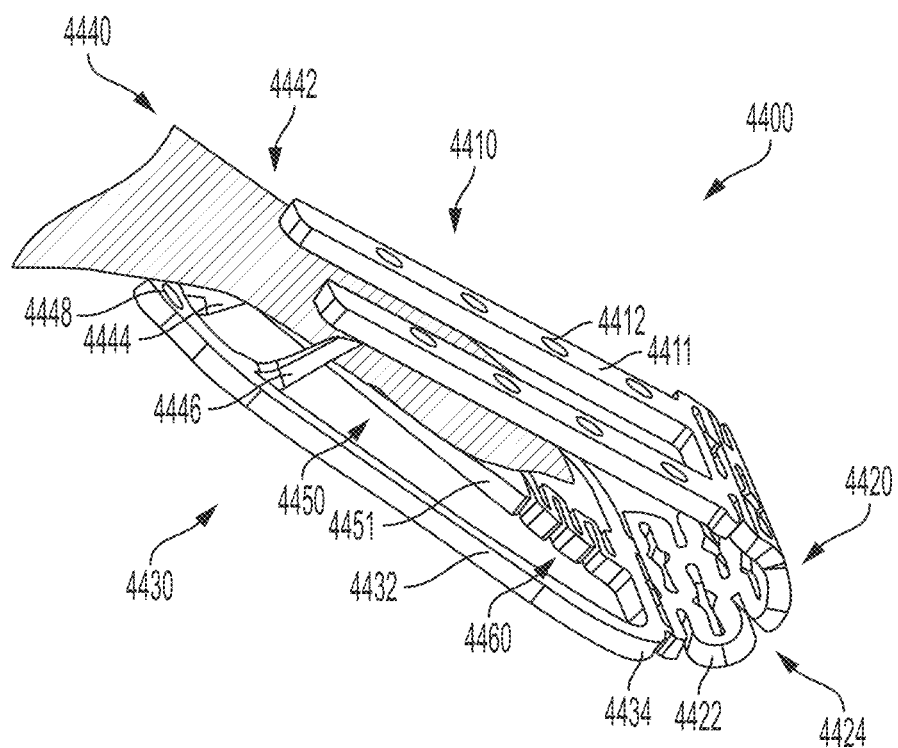

Referring now to FIGS. 120-122, the clasp 4400 is shown with the moveable arm 4430 and the indicator arm 4450 both in a closed position. When the clasp 4400 is closed, the moveable arm 4430 and the indicator arm 4450 exert a pinching force that retains the native leaflet tissue to be secured within the clasp 4400. The clasp 4400 is biased in the closed direction by the shape-setting of the moveable arm 4430 and the indicator arm 4450 in preloading positions. The closed clasp has captured a sufficient amount of leaflet tissue, that is, the depth of the leaflet in the clasp is sufficient for the clasp to be considered properly positioned, as indicated by the bump 1031 on the indicator arm being flattened. In FIGS. 120-122, the portion of the indicator arm having the bump 1031 is not visible because the leaflet blocks the view of that portion of the indicator arm and because the bump is flattened by engagement with the leaflet.

Figure 67:
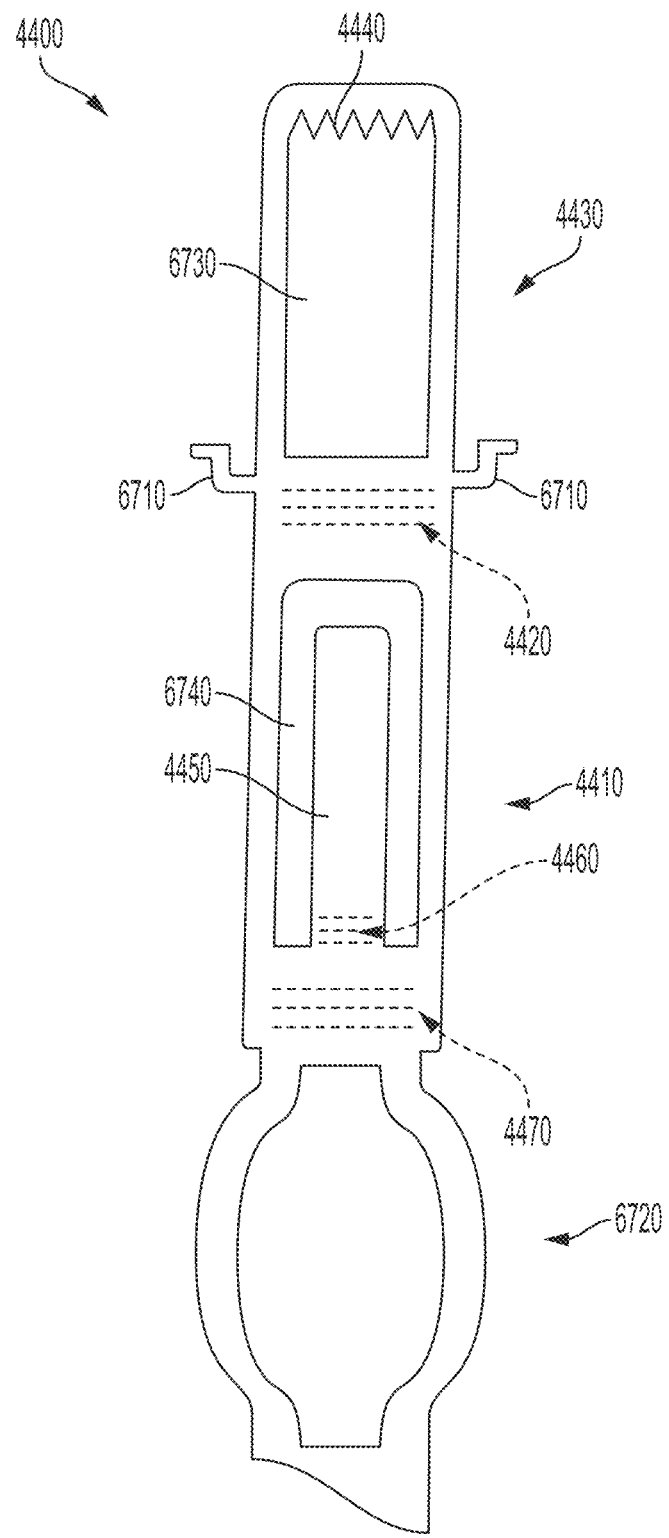
FIGS. 67 and 68 show an example embodiment of a laser cut clasp and indicator.

Referring now to FIGS. 67A-68A, an example embodiment of a laser cut clasp 4400 is illustrated. FIG. 67 illustrates a flat view of a portion of a laser cut clasp 4400, having a moveable arm 4430, a fixed arm 4410, and indicator arm 4450. In the example illustrated by FIGS. 67 and 68, a portion of a paddle 6720 is optionally also formed from the same piece of material as the clasp 4400. However, in some embodiments only the clasp is cut from the piece of material and the paddle portion 6720 is omitted. The moveable arm can have a cut-out section 6730 and barbs 4440 at the free end of the moveable arm, for securing to tissue of a native leaflet. The clasp can have flexible sections where bending of the clasp into a useable shape occurs. The flexible sections can each be a hinged portion, jointed portion, and/or an otherwise flexible portion. There is a flexible or hinged portion 4460 that permits the indicator arm to flex. There are also flex or hinge portions 4420 that permits dynamic flexing of the moveable arm 4430 relative to the fixed arm 4410. An optional flex or hinge portion 4470 allows flexing between the fixed arm 4410 and the optional paddle portion 6720. The clasp can also have optional feet 6710 extending outward from the sides of the clasp near the flexible portion 4420 between the moveable arm and the fixed arm. The feet 6710 can lock into a bushing type collar (not shown) or another connector. The connector can be attached to a spacer that coapts with native mitral valve leaflets. The clasp can be shape set so that its resting configuration has the indicator arm 4450 extending through or toward the opening 6730 of the moveable arm 4430.

Figure 68:
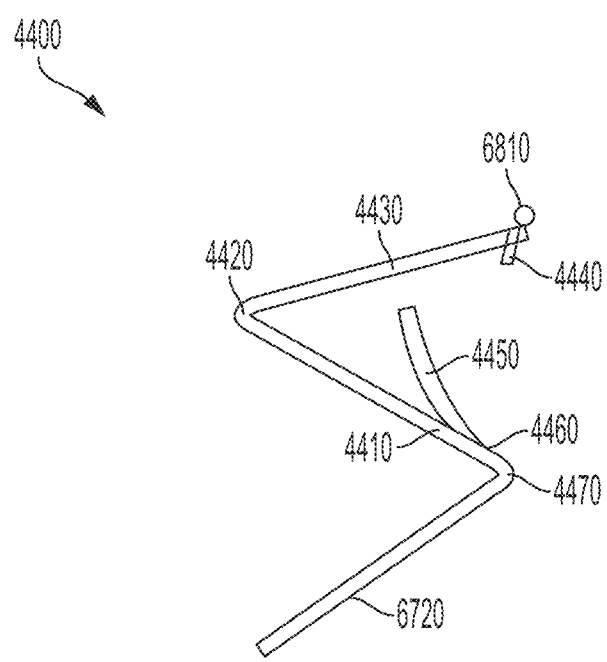

FIG. 68 illustrates the clasp 4400 in a partially open configuration. The clasp can be oriented to capture a valve leaflet. When the leaflet is inserted to a predetermined acceptable dept, the leaflet depresses the indicator arm 4450. The depression or flattening of the indicator arm 4450 indicates that a sufficient amount of the leaflet is disposed in the clasp. Once a sufficient amount of the leaflet is in the clasp, the clasp can be closed to capture the leaflet. In the example illustrated by FIG. 68, the indicator arm 4450 extends in the opposite or substantially the opposite direction of the moveable clasp arm 4430. FIG. 68 also illustrates an optional suture loop 6810, in which suture or other actuating line(s) pass through and/or connect, to actuate the clasp.

The indicator arm has a flexible or hinged section 4460 to permit flexing of the clasp. The indicator can pass through the opening 6730 of the moveable arm (see FIG. 67) when there is no leaflet captured. When there is a leaflet captured in the clasp, the indicator arm 4450 can sit on top of the leaflet. The length and/or the position of the indicator can be chosen to represent the minimum capture depth required for the device. The optional integral paddle 6720 can be used to approximate the leaflets and/or can be configured to allow elongation of the laser cut paddle. The flex or hinge regions 4420, 4470, and 4460 permit shape setting in a desired shape and/or facilitate relative flexing of the moveable clasp portion, the fixed clasp portion, the indicator arm, and/or the paddle portion 6720.

Figure 67A:
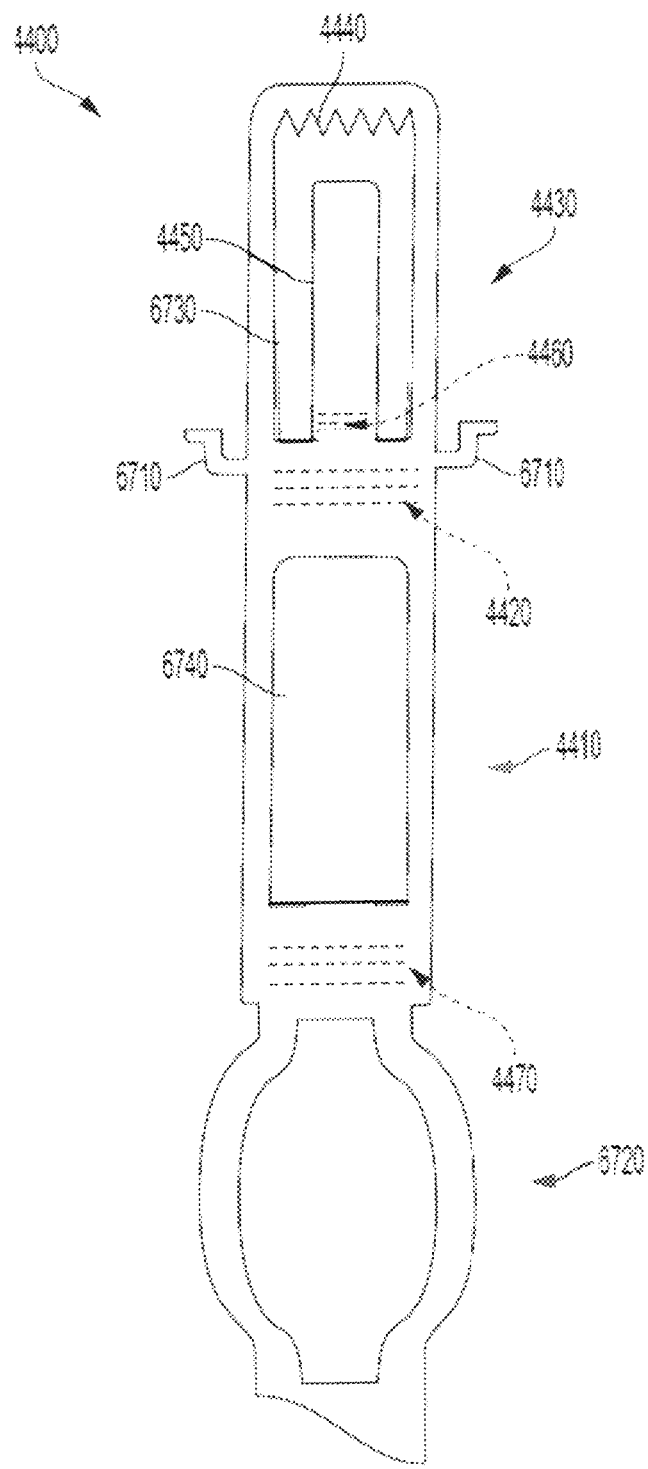
FIGS. 67A and 68A show an example embodiment of a laser cut clasp and indicator.
Figure 68A:
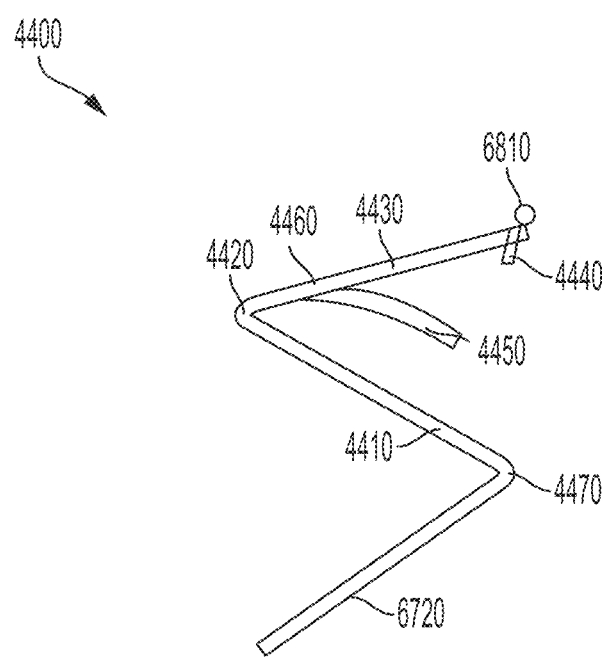

Referring now to FIGS. 67A and 68A, an example embodiment of the clasp similar to that in FIGS. 67 and 68 is illustrated. FIG. 67A illustrates that the indicator arm 4450 is connected to the moveable arm 4430 at a flex or hinge region 4460. The indicator arm flexes toward the interior region of the clasp when there is no leaflet and the clasp is not yet closed, as illustrated in FIG. 68A. When the clasp is closed, the indicator arm 4450 can pass through opening 6740 of the fixed arm when there is no leaflet positioned deep enough within the clasp to engage the indicator arm 4450. When a leaflet is positioned sufficiently deep within the clasp so as to engage the indicator arm, the indicator arm can flex at a flexible or hinged region 4460 toward and through opening 6730 of moveable arm 4430.

Figure 69:
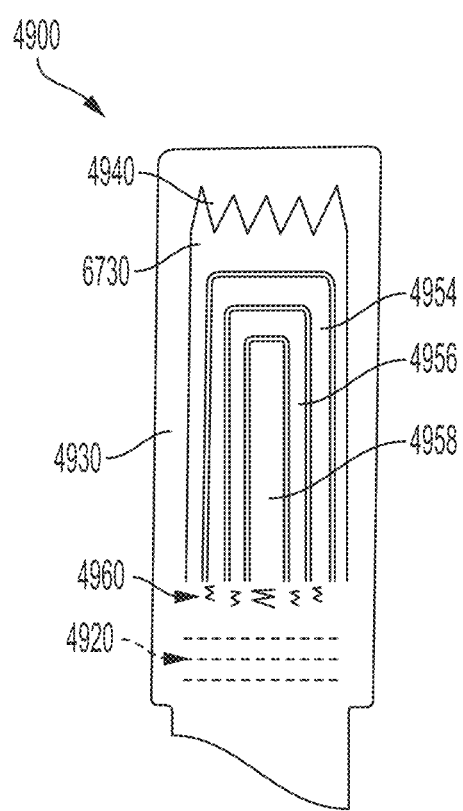
FIG. 69 shows an example embodiment of a laser cut clasp with a plurality of indicators.

Referring now to FIG. 69, a portion of an example laser cut clasp 4900 is illustrated. This laser cut clasp has a moveable arm 4930, a barbed portion 4940, and three indicator arms, 4954, 4956, and 4958. A fixed arm of the clasp 4900 is not illustrated in FIG. 69. A fixed arm can be included as in other embodiments described herein or the fixed arm can be omitted in any of the embodiments and the moveable arm can extend from and/or be connected to a spacer or a paddle.

As with the example embodiment described above in FIGS. 67-68, there is a flexible section of the laser cut sheet to permit shape setting of the moveable arm and/or to form flexible portions or hinge portions 4920, 4960 to permit flexing of the moveable arm and/or the indicator arms. The multiple indicators in the embodiment illustrated in FIG. 69, as well as the moveable arm, are all cut from one sheet. The indicators can be cut from one sheet, which does not require them to be individually attached to the moveable arm.

Figures 70, 70A:
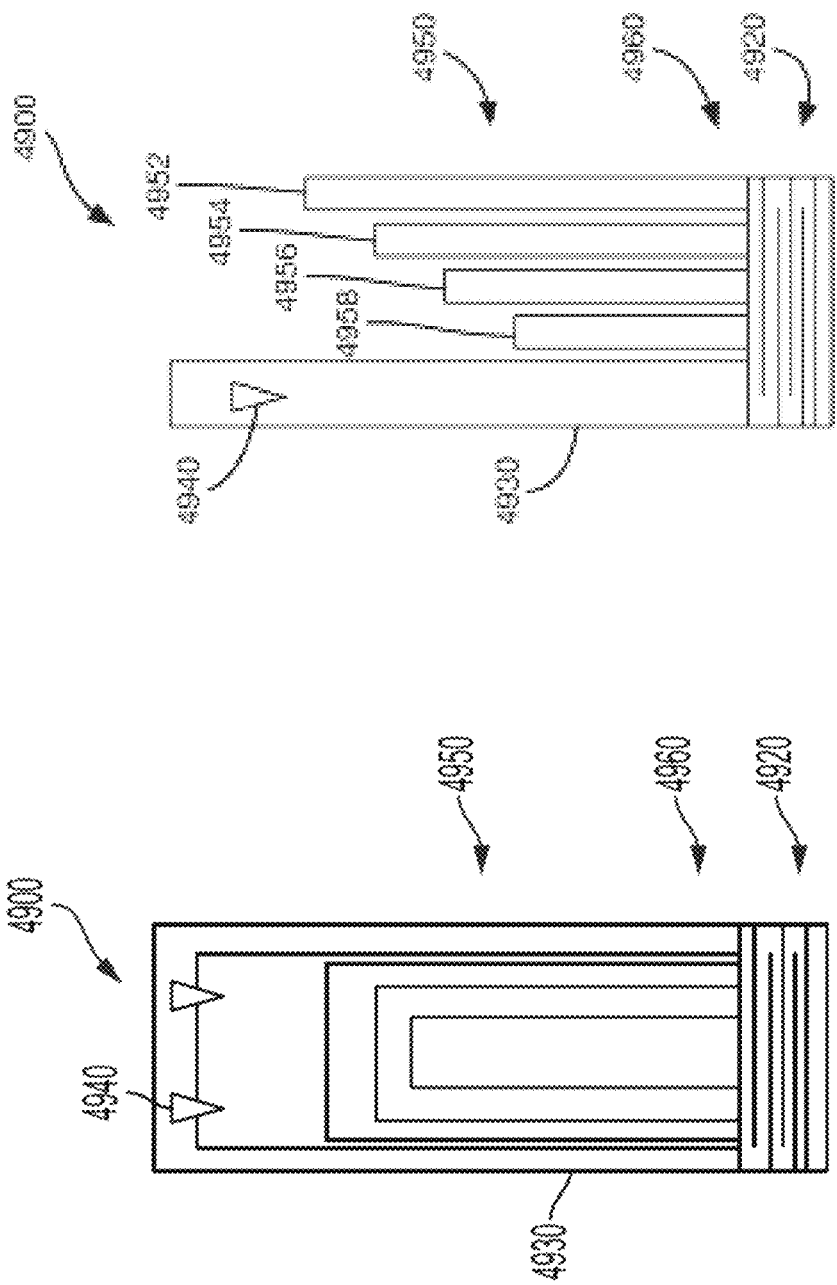
Figure 71A:
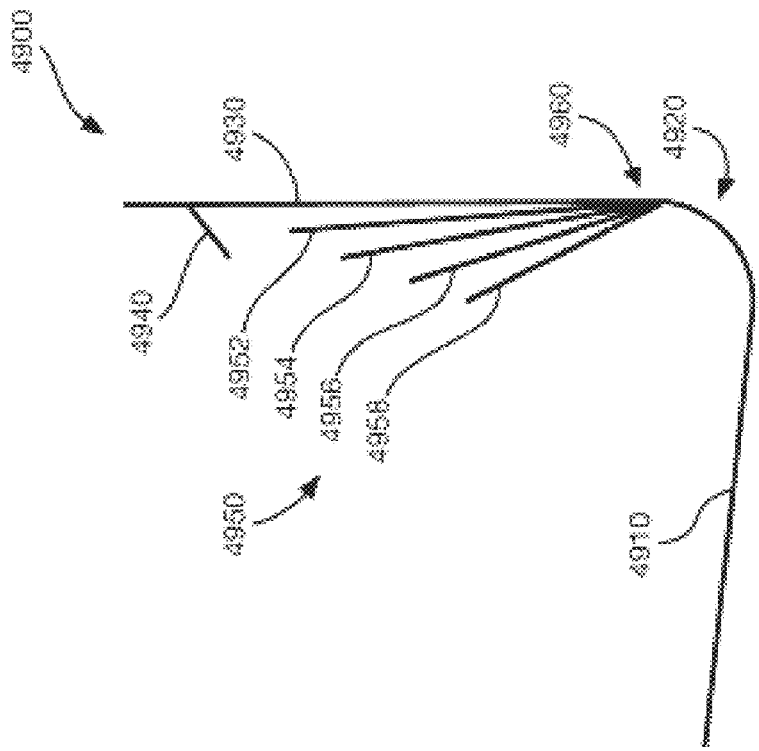
Figure 71:
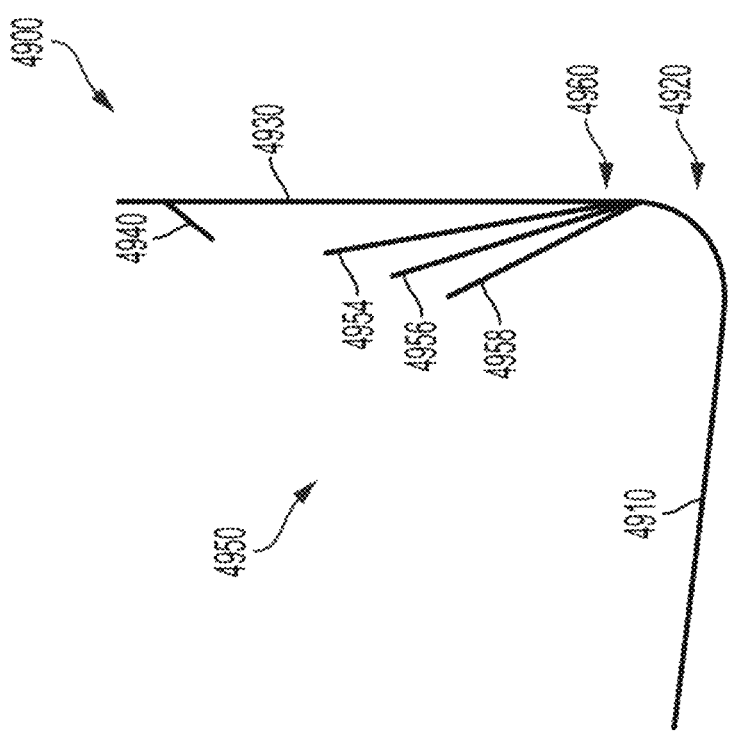

FIGS. 70-71 and 70A-71A schematically illustrate examples of how the moveable arm with indicators of FIG. 69 can be used in a clasp 4900. FIGS. 70-71 and 70A-71A illustrate that indicators having very different physical constructions can operate in the same or substantially the same manner. In the example of FIGS. 70A and 71A, each of the moveable clasp arm 4930 and the indicators 4952, 4954, 4956, 4958 are elongated and positioned adjacent to one another. In the example of FIGS. 70 and 71, the moveable clasp arm 4930 is disposed around the indicators and the indicators 4954, 4956, 4958, the indicator 4954 is disposed around the indicators 4956, 4958, and the indicator 4956 is disposed around the indicator 4958. The clasps illustrated by the schematic illustrations of FIGS. 70-75 can be, but are not required to be, laser cut from a flat sheet.

Referring now to FIGS. 70-71, an example clasp 4900 (illustrated as a barbed clasp) for use in implantable prosthetic devices, such as devices 100, 200, 300 described above, is shown. Like the clasp 3500 described above, the clasp 4900 includes a fixed arm 4910, a flex or hinge portion 4920, and a moveable arm 4930 having a barbed portion 4940 (though other friction-enhancing portions can be used). The clasp 4900 can be used in any of the implantable prosthetic devices of the present application and can include any of the features or combinations of features of the other clasps described herein.

The clasp 4900 also includes an indicator portion 4950 formed from first, second, and third indicator arms 4954, 4956, 4958 adjacent to the moveable arm 4930 and each extending from an indicator flex or hinge portion 4960. The indicator flex or hinge portions 4960 allow the indicator arms 4954, 4956, 4958 to be actuated individually and separately from the moveable arm 4930. The indicator flex or hinge portions 4960 can be formed from a portion of the indicator arms 4954, 4956, 4958, can be formed from a series of cutouts and/or the indicator flex or hinge portion 4960 can be part of the flex or hinge portion 4920.

The indicator arms 4954, 4956, 4958 can be separately actuated from the moveable arm 4930 and optionally from one another to facilitate detection of the depth of engagement of the native leaflet between the moveable arm 4930 and the fixed arm 4910 of the clasp 4900. In some example embodiments, the indicator arms 4954, 4956, 4958 are released from the valve tissue in unison (i.e. release or retraction of one indicator arm releases or retracts all of the indicator arms). In the illustrated embodiment, the indicator arms 4954, 4956, 4958 are narrower than the moveable arm 4930 and have lengths that are each less than a distance from the flex or hinge portion 4920 to the barbed portion 4940. The first indicator arm 4954 can have a length that is about 75 percent to about 100 percent of the distance between the flex or hinge portion 4920 and the barbed portion 4940. The second indicator arm 4956 can have a length that is about 65 percent to about 95 percent of the distance between the flex or hinge portion 4920 and the barbed portion 4940. The third indicator arm 4958 can have a length that is about 50 percent to about 80 percent of the distance between the flex or hinge portion 4920 and the barbed portion 4940. In some embodiments, the first indicator arm 4954 has a length that is about 60 percent to about 100 percent of the distance between the flex or hinge portion 4920 and the barbed portion 4940. The second indicator arm 4956 has a length that is about 50 percent to about 75 percent of the distance between the flex or hinge portion 4920 and the barbed portion 4940. The third indicator arm 4958 has a length that is about 30 percent to about 60 percent of the distance between the flex or hinge portion 4920 and the barbed portion 4940. Any combination of the lengths of indicator arms can be used, as long as the length continues to decrease with each successive indicator arm, to provide indication of the depth the leaflet is positioned within the clasp. There can also be a fourth indicator arm (not shown). Any number of different indicator arms can be included.

The different lengths of the indicator arms 4954, 4956, 4958 are used to determine a desired minimum engagement depth as measured from the end of the moveable arm 4930 of the clasp 4900. Configuring the length of the first indicator arm 4954 to be less than a distance from the flex or hinge portion 4920 to the barbed portion 4940 ensures that the barbed portion 4940 will engage a leaflet that is positioned at the minimum engagement depth as indicated by the first indicator arm 4954. That is, if a native leaflet positioned within the clasp 4900 is engaged by the first indicator arm 4954 when the first indicator arm 4954 is actuated, then the leaflet will be engaged by the barbed portion 4940 of the moveable arm 4930. The opposite is also true. That is, if a native leaflet positioned within the clasp 4900 is not engaged by the first indicator arm 4954 when the first indicator arm is actuated, then the leaflet will not be adequately engaged by the barbed portion 4940 of the moveable arm 4930.

The second and third indicator arms 4956, 4958 are configured with decreasing lengths so that the surgeon to determine how far beyond the minimum engagement depth the native leaflet has been inserted into the clasp 4900. That is, whether or not the native leaflet is engaged by the second and third indicator arms 4956, 4958 indicates that the native leaflet has or has not reached the engagement depth measured by each of the second and third indicator arms 4956, 4958. For example, if a native leaflet positioned within the clasp 4900 is engaged by the third indicator arm 4958 when the third indicator arm 4958 is actuated, then the leaflet has been inserted about 50 percent to about 80 percent of the distance from the barbed portion 4940 to the flex or hinge portion 4920, for example. The opposite is also true. That is, if a native leaflet positioned within the clasp 4900 is not engaged by the third indicator arm 4958 when the third indicator arm 4958 is actuated, then the leaflet has not reached about 50 percent of the distance between the barbed portion 4940 and the flex or hinge portion 4920.

Referring now to FIGS. 70A-71A, an example clasp 4900 for use in implantable prosthetic devices, such as devices 100, 200, 300 described above, is shown. The barbed clasp 4900 includes a fixed arm 4910, a hinge portion 4920, and a moveable arm 4930. Moveable arm 4930 can include a barbed portion 4940 and/or some other friction-enhancing portion(s). The clasp 4900 can be used in any of the implantable prosthetic devices of the present application and can include any of the features or combinations of features of the clasps or barbed clasps described herein.

The clasp 4900 also includes an indicator portion 4950 formed from first, second, third, and fourth indicator arms 4952, 4954, 4956, 4958 adjacent to the moveable arm 4930 and each extending from an indicator hinge portion 4960. The indicator hinge portions 4960 allow the indicator arms 4952, 4954, 4956, 4958 to be actuated individually and separately from the moveable arm 4930. The indicator hinge portions 4960 can be formed from a portion of the indicator arms 4952, 4954, 4956, 4958 or can be formed from a series of cutouts similar to the patterned hinge of the clasp 2100 described above.

The indicator arms 4952, 4954, 4956, 4958 can be separately actuated from the moveable arm 4930 to facilitate detection of the depth of engagement of the native leaflet between the moveable arm 4930 and the fixed arm 4910 of the clasp 4900. In the illustrated embodiment, the indicator arms 4952, 4954, 4956, 4958 are narrower than the moveable arm 4930 and have lengths that are each less than a distance from the hinge portion 4920 to the barbed portion 4940. In some embodiments, the first indicator arm 4952 has a length that is about 75 percent to about 100 percent of the length of a distance between the hinge portion 4920 and a barbed portion 4940. In some embodiments, the second indicator arm 4954 has a length that is about 65 percent to about 95 percent of the length of a distance between the hinge portion 4920 and the barbed portion 4940. In some embodiments, the third indicator arm 4956 has a length that is about 50 percent to about 80 percent of the length of a distance between the hinge portion 4920 and the barbed portion 4940. In some embodiments, the fourth indicator arm 4958 has a length that is about 35 percent to about 65 percent of the length of a distance between the hinge portion 4920 and the barbed portion 4940.

The different lengths of the indicator arms 4952, 4954, 4956, 4958 are used to determine a desired minimum engagement depth as measured from the end of the moveable arm 4930 of the clasp 4900. In some embodiments, configuring the length of the first indicator arm 4952 to be less than a distance from the hinge portion 4920 to the barbed portion 4940 ensures that the barbed portion 4940 will engage a leaflet that is positioned at the minimum engagement depth as indicated by the first indicator arm 4952. That is, if a native leaflet positioned within the clasp 4900 is engaged by the first indicator arm 4952 when the first indicator arm 4952 is actuated, then the leaflet will be engaged by the barbed portion 4940 of the moveable arm 4930. The opposite is also true. That is, if a native leaflet positioned within the clasp 4900 is not engaged by the first indicator arm 4952 when the first indicator arm 4952 is actuated, then the leaflet will not be adequately engaged by the barbed portion 4940 of the moveable arm 4930.

The second, third, and fourth indicator arms 4954, 4956, 4958 are configured with decreasing lengths so that the surgeon to determine how far beyond the minimum engagement depth the native leaflet has been inserted into the clasp 4900. That is, whether or not the native leaflet is engaged by the second, third, and fourth indicator arms 4954, 4956, 4958 indicates that the native leaflet has or has not reached the engagement depth measured by each of the second, third, and fourth indicator arms 4954, 4956, 4958. For example, in some embodiments, if a native leaflet positioned within the clasp 4900 is engaged by the third indicator arm 4956 when the third indicator arm 4956 is actuated, then the leaflet has been inserted about 50 percent to about 80 percent of the distance from the barbed portion 4940 to the hinge portion 4920. The opposite is also true. That is, if a native leaflet positioned within the clasp 4900 is not engaged by the third indicator arm 4956 when the third indicator arm 4956 is actuated, then the leaflet has not reached about 50 percent of the distance between the barbed portion 4940 and the hinge portion 4920.

Figure 72:
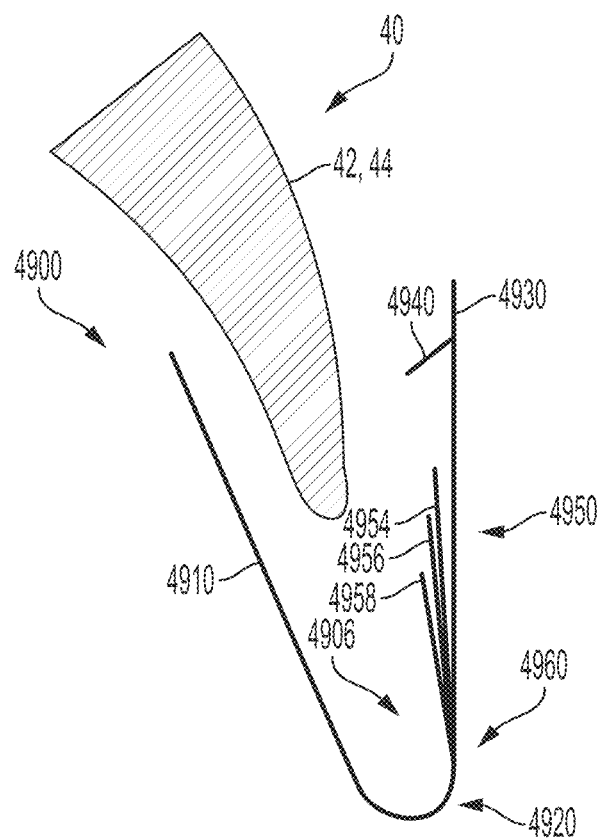
FIGS. 72-75 show the example clasp of FIGS. 70-71 or FIGS. 70A-71A being deployed to engage with a leaflet of a native valve.
Figure 73:
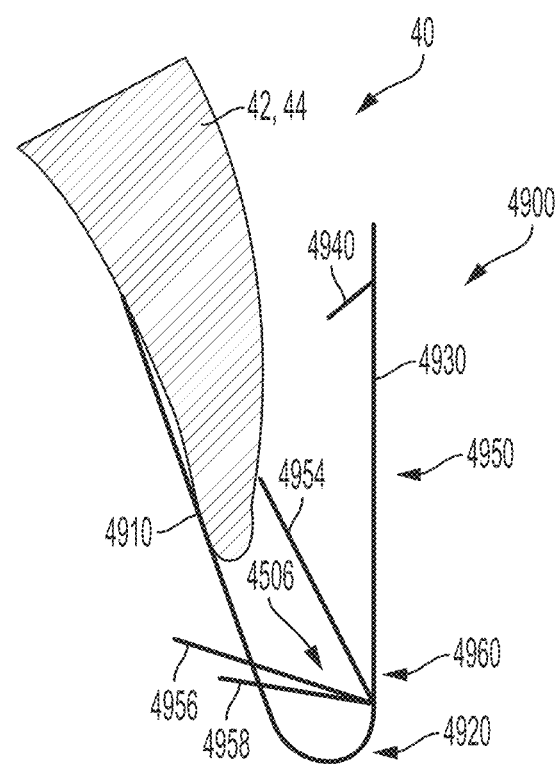
Figure 74:
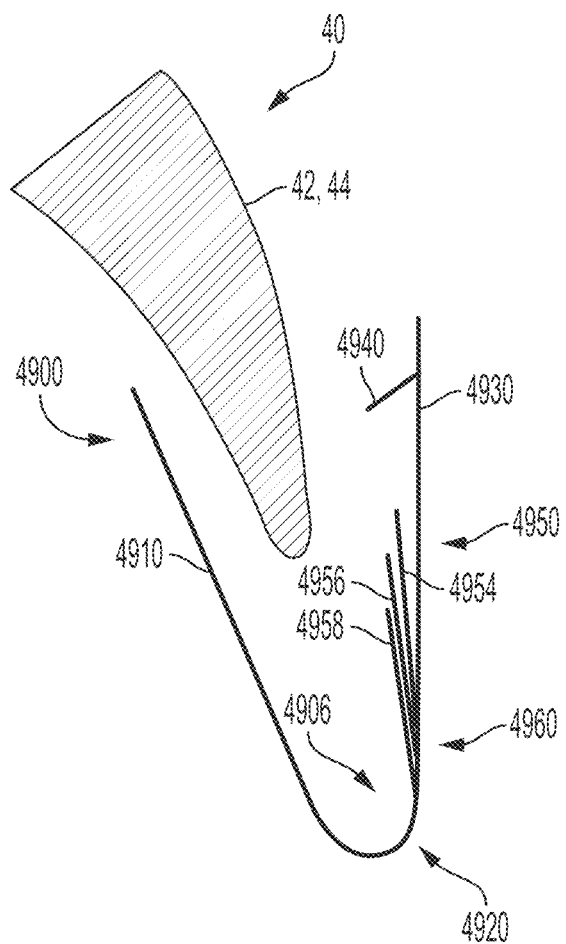

FIGS. 72-74 illustrate schematically illustrate the clasp 4900 of FIG. 70-71 (or 70A-71A) being deployed to secure a native leaflet of a native valve (e.g., a native mitral valve, etc.). The example clasp 4900 is shown being deployed within the native valve 40 to secure an implantable device (not shown), such as the devices 100, 200, 300 described above, to one of the native leaflets 42, 44. Referring now to FIG. 72, the clasp 4900 is shown in an open condition with a native leaflet 42, 44 partially inserted into an opening 4906 of the clasp 4900 formed between the fixed and moveable arms 4910, 4930. To determine whether the leaflet 42, 44 has reached the desired engagement depth, the indicator arms 4954, 4956, 4958 are actuated, either individually or all at once, by one or more actuation lines (not shown in FIGS. 72-75) as shown in FIGS. 73 and 75.

Referring now to FIG. 73, the indicator arms 4954, 4956, 4958 are shown in an actuated or released condition. Because the leaflet 42, 44 is inserted into the opening 4906 of the clasp 4900 about half way between the barbed portion 4940 and the flex or hinged portion 4920, the first indicator arm 4954 engages the leaflet while the second and third indicator arms 4956, 4958 miss or slip off of the leaflet 42, 44 to move to fully actuated positions at or beyond the fixed arm 4910. In the illustrated example, the second and third indicator arms 4956, 4958 form X or crossing shapes with the fixed arm that are visible via imaging devices used to monitor implantation and deployment of the prosthetic device. In an example embodiment, the second and third indicator arms would engage the fixed arm or a covering on the fixed arm, so that there would not be a crossing or X shape, but the lack of space between the indicator arms and the fixed arms would still indicate the lack of leaflet tissue. In addition, or instead, the indicator arms 4954, 4956 that engage the valve leaflet bounce or pulse as the heart beats, while the arm 4958 does not. This bouncing or pulsing can be seen on imaging. Thus, the depth of engagement can be determined from the relative positions of the indicator arms 4954, 4956, 4958 with respect to the fixed arm 4910 and/or the number of indicator arms that bounce or pulse versus the number that do not.

Referring now to FIG. 74, the indicator arms 4954, 4956, 4958 are retracted by applying tension to the actuation line(s) and the clasp 4900 is repositioned so that the leaflet 42, 44 is more deeply inserted into the opening 4906 of the clasp 4900. However, in some cases engagement by only some of the indicator arms can indicate correct leaflet positioning. The indicator arms 4954, 4956, 4958 are then actuated by releasing tension on the actuating lines, as can be seen in FIG. 75. Because the leaflet 42, 44 has been inserted into the clasp 4900 at or beyond the minimum desired engagement depth of the third indicator arm 4958, all three of the indicator arms 4954, 4956, 4958 engage and pinch the leaflet 42, 44 against the fixed arm 4910. Engagement with the leaflet 42, 44 prevents the indicator arms 4954, 4956, 4958 from moving to or past the fixed arm 4910 of the clasp 4900 to form the X-shapes shown in FIG. 73 (or another shape indicating the lack of the presence of valve leaflet tissue). Thus, the indicator arms 4954, 4956, 4958 indicate to an observer observing the installation via an imaging device that the leaflet 42, 44 is inserted into the opening 4906 beyond at least the depth established by the third indicator arm 4958.

Figure 75:
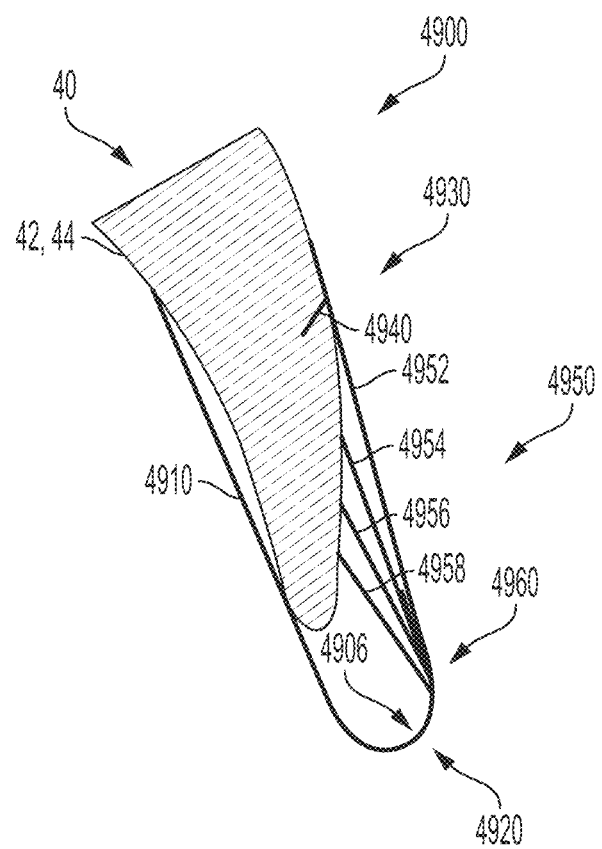

Referring now to FIG. 75, once the indicator arms 4954, 4956, 4958 indicate that the leaflet 42, 44 is sufficiently inserted into the opening 4906, the moveable arm 4930 is actuated by releasing tension on the actuating line (not shown) so that the leaflet 42, 44 is pinched between the barbed portion 4940 and the fixed arm 4910 to secure the leaflet 42, 44 firmly within the clasp 4900.

Figure 76:
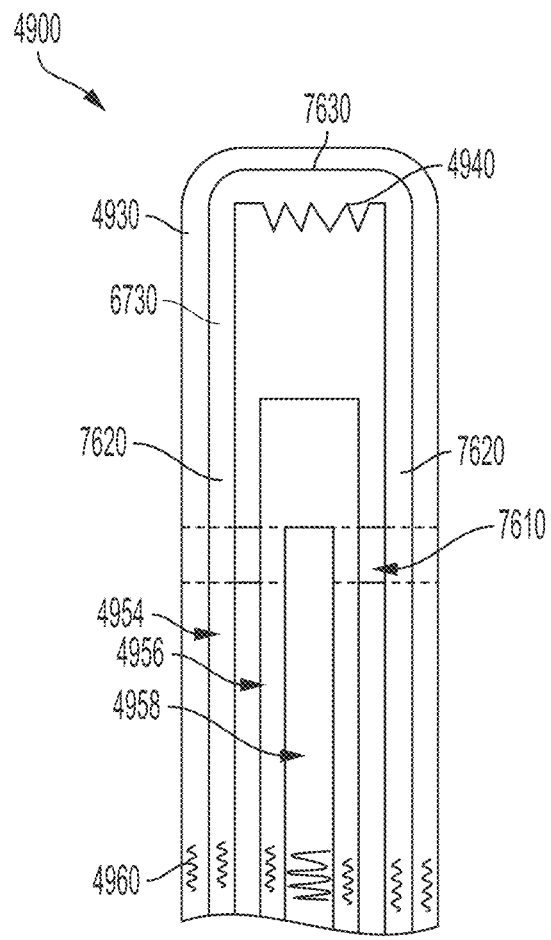
FIGS. 76-77 each show a moveable arm and indicator arms according to example embodiments of an implantable prosthetic device having a T-bar.
Figure 77:
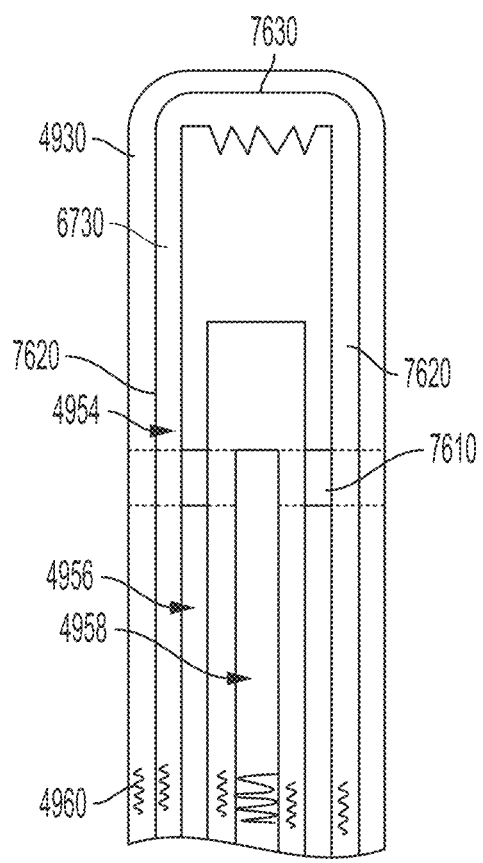

Referring now to FIGS. 76-77, the moveable arm 4930 and indicator arms 4954, 4956, and 4958 of a laser cut embodiment of a clasp 4900 are illustrated. The embodiments illustrated in FIGS. 76-77 are similar to that described above with respect to FIG. 69, having a moveable arm 4930 with a cut-out opening 6730, and multiple indicator arms 4954, 4956, 4958 all cut from the same sheet, where the moveable arm and each of the indicator arms have a flexible section 4960 to permit bending and/or flexing relative to the fixed arm and/or to allow shape-setting of the unflexed position of the clasp. In these embodiments, the multiple indicators assist with identifying the depth of the leaflet.

The embodiments in FIGS. 76-77 further include a bar 7610 on the shortest indicator arm 4958 that forms the shape of a "T" with the shortest indicator arm 4958, referred to herein as a T-bar. The T-bar can allow the multiple indicators and optionally the movable clasp arm 4930 to be lifted together (i.e. opened relative to the fixed arm). The T-bar can be attached to the indicator arm 4958 by welding, attachment with a rivet, or other known means for attachment. In FIG. 76, the T-bar extends all the way to the outermost layer of the moveable arm 4930, which can be a moveable arm with optional barbs (barbs not shown) that is closed after the leaflet is properly positioned within the clasp.

In FIG. 77, an example embodiment is illustrated in which the T-bar 7610 extends outward to the outermost indicator arm 4954 but is positioned inside of the moveable. The indicator arms here increase in length as they move outward from the centrally located indicator arm 4958, being centrally located along the width of the moveable arm frame. The indicator arms 4956, 4958 having a longer length than the centrally located indicator arm can be "U" shaped or other shape where the indicator arm has sides 7620 and a distal end 7630.

The indicator arms can be pulled up or opened by the T-bar with a suture line attached to the T-bar or by another actuator means. The moveable arm can be pulled up or opened by another suture line or other actuator means. Similar to other embodiments having a suture line described herein, the suture line connected to the T-bar or the shortest indicator arm is given slack prior to the suture line connected to the moveable arm. This slack allows the shortest indicator arm to fall towards the fixed arm (or leaflet if a leaflet is positioned within the clasp). The falling of the shortest indicator arm, and thus T-bar, permits the remaining indicator arms and optionally the moveable arm 4930 to fall towards the fixed arm as well. If the leaflet is partially captured, some of the indicator arms, but not those overlapping with the leaflet, will still fall past the leaflet. FIGS. 80-83 illustrate the falling of the indicator arms based on the position of the leaflet and are described below.

Figure 78:
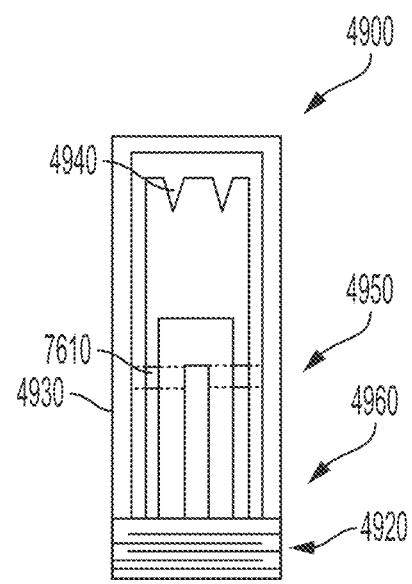
FIGS. 78-79 show an example embodiment of a clasp with indicator arms and a T-bar for an implantable prosthetic device.
Figure 79:
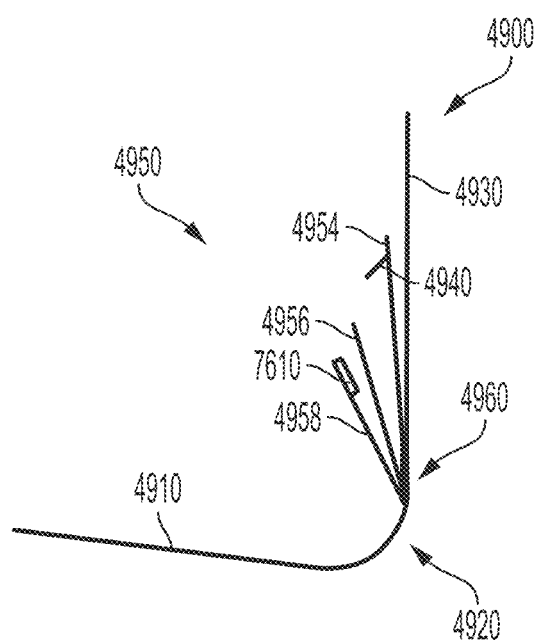

Referring now to FIGS. 78-79, an example clasp 4900 for use in implantable prosthetic devices, such as devices 100, 200, 300 described above, is shown. Like the clasp 3500 described above, the clasp 4900 includes a fixed arm 4910, a flex or hinge portion 4920, and a moveable arm 4930. As with FIGS. 76 and 77, the shortest indicator arm 4958 has a T-bar connected to it, to lift all the indicator arms together at the same time when positioning the clasp. The clasp 4900 can be used in any of the implantable prosthetic devices of the present application and can include any of the features or combinations of features of the clasps described herein. Although the example illustrated by FIGS. 78 and 79 does not illustrate barbs on the moveable arm 4930, the moveable arm can have one or more barbs in this or any other embodiment disclosed herein (see for example, barb 3540 in FIGS. 24-29.

The clasp 4900 also includes an indicator portion 4950 formed from first, second, and third indicator arms 4954, 4956, 4958 adjacent to the moveable arm 4930 and each extending from an indicator flex or hinge portion 4960. The indicator flex or hinge portions 4960 allow the indicator arms 4954, 4956, 4958 to be actuated individually and separately from the moveable arm 4930. The indicator flex or hinge portions 4960 can be formed from a portion of the indicator arms 4954, 4956, 4958, can be formed from a series of cutouts, and/or can be a portion of the flex or hinge portion 4920. The T-bar can be connected by welding, or using a rivet, or other known means. The T-bar can be made of the same material as the indicator arms. The T-bar is used to lift the indicator arms together. As explained below, during deployment of the clasp on a native leaflet, the indicator arms that fall to or beyond the fixed arm of the clasp indicate that the leaflet is not positioned within the clasp to the depth indicated by that particular indicator arm. The T-bar does not affect the functioning of the indicator arms, which operate, as explained below, similarly to the example embodiment described in FIGS. 70-75.

The indicator arms 4954, 4956, 4958 can be separately actuated from the moveable arm 4930 to facilitate detection of the depth of engagement of the native leaflet between the moveable arm 4930 and the fixed arm 4910 of the clasp 4900. In the illustrated embodiment, the indicator arms 4954, 4956, 4958 are narrower than the moveable arm 4930 and have lengths that are each less than a distance from the flex or hinge portion 4920 to the barbed portion 4940. The first indicator arm 4954 has a length that is about 75 percent to about 100 percent of the distance between the flex or hinge portion 4920 and the barbed portion 4940. The second indicator arm 4956 has a length that is about 65 percent to about 85 percent of the length between the flex or hinge portion 4920 and the barbed portion 4940. The third indicator arm 4958 has a length that is about 50 percent to about 70 percent of the distance between the flex or hinge portion 4920 and the barbed portion 4940. Any combination of the lengths of indicator arms can be used, as long as the length continues to decrease with each successive indicator arm, to provide indication of the depth the leaflet is positioned within the clasp. There can also be a fourth indicator arm (not shown) or any number of indicator arms.

The different lengths of the indicator arms 4954, 4956, 4958 are used to determine a desired minimum engagement depth as measured from the end of the moveable arm 4930 of the clasp 4900. Configuring the length of the first indicator arm 4954 to be less than a distance from the flex or hinge portion 4920 to the barbed portion 4940 ensures that the barbed portion 4940 will engage a leaflet that is positioned at the minimum engagement depth as indicated by the first indicator arm 4954. That is, if a native leaflet positioned within the clasp 4900 is engaged by the first indicator arm 4954 when the first indicator arm is actuated, then the leaflet will be engaged by the barbed portion 4940 of the moveable arm 4930. The opposite is also true. That is, if a native leaflet positioned within the clasp 4900 is not engaged by the first indicator arm 4954 when the first indicator arm is actuated, then the leaflet will not be adequately engaged by the barbed portion 4940 of the moveable arm 4930.

The first, second, and third indicator arms 4954, 4956, 4958 are configured with decreasing lengths so that the surgeon can determine how far beyond the minimum engagement depth the native leaflet has been inserted into the clasp 4900. That is, whether or not the native leaflet is engaged by the second and third indicator arms 4956, 4958 indicates that the native leaflet has or has not reached the engagement depth measured by each of the first, second, and third indicator arms 4954, 4956, 4958. For example, if a native leaflet positioned within the clasp 4900 is engaged by the third indicator arm 4958 when the third indicator arm 4958 is actuated, then the leaflet has been inserted about 50 percent to about 80 percent of the distance from the barbed portion 4940 to the flex or hinge portion 4920. The opposite is also true. That is, if a native leaflet positioned within the clasp 4900 is not engaged by the third indicator arm 4958 when the third indicator arm 4958 is actuated, then the leaflet has not reached about 50 percent of the distance between the barbed portion 4940 and the flex or hinge portion 4920.

Figure 80:
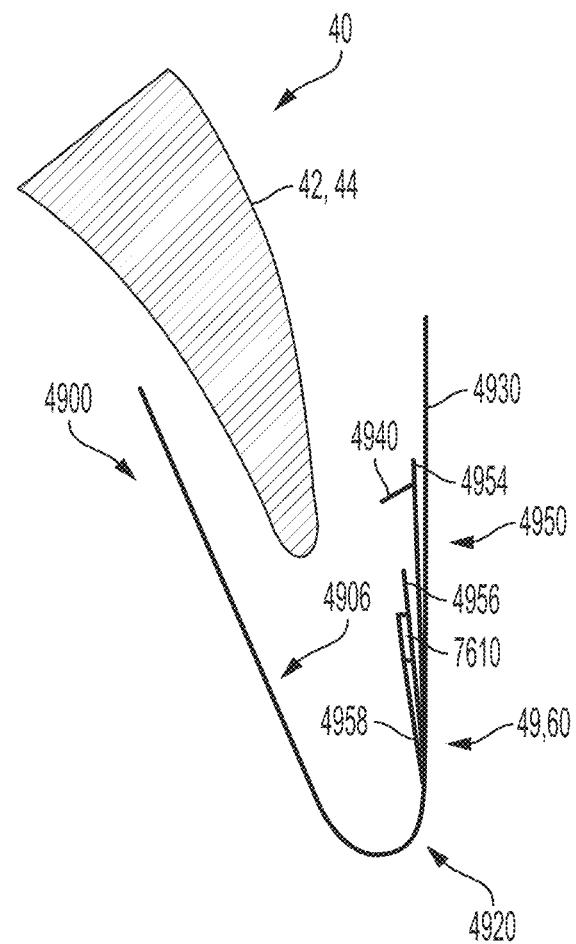
FIGS. 80-83 show the example clasp of FIGS. 78-79 being deployed to engage with a leaflet of a native valve.
Figure 81:
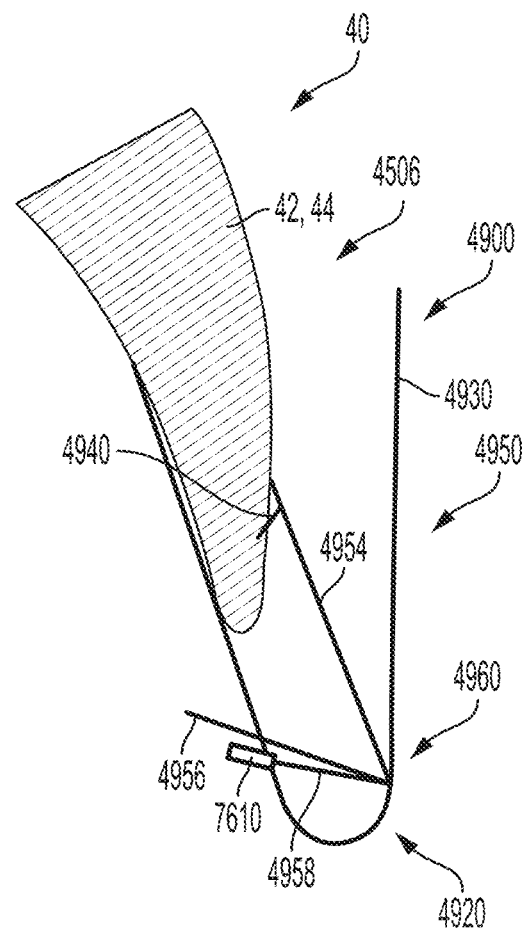
Figure 82:
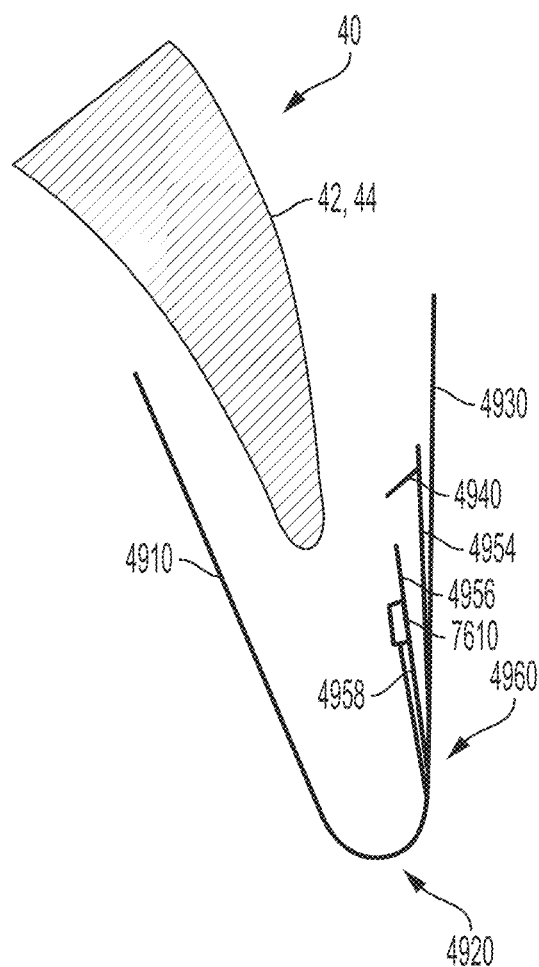
Figure 83:
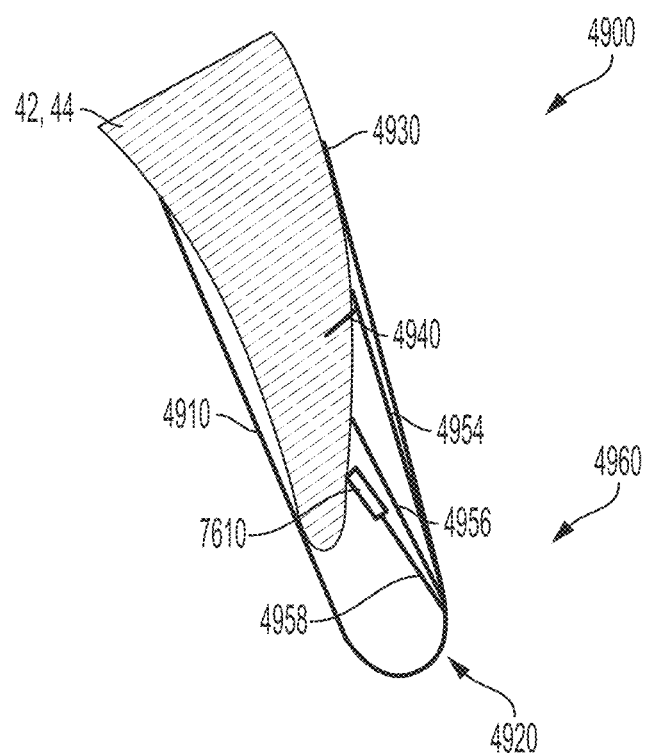

Referring now to FIGS. 80-83, the example clasp 4900 is shown being deployed within a native valve 40 to secure an implantable device (not shown), such as the devices 100, 200, 300 described above, to one of the native leaflets 42, 44. Referring now to FIG. 80, the clasp 4900 is shown in an open condition with a native leaflet 42, 44 partially inserted into an opening 4906 of the clasp 4900 formed between the fixed and moveable arms 4910, 4930. To determine whether the leaflet 42, 44 has reached the desired engagement depth, the indicator arms 4954, 4956, 4958 are individually actuated via a plurality of actuation lines (not shown) as shown in FIGS. 81 and 83. Or, a single actuation line can be connected to the indicator arm 4958 with the T-bar 7610, such that pulling on the single line opens all of the indicator arms 4954, 4956, 4958 with the T-bar 7610 and releasing the single line allows all of the indicator arms 4954, 4956, 4958 to fall or close.

Referring now to FIG. 81, the indicator arms 4954, 4956, 4958 are shown in a released condition. Because the leaflet 42, 44 is inserted into the opening 4906 of the clasp 4900 about half way between the barbed portion 4940 and the flexible or hinged portion 4920, the first indicator arm 4954 engages the leaflet while the second and third indicator arms 4956, 4958 miss or slip off of the leaflet 42, 44 to move to fully actuated positions at or beyond the fixed arm 4910. The second and third indicator arms 4956, 4958 forms a shape with the fixed arm that is visible via imaging devices used to monitor implantation and deployment of the prosthetic device. In addition, or instead, the indicator arm 4954 that engages the valve leaflet bounce or pulse as the heart beats, while the arms 4956, 4958 do not. This bouncing or pulsing can be seen on imaging. Thus, the depth of engagement can be determined from the number of visible shapes formed by the indicator arms 4954, 4956, 4958 and the fixed arm 4910 and/or the number of indicator arms that bounce or pulse versus the number that do not.

Referring now to FIG. 82, the indicator arms 4954, 4956, 4958 are retracted by applying tension to an actuation lines that is connected to the indicator arm 4958 with the T-bar 7610 and the clasp 4900 is repositioned so that the leaflet 42, 44 is more deeply inserted into the opening 4906 of the clasp

4900. (In the illustration, space is shown between the indicator arms 4958, 4956, 4954 so that they are visible in the drawing. However, in reality, the indicator arms 4956, 4954 rest on the T-bar 7610 and there is no space.) However, in some cases engagement by only some of the indicator arms can indicate correct leaflet positioning. The indicator arms 4954, 4956, 4958 are then actuated by releasing tension on the actuating line (not shown) that is attached to the indicator arm 4958 or T-bar 7610, as can be seen in FIG. 83. Because the leaflet 42, 44 has been inserted into the clasp 4900 at or beyond the minimum desired engagement depth of the third indicator arm 4958, all three of the indicator arms 4954, 4956, 4958 engage and pinch the leaflet 42, 44 against the fixed arm 4910. Engagement with the leaflet 42, 44 prevents the indicator arms, 4954, 4956, 4958 from moving past the fixed arm 4910 of the clasp 4900 to form the shapes shown in FIG. 81. Thus, the indicator arms 4954, 4956, 4958 indicate to an observer observing the installation via an imaging device that the leaflet 42, 44 is inserted into the opening 4906 beyond at least the depth established by the third indicator arm 4958.

Referring now to FIG. 83, once the indicator arms 4954, 4956, 4958 indicate that the leaflet 42, 44 is sufficiently inserted into the opening 4906, the moveable arm 4930 is actuated by releasing tension on the actuating line (not shown) so that the leaflet 42, 44 is pinched between the moveable arm 4930 and the fixed arm 4910 to secure the leaflet 42, 44 firmly within the clasp 4900.

Figure 123:
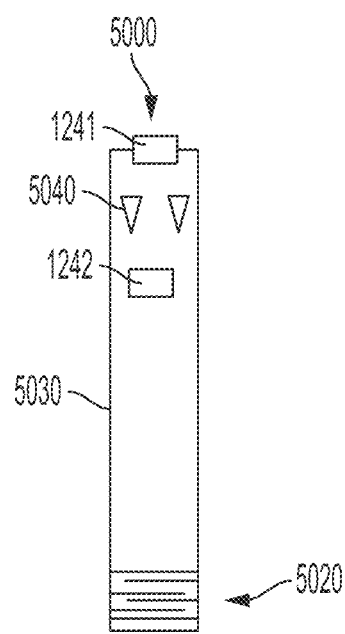
FIGS. 123 and 124 show schematic views of an example embodiment of a clasp having deflecting indicators on the moveable arm, for an implantable prosthetic device.
Figure 124:
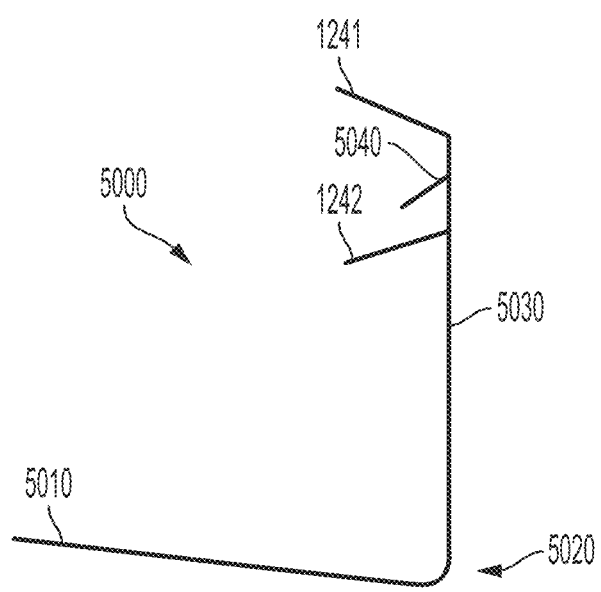

Referring now to FIGS. 123 and 124, an example clasp 5000 (illustrated as a barbed clasp) for use in implantable prosthetic devices, such as devices 100, 200, 300 described above, is shown. Like the clasp 3500 described above, the clasp 5000 includes a fixed arm 5010, a flex or hinge portion 5020, and a moveable arm 5030 having a barbed portion 5040 (though other friction-enhancing portions can be used). The moveable arm 5030 also includes an optional first indicating lever 1241 disposed at a distance from the flex portion or hinge that is greater than the distance of the barb 5040. The moveable arm 5030 also includes a second indicating lever 1242 disposed at a distance from the flex or hinge portion 5020 that is less than a distance between the barbed portion 5040 and the flex or hinge portion 5020. The indicating levers 1241, 1242 deform when the native leaflet tissue is pressed against the fixed arm 5010 by the moveable arm 5030 to indicate the engagement depth that the leaflet tissue has reached. The first indicating lever 1241 deforms when the native leaflet is partially inserted into the clasp. The second indicating lever 1242 deforms when the native leaflet has reached the minimum desired engagement depth. The clasp is not limited to two indicating levers but can have additional indicating levers, placed between the first and second indicating lever (as described in U.S. App. Ser. No. 62/805,847, filed on Feb. 14, 2019, incorporated herein by reference in its entirety, and described below with reference to FIGS. 123A-127A). Thus, the second indicating lever 1242 will not indicate that the native leaflet 42, 44 has reached the desired engagement depth until the leaflet 42, 44 is inserted at or beyond the location of the second indicating lever 1242. Once the leaflet 42, 44 has reached the desired engagement depth, actuation of the moveable arm 5030 squeezes the leaflet tissue 42, 44 against the indicating lever 1242 to cause the indicating lever 1242 to flatten or flex against the valve leaflet and thereby indicate that the leaflet 42, 44 has been inserted into the clasp 5000 at or beyond the desired engagement depth. The clasp 5000 can be used in any of the implantable prosthetic devices of the present application and can include any of the features or combinations of features of the other clasps described herein.

Figure 125:
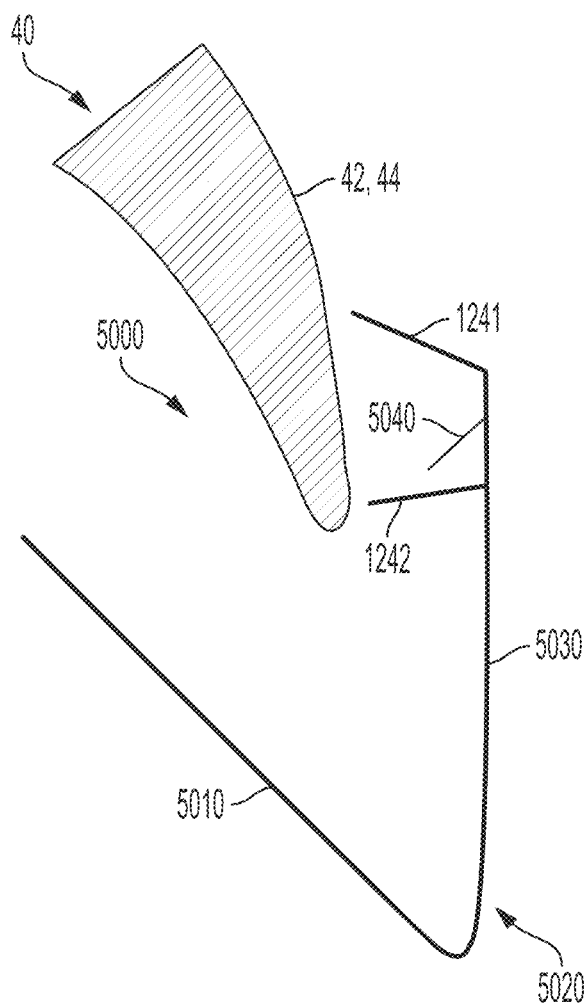
FIGS. 125, 126, and 127 show the example clasp of FIGS. 123 and 124 being deployed to engage with a leaflet of a native valve.
Figure 126:
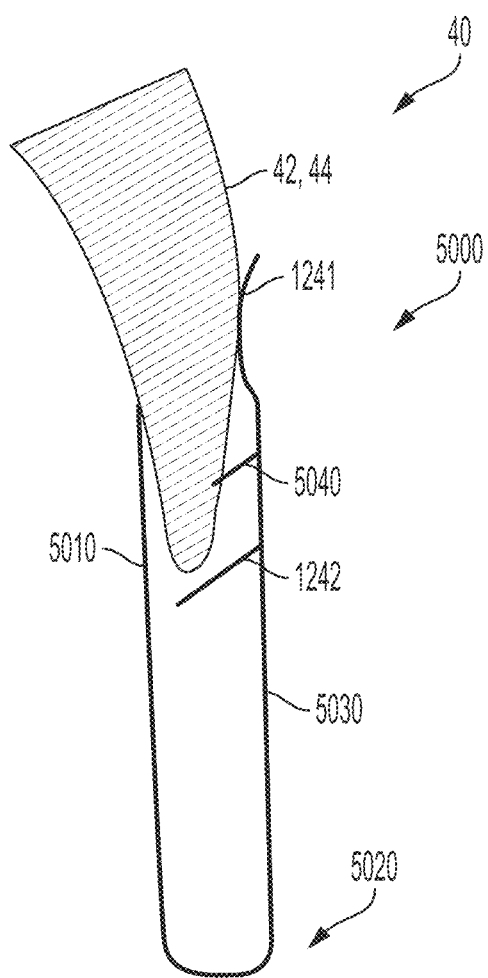
Figure 127:
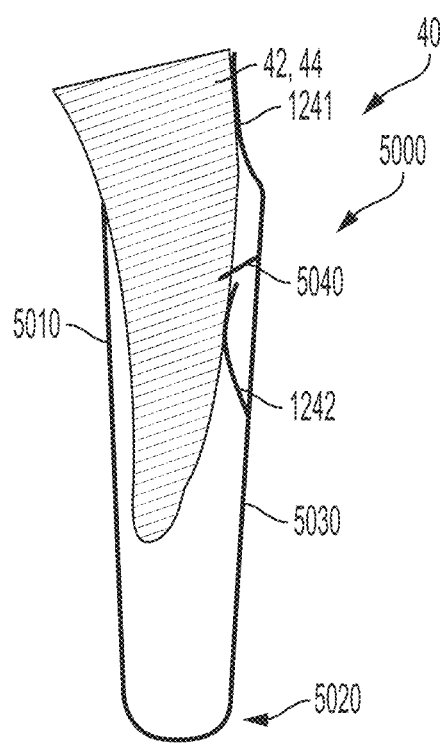

Referring now to FIGS. 125, 126, and 127, the example clasp 5000 is shown being deployed within a native valve 40 to secure an implantable device (not shown), such as the devices 100, 200, 300 described above, to one of the native leaflets 42, 44. Referring now to FIG. 125, the clasp 5000 is shown in an open condition with a native leaflet 42, 44 partially inserted into an opening of the clasp 5000 formed between the fixed and moveable arms 5010, 5030. With the clasp in the open condition, neither of the indicator levers, 1241,1242 are flexed or flattened. To determine whether the leaflet 42, 44 has reached the desired engagement depth, the moveable arm 5030 is actuated via actuation lines (not shown) as shown in FIGS. 126-127.

Referring now to FIG. 126, when the moveable arm 5030 is actuated to push the leaflet 42, 44 against the fixed arm 5010, the leaflet 42, 44 may contact a portion of the moveable arm 5030, contacting only the first indicator lever 1241 but not the second indicating lever 1242 when the engagement depth of the leaflet 42, 44 is less than the minimum desired engagement depth. As can be seen in FIG. 126, the first indicating lever 1241 is flexed out of the way of the moveable arm due to contact with the leaflet 42, 44 when the leaflet 42, 44 is partially inserted into the clasp 5000 and is pressed against the first indicating lever 1241 by the fixed arm 5010. That is, the first indicating lever 1241 is deformed by the leaflet 42, 44 to indicate that the leaflet 42, 44 has been partially inserted into the clasp. In some embodiments, actuation of the moveable arm 5030 also causes the barbed portion 5040 to engage and secure the leaflet 42, 44 within the barbed clasp 5000. Because the second indicating lever 1242 has not been flexed and/or flattened, this indicates to the operator that the leaflet has not been inserted into the clasp at or beyond a minimum engagement depth. If the indicating lever 1242 indicates that the leaflet 42, 44 is not inserted to the desired depth, the clasp 5000 can be opened to allow for repositioning of the leaflet 42, 44.

Referring now to FIG. 127, when the moveable arm 5030 is actuated to push the leaflet 42, 44 against the fixed arm 5010, the leaflet 42, 44 may contact a portion of the moveable arm 5030, contacting the first indicator lever 1241 and the second indicating lever 1242 when the engagement depth of the leaflet 42, 44 is greater than or equal to the minimum desired engagement depth. As can be seen in FIG. 127, the first indicating lever 1241 and second indicating lever 1242 are both flexed out of the way of the moveable arm due to contact with the leaflet 42, 44 when the leaflet 42, 44 is inserted into the clasp 5000 at or beyond the minimum engagement depth and is pressed against both the first indicating lever 1241 and the second indicating lever 1242 by the fixed arm 5010. That is, the first indicating lever 1241 and the second indicating lever 1242 are each deformed by the leaflet 42, 44 to indicate that the leaflet 42, 44 has been inserted into the clasp at or beyond the minimum engagement depth. In some embodiments, actuation of the moveable arm 5030 also causes the barbed portion 5040 to engage and secure the leaflet 42, 44 within the barbed clasp 5200. The indicating lever 1241 is optional, and in some example embodiments, there is no indicating lever 1241 positioned above the barb 5040.

Referring now to FIGS. 123A-127A, an example clasp 5000 (illustrated as a barbed clasp) such as that shown in FIGS. 123-127, with a plurality of flexible indicating levers 1242, is illustrated. Referring to FIGS. 123A and 124A, an example clasp 5000 for use in implantable prosthetic devices, such as devices 100, 200, 300 described above, is shown or any other implantable prosthetic device. Like the clasp 3500 described above, the clasp 5000 includes a fixed arm 5010, a flex or hinge portion 5020, and a moveable arm 5030 having a barbed portion 5040 (though other friction-enhancing portions can be used). The moveable arm 5030 also includes an optional first indicating lever 1241 disposed at a distance from the flexible portion or hinge that is greater than the distance of the barb 5040. The moveable arm 5030 also includes a plurality of additional indicating levers 1242 disposed at distances from the flex or hinge portion 5020 that are less than a distance between the barbed portion 5040 and the flex or hinge portion 5020. The indicating levers 1241, 1242 deform when the native leaflet tissue is pressed against the fixed arm 5010 by the moveable arm 5030 to indicate the engagement depth that the leaflet tissue has reached. The first indicating lever 1241 deforms when the native leaflet is partially inserted into the clasp. Each of the plurality of indicating levers 1242 deform when the native leaflet has reached the engagement depth at which each indicating lever 1242 is positioned.

Once the leaflet 42, 44 has reached the desired engagement depth, actuation of the moveable arm 5030 squeezes the leaflet tissue 42, 44 against at least one indicating lever 1242 to cause the indicating lever 1242 to flatten or flex against the valve leaflet and thereby indicate that the leaflet 42, 44 has been inserted into the clasp 5000 at or beyond the desired engagement depth. The indicating levers 1242 can also be used to indicate whether the leaflet 42, 44 has been inserted too far into the clasp. For example, if the leaflet deforms the indicating lever 1242 closest to the flex or hinge portion 5020, this can indicate to the operator that the leaflet has been inserted too far into the clasp.

Figure 125A:
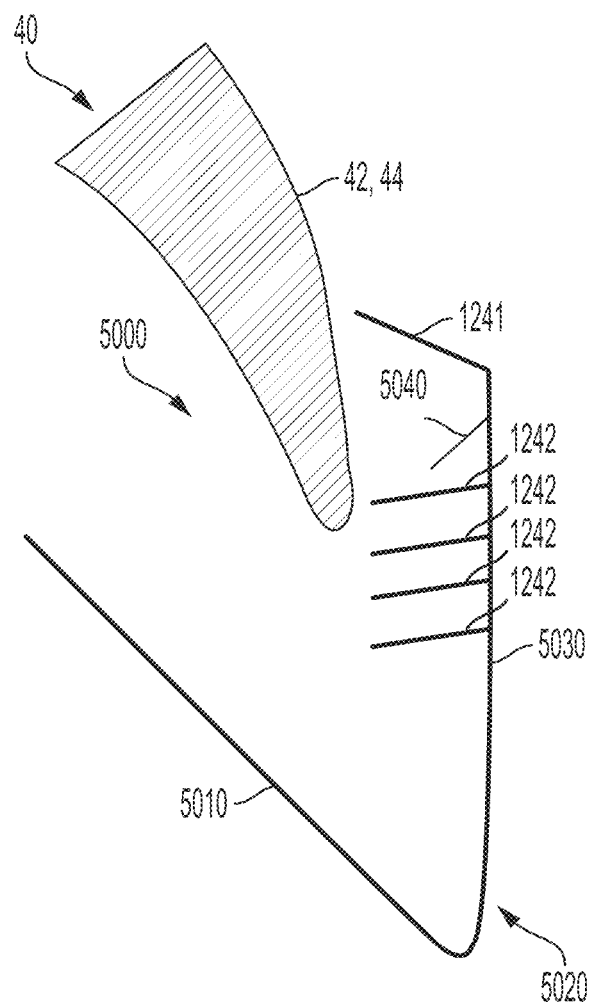
FIGS. 125A, 126A, and 127A show the example clasp of FIGS. 123A and 124A being deployed to engage with a leaflet of a native valve.
Figure 126A:
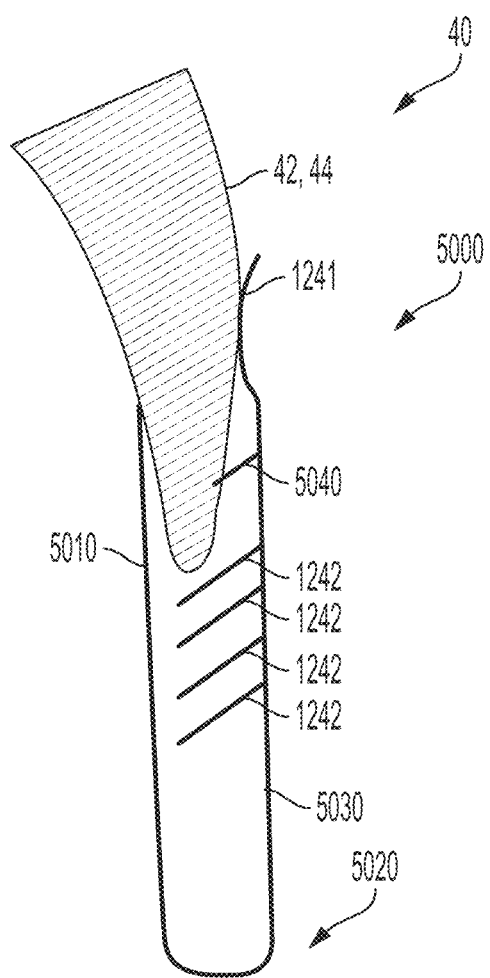
Figure 127A:
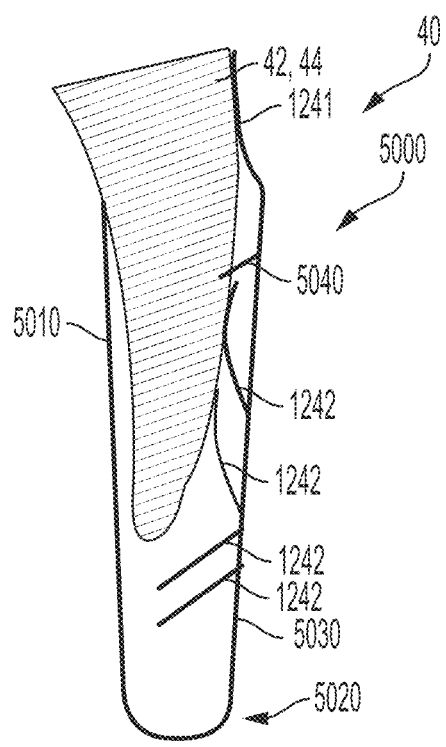

Referring now to FIGS. 125A, 126A, and 127A, the example clasp 5000 is shown being deployed within a native valve 40 to secure an implantable device (not shown), such as the devices 100, 200, 300 described above, to one of the native leaflets 42, 44. Referring now to FIG. 125A, the clasp 5000 is shown in an open condition with a native leaflet 42, 44 partially inserted into an opening of the clasp 5000 formed between the fixed and moveable arms 5010, 5030. With the clasp in the open condition, none of the indicator levers, 1241, 1242 are flexed or flattened. To determine whether the leaflet 42, 44 has reached the desired engagement depth, the moveable arm 5030 is actuated as shown in FIGS. 126A and 127A.

Referring now to FIG. 126A, when the moveable arm 5030 is actuated to push the leaflet 42, 44 against the fixed arm 5010, the leaflet 42, 44 may contact a portion of the moveable arm 5030, contacting only the first indicator lever 1241 but none of the plurality of indicating levers 1242 when the engagement depth of the leaflet 42, 44 is less than the minimum desired engagement depth. As can be seen in FIG. 126A, the first indicating lever 1241 is flexed out of the way of the moveable arm due to contact with the leaflet 42, 44 when the leaflet 42, 44 is partially inserted into the clasp 5000 and is pressed against the first indicating lever 1241 by the fixed arm 5010. That is, the first indicating lever 1241 is deformed by the leaflet 42, 44 to indicate that the leaflet 42, 44 has been partially inserted into the clasp. In some embodiments, actuation of the moveable arm 5030 also causes the barbed portion 5040 to engage and secure the leaflet 42, 44 within the barbed clasp 5000. All of the indicating levers 1242 not being flexed and/or flattened indicates to the operator that the leaflet has not been inserted into the clasp at or beyond a minimum engagement depth. If the indicating levers 1242 indicate that the leaflet 42, 44 is not inserted to the desired depth, the clasp 5000 can be reopened to allow for repositioning of the leaflet 42, 44.

Referring now to FIG. 127A, when the moveable arm 5030 is actuated to push the leaflet 42, 44 against the fixed arm 5010. In FIG. 127A, the leaflet 42, 44 contacts the first indicator lever 1241 and the two indicating levers 1242. This indicates that the depth of the leaflet 42, 44 is greater than or equal to the minimum desired engagement depth. In FIG. 127A, the two indicating levers 1242 closest to the flex or hinge region 5020 are not deformed, which can indicate to the operator that the leaflet is not inserted too far into the clasp. If the leaflet is inserted too far into the clasp, the clasp can be re-opened, and the leaflet can be repositioned. In some embodiments, actuation of the moveable arm 5030 also causes the barbed portion 5040 to engage and secure the leaflet 42, 44 within the barbed clasp 5200. The indicating lever 1241 is optional, and in some example embodiments, there is no indicating lever 1241 positioned above the barb 5040.

Figure 129:
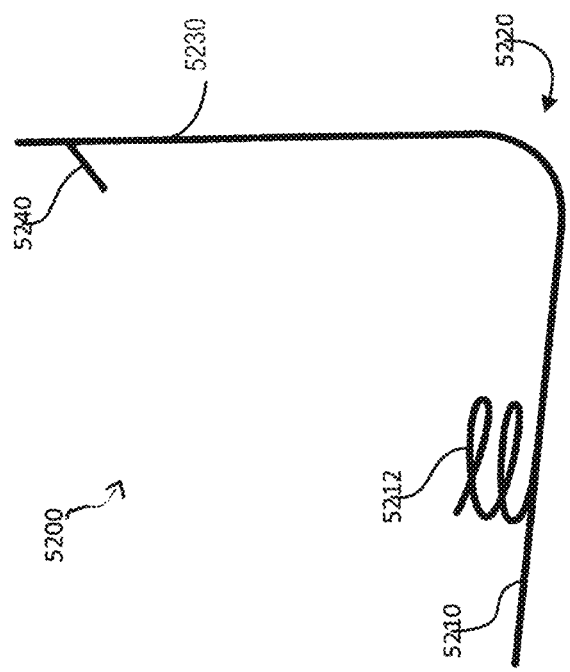
Figure 128:
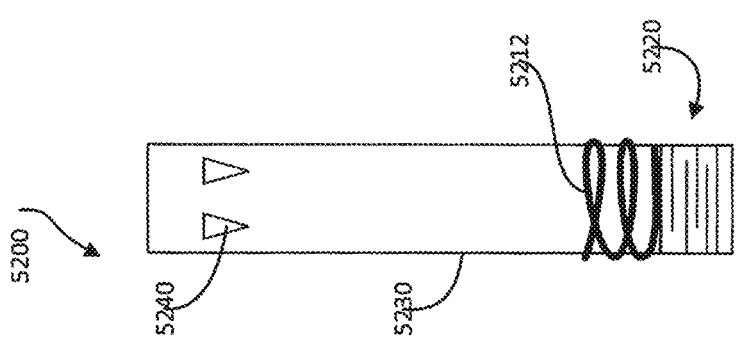
Figure 128A:
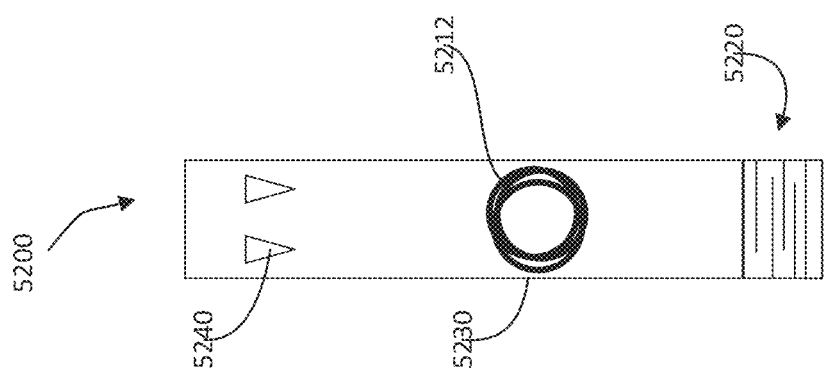

Referring now to FIGS. 128-129, an example clasp 5200 (illustrated as a barbed clasp) for use in implantable prosthetic devices, such as devices 100, 200, 300 described above, is shown. Like the clasp 3500 described above, the clasp 5200 includes a fixed arm 5210, a flex or hinge portion 5220, and a moveable arm 5230 having a barbed portion 5240 (though other friction-enhancing portions can be used). The fixed arm 5210 also includes an indicating spring 5212 disposed at a distance from the flex or hinge portion that is less than a distance between the barbed portion 5240 and the flex or hinge portion 5220. In an example embodiment, the movable arm 5230 also includes an indicating spring 5212 disposed at a distance from the flex or hinge portion that is less than a distance between the barbed portion 5240 and the flex or hinge portion 5220. The indicating spring is schematically illustrated and can take a wide variety of different forms. For example, the indicating spring can be any resiliently deformable component. The indicating spring 5212 can include closed ends and/or can be covered with cloth or other material to prohibit damage to the leaflet tissue. The indicating spring 5212 deforms when the native leaflet tissue is pressed against the indicating spring 5212 by the moveable arm 5230 to indicate that the leaflet tissue has reached a minimum desired engagement depth. Thus, the indicating spring 5212 will not indicate that the native leaflet 42, 44 has reached the desired engagement depth until the leaflet 42, 44 is inserted at or beyond the location of the indicating spring 5212. Once the leaflet 42, 44 has reached the desired engagement depth, actuation of the moveable arm 5230 squeezes the leaflet tissue 42, 44 against the indicating spring 5212 of the fixed arm 5210 to cause the indicating spring 5212 to flatten and thereby indicate that the leaflet 42, 44 has been inserted into the clasp 5200 at or beyond the desired engagement depth. The clasp 5200 can be used in any of the implantable prosthetic devices of the present application and can include any of the features or combinations of features of the other clasps described herein.

Figure 130:
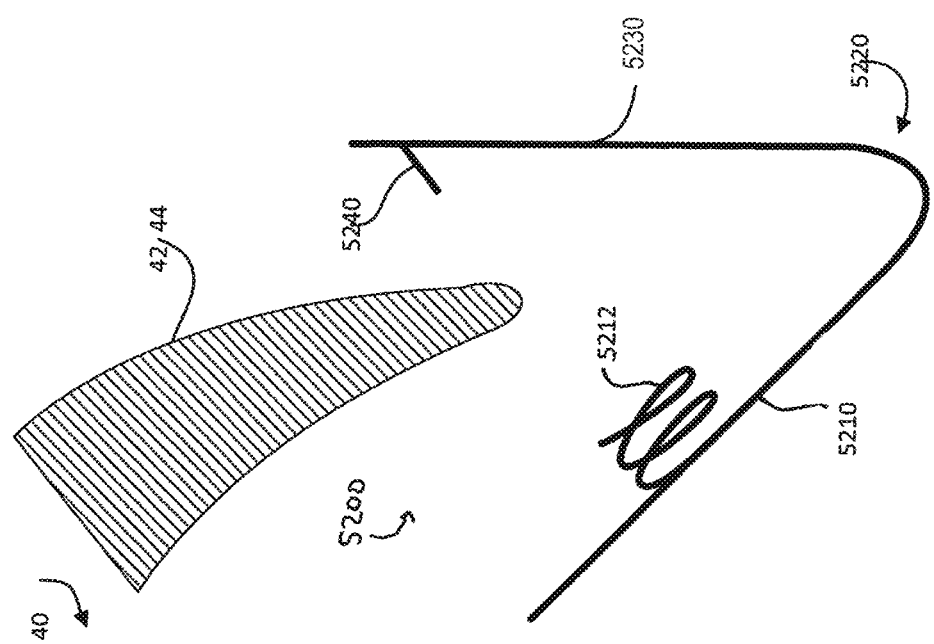
FIGS. 130, 131, and 132 show the example clasp of FIGS. 128 and 129 being deployed to engage with a leaflet of a native valve.
Figure 130A:
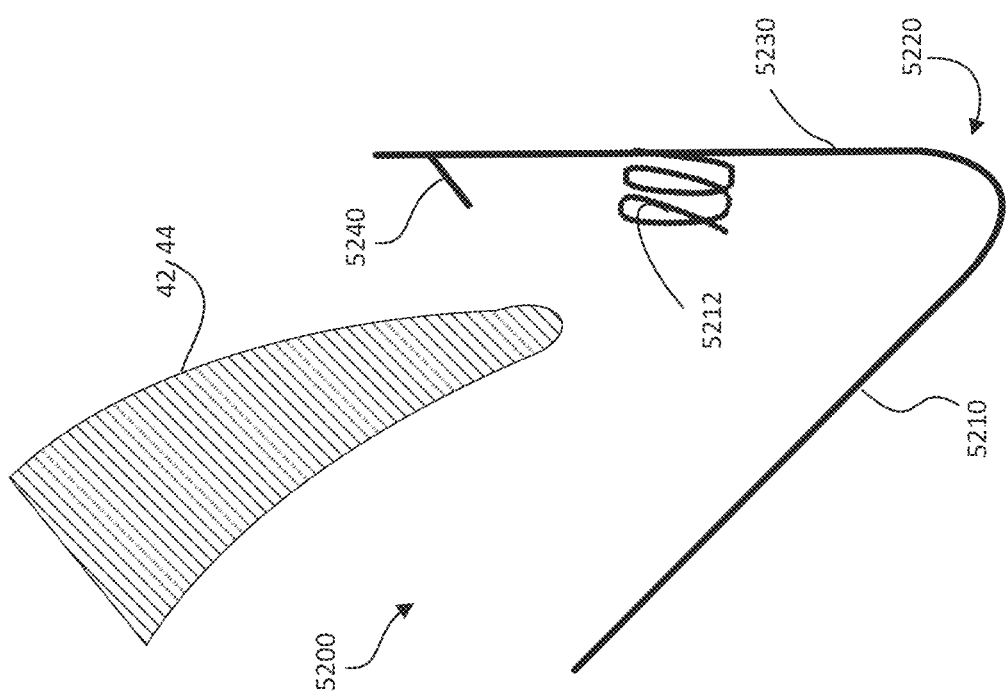
FIGS. 130A, 131A, and 132A show the example clasp of FIGS. 128A and 129A being deployed to engage with a leaflet of a native valve.
Figure 131:
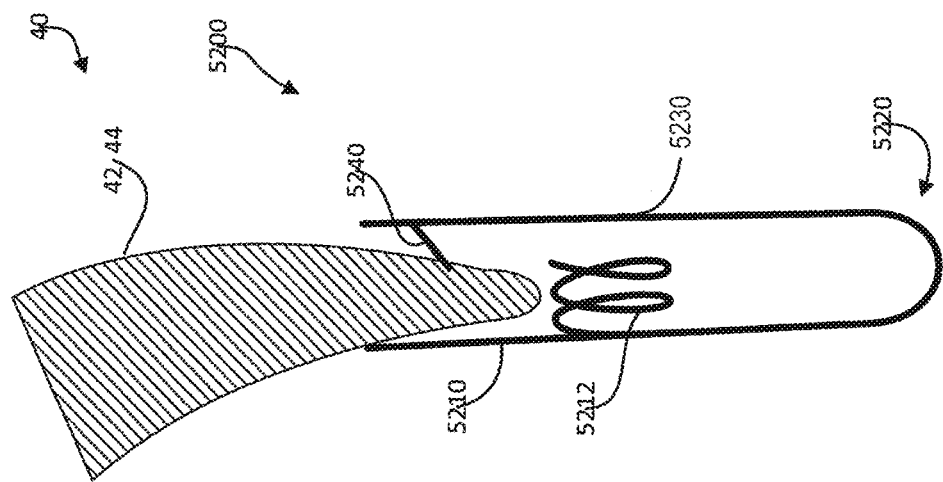
Figure 131A:
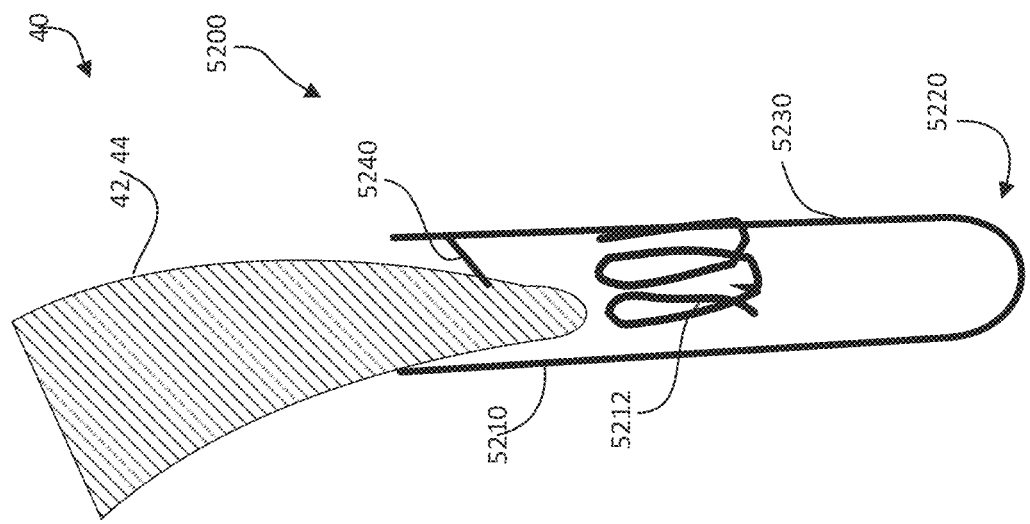
Figure 132:
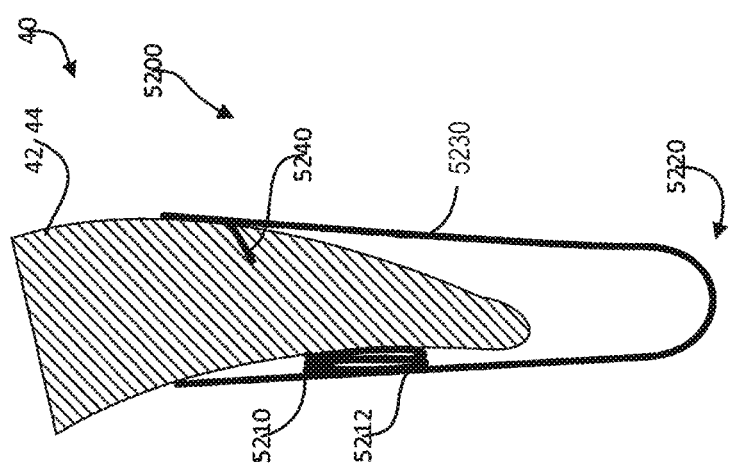
Figure 132A:
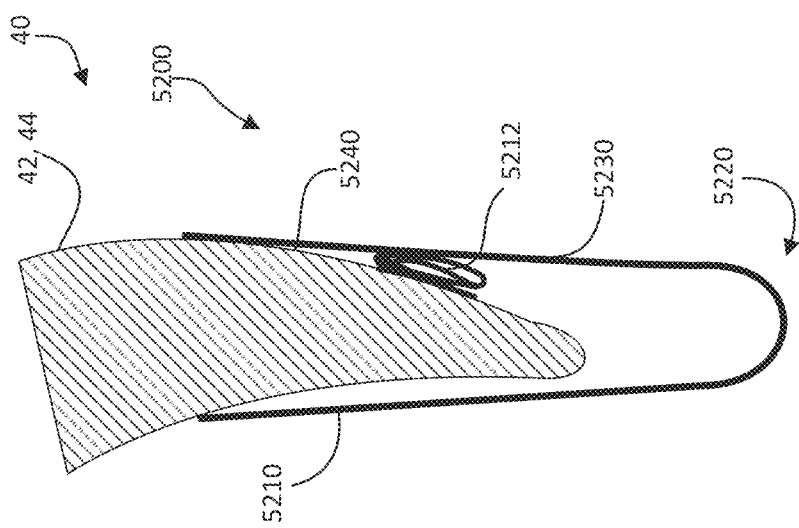

Referring now to FIGS. 130-132, the example clasp 5200 is shown being deployed within a native valve 40 to secure an implantable device (not shown), such as the devices 100, 200, 300 described above, to one of the native leaflets 42, 44. Referring now to FIG. 130, the clasp 5200 is shown in an open condition with a native leaflet 42, 44 partially inserted into an opening 5206 of the clasp 5200 formed between the fixed and moveable arms 5210, 5230. To determine whether the leaflet 42, 44 has reached the desired engagement depth, the moveable arm 5230 is actuated via actuation lines (not shown) as shown in FIGS. 131-132.

Referring now to FIG. 131, when the moveable arm 5230 is actuated to push the leaflet 42, 44 against the fixed arm 5210, the leaflet 42, 44 may contact a portion of the fixed arm 5210 without contacting the indicating spring 5212 when the engagement depth of the leaflet 42, 44 is less than the minimum desired engagement depth. As can be seen in FIG. 132, the indicating spring 5212 is deformed or flattened from contact with the leaflet 42, 44 when the leaflet 42, 44 is inserted into the clasp 5200 at or beyond the minimum engagement depth and is pressed against the indicating spring 5212 by the moveable arm 5230. That is, the indicating spring 5212 is deformed by the leaflet 42, 44 to indicate that the leaflet 42, 44 has been inserted at or beyond the minimum engagement depth. In some embodiments, actuation of the moveable arm 5230 also causes the barbed portion 5240 to engage and secure the leaflet 42, 44 within the barbed clasp 5200. If the indicating spring 5212 indicates that the leaflet 42, 44 is not inserted to the desired depth, the clasp 5200 can be opened to allow for repositioning of the leaflet 42, 44.

Referring now to FIGS. 129B-129C, additional views and configurations of the clasp 5200 and indicator spring 5212 are illustrated. FIG. 129B illustrated the indicator spring 5212 is attached to the fixed arm 5210. The spring 5212 can be depressed by a force as indicated by arrow 5214. The arrow 5214 represents the force of a leaflet 42, 44 pressed against the spring. The rings of the indicator spring 2512 stack on top of each other in the example embodiment of FIG. 129B, because they are all the same or approximately the same size. FIG. 129C illustrates a top view of the indicator spring 5212.

Figure 129A:
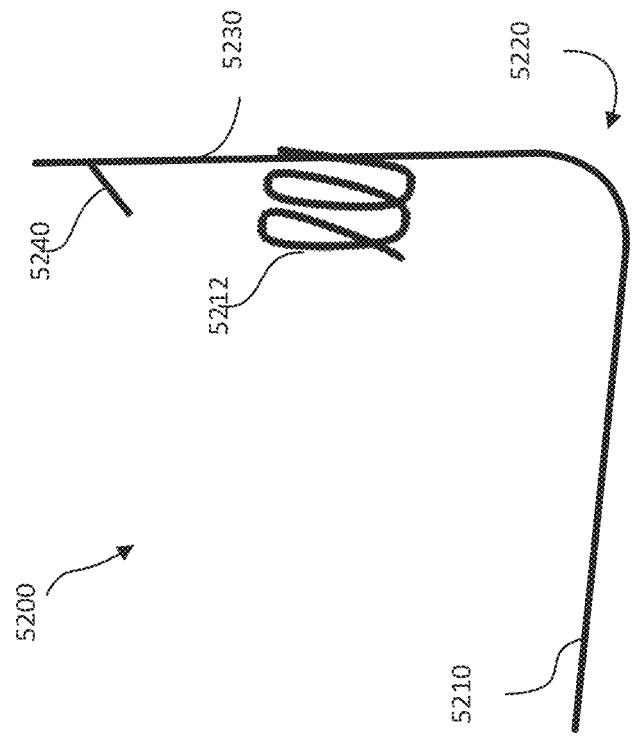
FIGS. 128A and 129A show an example embodiment of a clasp with a spring indicator for an implantable prosthetic device.
Figure 129E:
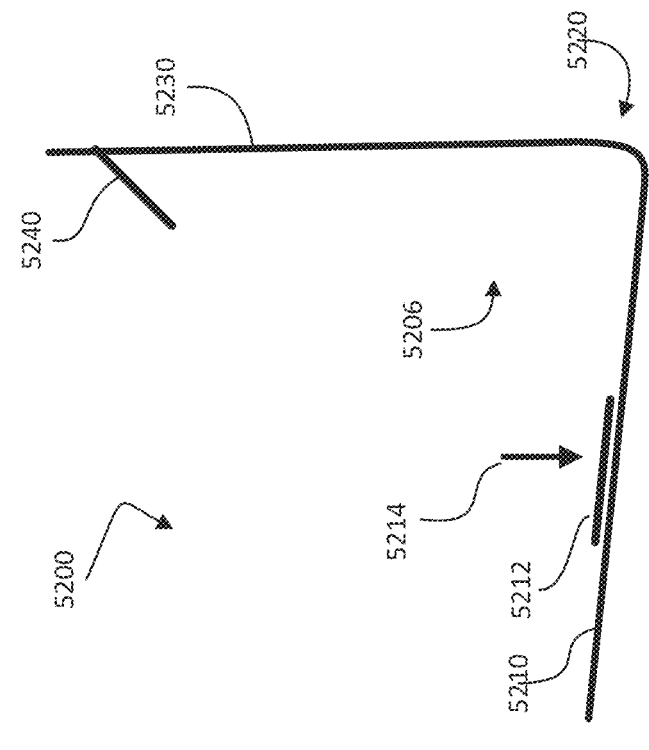
FIGS. 129D and 129E show an example embodiment of a clasp with a spring indicator for an implantable prosthetic device.
Figure 129F:
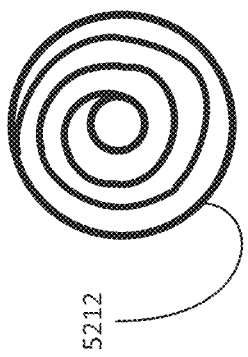
FIG. 129F shows an example embodiment of a spring indicator for a clasp.
Figure 129D:
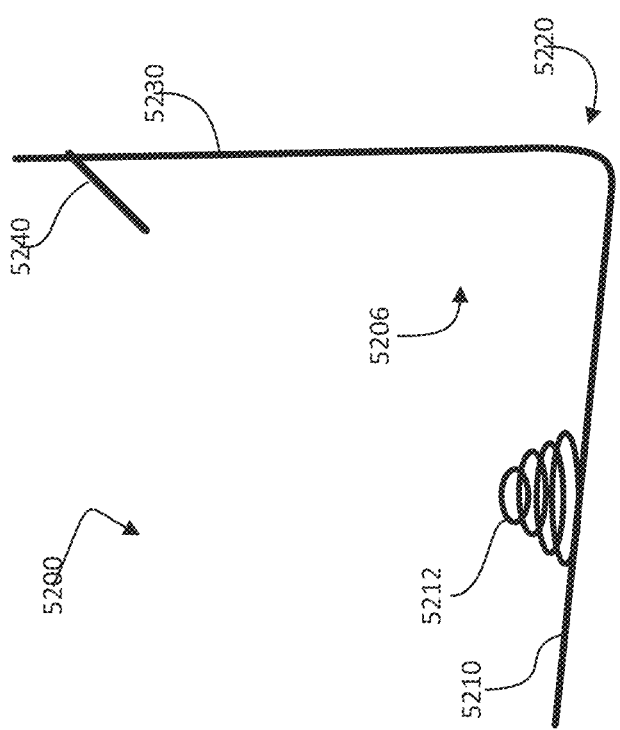

Referring now to FIGS. 129D-129F, an example clasp 5200 having a conical indicator spring 5213 is illustrated. FIG. 129D illustrates a clasp 5200 in an open configuration having a conical indicator spring 5213 attached to the fixed arm 5210. In some example embodiments, the conical indicator spring 5213 can be attached to the moveable arm 5230. FIG. 129E illustrates the conical indicator spring 5213 in a compressed configuration. Arrow 5214 represents the force of a leaflet pressed against the spring. The outermost, widest diameter ring of the conical indicator spring 5213 is visible. The rest of the rings, in which the diameter decreases with each successive ring to form the conical shape, nest within each other, to form the concentric circles seen in the top-down view of the spring 5213 in FIG. 129F. As a result, the spring 5212 is flat or substantially flat. In FIGS. 129D-129F, the conical indicator spring 5213 is positioned on the fixed arm 5230, but in some example embodiments, it can be fixed on the moveable arm.

Figure 129H:
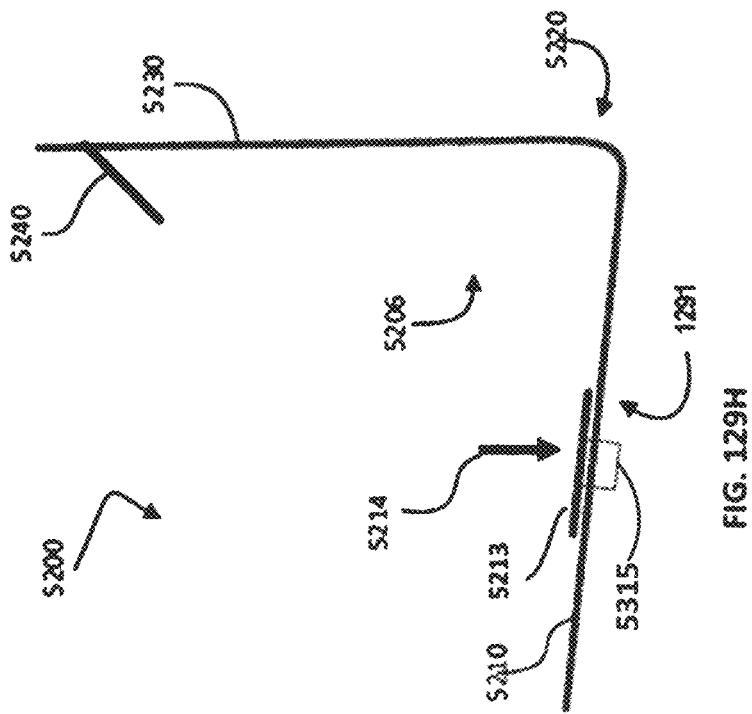
FIGS. 129G and 129H show an example embodiment of a spring indicator for a clasp.
Figure 129G:
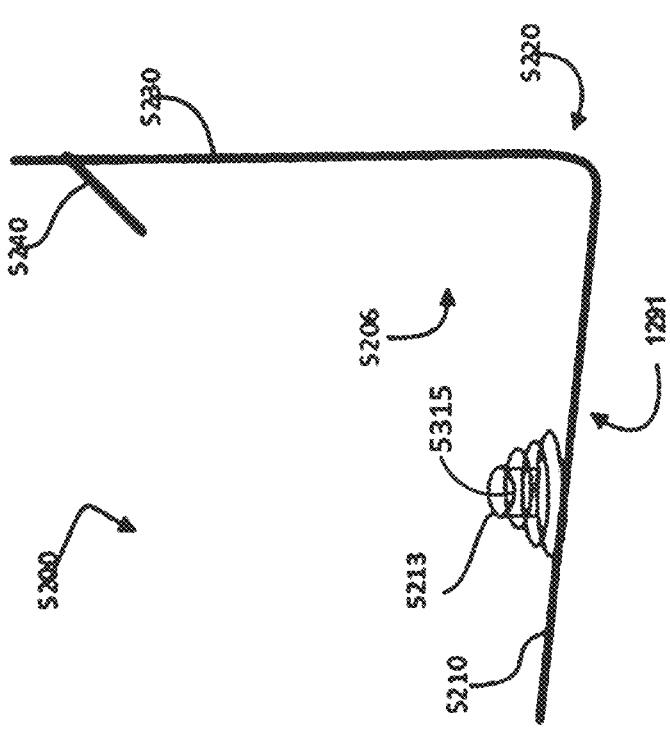

Referring now to FIGS. 129G-129H, example embodiments of clasps having a supplemental indicator element 513 on a conical indicator spring 5213 are illustrated. Referring to FIGS. 129G and 129H, an indicator element 5215, or 5215 can be attached to the conical indicator spring 5213 at the free end of the spring 5213. When in a resting configuration as shown in FIG. 129G, the indicator element 5215 extends downward from the free end of the spring 5213 towards the fixed arm 5210. When in a compressed configuration, as shown in FIG. 129H, due to forces as indicated by arrow 5214, the spring 5213 flattens and indicating element 5215 extends through an opening 129I in the fixed arm, so that the indicator element 5215 is visible on the exterior side of the fixed arm 5210.

Figure 129J:
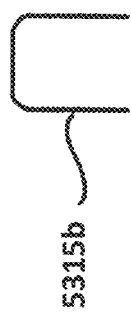
FIGS. 129I and 129J show example embodiments of indicator elements for a spring indicator of a clasp.
Figure 129I:

Referring now to FIGS. 129I and 129J, example embodiments of the indicator element 5215 are illustrated. In FIG. 129I, the indicator element 5215*a* is a conical spring or a conical spring portion having its greatest diameter coil attached to the free end of the conical indicator spring 5213 and its smallest diameter coil positioned closest to the fixed arm 5210. In one example embodiment, the spring 5213 and the conical spring indicator element 5213*a* are formed from a single piece of material, such as a single piece of wire. In the example illustrated by FIG. 129J the indicator element 5213*b* is a piece of material that is secured to the free end of the conical indicator spring. The indicator element 5213*b* can take a wide variety of different forms. The indicator element 5213*b* can be a U-shaped, cup-shaped, or rod-shaped piece of radiopaque material that is secured to the free end of the conical indicator spring. In the illustrated example, the bottom curve of the "U" extends downward toward the fixed arm and the free ends of the "U" are attached to the conical indicator spring 5213. In some example embodiments, the indicator elements 5215 can be attached to a spring indicator having coils of the same diameter, and/or the spring indicator 5213 can be attached to the moveable arm. The indicating elements 5215 can be wrapped in a radiopaque material, made of a radiopaque material, covered in a radiopaque fabric sheath and/or printed with radiopaque ink.

Referring now to FIGS. 128A, 129A, 130A, 131A, and 132A, an example clasp is shown, having similar features to the clasp illustrated in FIGS. 128-132. In FIGS. 128-132A, the clasp 5200 and indicating spring 5212 operate the same way as in the embodiment illustrated in FIGS. 128-132, with one difference. In FIGS. 128A, 129A, 130A, 131A, and 132A, the indicating spring 5213 is positioned on the moveable arm 5230.

Figure 133:
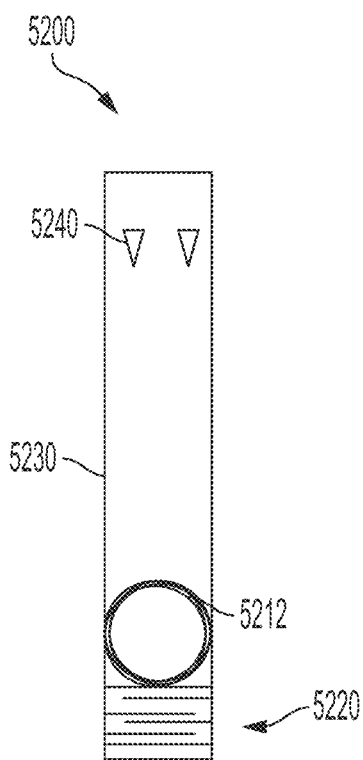
FIGS. 133 and 134 show an example embodiment of a clasp with a spring indicator for an implantable prosthetic device.
Figure 134:
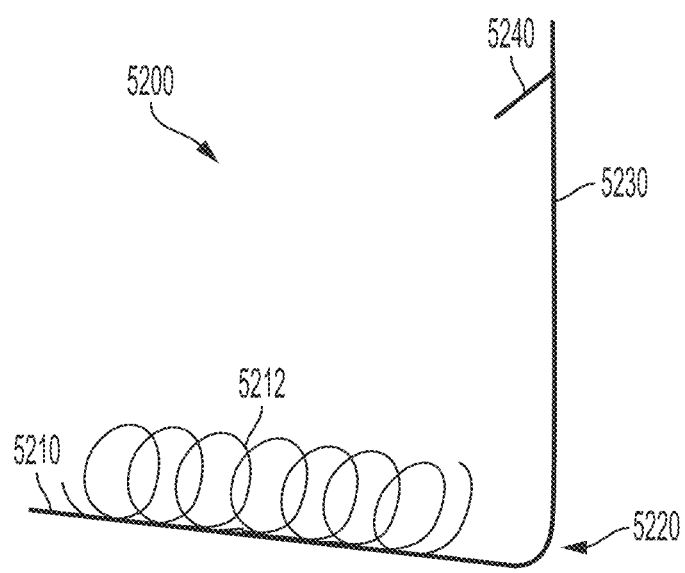

Referring now to FIGS. 133-134, an example clasp 5200 having an indicator on the fixed arm is shown. The clasp can be used in implantable prosthetic devices, such as devices 100, 200, 300 described above. The clasp 5200 includes a fixed arm 5210, a flex or hinge portion 5220, and a moveable arm 5230 having a barbed portion 5240 (though other friction-enhancing portions can be used). The fixed arm 5210 also includes an indicating spring 5212 disposed at a distance between the flex or hinge 5220 portion and the barbed portion 5240. The indicating spring 5212 pictured in FIGS. 133-134 is one having coils aligned so that the spring extends longitudinally along the fixed arm. The indicating spring is schematically illustrated and can take a wide variety of different forms. For example, the indicating spring can be any resiliently deformable component. The indicating spring 5212 can include closed ends and/or can be covered with cloth or other material to prohibit damage to the leaflet tissue. The indicating spring 5212 deforms when the native leaflet tissue is pressed against the indicating spring 5212 by the moveable arm 5230 to indicate that the leaflet tissue has reached a minimum desired engagement depth. Thus, the indicating spring 5212 will not indicate that the native leaflet 42, 44 has reached the desired engagement depth until the leaflet 42, 44 is inserted at or beyond the location of the indicating spring 5212. Once the leaflet 42, 44 has reached the desired engagement depth, actuation of the moveable arm 5230 squeezes the leaflet tissue 42, 44 against the indicating spring 5212 or a portion of the indicating spring of the fixed arm 5210 to cause the indicating spring 5212 or a portion of the indicating spring to flatten and thereby indicate that the leaflet 42, 44 has been inserted into the clasp 5200 at or beyond the desired engagement depth. The indicating spring 5212 can also provide a precise visual indication of leaflet insertion, since the amount of the indicating spring that is depressed is directly related to the amount of leaflet insertion. The clasp 5200 can be used in any of the implantable prosthetic devices of the present application and can include any of the features or combinations of features of the clasps described herein.

Figure 135:
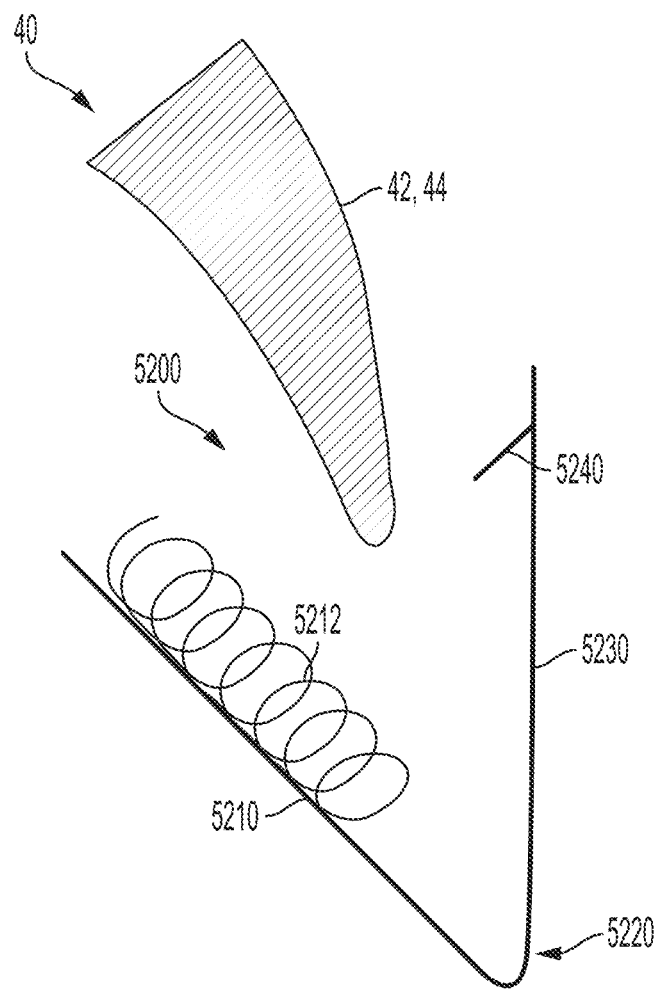
FIGS. 135, 136, and 137 show the example clasp of FIGS. 133 and 134 being deployed to engage with a leaflet of a native valve.
Figure 136:
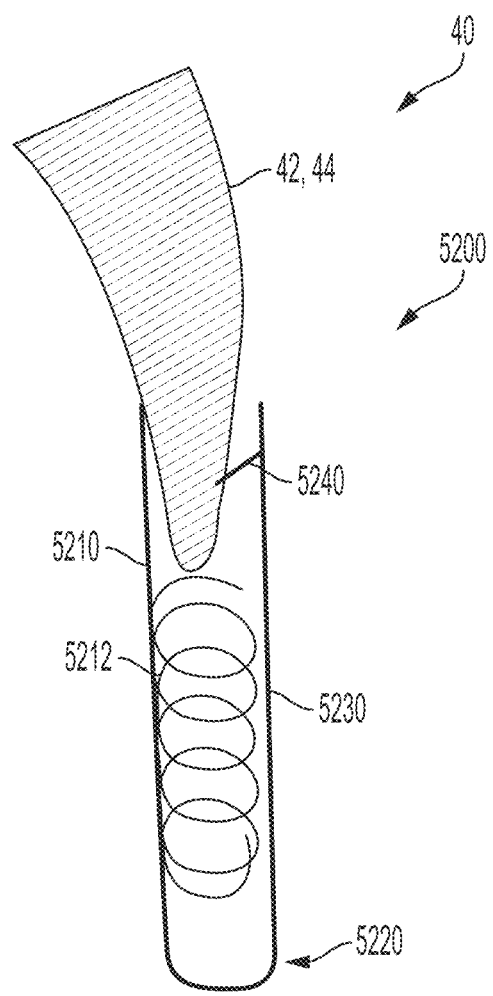
Figure 137:
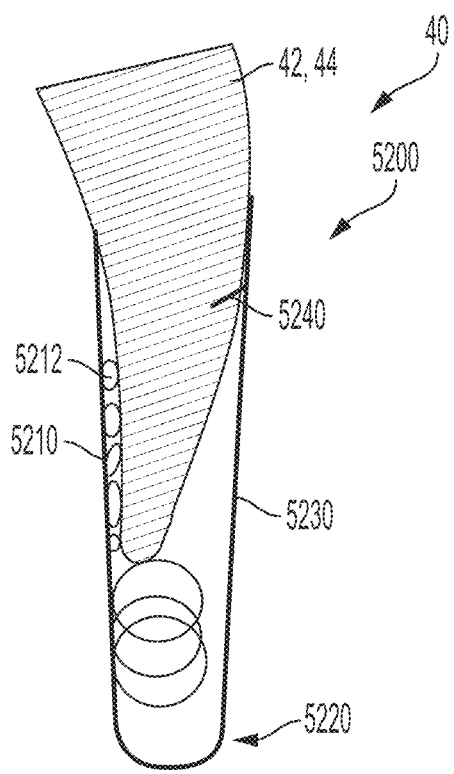

Referring now to FIGS. 135-137, the example clasp 5200 is shown being deployed within a native valve 40 to secure an implantable device (not shown), such as the devices 100, 200, 300 described above, to one of the native leaflets 42, 44. Referring now to FIG. 135, the clasp 5200 is shown in an open condition with a native leaflet 42, 44 partially inserted into an opening 5206 of the clasp 5200 formed between the fixed and moveable arms 5210, 5230. To determine whether the leaflet 42, 44 has reached the desired engagement depth, the moveable arm 5230 is actuated via actuation lines (not shown) as shown in FIGS. 136-137.

Referring now to FIG. 136, when the moveable arm 5230 is actuated to push the leaflet 42, 44 against the fixed arm 5210, the leaflet 42, 44 may contact a portion of the fixed arm 5210 without contacting the indicating spring 5212 when the engagement depth of the leaflet 42, 44 is less than the minimum desired engagement depth. As can be seen in FIG. 137, the indicating spring 5212 is deformed or flattened from contact with the leaflet 42, 44 when the leaflet 42, 44 is inserted into the clasp 5200 at or beyond the minimum engagement depth and is pressed against the indicating spring 5212 by the moveable arm 5230. That is, the indicating spring 5212 is deformed by the leaflet 42, 44 to indicate that the leaflet 42, 44 has been inserted at or beyond the minimum engagement depth. In some embodiments, actuation of the moveable arm 5230 also causes the barbed portion 5240 to engage and secure the leaflet 42, 44 within the barbed clasp 5200. If the indicating spring 5212 indicates that the leaflet 42, 44 is not inserted to the desired depth, the clasp 5200 can be opened to allow for repositioning of the leaflet 42, 44.

Referring now to FIGS. 133A, 134A, 135A, 136A, and 137A, in an example embodiment of a clasp, the indicating spring 5212 as illustrated in FIGS. 133-137 can be secured to the moveable arm 5230 rather than the fixed arm 5210. The indicating spring 5212 can be made from one or more materials visible with fluoroscopy. The indicating spring 2512 can be made with Nitinol or other material visible with fluoroscopy. The indicating spring can be fixed between the barb 5240 and the flex or hinge region 5220. The indicator spring 5212 secured to the moveable arm 5230 operates in the same way to indicate when a leaflet 42, 44 is inserted sufficiently into the clasp, as the indicator spring 5212 with regard to FIGS. 133-134.

Referring to FIGS. 133A and 134A, the clasp 5200 is in an open configuration with no leaflet positioned between the arms of the clasp. The indicating spring 5212 is secured to the interior side of the moveable arm 5230 at a location between the barbed portion 5240 and the flex or hinge portion 5220.

Figure 136A:
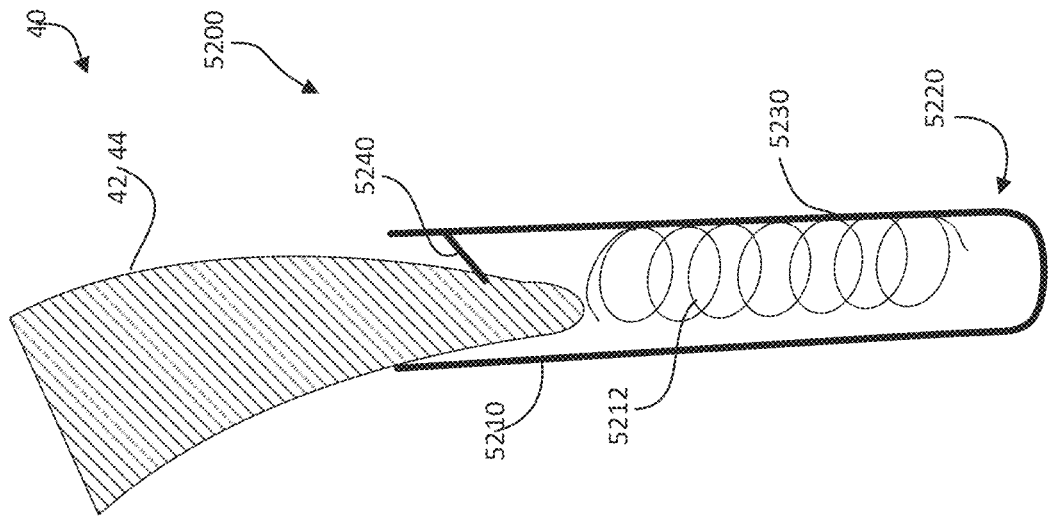
Figure 137A:
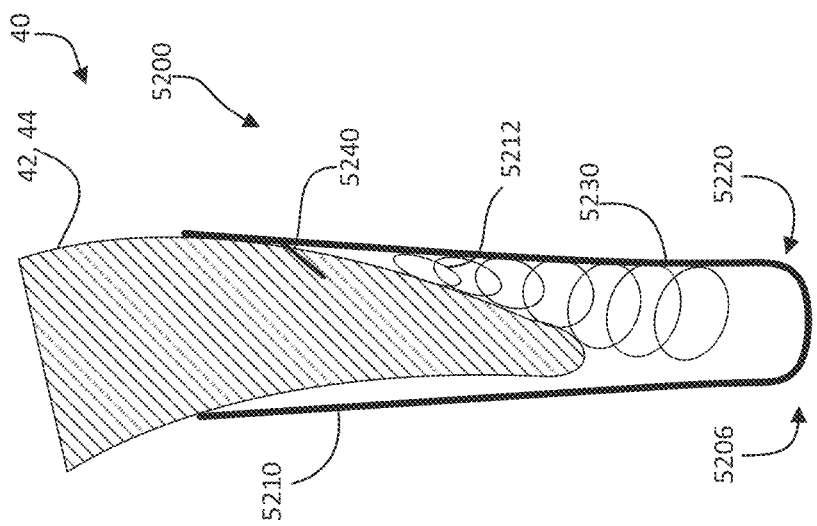

Referring to FIG. 135A, the leaflet 42, 44 is positioned partially within the clasp 5200 and the clasp is in an open configuration. Referring to FIG. 136A, the clasp 5220 is closed on the leaflet 42, 44 and the indicating spring 5212 is not compressed because the leaflet 42, 44 is not inserted at or beyond the minimum depth in the clasp. Referring to FIG. 137A, the indicating spring 5212 is partially compressed to indicate the depth of the leaflet within the clasp. The compression of the indicating spring 5212 can indicate that the leaflet is sufficiently engaged by the clasp. The barbed region 5240 can pierce the leaflet to hold it in place within the clasp. The clasp can be reopened so that the leaflet can be repositioned, until the leaflet is positioned at or beyond a minimum depth as desired by the operator.

In the example embodiments having a coil indicator, the coil can be Nitinol, a Nitinol wire with a platinum core, or Nitinol wrapped with a platinum wire. The coil can be any other combination of materials that can be visualized with fluoroscopy imaging techniques.

Referring now to FIGS. 133B, 134B, 135B, 136B, and 137B, in an example embodiment of a clasp, the indicating spring 5212 as illustrated in FIGS. 133-137 can be secured at or near the flex or hinge region 5220. The indicating spring is fixed to the clasp at one end of the indicating spring, and when in its resting state, extends away from the flex or hinge region toward the central region of the interior of the clasp, where a leaflet would be positioned, and the other end of the indicating spring is free and unattached. The indicating spring 5212 can be made from one or more materials visible with fluoroscopy. The indicating spring 2512 can be made with Nitinol or other material visible with fluoroscopy.

Referring to FIGS. 133B and 134B, the clasp 5200 is in an open configuration with no leaflet positioned between the arms of the clasp.

Figure 135B:
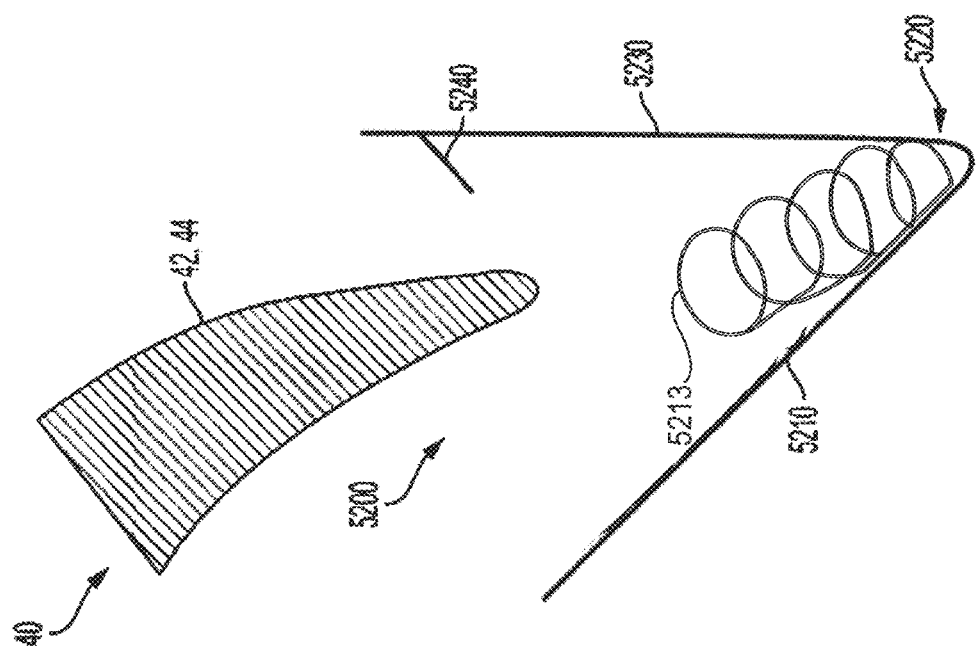
FIGS. 135B, 136B, and 137B show the example clasp of FIGS. 133B and 134B being deployed to engage with a leaflet of a native valve.
Figure 136B:
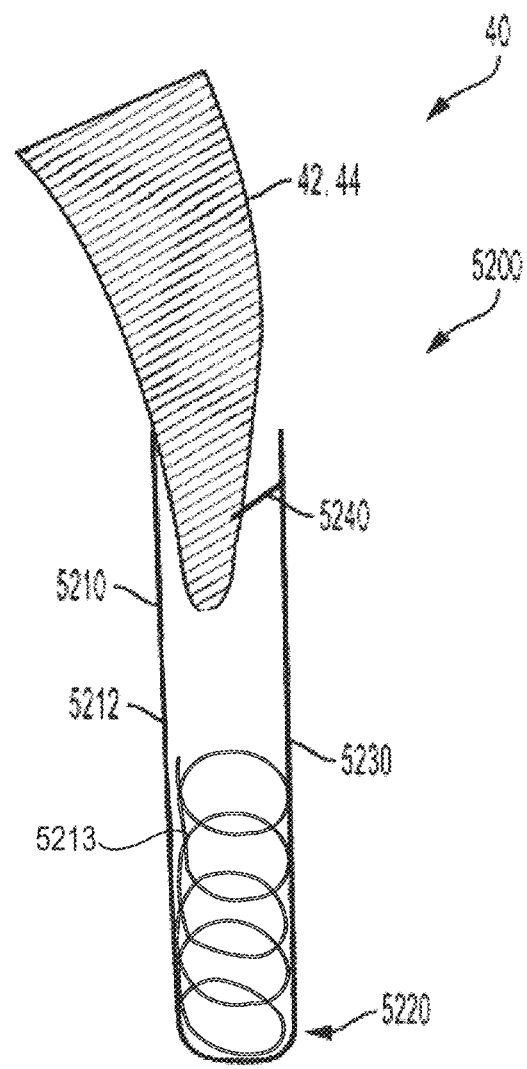
Figure 137B:
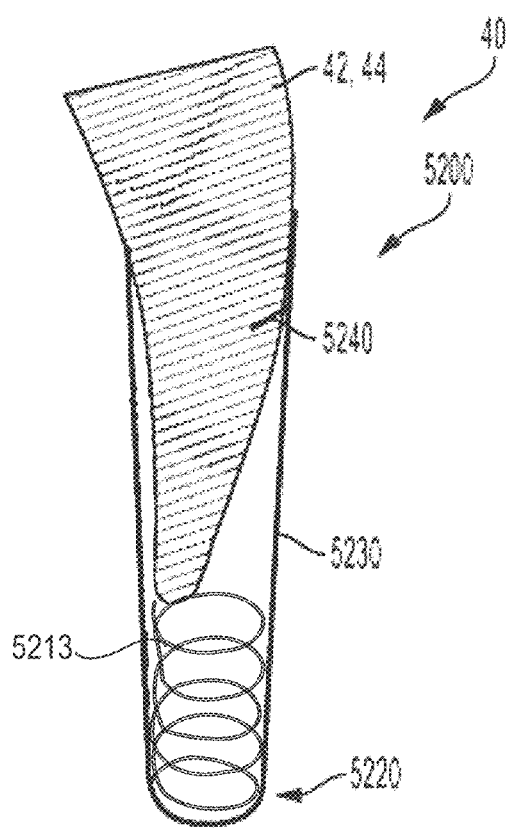

Referring to FIG. 135B, the leaflet 42, 44 is positioned partially within the clasp 5200 and the clasp is in an open configuration. Referring to FIG. 136B, the clasp 5220 is closed on the leaflet 42, 44 and the indicating spring 5212 is not compressed because the leaflet 42, 44 is not inserted at or beyond the minimum depth in the clasp. Referring to FIG. 137B, the indicating spring 5212 is partially compressed to indicate the depth of the leaflet within the clasp. The compression of the indicating spring 5212 can indicate that the leaflet is sufficiently engaged by the clasp. The barbed region 5240 can pierce the leaflet to hold it in place within the clasp. The clasp can be reopened so that the leaflet can be repositioned, until the leaflet is positioned at or beyond a minimum depth as desired by the operator.

Referring now to FIGS. 138-142, an example clasp 6400 for use in implantable prosthetic devices, such as devices 100, 200, 300 described above, is shown. Like the clasp 3500 described above, the clasp 6400 includes a fixed arm 6410, a flex or hinge portion 6420, and a moveable arm 6430 having a barbed portion 6440 (though other friction-enhancing portions can be used). The fixed arm 6410 also includes an indicating pad 6450 disposed at a distance from the flex or hinge portion that is less than a distance between the barbed portion 6440 and the flex or hinge portion 6420. The indicating pad 6450 can take a wide variety of different forms. For example, the indicating pad can comprise upstanding strands, (like carpet strands, toothbrush bristles, etc.), braided wire mesh, compressible foam, non-woven fabrics (such as spun bond, air laid, and/or lofted plastics, such as polyethylene terephthalate ("PET"), woven fabrics, etc. The indicating pad 6450 can be made from a radio opaque material, be covered with a radio opaque material and/or be partially made from a radio opaque material, such as PET and partially made from a non-radio opaque material. In some embodiments, the indicating pad 6450 can be formed by hoops of wire extending from the fixed arm 6410. In some embodiments, the indicating pad 6450 is arranged on the moveable arm 6430 instead of the fixed arm 6410. The clasp 6400 can also include a separate indicating arm (not shown) to press the leaflet 42, 44 against the indicating pad 6450 without actuating the movable arm 6430. An indicating pad can be included on any of the fixed arms, moveable arms, and or indicating arms disclosed herein.

Figure 139A:
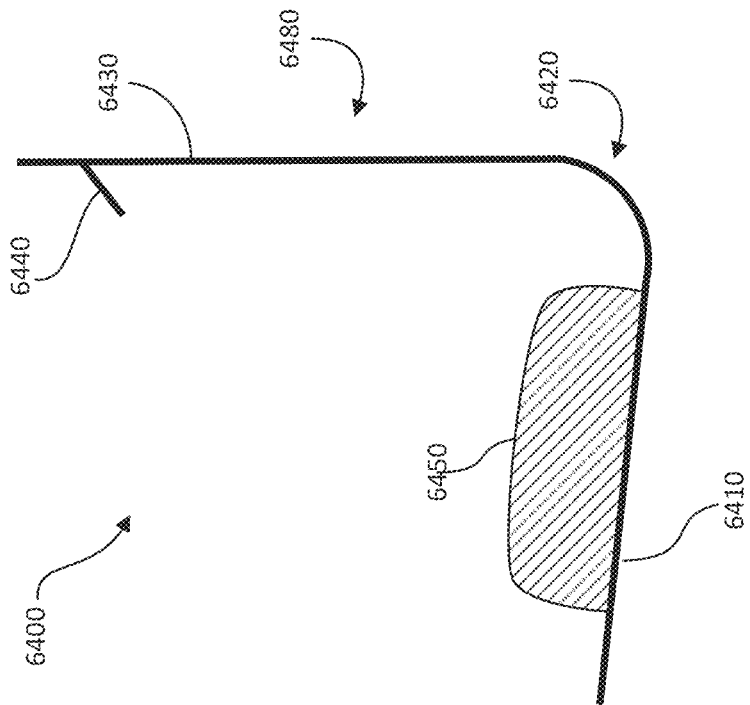
FIGS. 138A and 139A show an example embodiment of a clasp with an indicator pad for an implantable prosthetic device.
Figure 138A:
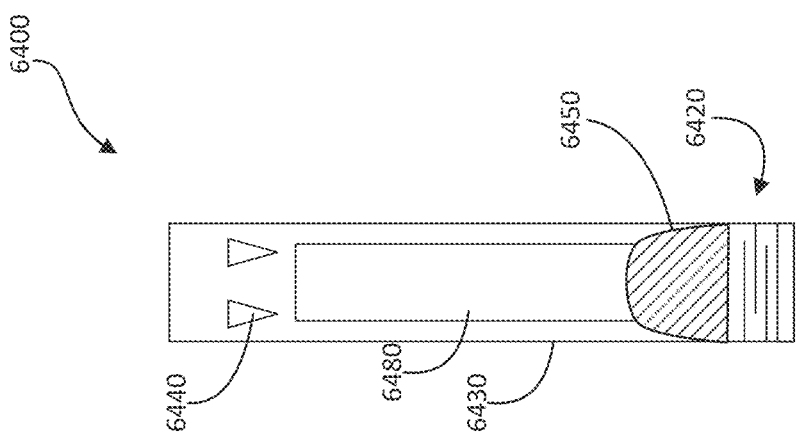

FIGS. 138A and 139A illustrate an example clasp 6400 similar to that described above with reference to FIGS. 138 and 139. Like the clasp 3500 described above, the clasp 6400 includes a fixed arm 6410, a flex or hinge portion 6420, and a moveable arm 6430 having a barbed portion 6440 (though other friction-enhancing portions can be used). The fixed arm 6410 also includes an indicating pad 6450 disposed at a distance from the flex or hinge portion that is less than a distance between the barbed portion 6440 and the flex or hinge portion 6420. The moveable arm 6430 also includes an opening 6480 in which the indicating pad 6450 can pass through when the clasp is closed and the leaflet 42, 44 is not fully engaged.

The indicating pad 6450 is configured to deform, such as elastically deform, when engaged by the native leaflet tissue that is pressed against the indicating pad 6450 by the fixed and moveable arms 6410, 6430. When the tissue disengages the indicating pad 6450 the indicating pad 6450 optionally returns to a neutral position. More specifically, the indicating pad 6450 deforms only in the areas that are engaged by the leaflet and the areas not engaged by the leaflet remain in substantially an initial or resting condition in one example embodiment. Thus, the indicating pad 6450 can indicate that the native leaflet 42, 44 has reached the desired engagement depth when a predetermined portion or the entirety of the indicating pad 6450 has been deformed by the leaflet 42, 44. Once the leaflet 42, 44 has reached the desired engagement depth, actuation of the moveable arm 6430 squeezes the leaflet tissue 42, 44 against the indicating pad 6450 of the fixed arm 6410 to cause the indicating pad 6450 to deform and thereby indicate that the leaflet 42, 44 has been inserted into the clasp 6400 at or beyond the desired engagement depth. The clasp 6400 can be used in any of the implantable prosthetic devices of the present application and can include any of the features or combinations of features of the other clasps described herein.

Figure 141:
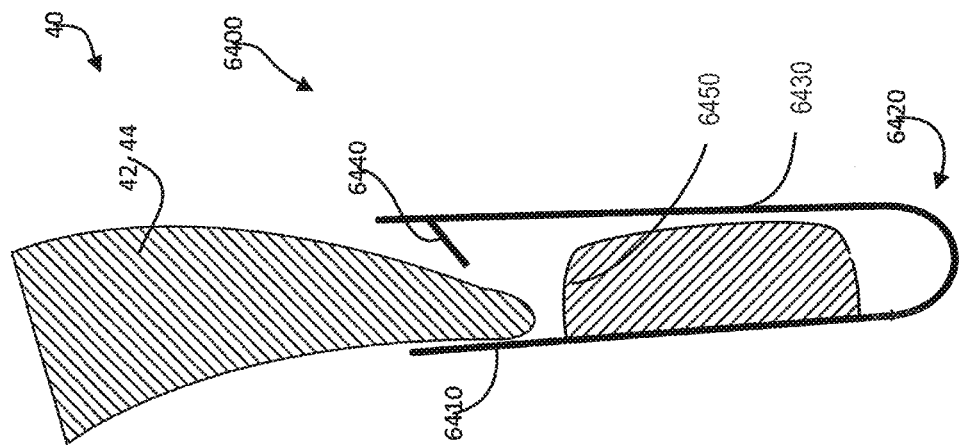

Referring now to FIGS. 140-142, the example clasp 6400 having an indicating pad 6450 as a leaflet depth indicator is shown being deployed within a native valve 40 to secure an implantable device (not shown), such as the devices 100, 200, 300 described above, to one of the native leaflets 42, 44. FIGS. 141 and 142 illustrate an indicating pad 6450 that can deform or flatten upon contact with a leaflet. Referring now to FIG. 140, the clasp 6400 is shown in an open condition with a native leaflet 42, 44 partially inserted into an opening 6406 of the clasp 6400 formed between the fixed and moveable arms 6410, 6430. To determine whether the leaflet 42, 44 has reached the desired engagement depth, the moveable arm 6430 is actuated via actuation lines (not shown) as shown in FIGS. 141-142.

Referring now to FIG. 141, when the moveable arm 6430 is actuated to push the leaflet 42, 44 against the fixed arm 6410, the leaflet 42, 44 may contact a portion of the fixed arm 6410 without contacting the indicating pad 6450 when the engagement depth of the leaflet 42, 44 is less than the minimum desired engagement depth.

Referring now to FIG. 142, the indicating pad 6450 is deformed or flattened from contact with the leaflet 42, 44 when the leaflet 42, 44 is inserted into the clasp 6400 at or beyond the minimum engagement depth and is pressed against the indicating pad 6450 by the moveable arm 6430. That is, the portion of the indicating pad 6450 that is deformed by the leaflet 42, 44 indicates that the leaflet 42, 44 has been inserted at or beyond the minimum engagement depth. In some embodiments, actuation of the moveable arm 6430 also causes the barbed portion 6440 to engage and secure the leaflet 42, 44 within the barbed clasp 6400. If the indicating pad 6450 indicates that the leaflet 42, 44 is not inserted to the desired depth, the clasp 6400 can be opened to allow for repositioning of the leaflet 42, 44.

Figure 141A:
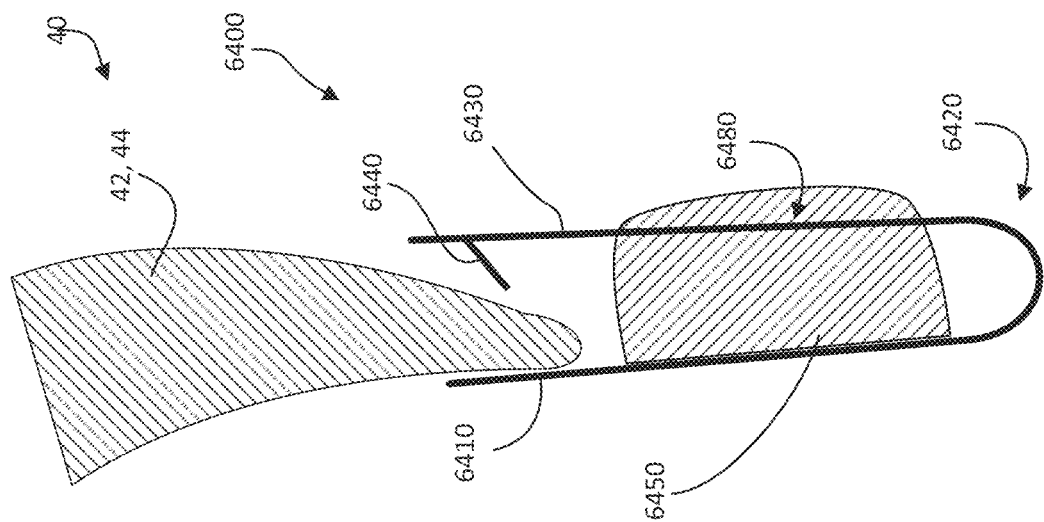
Figure 142A:
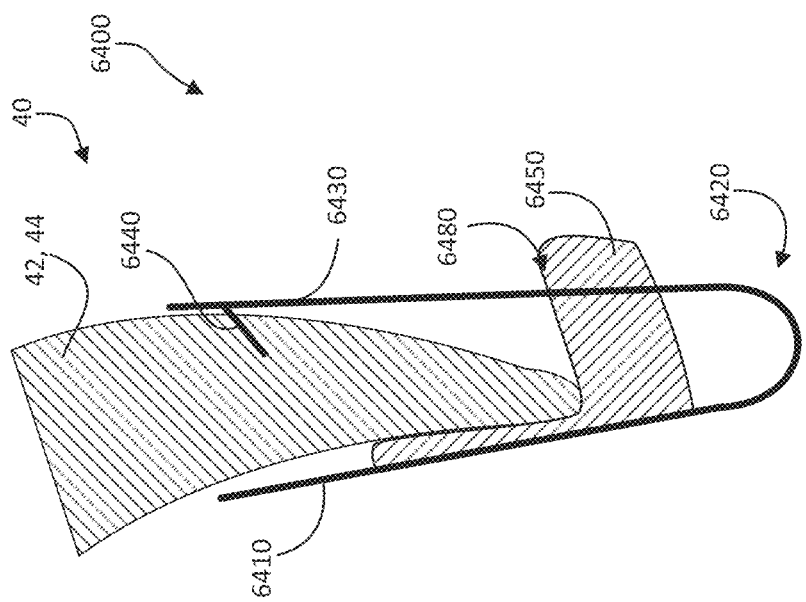

Referring now to FIGS. 140A, 141A, and 142A, the indicating pad can pass through opening 6480 of the moveable arm 6430 when the clasp is closed, and the leaflet is not fully engaged. Referring to FIG. 140A, similar to FIG. 140, clasp 6400 is open and leaflet 42, 44 is partially inserted into the clasp. Referring to FIG. 141A, clasp 6400 is closed and leaflet 42, 44 is not inserted at or beyond the minimum depth in the clasp. Indicating pad 6450 is not deformed, and instead passes through opening 6480 in moveable arm 6430. The indicating pad positioned through the opening 6480 is visible to the operator to indicate that the leaflet is not inserted at a sufficient depth in the clasp. Referring to FIG. 142A, the indicating pad 6450 is deformed or flattened from contact with the leaflet 42, 44 when the leaflet 42, 44 is inserted into the clasp 6400 at or beyond the minimum engagement depth and is pressed against the indicating pad 6450 by the moveable arm 6430. That is, the portion of the indicating pad 6450 that is deformed by the leaflet 42, 44 indicates that the leaflet 42, 44 has been inserted at or beyond the minimum engagement depth. In some embodiments, actuation of the moveable arm 6430 also causes the barbed portion 6440 to engage and secure the leaflet 42, 44 within the barbed clasp 6400. A portion of the indicating pad 6450 that is not deformed or flattened by the leaflet 42, 44 extends through the opening 6480 of the moveable arm 6430 when the clasp is closed. If the indicating pad 6450 indicates that the leaflet 42, 44 is not inserted to the desired depth, the clasp 6400 can be opened to allow for repositioning of the leaflet 42, 44.

Figure 143:
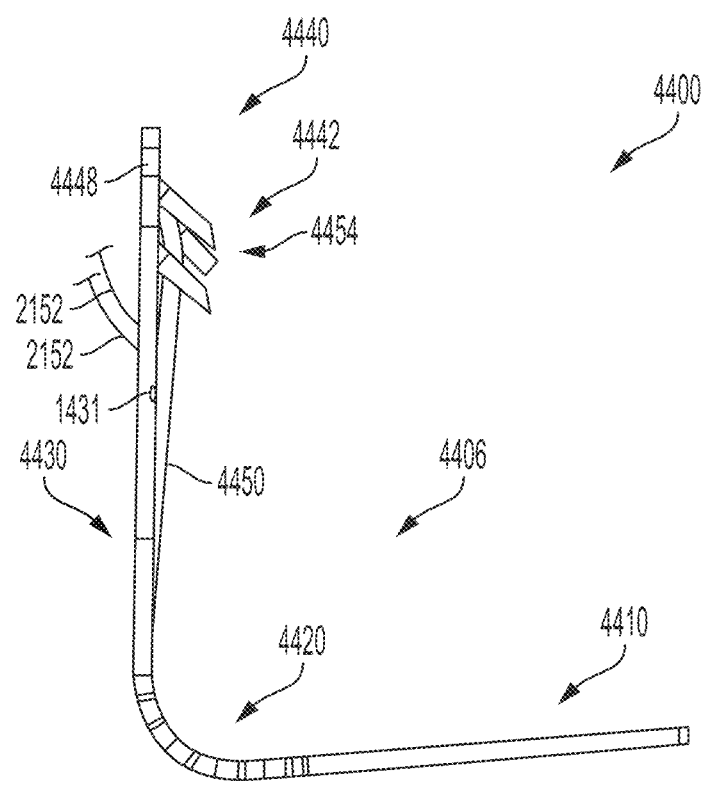
FIGS. 143-152 show an example embodiment of a clasp for an implantable prosthetic device having suture holes.
Figure 144:
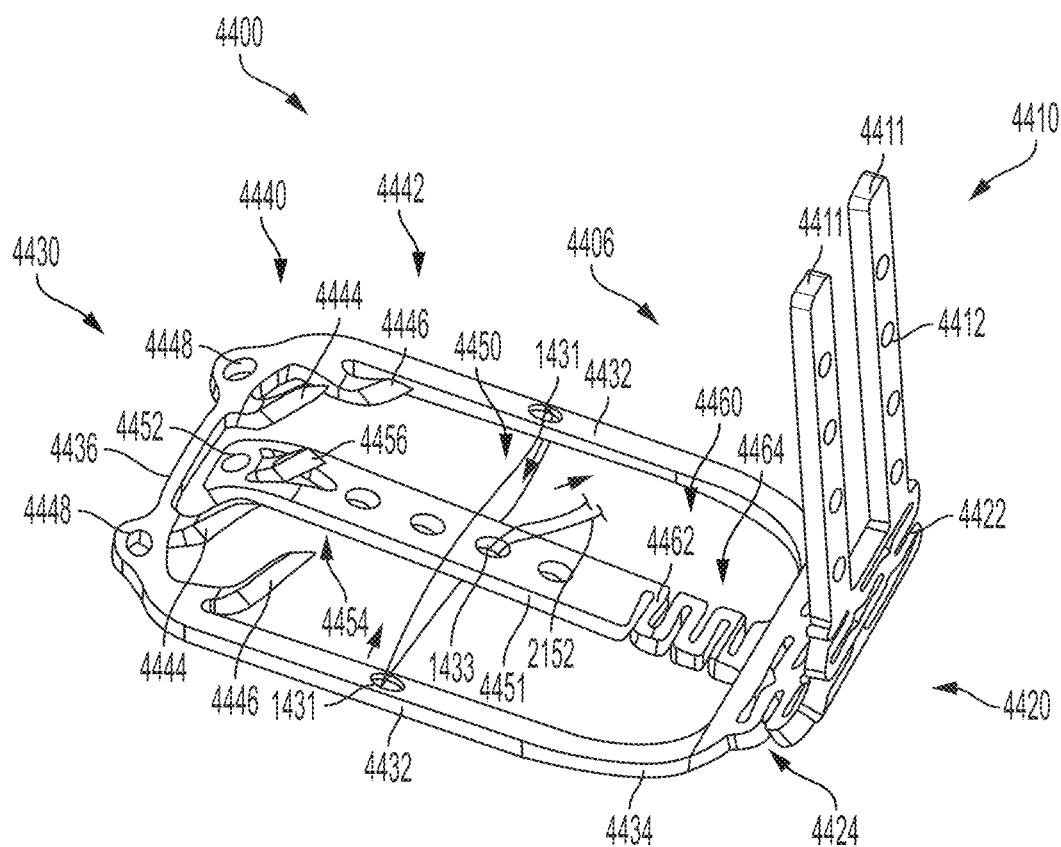
Figure 145:
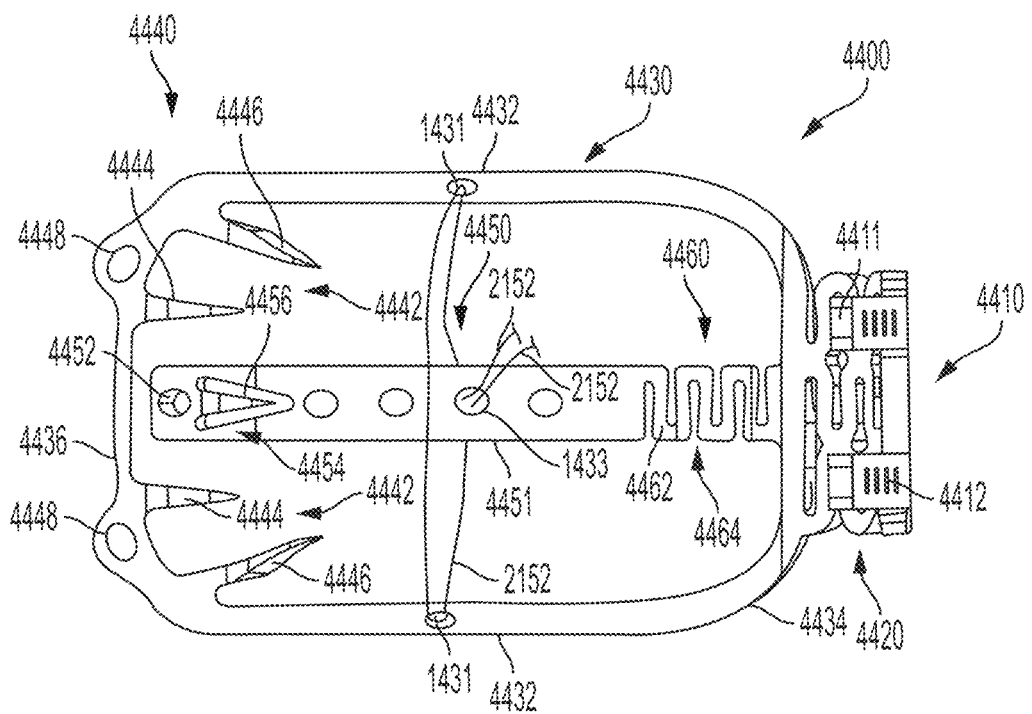

Referring now to FIGS. 143-154, an example clasp 4400 that is the same or substantially the same as the embodiment illustrated by FIGS. 48-66 or FIGS. 111-122, except the clasp is actively collapsible by lines, such as suture lines. Referring to FIGS. 144 and 145, the moveable arm 4430 includes side beams that are flexible, particularly in the lateral direction. The moveable arm 4430 includes holes 1431 for receiving one or more actuation sutures 2152 that are used to collapse the moveable arm 2130. For example, the sutures 2152 an be pulled on to pull the side beams inward of the moveable arm 4430 inward as the clasp is routed through the native valve, such as the native mitral valve and associated chordae tendinea. In the illustrated example, the lines 2152 are routed through the holes 1431 and through a hole 1433 in the indicator arm 4450. The hole 1433 in the indicator arm can be centered between the holes 1431 in the movable arm 4430 to efficiently and/or symmetrically pull the side beams of the moveable arm inward. For example, arranging the hole 1433 in the indicator arm closer to the holes 1431 causes the forces applied to the clasp 4400 by the sutures 2152 to be directed in a more lateral rather than longitudinal direction.

The rounded hoop shape of the clasp 4400 allows the clasp 2100 to be collapse by merely retracting the clasp 2100 into the delivery sheath. In certain embodiments, the expansion and contraction of the clasp 4400 is controllable by the actuation sutures 2152.

The clasp illustrated by FIGS. 143-154 can be used in implantable prosthetic devices, such as devices 100, 200, 300 described above, is shown. The clasp 4400 has a fixed arm 4410, a patterned flex portion or patterned hinge portion 4420, a moveable arm 4430 formed in the shape of a hoop or loop having side beams 4432, and a barbed portion 4440 of the moveable arm 4430. The clasp 4400 also includes an indicator arm 4450 extending from an indicator flex or hinge portion 4460 that joins the indicator arm to the flex or hinge portion 4420. The illustrated clasp also includes the suture holes 1431 positioned part-way down on the moveable arm 4430 and a suture hole 1433 in the indicator arm 4450. The suture holes can be positioned one on each of the side beams 4432 of the moveable arm, such that each suture hole is positioned at a location between the barb 4446 and the patterned flex portion or patterned hinge portion 4420. The suture holes 1431 are used for the actuation lines 2152, which can be suture lines. As mentioned above, the actuation lines are used to control the expansion and contraction of the clasp 4400. The same suture line can be used to raise and lower both the moveable arm and/or the indicator arm. The indicator arm can also have an optional suture hole 4452 at its free end (see FIG. 144).

In one example embodiment, the actuation lines are attached to suture holes 1431 in the illustrated position on the side beams to reduce the moment arm, as compared to suture holes at the free end of the moveable arm side beams. This allows the operator to raise the moveable arm first, and then raise the indicator arm, when opening the clasp with a single suture line. Likewise, when closing the clasp, the indicator arm can will be lowered first before the moveable arm is lowered.

The clasp 4400 can be used in any of the implantable prosthetic devices of the present application and can include any of the features or combinations of features of the other clasps described herein. For example, the clasp 4400 can be laser cut from a flat sheet or a tube of shape-memory alloy, such as Nitinol, and then shape-set into a desired shape.

The illustrated fixed arm 4410 has two tongue portions 4411 that each include holes 4412 for attaching the fixed arm 4410 to an implantable device. A central opening 4454 arranged between the tongue portions 4411 is wider than the indicator arm 4450 so that the indicator arm 4450 can optionally pass through the fixed arm 4410 between the tongue portions 4411.

The patterned flex portion or patterned hinge portion 4420 is formed from a plurality of spring segments 4422 and cutouts 4424. The two tongue portions 4411 of the fixed arm 4410 extend from one end of the patterned flex/hinge portion 4420 and the moveable arm 4430 extends from the other end of the flex/hinge portion 4420.

The moveable arm 4430 of the clasp 4400 has a hoop-like shape. The hoop-shaped moveable arm 4430 includes side beams 4432 that are thinner and more flexible, particularly in the lateral direction. The side beams 4432 can optionally include a first flex or hinge portion 4434 arranged toward the proximate end of the moveable arm 4430 and a second flex or hinge portion 4436 arranged at the distal end of the moveable arm 4430. The first flex or hinge portion 4434 is formed by one or more bends in the side beams 4432. The second flex or hinge portion 4436 includes a thinner—and therefore more flexible—portion to reduce the force required to collapse the clasp 4400.

The hoop-like shape of the moveable arm 4430 provides for a wider barbed portion 4440 that can include more barbs 4442 with the same or greater lateral spacing than other clasps. The wider spacing of the barbs 4442 improves capture of the native leaflets. The barbs 4442 are also longitudinally staggered as a result of their position on the hoop-like shape of the moveable arm 4430. That is, two center barbs 4444 are arranged further away from the flex or hinge portion 4420 and two outer barbs 4446 are arranged closer to the flex or hinge portion 4420. The barbed portion 4440 of the moveable arm 4430 can include optional additional holes 4448 for receiving an additional actuation suture (not shown). In certain embodiments, the hoop shape of the moveable arm 4430 is similar to the shape of wide outer paddles of an implantable device so that pinching forces of the paddles are spread out evenly on the barbs, further improving the retention of the native leaflets. The ends of the barbs 4442 can be further sharpened using any suitable sharpening means.

The indicator arm 4450 includes a beam 4451 that extends from the flex or hinge portion 4420 in the interior of the hoop-shaped moveable arm 4430 between the two side arms 4432 to a barbed portion 4456. The indicator arm 4450 includes an optional hole 4452 at the end for receiving an optional actuation line (not shown) for actuating the indicator arm 4450. The optional barbed portion 4456 is arranged at the end of the beam 4451 of the indicator arm 4450 and can include at least one barb 4456. The barbed portion 4456 helps the indicator arm 4450 secure the leaflet until the moveable arm 4430 is closed. The barb 4456 can be laser cut from the indicator arm 4450 and bent outwards so that it protrudes away from the indicator arm 4450 at about the same angle as the barbs 4442 protrude from the moveable arm 4430. In some embodiments, the indicator arm 4450 includes barbs that, like the barbs 2244 of the clasp 2200, are cut from a flat sheet of material and then rotated 90 degrees to protrude outward at an angle.

The barbed portion 4456 of the indicator arm 4450 is arranged at a distance from the flex or hinge portion 4420 such that the optional barb 4456 of the indicator arm 4450 is longitudinally arranged between the center barbs 4444 and the outer barbs 4446 of the barbed portion 4440. This arrangement ensures that the barbed portion 4440 will engage a leaflet that is engaged by the indicator arm 4450. That is, if a native leaflet positioned within the clasp 4400 is engaged by the barbed portion 4456 of the indicator arm 4450 when the indicator arm 4450 is actuated, then the leaflet will also be engaged by the barbed portion 4440 of the moveable arm 4430. The opposite is also true. That is, if a native leaflet positioned within the clasp 4400 is not engaged by the indicator arm 4450 when the indicator arm 4450 is actuated, then the leaflet will not be sufficiently engaged by the barbed portion 4440 of the moveable arm 4430.

The indicator flex or hinge portion 4460 allows the indicator arm 4450 to be actuated separately from the moveable arm 4430 to facilitate detection of the depth of engagement of the native leaflet arranged between the moveable arm 4430 and the fixed arm 4410 of the clasp 4400. The indicator flex or hinge portion 4460 is similar to the patterned flex or hinge portion 4420 and is formed from a series of spring segments 4462 and cutouts 4464. In some embodiments, the spring force of the indicator flex or hinge portion 4460 is less than the pinching force imparted to the moveable arm 4430 by the flex or hinge portion 4420 so that the indicator arm 4450 can be actuated many times to detect the position of the leaflet while the moveable arm 4430 with a stronger pinching force is actuated once the leaflet is with barbs is held in a desirable position by the indicator arm 4450. The lower pinching force of the indicator arm 4450 reduces the force imparted onto the leaflet tissue so that the indicator arm 4450 can be repositioned repeatedly and be less likely to puncture or otherwise damage the leaflet tissue. The lower pinching force also allows the indicator arm 4450 to pulse or jump as the heart beats.

Referring now to FIGS. 143-145, the clasp 4400 is shown in an open position. The moveable arm 4430 and indicator arm 4450 are biased or spring-loaded in a closing direction and can be moved to and held in the open position by tension applied to the line 2152 routed through the holes 1431, 1433 in each of the moveable arm 4430 and indicator arm 4450, respectively.

Figure 146:
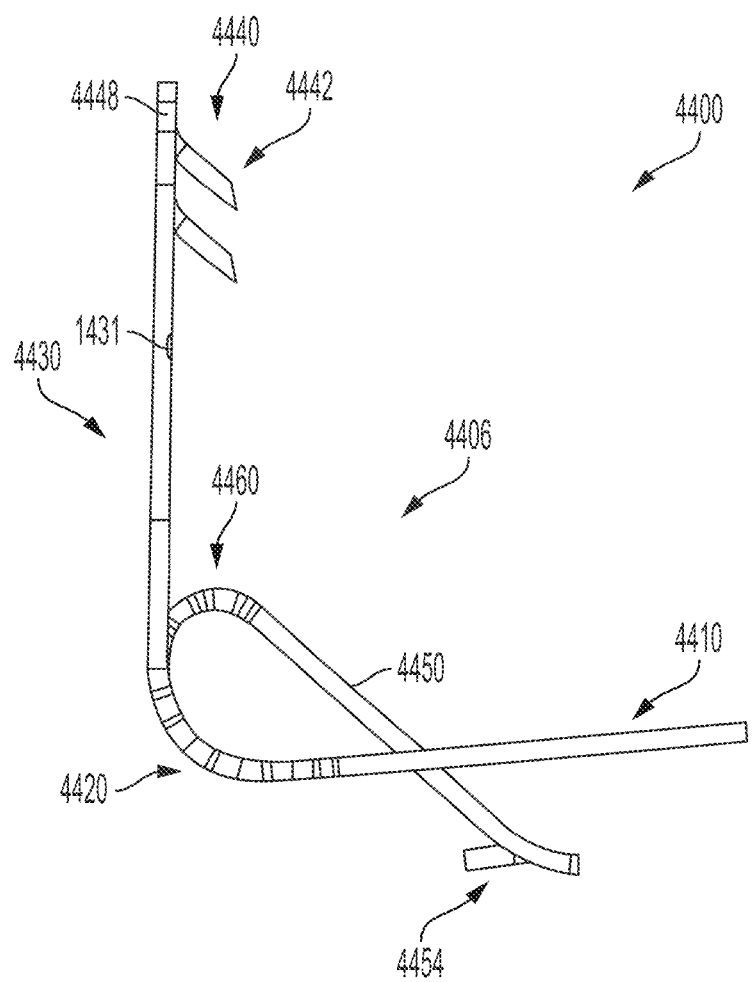
Figure 147:
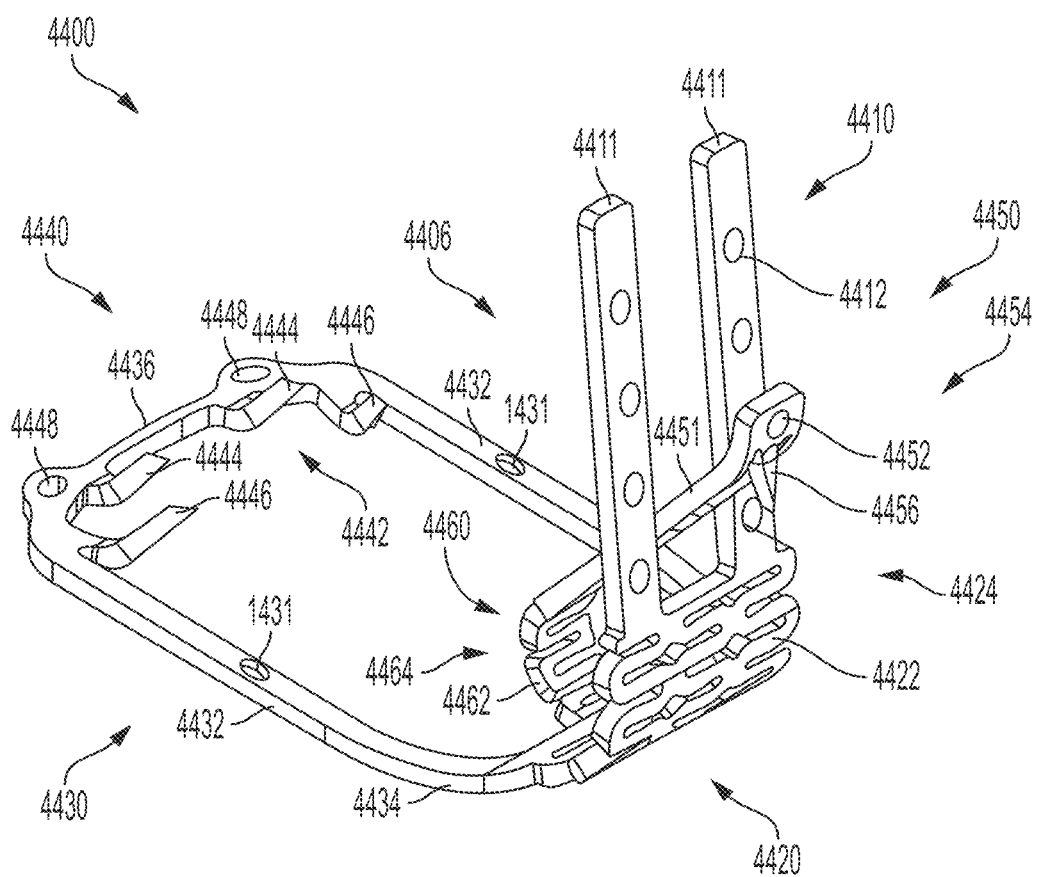
Figure 148:
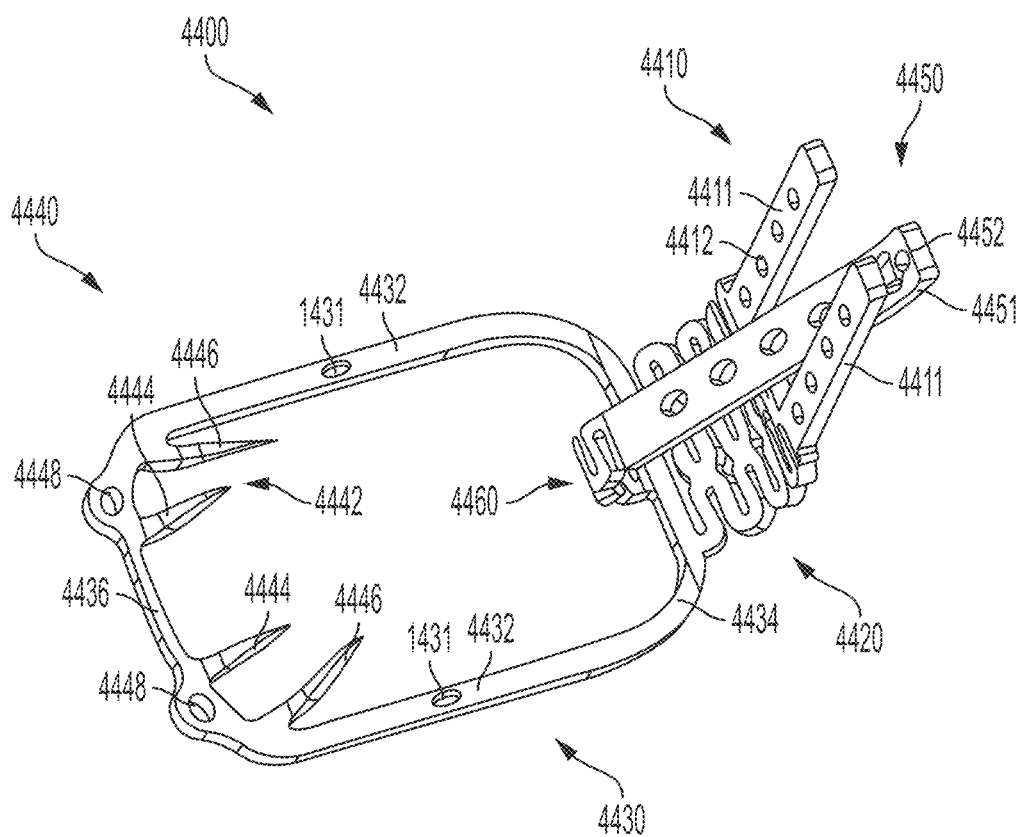

Referring now to FIGS. 146-148, the clasp 4400 is shown with the indicator arm 4450 in a fully deployed or actuated position, that is, the furthest extent that the indicator arm 4450 is capable of reaching when the indicator arm 4450 does not engage with the leaflet tissue during actuation. The indicator arm 4450 is allowed to close when tension on actuation lines 2152 is decreased. In the fully actuated position, the indicator arm 4450 forms an X-shape or other shape with the fixed arm 4410 that is visible via imaging devices so that the operator knows that the indicator arm 4450 has not engaged the leaflet.

Figure 149:
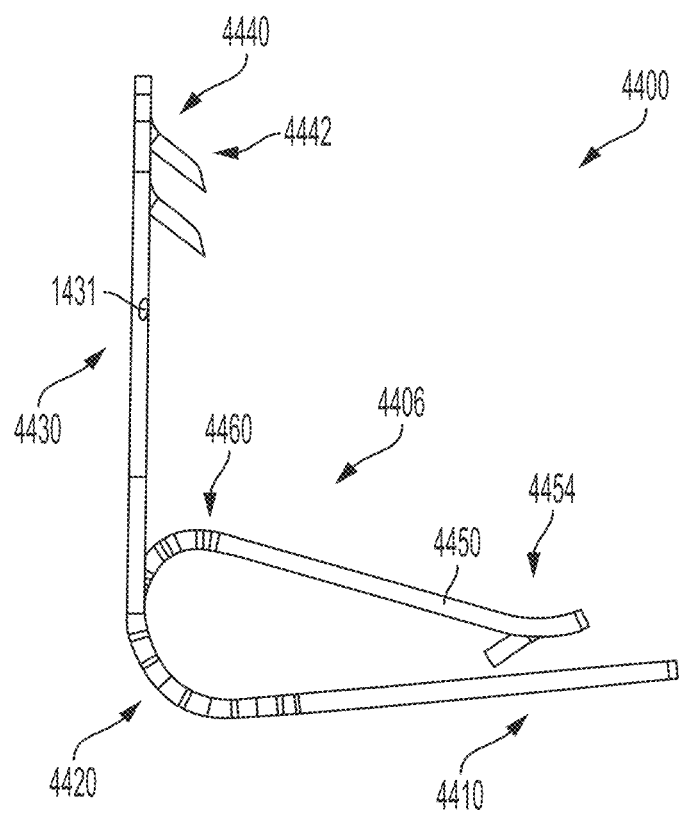
Figure 150:
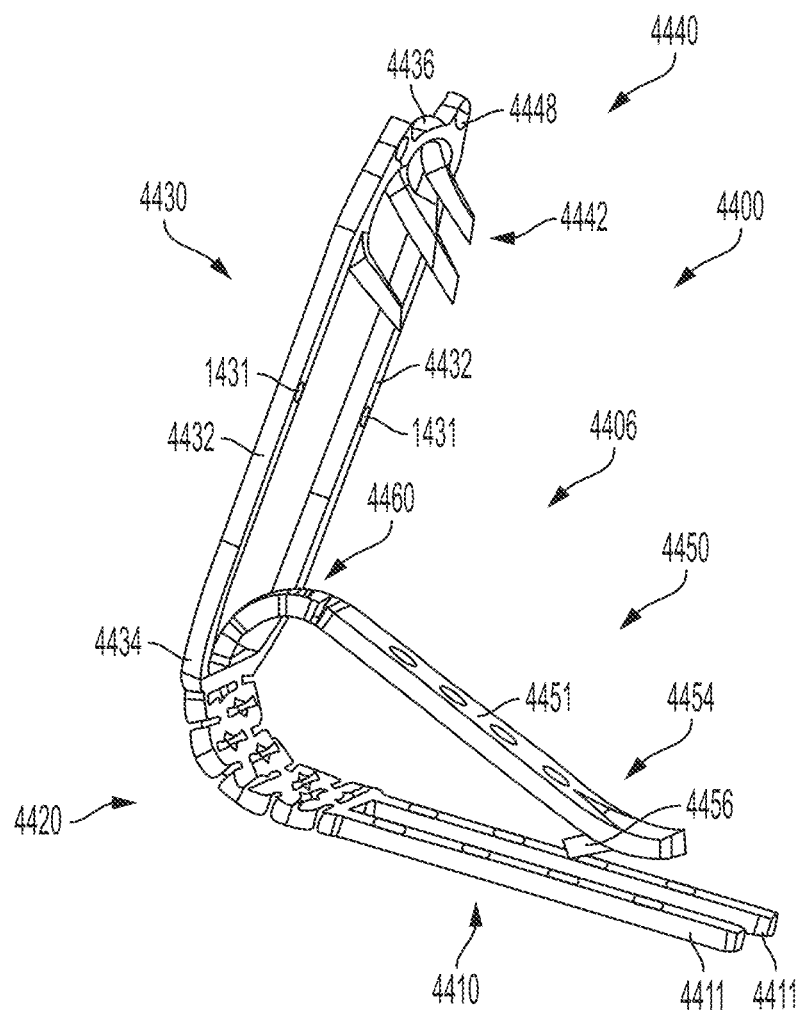
Figure 151:
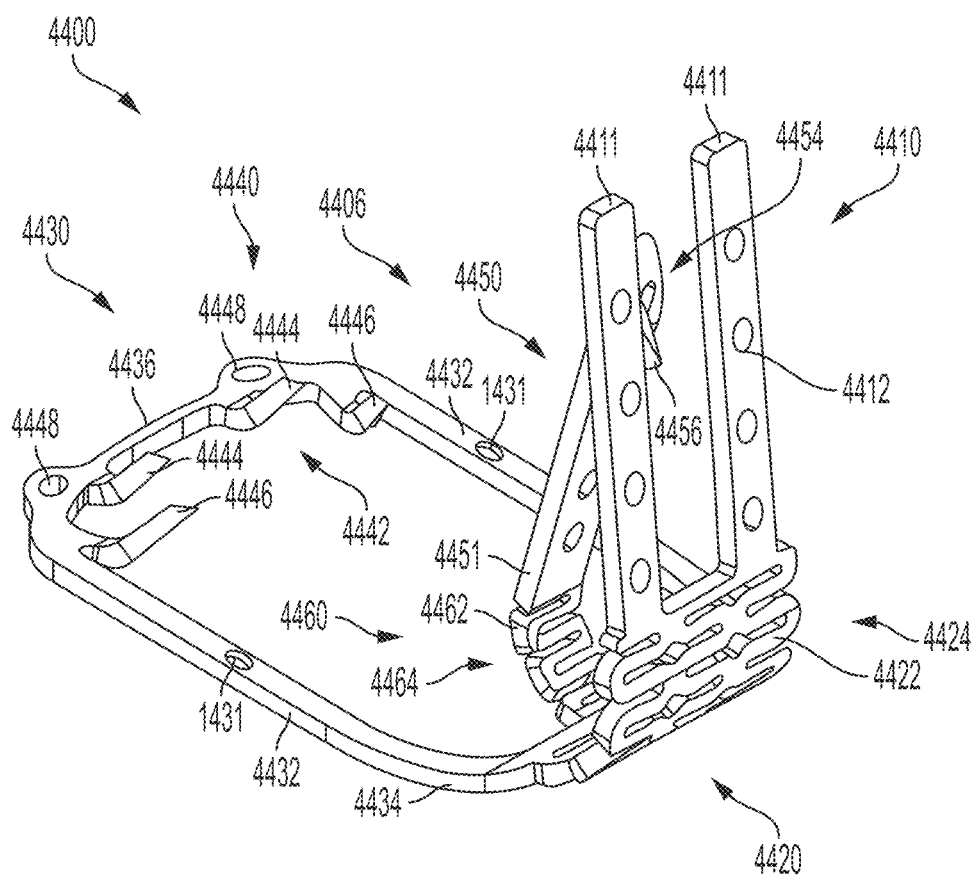

Referring now to FIGS. 149-151, the clasp 4400 is shown with the indicator arm 4450 in an engaged or closed position. That is, the position that the indicator arm 4450 would be in when the leaflet tissue has been engaged during actuation. The indicator arm 4450 is allowed to close when tension on actuation line 2152 (not shown in FIGS. 149-151) is decreased. In the closed position, the indicator arm 4450 is spaced apart from the fixed arm 4410 and/or does not form an X-shape with the fixed arm 4410. Thus, the operator knows that the indicator arm 4450 has engaged the leaflet tissue when the indicator arm 4450 has been actuated when the clasp 4400 is viewed with an imaging device. In addition, or instead, the indicator arm 4450 can be optically monitored to detect pulsing or jumping of the indicator arm as the heart beats. This jumping or bouncing of the indicator arm indicates to the operator that the indicator arm has engaged leaflet tissue.

Figure 152:
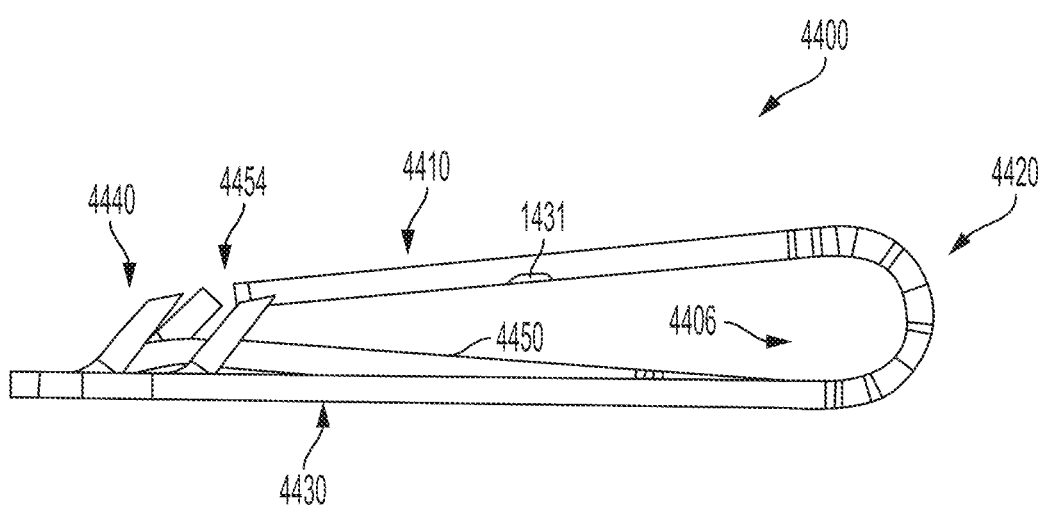
Figure 153:
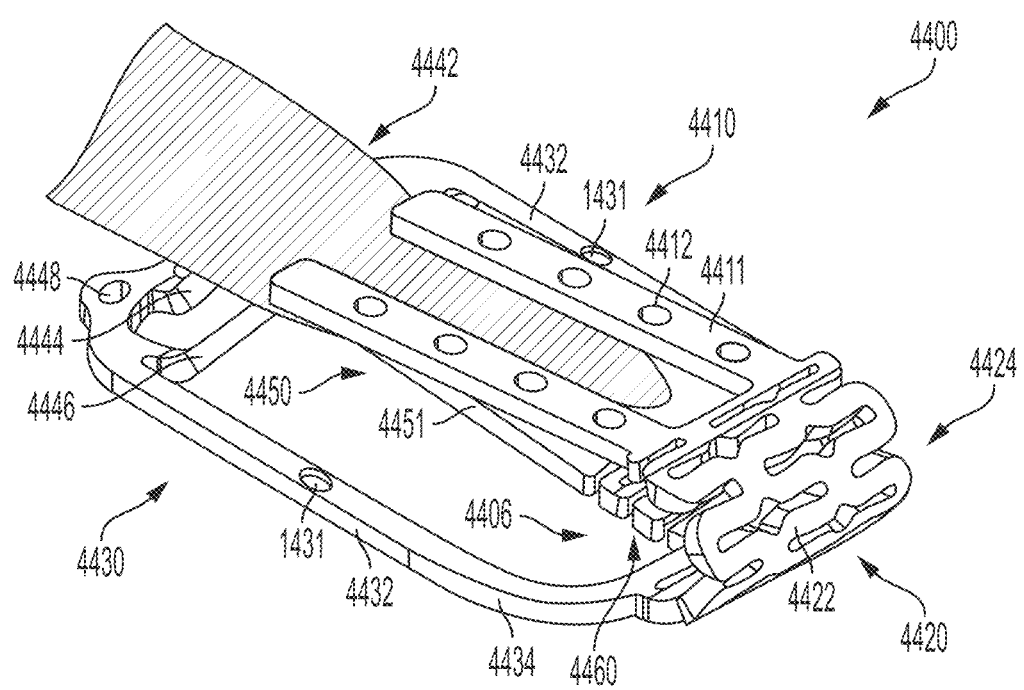
FIGS. 153-154 show the example clasp of FIG. 143 being deployed to engage with a leaflet of a native valve.
Figure 154:
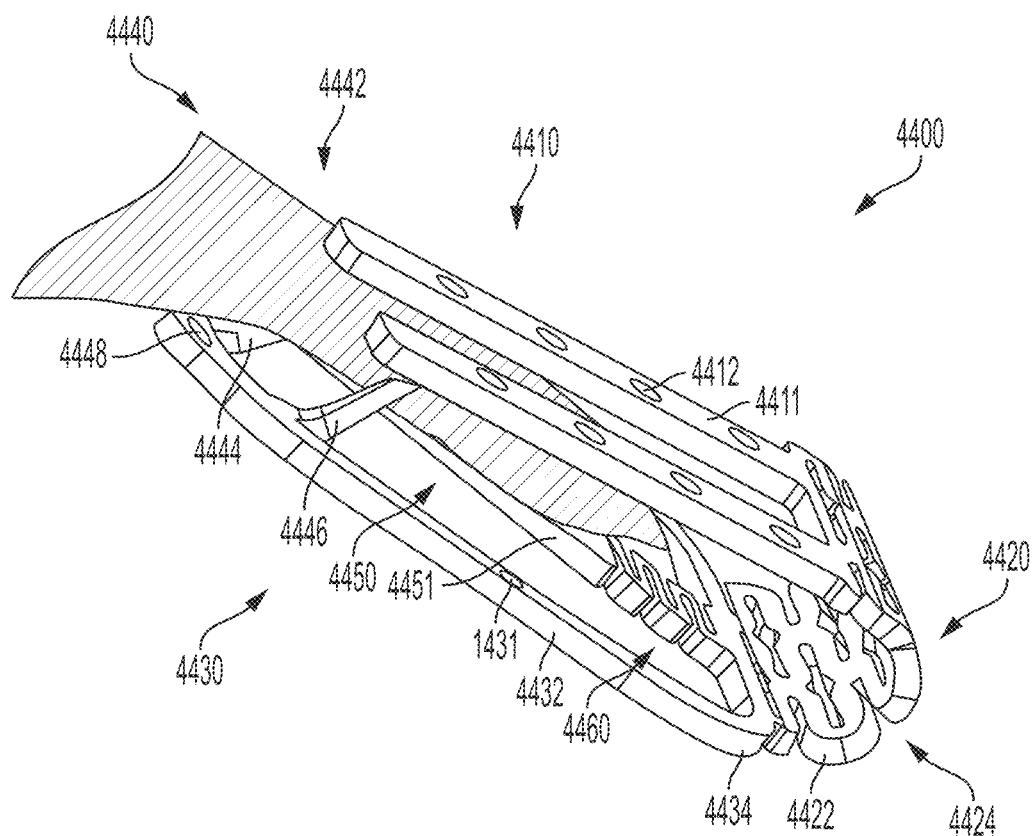

Referring now to FIGS. 152-154, the clasp 4400 is shown with the moveable arm 4430 and the indicator arm 4450 both in a closed position. The indicator arm and moveable arm are both closed by continued release of tension on the actuation line 2152. The initial release of tension releases the indicator arm so that it can close, and by continuing to release tension on the actuation line, the moveable arm then closes. The suture holes 1451 in the moveable arm can be positioned so that the indicator arm can close entirely before the moveable arm begins to close. In some embodiments, the suture holes 1451 can be positioned so that the indicator arm begins to close first but the moveable arm can begin to close before the indicator arm has tension on it released enough to allow it to fully close.

When the clasp 4400 is closed, the moveable arm 4430 and the indicator arm 4450 exert a pinching force that retains the native leaflet tissue to be secured within the clasp 4400. Additionally, a tortuous path for retaining the captured leaflet tissue is formed by the fixed arm 4410, the moveable arm 4430, and the barbed portion 4440. The clasp 4400 is biased in the closed direction by the shape-setting of the moveable arm 4430 and the indicator arm 4450.

The effect of allowing the indicator arm to close first can be achieved in other embodiments as well. These embodiments permit semi-independent control of a weaker shorter indicator arm to close first and open second. For example, the actuator line can be pulled from an angle not parallel to the direction of motion, i.e., increasing the tension force required to lift the clasp. In another example, the suture loop can be doubled back through the clasp connection so that the suture tension force is doubled on the main clasp, causing it to lift first.

Figure 216:
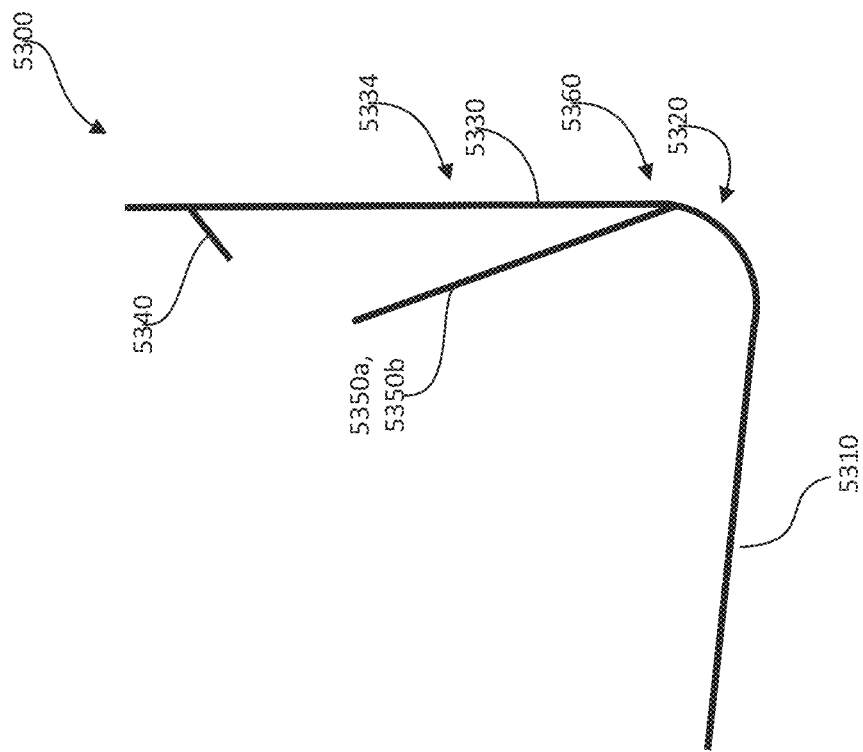
FIGS. 215-216 show schematic views of an example embodiment of a clasp having an indicator.
Figure 215:
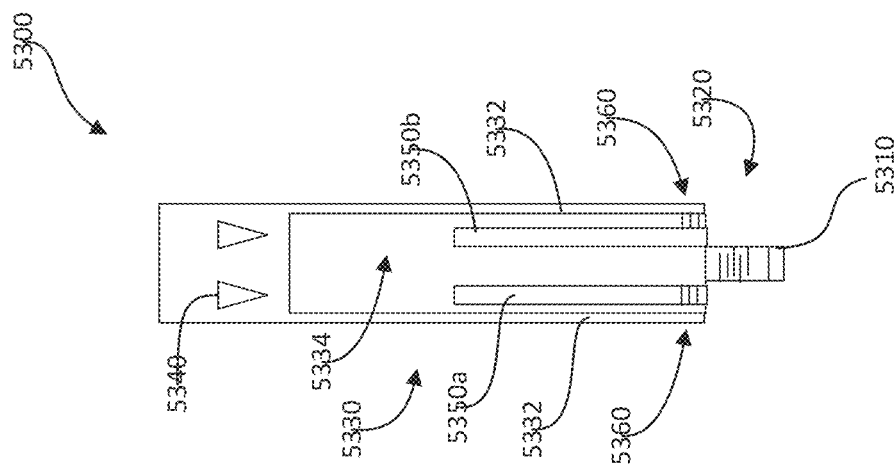

Referring now to FIGS. 215-216, schematic views of example embodiments of a clasp for use in an implantable prosthetic device, such as devices 100, 200, and 300 described above, are shown. Like the clasp 3500 described above, the clasp 5200 includes a fixed arm 5310, a flex or hinge portion 5320, and a moveable arm 5330 having a barbed portion 5340 (though other friction-enhancing portions can be used), an opening 5334, and two side arms 5332. In the example illustrated by FIG. 215, the clasp has two flexible indicators 5350a, 5350b, positioned between side arms 5332 of the moveable arm 5330. Having two indicator arms 5350a, 5350b that are independently moveable with respect to each other, along the width of the moveable arm, can be used to indicate the proper rotational orientation of the clasp on the leaflet 42, 44. The flexible indicators can be part of the laser cut clasp or can be attached to the laser-cut clasp frame by welding or rivets or other known means.

FIG. 216 illustrates a side schematic view of the embodiment illustrated in FIG. 215. From the side view in the open configuration, only one flexible indicator is visible because both the flexible indicators, 5350a and 5350b are aligned with each other.

Figure 217:
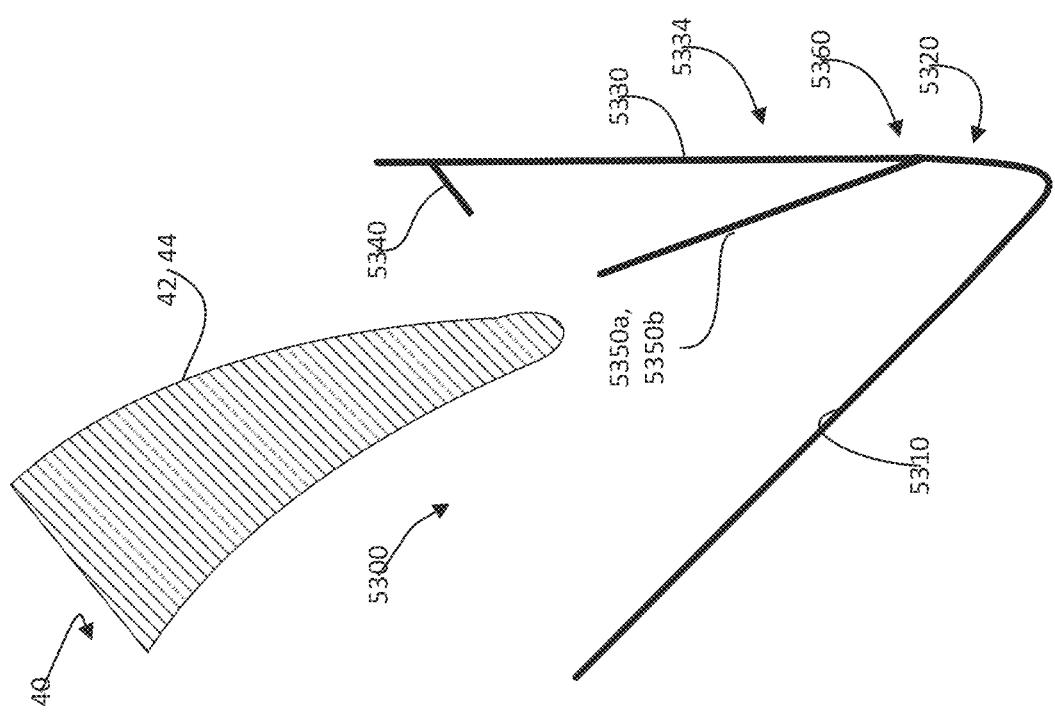

Referring now to FIGS. 217-220, the example clasp 5300 illustrated in FIGS. 215-216 is shown being deployed within a native valve 40 to secure an implantable device (not shown), such as the devices 100, 200, 300 described above, to one of the native leaflets 42, 44. Referring now to FIG. 217, the clasp 5300 is shown in an open condition with a native leaflet 42, 44 partially inserted into an opening of the clasp 5300 formed between the fixed and moveable arms 5310, 5330.

Figure 218:
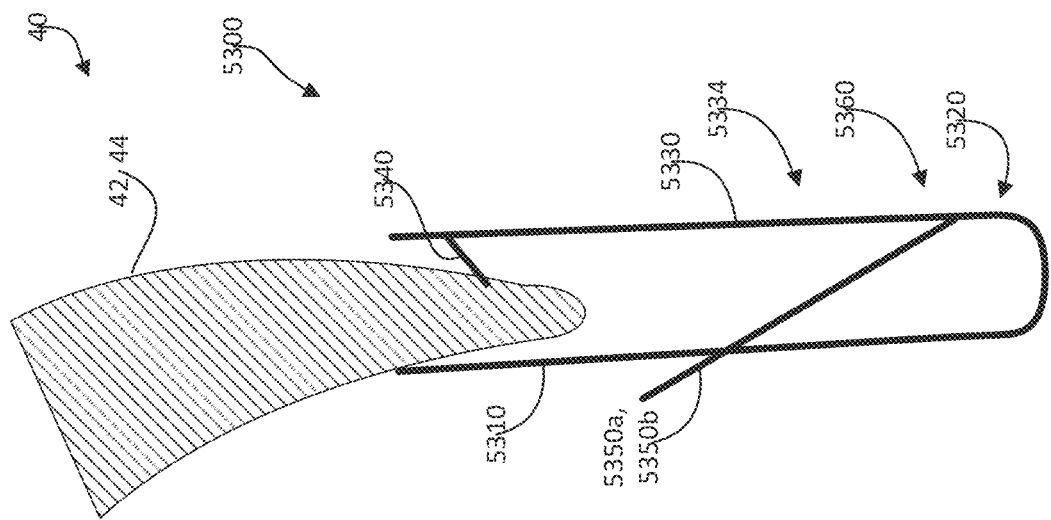
Figure 219:
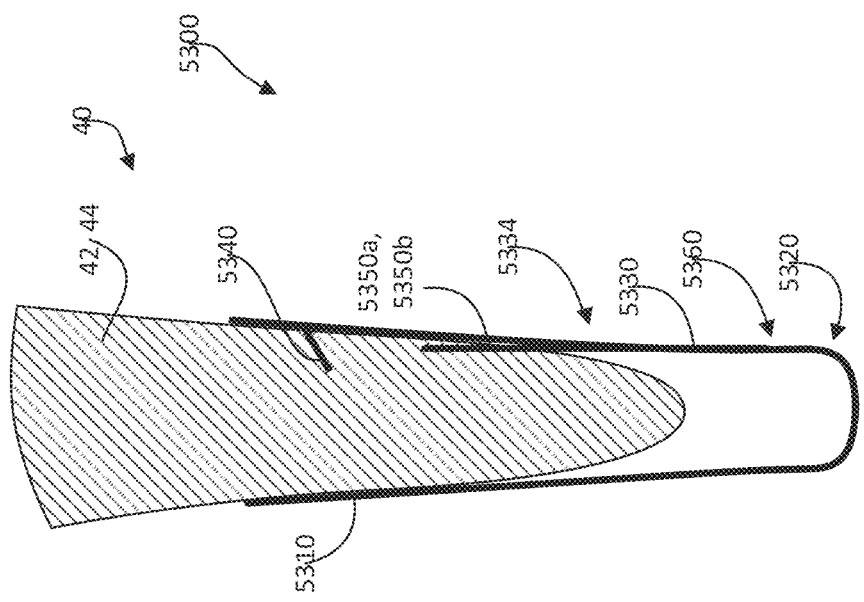

Referring now to FIG. 218, when the moveable arm 5330 is actuated to push the leaflet 42, 44 against the fixed arm 5310, the leaflet 42, 44 may contact a portion of the fixed arm 5310 without contacting either indicator arm 5350a, 5350b when the engagement depth of the leaflet 42, 44 is less than the minimum engagement depth. As can be seen in FIG. 219, the indicator arms 5350a, 5350b are moved by the pressure of the leaflet towards the moveable arm 5330. The indicator arms flex at the flex or hinge region 5360 of each indicator arm. The indicator arms can optionally have portions (not shown) that pass through the opening 5334 of the moveable arm to indicate to the operator that the leaflet is inserted into the clasp 5300 at or beyond the minimum engagement depth.

Referring now to FIG. 220, one indicator arm 5350a is moved by the pressure of the leaflet towards the moveable arm 5330. The second indicator arm 5350b has fallen past the fixed arm 5310 of the clasp to indicate that the leaflet is not positioned over that indicator arm 5350b. The first indicator arm 5350a can indicate that the leaflet is positioned sufficiently far enough in towards the flex or hinge region 5320 of the clasp, but the position of the second indicator arm 5350b indicates that the leaflet is not sufficiently engaged by the clasp because the entire width of the clasp has not engaged the leaflet. This can occur due to incorrect orientation of the clasp relative to the leaflet (i.e. the clasp is tilted or canted relative to the valve leaflet). The clasp can be reopened to reposition the clasp to obtain a proper positioning both as to the depth of the leaflet within the clasp and to ensure that the clasp is properly oriented relative to the leaflet tissue. The indicator arms can be detected by fluoroscopy or other imaging techniques. In the embodiments described herein, the indicator arms 5350a, 5350b can be integrated with the clasp, such as in the embodiments formed from a laser-cut sheet. However, the indicator arm can also be a separate piece that is fixed to the clasp in the example embodiments described herein. The indicator arm can be formed from another laser cut sheet having a thickness different than that of the clasp; i.e., the indicator arm can be thinner than the clasp arms to create an indicator that is more flexible than the remainder of the clasp. The indicator arm can be connected via rivets, welding, and/or any other technique known in the art to secure two elements together.

Referring now to FIGS. 155, 155A, 156-164, 164A, 164B, and 203-205, example actuation mechanisms are shown for actuating clasps (e.g., barbed clasps, clasps with other friction enhancing elements, plain clasps, etc.); in particular, clasps with at least two actuatable portions such as the clasps with indicator arms described above. These actuation mechanisms employ one or more actuation lines or sutures to open and close the components of the clasps described herein. The actuation lines are removably attached to the clasps so that the actuation lines can be withdrawn through the delivery device once the implantable device has been deployed.

Figure 155A:
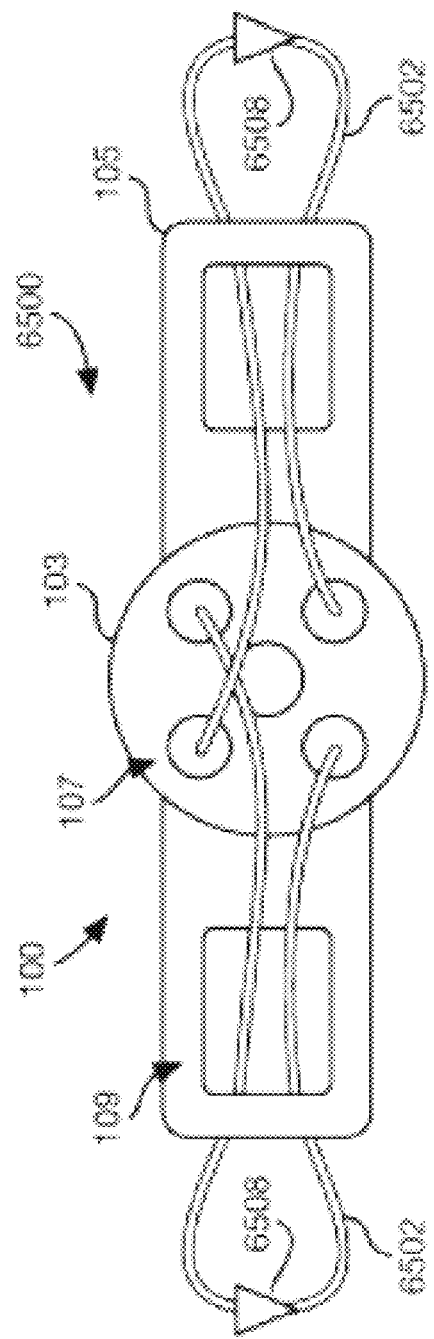
FIG. 155A shows an example actuation mechanism for use with implantable devices described herein.
Figure 164A:
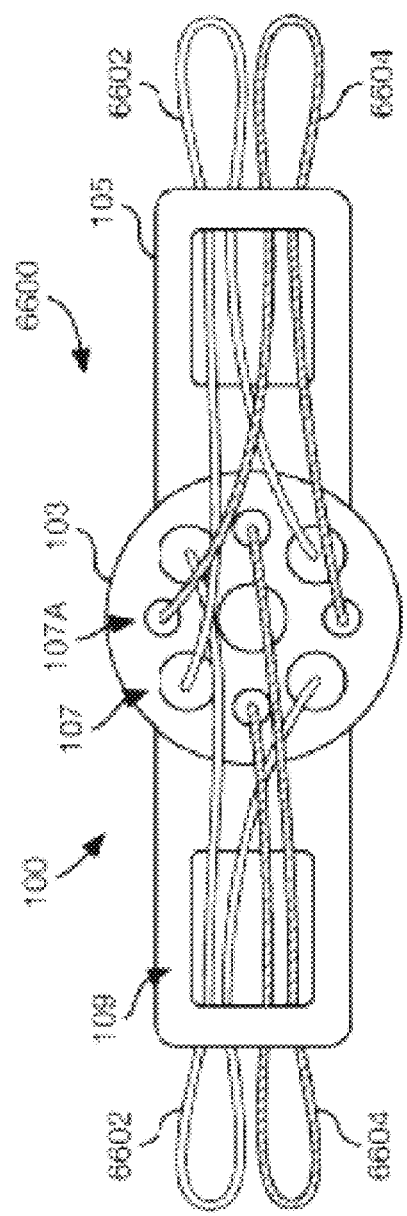
FIGS. 164A and 164B show example actuation mechanisms for use with implantable devices described herein.
Figure 164B:
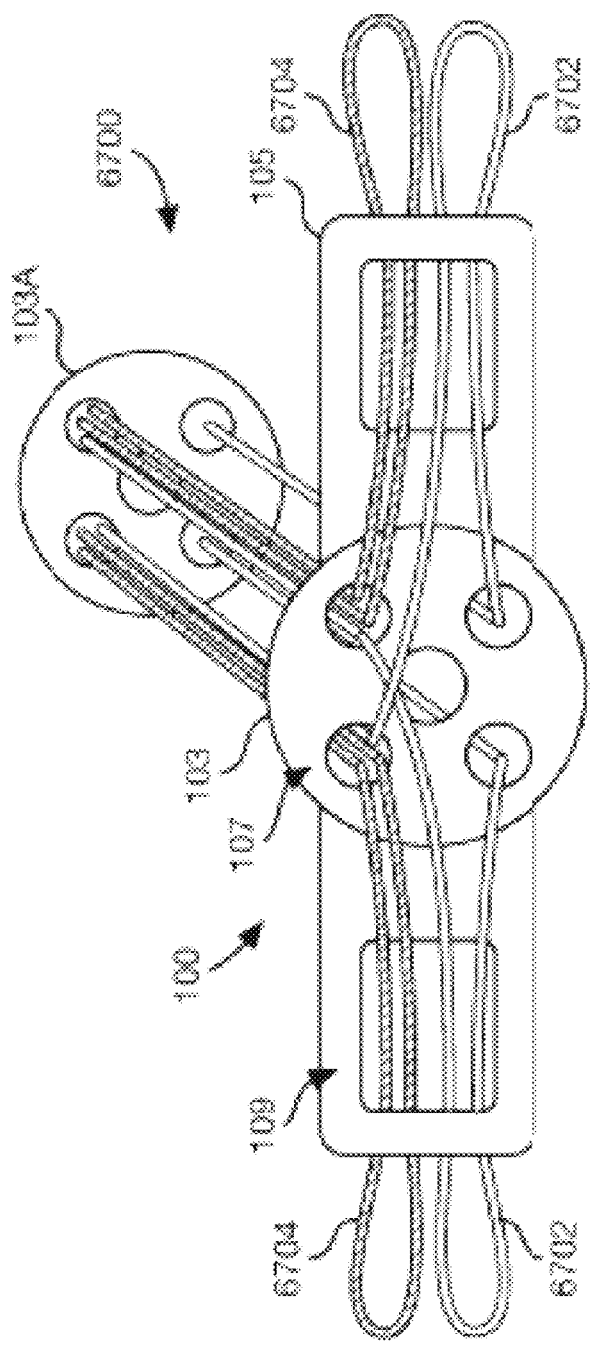

FIGS. 155A, 164A, and 164B illustrate delivery sheaths 102 with actuation lines for example actuation mechanisms for actuating clasps (e.g., barbed clasps, etc.) with at least two actuatable portions, such as the clasps with indicator arms described above. The delivery sheath 102 is connected to a collar or coupler 103 with moveable fingers 105 that couple to the device 100. The moveable fingers 105 are schematically illustrated in the outwardly spread or release configuration in FIGS. 155A, 164A, and 164B. In this condition, the device 100 is released from the collar or coupler 103. The actuation lines extend through lumens or openings 107 in the collar 103 and then through openings 109 in the moveable fingers 105 to engage the moveable arm 134, indicator arm 150, and/or loops attached to either or both of the moveable arm 134 and indicator arm 150.

Referring now to FIG. 155A, an actuation mechanism 6500 is shown extending through the collar 103 and the moveable fingers 105. The actuation mechanism 6500 includes actuation lines 6502 that each include a one-way catch 6508. The one-way catch 6508 can be a knot in the actuation line 6502 or can be an object attached to the actuation line 6502, such as, for example, a bead threaded onto the actuation line 6502 and affixed in place by wrapping the actuation line 6502 around the bead or with any other suitable mechanical or adhesive means. As can be seen in FIG. 155A, the one-way catch 6508 can have a conical shape so that it passes through a loop in a first direction and catches on the loop when moved in a second direction.

Referring now to FIGS. 164A and 164B, example actuation mechanisms are shown that use separate actuation lines to actuate the moveable and indicator arms, unlike the actuation mechanism shown in FIG. 155A that uses a single actuation line to actuate both the moveable clasp and indicator arms. Referring now to FIG. 164A, an example actuation mechanism 6600 is shown. The actuation mechanism 6600 includes first actuation lines 6602 and second actuation lines 6604. The first actuation lines 6602 are for actuating the moveable arms and the second actuation lines 6604 are for actuating the indicator arms. Each of the actuation lines 6602, 6604 can be separately actuated to control the moveable arms 134 and the indicator arms 150 of the device 100. As can be seen in FIG. 164A, the first and second actuation lines 6602, 6604 are shown extending through the collar 103 and the moveable fingers 105. The first actuation lines 6602 extend through the lumens 107 in the collar 103 and the second actuation lines 6604 extend through secondary lumens 107A in the collar 103. Each of the first and second actuation lines 6602, 6604 extends from one lumen 107, 107A, respectively, and returns through a different lumen 107, 107A, respectively. In some embodiments, the second actuation lines 6604 and the secondary lumens 107A have a smaller diameter than the first actuation lines 6602 and lumens 107, respectively.

Referring now to FIG. 164B, an example actuation mechanism 6700 is shown. The actuation mechanism 6700 includes first actuation line(s) 6702 and second actuation line(s) 6704. The first actuation line(s) 6702 are for actuating the moveable arms (not shown) and the second actuation line(s) 6704 are for actuating the indicator arms (not shown). Each of the actuation lines 6702, 6704 can be separately actuated to control the moveable arms 134 and the indicator arms 150 of the device 100. As can be seen in FIG. 164B, the first and second actuation lines 6702, 6704 are shown extending through the collar 103 and the moveable fingers 105. Unlike the collar 103 of FIG. 164A, the collar 103 of FIG. 225 does not have secondary lumens 107A. Thus, each of the first actuation line(s) 6702 extends from one lumen 107 and returns through a different lumen 107, while the second actuation line(s) 6704 extend from one lumen 107 alongside the first actuation line(s) 6702. In some embodiments, the second actuation line(s) 6704 have a smaller diameter than the first actuation line(s) 6702. In some embodiments, the actuation lines 6702, 6704 also extend through a secondary collar 103A and are pulled from beyond the secondary collar 103A so that friction between the actuation lines 6702, 6704 is reduced.

Referring now to FIGS. 203-205, actuation mechanisms using a single actuation line to actuate both the moveable and indicator arms are shown on device 100. For example, the embodiment of FIG. 155A can optionally be used in the embodiment of FIGS. 203-205. The device 100 includes clasps 130 each having a fixed arm 132 and a moveable arm 134. The claps 130 can include barbs, other friction-enhancing elements, etc. or optionally, not include these. The clasps 130 shown in FIGS. 155-160 also include an indicator arm 150, such as the indicator arms described herein. The actuation mechanisms described below are used to actuate the moveable arm 134 and indicator arm 150 of the clasps 130. The components of the clasps 130 are shown in an open position on the left side of the device 100 to clearly illustrate the relationship between the components (the indicator is partially open, so that it is visible), while the clasps 130 on the right side of the device 100 are shown in various stages of actuation.

Referring now to FIGS. 203-205, the actuation mechanism 6500 is shown attached to the device 100, which can be the device illustrated and described in FIGS. 143-154, having suture holes positioned between a flexible bend and a barbed end of the moveable arm. The actuation mechanism 6500 includes a single actuation line 6502 on each side of the device, extending from the delivery sheath 102, through a first suture hole 1431 positioned on the moveable arm, a second suture hole 1433 positioned on the indicator arm 4450, and returning into the delivery sheath 102. The first and second suture holes 1431, 1433 are through or attached to the moveable arm 134 and indicator arm 150, respectively. The first suture hole 1431 is near a midpoint of the moveable arm 134. The second suture hole 4452 is near the end of the indicator arm 150 in the example illustrated by FIGS. 203-205. The actuation line 6502 and the suture holes 1431, 1433 can be formed from sutures, wires, or the like. In some embodiments, the suture holes are integrally formed with a cover that covers the clasps 130 and coaption element 110.

Still referring to FIGS. 203-205, in one example embodiment, a one-way catch or stop 6508 of the actuation line 6502 is unable to pass through the hole or loop 1431 while being able to pass through the hole or loop loop 1431 (See FIG. 155A). The optional one-way catch 6508 can be a knot in the actuation line 6502 or can be an object attached to the actuation line 6502, such as, for example, a bead threaded onto the actuation line 6502 and affixed in place by wrapping the actuation line 6502 around the bead or with any other suitable mechanical or adhesive means. In some embodiments, the one-way catch 6508 has a conical shape so that it passes through the first hole or loop 1431 in a first direction and catches on the first hole or loop 1431 when moved in a second direction. Consequently, the actuation line 6502 can be pulled so that the one-way catch 6508 engages the first hole or loop 1431 to actuate the moveable arm.

Referring now to FIG. 203, the actuation line 6502 is relaxed on the right side of the device 100, and the clasp 130 on the right side is shown in a closed position. The clasp 130 is biased in a closing direction so that the clasp 130 will close when there is an absence of tension on the actuation lines 6502.

Referring now to FIG. 204, tension is applied to the actuation line 6502 to actuate the moveable arm 134. This is done by pulling on the first end 6510 of the actuation line 6502 until the one-way catch 6508 engages the first hole or loop 1431. The pulling force applied to the actuation line 6502 is transferred to the first hole or loop 1431 via the one-way catch 6508 to cause the moveable arm 134 to open from the closed position shown in FIG. 203 to the open position shown in FIG. 204.

Referring now to FIG. 205, tension is maintained on the first end of the actuation line 6502 to maintain the moveable arm 134 in the open position. Tension is then applied to the second end of the actuation line 6502 to cause the length of the loop of actuation line 6502 to shorten and to pull on the second moveable hole or loop 1431 of the indicator arm 150 to cause the indicator arm 150 to open from the closed position shown in FIG. 204 to the open position shown in FIG. 205.

Figure 222:
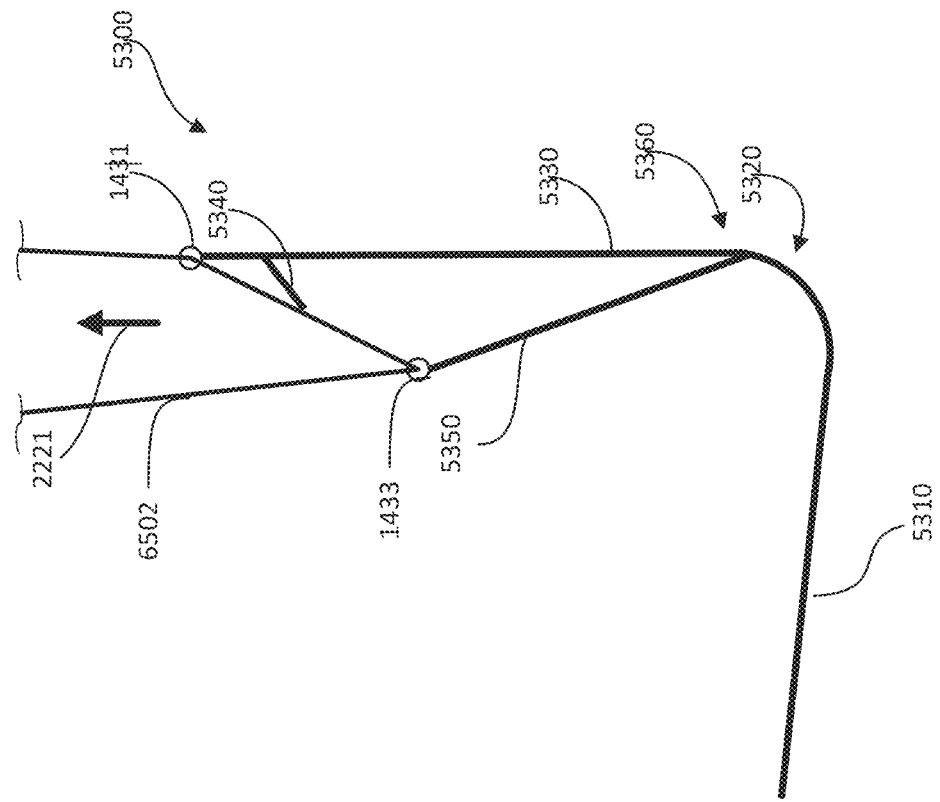
FIGS. 221-222 show schematic views of an example embodiment of a clasp having an indicator and actuatable by a single suture line.
Figure 221:
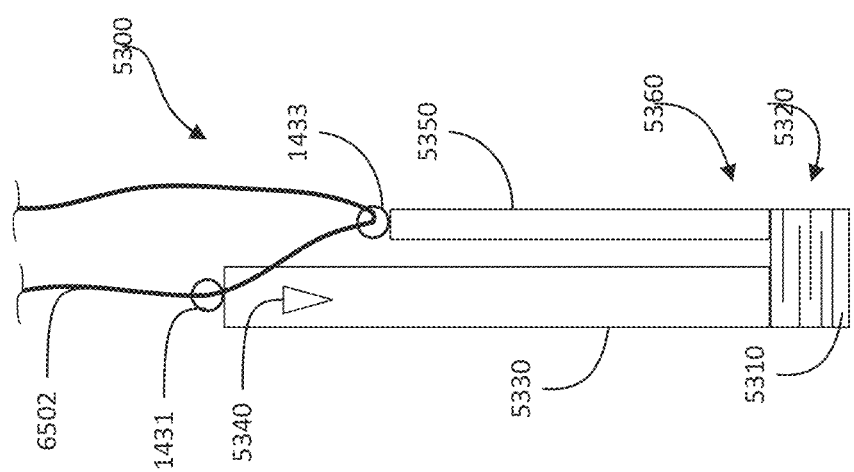

Referring now to FIGS. 221-222, an example clasp 3500 (illustrated as a barbed clasp) for use in implantable prosthetic devices, such as devices 100, 200, 300 described above, is shown. The clasp 5300 is configured to capture the native tissue when the implantable prosthetic device—e.g., any device described in the present application—is attached to the native tissue. Like the clasps described above, the clasp 5300 includes a fixed arm 5310, a flex or hinge portion 5320, and a moveable arm 5330 having a barbed portion 5340 (though other friction-enhancing portions can be used). The clasp 5300 also includes an indicator arm 5350 adjacent to the moveable arm 5330 and extending from an indicator flex or hinge portion 5360. The clasp 5300 can be used in any of the implantable prosthetic devices of the present application and can include any of the features or combinations of features of the other clasps described herein.

The clasp 5300 of FIGS. 221-225 also includes a first suture hole, eyelet, loop, or ring 1431 positioned at the end of moveable arm 5330 and a second suture hole, eyelet, loop, or ring 1433 positioned at the end of the indicator arm 5350. A single actuation line 6502 can be threaded through both the first and second suture holes, eyelets, loops, or rings 1431, 1433. The single actuation line 6502 can be used to open and close both the moveable arm and the indicator arm. In one example embodiment, the indicator arm 5350 closes before the moveable clasp arm 5330 and the moveable clasp arm opens before the indicator arm. In an example embodiment, the moveable arm and indicator arm can be opened simultaneously. In an example embodiment, the indicator arm partially closes before the moveable clasp arm begins to close and the moveable clasp arm partially opens before the indicator arm begins to open. The actuation line can be a suture, thread, wire, a biocompatible filament, etc. that can be threaded through the suture holes 1431, 1433. A single actuation line can be used to open and close the moveable arm and indicator arm(s) on any of the example embodiments described herein. In one example embodiment, the single actuation line does not include a one-way knot, stop, cone, or other structure.

Figure 223:
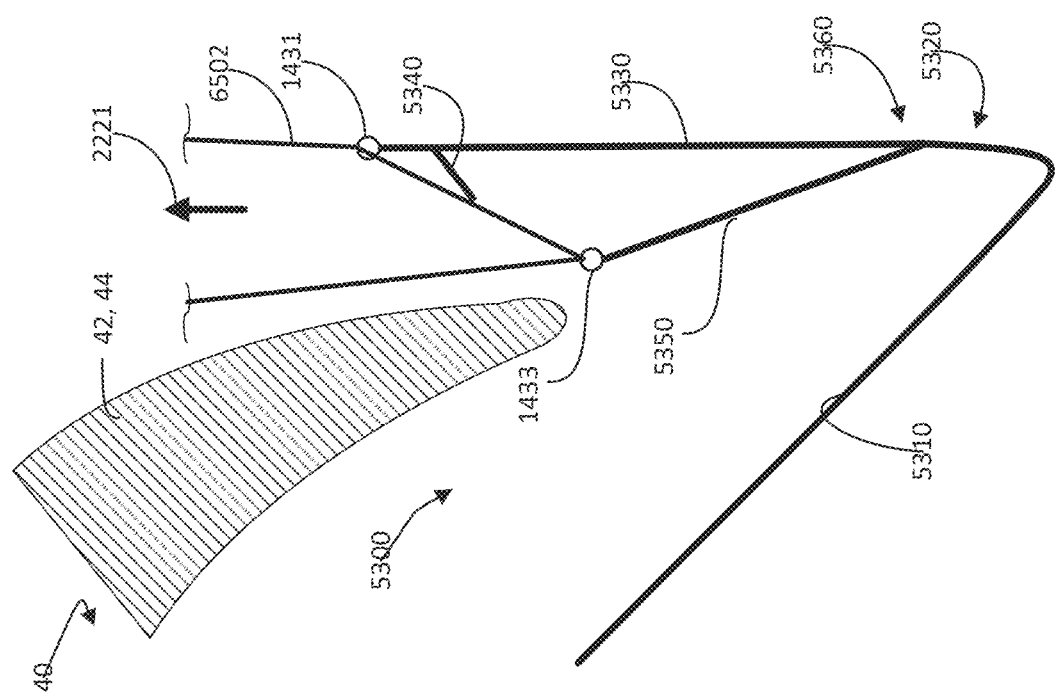
FIGS. 223-225 show the example clasp of FIGS. 221-222 being deployed by using a single actuation line to engage a leaflet of a native valve.
Figure 224:
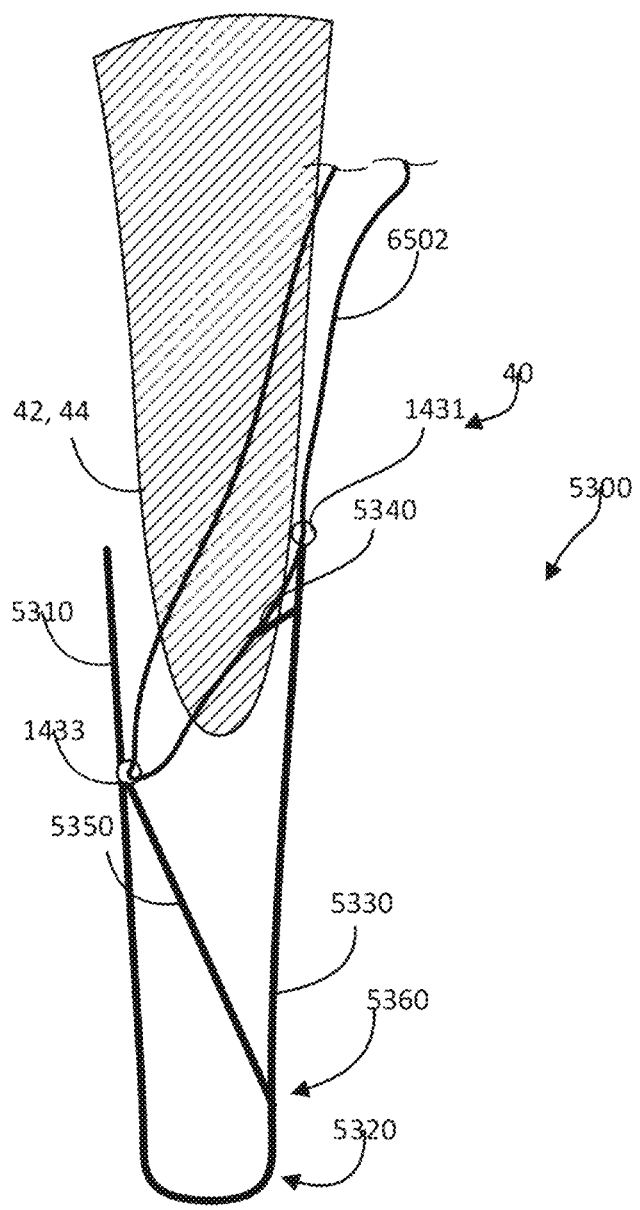
Figure 225:
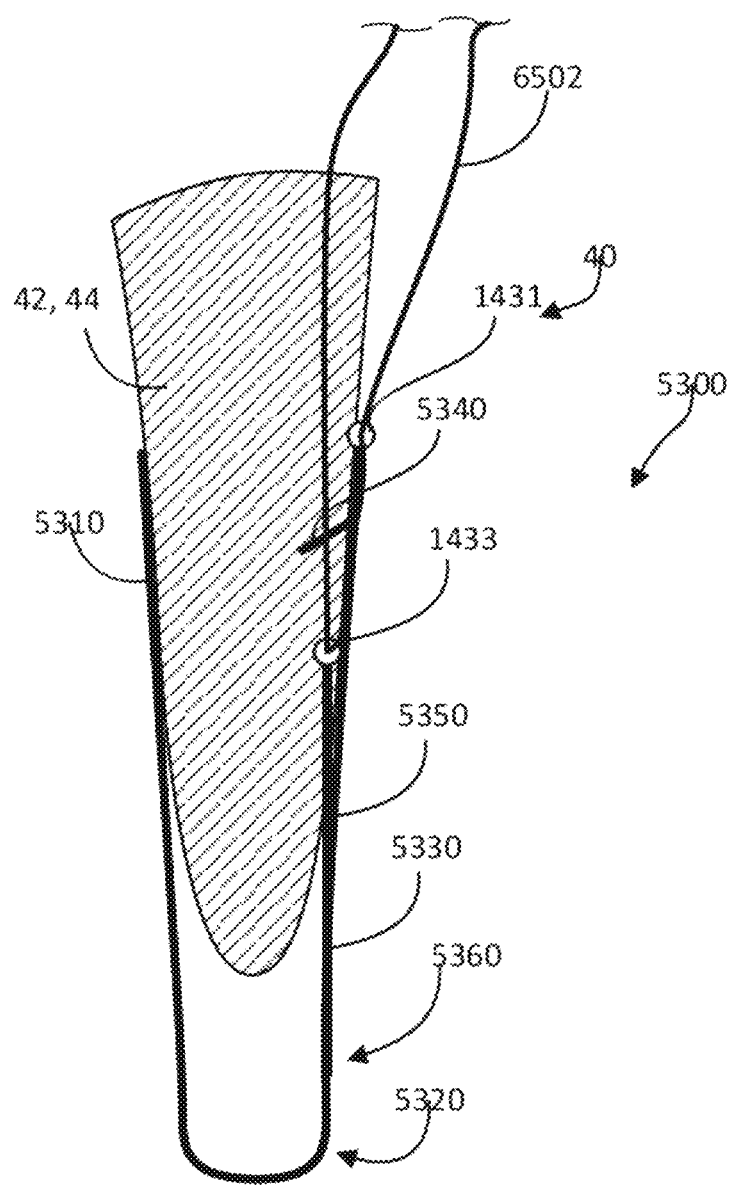

Referring now to FIGS. 223-225, the example clasp 5300 is shown being deployed within a native valve 40 to secure an implantable device (not shown), such as the devices 100, 200, 300 described above, to one of the native leaflets 42, 44. Referring now to FIG. 223, the clasp 5300 is shown in an open condition with a native leaflet 42, 44 partially inserted into an opening of the clasp 5300 formed between the fixed and moveable arms 5310, 5330. The indicator arm 5350 and moveable arm 5330 are in a raised (or open) position due to the tension on the suture line 6502 caused by pulling both ends of the suture line towards the operator in a direction indicated by arrow 2221. To determine whether the leaflet 42, 44 has reached the desired engagement depth, the indicator arm 3550 can be actuated by reducing tension on the actuation line 6502.

Referring now to FIG. 224, the tension on the actuation line 6502 has been released, and the clasp is shown in a closed configuration, closed on the leaflet 42, 44. The indicator arm and moveable arm are actuated (i.e., lowered in the direction towards the fixed arm). Because the leaflet 42, 44 is inserted into the opening of the clasp 5300 about half way between the barbed portion 5340 and the flex or hinged portion 5320 and is not inserted far enough into the clasp to overlap with the length of the indicator arm 5350, the indicator arm 3550 does not engage the leaflet 42, 44. Instead, the indicator arm swings toward the fixed arm 3510. The indicator arm's position is visible via imaging devices used to monitor implantation and deployment of the prosthetic device. The actuation line can be pulled and released multiple times to open and close the clasp and/or indicator, so that the leaflet can be repositioned if needed.

Referring now to FIG. 225, the clasp is closed on the leaflet 42, 44, by release of the tension on actuation line 6502, and the leaflet is positioned deep enough into the clasp 5300 such that it overlaps with the indicator arm 5350. The barb 5340 on the moveable arm 5330 has pierced the native leaflet. The indicator arm rests on the leaflet tissue, and the leaflet prevents the indicator arm from moving all the way toward the fixed arm 5310 of the clasp. Although the indicator arm as illustrated in FIGS. 221-225 does not have a barb on it, in some example embodiments, it can have a barb to further secure the leaflet in place.

As has been described above, because of the arrangement of the first and second suture holes 1431, 1433 and the one-way catch 6508 the moveable and indicator arms 134, 150 can be opened in sequence with a single looped actuation line. In an example embodiment, the one-way catch is omitted and the moveable and indicator arms 134, 150 are opened in sequence due to the combined effect of the relative flexibility of the flex or hinge portions of the moveable and indicator arms 134, 150 and the relative distances of the holes or loops 1431, 1433 to the flex or hinge portions of the moveable and indicator arms 134, 150. The moveable and indicator arms 134, 150 are closed in the reverse sequence when tension on the actuation line 6502 is reduced. That is, the indicator arm 150 closes first, followed by the moveable arm 134.

Referring now to FIGS. 155-160, actuation mechanisms using a single actuation line to actuate both the moveable and indicator arms are shown on device 100. For example, the embodiment of FIG. 155A can optionally be used in the embodiment of FIGS. 155—The device 100 includes clasps 130 each having a fixed arm 132 and a moveable arm 134. The clasps 130 shown in FIGS. 155-160 also include an indicator arm 150, such as the indicator arms described herein. The actuation mechanisms described below are used to actuate the moveable arm 134 and indicator arm 150 of the clasps 130. The components of the clasps 130 are shown in an open position on the left side of the device 100 to clearly illustrate the relationship between the components, while the clasps 130 on the right side of the device 100 are shown in various stages of actuation.

Referring now to FIGS. 155-157, the actuation mechanism 6500 is shown attached to the device 100. The actuation mechanism 6500 includes actuation lines 6502 extending at a first end 6510 from the delivery sheath 102, through a first loop 6504, a second loop 6506, and returning into the delivery sheath 102 at a second end 6512. The first and second loops 6504, 6506 are attached to the moveable arm 134 and indicator arm 150, respectively. The first loop 6504 is attached near the end of the moveable arm 134. The second loop 6506 is attached near the middle of the indicator arm 150. The actuation lines 6502 and the loops 6504, 65, can be formed from sutures, wires, or the like. In some embodiments, the loops 6504, 6506, are integrally formed with a cover that covers the clasps 130 and coaption element 110.

The one-way catch 6508 of the actuation lines 6502 is unable to pass through the first loop 6504 while being able to pass through the second loop 6506. The one-way catch 6508 can be a knot in the actuation line 6502 or can be an object attached to the actuation line 6502, such as, for example, a bead threaded onto the actuation line 6502 and affixed in place by wrapping the actuation line 6502 around the bead or with any other suitable mechanical or adhesive means. In some embodiments, the one-way catch 6508 has a conical shape so that it passes through the first loop 6504 in a first direction and catches on the first loop 6504 when moved in a second direction. Consequently, the actuation line 6502 can be pulled so that the one-way catch 6508 engages the first loop 6504 to actuate the moveable arm.

Referring now to FIG. 155, the actuation line 6502 is relaxed on the right side of the device 100, and the clasp 130 on the right side is shown in a closed position. The clasp 130 is biased in a closing direction so that the clasp 130 will close when there is an absence of tension on the actuation lines 5102.

Referring now to FIG. 156, tension is applied to the actuation line 6502 to actuate the moveable arm 134. This is done by pulling on the first end 6510 of the actuation line 6502 until the one-way catch 6508 engages the first loop 6504. The pulling force applied to the actuation line 6502 is transferred to the first loop 6504 via the one-way catch 6508 to cause the moveable arm 134 to open from the closed position shown in FIG. 155 to the open position shown in FIG. 156.

Referring now to FIG. 157, tension is maintained on the first end 6510 of the actuation line 6502 to maintain the moveable arm 134 in the open position. Tension is then applied to the second end 6512 of the actuation line 6502 to cause the length of the loop of actuation line 6502 to shorten and to pull on the second moveable loop 6506 attached to the indicator arm 150 to cause the indicator arm 150 to open from the closed position shown in FIG. 156 to the open position shown in FIG. 157.

As has been described above, because of the arrangement of the first and second moveable loops 6504, 6506 and the one-way catch 6508 the moveable and indicator arms 134, 150 can be opened in sequence with a single looped actuation line. The moveable and indicator arms 134, 150 are closed in the reverse sequence when tension on the actuation line 6502 is reduced. That is, the indicator arm 150 closes first, followed by the moveable arm 134. Similar concepts may be applied to clasps having two or more moveable portions, such as the clasp 2200 described above. In some embodiments, a plurality of catches of different sizes may interact with a plurality of loops of different sizes to control the opening and closing of a plurality of moveable portions of a clasp.

Referring now to FIGS. 158-160, the device 100 is shown with an actuation mechanism 6800. The actuation mechanism 6800 includes actuation lines 6802 extending at a first end 6810 from the delivery sheath 102, through a first moveable loop 6804, a first stationary loop 6814, a second stationary loop 6816, a second moveable loop 6806, and then back through the second stationary loop 6816, the first stationary loop 6814, the first moveable loop 6804, and returning into the delivery sheath 102 at a second end 6812. The first and second moveable loops 6804, 6806 are attached to the moveable arm 134 and indicator arm 150, respectively. The first loop 6804 is attached near the end of the moveable arm 134. The second loop 6806 is attached near the middle of the indicator arm 150.

In some embodiments, the first and second stationary loops 6814, 6816 are attached to the coaption element 110 of the device 100. The first stationary loop 6814 is attached near the proximal end of the coaption element 110. The second stationary loop 6816 is attached near the middle of the coaption element 110. The actuation lines 6802 and the loops 6804, 6806, 6814, 6816 can be formed from sutures, wires, or the like. In some embodiments, the loops 6804, 6806, 6814, 6816 are integrally formed with a cover that covers the clasps 130 and coaption element 110.

Referring now to FIG. 158, the actuation line 6802 is relaxed on the right side of the device 100, and the clasp 130 on the right side is shown in a closed position. The clasp 130 is biased in a closing direction so that the clasp 130 will close when there is an absence of tension on the actuation lines 6802.

Referring now to FIG. 159, tension is applied to the actuation line 6802 to actuate the moveable arm 134. This may be done by pulling on one end 6810, 6812 of the actuation line 6802 while holding the other end 6812, 6810 so that the length of the actuation line 6802 shortens or can be done by pulling on both ends 6810, 6812 simultaneously. As force is applied to the actuation line 6802, the actuation line 6802 is pulled through the moveable loops 6804, 6806 attached to the moveable arm 134 and indicator arm 150, respectively, and the stationary loops 6814, 6816 attached to the coaption element 110. In embodiments where both ends 6810, 6812 are pulled, the actuation line 6802 moves through the first moveable loop 6804 and does not move through the second moveable loop 6806. That is, the second moveable loop 6806 is located at the midpoint of the actuation line 6802 such that tension applied to both ends 6810, 6812 is transmitted to the second moveable loop 6806. Though an opening force is exerted on both of the first and second moveable loops 6804, 6806 by the actuation line 6802, the moveable arm 134 opens before the indicator arm 150 because of the greater mechanical advantage provided by the location of the first moveable loop 6804 near the end of the moveable arm 134. The routing of the actuation lines 6802 through the first moveable loop 6804 and the first stationary loop 6814 operates as a pulley that provides additional mechanical advantage. Thus, the moveable arm 134 moves from the closed position shown in FIG. 158 to the open position shown in FIG. 159.

Referring now to FIG. 160, further tension is applied to one or both ends 6810, 6812 of the actuation line 6802 to cause the length of the loop of actuation line 6802 to shorten further and continue to pull on the first and second moveable loops 6804, 6806 and the first and second stationary loops 6814, 6816. The pulling force exerted by the actuation line 6802 is focused on the second moveable loop 6806 because the moveable arm 134 has already been moved to the open position, thereby causing the indicator arm 150 to open from the closed position shown in FIG. 159 to the open position shown in FIG. 160.

As has been described above, because of the arrangement of the first and second moveable loops 6804, 6806 at different distances from the flex, hinge, or pivot points of the moveable and indicator arms 134, 150, respectively, the opening of the moveable and indicator arms 134, 150 can be opened in sequence. The moveable and indicator arms 134, 150 are closed in the reverse sequence when tension on the actuation line 6802 is reduced. That is, the indicator arm 150 closes first, followed by the moveable arm 134.

The left sides of FIGS. 158-160 illustrate an embodiment where the moveable arm 134 and indicator arm 150 do not open and close in sequence. Rather, the force of the actuation line is shared between the moveable arm 134 and the indicator arm 150 and the movable arm 134 and indicator arm 150 move at different rates. The relative rate at which the moveable arm 134 and indicator arm 150 open and close depends on the spring force of the moveable arm 134, the spring force of the indicator arm 150, and the positions of the loops 6814, 6816, 6806, and 6804.

In the embodiment illustrated by the left side of FIGS. 158-160, the moveable arm 134 opens more quickly than the indicator arm 150, but the indicator arm opens to some degree as the moveable arm opens. In this embodiment, the indicator arm 150 closes more quickly than the movable arm 134, but the moveable arm closes to some degree as the indicator arm closes.

In the embodiment illustrated by the right side of FIGS. 158-160, the spring force of the moveable arm 134, the spring force of the indicator arm 150, and the positions of the loops 6814, 6816, 6806, and 6804 are selected such that the moveable arm 134 opens completely before the indicator arm 150 begins to open. In this embodiment, the indicator arm 150 closes completely before the movable arm 134 begins to close.

The opening and closing sequence of the moveable and indicator arms 134, 150 can be changed by altering the spring force of the flex or hinge portions of the moveable and indicator arms 134, 150 and by changing the locations of the first and second loops 6804, 6806. That is, in certain embodiments, the indicator arm 150 can be caused to open first by moving the second loop 6806 to the end of the indicator arm 150 and the first loop 6804 closer to the coaption element 110, while also increasing the spring force applied to the moveable arm 134 and decreasing the spring force applied to the indicator arm 150. Optionally, the actuation line 6802 could be routed through the second moveable loop 6806 before routing through the second stationary loop 6816 to provide a mechanical advantage when opening the indicator arm 150. Similar concepts may be applied to clasps having two or more moveable portions, such as the clasp 2200 described above.

Referring now to FIGS. 161-163, the device 100 is shown with an actuation mechanism 6900. The actuation mechanism 6900 includes actuation lines 6902 extending at a first end 6910 from the delivery sheath 102, passing through first and second loops 6904, 6906, and returning into the delivery sheath 102 at a second end 6912. The first and second loops 6904, 6906 are attached to the moveable arm 134 and indicator arm 150, respectively. The first loop 6904 is attached near the end of the moveable arm 134. The second loop 6906 is attached near the middle of the indicator arm 150. The actuation lines 6902 and the loops 6904, 6906 can be formed from sutures, wires, or the like. In some embodiments, the loops 6904, 6906 are integrally formed with a cover that covers the clasps 130.

Referring now to FIG. 161, the actuation line 6902 is relaxed on the right side of the device 100, and the clasp 130 on the right side is shown in a closed position. The clasp 130 is biased in a closing direction so that the clasp 130 will close when there is an absence of tension on the actuation lines 6902.

Referring now to FIG. 162, tension is applied to the actuation line 6902 to actuate the moveable arm 134. This may be done by pulling on one end 6910, 6912 of the actuation line 6902 while holding the other end 6912, 6910 so that the length of the actuation line 6902 shortens. For example, a pulling force can be applied to the first end 6910 of the actuation line 6902 while the second end 6912 is held in a fixed position. As force is applied to the actuation line 6902, the actuation line 6902 pulls against the loops 6904, 6906 attached to the moveable arm 134 and indicator arm 150, respectively. Though an opening force is exerted on both of the first and second loops 6904, 6906 by the actuation line 6902, the moveable arm 134 opens before the indicator arm 150 because of the greater mechanical advantage provided by the location of the first loop 6904 near the end of the moveable arm 134. Thus, the moveable arm 134 moves from the closed position shown in FIG. 232 to the open position shown in FIG. 162.

Referring now to FIG. 163, further tension is applied to the first end 6910 of the actuation line 6902 to cause the length of the loop of actuation line 6902 to shorten and continue to pull on the loops 6904, 6906 attached to the moveable arm 134 and indicator arm 150, respectively. The pulling force exerted by the actuation line 6902 is focused on the second loop 6906 because the moveable arm 134 has already been moved to the open position, thereby causing the indicator arm 150 to open from the closed position shown in FIG. 162 to the open position shown in FIG. 163.

The left sides of FIGS. 161-163 illustrate an embodiment where the moveable arm 134 and indicator arm 150 do not open and close in sequence. Rather, the force of the actuation line is shared between the moveable arm 134 and the indicator arm 150 and the movable arm 134 and indicator arm 150 move at different rates. The relative rate at which the moveable arm 134 and indicator arm 150 open and close depends on the spring force of the moveable arm 134, the spring force of the indicator arm 150, and the positions of the loops 6806, and 6804.

In the embodiment illustrated by the left side of FIGS. 161-163, the moveable arm 134 opens more quickly than the indicator arm 150, but the indicator arm opens to some degree as the moveable arm opens. In this embodiment, the indicator arm 150 closes more quickly than the movable arm 134, but the moveable arm closes to some degree as the indicator arm closes.

In the embodiment illustrated by the right side of FIGS. 161-163, the spring force of the moveable arm 134, the spring force of the indicator arm 150, and the positions of the loops 6806 and 6804 are selected such that the moveable arm 134 opens completely before the indicator arm 150 begins to open. In this embodiment, the indicator arm 150 closes completely before the movable arm 134 begins to close.

As has been described above, because of the arrangement of the loops 6904, 6906 at different distances from the flex, hinge, or pivot points of the moveable and indicator arms 134, 150, respectively, the opening of the moveable and indicator arms 134, 150 can be opened in sequence. The moveable and indicator arms 134, 150 are closed in the reverse sequence when tension on the actuation line 6902 is reduced. That is, the indicator arm 150 closes first, followed by the moveable arm 134. The opening and closing sequence of the moveable and indicator arms 134, 150 can be changed by altering the spring force of the flex or hinge portions of the moveable and indicator arms 134, 150 and by changing the locations of the first and second loops 6904, 6906. That is, in certain embodiments, the indicator arm 150 can be caused to open first by moving the second loop 6906 to the end of the indicator arm 150 and the first loop 6904 closer to the coaption element 110 while also increasing the spring force applied to the moveable arm 134 and decreasing the spring force applied to the indicator arm 150. Similar concepts may be applied to clasps having two or more moveable portions, such as the clasp 2200 described above.

Referring now to FIGS. 164-166, the device 100 is shown with an actuation mechanism 7000. In the example illustrated by FIGS. 164-166, the moveable clasp arms and the indicator arms are each independently controllable by a separate actuation line 7002. In one example embodiment, the embodiments of FIG. 164A or 164B can be used in the embodiment of FIGS. 164-166. The illustrated actuation mechanism 7000 includes an actuation line 7002 extending at a first end 7010 from the delivery sheath 102, passing through an actuation loop 7004 attached to one of the moveable or indicator arms 134, 150, forming a loop 7006 around the actuation element 112, passing through the loop 7004 again, and returning into the delivery sheath 102 at a second end 7012. The actuation lines 7002 and the loops 7004 can be formed from sutures, wires, or the like. In some embodiments, the loops 7004 are integrally formed with a cover that covers the clasps 130. Forming the loop 7006 around the actuation element 112 allows the actuation line 7002 to be decoupled from the moveable or indicator arms 134, 150 without releasing the first or second end 7010, 7012 and pulling the entire actuation line 7002 through the delivery sheath 102 from one end. That is, the actuation line 7002 can be disengaged from the moveable or indicator arm 134, 150 by retracting the actuation element 112 and withdrawing both the first and second ends 7010, 7012 of the actuation line 7002 a short distance to retract the loop 7006 into the delivery sheath 102.

Referring now to FIG. 164, the actuation element 112 is secured to the cap 114 and the loops 7006 of the actuation lines 7002 are circled around the actuation element 112 between the coaption element 110 and the delivery sheath 102. To decouple the actuation lines 7002 from the device 100, the actuation element 112 is retracted into the delivery sheath 102 to form a gap between the actuation element 112 and the coaption element 110, as can be seen in FIG. 165.

The retraction of the actuation element 112 releases all of the retraction lines 7002 at once. When the retraction lines are released, all of the indicating arms 150 and moveable arms 134 close due to the closing spring force of the clasps.

Referring to FIG. 165, both ends 7010, 7012 of the actuation lines 7002 are then withdrawn into the delivery sheath 102, causing the loops 7006 in the actuation lines 7002 to slide downward and off of the actuation element 112. Referring now to FIG. 166, further retraction of the actuation lines 7002 disengages the actuation lines 7002 from the loops 7004 on the moveable and indicator arms 134, 150 so that the device 100 is decoupled from the delivery sheath 102. The actuation mechanism 7000 can be used with any of the clasps and implantable prosthetic devices described herein. Similar concepts can also be applied to other actuation mechanisms described herein to reduce the time and effort required to decouple actuation lines from the implantable prosthetic device.

Figure 193:
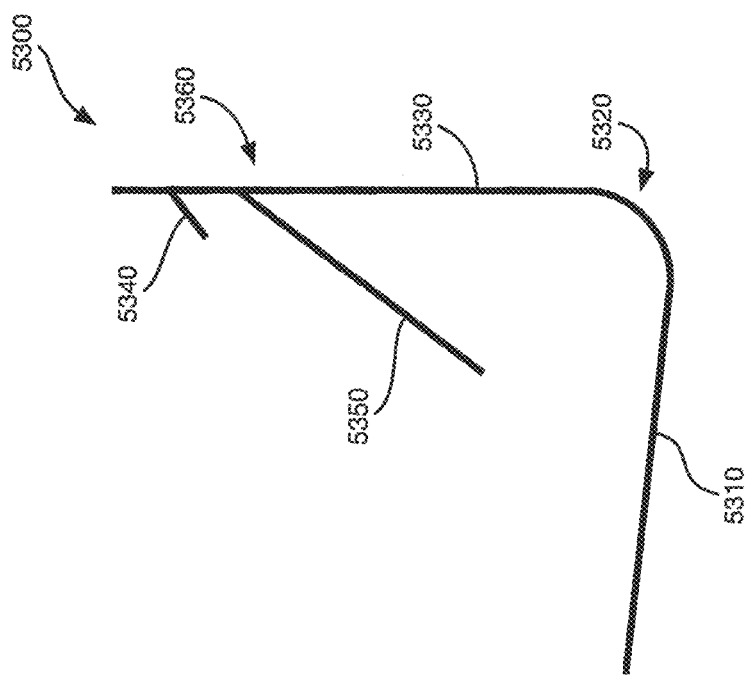
FIGS. 192-193 show schematic views of an example embodiment of a clasp having an indicator.
Figure 192:
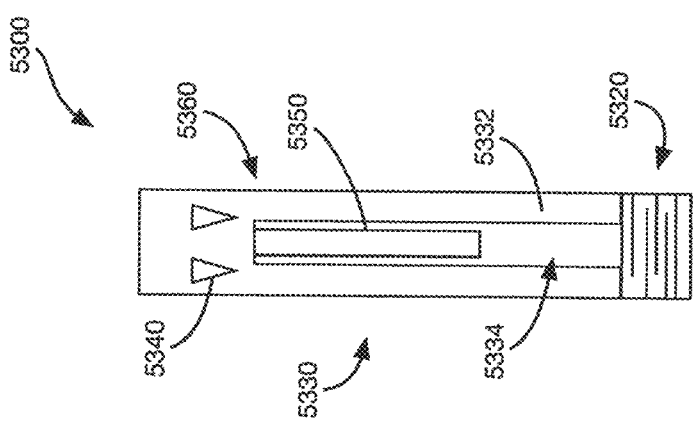

Referring now to FIGS. 192-193, an example clasp 5300 for use in implantable prosthetic devices, such as devices 100, 200, 300 described above, is shown. Like the clasp 3500 described above, the clasp 5300 includes a fixed arm 5310, a flex or hinge portion 5320, and a moveable arm 5330 having a barbed portion 5340. The clasp 5300 also includes an indicator arm 5350 extending from an indicator flex or hinge portion 5360 arranged toward the distal end of the moveable arm 5330. The indicator arm 5350 need not be actuated separately from the moveable arm 5330. The indicator flex or hinge portion 5360 can be formed from a portion of the indicator arm. The clasp 5300 can be used in any of the implantable prosthetic devices of the present application and can include any of the features or combinations of features of the clasps described herein.

The indicator arm 5350 can be moved relative to the moveable arm 5330 to facilitate detection of the depth of engagement of the native leaflet between the moveable arm 5330 and the fixed arm 5310 of the clasp 5300. The moveable arm 5330 is optionally formed in a hoop or loop shape having two side arms 5332 surrounding a central opening 5334 that extends from the flex or hinge portion 5320 to the barbed portion 5340 of the moveable arm 5330 as illustrated. In some embodiments, the moveable arm 5330 is not hoop shaped and the indicator arm 5350 is disposed next to a single moveable arm 5330. The indicator arm 5350 is disposed in the central opening 5334 between the two side arms 5332. In the illustrated example, because the moveable arm 5330 spans the full width of the clasp 5300, the barbed portion 5340 of the moveable arm 5330 is as wide as the clasp 5300 so that a larger area of the barbed portion 5340 engages with the native leaflet tissue.

As can be seen in FIGS. 192-193, the indicator flex or hinge portion 5360 is arranged near the barbed portion 5340 of the moveable arm 5330. The indicator flex or hinge portion 5360 is configured to bias the indicator arm 5350 at an angle from the moveable arm 5330 and toward the fixed arm 5310. The desired minimum engagement depth is determined by the angle of the indicator arm 5350 with respect to the moveable arm 5330, the distance between the indicator flex or hinge portion 5360 and the flex or hinge portion 5320, and the length of the indicator arm 5350. The minimum engagement depth decreases the further the flex or hinge portion 5360 is from the flex or hinge portion 5320, the greater the angle between the indicator arm 5350 and the moveable arm 5330, and the greater the length of the indicator arm 5350. When the clasp 5300 is closed without the indicator arm 5350 being engaged by the leaflet, the indicator arm 5350 moves to or beyond the fixed arm 5310.

Figure 195:
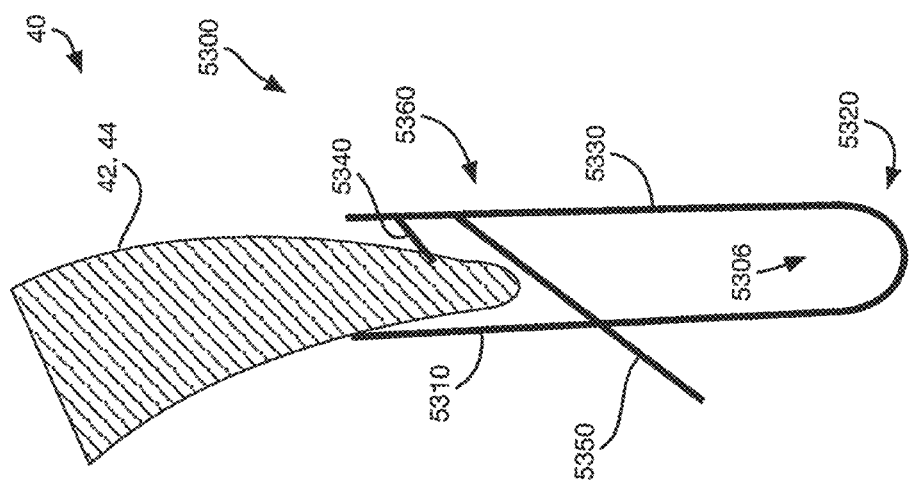

The indicator arm 5350 reaching the fixed arm 5310 forms a shape that is visible via imaging devices used to monitor implantation and deployment of the device, as can be seen in FIG. 195. When the leaflet is inserted into the clasp 5300 beyond the minimum desired engagement depth, the leaflet pushes the indicator arm 5350 back toward the moveable arm 5330 such that the indicator arm 5350 does not cross the fixed arm 5310 to form the indicating shape, such as the X-shape shown in FIG. 195. In addition, or instead, the indicator arm bounces or pulses when engaged with the valve leaflet when the heart beats. Thus, the indicator arm 5350 indicates to an observer observing the installation via an imaging device that the leaflet is inserted into the opening 5306 beyond the minimum desired engagement depth.

Figure 196:
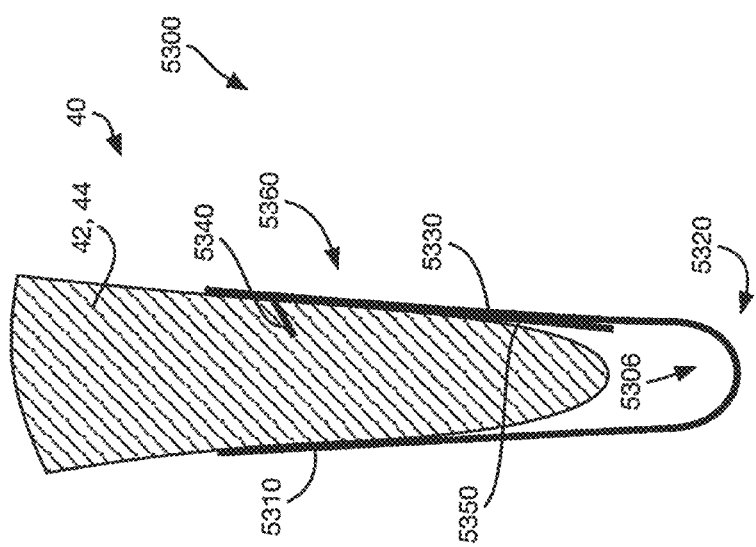

Referring now to FIGS. 194-196, the example clasp 5300 is shown being deployed within a native valve 40 to secure an implantable device (not shown), such as the devices 100, 200, 300 described above, to one of the native leaflets 42, 44. Referring now to FIG. 194, the clasp 5300 is shown in an open condition with a native leaflet 42, 44 partially inserted into an opening 5306 of the clasp 5300 formed between the fixed and moveable arms 5310, 5330. To determine whether the leaflet 42, 44 has reached the desired engagement depth, the moveable arm 5330 is actuated via actuation lines (not shown) as shown in FIGS. 195-196.

Referring now to FIG. 195, when the moveable arm 5330 is actuated toward the fixed arm 5310, the leaflet 42, 44 may contact portions of the fixed and moveable arms 5310, 5330 without contacting the indicator arm 5350 when the engagement depth of the leaflet 42, 44 is less than the minimum desired engagement depth. Thus, the indicator arm 5350 extends to or beyond the fixed arm 5310 to form a shape with the fixed arm 5310 that indicates insufficient leaflet insertion. In addition, or instead, the indicator arm bounces or pulses when engaged with the valve leaflet when the heart beats.

Figure 197:
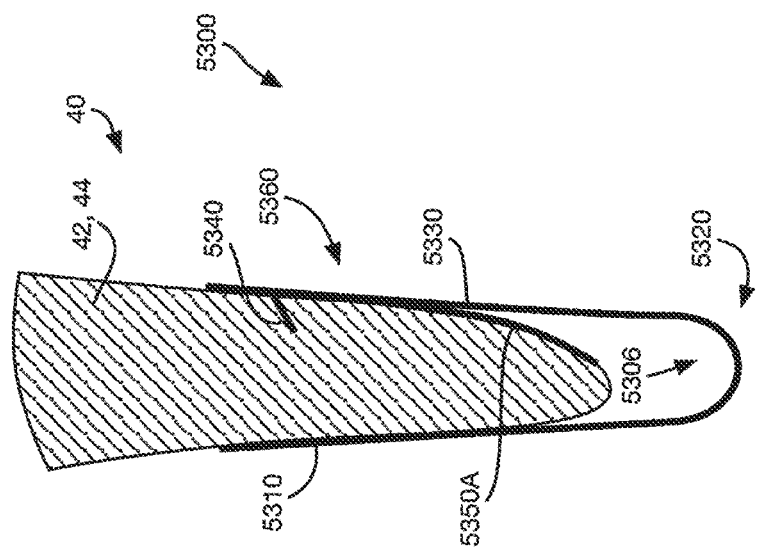

As can be seen in FIG. 196, the indicator arm 5350 is prevented from reaching or crossing the fixed arm 5310 when the leaflet 42, 44 is inserted far enough into the clasp 5300. That is, the indicator arm 5350 is deflected by the leaflet 42, 44 to indicate that the leaflet 42, 44 has been inserted at or beyond the minimum engagement depth. In some embodiments, actuation of the moveable arm 5330 also causes the barbed portion 5340 to engage and secure the leaflet 42, 44 within the barbed clasp 5300. If the indicator arm 5350 indicates that the leaflet 42, 44 is not inserted to the desired depth, the clasp 5300 can be opened to allow for repositioning of the leaflet 42, 44. As can be seen in FIG. 197, an indicator arm 5350A can optionally conform to the shape of the leaflet 42, 44 when engaged by the leaflet 42, 44 as the clasp 5300 is closed. This conforming to the shape of the leaflet can indicate the degree of insertion of the valve leaflet 42, 44 into the opening 5306.

Referring now to FIGS. 198-199, an example clasp 5400 for use in implantable prosthetic devices, such as devices 100, 200, 300 described above, is shown. Like the clasp 3500 described above, the clasp 5400 includes a fixed arm 5410, a flex or hinge portion 5420, and a moveable arm 5430 having a barbed portion 5440 (though other friction-enhancing portions can be used). The clasp 5400 also includes an indicator arm 5450 extending from an indicator flex or hinge portion 5460 arranged toward the distal end of the fixed arm 5410. The indicator arm 5450 need not be actuated separately from the fixed arm 5410. The indicator flex or hinge portion 5460 can be formed from a portion of the indicator arm 5450 or can be formed from a series of cutouts. The clasp 5400 can be used in any of the implantable prosthetic devices of the present application and can include any of the features or combinations of features of the other clasps described herein.

The illustrated moveable arm 5430 is formed in a hoop or loop shape having two side arms 5432 surrounding a central opening 5434 that extends from the flex or hinge portion 5420 to the barbed portion 5440 of the moveable arm 5430. The indicator arm 5450 is disposed in the central opening 5434 between the two side arms 5432. Because the moveable arm 5430 spans the full width of the clasp 5400, the barbed portion 5440 of the moveable arm 5430 is as wide as the clasp 5400 so that a larger area of the barbed portion 5440 engages with the native leaflet tissue. In one embodiment, the moveable arm 5430 is not formed in a hoop shape. For example, the moveable arm 5430 can be a single arm.

Figure 201:
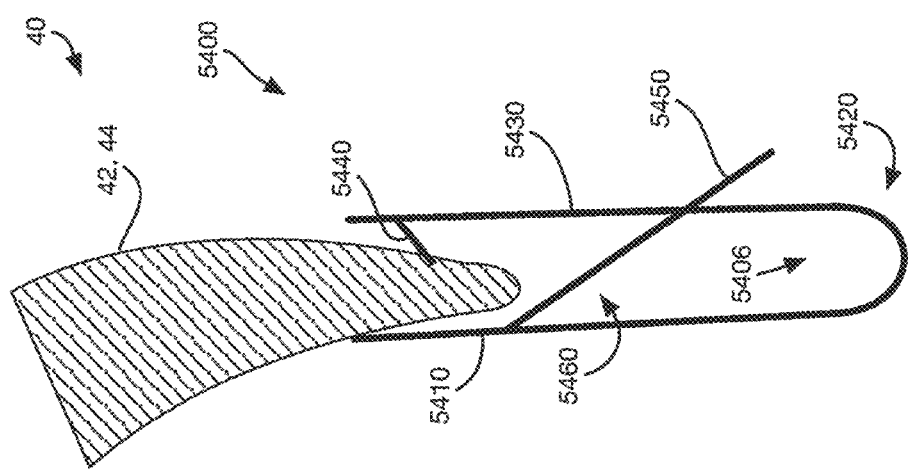

As can be seen in FIG. 199, the indicator flex or hinge portion 5460 is arranged near the distal end of the fixed arm 5410. Optionally, the indicator flex or hinge portion 5460 can be attached to a paddle (not shown) of the implantable prosthetic device. The indicator flex or hinge portion 5460 is configured to bias the indicator arm 5450 at an angle from the fixed arm 5410 and toward the moveable arm 5430. The desired minimum engagement depth is determined by the angle of the indicator arm 5450 with respect to the fixed arm 5410, the distance between the indicator flex or hinge portion 5460 and the flex or hinge portion 5420, and the length of the indicator arm 5450. The minimum engagement depth decreases the further the flex or hinge portion 5460 is from the flex or hinge portion 5420, the greater the angle between the indicator arm 5450 and the fixed arm 5410, and the greater the length of the indicator arm 5450. When the clasp 5400 is closed without the indicator arm 5450 being engaged by the leaflet, the indicator arm 5450 moves beyond the moveable arm 5430. The indicator arm 5450 crossing the moveable arm 5430 forms a closed shape or an X-shape that is visible via imaging devices used to monitor implantation and deployment of the device, as can be seen in FIG. 201. In addition, or instead, the indicator arm bounces or pulses when engaged with the valve leaflet when the heart beats. When the leaflet is inserted into the clasp 5400 beyond the minimum desired engagement depth, the leaflet pushes the indicator arm 5450 back toward the fixed arm 5410 such that the indicator arm 5450 does not reach or cross the moveable arm 5430 to form closed or the X-shape shown in FIG. 201. Thus, the indicator arm 5450 indicates to an observer observing the installation via an imaging device that the leaflet is inserted into the opening 5406 beyond the minimum desired engagement depth.

Figure 200:
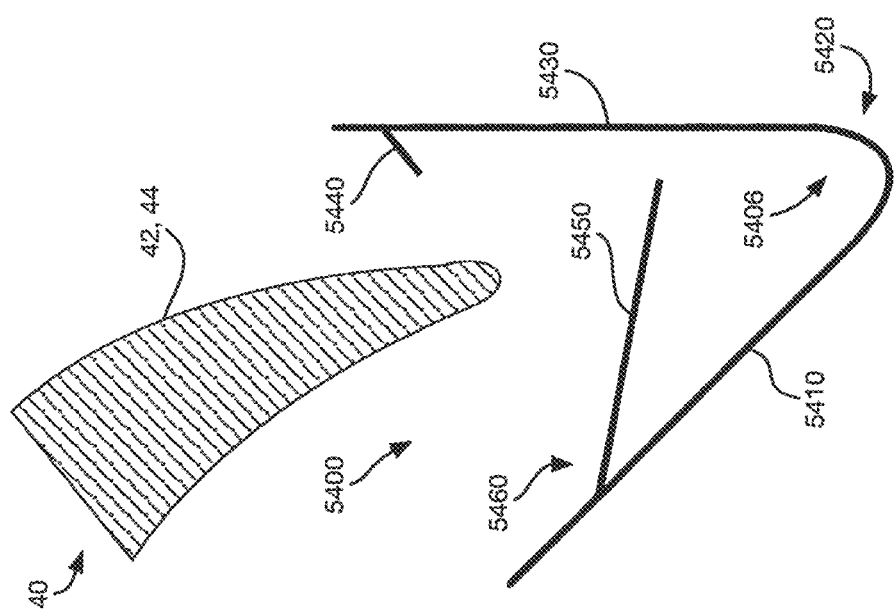
FIGS. 200-202 show the example clasp of FIGS. 198-199 being deployed to engage a leaflet of a native valve.
Figure 202:
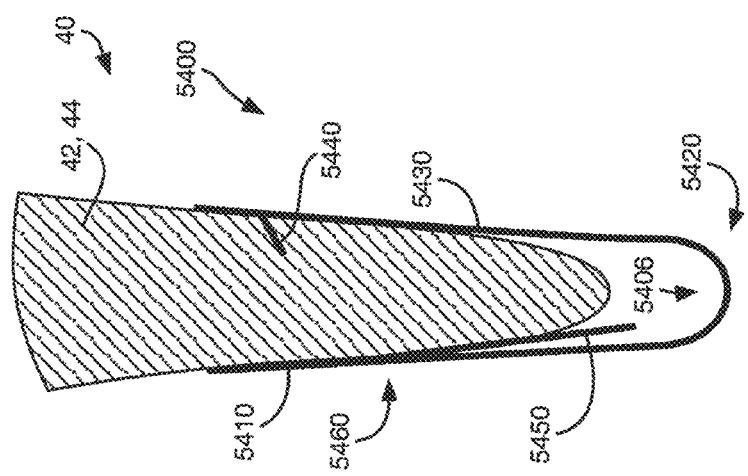

Referring now to FIGS. 200-202, the example clasp 5400 is shown being deployed within a native valve 40 to secure an implantable device (not shown), such as the devices 100, 200, 300 described above, to one of the native leaflets 42, 44. Referring now to FIG. 200, the clasp 5400 is shown in an open condition with a native leaflet 42, 44 partially inserted into an opening 5406 of the clasp 5400 formed between the fixed and moveable arms 5410, 5430. To determine whether the leaflet 42, 44 has reached the desired engagement depth, the moveable arm 5430 is actuated via actuation lines (not shown) as shown in FIGS. 201-202.

Figure 202A:
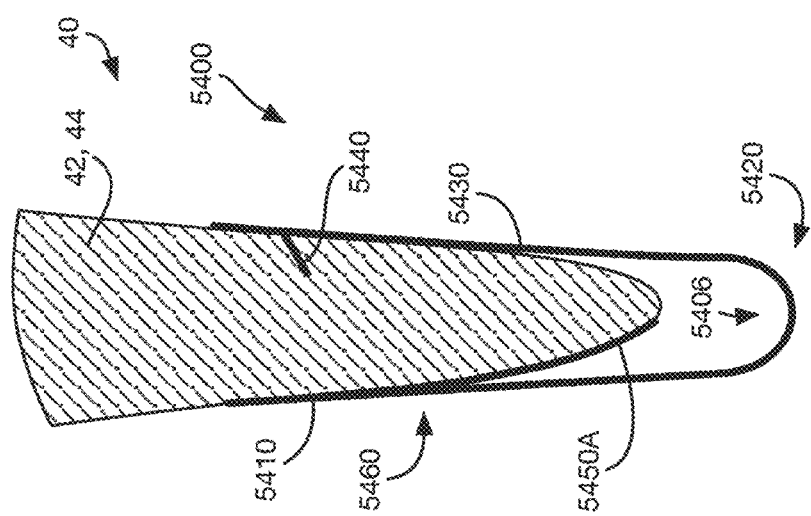
FIG. 202A illustrates an embodiment similar to FIG. 202 where the indicator arm conforms to the shape of the valve leaflet.

Referring now to FIG. 201, when the moveable arm 5430 is actuated toward the fixed arm 5410, the leaflet 42, 44 may contact portions of the fixed and moveable arms 5410, 5430 without contacting the indicator arm 5450 when the engagement depth of the leaflet 42, 44 is less than the minimum desired engagement depth. Thus, the indicator arm 5450 extends to or beyond the moveable arm 5430 to form a closed shape or an X-shape with the moveable arm 5430. In addition, or instead, the indicator arm bounces or pulses when engaged with the valve leaflet when the heart beats. As can be seen in FIG. 202, the indicator arm 5450 is prevented from crossing the moveable arm 5430 when the leaflet 42, 44 is inserted far enough into the clasp 5400. That is, the indicator arm 5450 is deflected by the leaflet 42, 44 to indicate that the leaflet 42, 44 has been inserted at or beyond the minimum engagement depth. In addition, or instead, the indicator arm bounces or pulses when engaged with the valve leaflet when the heart beats. In some embodiments, actuation of the moveable arm 5430 also causes the barbed portion 5440 to engage and secure the leaflet 42, 44 within the barbed clasp 5400. If the indicator arm 5450 indicates that the leaflet 42, 44 is not inserted to the desired depth, the clasp 5400 can be opened to allow for repositioning of the leaflet 42, 44. As can be seen in FIG. 202A, an indicator arm 5450A can optionally conform to the shape of the leaflet 42, 44 when engaged by the leaflet 42, 44 as the clasp 5400 is closed.

Referring now to FIGS. 206-214, an example clasp 5200 having an indicator arm 5250 with a shaped end 5260 for use in implantable prosthetic devices, such as devices 100, 200, 300 described above, is shown. The shaped end can have a variety of different shapes. For example, the shaped end can be round or coiled as illustrated, semi-circular, ovoid, polygonal, etc. Any shape that is visibly discernable from the remainder of the clasp can be used. Like the clasp 3500 described above, the clasp 5200 includes a fixed arm 5210, a flex or hinge portion 5220, a moveable arm 5230 having a barbed portion 5240 (though other friction-enhancing portions can be used), and an indicator arm 5220 connected to the moveable arm 5230 via an indicator flex or hinge portion 5290. The indicator arm 5250 includes a coil 5260 at its end opposite the indicator flex or hinge portion. The shaped end 5260 can have a laser cut pattern or other indicators, such as radiopaque indicators, to increase its visibility when being imaged. The indicator arm is used to indicate whether the leaflet has reached a desired depth. The moveable arm can have at least one opening 5280 in it, through which the indicator arm passes through. Thus, the shaped end 5260 of the indicating arm 5250 will not indicate that the native leaflet has reached a minimum desired engagement depth until the leaflet is inserted at or beyond the location of the shaped end 5260. Once the leaflet 42, 44 has reached the desired engagement depth, the indicator arm 5250 is pressed toward the moveable arm 5230 by the leaflet 42, 44, causing the shaped end 5260 of the indicator arm to pass through the opening 5280 of the moveable arm 5230. Thus, the shaped end 5260 positioned on the exterior of the moveable arm, as opposed to the interior space between the moveable and fixed arms 5230, 5210 of the clasp, indicates that the leaflet 42, 44 has reached a sufficient depth. The clasp 5200 can be used in any of the implantable prosthetic devices of the present application and can include any of the features or combinations of features of the other clasps described herein.

Figure 206:
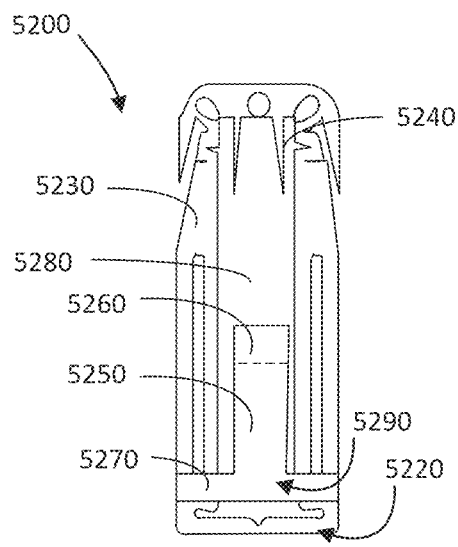
FIGS. 206-209 show an example embodiment of a clasp having an indicator with a shaped end.
Figure 207:
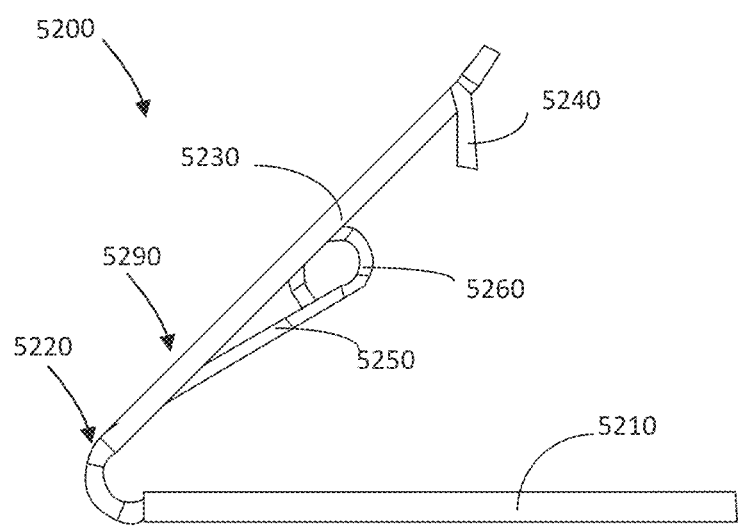

Referring now to FIGS. 206 and 207, a clasp 5200 having an indicator arm 5250 with a shaped end 5260 in a resting state is illustrated. The clasp can be a laser cut clasp or any other embodiment of clasp described herein. The indicator arm 5250 can be made from a flat sheet that is shape set to have a shaped end 5260. The flat sheet can be laser cut. In some example embodiments, the indicator arm can be braided wires and/or a bundle of wires, which are shape set. The indicator arm can be a separate piece attached to the clasp, as described in the example embodiment of FIGS. 206-214, or it can be laser cut from the same sheet of material as the clasp. As a separate piece, the indicator arm can have a base 5270 that is optionally a flex or hinge region of the indicator arm, at the end of the indicator arm that is attached to the moveable arm 5230. As is illustrated by FIG. 207, the clasp is open, and the indicator arm is in a resting state. In its resting state, the shaped end 5260 is positioned on the side of the moveable arm facing the fixed arm.

Figure 208:
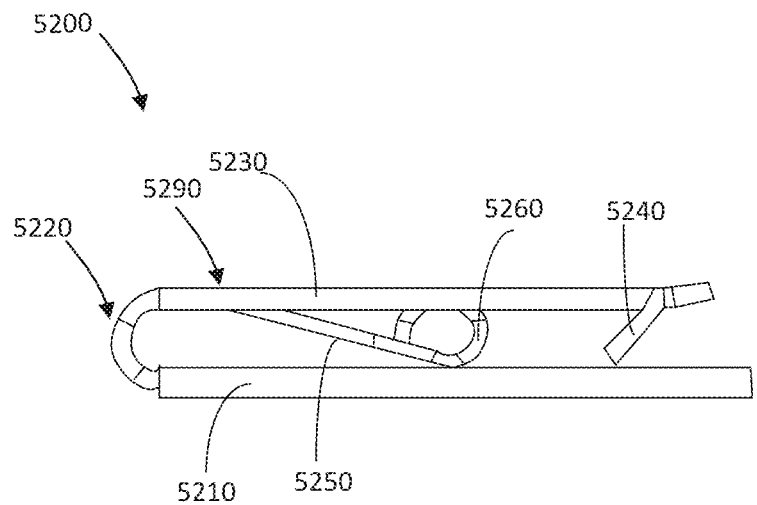
Figure 209:
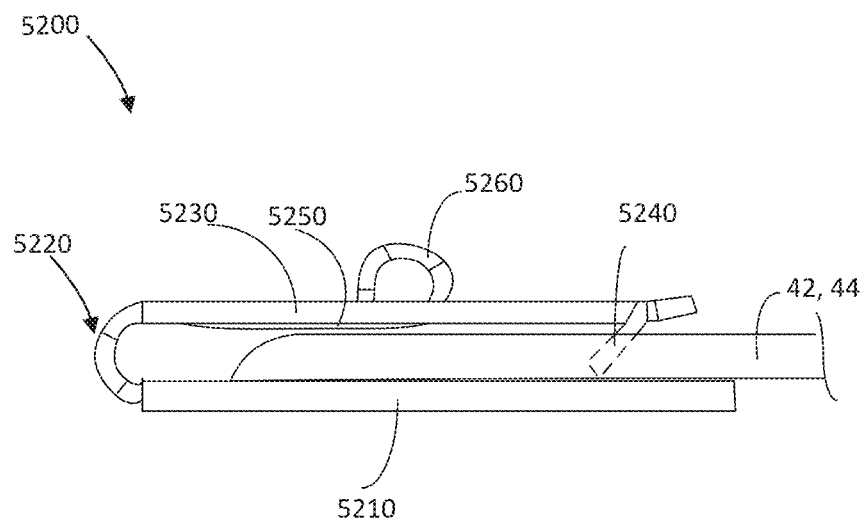

Referring now to FIGS. 208-209, the clasp 5200 is in a closed position. In FIG. 208, the clasp is closed without a leaflet between the moveable arm 5230 and the fixed arm 5210. Because there is no leaflet that has reached a sufficient depth within the clasp in FIG. 208, the indicator arm 5250 is in its resting configuration, and the shaped end 5260 is inside the outer boundaries of the profile of the clasp. In FIG. 209, a leaflet 42, 44 has been captured by the clasp. The leaflet is sufficiently deep within the clasp, as indicated by the shaped end 5260 of the indicator arm 5250 being positioned exterior to the profile of the moveable arm 5230 of the clasp. The leaflet has pushed the indicator arm towards the moveable arm, such that the indicator arm pivoted at the indicator arm hinge region 5230, and the shaped end 5260 has passed through the opening 5280 (visible in FIG. 206) of the moveable arm 5230.

Referring now to FIGS. 210-214, schematic views of the example embodiment of a clasp having an indicator arm with a shaped end such as that illustrated in FIGS. 208-209, are shown. FIGS. 210-211 illustrate the clasp 5200 in an open position where the indicator arm 5250 having a shaped end 5260 is in a resting configuration, that can be shape set as explained above.

Figure 212:
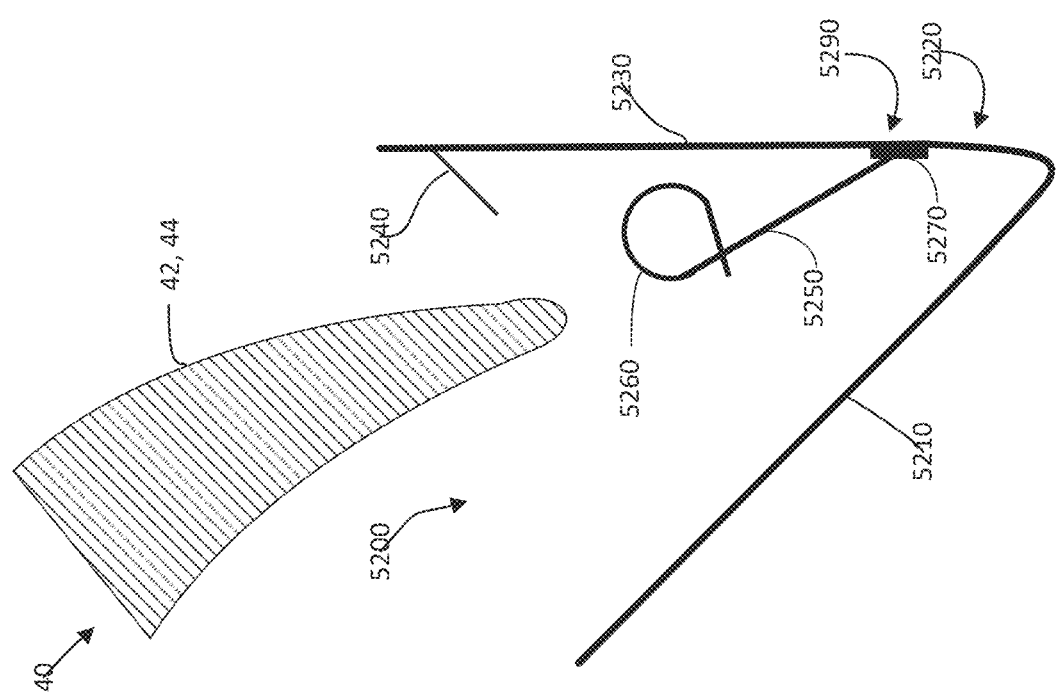
Figure 213:
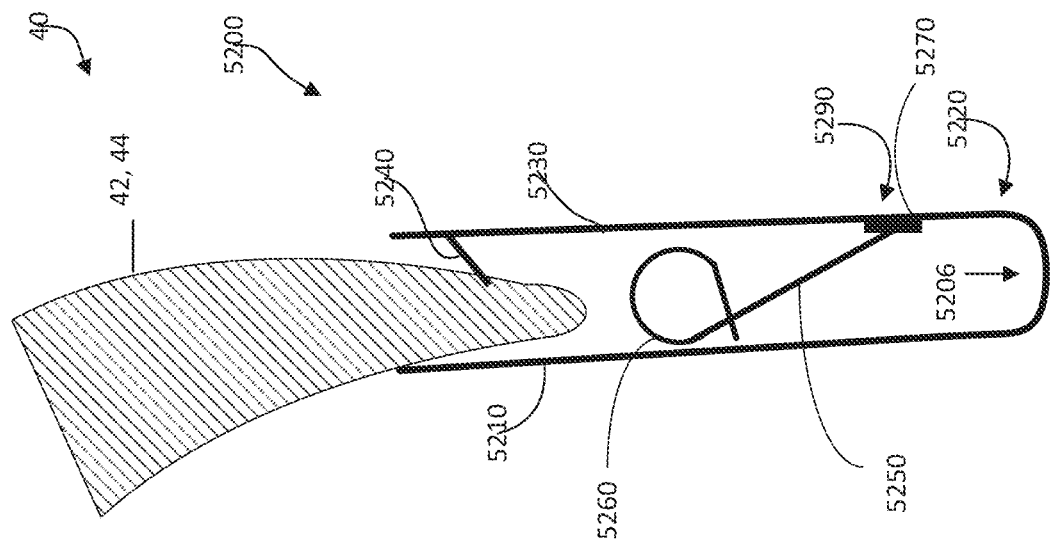

Referring now to FIGS. 212-214, the example clasp 5200 is shown being deployed within a native valve to secure an implantable device (not shown), such as the devices 100, 200, 300 described above, to one of the native leaflets 42, 44. Referring now to FIG. 212, the clasp 5200 is shown in an open condition with a native leaflet 42, 44 partially inserted into an opening of the clasp 5200 formed between the fixed and moveable arms 5210, 5230. To determine whether the leaflet 42, 44 has reached the desired engagement depth, the moveable arm 5230 is actuated to close the clasp, such that the moveable arm and the fixed arm move closer together. The indicator arm is free to flex, move, or pivot about the indicator flex or hinge portion 5290 when pressure is applied to the indicator arm, either by leaflet 42, 44 or the fixed arm 5210.

Referring now to FIG. 213, when the moveable arm 5230 is actuated to close the clasp on the leaflet 42, 44, the indicator arm will not be forced out of its resting configuration if the leaflet is not sufficiently deep within the clasp. That is, when the leaflet is not positioned sufficiently deep within the clasp, the indicator arm and shaped end 5260 will remain in its resting configuration between the moveable arm and the fixed arm.

Referring now to FIG. 214, the moveable arm 5230 has been actuated to close the clasp on the leaflet 42, 44, when the leaflet is positioned sufficiently deep within the clasp. The indicator arm 5250 and its shaped end 5260 indicate to the operator that the leaflet 42, 44 is sufficiently deep. When the leaflet is sufficiently deep and the moveable arm 5230 is actuated, the leaflet applies pressure to the indicator arm. This pressure moves the indicator arm 5250 towards the moveable arm such that the shaped end 5260 of the indicator arm 5250 passes through the opening 5280 of the moveable arm, to the side of the moveable arm facing away from the fixed arm.

Figure 168:
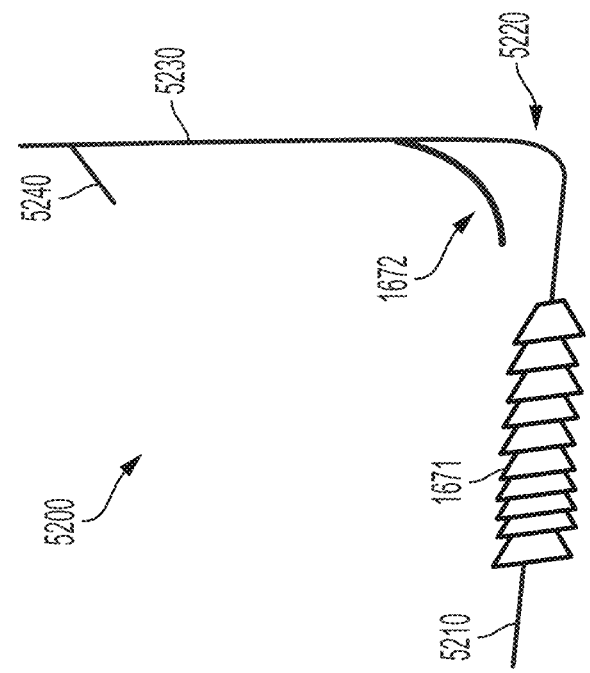
FIGS. 167-168 show schematic views of an example embodiment of a clasp having a screw drive to capture tissue.
Figure 167:
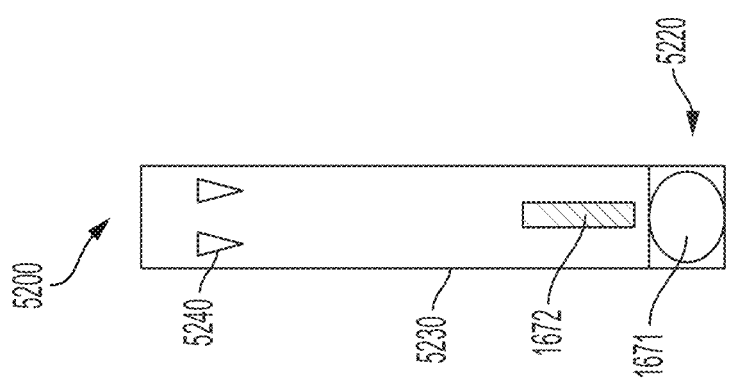

Referring now to FIGS. 167-168, an example clasp 5200 for use in implantable prosthetic devices, such as devices 100, 200, 300 described above, is shown. Like the clasp 3500 described above, the clasp 5200 includes a fixed arm 5210, a flex or hinge portion 5220, and a moveable arm 5230 having a barbed portion 5240 (though other friction-enhancing portions can be used). The moveable arm can include an optional indicator 1672 that can be positioned between the flex or hinge portion 5220 and the barbed portion 5240. In one embodiment, the indicator 1672 can be positioned closer to the flex or hinge portion than the barbed portion.

The fixed arm 5210 can include a rotating component 1671 to draw the leaflet tissue into the clasp, in a direction towards the flex or hinge portion 5220. The rotating component 1671 can be positioned on the fixed arm (and/or the moveable arm) at a position that is between the flex or hinge portion and the end of the fixed arm farthest from the flex portion or hinged portion. The rotating component is schematically illustrated and can be a variety of different rotating components. In FIGS. 167-168, the rotating component 1671 is a gear such as a worm gear or a crank, that can rotate to pull the tissue in towards the flex portion or hinged portion of the clasp.

In operation, the leaflet is captured by closing the clasp on it. The optional indicator can be used to determine whether the leaflet is positioned at a sufficient depth within the clasp. The leaflet is not sufficiently deep within the clasp if it is not contacting the indicator 1672. Thus, the indicator 1672 will not indicate that the leaflet 42, 44, has reached the desired engagement depth until the leaflet is inserted at or beyond the location of the indicator 1672.

The rotating component 1671 rotates and pulls in the leaflet tissue. After the clasp is closed onto leaflet tissue, the rotating component 1671 can be actuated without reopening the clasp to pull the leaflet tissue to the desired depth within the clasp by rotating the rotating component.

The rotating component 1671 can be used in any of the implantable prosthetic devices of the present application and can include any of the features or combinations of features of the other clasps described herein.

Figure 169:
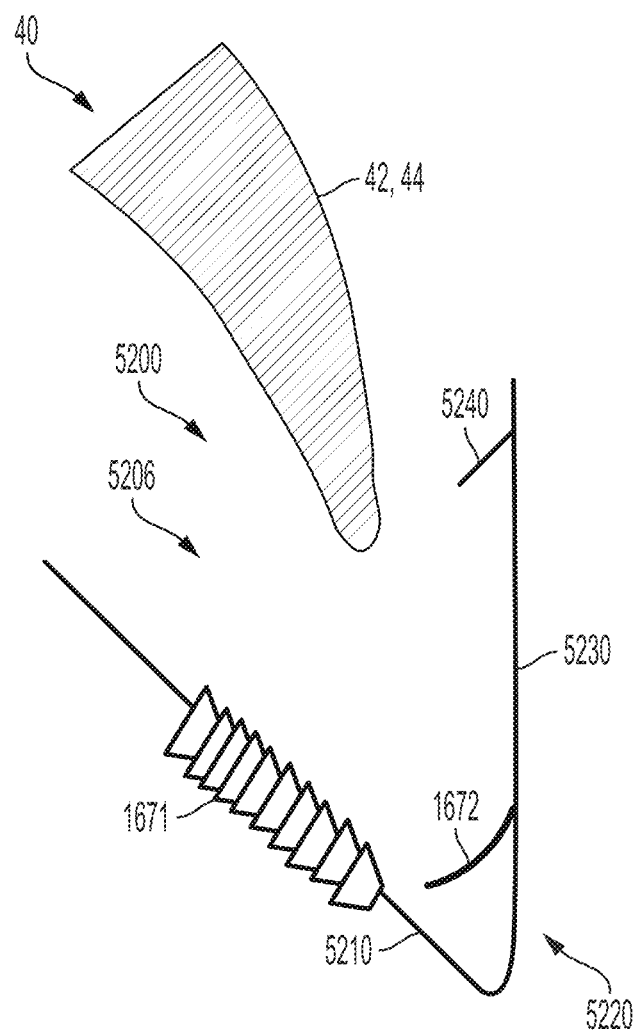
FIGS. 169-171 show the example clasp of FIGS. 167-168 being deployed to engage with a leaflet of a native valve.
Figure 170:
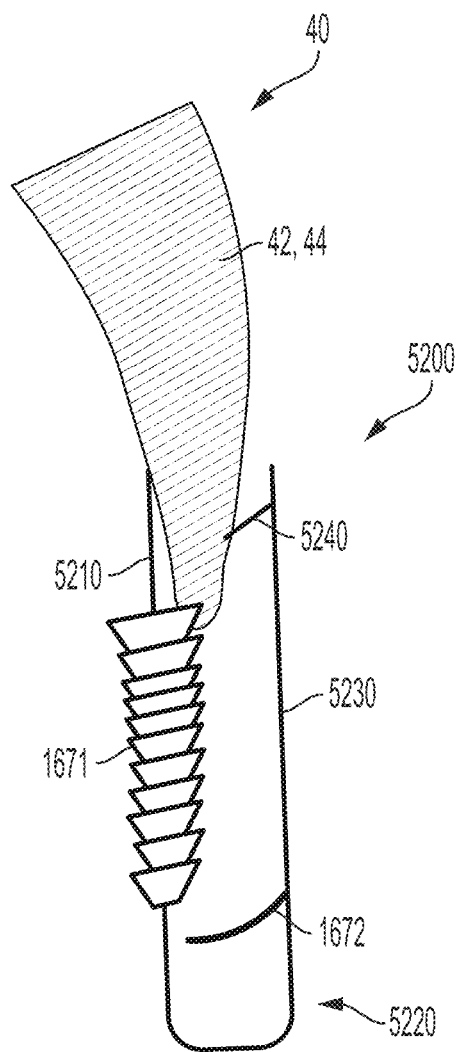
Figure 171:
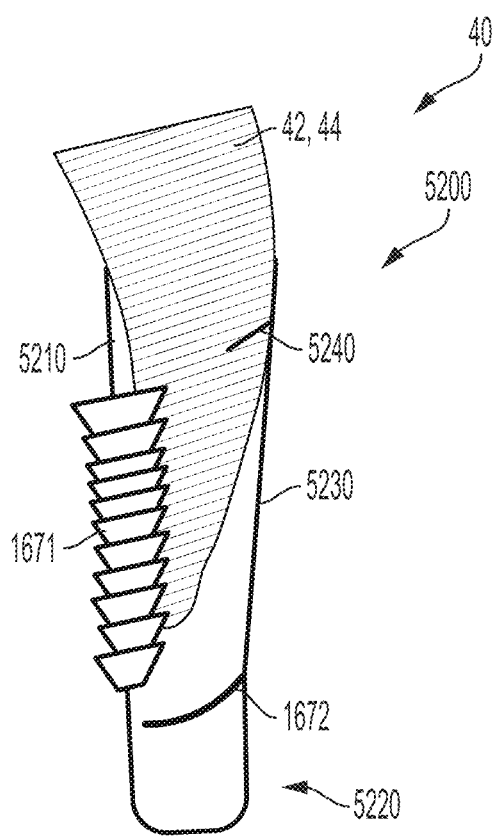

Referring now to FIGS. 169-171, the example clasp 5200 having a rotating component 1671 is shown being deployed within a native valve 40 to secure an implantable device (not shown), such as the devices 100, 200, 300 described above, to one of the native leaflets 42, 44. Referring now to FIG. 169, the clasp 5200 is shown in an open condition with a native leaflet 42, 44 partially inserted into an opening 5206 of the clasp 5200 formed between the fixed and moveable arms 5210, 5230. To draw the leaflet in to the desired engagement depth once the clasp is closed, the rotating component is rotated to pull the leaflet in towards the indicator 1672 as shown in FIGS. 170-171.

Referring now to FIG. 170, when the moveable arm 5230 is actuated to push the leaflet 42, 44 against the fixed arm 5210, the leaflet 42, 44 may contact a portion of the fixed arm 5210 and at least a portion of the rotating element 1671 without contacting the indicator 1672 when the engagement depth of the leaflet 42, 44 is less than the minimum desired engagement depth. As can be seen in FIG. 171, the rotating component 1671 has been rotated to pull the leaflet tissue into the clasp. In FIG. 171 the leaflet is pulled partially into the clasp. The leaflet is sufficiently pulled into the clasp by the rotating component when the leaflet contacts the indicator. In some embodiments, actuation of the moveable arm 5230 also causes the barbed portion 5240 to engage and secure the leaflet 42, 44 within the barbed clasp 5200. If the indicator is not contacted by the leaflet, as in FIG. 171, the rotating component 1671 can be rotated more to pull the leaflet farther in to the desired depth within the clasp.

Referring now to FIGS. 172-173, an example clasp 5200 for use in implantable prosthetic devices, such as devices 100, 200, 300 described above, is shown. Like the clasp 3500 described above, the clasp 5200 includes a fixed arm 5210, a flex or hinge portion 5220, and a moveable arm 5230 having a barbed portion 5240 (though other friction-enhancing portions can be used). The clasp can include a flexible indicator 1731 connected to the fixed arm 5210 at a fixed end 1732 and slidably positioned at a moveable end 1733 on the moveable arm 5230. The flexible indicator can be connected to the fixed arm at a location between the barbed portion 5240 and the flex or hinge portion 5220, at the end farther away from the flex or hinge portion 5220. The flexible indicator can be slidably positioned on the moveable arm at a location anywhere from the flex portion or hinged portion 5220 to the barbed portion 5240. The flexible indicator can have a hammock-like configuration in that it is attached to the arms of the clasp and has a slack region in between its ends that are connected to the arms. The indicator can be a suture, a nitinol wire, cloth, and/or a nitinol hammock that the tissue moves as it is captured and moves deeper into the clasp. If the leaflet tissue is not captured at a sufficient depth, the hammock is not moved, and its moveable end does not glide along the moveable arm. As tissue is captured, the mobile end of the flexible indicator can slide along the arm towards the flex portion or hinged portion 5220 of the apex of the clasp. The sliding of the indicator indicates the depth of the leaflet that has been captured by the clasp. There can be a spring 1734 along the moveable arm between the mobile end of the flexible indicator and the flex portion or hinged portion of the clasp. The spring can return the flexible feature to its rest state if the clasp is reopened to reposition it on the native leaflet. In the schematic illustrations the spring is drawn as a coil spring around the exterior of the moveable arm. However, the spring can be any known spring, and can be positioned along the interior surface of the arm of the clasp along which it extends. In some example embodiments, the flexible indicator can be shape set to return to a resting state where its moveable end moves away from the flex portion or hinged portion 5220. In some example embodiments, the flexible indicator can be fixed to the moveable arm, and slidably positioned on the fixed arm.

Figure 174:
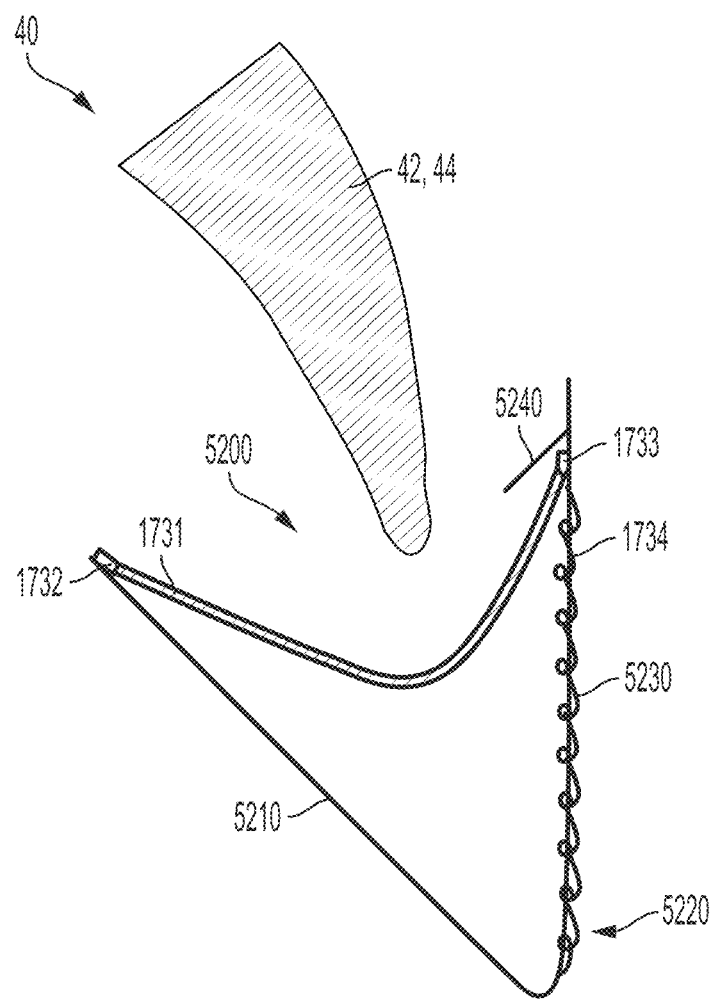
FIGS. 174-176 show the example clasp of FIGS. 172-173 being deployed to engage with a leaflet of a native valve.
Figure 175:
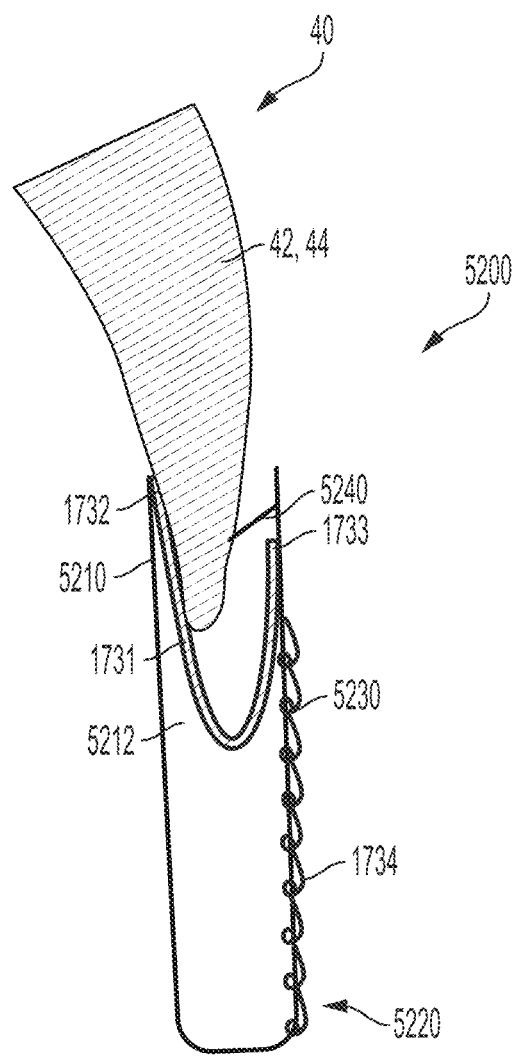
Figure 176:
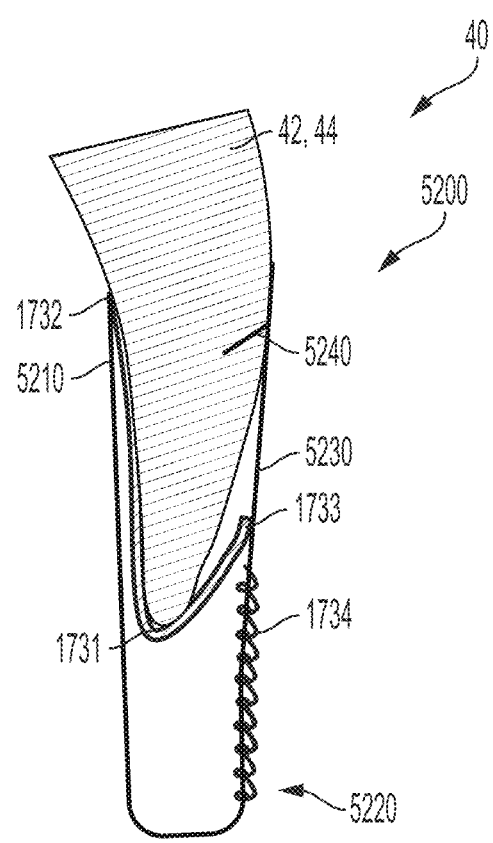

Referring now to FIGS. 174-176, the example clasp 5200 having a flexible indicator 1731 is shown being deployed within a native valve 40 to secure an implantable device (not shown), such as the devices 100, 200, 300 described above, to one of the native leaflets 42, 44. Referring now to FIG. 174, the clasp 5200 is shown in an open condition with a native leaflet 42, 44 partially inserted into an opening 5206 of the clasp 5200 formed between the fixed and moveable arms 5210, 5230.

Referring now to FIG. 175, when the moveable arm 5230 is actuated to push the leaflet 42, 44 against the fixed arm 5210, the leaflet 42, 44 may contact a portion of the fixed arm 5210 and at least a portion of the flexible indicator 1731 when the engagement depth of the leaflet 42, 44 is less than the minimum desired engagement depth. As can be seen in FIG. 175, the flexible indicator has not been flexed by the leaflet in the direction of the flex portion or hinged portion 5220. This is indicated to the operator because the slidable end of the flexible indicator has not moved in a direction from the barbed portion 5240 to the flex or hinge portion 5220 of the clasp.

Referring now to FIG. 176, the leaflet 42, 44 is pulled farther into the clasp 5200. The flexible feature is engaged by more of the leaflet tissue than in FIG. 175, because the leaflet is farther into the clasp. This has pulled the moveable end 1733 of the flexible indicator 1731 down along the length of the moveable arm, in a direction from the barbed portion 5240 towards the flex or hinge portion 5220. The spring 1734 is compressed due to the sliding of the moveable end of the flexible feature. With the leaflet in this position, the barb 5240 is engaged with the leaflet tissue as well.

Referring now to FIGS. 177-178, a schematic view of an example clasp 5200 for use in implantable prosthetic devices, such as devices 100, 200, 300 described above, is shown. Like the clasp 3500 described above, the clasp 5200 includes a fixed arm 5210, a flex or hinge portion 5220, and a moveable arm 5230. At the free end of the moveable arm is a rotating wheel 1771 with directional barbs 5240. The wheel 1771 can rotate by a line loop, such as a suture loop, to help draw a native mitral valve leaflet into the clasp, toward the flex or hinge portion 5220. The suture loop operates similar to a conveyor roller and rotates the wheel. The wheel can be a cog wheel or a spool, and the suture line can be used to rotate the wheel and draw the leaflet into the clasp. The barbs 5240 on the wheel engage with the leaflet tissue, and when the wheel is rotated in a first direction, the barbs pull the leaflet into the clasp. Should the leaflet be pulled too far into the clasp, the wheel can be rotated in a second direction, opposite to the first direction, to decrease the depth of which the leaflet is inserted into the clasp.

The leaflet depth can be indicated by an echo evaluation of regurgitation through the valve. After at least one of the barbs on the wheel engages with the leaflet, the wheel is rotated in the direction of arrow 1781. The rotation of the wheel translates to a linear distance that can be used to indicate to the operator that there is adequate engagement of the leaflet within the clasp. In this way, the operator can determine how far the leaflet has been pulled within the clasp by the number of rotations of the wheel. The wheel can have a clutch stop mechanism to provide a maximum distance and/or force into the clasp which the leaflet can be pulled.

Figure 179:
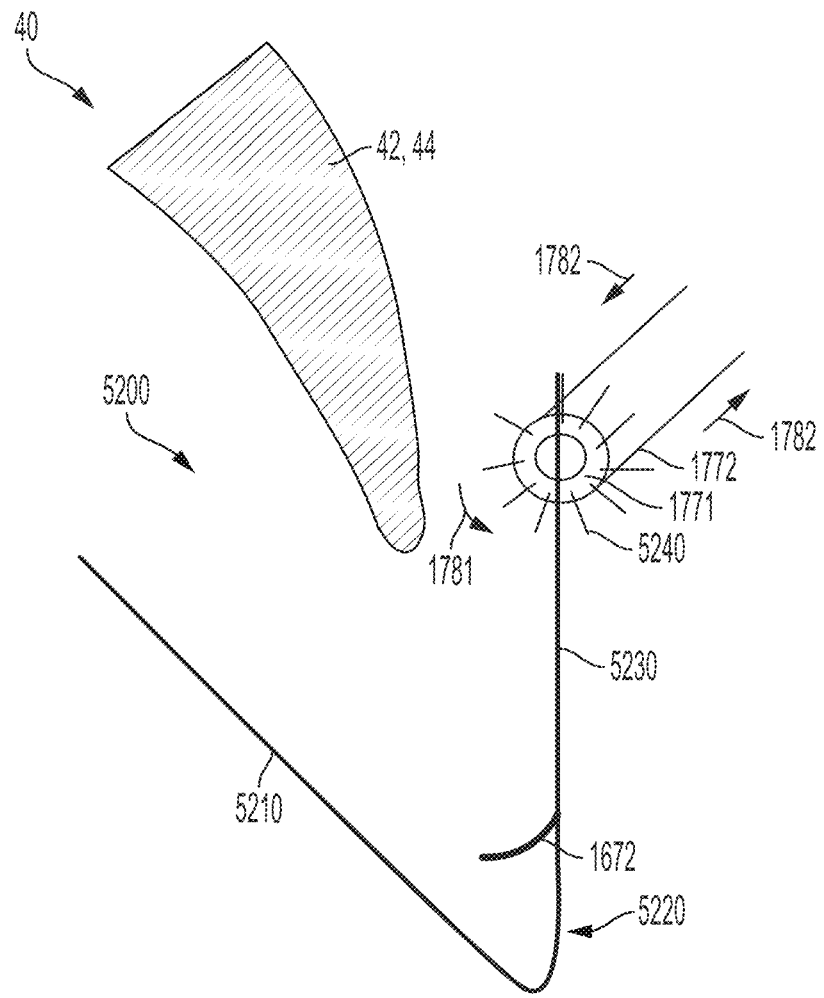
FIGS. 179-181 show the example clasp of FIGS. 177-178 being deployed to engage with a leaflet of a native valve.
Figure 180:
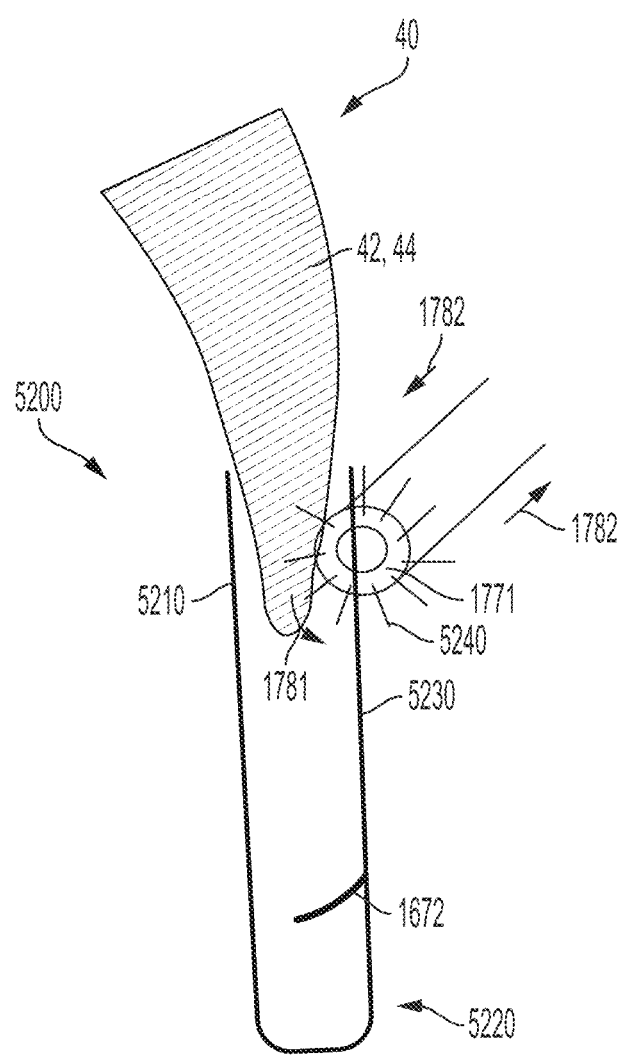
Figure 181:
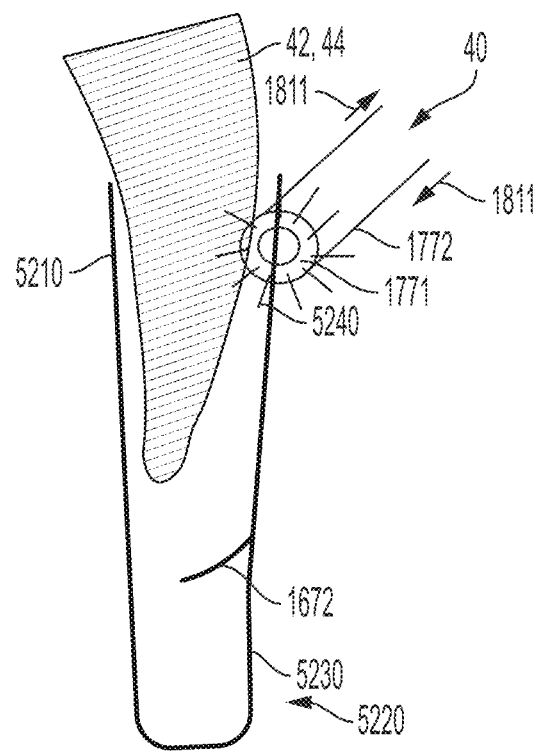

Referring now to FIGS. 179-181, the example clasp having a barbed wheel 1771 is shown being deployed within a native valve to secure an implantable device (not shown), such as the devices 100, 200, 300 described above, to one of the native leaflets 42, 44. Referring now to FIG. 179, the clasp 5200 is shown in an open condition with a native leaflet 42, 44 partially inserted into an opening 5206 of the clasp 5200 formed between the fixed and moveable arms 5210, 5230. To draw the leaflet in to the desired engagement depth once the clasp is closed, the wheel 1771 is rotated in the direction of arrow 1781 to pull the leaflet in towards the flex portion or hinged portion 5220 of the clasp, as shown in FIGS. 180-181. The wheel can be rotated in the direction of arrow 1781 by moving the actuating line in the direction of arrows 1782.

Referring now to FIG. 180, when the moveable arm 5230 is actuated to push the leaflet 42, 44 against the fixed arm 5210, the leaflet 42, 44 may contact a portion of the fixed arm 5210 and at least a portion of the rotating element 1771 without contacting the (optional) indicator 1672 when the engagement depth of the leaflet 42, 44 is less than the minimum desired engagement depth. As can be seen in FIG. 181, the rotating component 1771 has been rotated in the direction of arrow 1782 to pull the leaflet tissue into the clasp a sufficient distance as indicated by the indicator 1672. In FIG. 180 the leaflet is pulled partially into the clasp. In one example embodiment, the leaflet is sufficiently pulled into the clasp by the rotating component when the leaflet contacts the indicator. In some embodiments, actuation of the moveable arm 5230 also causes the barbed portion 5240 to engage and secure the leaflet 42, 44 within the barbed clasp 5200. If the indicator is not contacted by the leaflet, as in FIG. 180, the rotating component 1771 can be rotated more to pull the leaflet farther in to the desired depth within the clasp. Referring now to FIG. 181, the leaflet is pulled farther into the clasp. If the operator wants to lessen the distance the leaflet has been pulled into the clasp, the operator can rotate the wheel 1771 in the opposite direction, by moving the actuating lines in the direction of arrows 1811.

Figure 183:
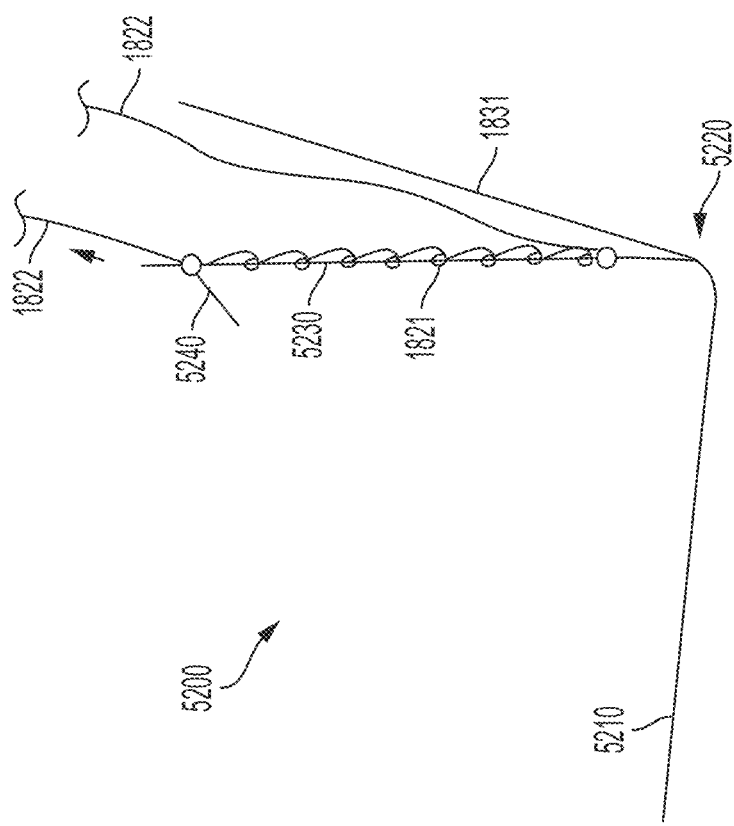
FIGS. 182-183 show schematic views of an example embodiment of a clasp.
Figure 182:
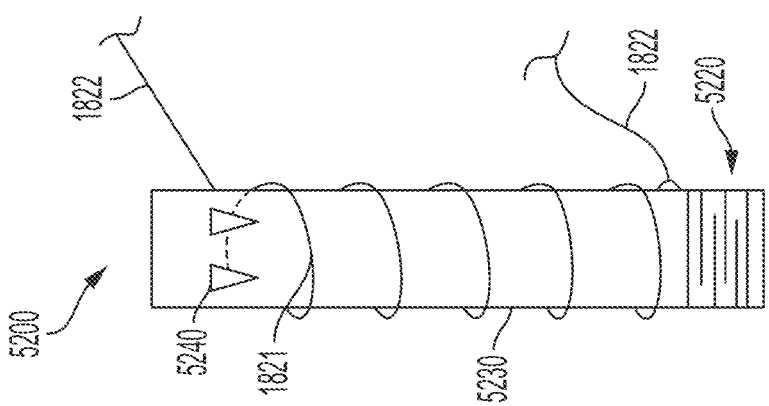

Referring now to FIGS. 182-183, a schematic view of an example clasp 5200 for use in implantable prosthetic devices, such as devices 100, 200, 300 described above, is shown. Like the clasp 3500 described above, the clasp 5200 includes a fixed arm 5210, a flex or hinge portion 5220, and a moveable arm 5230. Positioned on the moveable arm is a hinged barb(s) 5240 pivotally and/or slidably attached to the moveable arm. The hinged barb 5240 is further connected to a spring 1821. The hinged barb and spring pull the leaflet toward the flex portion or hinged portion 5220 and into the clasp. The barb(s) can move back and forth along the length of the clasp. The spring can be pulled on by a line 1822 to angle the barb(s) to disengage tissue and pulls the barb out to full length. That is, to the farthest point along the moveable arm away from the flex portion or hinged portion 5220. Releasing the suture line 1822 causes the spring to angle the barb to engage tissue and/or allow the spring to retract, pulling the tissue in to the clasp, towards the flex portion or hinged portion 5220. The barb(s) can be angled and positioned by applying tension to the suture line. Changing the angle of the barb 5240 permits the barb to atraumatically slide up the leaflet as the leaflet 42, 44 is positioned further into the clasp, towards the flex or hinge portion 5220. The changing angle of the barb 5240 changes when tension is applied to the leaflet in a direction away from the flex or hinge portion 5220, so that the barb engages the leaflet and can prevent it from being removed from the clasp. The change in the angle of the barb 5240 can be passive, and the angle can change to an angle that engages the leaflet by releasing the moveable arm 5230 on to the leaflet to close the clasp on the leaflet. The release of the moveable arm 5230 releases the tension in the spring 1821, thereby changing the angle of the barb.

There can be an optional second moveable arm 1831 that is connected to the clasp at the flex or hinge portion 5220 and is exteriorly positioned to the moveable arm 523 having the barb(s) and spring. The second moveable arm 1831 can be dropped and/or lowered onto the moveable arm 5230 once the tissue is pulled into the leaflet, thereby completing the process of securing the leaflet into the clasp.

Figure 184:
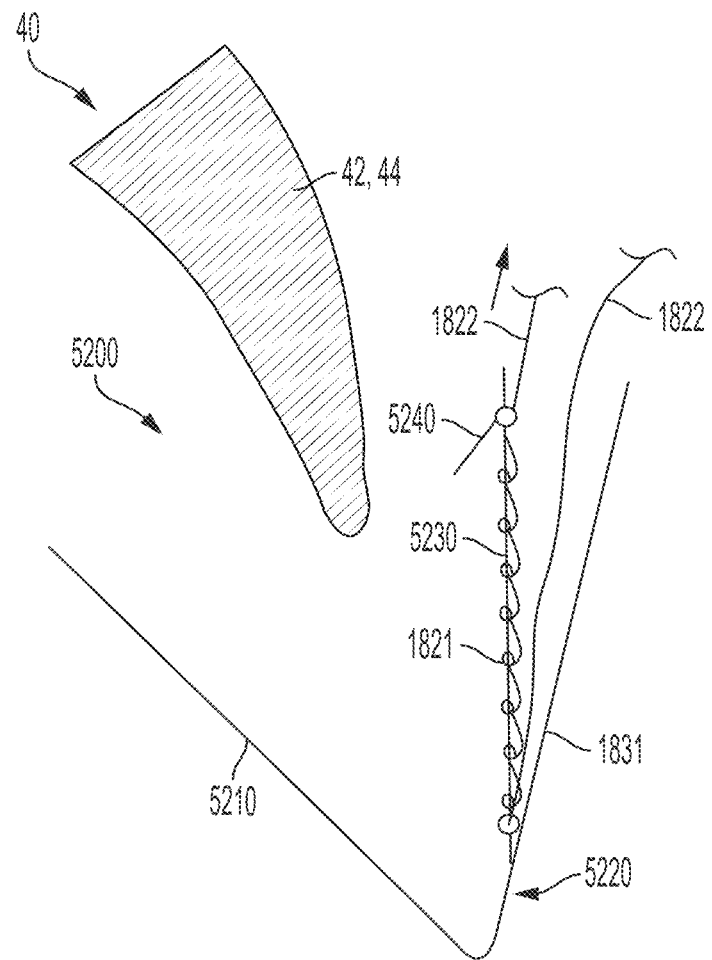
FIGS. 184, 185, 186A, and 186B show the example clasp of FIGS. 182-183 being deployed to engage with a leaflet of a native valve.
Figure 185:
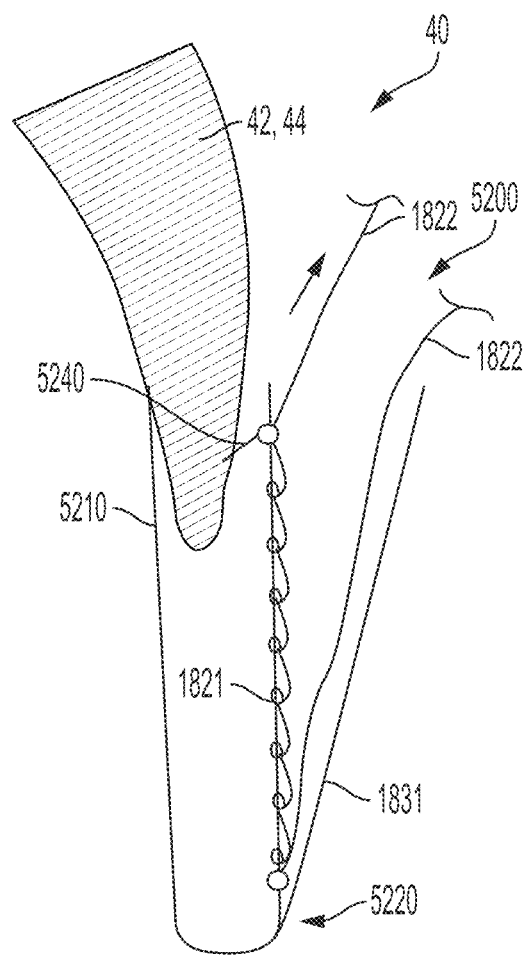

Referring now to FIGS. 184-186B, the example clasp having optionally hinged barbs 5240 and a spring 1821 to provide a mechanism for drawing a leaflet in to the clasp. The clasp 5200 is shown being deployed within a native valve to secure an implantable device (not shown), such as the devices 100, 200, 300 described above, to one of the native leaflets 42, 44. Referring now to FIG. 184, the clasp 5200 is shown in an open condition with a native leaflet 42, 44 partially inserted into an opening 5206 of the clasp 5200 formed between the fixed and moveable arms 5210, 5230. FIG. 185 illustrates the clasp 5200 in a closed position, where the barbs 5240 have engaged leaflet tissue. In this position, the suture line 1822 is taught and the spring 1821 extended by the line 1822.

Figure 186A:
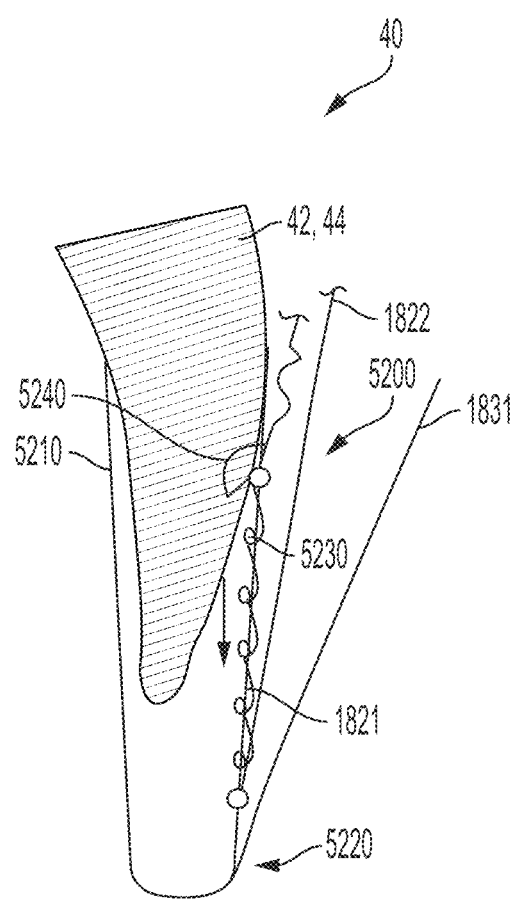
Figure 186B:
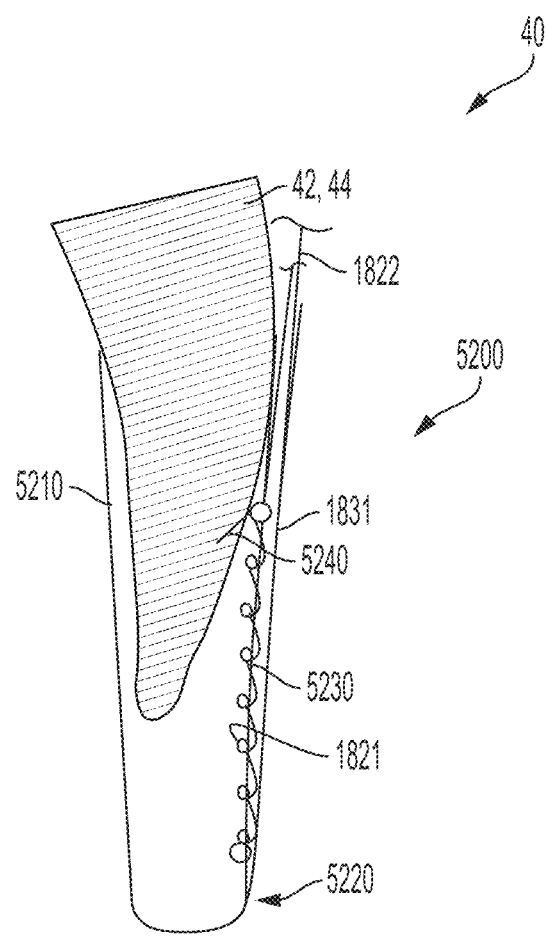

Referring now to FIGS. 186A and 186B, the leaflet is pulled into the clasp towards the flex portion or hinged portion 5220 by relaxing the portion of the suture that is connected to the spring, allowing the spring to pull the barb 5240 and leaflet into the clasp. In the illustrated example, the barb is optionally angled down towards the flex or hinge region of the clasp, holding the leaflet tissue in place. The suture line can be slackened and pulled taught as many times as is necessary to properly engage the leaflet in the clasp. Once the leaflet is engaged positioned, as illustrated in FIG. 186B, the optional second moveable arm is lowered onto the first moveable arm, to further secure the leaflet.

Referring now to FIGS. 187-188, a schematic view of an example clasp 5200 for use in implantable prosthetic devices, such as devices 100, 200, 300 described above, is shown. Like the clasp 3500 described above, the clasp 5200 includes a fixed arm 5210, a flex or hinge portion 5220, and a moveable arm 5230. Positioned on the moveable arm is a set of mobile barbs 5230 attached to a belt 1871 or other rotating mechanism and are moveable in a conveyor belt fashion. The illustrated wheels 1872 are rotatably connected to the moveable arm 5240 of the clasp at two points. One of the wheels 1872 of the conveyor belt is rotatably connected to the moveable arm at a first point that is closer to the flex portion or hinged portion 5220 and the second wheel is attached to the moveable arm to the second point, which is closer to the free end of the moveable arm.

One of the wheels 1872 can be rotated by an actuator line (see FIGS. 177-181) to help draw a native mitral valve leaflet into the clasp, toward the flex portion or hinged portion 5220. Similar in operation to the embodiment described in FIGS. 177-181, the barbs 5240 on the belt 1871 engage with the leaflet tissue, and when the belt is rotated in a first direction, indicated by arrow 1881, the barbs pull the leaflet into the clasp. Should the leaflet be pulled too far into the clasp, the wheel can be rotated in a second direction, indicated by arrow 1882, opposite to the first direction, to decrease the depth of which the leaflet is inserted into the clasp.

The leaflet depth can be indicated by an echo evaluation of regurgitation through the valve. After at least one of the barbs on the wheel engages with the leaflet, the wheel is rotated. The rotation of the wheel and belt translates to a linear distance that can be used to indicate to the operator that there is adequate engagement of the leaflet within the clasp. In this way, the operator can determine how far the leaflet has been pulled within the clasp by the number of rotations of the wheel. At least one-wheel 1872 can have a clutch stop mechanism to provide a maximum distance into the clasp which the leaflet can be pulled.

Figure 189:
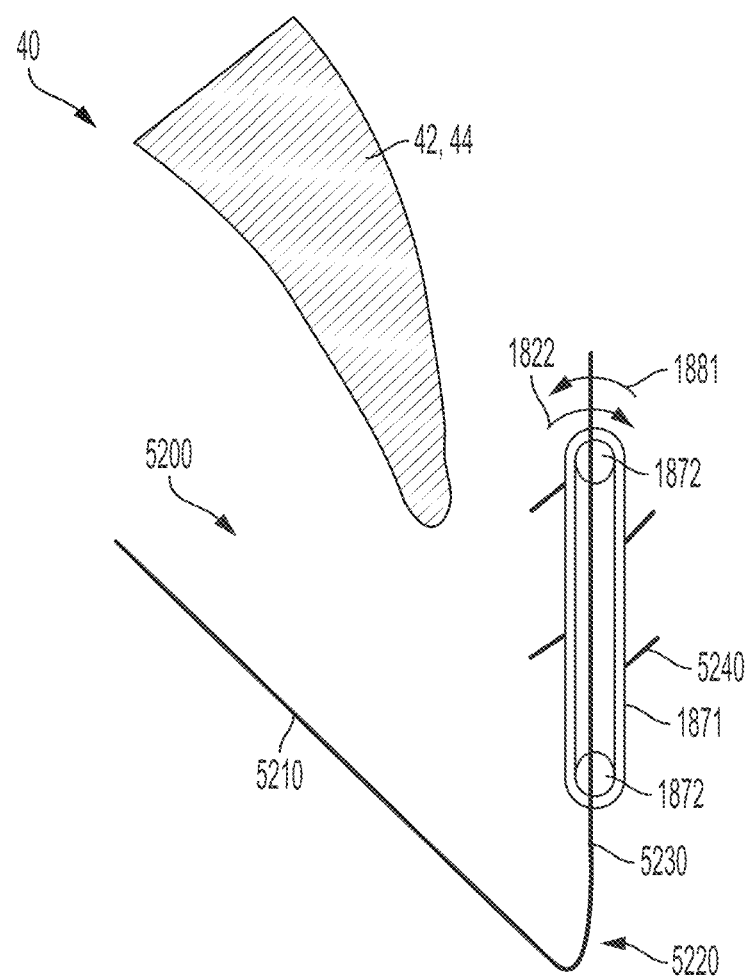
FIGS. 189-191 show the example clasp of FIGS. 187-188 being deployed to engage a leaflet of a native valve.
Figure 190:
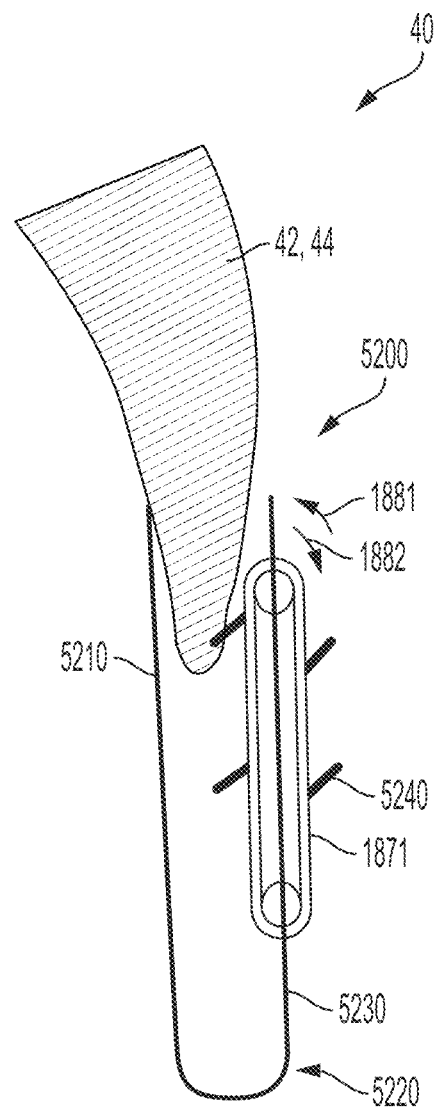
Figure 191:
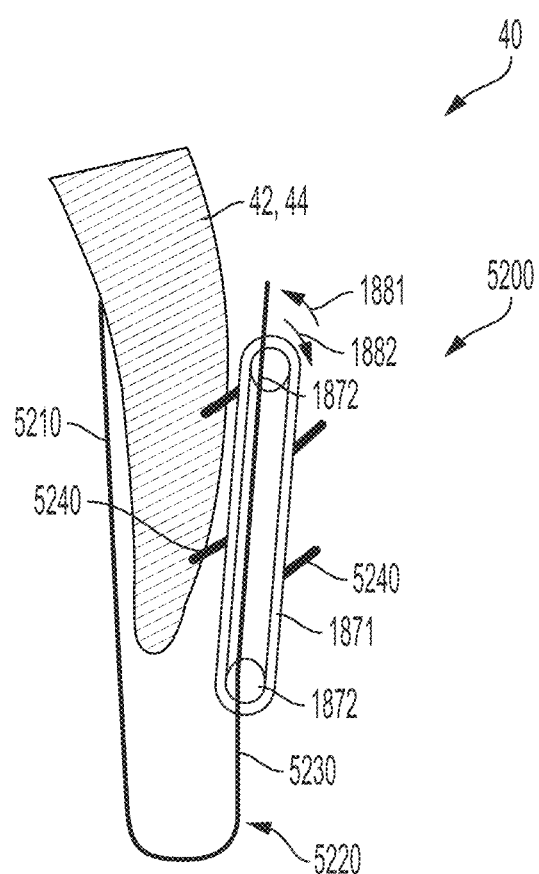

Referring now to FIGS. 189-191, the example clasp having a rotating belt 1871 with barbs 5240 is shown being deployed within a native valve to secure an implantable device (not shown), such as the devices 100, 200, 300 described above, to one of the native leaflets 42, 44. Referring now to FIG. 179, the clasp 5200 is shown in an open condition with a native leaflet 42, 44 partially inserted into an opening 5206 of the clasp 5200 formed between the fixed and moveable arms 5210, 5230. To draw the leaflet into the desired engagement depth once the clasp is closed, the wheel 1872 is rotated in the direction of arrow 1881 to pull the leaflet in towards the flex portion or hinged portion 5220 of the clasp, as shown in FIGS. 190-191. The wheel can be rotated in the direction of arrow 1881 by moving an actuating line as explained with respect to the embodiment of FIGS. 177-181.

Referring now to FIG. 190, when the moveable arm 5230 is actuated to push the leaflet 42, 44 against the fixed arm 5210, the leaflet 42, 44 may contact a portion of the fixed arm 5210 and at least a portion of the rotating belt 1871 when the engagement depth of the leaflet 42, 44 is less than the minimum desired engagement depth. As can be seen in FIG. 191, the rotating component 1872 has been rotated in the direction of arrow 1881 to pull the leaflet tissue into the clasp a sufficient distance in FIG. 190 the leaflet is pulled partially into the clasp. In some embodiments, actuation of the moveable arm 5230 also causes the barbed portion 5240 to engage and secure the leaflet 42, 44 within the barbed clasp 5200. The belt 1871 can be rotated more to pull the leaflet farther in to the desired depth within the clasp. Referring now to FIG. 191, the leaflet is pulled farther into the clasp. If the operator wants to lessen the distance the leaflet has been pulled into the clasp, the operator can rotate the belt 1871 in the opposite direction, as indicated by arrow 1882.

Figure 242:
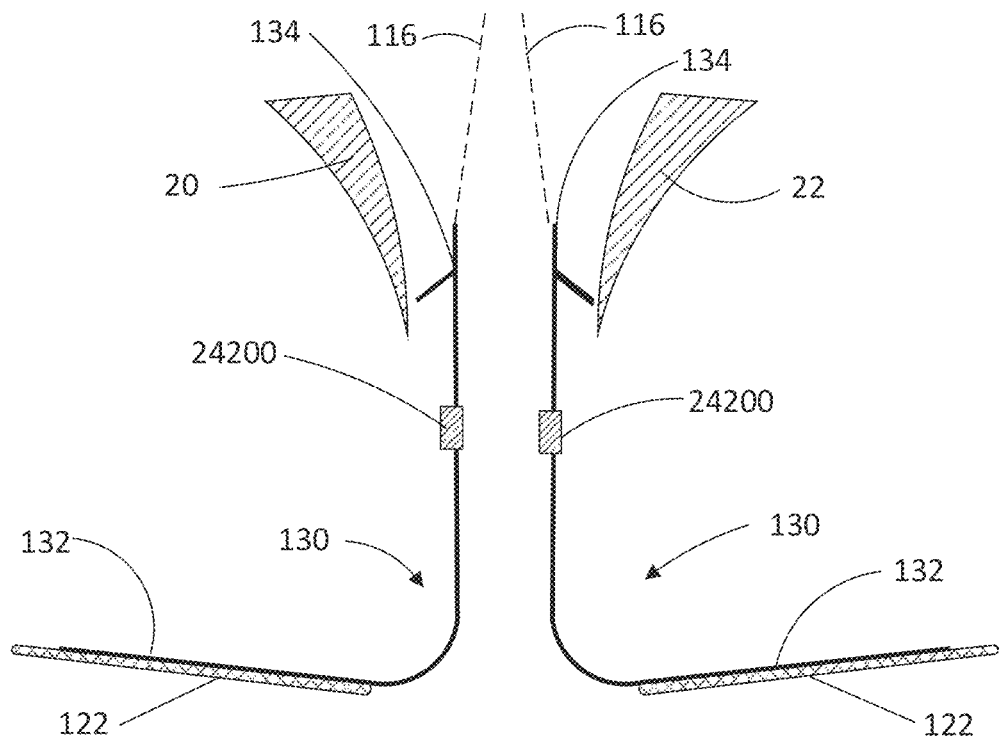
FIGS. 242-247 illustrate an example embodiment of a clasp with a leaflet insertion sensor.
Figure 243:
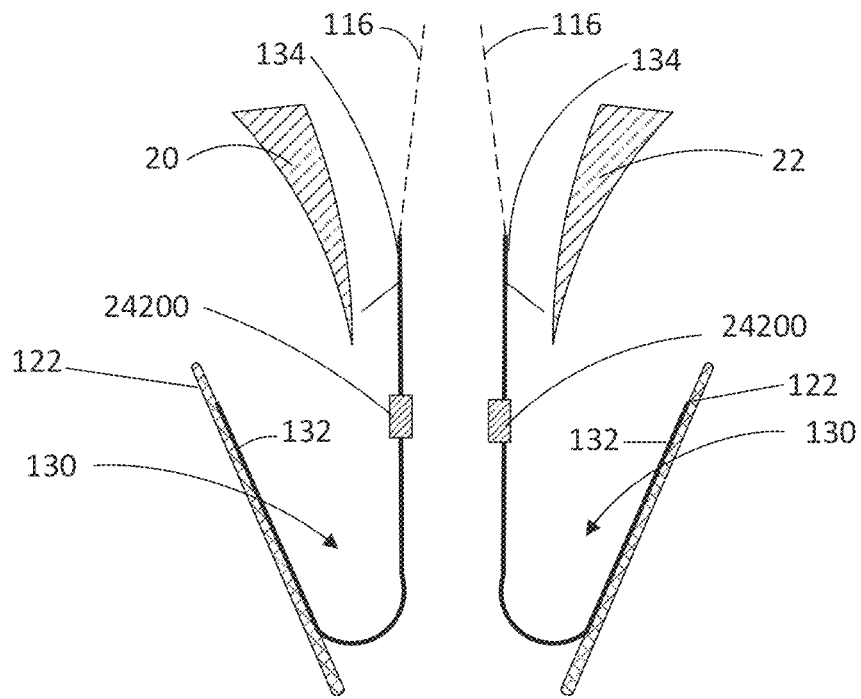
Figure 244:
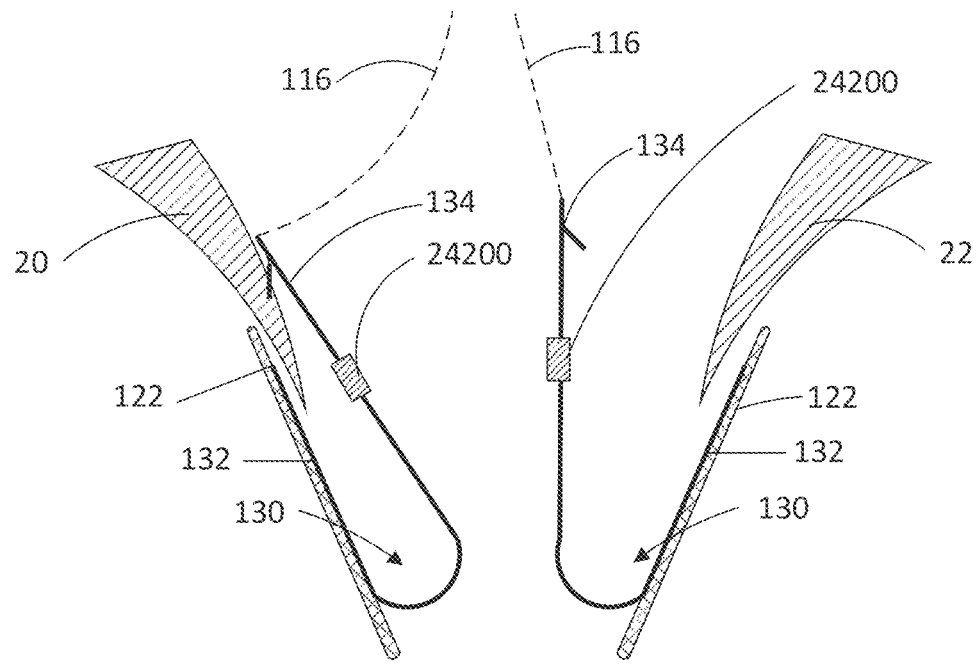
Figure 245:
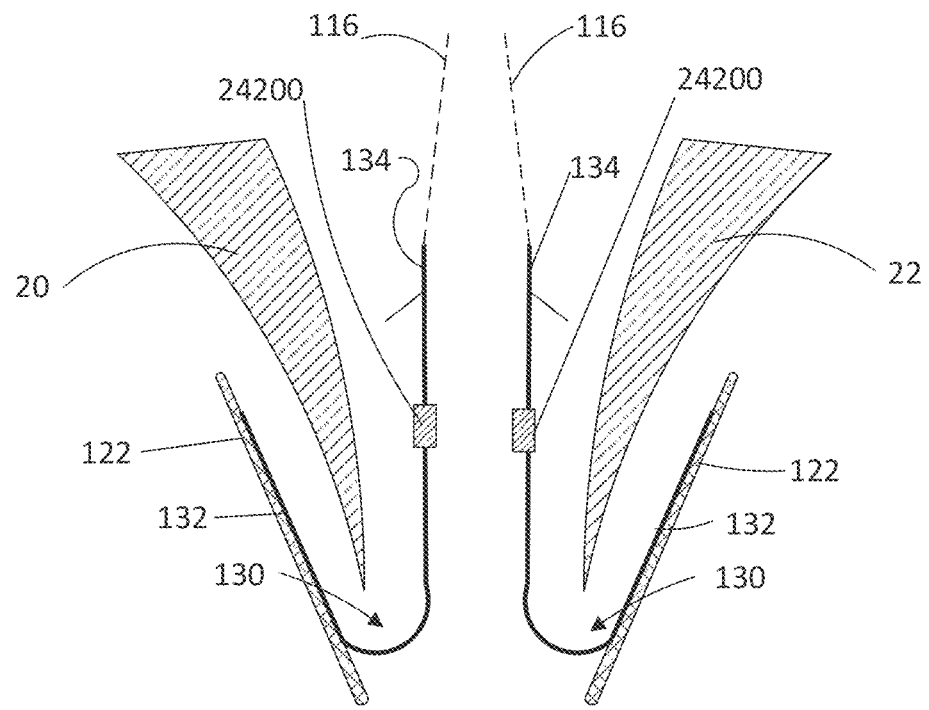
Figure 246:
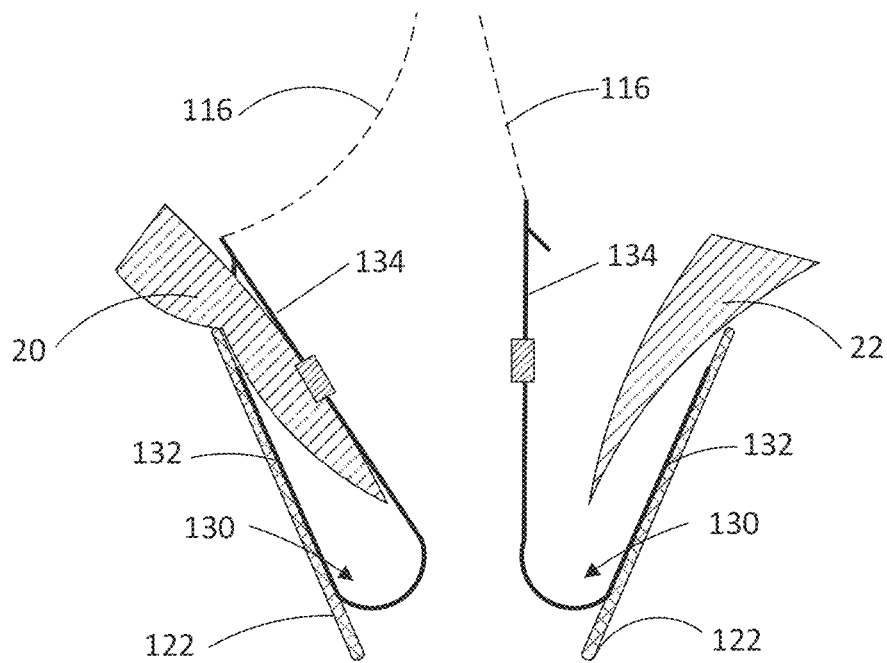
Figure 247:
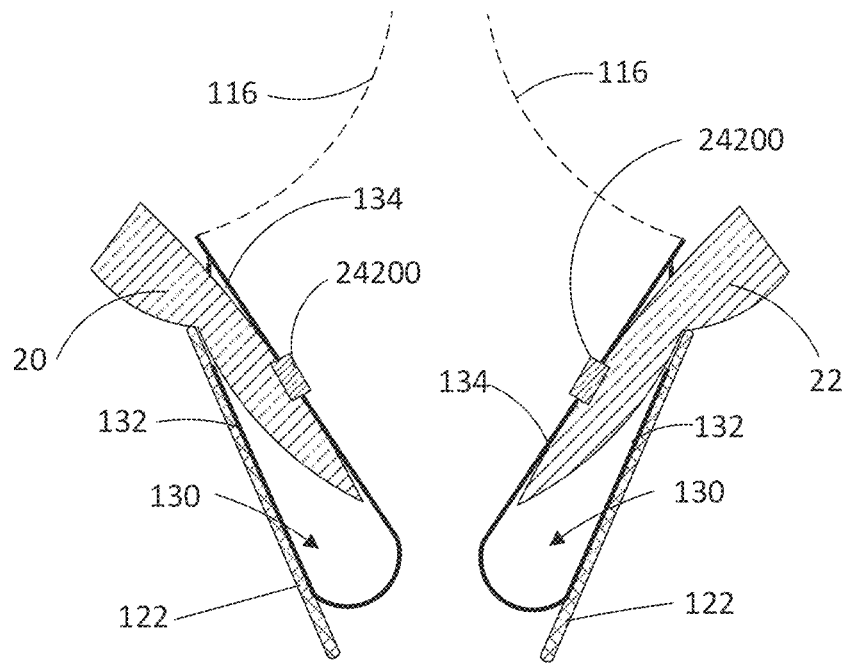
Figure 260:
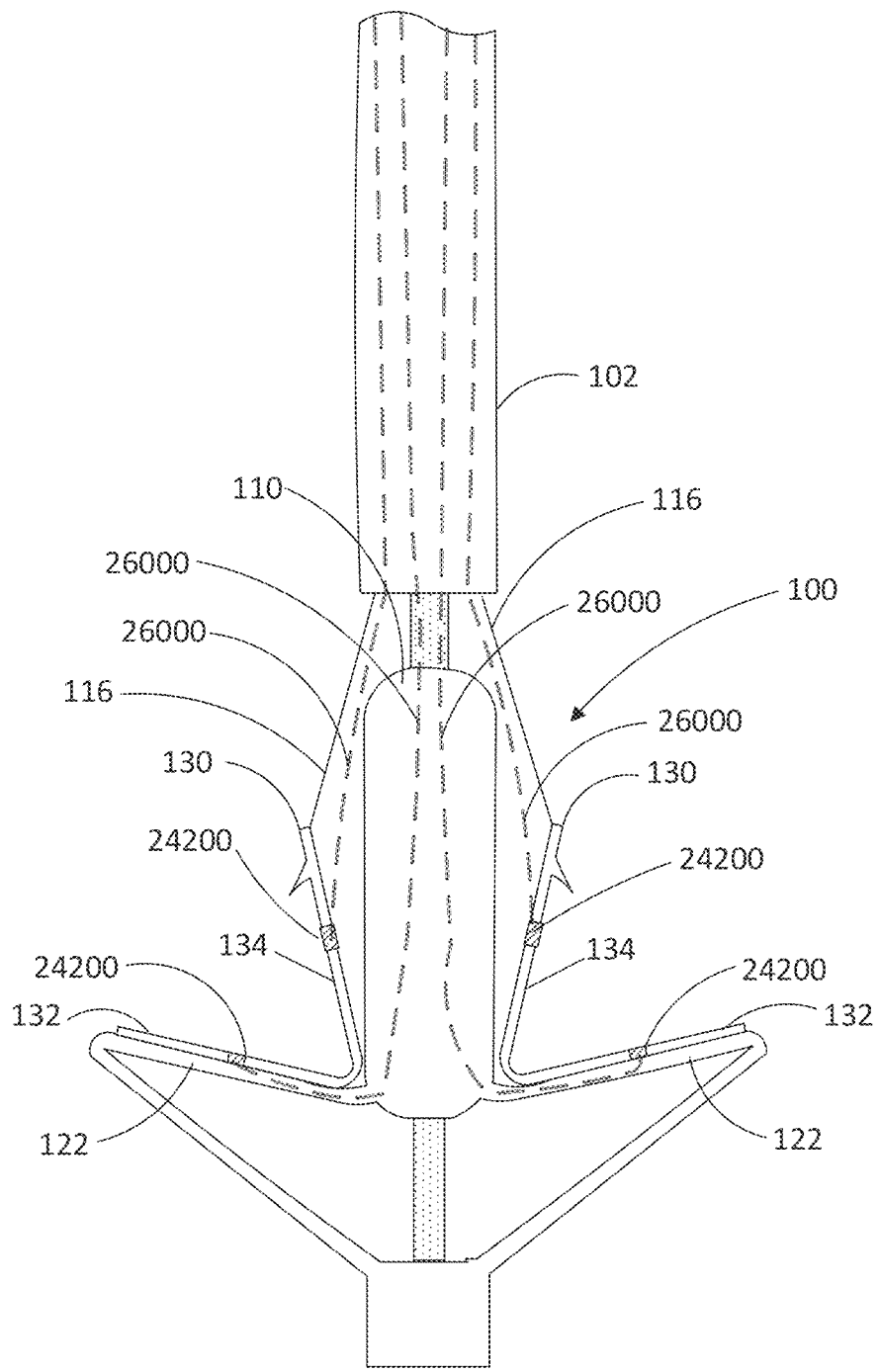
FIGS. 260-261 illustrate an example embodiment of a valve repair device with a leaflet insertion sensor.

In some example embodiments, a sensor 24200 can be used to determine whether a leaflet 20, 22 is sufficiently inserted into a clasp 130, which can be any of the clasps disclosed herein or any other clasp. The sensor 24200 can take a wide variety of different forms. The sensor 24200 can be a sensor that senses electrical, pressure, positional and/or optical characteristics of its surroundings. For example, an electrical sensor can sense resistance, capacitance, current, pressure, contact, opacity, and/or voltage. The sensor can be a wired sensor or a wireless sensor. The sensor 24200 can be configured to be removed from the device 100 and the patient or the sensor 24200 or a portion of the sensor can be configured to be left with the device 100 (See FIG. 260) after the device 100 is implanted in a patient. The device 100 can be any of the devices disclosed herein or any valve repair device. FIGS. 243-247 illustrate an example embodiment where sensors 24200 are provided on moveable arms 134 of the clasps 130. In FIG. 242, paddle portions 122 and the clasps 130 are open. The clasps 130 are positioned to grasp the leaflets 20, 22, but not at a position where the leaflets are sufficiently inserted into the device. In FIG. 243, the paddle portions 122 and the clasps are in a partially closed position. The leaflets 20, 22, are still not sufficiently inserted into the clasps. In FIG. 244, one of the clasps 130 is closed and the sensor 24200 on the closed clasp is spaced apart from the leaflet 20. The sensor 24200 provides a signal (or no signal) in response to spacing between the sensor on the closed clasp and the leaflet 20. This signal indicates that the leaflet is not sufficiently inserted into the closed clasp 130. Referring to FIG. 245, the clasp 130 is reopened and the positions of both clasps are adjusted, such that the leaflets 20, 22 become disposed in the clasps 130 at a sufficient depth. Referring to FIG. 246, one of the clasps 130 is closed and the sensor 24200 on the closed clasp contacts the leaflet 20. The sensor 24200 provides a signal (or no signal) in response to contact between the sensor on the closed clasp and the leaflet 20. This signal indicates that the leaflet is sufficiently inserted into the closed clasp 130. Referring to FIG. 247, the second clasp 130 is closed and the sensor 24200 on the second clasp contacts the leaflet 22. The sensor 24200 on the second clasp provides a signal (or no signal) in response to contact between the sensor on the second closed clasp and the leaflet 20. This signal indicates that the leaflet 22 is sufficiently inserted into the closed clasp 130. If the second sensor were spaced apart from the leaflet 22, the second sensor would provide a signal indicating that the second leaflet was not at an appropriate depth and the second clasp could be reopened and repositioned on the leaflet 22.

Figure 248:
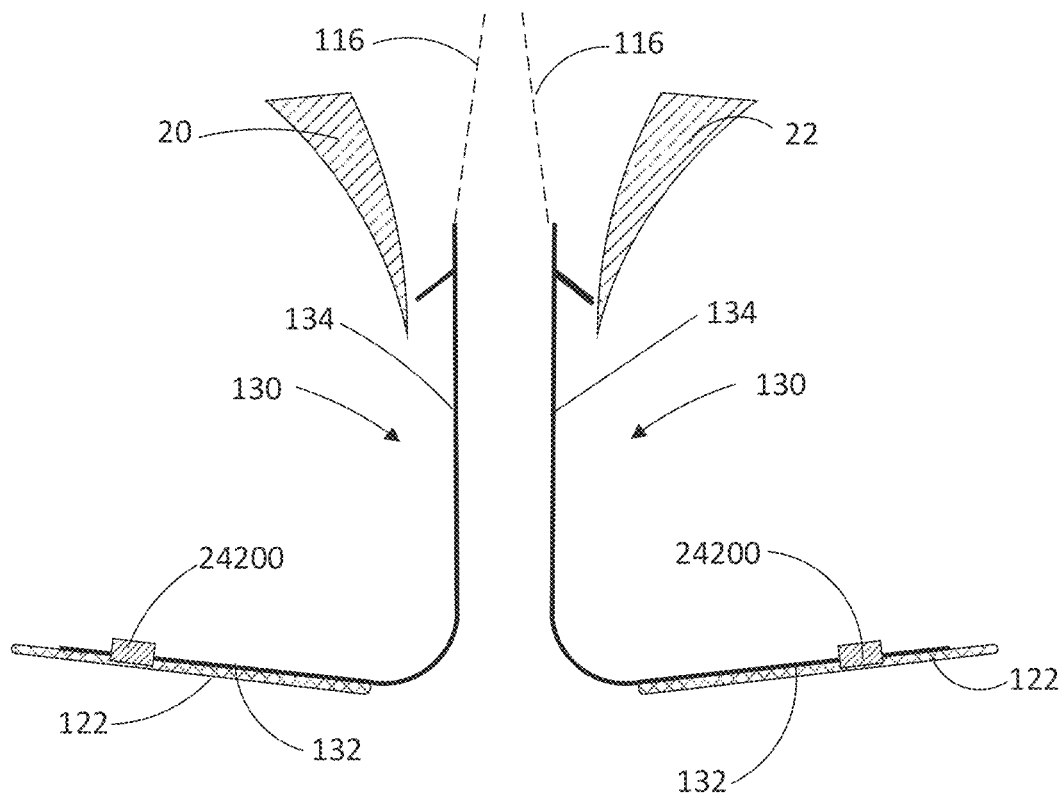
FIGS. 248-253 illustrate an example embodiment of a clasp with a leaflet insertion sensor.
Figure 249:
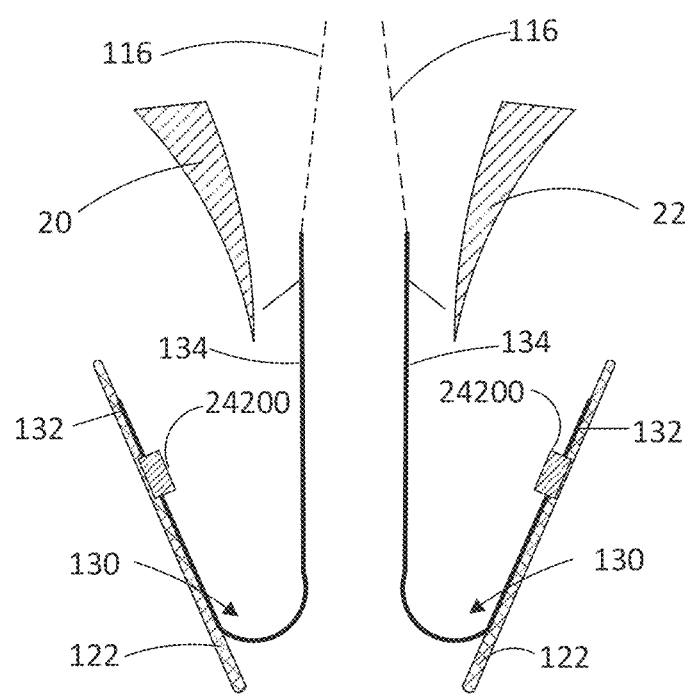
Figure 250:
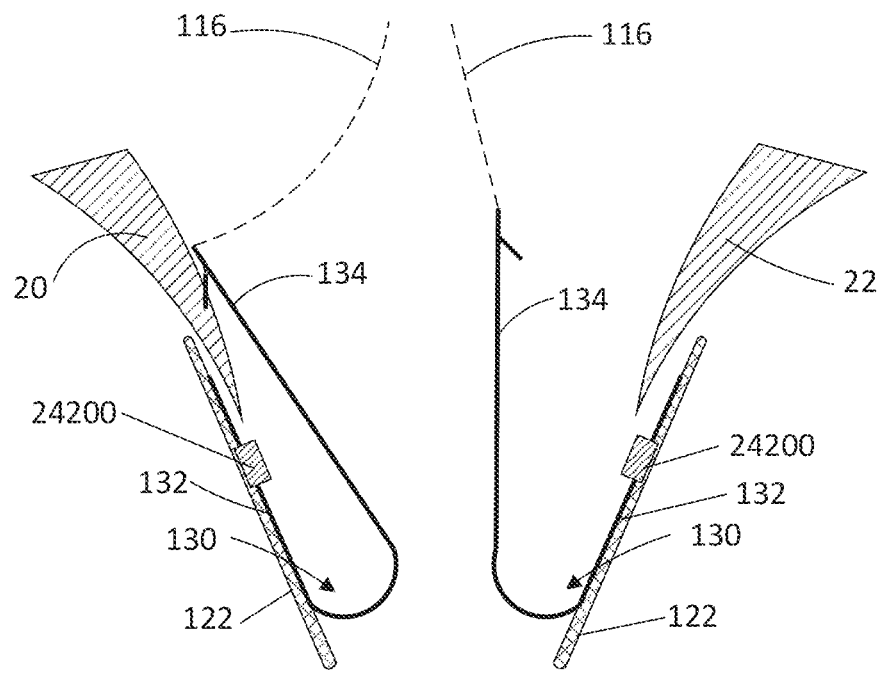
Figure 251:
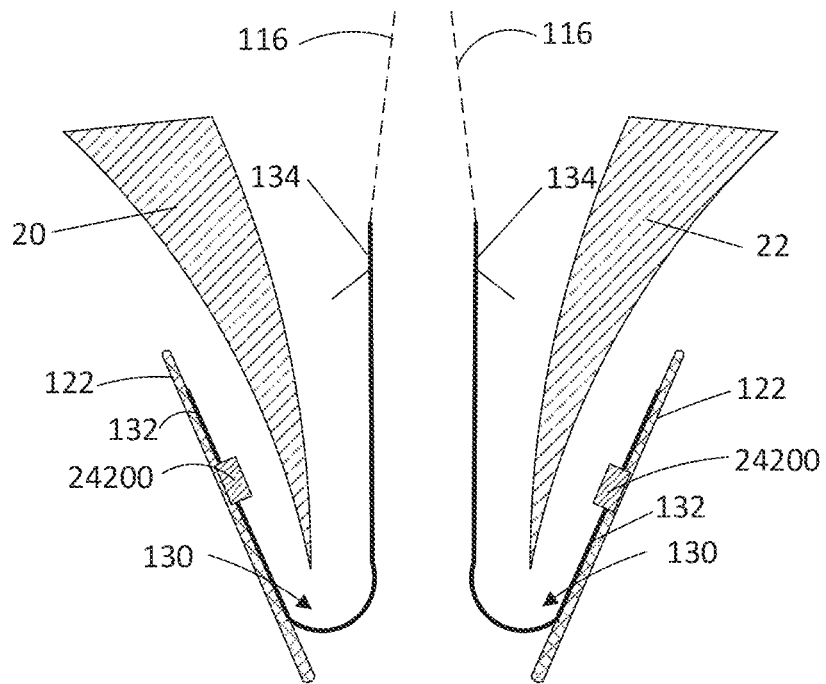
Figure 252:
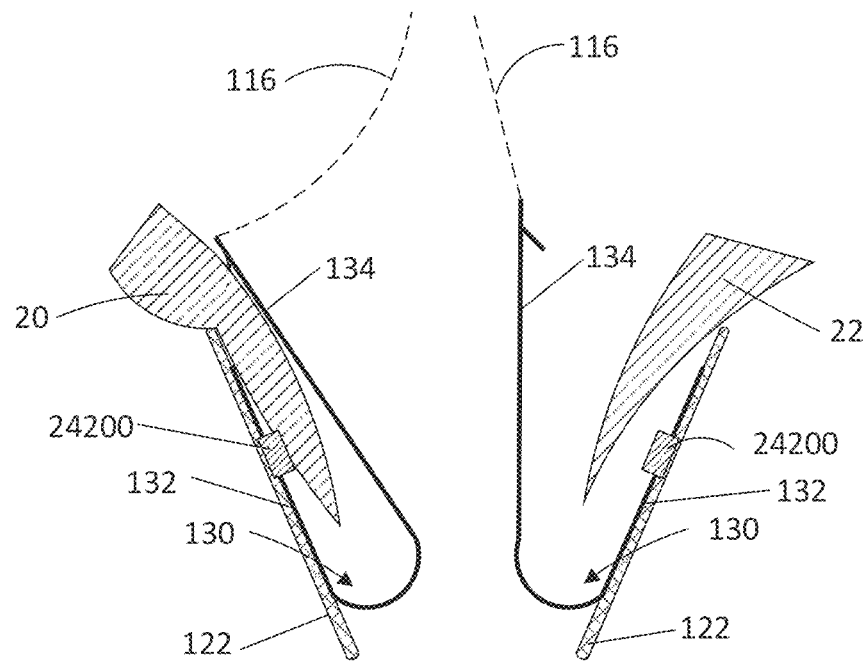
Figure 253:
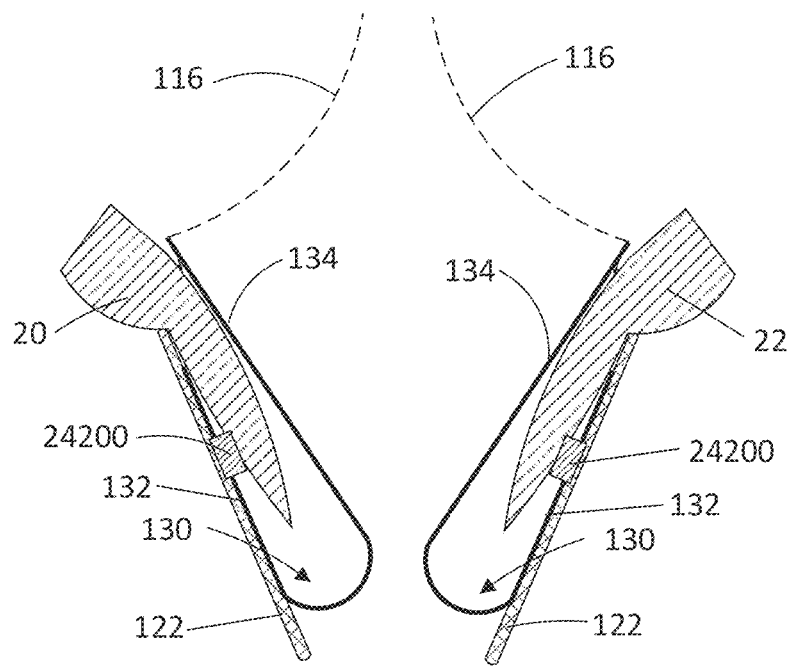

FIGS. 248-253 illustrate an example embodiment where sensors 24200 are provided on fixed arms 132 of the clasps 130. In FIG. 248, paddle portions 122 and the clasps 130 are open. The clasps 130 are positioned to grasp the leaflets 20, 22, but not at a position where the leaflets are sufficiently inserted into the device. In FIG. 249, the paddle portions 122 and the clasps are in a partially closed position. The leaflets 20, 22, are still not sufficiently inserted into the clasps. In FIG. 250, one of the clasps 130 is closed and the sensor 24200 on the closed clasp is spaced apart from the leaflet 20. The sensor 24200 provides a signal (or no signal) in response to spacing between the sensor on the closed clasp and the leaflet 20. This signal indicates that the leaflet is not sufficiently inserted into the closed clasp 130. Referring to FIG. 251, the clasp 130 is reopened and the positions of both clasps are adjusted, such that the leaflets 20, 22 become disposed in the clasps 130 at a sufficient depth. Referring to FIG. 252, one of the clasps 130 is closed and the sensor 24200 on the closed clasp contacts the leaflet 20. The sensor 24200 provides a signal (or no signal) in response to contact between the sensor on the closed clasp and the leaflet 20. This signal indicates that the leaflet is sufficiently inserted into the closed clasp 130. Referring to FIG. 253, the second clasp 130 is closed and the sensor 24200 on the second clasp contacts the leaflet 22. The sensor 24200 on the second clasp provides a signal (or no signal) in response to contact between the sensor on the second closed clasp and the leaflet 20. This signal indicates that the leaflet 22 is sufficiently inserted into the closed clasp 130. If the second sensor were spaced apart from the leaflet 22, the second sensor would provide a signal indicating that the second leaflet was not at an appropriate depth and the second clasp could be reopened and repositioned on the leaflet 22.

Figure 254:
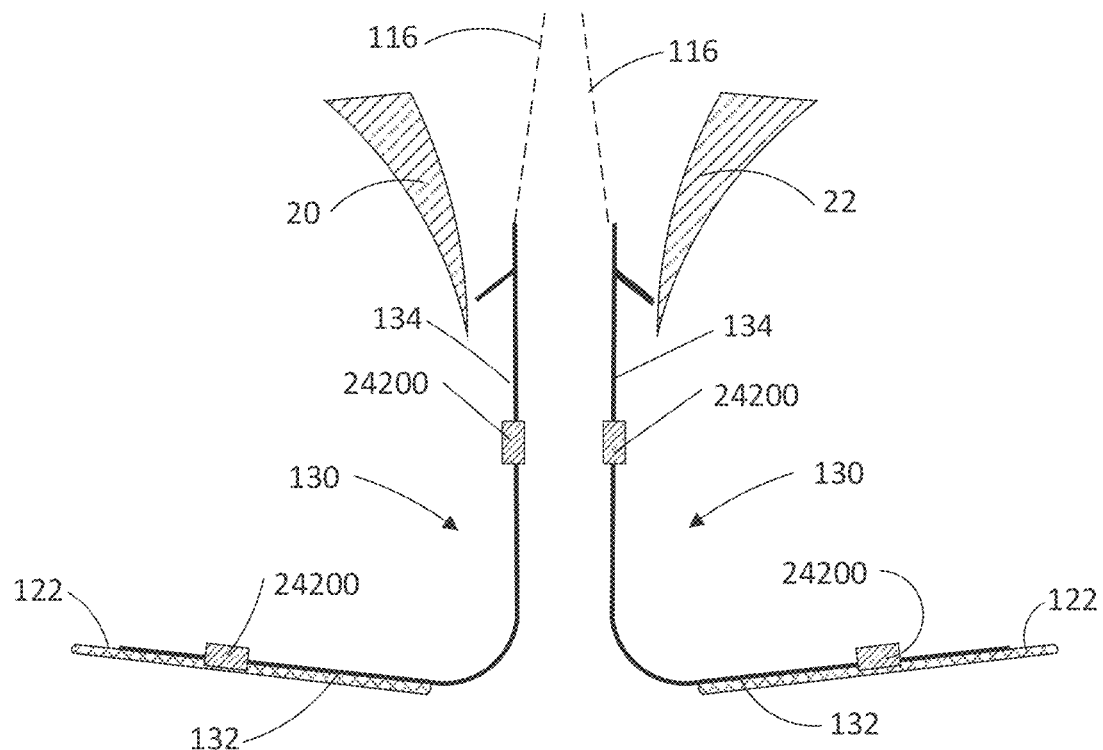
FIGS. 254-259 illustrate an example embodiment of a clasp with a leaflet insertion sensor.
Figure 255:
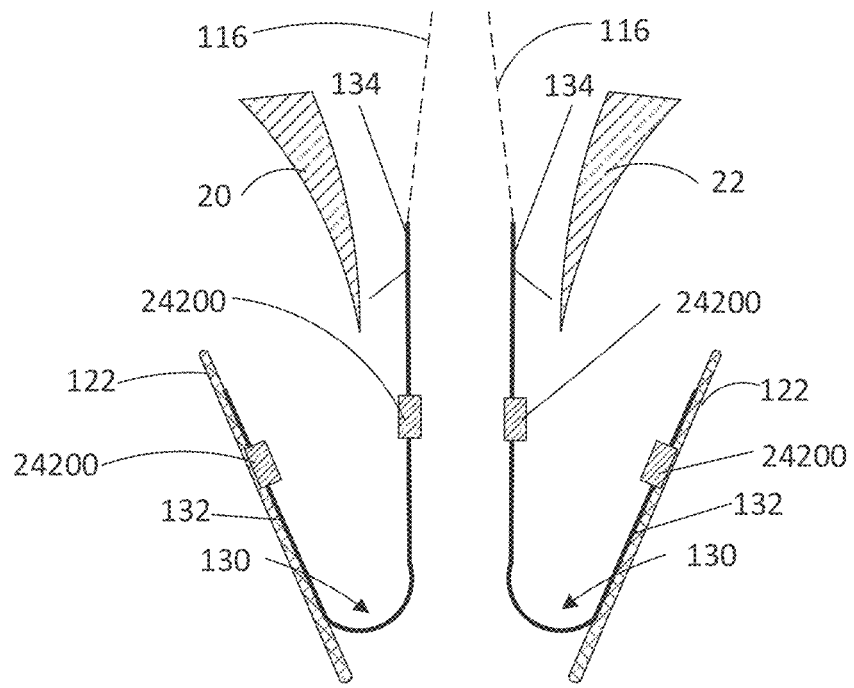
Figure 256:
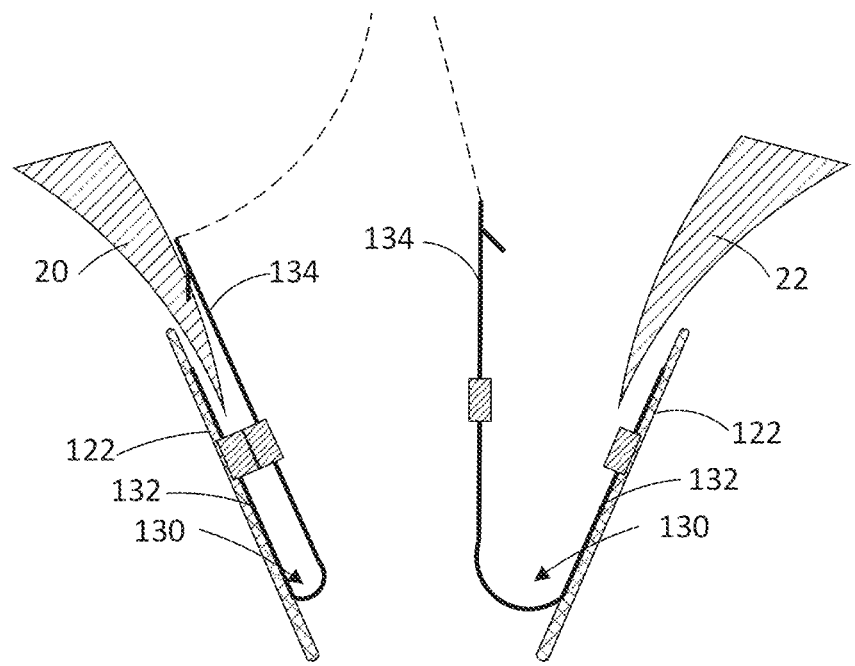
Figure 257:
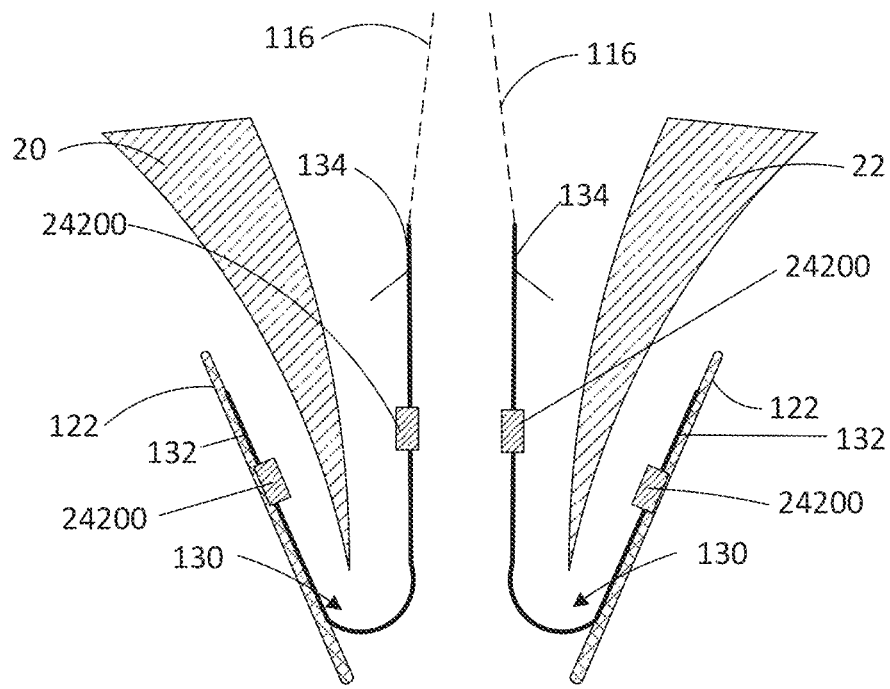
Figure 258:
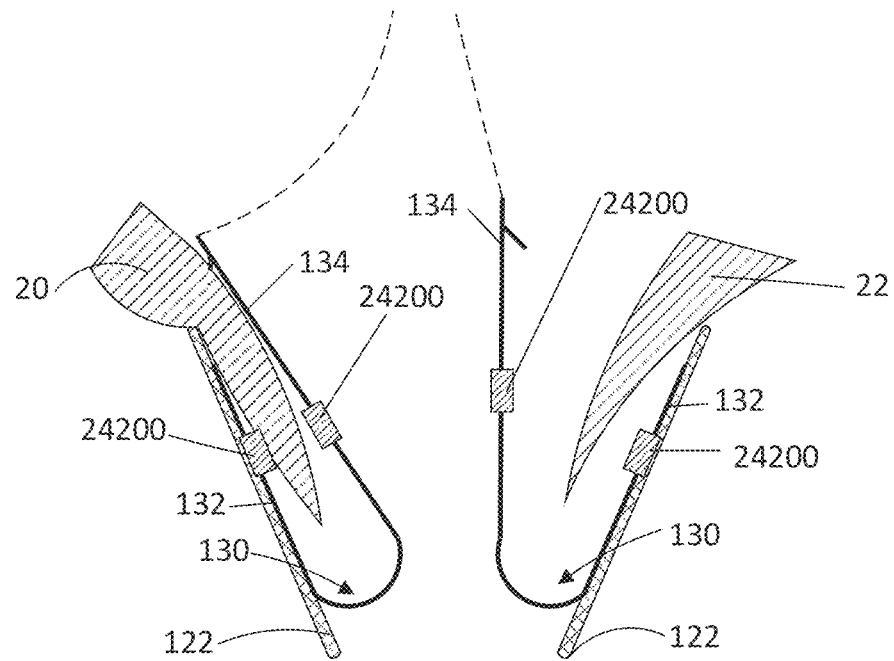
Figure 259:
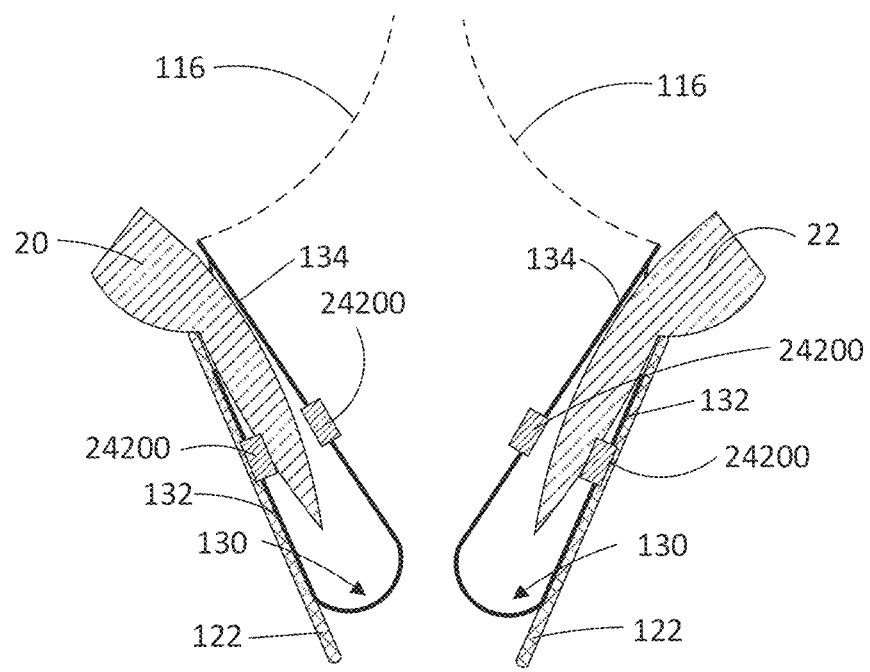

FIGS. 254-259 illustrate an example embodiment where sensors 24200 are provided on fixed arms 132 and moveable arms of the clasps 130. In FIG. 254, paddle portions 122 and the clasps 130 are open. The clasps 130 are positioned to grasp the leaflets 20, 22, but not at a position where the leaflets are sufficiently inserted into the device. In FIG. 255, the paddle portions 122 and the clasps are in a partially closed position. The leaflets 20, 22, are still not sufficiently inserted into the clasps. In FIG. 256, one of the clasps 130 is closed and two sensors 24200 on the closed clasp contact one another. The sensors 24200 provide a signal (or no signal) in response to the sensor-to-sensor contact. This signal indicates that the leaflet is not sufficiently inserted into the closed clasp 130. Referring to FIG. 257, the clasp 130 is reopened and the positions of both clasps are adjusted, such that the leaflets 20, 22 become disposed in the clasps 130 at a sufficient depth. Referring to FIG. 258, one of the clasps 130 is closed and the sensors 24200 on the closed clasp contact the leaflet 20 and/or are spaced apart by the leaflet 20. The sensors 24200 provide a signal (or no signal) in response to contact between the sensors on the closed clasp and the leaflet 20 and/or in response to the spacers being spaced apart. This signal indicates that the leaflet is sufficiently inserted into the closed clasp 130. Referring to FIG. 259, the second clasp 130 is closed and the sensors 24200 on the second clasp contacts the leaflet 22 and/or the sensors are held apart by the leaflets. The sensors 24200 on the second clasp provide a signal (or no signal) in response to contact between the sensors on the second closed clasp and the leaflet 20 and/or in response to being spaced apart. This signal indicates that the leaflet 22 is sufficiently inserted into the closed clasp 130. If the sensors on the second clasp contacted one another, the second pair of sensors would provide a signal indicating that the second leaflet was not at an appropriate depth and the second clasp could be reopened and repositioned on the leaflet 22.

Figure 261:
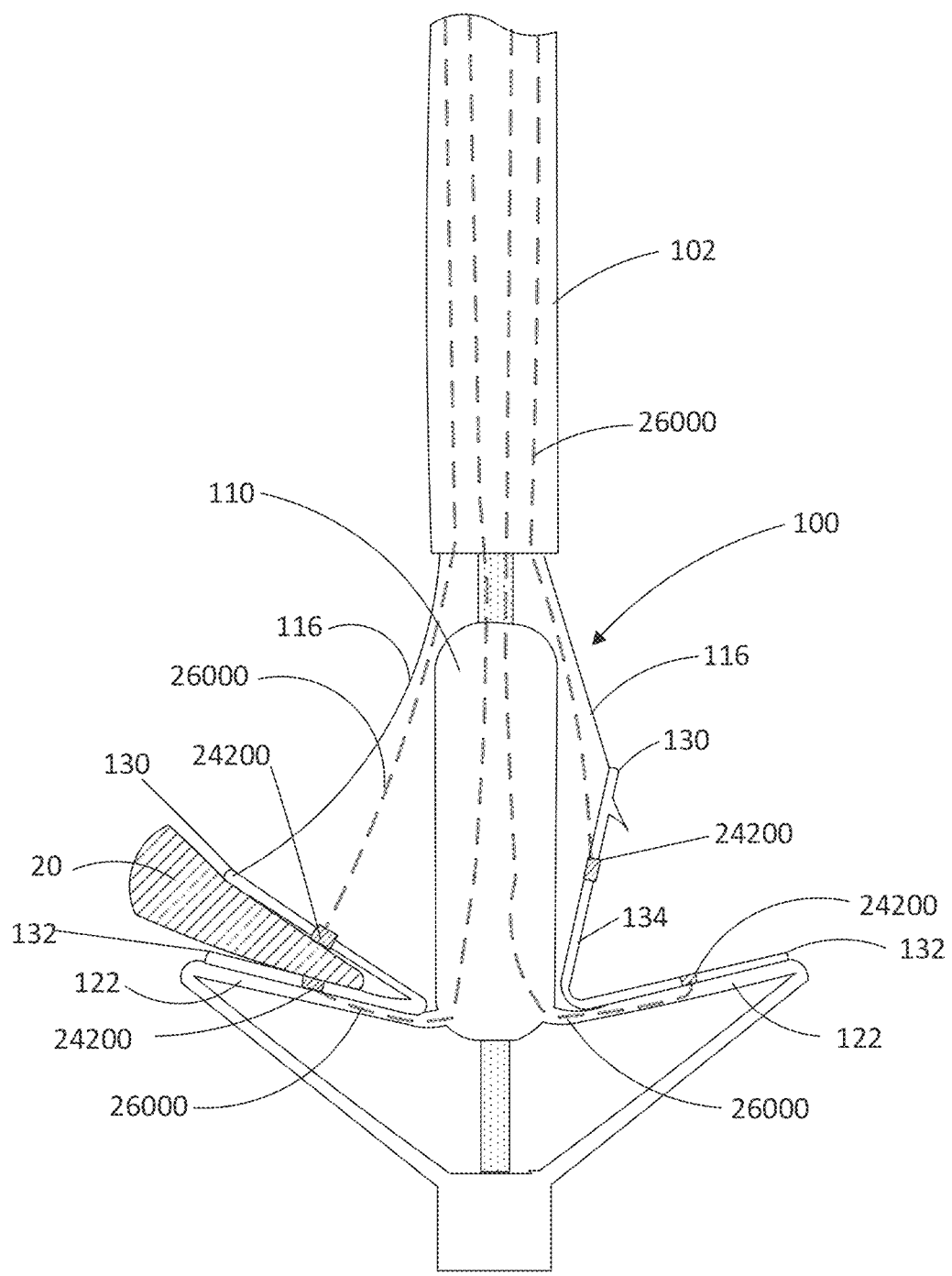

In one example embodiment, the sensors 24200 are connected to communication lines 26000, such as wires and/or optical fibers. The communication lines 26000 can be routed to the sensors in a wide variety of different ways. In the example illustrated by FIGS. 260 and 261, complimentary sensors 24200 are disposed on the moveable and fixed arms 134, 132 of the clasp 130. Communication lines 26000 that are connected to the sensors 24200 on the moveable arms 134, extend from the moveable arms and through the implant catheter 102. Communication lines 26000 that are connected to sensors on the fixed arms 132 extend from the fixed arms 132, through an optional coaption member 110, and through the implant catheter. The communication lines 26000 extend from the device, in the patient's heart, through the catheter 102, and out of the patient's body, so that proper leaflet insertion can be monitored. The sensors shown in FIGS. 260 and 261 can be used in the manner described by FIGS. 254-259 to detect proper insertion and/or capture of the leaflets 20, 22 in the clasp 130.

Figure 262:
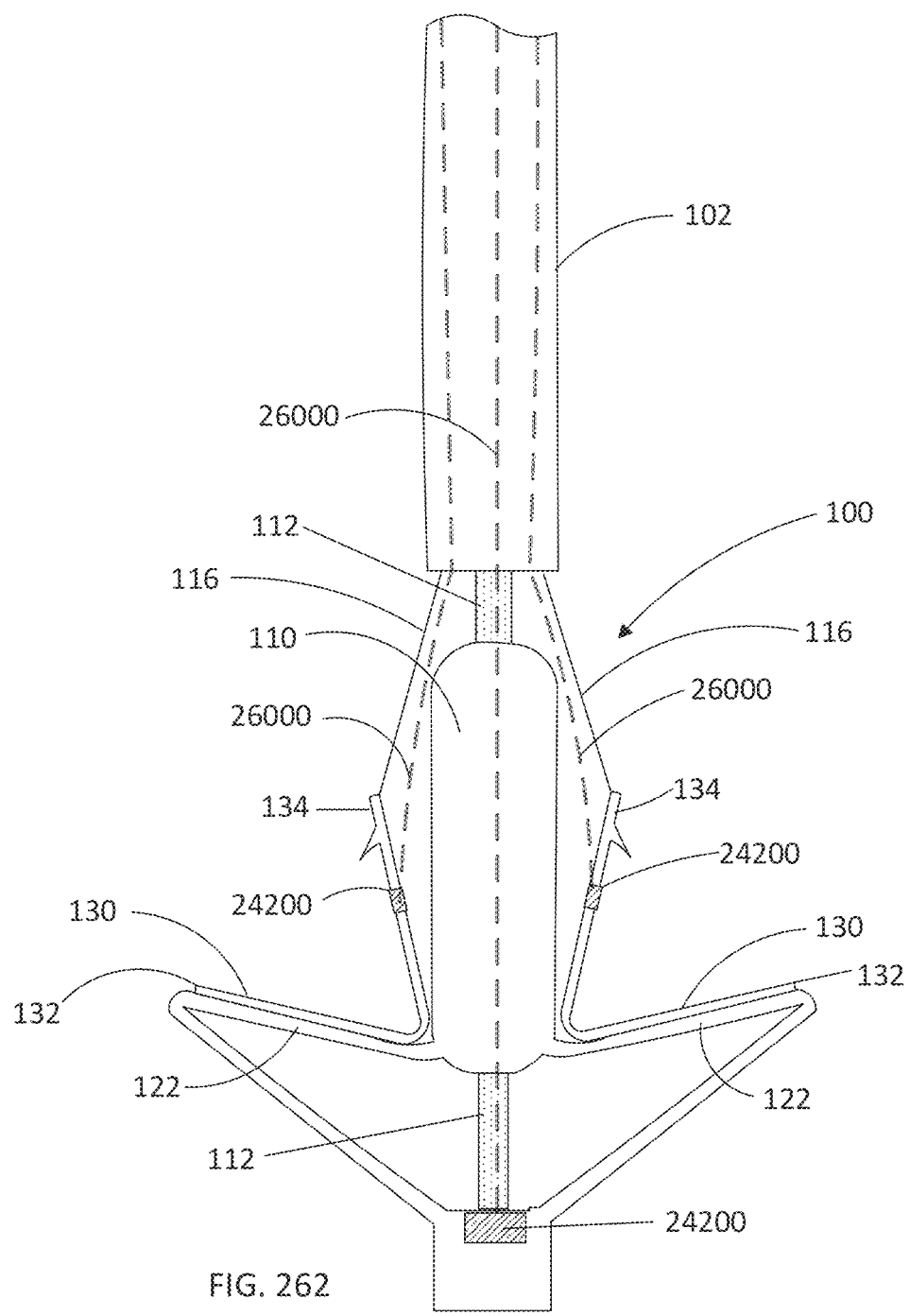
FIGS. 262-263 illustrate an example embodiment of a valve repair device with a leaflet insertion sensor.
Figure 263:
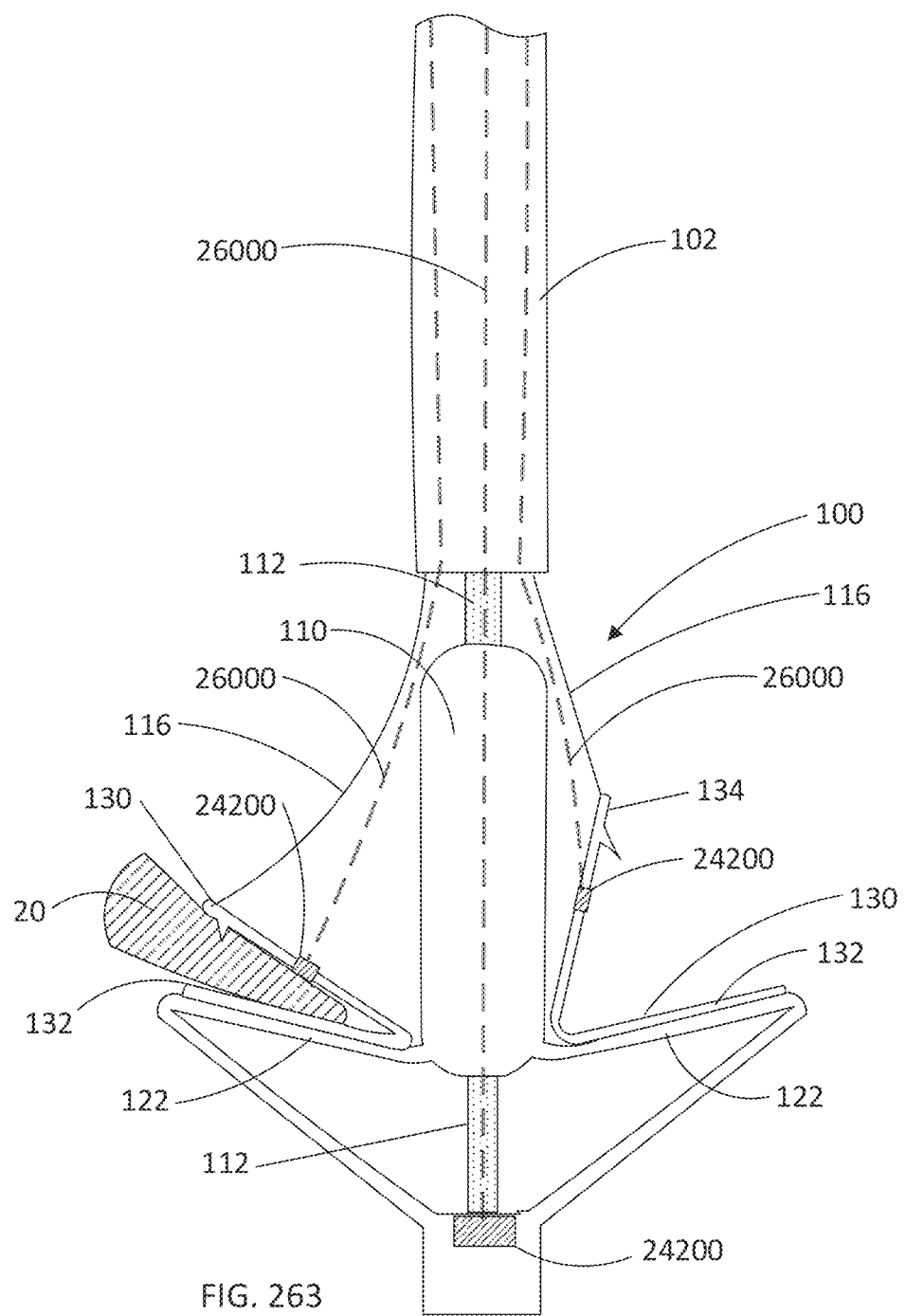

FIGS. 262 and 263 illustrates an example embodiment where sensors 24200 are connected to the moveable arms 130 and to the control wire or shaft 112. In this illustrated example, a communication line 26000 is connected to the sensor on the control wire or shaft 112 and extends through the coaption element 110, and through the catheter 102. Communication lines 26000 that are connected to the sensors 24200 on the moveable arms 134 extend from the moveable arms and through the implant catheter 102. The sensors 24200 can detect proper leaflet insertion based on the distances between the sensors on the moveable arms 134 and the sensor on the control wire 112.

Figure 264:
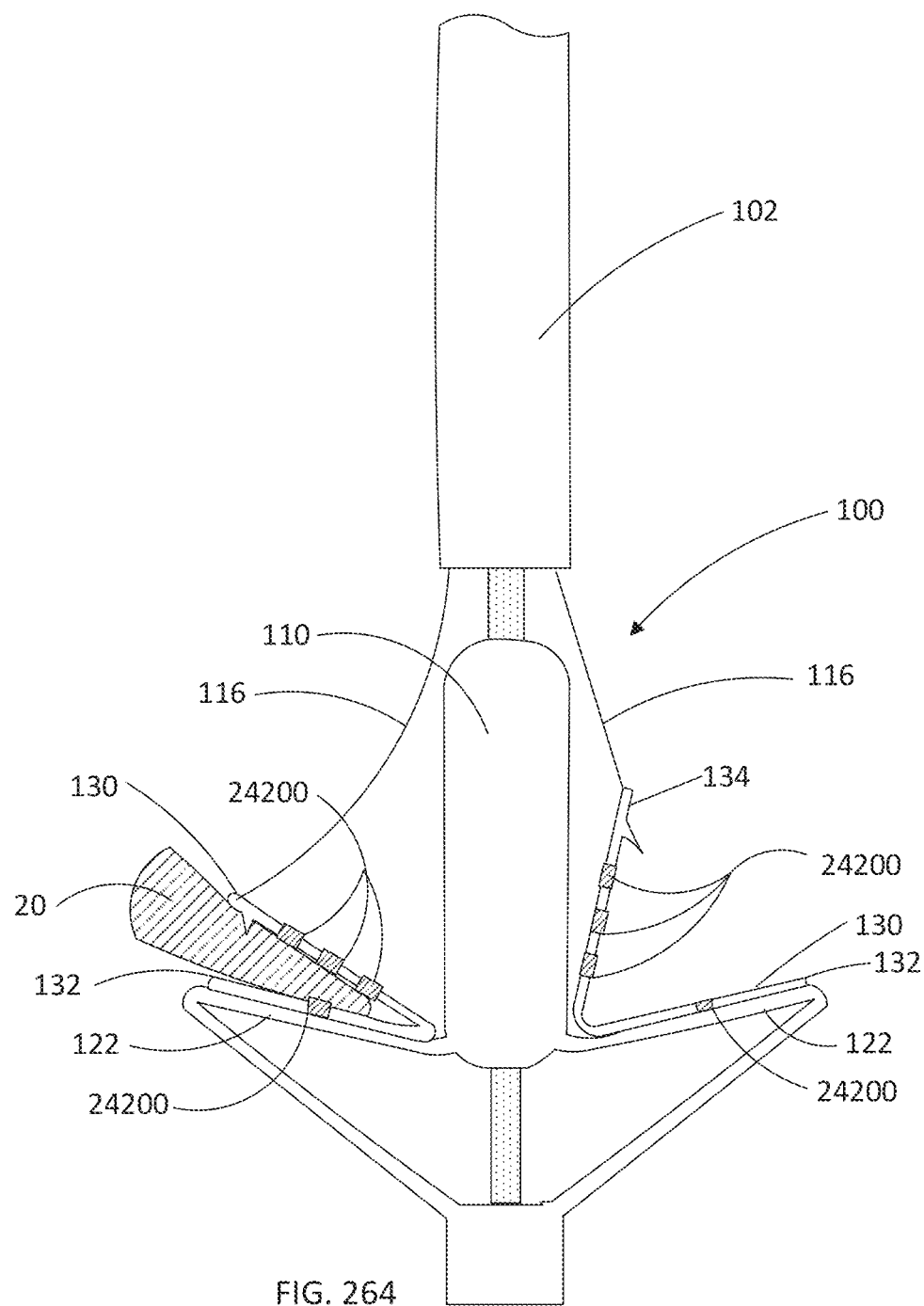
FIG. 264 illustrates an example embodiment of a valve repair device with a leaflet insertion sensor.
Figure 265:
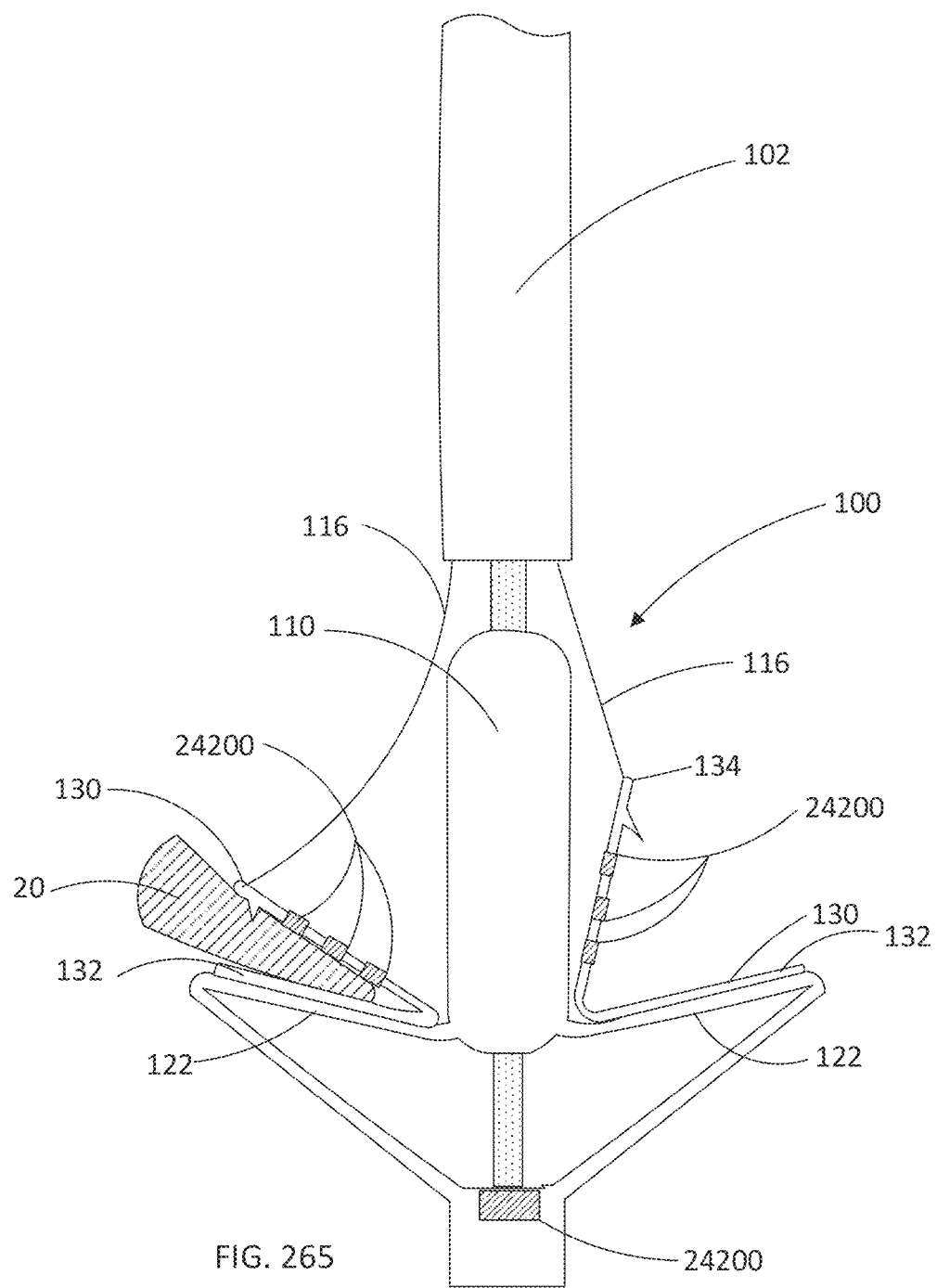
FIG. 265 illustrates an example embodiment of a valve repair device with a leaflet insertion sensor.

In some example embodiments, multiple sensors 24200 can be included to determine how far the leaflets 20, 22 are inserted into the clasp. FIGS. 264 and 265 illustrate example embodiments that are similar to the embodiments illustrated by FIGS. 262 and 263 where the moveable arm 134 of the clasp 130 includes multiple sensors for detecting the insertion depth of the leaflets 20, 22 in the clasp 130. For example, each sensor on the movable arm 134 can be used to sense contact with a leaflet 20, 22 to indicate the insertion depth of the leaflet in the clasp.

Figure 266:
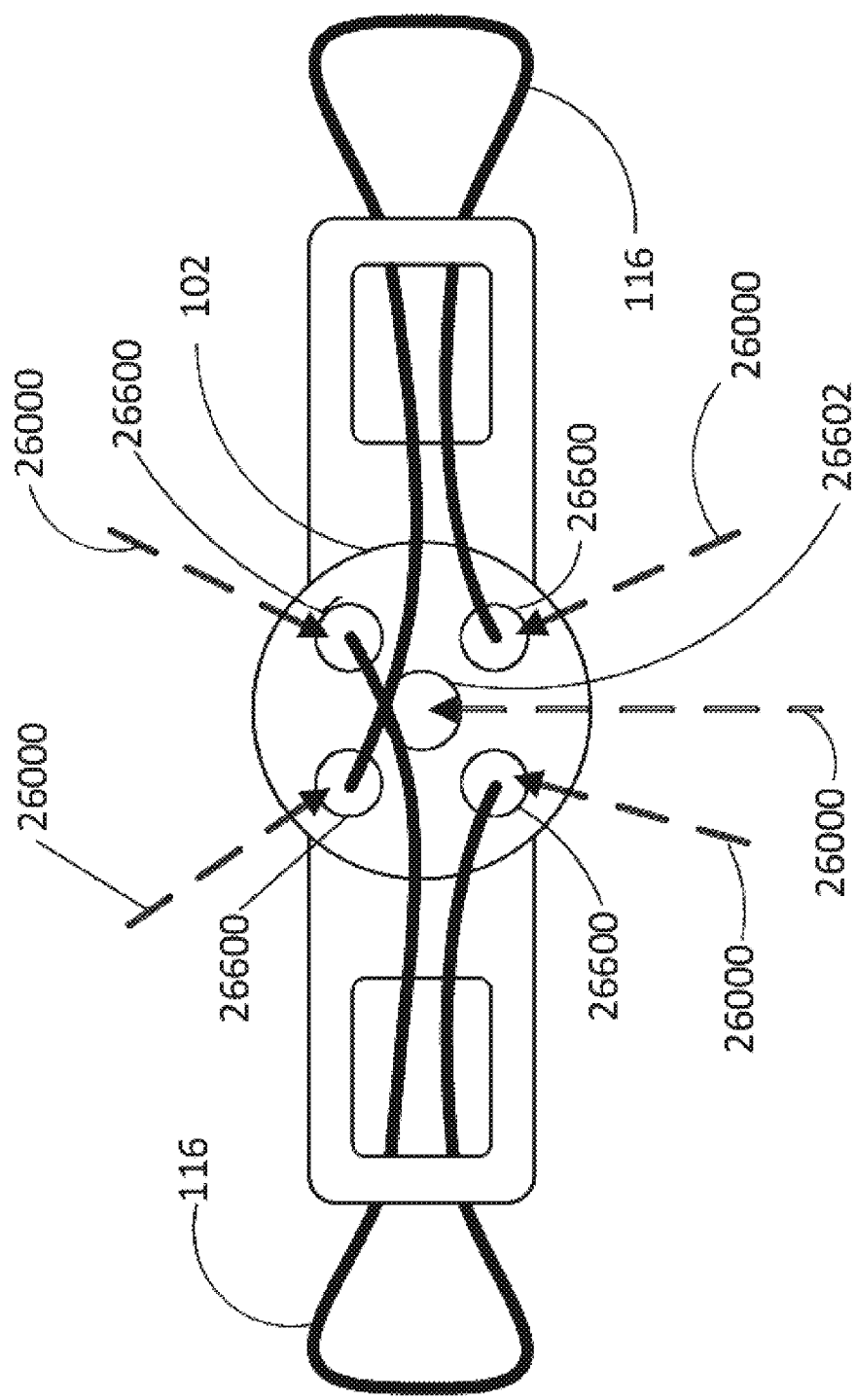
FIG. 266 illustrates an example embodiment of a catheter for a valve actuation catheter.

FIG. 266 illustrates an end of an implant catheter 102 and a coupler. Clasp actuation lines 116 extend through lumens 26600 in the catheter 102. The control wire or shaft 112 extends through a central lumen 26602 of the catheter. In one example embodiment, communication lines 26000 extend through the lumens 26600, 26602 to the sensors 24200. In one example embodiment, the control wire or shaft 112 is used as one of the communication lines 26000. In one example embodiment, the clasp actuation lines 116 act as communication lines 26000 or act as part of a communication line.

As mentioned above, the sensors 24200 can take a wide variety of different forms and the leaflets 20, 22 can be detected in a wide variety of different ways. In one example embodiment, the sensors 24200 comprise electrodes. A short, subthreshold (nA–µA), biphasic current can be applied via the electrodes incorporated in the implant to obtain a measurement of Impedance (Rz) and/or Capacitance (C). Impedance and/or capacitance changes before, during and after grasping of the leaflet with the device can be used to indicate the quality and quantity of the implant's grasp onto the leaflets.

In one example embodiment, Impedance can be measured by providing a known current (Rz=U/I) and monitoring the voltage with a current voltage converter. The capacitance (C) can be derived e.g. from the time constant ($\tau$) of the voltage change (C=$\tau$/Rz) in response to the provided current I.

In one example embodiment, Impedance rise indicates that a predetermined amount of native valve leaflet, such as 6 mm, is inserted into the clasp (See FIG. 259). Impedance drop (or short circuit—See FIG. 256) will indicate no or less than the predetermined amount of leaflet has been captured.

Capacitance increase indicates that the predetermined amount of native valve leaflet has been captured. In addition, the capacitance increase can be used to determine thickness of the captured leaflet. Detected thicknesses outside of an expected range can be used to identify a curled or rolled-in leaflet.

Referring back to FIGS. 260 and 261, in one example embodiment, the two sensors 24200 on the fixed arms 132 can be ground electrodes and the two sensors 24200 on the moveable arms 134 can be simulation electrodes (or vice versa). The position of the stimulation electrodes is aligned with the positions of the ground or reference electrodes when the clasp is closed (See FIG. 256). In one example embodiment, biphasic, subthreshold current flows from each stimulation electrode to each ground or reference electrode.

Referring back to FIGS. 262 and 263, two sensors 24200 on the moveable arms 134 can be stimulation electrodes and one sensor 24200 on the control wire 112 can be a ground electrode. That is, there is only a single ground or reference electrode in this embodiment. In the illustrated example, the ground or reference electrode is located at the distal or ventricular tip of the implant 100. In this example embodiment, the current flows from the stimulation electrodes to the ground or reference electrode. This current can be monitored during deployment of the implant 100 to detect proper leaflet insertion and capture by the clasps.

In one example embodiment, the electrodes described with respect to FIGS. 260-263 are electrically isolated from a metal frame or backbone of the device. This isolation prevents short circuiting between the stimulation and ground electrodes when the stimulation and ground electrodes are spaced apart. The electrodes can take a wide variety of different forms. For example, the electrodes can be uninsulated ends of platinum wires (simply blunt or coiled up), discs, patches of platinum or another conductive material.

Figure 267:
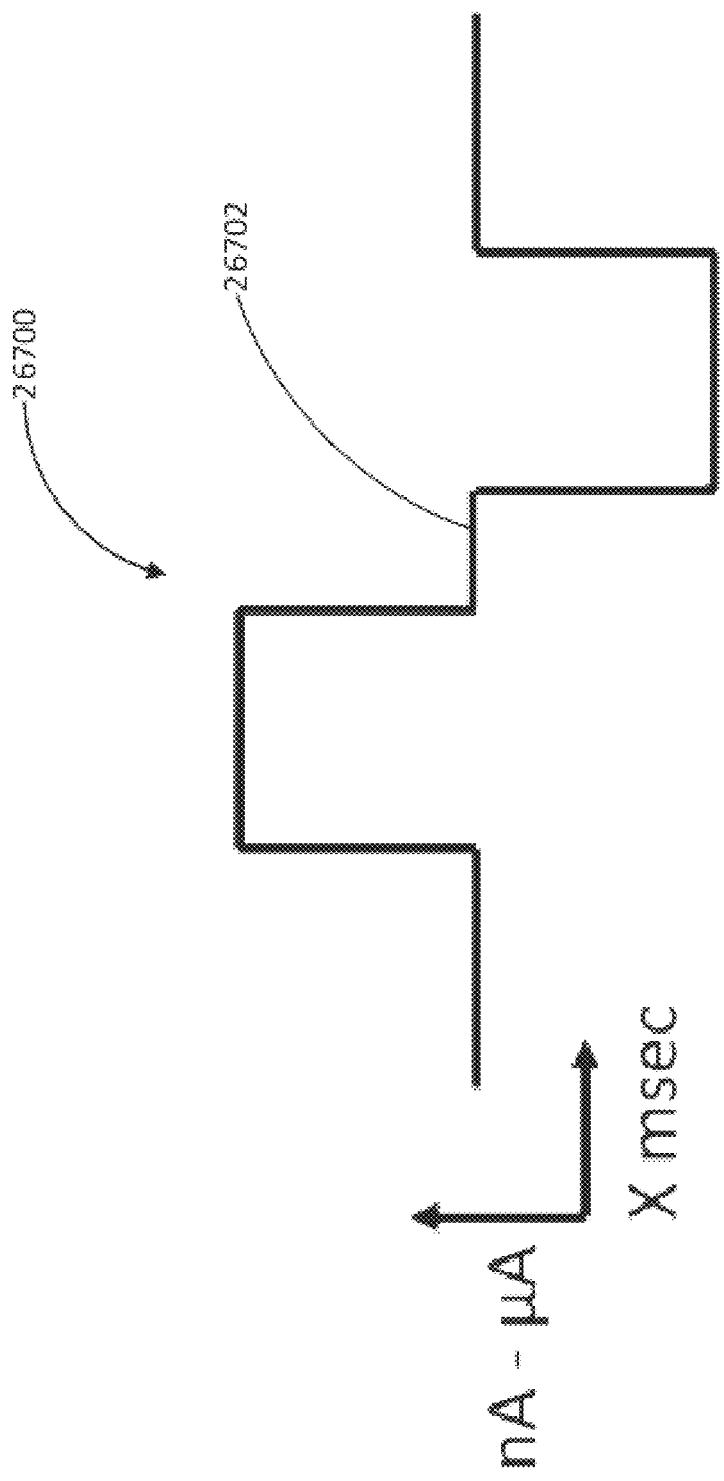
FIG. 267 is a plot of current versus time of an example method for sensing leaflet capture.

In one example embodiment, the current can be applied to the electrodes in phases. Referring to FIG. 267, the current 26700 between the stimulation electrode(s) and the ground or reference electrodes can be biphasic. The phases can each last a few to hundreds of a milliseconds (msec) with an interphase interval 26702 and are equal in charge. An external amplifier including a current voltage converter (common commercial products e.g. like in a patch clamp amplifier) can be used to measure the voltage. As a result, the impedance can be calculated in real time. The amplitude of the current is subthreshold and can be in the range of 0.1-100 µAmpere. The capacitance can be derived from the time ($\pi$) the voltage increases according to the formula:

$$C = R * \pi$$

Where C is capacitance, R is impedance, and $\pi$ is rise time (of exponential function).

Figure 268:
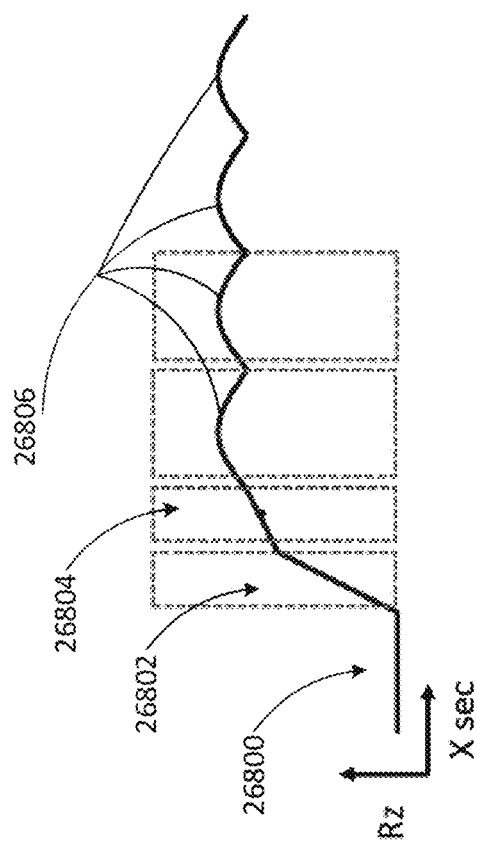

Referring to FIG. 268, impedance changes can be observed depending on the configuration of the implant and the insertion length of the leaflet. In region 26800, the implant is ready to capture the native valve leaflet. In region 26802, if enough leaflet is inserted impedance will rise when the clasps are dropped. In region 26804, the impedance will further rise when the implant is closed and reaches a plateau. In regions 26806, the impedance will periodically change from this plateau according to the opening and closing of the mitral valve.

Figure 269:
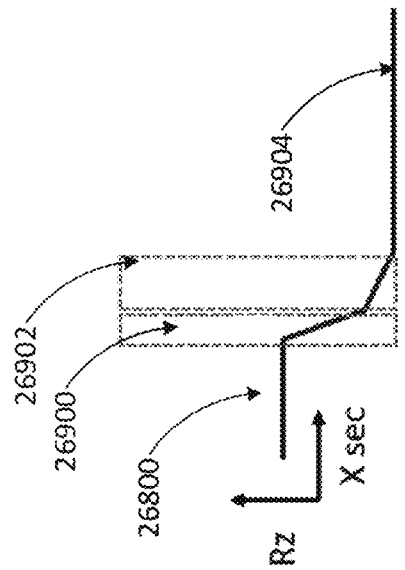
FIGS. 268 and 269 are plots of resistance versus time of an example method for sensing leaflet capture.

Referring to FIG. 269, in region 26800, the implant is ready to capture the native valve leaflet. In region 26900, if the leaflet is not inserted enough, impedance will decrease when dropping the clasps. In region 26902, the impedance will even further decrease and reach a floor 26904 when the implant is subsequently closed. No or very little impedance fluctuation can be observed when the mitral valve is opening and closing. These impedance changes therefore allow direct and instantaneous evaluation of the quality of the grasp or capture.

Figure 271:
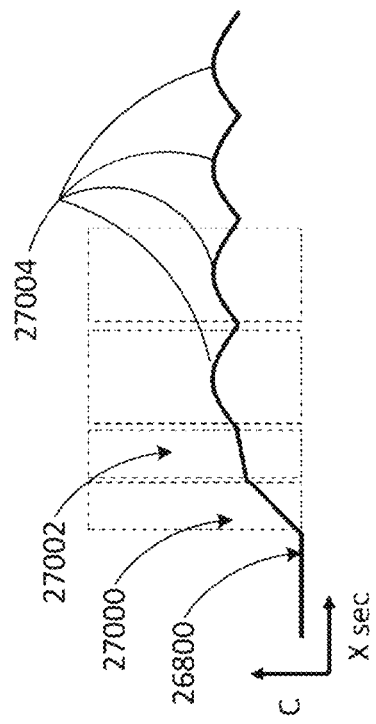
FIGS. 270 and 271 are plots of capacitance versus time of an example method for sensing leaflet capture.
Figure 270:
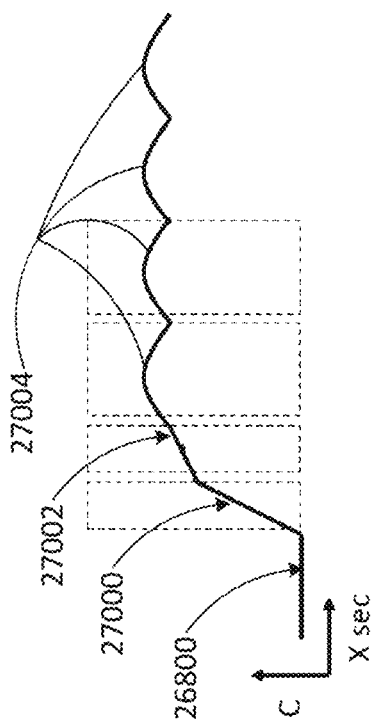

The second parameter besides impedance R that can be measured is the capacitance C between stimulation electrode and the ground or reference electrode. Referring to FIG. 270, in region 26800 low capacitance is observed in the capture ready configuration. Low capacitance is also observed when no leaflet is between the stimulation and ground or reference electrodes. In region 27000, when the leaflet is captured by the clasps, the capacitance rises. In region 27002, the paddles are closed, and the capacitance continues to rise. In regions 27004, the capacitance will periodically change according to the opening and closing of the mitral valve. FIG. 271 is the same or substantially the same as FIG. 270, except the leaflet is thicker or has curled or folded upon itself when captured by the clasp. As can be seen by comparing FIGS. 270 and 271, thinner leaflet results in higher capacitance and thicker leaflets or leaflet curling in lower capacitance. The capacitance can be related to the leaflet thickness (or folded leaflet thickness) according to the formula:

$$C = \varepsilon 0 * \frac{A}{d}$$

where:
C is Capacitance. A is the Area of the capacitator plate (i.e. the size of the electrode). d is the distance between the electrodes. And, ε0 is the electrical field constant.

In one example embodiment, to judge thickness, and flattening of the leaflet between clasp and paddle, the measured capacitance can be compared to norm values measured for known different leaflet thicknesses. Large differences can indicate curling or folding of one of the leaflets.

Referring now to FIGS. 272-274, schematic views of example embodiments of a clasp for use in an implantable prosthetic device, such as devices 100, 200, and 300 described above, are shown. Like the clasp 3500 described above, the clasp 5200 includes a fixed arm 5210, a flex or hinge portion 5220, and a moveable arm 5230 having an optional barbed portion 5240 and/or other type of friction-enhancing portion. FIG. 272 illustrates a schematic view of a clasp 5200 that has one flexible indicator 1031 on the fixed arm that fits through an opening 6730 in the moveable arm 5230. FIG. 273 illustrates a schematic view of a clasp that has two flexible indicators 1031 on the fixed arm that fit between two cutout openings 6730 on the moveable arm. When there are a plurality of flexible indicators, the flexible indicators can be aligned or offset along the length of the fixed arm.

In the example illustrated by FIG. 274, the flexible indicator 1031 has a fixed end 27402 attached to the fixed arm 5210 and a free end 27404. In the example illustrated by FIG. 274, the fixed end 27402 is farther away from the flex or hinge portion 5220 than the free end 27404. However, this orientation can be reversed. In an example embodiment, the flexible indicator 1031 is attached to the moveable arm 5230.

The flexible indicators 1031 can be part of the laser cut clasp or can be attached to the laser-cut clasp frame by welding or rivets or other known means. FIG. 274 illustrates a side schematic view of the embodiments illustrated in FIGS. 272 and 273. From the side view, the clasp appears the same, whether there is one flexible indicator 1031 or two, since the two indicators are aligned in the illustrated example. In FIG. 274, the clasp is in an open position and the flexible indicator is curved or bent into a "bump" configuration. FIGS. 274-277 also illustrate optional radiopaque indicators 1030 on the indicator 1031. The radiopaque indicator can be printed or attached as a separate piece of material to the indicator 1031. For example, the radiopaque material can be a coil made of platinum or another radiopaque material. The radiopaque indicator can be printed directly on the bump, a coil wrapped directly around the bump, or printed on a fabric covering the bump, or otherwise fixed to the bump. The radiopaque indicator is visible with fluoroscopy and/or other imaging techniques and can assist the user in determining whether the leaflet is properly positioned in the clasp.

Figure 275:
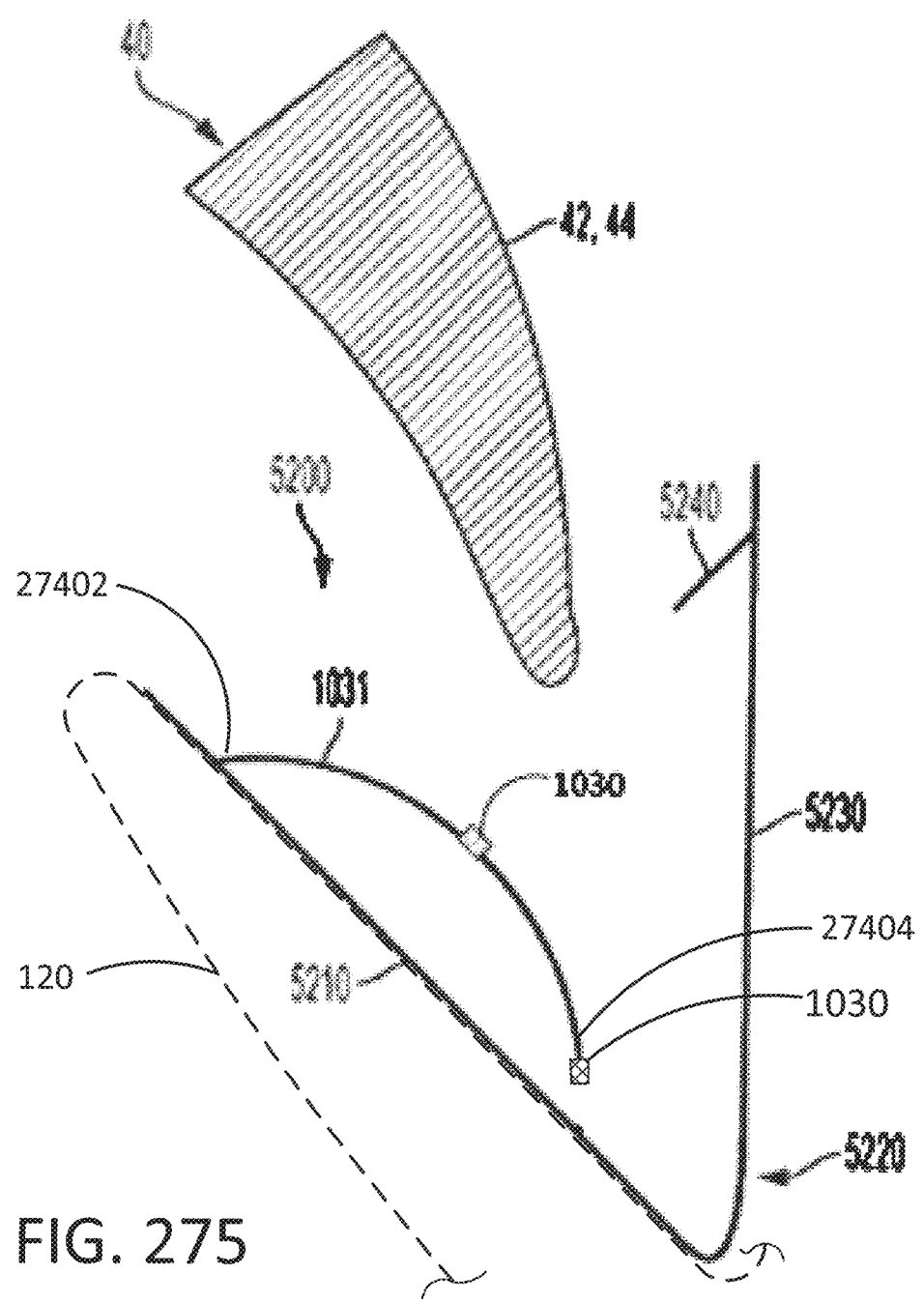
FIGS. 275-277 show the example indicator and example clasp of FIGS. 272-274 being deployed to engage with a leaflet of a native valve.
Figure 276:
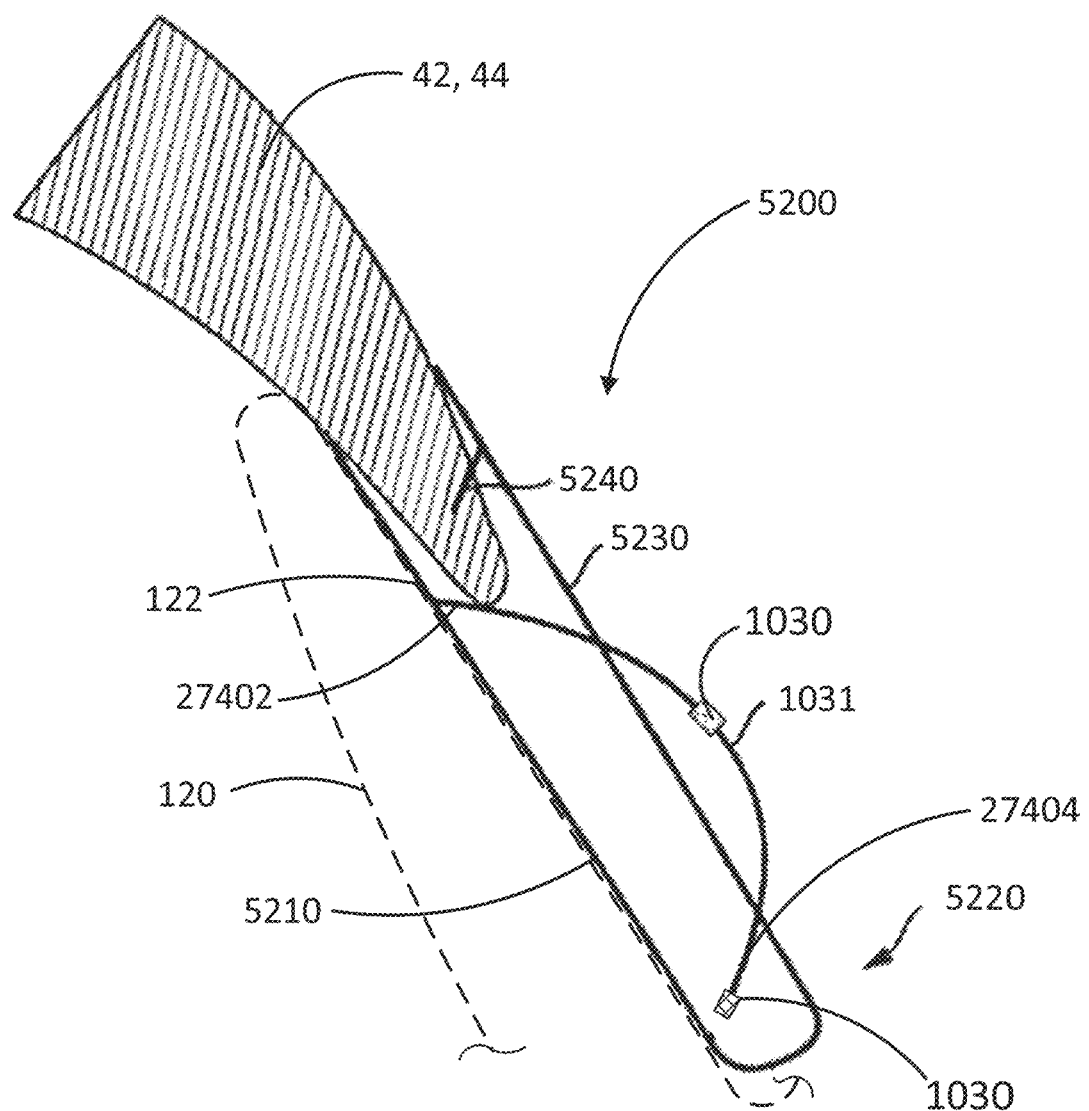
Figure 277:
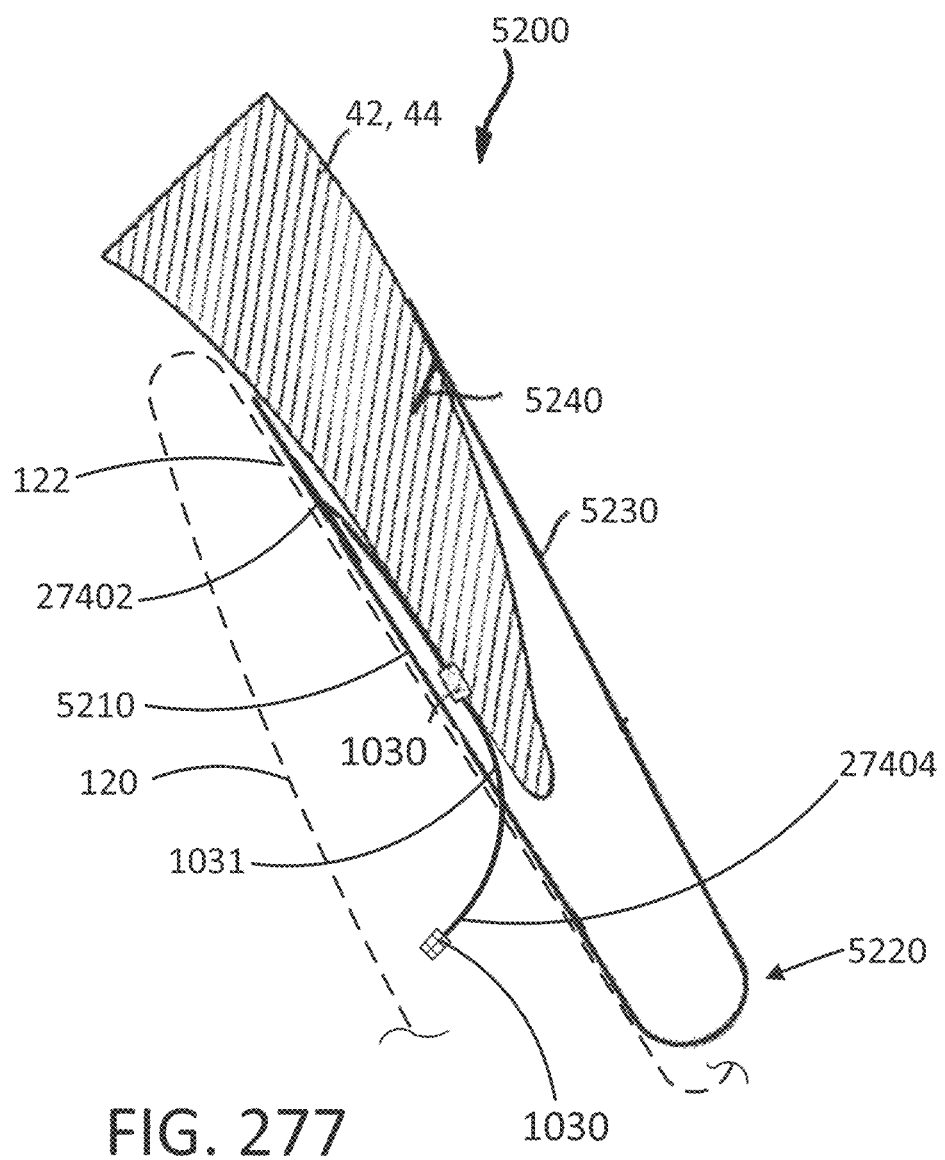

Referring to FIGS. 275-277, the indicator 1031 deforms and/or is pressed through the fixed arm 5210 when the native leaflet tissue 42 or 44 is pressed against the indicator 1031 by the moveable arm 5230 to indicate that the leaflet tissue has reached a minimum desired engagement depth. Thus, the indicator 1031 will not indicate that the native leaflet 42, 44 has reached the desired engagement depth until the leaflet 42, 44 is inserted at or beyond the location of the indicator 1031. Once the leaflet 42, 44 has reached the desired engagement depth, actuation of the moveable arm 5230 squeezes the leaflet tissue 42, 44 against the indicator 1031 on the fixed arm 5210 to cause the indicator 1031 to flatten and thereby indicate that the leaflet 42, 44 has been inserted into the clasp 5200 at or beyond the desired engagement depth. The clasp 5200 can be used in any of the implantable prosthetic devices of the present application and can include any of the features or combinations of features of the other clasps described herein.

Referring now to FIGS. 275-277, the example clasp 5200 illustrated in FIGS. 272-274 is shown being deployed within a native valve 40 to secure an implantable device (only portions of inner paddles 122 (or 222 or 322) and outer paddles 120 (or 220, 320), such as the devices 100, 200, 300 described above, to one of the native leaflets 42, 44. Referring to FIG. 275, the clasp 5200 is shown in an open condition with a native leaflet 42 or 44 partially inserted into an opening of the clasp 5200 formed between the fixed and moveable arms 5210, 5230. In the example illustrated by FIG. 275, all or substantially all of the indicator 1031 is disposed in the space between the fixed arm 5210 and the moveable arm 5230 then the clasp 5200 is open.

Referring now to FIG. 276, when the moveable arm 5230 is closed to push the leaflet 42 or 44 against the fixed arm 5210, the leaflet 42 or 44 contacts a portion of the fixed arm 5210, while not contacting the indicator 1031 or only contacting a small portion of the indicator. In the example illustrated by FIG. 276, all or substantially all of the indicator 1031 remains positioned on the side of the fixed arm 5210 that faces away from the inner paddle portion 120. This indicates that the engagement depth of the leaflet 42 or 44 is less than the minimum engagement depth.

In the insufficient leaflet engagement example illustrated by FIG. 276, the indicator 1031 extends through the moveable arm 5230. In this example, a marker 1030 on a middle portion of the indicator 1030 is disposed on a side of the moveable arm 5230 that faces away from the fixed arm 5210 and a marker 1030 on the free end 27404 is in the space between the fixed arm 5210 and the moveable arm 5230. However, the indicator 1031, clasp 5200, and/or optional markers can be configured to indicate insufficient leaflet engagement in a wide variety of different ways.

Referring now to FIG. 277, when the moveable arm 5230 is closed to push the leaflet 42 or 44 against the fixed arm 5210, the leaflet 42 or 44 contacts a substantial portion of the indicator, such as ¼, ½, or more of the indicator 1031. In the example illustrated by FIG. 277, a portion of the indicator 1031 is flattened and/or a portion of the indicator is pressed through the fixed arm 5210. This indicates that the engagement depth of the leaflet 42 or 44 is greater than or equal to the minimum engagement depth.

In the sufficient leaflet engagement example illustrated by FIG. 277, the indicator 1031 extends through the fixed arm 5210 and the inner paddle 122. In this example, the portion of the indicator 1031 that extends through the fixed arm 5210 is disposed in a space between the inner paddle 122 and the outer paddle 120. As such, the indicator 1031 is completely disposed inside the device, such as the device 100, 200, 300. In this example, the marker 1030 on a middle portion of the indicator 1030 becomes adjacent to the fixed arm 5210 and the marker 1030 on the free end 27404 moves toward the outer paddle 120, in the space between the inner paddle 122 and the outer paddle 120. However, the indicator 1031, clasp 5200, and/or optional markers can be configured to indicate sufficient leaflet engagement in a wide variety of different ways.

Figure 278:
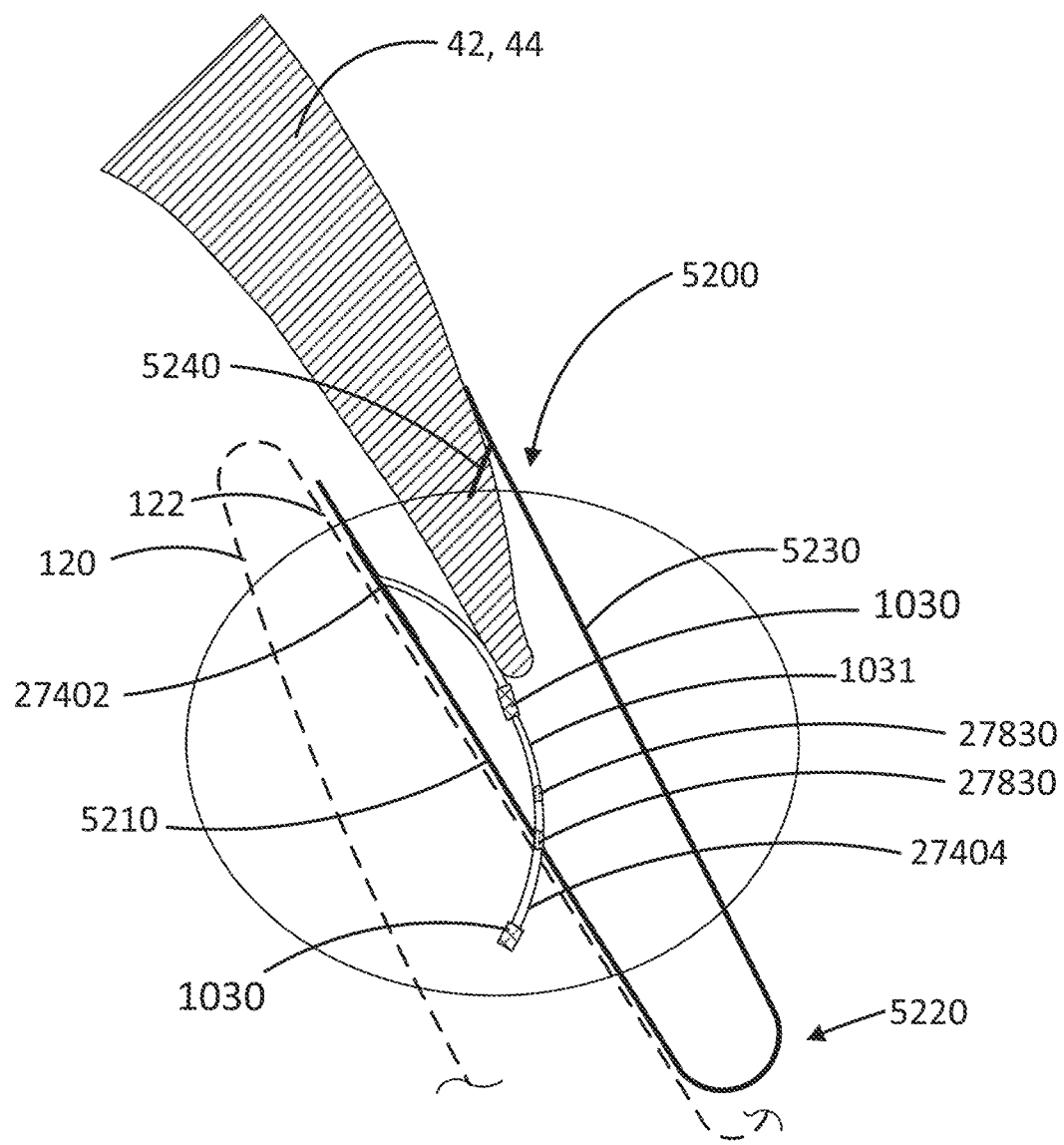
FIGS. 278 and 279 illustrate an embodiment similar to the embodiment of FIGS. 272-274 where the curved indicator includes leaflet depth markers.
Figure 279:
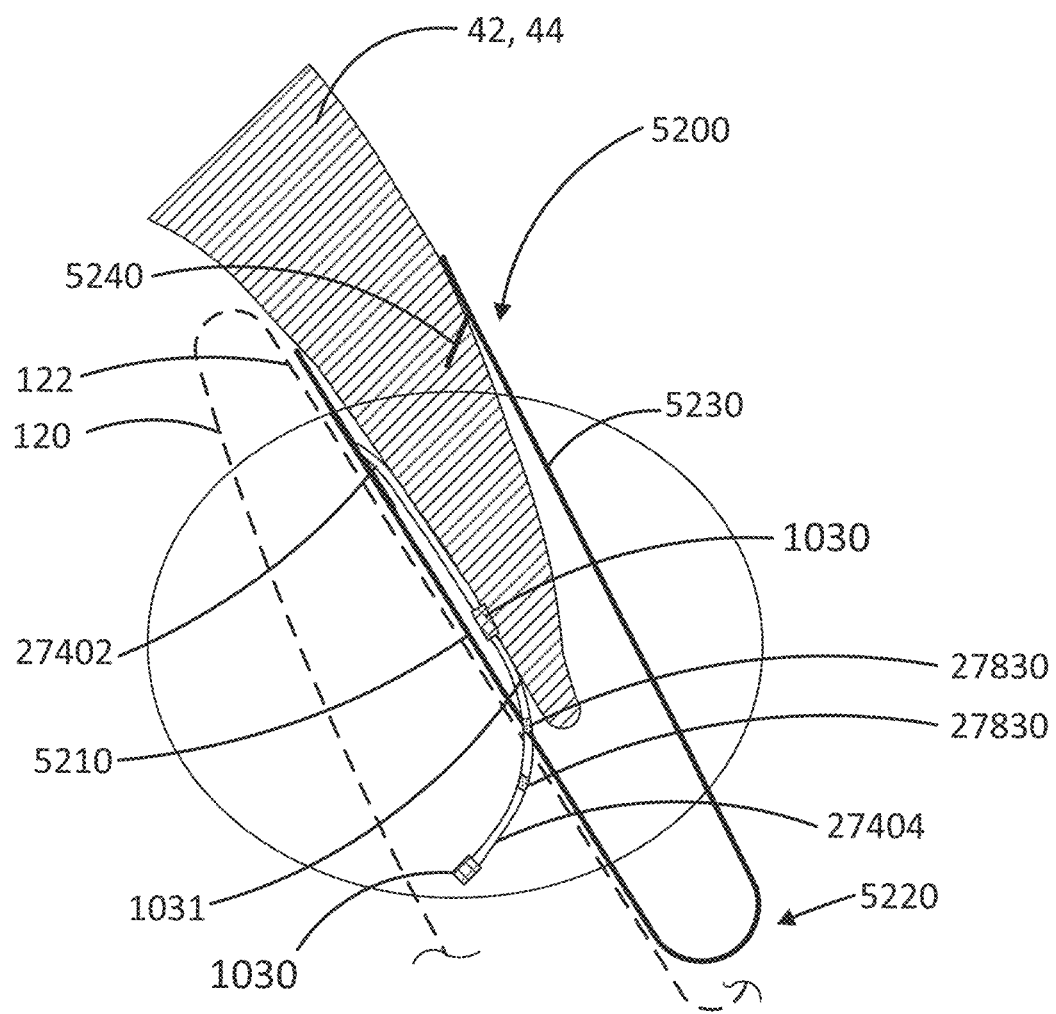
Figure 279A:
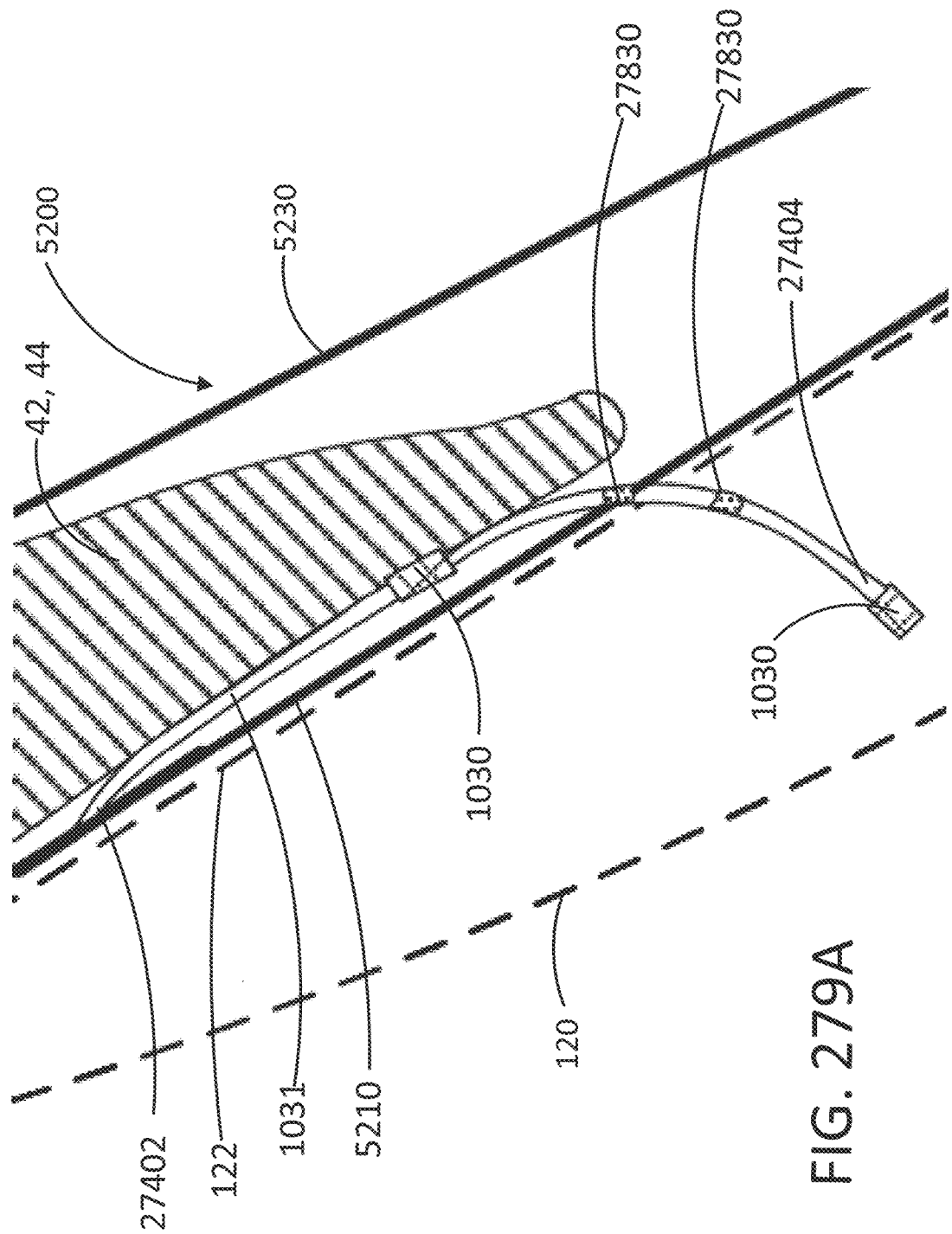

Referring to FIGS. 278, 278A, 279, and 279A, in some example embodiments, one or more secondary markers 27830 can be included to determine how far the leaflets 42 or 44 are inserted into the clasp. The secondary markers 27830 can be formed in any of the ways that the markers 1030 are formed or the secondary markers can take other forms. FIGS. 278, 278A, 279, and 279A illustrate example embodiments that are similar to the embodiments illustrated by FIGS. 272-277 where the indicator 1031 includes one or more additional markers 27830 that indicate the insertion depth of the leaflets 20, 22 in the clasp 130. For example, each additional marker 27830 will cross the fixed arm 5210 at a predetermined amount of leaflet insertion. In FIG. 278 an additional indicator 27830 that is closest to the flex or hinge 5220 crosses the fixed arm 5210 to indicate a first insertion depth. In FIG. 279 the next additional indicator 27830 crosses the fixed arm 5210 to indicate another, deeper insertion depth.

The indicators 1031 shown in and described with respect to FIGS. 272-277 can take a wide variety of different forms and can be used with a wide variety of different clasps. For example, the indicators shown in FIG. 272-277 can include any of the features of any of the indicators shown and described herein and can be used with any of the clasps shown and described herein.

Figure 280:
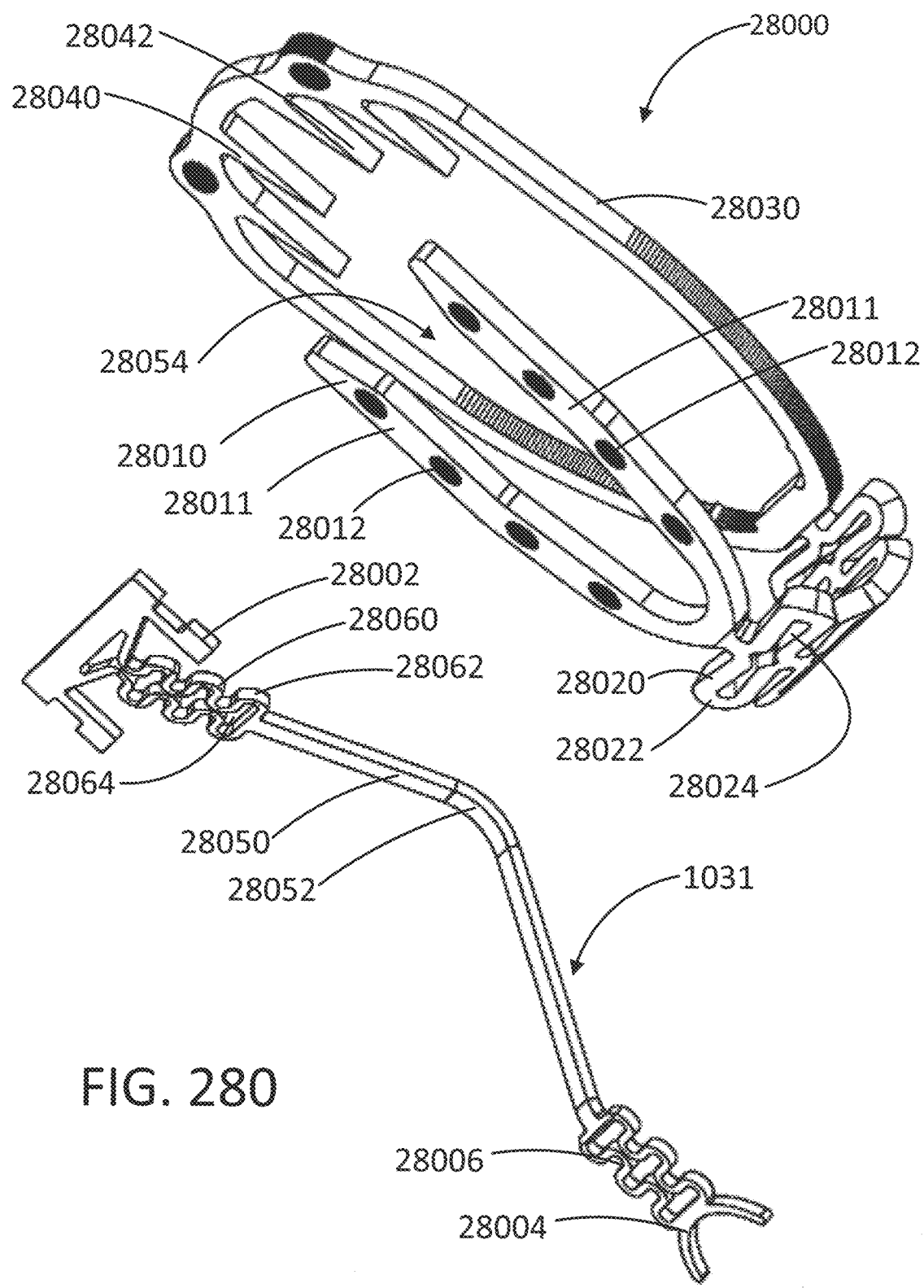
FIG. 280 is an exploded perspective view of an example embodiment of a clasp and indicator.
Figure 281:
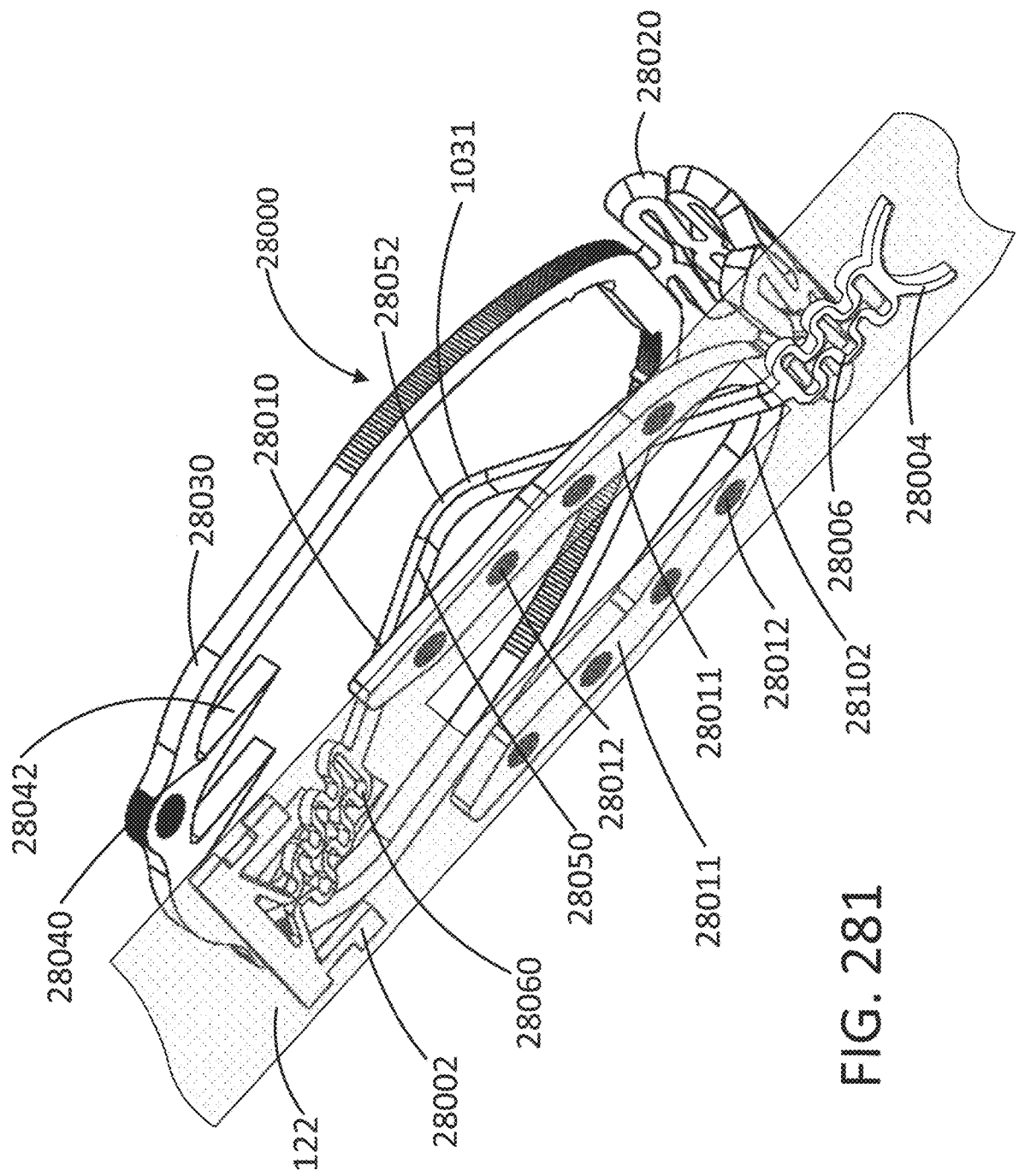
FIG. 281 is a perspective view of the example clasp and example indicator of FIG. 280 assembled with an inner paddle of a valve repair device.

FIGS. 280 and 281 illustrate one of the many different configurations that the clasp and indicator of FIGS. 272-277 can take. In the example illustrated by FIGS. 280 and 281, an example clasp 28000 and an indicator 1031 for use in implantable prosthetic devices, such as devices 100, 200, 300 described above, are shown. The clasp 28000 has a fixed arm 28010, a patterned flex portion or patterned hinge portion 28020, a moveable arm 28030 formed in the shape of a hoop or loop with a barbed portion 28040.

In the example illustrated by FIGS. 280 and 281, the indicator 1031 is formed separately from the clasp 28000. The indicator 1031 can be connected to the clasp in a wide variety of different ways. In the example illustrated by FIGS. 281-284, both the fixed arm 28010 of the clasp and the indicator 1031 are attached to the inner paddle 122.

In the example illustrated by FIGS. 280 and 281, the indicator 1031 includes a connector 28002, a flex or hinge portion 28060, an indicator arm 28050, and a marker support 28004. The flex or hinge portion 28060 extends from the connector 28002. The indicator arm 28050 extends from the indicator flex or hinge portion 28060. The marker support 28004 is connected to the indicator arm 28050 by an optional flex or hinge portion 28006. In some example embodiments, the marker support 28004 is connected directly to the indicator arm 28050 or is part of the indicator arm 28050.

The clasp 28000 and indicator 1031 can be used in any of the implantable prosthetic devices of the present application and can include any of the features or combinations of features of the other clasps described herein. For example, the clasp 28000 can be laser cut from a flat sheet or a tube of shape-memory alloy, such as Nitinol, and then shape-set into a desired shape.

The illustrated fixed arm 28010 has two tongue portions 28011 that each include holes 28012 for attaching the fixed arm 28010 to a paddle of an implantable device (See FIG. 281). A central opening 28054 arranged between the tongue portions 28011 is wider than the indicator arm 28050 so that the indicator arm 28050 can pass through the fixed arm 28010 between the tongue portions 28011. In the example illustrated by FIG. 281, the inner paddle 122 also includes a cutout or slot 28102 that the indicator arm 28050 passes through.

The patterned flex portion or patterned hinge portion 28020 is formed from a plurality of spring segments 28022 and cutouts 28024. The two tongue portions 28011 of the fixed arm 28010 extend from one end of the patterned flex portion or patterned hinge portion 28020 and the moveable arm 28030 extends from the other end of the flex or hinge portion 28020.

The moveable arm 28030 of the clasp 28000 has a hoop-like shape. The hoop-like shape of the moveable arm 28030 provides for a wider barbed portion 28040 that can include more barbs 28042 with the same or greater lateral spacing than other clasps. The wider spacing of the barbs 28042 improves capture of the native leaflets. The barbs 28042 are also longitudinally staggered as a result of their position on the hoop-like shape of the moveable arm 28030. That is, two center barbs are arranged further away from the flex or hinge portion 28020 and two outer barbs are arranged closer to the flex or hinge portion 28020.

In the example illustrated by FIGS. 280 and 281, the flex or hinge portion 28060 is bent, a central portion 28052 of the indicator arm 28050 is bent, and the flex or hinge portion 28006 is bent to form an inverted "V" or other "bump" shape. Referring to FIG. 281, the fixed arm 28010 of the clasp 28000 and the connector 28002 are aligned and connected to the inner paddle 122. Once the fixed arm 28010 and the connector 28002 are connected to the inner paddle, the indicator arm 28050 extends into the interior of the hoop-shaped moveable arm 28030 when the clasp is closed, and the indicator is not obstructed. In the examples illustrated by FIGS. 272-284, the indicator arm is passive or automatic (i.e. separate actuation of the indicator 1031, such as by an actuation line, relative to the clasp is not required).

The indicator flex or hinge portion 28060 allows the indicator arm 28050 to move relative to the fixed arm 28010 and the moveable arm 28030. This facilitates detection of the depth of engagement of the native leaflet 42 or 44 arranged between the moveable arm 28030 and the fixed arm 28010 of the clasp 4400. The indicator flex or hinge portion 28060 can be similar to the patterned flex/hinge portion 28020 and can be formed from a series of spring segments 28062 and cutouts 28064 as illustrated. In some embodiments, the spring force of the indicator flex or hinge portion 28060 is less than the pinching force imparted to the moveable arm 28030 by the flex or hinge portion 4420.

Figure 282:
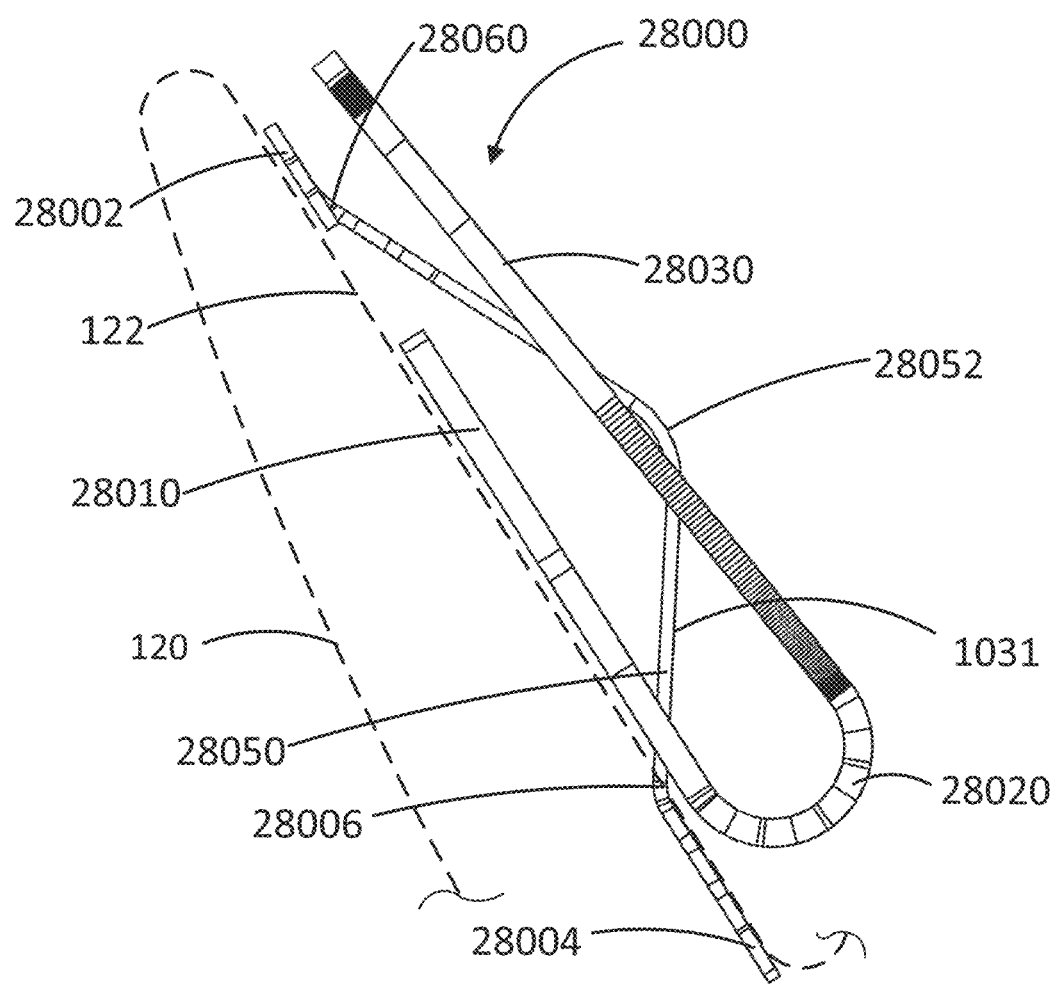
FIG. 282 is a side view of the example clasp and example indicator of FIG. 280 assembled with a paddle of a valve repair device.
Figure 283:
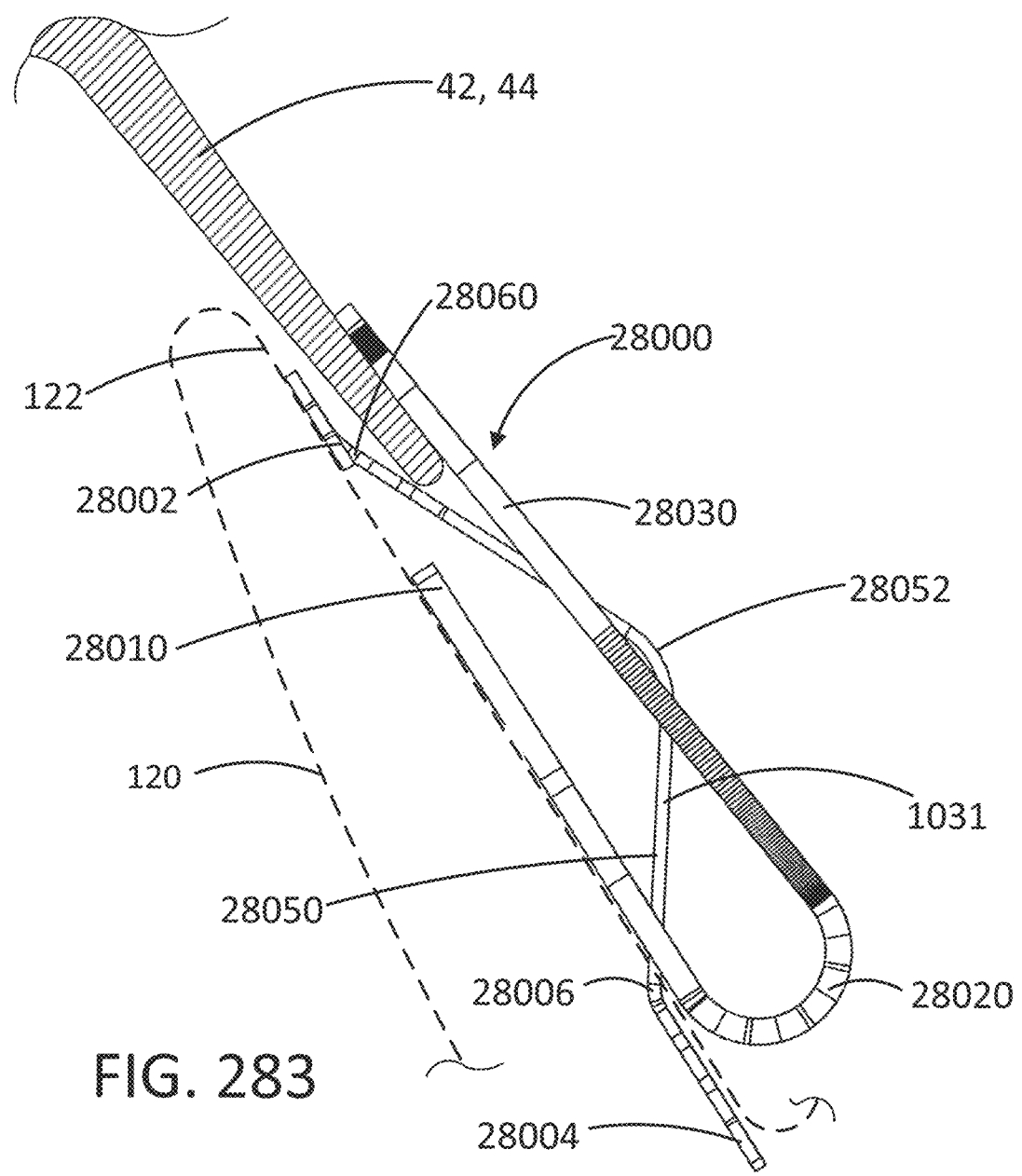
FIG. 283 shows the example indicator and example clasp of FIG. 282 with a native valve leaflet inserted into the clasp to a less than sufficient predetermined depth.

Referring now to FIGS. 281-283, the clasp 28000 is shown with the indicator arm 28050 in a fully deployed or extended position. That is, the furthest extent that the indicator arm 28050 is capable of reaching when the indicator arm 28050 does not engage with the leaflet tissue during actuation. In the fully actuated position, the indicator arm 28050 crosses the moveable arm 28030 that is visible via imaging devices so that the operator knows that the indicator arm 28050 has not engaged the leaflet (FIG. 282) or not properly engaged the leaflet (FIG. 283).

Figure 284:
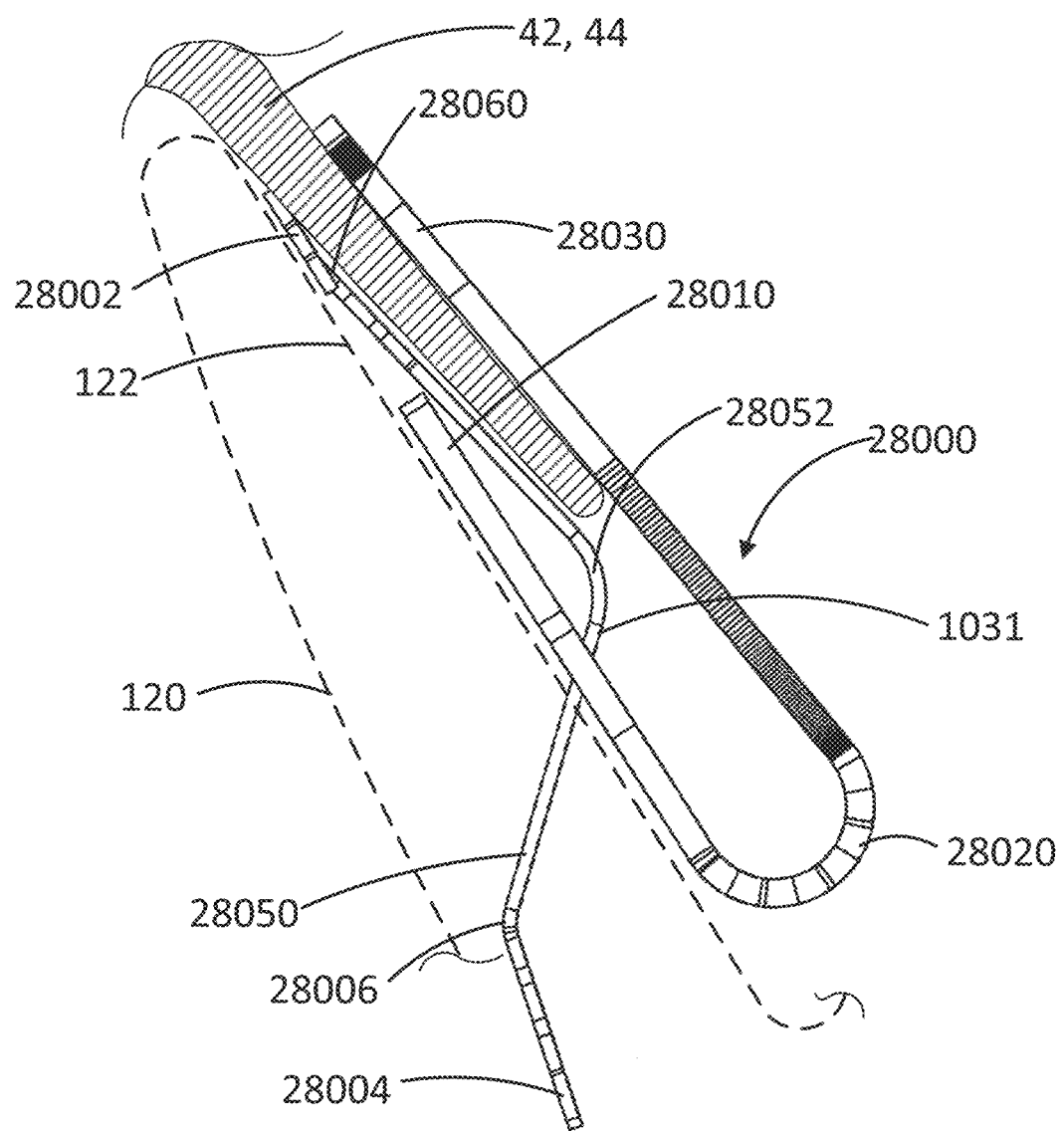
FIG. 284 shows the example indicator and example clasp of FIG. 282 with a native valve leaflet inserted into the clasp to a sufficient predetermined depth.

Referring now to FIG. 284, the clasp or barbed clasp 28000 is shown with the indicator arm 28050 in an engaged position. That is, the position that the indicator arm 28050 is moved by the leaflet 42 or 44. In the closed position, the indicator arm 28050 no longer crosses the moveable arm 28050 and extends past the fixed arm 28010 and into the space between the inner paddle 122 and the outer paddle 120. Thus, the operator knows that the indicator arm 28050 has engaged the leaflet tissue 42 or 44 when the indicator arm 28050 has been moved such that no indicator arm is visible past the clasp moveable arm 28030 and a portion of the moveable arm extends past the clasp fixed arm 28010 when the clasp 28000 is viewed with an imaging device. In addition, or instead, the indicator arm 28050 can be optically monitored to detect pulsing, jumping, and/or flexing of the indicator arm as the heart beats. This jumping, bouncing and/or flexing of the indicator arm indicates to the operator that the indicator arm has engaged leaflet tissue.

Still referring to FIG. 284, the clasp 28000 is shown with the moveable arm 28030 in a closed position. When the clasp 28000 is closed, the moveable arm 28030 exerts a pinching force that retains the native leaflet tissue within the clasp 28000. The clasp 28000 is biased in the closed direction by the shape-setting of the moveable arm 28030 in a preloading position.

The example clasp 28000 can be deployed within a native valve 40 to secure the implantable device, such as the devices 100, 200, 300 described above, to one of the native leaflets 42, 44 in any of the manners described herein. The clasp 28000 is opened with a native leaflet 42, 44 partially inserted into the opening of the clasp 28000 formed between the fixed and moveable arms 28010, 28030. To determine whether the leaflet 42, 44 has reached the desired engagement depth, the clasp 28000 is closed or partially closed. In FIG. 283, because the leaflet 42, 44 is not at or beyond the minimum engagement depth the indicator arm 28050 misses the leaflet 42, 44 and a portion of the indicator arm moves to a position that is beyond the movable arm 28010 of the clasps 28000. In FIG. 284, because the leaflet 42, 44 has been inserted into the clasp 4400 at or beyond the minimum desired engagement depth, the indicator arm 28050 is engaged by the leaflet 42, 44 and a portion of the indicator arm is moved past the fixed arm 28010.

Referring now to FIGS. 285-286, an example clasp 5000 for use in implantable prosthetic devices, such as devices 100, 200, 300 described above, is shown. Like the clasp 3500 described above, the clasp 5000 includes a fixed arm 5010, a hinge portion 5020, and a moveable arm 5030 having a barbed portion 5040 (though other friction-enhancing portions can be used). The moveable arm 5030 also includes an indicating lever 5032 disposed at a distance from the hinge portion 5020 that is less than a distance between the barbed portion 5040 and the hinge portion 5020. The indicating lever 5032 deforms when the native leaflet tissue is pressed against the fixed arm 5010 by the moveable arm 5030 to indicate that the leaflet tissue has reached a minimum desired engagement depth. Thus, the indicating lever 5032 will not indicate that the native leaflet 42, 44 has reached the desired engagement depth until the leaflet 42, 44 is inserted at or beyond the location of the indicating lever 5032. Once the leaflet 42, 44 has reached the desired engagement depth, actuation of the moveable arm 5030 squeezes the leaflet tissue 42, 44 against the indicating lever 5032 to cause the indicating lever 5032 to flatten against the moveable arm 5030 and thereby indicate that the leaflet 42, 44 has been inserted into the clasp 5000 at or beyond the desired engagement depth. The clasp 5000 can be used in any of the implantable prosthetic devices of the present application and can include any of the features or combinations of features of the other clasps described herein.

Figure 287:
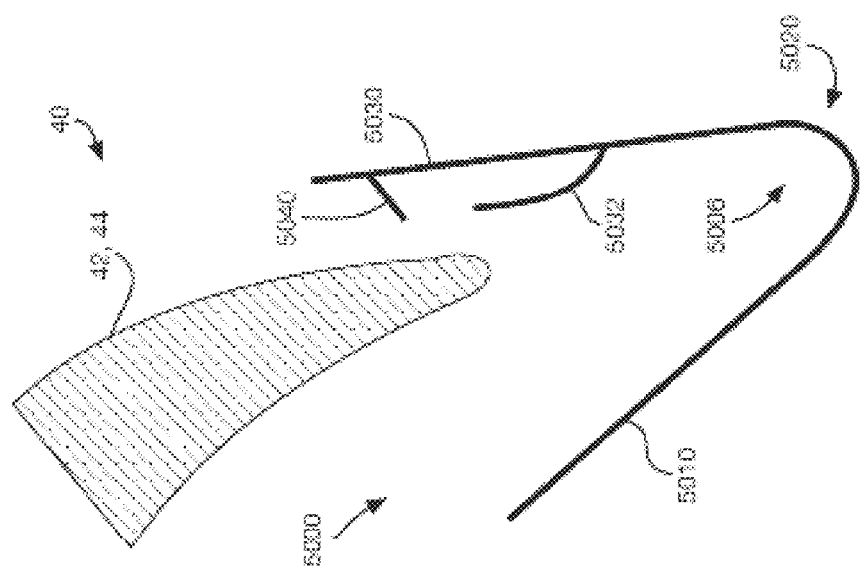
FIGS. 287-289 show the clasp of FIGS. 285-286 being deployed to engage with a leaflet of a native valve.
Figure 288:
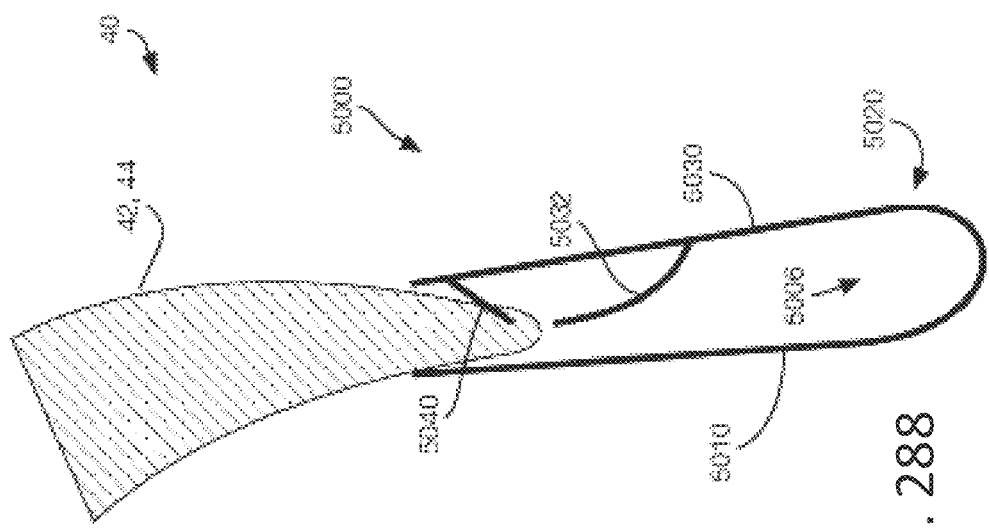
Figure 289:
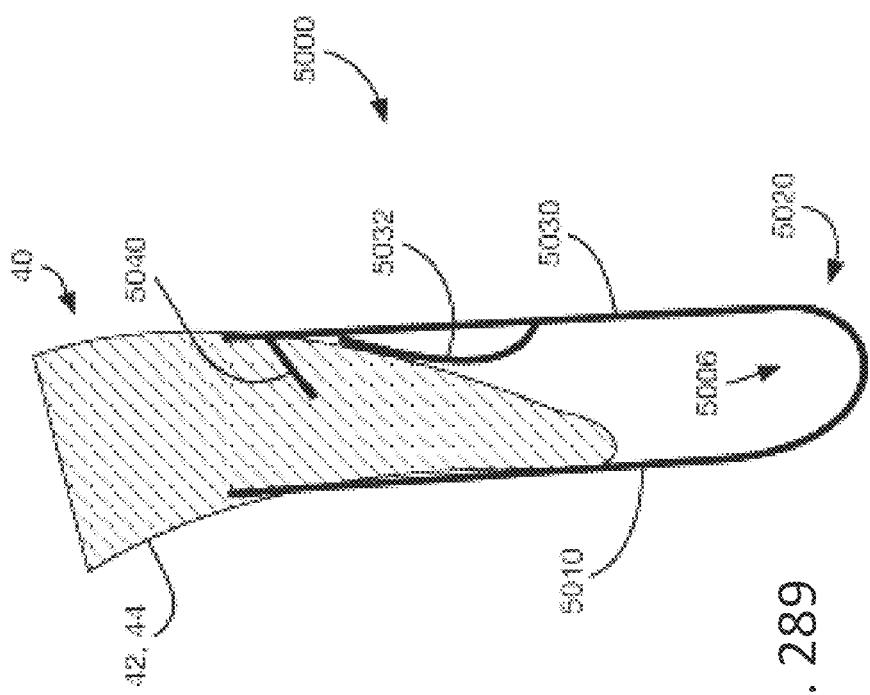

Referring now to FIGS. 287-289, the example clasp 5000 is shown being deployed within a native valve 40 to secure an implantable device (not shown), such as the devices 100, 200, 300 described above, to one of the native leaflets 42, 44. Referring now to FIG. 287, the clasp 5000 is shown in an open condition with a native leaflet 42, 44 partially inserted into an opening 5006 of the clasp 5000 formed between the fixed and moveable arms 5010, 5030. To determine whether the leaflet 42, 44 has reached the desired engagement depth, the moveable arm 5030 is actuated via actuation lines (not shown) as shown in FIGS. 288-289.

Referring now to FIG. 288, when the moveable arm 5030 is actuated to push the leaflet 42, 44 against the fixed arm 5010, the leaflet 42, 44 may contact a portion of the moveable arm 5030 without contacting the indicating lever 5032 when the engagement depth of the leaflet 42, 44 is less than the minimum desired engagement depth. As can be seen in FIG. 289, the indicating lever 5032 is deformed or flattened from contact with the leaflet 42, 44 when the leaflet 42, 44 is inserted into the clasp 5000 at or beyond the minimum engagement depth and is pressed against the indicating lever 5032 by the fixed arm 5010. That is, the indicating lever 5032 is deformed by the leaflet 42, 44 to indicate that the leaflet 42, 44 has been inserted at or beyond the minimum engagement depth. In some embodiments, actuation of the moveable arm 5030 also causes the barbed portion 5040 to engage and secure the leaflet 42, 44 within the barbed clasp 5000. If the indicating lever 5032 indicates that the leaflet 42, 44 is not inserted to the desired depth, the clasp 5000 can be opened to allow for repositioning of the leaflet 42, 44.

Referring now to FIGS. 290-291, an example clasp 5100 for use in implantable prosthetic devices, such as devices 100, 200, 300 described above, is shown. Like the clasp 3500 described above, the clasp 5100 includes a fixed arm 5110, a hinge portion 5120, and a moveable arm 5130 having a barbed portion 5140 (though other friction-enhancing portions can be used). The fixed arm 5110 also includes an indicating lever 5112 disposed at a distance from the hinge portion that is less than a distance between the barbed portion 5140 and the hinge portion 5120. The indicating lever 5112 deforms when the native leaflet tissue is pressed against the indicating lever 5112 by the moveable arm 5130 to indicate that the leaflet tissue has reached a minimum desired engagement depth. Thus, the indicating lever 5112 will not indicate that the native leaflet 42, 44 has reached the desired engagement depth until the leaflet 42, 44 is inserted at or beyond the location of the indicating lever 5112. Once the leaflet 42, 44 has reached the desired engagement depth, actuation of the moveable arm 5130 squeezes the leaflet tissue 42, 44 against the indicating lever 5112 of the fixed arm 5110 to cause the indicating lever 5112 to flatten and thereby indicate that the leaflet 42, 44 has been inserted into the clasp 5100 at or beyond the desired engagement depth. The clasp 5100 can be used in any of the implantable prosthetic devices of the present application and can include any of the features or combinations of features of the other clasps described herein.

Referring now to FIGS. 292-294, the example clasp 5100 is shown being deployed within a native valve 40 to secure an implantable device (not shown), such as the devices 100, 200, 300 described above, to one of the native leaflets 42, 44. Referring now to FIG. 292, the clasp 5100 is shown in an open condition with a native leaflet 42, 44 partially inserted into an opening 5106 of the clasp 5100 formed between the fixed and moveable arms 5110, 5130. To determine whether the leaflet 42, 44 has reached the desired engagement depth, the moveable arm 5130 is actuated via actuation lines (not shown) as shown in FIGS. 293-294. As can be seen in FIGS. 292A, 293A, and 294A, the indicating lever 5112 can optionally extend from the distal end of the fixed arm 5110A or be formed from a distal portion of the fixed arm 5110A that is bent or biased towards the moveable arm.

Referring now to FIG. 293, when the moveable arm 5130 is actuated to push the leaflet 42, 44 against the fixed arm 5110, the leaflet 42, 44 may contact a portion of the fixed arm 5110 without contacting the indicating lever 5112 when the engagement depth of the leaflet 42, 44 is less than the minimum desired engagement depth. As can be seen in FIG. 294, the indicating lever 5112 is deformed or flattened from contact with the leaflet 42, 44 when the leaflet 42, 44 is inserted into the clasp 5100 at or beyond the minimum engagement depth and is pressed against the indicating lever 5112 by the moveable arm 5130. That is, the indicating lever 5112 is deformed by the leaflet 42, 44 to indicate that the leaflet 42, 44 has been inserted at or beyond the minimum engagement depth. In some embodiments, actuation of the moveable arm 5130 also causes the barbed portion 5140 to engage and secure the leaflet 42, 44 within the barbed clasp 5100. If the indicating lever 5112 indicates that the leaflet 42, 44 is not inserted to the desired depth, the clasp 5100 can be opened to allow for repositioning of the leaflet 42, 44.

Referring now to FIGS. 295-296, an example clasp 5500 for use in implantable prosthetic devices, such as devices 100, 200, 300 described above, is shown. Like the clasp 3500 described above, the clasp 5500 includes a fixed arm 5510, a hinge portion 5520, and a moveable arm 5530 having a barbed portion 5540 (though other friction-enhancing portions can be used). The moveable arm 5530 also includes a plurality of indicating levers 5532 arranged at intervals along the moveable arm 5530 between the hinge portion 5520 and the barbed portion 5540. The indicating levers 5532 deform when the native leaflet tissue is pressed against the fixed arm 5510 by the moveable arm 5530 to indicate that the leaflet tissue has reached a particular engagement depth depending on the number of indicating levers 5532 engaged by the leaflet. Thus, the engagement depth of the leaflet can be determined by the number of indicating levers 5532 engaged by the leaflet. The clasp

5500 can be used in any of the implantable prosthetic devices of the present application and can include any of the features or combinations of features of the other clasps described herein.

Referring now to FIGS. 178-180, the example clasp 5500 is shown being deployed within a native valve 40 to secure an implantable device (not shown), such as the devices 100, 200, 300 described above, to one of the native leaflets 42, 44.

Referring now to FIG. 297, the clasp 5500 is shown in an open condition with a native leaflet 42, 44 partially inserted into an opening 5506 of the clasp 5500 formed between the fixed and moveable arms 5510, 5530. To determine whether the leaflet 42, 44 has reached the desired engagement depth, the moveable arm 5530 is actuated via actuation lines (not shown) as shown in FIGS. 298-299.

Referring now to FIG. 298, when the moveable arm 5530 is actuated to push the leaflet 42, 44 against the fixed arm 5510, the leaflet 42, 44 engages two out of the four of the indicating levers 5532, which may, depending on the patient, be less than a minimum desired engagement depth of three or more indicating levers 5532. However, engagement of two of the indicating levers can indicate that leaflet is inserted far enough for some patients.

As can be seen in FIG. 299, all four of the indicating levers 5532 are deformed or flattened from contact with the leaflet 42, 44 when the leaflet 42, 44 is inserted into the clasp 5000 at or beyond the minimum engagement depth and is pressed against the indicating levers 5532 by the fixed arm 5510. In some embodiments, actuation of the moveable arm 5530 also causes the barbed portion 5540 to engage and secure the leaflet 42, 44 within the barbed clasp 5500. If the indicating levers 5532 indicate that the leaflet 42, 44 is not inserted to the desired depth, the clasp 5500 can be opened to allow for repositioning of the leaflet 42, 44.

Referring now to FIGS. 300-301, an example clasp 5600 for use in implantable prosthetic devices, such as devices 100, 200, 300 described above, is shown. Like the clasp 3500 described above, the clasp 5600 includes a fixed arm 5610, a hinge portion 5620, and a moveable arm 5630 having a barbed portion 5640 (though other friction-enhancing portions can be used). The fixed arm 5610 also includes a plurality of indicating levers 5612 arranged at intervals along the length of the fixed arm 5610. The indicating levers 5612 deform when the native leaflet tissue is pressed against the fixed arm 5610 by the moveable arm 5630 to indicate that the leaflet tissue has reached a particular engagement depth depending on the number of indicating levers 5612 engaged by the leaflet. Thus, the engagement depth of the leaflet can be determined by the number of indicating levers 5612 engaged by the leaflet. The clasp 5600 can be used in any of the implantable prosthetic devices of the present application and can include any of the features or combinations of features of the other clasps described herein.

Referring now to FIGS. 302-304, the example clasp 5600 is shown being deployed within a native valve 40 to secure an implantable device (not shown), such as the devices 100, 200, 300 described above, to one of the native leaflets 42, 44. Referring now to FIG. 302, the clasp 5600 is shown in an open condition with a native leaflet 42, 44 partially inserted into an opening 5606 of the clasp 5600 formed between the fixed and moveable arms 5610, 5630. To determine whether the leaflet 42, 44 has reached the desired engagement depth, the moveable arm 5630 is actuated via actuation lines (not shown) as shown in FIGS. 303-304.

Referring now to FIG. 303, when the moveable arm 5630 is actuated to push the leaflet 42, 44 against the fixed arm 5610, the leaflet 42, 44 engages two out of the four of the indicating levers 5612, which may, depending on the patient, be less than a minimum desired engagement depth of three or more indicating levers 5612. As can be seen in FIG. 304, all four of the indicating levers 5612 are deformed or flattened from contact with the leaflet 42, 44 when the leaflet 42, 44 is inserted into the clasp 5000 at or beyond the minimum engagement depth and is pressed against the indicating levers 5612 by the moveable arm 5630. In some embodiments, actuation of the moveable arm 5630 also causes the barbed portion 5640 to engage and secure the leaflet 42, 44 within the barbed clasp 5600. If the indicating levers 5612 indicate that the leaflet 42, 44 is not inserted to the desired depth, the clasp 5600 can be opened to allow for repositioning of the leaflet 42, 44.

Referring now to FIGS. 305-306, an example clasp 5700 for use in implantable prosthetic devices, such as devices 100, 200, 300 described above, is shown. Like the clasp 3500 described above, the clasp 5700 includes a fixed arm 5710, a hinge portion 5720, and a moveable arm 5730 having a barbed portion 5740 (though other friction-enhancing portions can be used). The clasp 5700 also includes an indicator arm 5750 extending from an indicator hinge portion 5760. The indicator hinge portion 5760 joins the indicator arm 5750 to an attachment portion 5752. Unlike the indicator arm 3550 of the clasp 3500, the indicator arm 5750 is formed from a separate piece of material than the rest of the clasp 5700. The indicator arm 5750 is attached to the clasp 5700 by welding or otherwise securing the attachment portion 5752 to the fixed arm 5710 of the clasp 5700. As can be seen in FIG. 306A, the attachment portion 5752 can alternatively be attached to the moveable arm 5730 of the clasp 5700. While the indicator arm 5750 being formed from a separate piece of material from the remainder of the clasp is illustrated as being similar to the indicator arm 3550 described above, the concept of forming the indicator from a separate piece of material that is attached to the clasp can be applied to any of the indicating features described herein. In addition, while the separate indicator arm 5750 is illustrated as being positioned next to the moveable arm 5730, in other embodiments the indicator arm 5750 can overlap with and/or be aligned with the moveable arm in the view of FIG. 305.

Referring now to FIGS. 307-336, example clasps for use in implantable prosthetic devices, such as devices 100, 200, 300 described above, are shown. These clasps include indicators that provide improved visibility to the position of the leaflet within the clasp during implantation, particularly when the clasp is observed via imaging devices. The indicators can be similar to any of the indicators disclosed herein with the addition of one or more markers that enhance imaging. The markers can take a wide variety of different forms. Radio opaque markers are referred to in this application, but any type of marker that enhances imaging can be used. Any type of image enhancing marker can be substituted of a radio opaque marker when a radio opaque marker is referred to herein. In the examples illustrated by FIGS. 307-336, the markers are shown as discrete components that are attached to the indicators. However, indicators themselves can be made from or comprise a marker material, such as radio opaque marker material, and/or can have portions treated (such as by coating) to act as markers. In yet other example embodiments, indicators can be provided on the fixed arm and/or the moveable arm of any of the clasps disclosed herein. Discreet markers can be provided on the fixed arm and/or the moveable arm, all or a portion of the fixed arm and/or the moveable arm can be made from a marker material, or all or a portion of the fixed arm and/or the moveable arm can be made from a marker material.

Radio opaque markers are formed from a material that reflects the electromagnetic radiation of the imaging device. That is, the markers appear opaque when viewed via an imaging device, in contrast to the surrounding tissue and, in some embodiments, the material of the clasps. Consequently, the markers appear as bright spots on the display of the imaging device and can be configured to provide improved visibility of the position of the leaflet within the clasp.

Referring now to FIGS. 307-308, an example clasp 5800 for use in implantable prosthetic devices, such as devices 100, 200, 300 described above, is shown. Like the clasp 3500 described above, the clasp 5800 includes a fixed arm 5810, a hinge portion 5820, and a moveable arm 5830 having a barbed portion 5840 (though other friction-enhancing portions can be used). The clasp 5800 also includes an indicator arm 5850 adjacent to the moveable arm 5830 and extending from an indicator hinge portion 5860. The indicator hinge portion 5860 allows the indicator arm 5850 to be actuated separately from the moveable arm 5830. The indicator hinge portion 5860 can be formed from a portion of the indicator arm 5830 or can be formed from a series of cutouts similar to the patterned hinge of the clasp 2100 described above. The indicator arm 5850 includes a radio opaque marker or other marker that enhances imaging 5852 at the distal end of the indicator arm 5850. The marker 5852 increases the visibility of the position of the indicator arm 5850 relative to the fixed and moveable arms 5810, 5830 when viewed through an imaging device. The clasp 5800 can be used in any of the implantable prosthetic devices of the present application and can include any of the features or combinations of features of the other clasps described herein. A radio opaque marker, such as the marker 5852 shown in FIGS. 307-308 can be used on any clasp with an indicator arm disclosed herein.

The indicator arm 5850 can be separately actuated from the moveable arm 5830 to facilitate detection of the depth of engagement of the native leaflet between the moveable arm 5830 and the fixed arm 5810 of the clasp 5800. In the illustrated embodiment, the indicator arm 5850 is narrower than the moveable arm 5830 and has a length that is less than a distance from the hinge portion 5820 to the barbed portion 5840.

The length of the indicator arm 5850 is used to determine a desired minimum engagement depth as measured from the end of the moveable arm 5830 of the clasp 5800. Configuring the length of the indicator arm 5850 to be less than a distance from the hinge portion 5820 to the barbed portion 5840 ensures that the barbed portion 5840 will engage a leaflet that is positioned at the minimum engagement depth as indicated by the indicator arm 5850. That is, if a native leaflet positioned within the clasp 5800 is engaged by the indicator arm 5850 when the indicator arm 5850 is actuated, then the leaflet will be engaged by the barbed portion 5840 of the moveable arm 5830. The opposite is also true. That is, if a native leaflet positioned within the clasp 5800 is not engaged by the indicator arm 5850 when the indicator arm 5850 is actuated, then the leaflet will not be adequately engaged by the barbed portion 5840 of the moveable arm 5830.

Referring now to FIGS. 309-311, the example clasp 5800 is shown being deployed within a native valve 40 to secure an implantable device (not shown), such as the devices 100, 200, 300 described above, to one of the native leaflets 42, 44. Referring now to FIG. 309, the clasp 5800 is shown in an open condition with a native leaflet 42, 44 partially inserted into the opening 5806 of the clasp 5800 formed between the fixed and moveable arms 5810, 5830. When the indicator arm 5850 is in the open condition the marker 5852 is proximate the moveable arm 5830 and spaced apart from the fixed arm 5810. To determine whether the leaflet 42, 44 has reached the desired engagement depth, the indicator arm 5850 is actuated as shown in FIGS. 310 and 311, e.g., via actuation lines (not shown).

Referring now to FIG. 310, the indicator arm 5850 can be actuated by releasing tension on an actuation line (not shown). Because the leaflet 42, 44 is not at or beyond the minimum engagement depth the indicator arm 5850 misses or slips off of the leaflet 42, 44 and moves to a fully actuated position that is beyond the fixed arm 5810 of the clasps 5800. The indicator arm 5850 crosses the fixed arm 5810 to form an X-shape that is visible via imaging devices used to monitor implantation and deployment of the prosthetic device. In the fully actuated position, the marker 5852 is disposed beyond the fixed arm 5810—i.e., outside of the opening 5806 formed between the fixed and moveable arms 5810, 5830—to clarify that the indicator arm 5850 has not engaged the leaflet 42, 44. In addition or instead, the marker 5852 does not bounce or jump with the beating of the heart when the indicator arm 5858 does not engage the leaflet.

Referring now to FIG. 311, the leaflet 42, 44 has been inserted into the clasp 5800 at or beyond the minimum desired engagement depth, the indicator arm 5850 engages and pinches the leaflet 42, 44 against the fixed arm 5810. Engagement with the leaflet 42, 44 prevents the indicator arm 5850 from moving past the fixed arm 5810 of the clasp 5800 to form the X-shape shown in FIG. 310. In addition or instead, the marker 5852 bounces or jumps with the beating of the heart when the indicator arm 5850 is engaged with the valve leaflet 42, 44. When the indicator arm 5850 is engaged by the leaflet 42, 44, the marker 5852 is located between the fixed and moveable arms 5810, 5830. Thus, the indicator arm 5850 and marker 5852 indicate to an observer observing the installation via an imaging device that the leaflet 42, 44 is inserted into the opening 5806 beyond the minimum desired engagement depth that is determined by the length of the indicator arm 5850. Once the indicator arm 5850 indicates that the leaflet 42, 44 is sufficiently inserted into the opening 5806, the moveable arm 5830 is actuated by releasing tension on the actuating line (not shown) so that the leaflet 42, 44 is pinched between the barbed portion 5840 and the fixed arm 5810 to secure the leaflet 42, 44 firmly within the clasp 5800.

Referring now to FIGS. 309A, 310A, and 311A, the clasp 5800 is shown having a second marker 5854 that is arranged on the fixed arm 5810 of the clasp 5800 in addition to the first marker 5852 on the indicator arm 5850. Any number of markers can be included to facilitate proper insertion of the leaflet into the opening 5806. The second marker 5854 can be a different shape than the marker 5852 so that the second marker 5854 can be distinguished from the first marker 5852 when both are viewed via an imaging device. For example, as is shown in FIG. 309A, the second marker 5854 can be longer than the first marker 5852. The combination of the first and second markers 5852, 5854 provides further information of the relative position of the indicator arm 5850 and the fixed arm 5810.

As can be seen in FIG. 310A, the first marker 5852 is arranged to the left of the second marker 5854 because the leaflet 42, 44 was not engaged when the indicator arm 5850 was actuated. In other embodiments, the first marker 5852 can touch, be close to, or otherwise be positioned relative to the second marker to indicate that the leaflet tissue was not engaged. When the indicator arm 5850 engages the leaflet 42, 44, however, the first marker 5852 is arranged to the right of the second marker 5854, as can be seen in FIG. 311A. In other embodiments, the first marker 5852 can be otherwise positioned relative to the second marker 5854 to indicate proper tissue engagement. Any detectable differences between the relative positions of the first and second markers 5852, 5854 when the indicator arm is in respective valve tissue engaged (FIG. 192A) and valve tissue not engaged (FIG. 191A) can be used to determine proper leaflet insertion into the opening 5806. Thus, the combination of the first and second markers 5852, 5854 provides an indication of the position of the leaflet 42, 44 without needing to directly ascertain the positions of the fixed arm 5810, moveable arm 5830, or indicator arm 5850. First and second radio opaque markers, such as the markers 5852, 5854 shown in FIGS. 309A, 310A, and 311A can be used on any clasp with an indicator arm disclosed herein.

Referring now to FIGS. 312-313, an example clasp 5900 for use in implantable prosthetic devices, such as devices 100, 200, 300 described above, is shown. Like the clasp 3500 described above, the clasp 5900 includes a fixed arm 5910, a hinge portion 5920, and a moveable arm 5930 having a barbed portion 5940 (though other friction-enhancing portions can be used). The moveable arm 5930 also includes an indicating feature or bump 5932 disposed between the barbed portion 5940 and the hinge portion 5920. The indicating feature 5932 includes a marker 5934 at the location on the indicating feature 5932 that is furthest from the moveable arm 5950. The marker 5934 increases the visibility of the position of the indicating feature 5932 relative to the fixed and moveable arms 5910, 5930 when viewed through an imaging device.

The indicating feature 5932 deforms when the native leaflet tissue is pressed against the indicating feature 5932 by the fixed arm 5910 to indicate that the leaflet tissue has reached a minimum desired engagement depth. Thus, the indicating feature 5932 will not indicate that the native leaflet has reached the desired engagement depth until the leaflet is inserted at or beyond the location of the indicating feature 5932. Once the leaflet 42, 44 has reached the desired engagement depth, actuation of the moveable arm 5930 squeezes the leaflet tissue 42, 44 between the fixed arm 5910 and the indicating feature 5932 to cause the indicating feature 5932 to flatten and thereby indicate that the leaflet 42, 44 has been inserted into the clasp 5900 at or beyond the desired engagement depth. The clasp 5900 can be used in any of the implantable prosthetic devices of the present application and can include any of the features or combinations of features of the other clasps described herein. A radio opaque marker, such as the marker 5934 shown in FIGS. 312-313 can be used on any clasp with an indicating feature disclosed herein.

Referring now to FIGS. 314-316, the example clasp 5900 is shown being deployed within a native valve 40 to secure an implantable device (not shown), such as the devices 100, 200, 300 described above, to one of the native leaflets 42, 44. Referring now to FIG. 314, the clasp 5900 is shown in an open condition with a native leaflet 42, 44 partially inserted into an opening 5906 of the clasp 5900 formed between the fixed and moveable arms 5910, 5930. To determine whether the leaflet 42, 44 has reached the desired engagement depth, the moveable arm 5930 is actuated via actuation lines (not shown) as shown in FIGS. 315-316.

Referring now to FIG. 315, when the moveable arm 5930 is actuated to push the leaflet 42, 44 against the fixed arm 5910, the leaflet 42, 44 may contact a portion of the moveable arm 5930 without contacting the indicating feature 5932 when the engagement depth of the leaflet 42, 44 is less than the minimum desired engagement depth. In this position, the marker 5934 is disposed in the opening 5906 between the fixed and moveable arms 5910, 5930—i.e., the marker 5934 is not aligned with the moveable arm 5930—to clarify that the indicating feature 5932 has not engaged the leaflet 42, 44.

Referring now to FIG. 316, the indicating feature 5932 is deformed or flattened from contact with the leaflet 42, 44 when the leaflet 42, 44 is inserted into the clasp 5900 at or beyond the minimum engagement depth and is pressed against the indicating feature 5932. That is, the indicating feature 5932 is deformed by the leaflet 42, 44 to indicate that the leaflet 42, 44 has been inserted at or beyond the minimum engagement depth. When the indicating feature 5932 is engaged by the leaflet 42, 44, the marker 5934 is pushed closer to the moveable arm 5930 and can align with the moveable arm 5930. Thus, the moveable arm 5930, indicating feature 5932, and marker 5934 indicate to an observer observing the installation via an imaging device that the leaflet 42, 44 is inserted into the opening 5906 beyond the minimum desired engagement depth that is determined by the length of the indicator 5950. In some embodiments, actuation of the moveable arm 5930 also causes the barbed portion 5940 to engage and secure the leaflet 42, 44 within the barbed clasp 5900. If the indicating feature 5932 indicates that the leaflet 42, 44 is not inserted to the desired depth, the clasp 5900 can be opened to allow for repositioning of the leaflet 42, 44.

Referring now to FIGS. 314A, 315A, and 316A, the clasp 5900 is shown with second markers 5936 that are arranged on the moveable arm 5930 of the clasp 5900 in addition to the first marker 5932 on the indicating feature 5932. In some embodiments, only one second marker 5934 is included. The second markers 5934 are located on both sides of the indicating feature 5932 in the illustrated embodiment. As the indicating feature 5932 is compressed or deformed by the leaflet 42, 44, the first marker 5932 moves relative to the second markers 5934, helping to distinguish the first and second markers 5932, 5934. In some embodiments, the second marker 5934 is a different shape than the first marker 5932 so that the second marker 5934 can be distinguished from the first marker 5932 when both are viewed via an imaging device.

The combination of the first and second markers 5932, 5934 provides further information of the relative position of the indicating feature 5932 and the moveable arm 5930. As can be seen in FIG. 315A, the first marker 5932 is out of alignment with the second markers 5934 because the leaflet 42, 44 was not engaged when the moveable arm 5930 was actuated. When the indicating feature 5932 engages the leaflet 42, 44, however, the first marker 5932 moves into or close to alignment with the second markers 5934, as can be seen in FIG. 316A. Thus, the combination of the first and second markers 5932, 5934 provides an indication of the position of the leaflet 42, 44 without needing to directly ascertain the positions of the fixed arm 5910, moveable arm 5930, or indicating feature 5932. First and second radio markers, such as the markers 5932, 5934 shown in FIGS. 314A, 315A, and 316A can be used on any clasp with an indicator disclosed herein.

Referring now to FIGS. 317-318, an example clasp 6000 for use in implantable prosthetic devices, such as devices 100, 200, 300 described above, is shown. Like the clasp 3500 described above, the clasp 6000 includes a fixed arm 6010, a hinge portion 6020, and a moveable arm 6030 having a barbed portion 6040 (though other friction-enhancing portions can be used). The moveable arm 6030 also includes an indicating lever 6032 disposed at a distance from the hinge portion 6020 that is less than a distance between the barbed portion 6040 and the hinge portion 6020. The indicating lever 6032 includes a radio opaque marker 6034 at the distal end of the indicating lever 6032. The marker 6034 increases the visibility of the position of the indicating lever 6032 relative to the fixed and moveable arms 6010, 6030 when viewed through an imaging device. The indicating lever 6032 deforms when the native leaflet tissue is pressed against the fixed arm 6010 by the moveable arm 6030 to indicate that the leaflet tissue has reached a minimum desired engagement depth. Thus, the indicating lever 6032 will not indicate that the native leaflet has reached the desired engagement depth until the leaflet is inserted at or beyond the location of the indicating lever 6032. Once the leaflet 42, 44 has reached the desired engagement depth, actuation of the moveable arm 6030 squeezes the leaflet tissue 42, 44 between the fixed arm 6010 and the indicating lever 6032 to cause the indicating lever 6032 to flatten against the moveable arm 6030 and thereby indicate that the leaflet 42, 44 has been inserted into the clasp 6000 at or beyond the desired engagement depth. The clasp 6000 can be used in any of the implantable prosthetic devices of the present application and can include any of the features or combinations of features of the other clasps described herein. A radio opaque marker, such as the marker 6034 shown in FIGS. 317-318 can be used on any clasp with an indicating feature disclosed herein.

Referring now to FIGS. 319-321, the example clasp 6000 is shown being deployed within a native valve 40 to secure an implantable device (not shown), such as the devices 100, 200, 300 described above, to one of the native leaflets 42, 44. Referring now to FIG. 319, the clasp 6000 is shown in an open condition with a native leaflet 42, 44 partially inserted into an opening 6006 of the clasp 6000 formed between the fixed and moveable arms 6010, 6030. To determine whether the leaflet 42, 44 has reached the desired engagement depth, the moveable arm 6030 is actuated via actuation lines (not shown) as shown in FIGS. 320-321.

Referring now to FIG. 320, when the moveable arm 6030 is actuated to push the leaflet 42, 44 against the fixed arm 6010, the leaflet 42, 44 may contact a portion of the moveable arm 6030 without contacting the indicating lever 6032 when the engagement depth of the leaflet 42, 44 is less than the minimum desired engagement depth. In this position, the marker 6034 is disposed in the opening 6006 between the fixed and moveable arms 6010, 6030—i.e., the marker 6034 is spaced apart from the moveable arm 6030—to clarify that the indicating feature 6032 has not engaged the leaflet 42, 44.

Referring now to FIG. 321, the indicating feature 6032 is deformed or flattened from contact with the leaflet 42, 44 when the leaflet 42, 44 is inserted into the clasp 6000 at or beyond the minimum engagement depth and is pressed against the indicating lever 6032 by the fixed arm 6010. That is, the indicating lever 6032 is deformed by the leaflet 42, 44 to indicate that the leaflet 42, 44 has been inserted at or beyond the minimum engagement depth. When the indicating lever 6032 is engaged by the leaflet 42, 44, the marker 6034 is pushed closer to the moveable arm 6030 and can align with the moveable arm 6030. Thus, the moveable arm 6030, indicating lever 6032, and marker 6034 indicate to an observer observing the installation via an imaging device that the leaflet 42, 44 is inserted into the opening 6006 beyond the minimum desired engagement depth that is determined by the length of the indicator arm 6050. In some embodiments, actuation of the moveable arm 6030 also causes the barbed portion 6040 to engage and secure the leaflet 42, 44 within the barbed clasp 6000. If the indicating lever 6032 indicates that the leaflet 42, 44 is not inserted to the desired depth, the clasp 6000 can be opened to allow for repositioning of the leaflet 42, 44.

Referring now to FIGS. 319A, 320A, and 321A, the clasp 6000 is shown with a second marker 6036 arranged on the moveable arm 6010 of the clasp 6000 in addition to the first marker 6034 on the indicating lever 6032. More than one additional marker 6036 can be included to indicate proper tissue insertion. In some embodiments, the second marker 6036 is arranged at the intersection of the moveable arm 6030 and indicating lever 6032. In some embodiments, the second marker 6036 is a different shape than the first marker 6034 so that the second marker 6036 can be distinguished from the first marker 6034 when both are viewed via an imaging device. The combination of the first and second markers 6034, 6036 provides further information of the relative position of the indicating lever 6032 and the moveable arm 6030. As can be seen in FIG. 320A, the first marker 6034 is out of alignment with the second marker 6036 because the leaflet 42, 44 was not engaged when the moveable arm 6030 was actuated. When the indicating lever 6032 engages the leaflet 42, 44, however, the first marker 6034 moves into or close to alignment with the second marker 6036, as can be seen in FIG. 321A. Thus, the combination of the first and second markers 6034, 6036 provides an indication of the position of the leaflet 42, 44 without needing to directly ascertain the positions of the fixed arm 6010, moveable arm 6030, or indicating lever 6032. First and second radio opaque markers, such as the markers 6034, 6036 shown in FIGS. 319A, 320A, and 321A can be used on any clasp with an indicator arm disclosed herein.

Referring now to FIGS. 322-323, an example clasp 6100 for use in implantable prosthetic devices, such as devices 100, 200, 300 described above, is shown. Like the clasp 3500 described above, the clasp 6100 includes a fixed arm 6110, a hinge portion 6120, and a moveable arm 6130 having a barbed portion 6140 (though other friction-enhancing portions can be used). The clasp 6100 also includes an indicator arm 6150 extending from an indicator hinge portion 6160 arranged toward the distal end of the moveable arm 6130. The indicating arm 6150 includes a marker 6152 at the distal end of the indicating arm 6150. The marker 6152 increases the visibility of the position of the indicating arm 6150 relative to the fixed and moveable arms 6110, 6130 when viewed through an imaging device.

The indicator hinge portion 6160 allows the indicator arm 6150 to be actuated separately from the moveable arm 6130. The indicator hinge portion 6160 can be formed from a portion of the indicator arm 6150 or can be formed from a series of cutouts similar to the patterned hinge of the clasp 2100 described above. The clasp 6100 can be used in any of the implantable prosthetic devices of the present application and can include any of the features or combinations of features of the other clasps described herein. A marker, such as the marker 6152 shown in FIGS. 322-323 can be used on any clasp with an indicating arm disclosed herein.

The indicator arm 6150 need not be separately actuated from the moveable arm 6130 to detect the depth of engagement of the native leaflet between the moveable arm 6130 and the fixed arm 6110 of the clasp 6100. The moveable arm 6130 is optionally formed in a hoop or loop shape having two side arms 6132 surrounding a central opening 6134 that extends from the hinge portion 6120 to the barbed portion 6140 of the moveable arm 6130. The indicator arm 6150 is optionally disposed in the central opening 6134 between the two side arms 6132. In another example embodiment, only a single side arm is included. In the illustrated embodiment, because the moveable arm 6130 spans the full width of the clasp 6100, the barbed portion 6140 of the moveable arm 6130 is as wide as the clasp 6100 so that a larger area of the barbed portion 6140 engages with the native leaflet tissue.

As can be seen in FIGS. 322-323, the indicator hinge portion 6160 is arranged near the barbed portion 6140 of the moveable arm 6130. The indicator hinge portion 6160 is configured to bias the indicator arm 6150 at an angle from the moveable arm 6130 and toward the fixed arm 6110. The desired minimum engagement depth is determined by the angle of the indicator arm 6150 with respect to the moveable arm 6130, the distance between the indicator hinge portion 6160 and the hinge portion 6120, and the length of the indicator arm 6150. The minimum engagement depth decreases the further the hinge portion 6160 is from the hinge portion 6120, the greater the angle between the indicator arm 6150 and the moveable arm 6130, and the greater the length of the indicator arm 6150.

When the clasp 6100 is closed without the indicator arm 6150 being engaged by the leaflet, the indicator arm 6150 moves beyond the fixed arm 6110. The indicator arm 6150 crossing the fixed arm 6110 forms an X-shape that is visible via imaging devices used to monitor implantation and deployment of the device, as can be seen in FIG. 325. When the leaflet is inserted into the clasp 6100 beyond the minimum desired engagement depth, the leaflet pushes the indicator arm 6150 back toward the moveable arm 6130 such that the indicator arm 6150 does not cross the fixed arm 6110 to form the X-shape shown in FIG. 325. Thus, the indicator arm 6150 indicates to an observer observing the installation via an imaging device that the leaflet is inserted into the openings 6106 beyond the minimum desired engagement depth.

Referring now to FIGS. 324-326, the example clasp 6100 is shown being deployed within a native valve 40 to secure an implantable device (not shown), such as the devices 100, 200, 300 described above, to one of the native leaflets 42, 44. Referring now to FIG. 324, the clasp 6100 is shown in an open condition with a native leaflet 42, 44 partially inserted into an opening 6106 of the clasp 6100 formed between the fixed and moveable arms 6110, 6130. To determine whether the leaflet 42, 44 has reached the desired engagement depth, the moveable arm 6130 is actuated via actuation lines (not shown) as shown in FIGS. 325-326.

Referring now to FIG. 325, when the moveable arm 6130 is actuated toward the fixed arm 6110, the leaflet 42, 44 may contact portions of the fixed and moveable arms 6110, 6130 without contacting the indicator arm 6150 when the engagement depth of the leaflet 42, 44 is less than the minimum desired engagement depth. Thus, the indicator arm 6150 can extend beyond the fixed arm 6110 to form an X-shape with the fixed arm 6110. In this position, the marker 6152 is disposed beyond the fixed arm 6110—i.e., outside of the opening 6106 formed between the fixed and moveable arms 6110, 6130—to clarify that the indicator arm 6150 has not engaged the leaflet 42, 44.

Referring now to FIG. 326, the indicator arm 6150 is prevented from crossing the fixed arm 6110 when the leaflet 42, 44 is inserted far enough into the clasp 6100. That is, the indicator arm 6150 is deflected by the leaflet 42, 44 to indicate that the leaflet 42, 44 has been inserted to or beyond the minimum engagement depth. When the indicator arm 6150 is engaged by the leaflet 42, 44, the marker 6152 is located between the fixed and moveable arms 6110, 6130. Thus, the indicator arm 6150 and marker 6152 indicate to an observer observing the installation via an imaging device that the leaflet 42, 44 is inserted into the opening 6106 beyond the minimum desired engagement depth that is determined by the length of the indicator arm 6150. In some embodiments, actuation of the moveable arm 6130 also causes the barbed portion 6140 to engage and secure the leaflet 42, 44 within the barbed clasp 6100. If the indicator arm 6150 indicates that the leaflet 42, 44 is not inserted to the desired depth, the clasp 6100 can be opened to allow for repositioning of the leaflet 42, 44.

Referring now to FIGS. 324A, 325A, and 326A, the clasp 6100 is shown having a second marker 6154 that is arranged on the fixed arm 6110 of the clasp 6100 in addition to the first marker 6152 on the indicator arm 6150. The second marker 6154 can be a different shape than the marker 6152 so that the second marker 6154 can be distinguished from the first marker 6152 when both are viewed via an imaging device. For example, as is shown in FIG. 324A, the second marker 6154 can be longer than the first marker 6152. The combination of the first and second markers 6152, 6154 provides further information or more visibly clear information on an imaging device of the relative position of the indicator arm 6150 and the fixed arm 6110.

As can be seen in FIG. 325A, the first marker 6152 is arranged to the left of the second marker 6154 because the leaflet 42, 44 was not engaged when the indicator arm 6150 was actuated. When the indicator arm 6150 engages the leaflet 42, 44, however, the first marker 6152 is arranged to the right of the second marker 6154, as can be seen in FIG. 326A. Thus, the combination of the first and second markers 6152, 6154 provides an indication of the position of the leaflet 42, 44 without needing to directly ascertain the positions of the fixed arm 6110, moveable arm 6130, or indicator arm 6150. First and second radio opaque markers, such as the markers 6152, 6154 shown in FIGS. 324A, 325A, and 326A can be used on any clasp with an indicator arm disclosed herein.

Referring now to FIGS. 327-328, an example clasp 6200 for use in implantable prosthetic devices, such as devices 100, 200, 300 described above, is shown. Like the clasp 3500 described above, the clasp 6200 includes a fixed arm 6210, a hinge portion 6220, and a moveable arm 6230 having a barbed portion 6240 (though other friction-enhancing portions can be used). The moveable arm 6230 also includes a plurality of indicating levers 6232 arranged at intervals along the moveable arm 6230 between the hinge portion 6220 and the barbed portion 6240. The indicating levers 6232 each include a marker 6234. The illustrated markers 6252 are disposed at the distal end of each indicating lever 6232. However, the markers 6252 can be proved at any moveable position on the indicating lever. The markers 6252 increase the visibility of the position of the indicating levers 6250 relative to the fixed and moveable arms 6210, 6230 when viewed through an imaging device. The indicating levers 6232 deform when the native leaflet tissue is pressed against the fixed arm 6210 by the moveable arm 6230 to indicate that the leaflet tissue has reached a particular engagement depth depending on the number of indicating levers 6232 engaged by the leaflet. Thus, the engagement depth of the leaflet can be determined by the number of indicating levers 6232 engaged by the leaflet. The clasp 6200 can be used in any of the implantable prosthetic devices of the present application and can include any of the features or combinations of features of the other clasps described herein.

Referring now to FIGS. 329-331, the example clasp 6200 is shown being deployed within a native valve 40 to secure an implantable device (not shown), such as the devices 100, 200, 300 described above, to one of the native leaflets 42, 44. Referring now to FIG. 329, the clasp 6200 is shown in an open condition with a native leaflet 42, 44 partially inserted into an opening 6206 of the clasp 6200 formed between the fixed and moveable arms 6210, 6230. To determine whether the leaflet 42, 44 has reached the desired engagement depth, the moveable arm 6230 is actuated via actuation lines (not shown) as shown in FIGS. 330-331.

Referring now to FIG. 330, when the moveable arm 6230 is actuated to push the leaflet 42, 44 against the fixed arm 6210, the leaflet 42, 44 engages two out of the four of the indicating levers 6232, which may be less than a minimum desired engagement depth of three or more indicating levers 6232. The markers 6234 on each of the engaged indicating levers 6232 are moved close to or against the moveable arm 6230 while the markers 6234 on the indicating levers 6232 that are not engaged by the leaflet 42, 44 remain spaced apart from the moveable arm 6230. The relative position of the markers 6234 provides a further indication that the leaflet 42, 44 has engaged only two of the four indicating levers 6232.

Referring now to FIG. 331, all four of the indicating levers 6232 are deformed or flattened from contact with the leaflet 42, 44 when the leaflet 42, 44 is inserted into the clasp 6200 at or beyond the minimum engagement depth and is pressed against the indicating levers 6232 by the fixed arm 6210. When the indicating levers 6232 are engaged by the leaflet 42, 44, the markers 6234 are located close to or against the moveable arm 6230. Thus, the indicating levers 6232 and markers 6234 indicate to an observer observing the installation via an imaging device that the leaflet 42, 44 is inserted into the opening 6206 beyond the minimum desired engagement depth that is determined by the number of engaged indicating levers 6232. Thus, the relative position of the markers 6234 provides an indication of the position of the leaflet 42, 44 without needing to directly ascertain the positions of the fixed arm 6210, moveable arm 6230, or indicating levers 6232. In some embodiments, actuation of the moveable arm 6230 also causes the barbed portion 6240 to engage and secure the leaflet 42, 44 within the barbed clasp 6200. If the indicating levers 6232 indicate that the leaflet 42, 44 is not inserted to the desired depth, the clasp 6200 can be opened to allow for repositioning of the leaflet 42, 44. The markers 6234 shown in FIGS. 329-331 can be used on any clasp with multiple indicator arms or levers disclosed herein.

Referring now to FIGS. 332-333, an example clasp 6300 for use in implantable prosthetic devices, such as devices 100, 200, 300 described above, is shown. Like the clasp 3500 described above, the clasp 6300 includes a fixed arm 6310, a hinge portion 6320, and a moveable arm 6330 having a barbed portion 6340 (though other friction-enhancing portions can be used). The clasp 6300 also includes an indicator arm 6350 adjacent to the moveable arm 6330 and extending from an indicator hinge portion 6360. The indicator hinge portion 6360 allows the indicator arm 6350 to be actuated separately from the moveable arm 6330. The indicator hinge portion 6360 can be formed from a portion of the indicator arm 6330 or can be formed from a series of cutouts similar to the patterned hinge of the clasp 2100 described above. The clasp 6300 can be used in any of the implantable prosthetic devices of the present application and can include any of the features or combinations of features of the other clasps described herein.

The indicator arm 6350 bends away from the moveable arm 6330 to form a protruding portion 6352. Beyond the rounded protruding portion 6352, the indicator arm 6350 bends gradually toward the moveable arm 6330. A first radio opaque marker 6354 is attached to the protruding portion 6352 of the indicator arm 6350 and a second radio opaque marker 6356 is attached to the distal end of the indicator arm 6350. The markers 6354, 6356 increase the visibility of the position of the indicator arm 6350 relative to the fixed and moveable arms 6310, 6330 when viewed through an imaging device.

The indicator arm 6350 can be separately actuated from the moveable arm 6330 to facilitate detection of the depth of engagement of the native leaflet between the moveable arm 6330 and the fixed arm 6310 of the clasp 6300. In the illustrated embodiment, the indicator arm 6350 is narrower than the moveable arm 6330 and has a length that is less than a distance from the hinge portion 6320 to the barbed portion 6340.

The length of the indicator arm 6350 is used to determine a desired minimum engagement depth as measured from the end of the moveable arm 6330 of the clasp 6300. Configuring the length of the indicator arm 6350 to be less than a distance from the hinge portion 6320 to the barbed portion 6340 ensures that the barbed portion 6340 will engage a leaflet that is positioned at the minimum engagement depth as indicated by the indicator arm 6350. That is, if a native leaflet positioned within the clasp 6300 is engaged by the indicator arm 6350 when the indicator arm 6350 is actuated, then the leaflet will be engaged by the barbed portion 6340 of the moveable arm 6330. The opposite is also true. That is, if a native leaflet positioned within the clasp 6300 is not engaged by the indicator arm 6350 when the indicator arm 6350 is actuated, then the leaflet will not be engaged by the barbed portion 6340 of the moveable arm 6330.

Referring now to FIGS. 334-336, the example clasp 6300 is shown being deployed within a native valve 40 to secure an implantable device (not shown), such as the devices 100, 200, 300 described above, to one of the native leaflets 42, 44. Referring now to FIG. 334, the clasp 6300 is shown in an open condition with a native leaflet 42, 44 partially inserted into the opening 6306 of the clasp 6300 formed between the fixed and moveable arms 6310, 6330. When the indicator arm 6350 is in the open condition the first marker 6354 is arranged between the fixed and moveable arms 6310, 6330 and the second marker 6356 is arranged proximate the moveable arm 6330 and spaced apart from the fixed arm 6310. To determine whether the leaflet 42, 44 has reached the desired engagement depth, the indicator arm 6350 is actuated via actuation lines (not shown) as shown in FIGS. 335 and 336.

Referring now to FIG. 335, the indicator arm 6350 is actuated by releasing tension on an actuation line (not shown). Because the leaflet 42, 44 is not at or beyond the minimum engagement depth the indicator arm 6350 misses or slips off of the leaflet 42, 44 and moves to a fully actuated position that is beyond the fixed arm 6310 of the clasps 6300. In the fully actuated position, the first and second markers 6354, 6356 are disposed beyond the fixed arm 6310—i.e., outside of the opening 6306 formed between the fixed and moveable arms 6310, 6330—to clarify that the indicator arm 6350 has not engaged the leaflet 42, 44. In some embodiments, the leaflet 42, 44, while not inserted beyond the minimum engagement depth, is engaged by the distal end of the indicator arm 6350 so that the second marker 6356 is disposed between the fixed and moveable arms 6310, 6330 while the first marker 6354 is disposed beyond the fixed arm 6310 because of the first marker's position on the protrusion 6352 of the indicator arm 6350.

Referring now to FIG. 336, the leaflet 42, 44 has been inserted into the clasp 6300 at or beyond the minimum desired engagement depth—that is, at or beyond the location of the protrusion portion 6352 of the indicator arm 6350—the indicator arm 6350 engages and pinches the leaflet 42, 44 against the fixed arm 6310. When the indicator arm 6350 is engaged by the leaflet 42, 44 at or beyond the protrusion portion 6352, the first and second markers 6354, 6356 are pressed against the moveable arm 6330. Thus, the indicator arm 6350 and markers 6354, 6356 indicate to an observer observing the installation via an imaging device that the leaflet 42, 44 is inserted into the opening 6306 beyond the minimum desired engagement depth that is determined by the length of the indicator arm 6350. Once the indicator arm 6350 indicates that the leaflet 42, 44 is sufficiently inserted into the opening 6306, the moveable arm 6330 is actuated by releasing tension on the actuating line (not shown) so that the leaflet 42, 44 is pinched between the barbed portion 6340 and the fixed arm 6310 to secure the leaflet 42, 44 firmly within the clasp 6300.

Referring to FIGS. 337-352, in some example embodiments an indicator 33750 can be configured to utilize snap-through buckling to enhance visualization of the leaflet engagement indication. For example, an indicator 33750 that is configured with snap-through buckling can create a greater deflection of the indicator than can be achieved by deflection only due to engagement with the native leaflet. In one example embodiment, an indicator 33750 uses snap-through buckling to create clear "leaflet sufficiently engaged" and "leaflet insufficiently engaged" regions. Such distinct regions can be easier to visualize or read and can prevent false positive leaflet engagement results.

Snap buckling, snap-through buckling, bifurcation buckling, and Euler buckling are all types of buckling that are referred to as snap-through buckling herein. FIGS. 337 and 338 illustrate the concept of snap-through buckling. In FIG. 337, a beam 33700 has a first stable state 33702 and a second stable state 33704. In the example illustrated by FIG. 337, the beam 33700 is bent and/or compressed to form an apex 33706. A load 33708 is applied to the beam 33700 at the apex 33706. While the apex 33706 remains above the horizontal (or other snap-through point), the compression in the beam 33700 resists buckling and the system is in the first stable state 33702. As soon as the apex drops a hair beneath the horizontal (or other snap-through point), however, the compression in the beam 33700 actually encourages buckling which takes place rapidly (the snap). The load on the beam 33700 decreases 33710 as the beam snaps from the first stable state 33702 to the second stable state 33704. The system eventually becomes stable again as the apex 33706 drops further and the beam goes into tension.

The beam 33700 can take a wide variety of different forms. For example, the beam 33700 can be fixed at both ends as illustrated. However, in some example embodiments, the beam 33700 can have any combination of fixed end(s), simply supported (pinned) end(s), a free end, and sliding end(s).

A snap-through indicator 33750 can take a wide variety of different forms, can be used on any of the clasps disclosed herein and can be used in place of any of the indicators disclosed herein. The snap-through indicator 33750 can be an integrally formed feature of the clasp or the snap-through indicator 33750 can be a separate component that is attached to the clasp.

Referring now to FIGS. 339-342, an example clasp 33900 for use in implantable prosthetic devices, such as devices 100, 200, 300 described above, is shown. The barbed clasp 33900 includes a fixed arm 33910, a hinge portion 33920, and a moveable arm 33930 having an optional barbed portion 33940 and/or other friction-enhancing portion. FIG. 341 illustrates that the moveable arm 33930 can include an optional cutout 33915.

In the example illustrated by FIGS. 339-342, the fixed arm 33910 of the clasp 33900 includes a snap-through indicator 33750. In this example, the snap-through indicator 33750 is integrally formed with the fixed arm 33910. For example, the snap through indicator 33750 can be formed by a pair of spaced apart cutouts 33902 that leave a strip that forms the snap-through indicator 33750 (See FIG. 340). The strip can be shape set to the first stable state 33702 to form the snap-through indicator 33750. The clasp 33900 can be used in any of the implantable prosthetic devices of the present application and can include any of the features or combinations of features of the other clasps described herein.

In the first stable state 33702, the snap-through indicator 33750 bends away from the fixed arm 33910 to the apex 33706. The size and position of the snap-through indicator 33750 is configured to determine whether a desired minimum depth is reached by the native leaflet. In the illustrated embodiment, the snap-through indicator 33750 is closer to the hinge portion 33920 than the barbed portion 33940. This positioning ensures that the snap-through indicator 33750 will snap to the second stable state 33704 when the barbed portion 33940 engages a leaflet that is positioned at the minimum engagement depth. That is, if a native leaflet positioned within the clasp 33900 snaps the indicator to the second stable state 33704, then the leaflet will be engaged by or has been properly engaged by the barbed portion 33940. The opposite is also true. That is, if a native leaflet positioned within the clasp 33900 does not snap the indicator to the second stable state, then a sufficient amount of leaflet is not engaged by or will not be engaged by the barbed portion 33940 of the moveable arm 33930.

Referring now to FIGS. 343-345, the example clasp 33900 is shown being deployed within a native valve 40 to secure an implantable device (not shown), such as the devices 100, 200, 300 described above, to one of the native leaflets 42, 44. Referring now to FIG. 343, the clasp 33900 is shown in an open condition with a native leaflet 42, 44 partially inserted into the opening 33906 of the clasp 33900 formed between the fixed and moveable arms 33910, 33930.

Referring now to FIG. 344, the clasp 33900 is closed, for example, by releasing tension on an actuation line (not shown). Because the leaflet 42, 44 is not at or beyond the minimum engagement depth the snap-through indicator 33750 misses or is not sufficiently engaged by the leaflet 42, 44 to snap the indicator 33750 from the first stable state 33702 to the second stable state 33704. As a result, the snap through indicator 33750 can be easily visualized in a "leaflet insufficiently engaged" zone between the fixed arm 33910 and the moveable arm 33930. The snap through indicator 33750 in the "leaflet insufficiently engaged zone" clearly indicates that the leaflet has not been properly grasped by the clasp.

Referring now to FIG. 345, the leaflet 42, 44 has been inserted into the clasp 33900 at or beyond the minimum desired engagement depth—that is, at or beyond the location of the snap-through indicator 33750. The moveable arm 33930 engages and pinches the leaflet 42, 44 against the snap-through indicator 33750 and the fixed arm 33910. Because the leaflet 42, 44 is at or beyond the minimum engagement depth, the snap-through indicator 33750 is snapped from the first stable state 33702, through the fixed arm 33910, to the second stable state 33704. As a result, the snap through indicator 33750 can be easily visualized in a "leaflet sufficiently engaged" zone outside the clasp 33900, on the side of the fixed arm 33910. The snap through indicator 33750 in the "leaflet sufficiently engaged zone" clearly indicates that the leaflet has been properly grasped by the clasp.

Referring now to FIGS. 346-349, an example clasp 34600 for use in implantable prosthetic devices, such as devices 100, 200, 300 described above, is shown. The clasp 34600 includes a fixed arm 33910, a hinge portion 33920, and a moveable arm 33930 having an optional barbed portion 33940 and/or other friction-enhancing portion. FIG. 348 illustrates that the moveable arm 33930 can include an optional cutout 34615 that is used to form the barbed portion 33940 and/or other friction-enhancing portion.

In the example illustrated by FIGS. 346-349, the moveable arm 33930 of the clasp 33900 includes a snap-through indicator 33750. In this example, the snap-through indicator 33750 is integrally formed with the moveable arm 33930. For example, the snap through indicator 33750 can be formed by a pair of spaced apart cutouts 34602 that leave a strip that forms the snap-through indicator 33750 (See FIG. 348). The strip can be shape set to the first stable state 33702 to form the snap-through indicator 33750. The clasp 34600 can be used in any of the implantable prosthetic devices of the present application and can include any of the features or combinations of features of the other clasps described herein.

In the first stable state 33702, the snap-through indicator 33750 bends away from the moveable arm 33930 to the apex 33706. The size and position of the snap-through indicator 33750 is configured to determine whether a desired minimum depth is reached by the native leaflet. In the illustrated embodiment, the snap-through indicator 33750 is closer to the hinge portion 33920 than the barbed portion 33940. This positioning ensures that the snap-through indicator 33750 will snap to the second stable state 33704 when the barbed portion 33940 engages a leaflet that is positioned at the minimum engagement depth. That is, if a native leaflet positioned within the clasp 34600 snaps the indicator to the second stable state 33704, then the leaflet will be properly engaged or has been properly engaged by the barbed portion 33940. The opposite is also true. That is, if a native leaflet positioned within the clasp 34600 does not snap the indicator to the second stable state, then a sufficient amount of leaflet is not engaged by or will not be engaged by the barbed portion 33940 of the moveable arm 33930.

Referring now to FIGS. 350-352, the example clasp 34600 is shown being deployed within a native valve 40 to secure an implantable device (not shown), such as the devices 100, 200, 300 described above, to one of the native leaflets 42, 44. Referring now to FIG. 350, the clasp 34600 is shown in an open condition with a native leaflet 42, 44 partially inserted into the opening 33906 of the clasp 34600 formed between the fixed and moveable arms 33910, 33930.

Referring now to FIG. 351, the clasp 34600 is closed, for example, by releasing tension on an actuation line (not shown). Because the leaflet 42, 44 is not at or beyond the minimum engagement depth the snap-through indicator 33750 misses or is not sufficiently engaged by the leaflet 42, 44 to snap the indicator 33750 from the first stable state 33702 to the second stable state 33704. As a result, the snap through indicator 33750 can be easily visualized in a "leaflet insufficiently engaged" zone between the fixed arm 33910 and the moveable arm 33930. The snap through indicator 33750 in the "leaflet insufficiently engaged zone" clearly indicates that the leaflet has not been properly grasped by the clasp.

Referring now to FIG. 352, the leaflet 42, 44 has been inserted into the clasp 34600 at or beyond the minimum desired engagement depth—that is, at or beyond the location of the snap-through indicator 33750. The fixed arm 33910 engages and pinches the leaflet 42, 44 against the snap-through indicator 33750 and the moveable arm 33930. Because the leaflet 42, 44 is at or beyond the minimum engagement depth, the snap-through indicator 33750 is snapped from the first stable state 33702, through the moveable arm 33930, to the second stable state 33704. As a result, the snap through indicator 33750 can be easily visualized in a "leaflet sufficiently engaged" zone outside the clasp 33900, on the side of the moveable arm 33930. The snap through indicator 33750 in the "leaflet sufficiently engaged zone" clearly indicates that the leaflet has been properly grasped by the clasp.

FIGS. 353A-353D illustrate example embodiments of snap-through indicators 33750 that can be attached to a clasp. For example, the snap-through indicators 33750 illustrated by FIGS. 353A-353D can be used on any of the clasps disclosed herein and/or in place of any of the indicators disclosed herein. In the examples of FIGS. 353A-353C, the snap-through indicators 33750 can be formed from a flat sheet, such as being cut from a flat sheet. In these examples, snap-through indicators 33750 include a beam 33700 that is fixed to attachment portions 35302.

The beam 33700 can take a wide variety of different forms. In the examples of FIGS. 353A and 353B, the beams 33700 are straight or substantially straight and have a constant rectangular cross-section, except at the apex 33706. In FIGS. 353A and 353B, the beam 33700 includes an optional circular disk 35310 with an optional central opening 35312. The disk 35310 can be radiopaque and/or a radiopaque insert can be provided in the central opening. In an example embodiment, the disk 35310 is omitted and the beam has a constant or substantially constant rectangular cross-section.

In the example of FIG. 353C, the beam 33700 extends in a straight line or a substantially straight line and includes a plurality of spaced apart notches 35320 that form spaced apart projections 35322. The spaced apart notches 35320 and projections 35322 can be configured to set the force 33708 (See FIG. 337) at which the beam 33700 snaps from the first stable state 33702 to the second stable state 33704. That is, the size, shape, spacing, etc. of the notches 35320 and projections 35322 can be selected to create a beam 33700 with a desired snap-through force that corresponds to a force that will be applied to the beam when the clasp closes and presses the native valve leaflet against the beam 33700. In FIG. 353C, the beam 33700 includes an optional central opening 35312. A radiopaque insert can be provided in the central opening 35312. In an example embodiment, the central opening is omitted and the notches 35320 and projections 35322 can be uniformly spaced apart.

The attachment portions 35302 can take a wide variety of different forms. The attachment portions 35302 can be tailored to the clasp that the snap-through indicator 33750 will be attached to. In the examples illustrated by FIGS. 353A-353C, the attachment portions 35302 are rectangular or substantially rectangular and extend transversely away from the beam 33700. Optional stress relief cutouts 35350 can be provided between the attachment portions 35302 and the beam 33700. The optional stress relief cutouts 35350 can be configured to allow the beam 33700 to twist relative to the attachment portions 35302. In the examples of FIGS. 353A and 353C, the stress relief cutouts 35350 are semi-circular cutouts. In the example of FIG. 353B, the attachment portions 35302 taper inward to a stress relief radius 35350 between the attachment portion 35302 and the beam 33700. In the illustrated examples of FIGS. 353A-353C, the attachment portions 35302 include holes 35352 or other attachment features for connecting the attachment portions 35302 to the clasp.

Referring to FIG. 353D, in one example embodiment the flat parts illustrated by FIGS. 353A-353C are compressed and/or bent such that the beam 33700 has an upwardly bent shape (as viewed in FIG. 353D) and a corresponding first stable state 33702 to form the snap-through indicator 33750. In one example embodiment, the parts of FIGS. 353A-353C can be shape set such that the beam 33700 has the shape of the upper curved dashed line. In FIG. 353D, the beam 33700 of the snap-through indicator 33750 has a first stable state 33702 and a second stable state 33704. A load is applied to the beam 33700 when the clasp is closed, and the beam is engaged by the native valve leaflet. While the apex 33706 remains above the horizontal (or other snap-through point), the compression in the beam 33700 resists buckling and the system is in the first stable state 33702. As soon as the native valve leaflet pushes the apex 33706 a hair beneath the horizontal (or other snap-through point), however, the compression in the beam 33700 actually encourages buckling which takes place rapidly (the snap). The load on the beam 33700 decreases as the beam snaps from the first stable state 33702 to the second stable state 33704.

The snap through indicators 33750 can be used with a clasp in a wide variety of different ways. For example, the beam 33700 of the snap through indicator 33750 can run along the length of the clasp (See FIGS. 339, 340, 346, and 348) or across the width of the clasp.

While various inventive aspects, concepts and features of the disclosures may be described and illustrated herein as embodied in combination in the example embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein. For example, the various indicators herein can be used on any device that needs to indicate capture of something (e.g., tissue) therein.

Additionally, even though some features, concepts, or aspects of the disclosures may be described herein as being a preferred arrangement or method, such description is not intended to suggest that such feature is required or necessary unless expressly so stated. Still further, example or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of example methods or processes are not limited to inclusion of all steps as being required in all cases, nor is the order that the steps are presented to be construed as required or necessary unless expressly so stated. Further, the treatment techniques, methods, operations, steps, etc. described or suggested herein can be performed on a living animal or on a non-living simulation, such as on a cadaver, cadaver heart, simulator (e.g. with the body parts, tissue, etc. being simulated), etc. The words used in the claims have their full ordinary meanings and are not limited in any way by the description of the embodiments in the specification.

The invention claimed is:

1. A clasp for a heart valve treatment device, the clasp comprising:
   a fixed arm attachable to the heart valve treatment device;
   a movable arm that is movable between an open position and a closed position relative to the fixed arm;
   a hinge portion hingeably connecting the movable arm to the fixed arm;
   and an indicator arm hingeably connected to at least one of the fixed arm and the movable arm;
   wherein the indicator arm is movable between a resting position and an engaged position in which at least a portion of the indicator arm extends beyond a profile of the fixed arm and the movable arm;
   wherein the indicator arm moves through an opening of the movable arm to move to the engaged position; and
   wherein movement of the indicator arm from the resting position to the engaged position indicates capture of a leaflet of a native valve of a patient by the heart valve treatment device.

2. The clasp according to claim 1, wherein the indicator arm comprises a shaped end that extends beyond the profile of the fixed arm and the movable arm when the indicator arm is in the engaged position.

3. The clasp according to claim 2, wherein the indicator arm comprises a flat sheet that is shape set to include the shaped end.

4. The clasp according to claim 1, wherein the clasp and the indicator arm are formed from a single piece of laser cut material.

5. The clasp according to claim 1, wherein the movable arm comprises one or more barbs.

6. A valve repair device for repairing a native valve of a patient, the valve repair device comprising:
   a pair of paddles configured to attach to the native valve of the patient, wherein the paddles are movable between an open position and a closed position;

a clasp attached to each of the paddles, each clasp comprising:

a fixed arm attached to the paddle;

a movable arm connected to the fixed arm, wherein the movable arm is movable between an open position and a closed position relative to the fixed arm; and an indicator arm hingeably connected to at least one of the fixed arm and the movable arm of the clasp;

wherein the indicator arm is movable between a resting position in which the indicator arm is disposed within a profile of the fixed arm and the movable arm and an engaged position in which at least a portion of the indicator arm extends beyond a profile of the fixed arm and the movable arm;

wherein movement of the indicator arm from the resting position to the engaged position indicates capture of a leaflet of the native valve by the pair of paddles.

7. The valve repair device according to claim 6, wherein the clasp further comprises a hinge portion that hingeably connects the movable arm to the fixed arm.

8. The valve repair device according to claim 6, wherein the indicator arm moves through an opening of the movable arm to move to the engaged position.

9. The valve repair device according to claim 6, wherein the indicator arm moves through an opening of the fixed arm to move to the engaged position.

10. The valve repair device according to claim 6, wherein the indicator arm comprises a shaped end that extends beyond the profile of the fixed arm and the movable arm when the indicator arm is in the engaged position.

11. The valve repair device according to claim 10, wherein the indicator arm comprises a flat sheet that is shape set to include the shaped end.

12. The valve repair device according to claim 6, wherein the clasp and the indicator arm are formed from a single piece of laser cut material.

13. A valve repair system for repairing a native valve of a patient during a non-open heart procedure, the valve repair system comprising:

a delivery device having at least one lumen;

a valve repair device for delivering through the at least one lumen of the delivery device and attaching to the native valve of the patient, the valve repair device comprising:

a pair of paddles configured to attach to the native valve of the patient, wherein the paddles are movable between an open position and a closed position;

a clasp attached to each of the paddles, each clasp comprising:

a fixed arm attached to the paddle; a movable arm connected to the fixed arm, wherein the movable arm is movable between an open position and a closed position relative to the fixed arm;

and an indicator arm hingeably connected to at least one of the fixed arm and the movable arm of the clasp;

wherein the indicator arm is movable between a resting position and the movable arm and an engaged position in which at least a portion of the indicator arm extends beyond a profile of the fixed arm and the movable arm; and wherein movement of the indicator arm from the resting position to the engaged position indicates capture of a leaflet of the native valve by the pair of paddles.

14. The valve repair system according to claim 13, wherein the clasp further comprises a hinge portion that hingeably connects the movable arm to the fixed arm.

15. The valve repair system according to claim 13, wherein the indicator arm moves through an opening of the movable arm to move to the engaged position.

16. The valve repair system according to claim 13, wherein the indicator arm moves through an opening of the fixed arm to move to the engaged position.

17. The valve repair system according to claim 13, wherein the indicator arm comprises a shaped end that extends beyond the profile of the fixed arm and the movable arm when the indicator arm is in the engaged position.

18. The valve repair system according to claim 13, wherein the clasp and the indicator arm are formed from a single piece of laser cut material.

\* \* \* \* \*